US 12,005,115 B2

(12) United States Patent
Kanekiyo et al.

(10) Patent No.: US 12,005,115 B2
(45) Date of Patent: Jun. 11, 2024

(54) EPSTEIN-BARR VIRUS VACCINES

(71) Applicant: The USA, as represented by the Secretary, Dept. of Health and Human Services, Bethesda, MD (US)

(72) Inventors: Masaru Kanekiyo, North Bethesda, MD (US); Gary J. Nabel, Chestnut Hill, MA (US); Jeffrey Cohen, Silver Springs, MD (US); Wei Bu, Potomac, MD (US)

(73) Assignee: The United States of America as Represented By The Secretary of the Department of Health and Human Services, Rockville, MD (US)

( * ) Notice: Subject to any disclaimer, the term of this patent is extended or adjusted under 35 U.S.C. 154(b) by 301 days.

(21) Appl. No.: 16/922,322

(22) Filed: Jul. 7, 2020

(65) Prior Publication Data

US 2020/0330587 A1   Oct. 22, 2020

Related U.S. Application Data

(62) Division of application No. 15/028,655, filed as application No. PCT/US2014/060142 on Oct. 10, 2014, now Pat. No. 10,744,199.

(60) Provisional application No. 61/921,284, filed on Dec. 27, 2013, provisional application No. 61/889,840, filed on Oct. 11, 2013.

(51) Int. Cl.
| | |
|---|---|
| A61K 39/245 | (2006.01) |
| A61K 39/12 | (2006.01) |
| C07K 14/00 | (2006.01) |
| C07K 14/005 | (2006.01) |
| C07K 14/195 | (2006.01) |
| C07K 16/08 | (2006.01) |
| C12N 7/00 | (2006.01) |
| A61K 39/00 | (2006.01) |

(52) U.S. Cl.
CPC ............ *A61K 39/245* (2013.01); *A61K 39/12* (2013.01); *C07K 14/00* (2013.01); *C07K 14/005* (2013.01); *C07K 14/195* (2013.01); *C07K 16/085* (2013.01); *C12N 7/00* (2013.01); *A61K 2039/55505* (2013.01); *A61K 2039/575* (2013.01); *A61K 2039/64* (2013.01); *C07K 2317/33* (2013.01); *C07K 2317/76* (2013.01); *C07K 2319/00* (2013.01); *C07K 2319/40* (2013.01); *C07K 2319/735* (2013.01); *C12N 2710/16222* (2013.01); *C12N 2710/16234* (2013.01); *C12N 2710/16271* (2013.01)

(58) Field of Classification Search
None
See application file for complete search history.

(56) References Cited

U.S. PATENT DOCUMENTS

| | | |
|---|---|---|
| 7,094,598 B2 | 8/2006 | Nabel et al. |
| 7,097,841 B2 | 8/2006 | Carter et al. |
| 7,608,268 B2 | 10/2009 | Carter et al. |
| 9,441,019 B2 | 9/2016 | Nabel et al. |
| 10,137,190 B2 | 11/2018 | Nabel et al. |
| 2002/0054882 A1 | 5/2002 | Okuno et al. |
| 2003/0211996 A1 | 11/2003 | Gowans et al. |
| 2005/0042229 A1 | 2/2005 | Yang et al. |
| 2005/0108791 A1 | 5/2005 | Edgerton |
| 2006/0251679 A1 | 11/2006 | Carter et al. |
| 2007/0082054 A1 | 4/2007 | Mooter et al. |
| 2007/0224205 A1 | 9/2007 | Powell et al. |
| 2008/0299151 A1 | 12/2008 | Fomsgaard |
| 2009/0233377 A1 | 9/2009 | Iwahori et al. |
| 2010/0137412 A1 | 6/2010 | Zhou et al. |
| 2010/0285982 A1 | 11/2010 | Golding et al. |
| 2010/0297174 A1 | 11/2010 | Garcia-Sastre et al. |
| 2011/0020374 A1* | 1/2011 | Frazer .................... A61P 35/00 536/23.1 |
| 2011/0038025 A1 | 2/2011 | Naitou et al. |
| 2011/0059130 A1 | 3/2011 | Yusibov |
| 2011/0177122 A1 | 7/2011 | Nabel et al. |

(Continued)

FOREIGN PATENT DOCUMENTS

| | | |
|---|---|---|
| EP | 1504037 | 12/2009 |
| WO | WO 2003/094849 | 11/2003 |

(Continued)

OTHER PUBLICATIONS

A3KF33, UniProtKB A3KF33_I57A5, Sep. 21, 2011 [online]. [Retrieved on Feb. 26, 2013]. Retrieved from the internet <URL: http://www.uniprot.org/uniprot/A3KF33.txt?version=36>.

(Continued)

*Primary Examiner* — Stacy B Chen

(74) *Attorney, Agent, or Firm* — Sughrue Mion, PLLC

(57) ABSTRACT

Vaccines are provided that elicit neutralizing antibodies to Epstein-Barr virus (EBV). Some vaccines comprise nanoparticles that display envelope proteins from EBV on their surface. The nanoparticles comprise fusion proteins comprising a monomeric subunit of a self-assembly protein, such as ferritin, joined to at least a portion of an EBV envelope protein. The fusion proteins self-assemble to form the envelope protein-displaying nanoparticles. Such vaccines can be used to vaccinate an individual against infection by different types of Epstein-Barr viruses as well as Epstein-Barr viruses that are antigenically divergent from the virus from which the EBV envelope protein was obtained. Also provided are fusion proteins and nucleic acid molecules encoding such proteins.

1 Claim, 25 Drawing Sheets

Specification includes a Sequence Listing.

(56) References Cited

U.S. PATENT DOCUMENTS

| | | |
|---|---|---|
| 2011/0212128 A1 | 9/2011 | Galarza et al. |
| 2016/0303224 A1 | 10/2016 | Kanekiyo et al. |
| 2018/0021258 A1 | 1/2018 | Graham et al. |
| 2019/0192651 A1 | 6/2019 | Boyington et al. |

FOREIGN PATENT DOCUMENTS

| | | | |
|---|---|---|---|
| WO | WO 2009/109428 | | 9/2009 |
| WO | WO 2010/036948 | | 4/2010 |
| WO | WO 2010/115046 | A2 * | 10/2010 |
| WO | WO 2010/117786 | | 10/2010 |
| WO | WO 2011/035422 | | 3/2011 |
| WO | WO 2011/044152 | | 4/2011 |
| WO | WO 2011/050168 | A2 * | 4/2011 |
| WO | WO 2012/162428 | | 11/2012 |
| WO | WO 2013/044203 | | 3/2013 |
| WO | WO 2015/054639 | | 4/2015 |
| WO | WO 2015/183969 | | 12/2015 |
| WO | WO 2016/021209 | | 2/2016 |

OTHER PUBLICATIONS

GenBank Accession No. 3EGM_A submitted Sep. 11, 2008, 2 pages.
GenBank Accession No. AAP34324, submitted May 1, 2003, 2 pages.
Bachmann, M.F., et al., "Neutralizing antiviral B cell responses," Annu Rev Immunol, 1997, 15:235-270.
Bernacchioni et al. "Loop Electrostatics Modulates the Intersubunit Interactions in Ferritin," ACS Chemical Biology, 2014, vol. 9, pp. 2517-2525.
Caton, A.J., et al., "The antigenic structure of the influenza virus A/PR/8/34 hemagglutinin (H1 subtype)," Cell, 1982, 31:417-427.
Cohen et al., "Ferritin as an Endogenous MRI Reporter for Non-invasive Imaging Neoplasia of Gene Expression in C6 Glioma Tumors," Neoplasia, Feb. 2005, 7(2):109-117.
C0LT38, UniProtKB C0LT38_9INFB, Sep. 21, 2011 [online]. [Retrieved on Feb. 26, 2013]. Retrieved from the internet <URL: http://www.uniprot.org/uniprot/C0LT38.txt?version=18>.
Corti, D., et al., "Heterosubtypic neutralizing antibodies are produced by individuals immunized with a seasonal influenza vaccine," J Clin Invest, 2010, 120:1663-1673.
Corti, D., et al., "A neutralizing antibody selected from plasma cells that binds to group 1 and group 2 influenza A hemagglutinins," Science, 2011, 333:850-856.
Dintzis, H.M. et al., "Molecular determinants of immunogenicity: the immunon model of immune response," Proc Natl Acad Sci USA, 1976, 73:3671-3675.
Ekiert, D.C., et al., "A highly conserved neutralizing epitope on group 2 influenza A viruses," Science, 2011, 333:843-850.
Ekiert, D.C., et al., "Antibody recognition of a highly conserved influenza virus epitope," Science, 2009, 324:246-251.
Greenstone et al. "Chimeric papillomavirus virus-like particles elicit antitumor immunity against the E7 oncoprotein in an HPV16 tumor model," Proc. Natl. Acad. Sci. USA, Feb. 1998, vol. 95, pp. 1800-1805.
Harrison "The Structure and Function of Ferritin," Biochemical Education, 1986, vol. 14, No. 4, pp. 154-162.
Haynes, J.R., "Influenza virus-like particle vaccines," Expert Rev Vaccines, 2009, 8:435-445.
He et al. "Presenting native-like trimeric HIV-1 antigens with self-assembling nanoparticles," Nature Communications, Jun. 2016, vol. 7, 12041, 15 pages.
Kanekiyo, Masaru, et al., "Self-assembling influenza nanoparticle vaccines elicit broadly neutralizing H1N1 antibodies", Nature, Nature Publishing Group, United Kingdom, vol. 499, No. 7456, Jul. 4, 2013 (Jul. 4, 2013), pp. 102-106.
Kanekiyo et al. "Rational Design of an Epstein-Barr Virus Vaccine Targeting the Receptor-Binding Site," Cell, Aug. 2015, vol. 162, No. 5, pp. 1090-1100.
Kang, S.M., et al., "Influenza vaccines based on virus-like particles", Virus Research, Amsterdam, NL, vol. 143, No. 2, Aug. 1, 2009 (Aug. 1, 2009), pp. 140-146.
Kashyap, A.K., et al., "Combinatorial antibody libraries from survivors of the Turkish H5N1 avian influenza outbreak reveal virus neutralization strategies," Proc Natl Acad Sci USA, 2008, 105:5986-5991.
Kong, W.P., et al., "Protective immunity to lethal challenge of the 1918 pandemic influenza virus by vaccination," Proc Natl Acad Sci USA, 2006, 103:15987-15991.
Kossovsky et al. "Nanocrystalline Epstein-Barr virus decoys," Journal of Applied Biomaterials: An Official Journal of the Society for Biomaterials, Jan. 1991, vol. 2, No. 4, pp. 251-259.
Krause, J.C., et al., "A broadly neutralizing human monoclonal antibody that recognizes a conserved, novel epitope on the globular head of the influenza H1N1 virus hemagglutinin," J Virol, 2011, 85:10905-10908.
Lambert, L.C., et al., "Influenza vaccines for the future," N Engl J Med, 2010, 363, 2036-2044.
Lee, L.A., et al., "Adaptations of nanoscale viruses and other protein cages for medical applications", Nanomedicine: Nanotechnology, Biology and Medicine, Elsevier, NL, vol. 2, No. 3, Sep. 1, 2006 (Sep. 1, 2006), pp. 137-149.
Lee et al. "Viruses and Virus-Like Protein Assemblies—Chemically Programmable Nanoscale Building Blocks," Nano Res, 2009, vol. 2, pp. 349-364.
Li, C.Q. et al., "Ferritin nanoparticle technology: A new platform for antigen presentation and vaccine development," Industrial Biotechnol 2, 143-147 (2006).
Lopez-Sagaseta et al. "Self-assembling protein nanoparticles in the design of vaccines," Computational and Structural Biotechnology Journal, 2016, vol. 14, pp. 58-68.
Meldrum, F.C., et al., "Magnetoferritin: in vitro synthesis of a novel magnetic protein," Science, 1992, 257:522-523.
Nabel, G.J., et al., "Induction of unnatural immunity: prospects for a broadly protective universal influenza vaccine," Nat Med, 2010, 16:1389-1391.
Okuno, Y., et al., "A common neutralizing epitope conserved between the hemagglutinins of influenza A virus H1 and H2 strains," J Virol, 1993, 67:2552-2558.
Pulford et al. "Expression of the Epstein-Barr Virus Envelope Fusion Glycoprotein GB85 Gene by a Recombinant Baculovirus," Journal of General Virology, Nov. 1994, vol. 75, No. 11, pp. 3241-3248.
Roldao, A., et al., "Virus-like particles in vaccine development," Expert Rev Vaccines, 2010, 9:1149-1176.
Ruiss et al. "A Virus-Like Particle-Based Epstein-Barr Virus Vaccine," Journal of Virology, Dec. 2011, vol. 85, No. 24, pp. 13105-13113.
Sheridan, C., "Flu vaccine makers upgrade technology—and pray for time," Nat Biotechnol, 2009, 27:489-491.
Steel et al. "Influenza Virus Vaccine Based on the Conserved Hemagglutinin Stalk Domain," MBIO, American Society for Microbiology, May 2010, vol. 1, No. 1, pp. e00018-10/1-9.
Sui, J., et al., "Structural and functional bases for broad-spectrum neutralization of avian and human influenza A viruses," Nat Struct Mol Biol, 2009, 16:265-273.
Treanor, J.J., et al., "Safety and immunogenicity of a recombinant hemagglutinin vaccine for H5 influenza in humans," Vaccine, 2001, 19:1732-1737.
Treanor, J.J., "Safety and immunogenicity of a baculovirus-expressed hemagglutinin influenza vaccine: a randomized controlled trial," JAMA, 2007, 297:1577-1582.
Vallhov et al. "Exosomes Containing Glycoprotein 350 Released by EBV-Transformed B Cells Selectively Target B Cells through CD21 and Block EBV Infection in Vitro," The Journal of Immunology, Jan. 2011, vol. 186, No. 1, pp. 73-82.
Wang, T.T., et al., "Broadly protective monoclonal antibodies against H3 influenza viruses following sequential immunization with different hemagglutinins," PLoS Pathog, 2010, vol. 6, Issue 2, e1000796.
Wei, C.J., et al., Cross-neutralization of 1918 and 2009 influenza viruses: role of glycans in viral evolution and vaccine design. Sci Transl Med, 2010, 2, 24ra21.

(56) References Cited

OTHER PUBLICATIONS

Wei, C.J., et al., "Induction of broadly neutralizing H1N1 influenza antibodies by vaccination," Science, 2010, 329:1060-1064.
Wei, C.J., et al., "Comparative efficacy of neutralizing antibodies elicited by recombinant hemagglutinin proteins from avian H5N1 influenza virus," J Virol, 2008, 82:6200-6208.
Whittle, J.R., et al., "Broadly neutralizing human antibody that recognizes the receptor-binding pocket of influenza virus hemagglutinin," Proc Natl Acad Sci USA, 2011, 108:14216-14221.
WHO Reference on Animal Influenza Diagnosis and Surveillance, 2002, Department of Communicable Disease Surveillance and Response, World Health Organization).
Wu, C.Y., et al., "Mammalian expression of virus-like particles for advanced mimicry of authentic influenza virus," PLoS One 5, 2010, e9784.
Xiong, A.S., et al., "PCR-based accurate synthesis of long DNA sequences," Nat Protoc, 2006, 1(2):791-797.
Yamashita, I., et al., "Ferritin in the field of nanodevices," Biochim Biophys Acta, 2010, 1800:846-857.
Yang, Z.Y., et al., "Immunization by avian H5 influenza hemagglutinin mutants with altered receptor binding specificity," Science, 2007, 317:825-828).
Yassine et al. "Hemagglutinin-stem nanoparticles generate heterosubtypic influenza protection." Nature Medicine, Sep. 2015, vol. 21, No. 9, pp. 1065-1070.
Zhang, Y., et al., "Self-Assembly in the Ferritin Nano-Cage Protein Super Family," Int. J. Mol. Sci., 2011, 12:5406-5421.
Zhang et al. "Universal Influenza Vaccines, a Dream to Be Realized Soon," Viruses, 2014, vol. 6, pp. 1974-1991.
International Search Report and Written Opinion prepared by the European Patent Office dated Feb. 5, 2015, for International Application No. PCT/US2014/060142.
English Translation of Official Action for China Patent Application No. 201480066333.2, dated Sep. 17, 2018 15 pages.
English Translation of Official Action for China Patent Application No. 201480066333.2, dated Mar. 20, 2019 5 pages.
Official Action for European Patent Application No. 14799574.0, dated Nov. 13, 2017 4 pages.
Official Action for European Patent Application No. 14799574.0, dated Nov. 21, 2018 5 pages.
Official Action for U.S. Appl. No. 15/028,655, dated Apr. 26, 2017 11 pages Restriction Requirement.
Official Action for U.S. Appl. No. 15/028,655, dated Oct. 26, 2017 12 pages.
Official Action for U.S. Appl. No. 15/028,655, dated May 11, 2018 9 pages.
Official Action for U.S. Appl. No. 15/028,655, dated Dec. 27, 2018 10 pages.
Notice of Allowance for U.S. Appl. No. 15/028,655, dated Apr. 13, 2020 8 pages.
Joyce et al. "Vaccine-Induced Antibodies that Neutralize Group 1 and Group 2 Influenza A Viruses," Cell, Jul. 2016, vol. 166, No. 3, pp. 609-623.
Ni et al. "Structural Insights into the Membrane Fusion Mechanism Mediated by Influenza Virus Hemagglutinin," Biochemistry, 2014, vol. 53, pp. 846-854.
Scorza et al. "Universal influenza vaccines: Shifting to better vaccines," Vaccine, Mar. 2016, vol. 34, No. 26, pp. 2926-2933.
English Translation of Official Action for China Patent Application No. 201480066333.2, dated Jul. 17, 2019 5 pages.
Notice of Allowance with English Translation for China Patent Application No. 201480066333.2, dated Mar. 17, 2020 5 pages.
Official Action for European Patent Application No. 14799574.0, dated Jul. 12, 2019 4 pages.
Official Action for European Patent Application No. 14/799574.0, dated Feb. 7, 2020 4 pages.
Official Action for India Patent Application No. 201617016021, dated May 8, 2019 7 pages.

\* cited by examiner

EPSTEIN-BARR VIRUS VACCINES

CROSS REFERENCE TO RELATED APPLICATIONS

This application is a divisional of U.S. patent application Ser. No. 15/028,655, filed Apr. 11, 2016; which is a national stage application under 35 U.S.C. 371 and claims the benefit of PCT Application No. PCT/US2014/060142, having an international filing date of Oct. 10, 2014, which designated the United States; which PCT application claims the benefit of U.S. Provisional Application No. 61/889,840, filed Oct. 11, 2013, and U.S. Provisional Application No. 61/921,284, filed Dec. 27, 2013, the disclosure of each of which are incorporated herein by reference.

REFERENCE TO SEQUENCE LISTING

This application contains a Sequence Listing submitted as an electronic text file named "6137NIAID-34-PROV_Sequence_Listing_ST25.txt", having a size in bytes of 412 KB, and created on Oct. 11, 2013. The information contained in this electronic file is hereby incorporated by reference in its entirety pursuant to 37 CFR § 1.52(e)(5).

SUMMARY OF THE INVENTION

The present invention provides novel, nanoparticle-based vaccines for Epstein-Barr virus that are easily manufactured, potent, and which elicit neutralizing antibodies to Epstein-Barr virus. In particular, the present invention provides novel Epstein-Barr virus protein-ferritin nanoparticle (np) vaccines. Such nanoparticles comprise fusion proteins, each of which comprises a monomeric subunit of a self-assembly protein, such as ferritin, joined to an immunogenic portion of an Epstein-Barr virus envelope protein. Because such nanoparticles display Epstein-Barr virus proteins on their surface, they can be used to vaccinate an individual against Epstein-Barr virus.

One embodiment of the present invention is a nanoparticle that includes a first fusion protein that is joined to at least one immunogenic portion from a first Epstein-Barr virus envelope protein that is selected from the group consisting of gp350, gH, gL, gp42, gB and BMRF2. The first fusion protein includes at least 25 contiguous amino acids from a monomeric subunit protein capable of self-assembling into a nanoparticle. Further, the nanoparticle expresses the at least one immunogenic portion on its surface.

The monomeric subunit of the self-assembly protein can be selected from a monomeric ferritin subunit protein, a monomeric encapsulin protein, a monomeric O3-33 protein, a monomeric SOR protein, a monomeric LS protein and a monomeric PDC protein. In the embodiment of a monomeric ferritin subunit protein, it can be selected from a bacterial, plant, algal, insect, fungal, and mammalian ferritin. More specifically, the monomeric subunit protein can be selected from a monomeric subunit of a *Helicobacter pylori* ferritin protein, a monomeric subunit of a *Escherichia coli* protein and a monomeric subunit of a bullfrog ferritin protein. Also, the monomeric ferritin subunit protein can be a hybrid protein that includes at least a portion of a bullfrog ferritin protein joined to at least a portion of a ferritin protein that is selected from a *Helicobacter pylori* ferritin protein and *Escherichia coli* ferritin protein.

The monomeric subunit self-assembling protein can include at least 25 contiguous amino acids of, be at least about 80% identical to or comprise an amino acid sequence selected from SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26 and SEQ ID NO:29.

The first Epstein-Barr virus envelope protein can be from Epstein-Barr virus type 1 or Epstein-Barr virus type 2. Also, the at least one immunogenic portion from the first Epstein-Barr virus envelope protein can include at least 100 amino acids from an amino acid sequence selected from SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132, SEQ ID NO:134 and SEQ ID NO:136. Further, the at least one immunogenic portion can include at least one domain selected from EBV gp350 Domain I, EBV gp350 Domain II and EBV gp350 Domain III. In addition, the at least one immunogenic portion can include the amino acid sequences of EBV gp350 Domain I and Domain II. Further, the at least one immunogenic portion can include the EBV gp350 CR2-binding site.

In this embodiment, the first EBV envelope protein can include an amino acid sequence that is at least about 80% identical to, is identical to or can elicit an immune response to an amino acid sequence selected from SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132, SEQ ID NO:134 and SEQ ID NO:136.

The first fusion protein can comprise a linker sequence.

The nanoparticle can elicit an immune response against an Epstein-Barr virus, including a strain of Epstein-Barr virus that is heterologous to the strain Epstein-Barr virus from which the Epstein-Barr virus envelope protein was obtained, as well as to an Epstein-Barr virus that is antigenically divergent from the Epstein-Barr virus from which the Epstein-Barr virus envelope protein was obtained.

The first fusion protein can include an amino acid sequence that is at least about 80% identical to or is identical to a sequence selected from SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:128, SEQ ID NO:134, SEQ ID NO:142, SEQ ID NO:144 and SEQ ID NO:146, wherein the nanoparticle elicits an immune response against an Epstein-Barr virus.

The nanoparticle can further include a second fusion protein that includes at least one immunogenic portion from a second Epstein-Barr virus envelope protein that is selected from gp350, gH, gL, gp42, gB and BMRF2. In this embodiment, the first and second Epstein-Barr virus envelope proteins are not the same and the nanoparticle expresses the at least one immunogenic portion from a second fusion protein on its surface.

A further embodiment of the present invention is a vaccine composition that includes any one of the foregoing described nanoparticles. The vaccine composition can further include at least one additional nanoparticle that includes a second fusion protein with at least 25 contiguous amino acids from a monomeric subunit protein that can self-assemble into a nanoparticle and that is joined to at least one immunogenic portion from a second Epstein-Barr envelope protein that can be gp350, gH, gL, gp42, gB and BMRF2. In this embodiment, the at least one immunogenic portion of the second fusion protein is from an Epstein-Barr virus envelope protein from a different strain of Epstein-Barr virus than the first Epstein-Barr virus envelope protein and the nanoparticle expresses the at least one immunogenic portion of the second fusion portion on its surface.

A further embodiment of the present invention is a method to produce a vaccine against Epstein-Barr virus. The method includes expressing a fusion protein that includes at least 25 contiguous amino acids from a monomeric subunit protein that can self-assemble into a nanoparticle and that is joined to at least one immunogenic portion from a first Epstein-Barr virus envelope protein selected from gp350, gH, gL, gp42, gB and BMRF2. The step of expressing is conducted under conditions such that the fusion protein forms a nanoparticle displaying the at least one immunogenic portion of an Epstein-Barr virus envelope protein on its surface. The method further includes recovering the nanoparticle.

A further embodiment of the present invention is a method to vaccinate an individual against Epstein-Barr virus that includes administering a nanoparticle to an individual such that the nanoparticle elicits an immune response against Epstein-Barr virus. The nanoparticle includes a fusion protein that includes at least 25 contiguous amino acids from a monomeric subunit protein that can self-assemble into a nanoparticle and that is joined to at least one immunogenic portion of a first Epstein-Barr virus protein selected from gp350, gH, gL, gp42, gB and BMRF2. In this embodiment, the nanoparticle displays the at least one immunogenic portion from an Epstein-Barr virus envelope protein on its surface. In this method to vaccinate, the nanoparticle can elicit an immune response to an Epstein-Barr virus strain that is heterologous to the strain of Epstein-Barr virus from which the envelope protein was obtained, or to an Epstein-Barr virus that is antigenically divergent from the Epstein-Barr virus from which the envelope protein was obtained.

The method to vaccinate can include administering to the individual a first vaccine composition and then at a later time administering a second vaccine composition that includes a nanoparticle that comprises a fusion protein comprising at least 25 contiguous amino acids from a monomeric subunit protein that can self-assemble into a nanoparticle and that is joined to at least one immunogenic portion of the first Epstein-Barr virus envelope protein selected from gp350, gH, gL, gp42, gB and BMRF2. In this embodiment, the nanoparticle displays the at least one immunogenic portion of an Epstein-Barr virus envelope protein on its surface. In this embodiment, the fusion protein can include an amino acid sequence that is at least about 80% identical to or is identical to a sequence that is selected from SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, SEQ ID NO:98, SEQ ID NO:101 SEQ ID NO:104, SEQ ID NO:128, SEQ ID NO:134, SEQ ID NO:142, SEQ ID NO:144 and SEQ ID NO:146.

In this embodiment, the second vaccine composition may be administered between ten days and four weeks following administration of the first vaccine composition. In this embodiment, the second vaccine composition may be administered between ten days and two months following administration of the first vaccine composition. In one embodiment, a third vaccine composition may be administered six months after administration of the first vaccine composition.

A further embodiment of the present invention is a fusion protein that includes at least 25 contiguous amino acids from a monomeric subunit protein that can self-assemble into a nanoparticle and that is joined to at least one immunogenic portion from an Epstein-Barr virus envelope protein selected from gp350, gH, gL, gp42, gB and BMRF2. In this embodiment, the monomeric subunit can be selected from a monomeric ferritin subunit protein, a monomeric encapsulin protein, a monomeric O3-33 protein, a monomeric SOR protein, a monomeric LS protein and a monomeric PDC protein. The monomeric ferritin subunit protein can be selected from a bacterial, plant, algal, insect, fungal and mammalian ferritin. Further, the monomeric ferritin subunit protein can be selected from a monomeric subunit of a *Helicobacter pylori* ferritin protein, a monomeric subunit of an *Escherichia coli* ferritin protein and a monomeric subunit of a bullfrog ferritin protein. Further, the monomeric ferritin subunit protein can be a hybrid protein that includes at least a portion of a bullfrog ferritin protein joined to at least a portion of a *Helicobacter pylori* ferritin protein or an *Escherichia coli* ferritin protein. Still further, the monomeric ferritin subunit protein can comprise an amino acid sequence that is at least about 80% identical to or is identical to or comprises at least 25 contiguous amino acids selected from SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26 and SEQ ID NO:29, wherein the fusion protein can self-assemble into nanoparticles. The fusion protein can be an Epstein-Barr virus envelope protein type 1 or type 2.

The at least one immunogenic portion of the fusion protein can comprise at least 100 amino acids from an amino acid sequence selected from SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132 and SEQ ID NO:136. The at least one immunogenic portion can include at least one domain selected from EBV gp350 Domain I, EBV gp350 Domain II and EBV gp350 Domain III. Further, the at least one immunogenic portion can include the amino acid sequences of EBV gp350 Domain I and Domain II. Still further, the at least one immunogenic portion can include the EBV gp350 CR2-binding site.

The EBV envelope protein can include an amino acid sequence at least about 80% identical to or is identical to an amino acid sequence selected from SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132 and SEQ ID NO:136. The EBV envelope protein of the fusion protein can be capable of eliciting an immune response to the protein that includes an amino acid sequence selected from SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132 and SEQ ID NO:136.

The fusion protein can also include a linker sequence.

Further embodiments of the present invention include nucleic acid molecules that encode the foregoing described fusion proteins. The nucleic acid molecule can be functionally linked to a promoter.

A still further embodiment of the present invention is a recombinant cell that includes the foregoing nucleic acid molecule.

A further embodiment of the present invention is a recombinant virus that includes the foregoing described nucleic acid molecule.

BACKGROUND

Epstein-Barr virus (EBV), also referred to as human herpesvirus 4 (HHV-4), is the principle etiological agent of infectious mononucleosis (IM) and is also associated with several human cancers, with more than 300,000 people being affected each year worldwide. The World Health Organization estimates that 95% of adults worldwide have been infected with EBV and are carriers of the virus. For the majority of individuals, EBV does not cause any symptoms and is indistinguishable from common, mild childhood illnesses. Currently, there is no vaccine for EBV. However, prevention of IM and EBV-associated malignancies through vaccination would have a substantial public health and economic benefit.

EBV has a linear, double-stranded DNA genome comprising approximately 192 kilobases (KB) of DNA, surrounded by a protein capsid. The capsid is surrounded by a protein tegument, which in turn is surrounded by an envelope. The EBV envelope contains several proteins, including glycoprotein gp350, gH, gB, gM, gp42, gL, gp78, gp150 and gN. The most abundant envelope glycoprotein is 350/220 (gp350), which binds complement receptor 2 (CR2 or CD21) enabling EBV infection of B cells, while glycoproteins gH and gp42 bind integrins and human leukocyte antigen class II molecules, respectively. Antibodies directed toward the putative CR2-binding site (CR2BS) on gp350 have been shown to potently inhibit EBV infections of B cells, and thus vaccine efforts against EBV have been largely focused on gp350.

In addition to infecting B cells, EBV also infects epithelial cells in the oropharynx where it is thought to spread to B cells. Current data suggests that infection of epithelial cells by EBV is initiated by attachment of EBV BMRF2 protein to epithelial cells followed by binding of EBV gH/gL to integrins, which serve as receptors for the virus on epithelial cells. Antibodies to gH/gL in human plasma blocks EBV infection of epithelial cells (Bu and Cohen, unpublished data) suggesting that a vaccine capable of inducing antibodies to EBV gH/gL may help to prevent infection or human disease due to EBV.

While work on EBV vaccines has continued, to date there is no efficacious EBV vaccine. For example, a recently completed phase 2 clinical trial of an adjuvanted recombinant gp350 protein vaccine showed that the vaccine did not protect against EBV infection but did reduce the incidence of IM by 78% (Sokal, E. M., et al. J Infect Dis. 196:1749-53, 2007). Thus, there remains a need for an efficacious Epstein-Barr virus vaccine that provides robust protection against EBV. The present invention meets this need by providing a novel ENV-SA protein-based nanoparticle (ENV-SA np) vaccine that is easily manufactured, potent, and elicits neutralizing antibodies against EBV.

and gp42 (B) in immune sera at week 5 were measured by a luciferase immunoprecipitation system (LIPS) assay. LIPS assay was preformed as previously described (Sashihara J., et al., Virology. 391, 249-256, 2009). Bar indicates the median with range. *, p<0.05; , p<0.01; *, p<0.001; ns, no significant difference.

Figure 16:
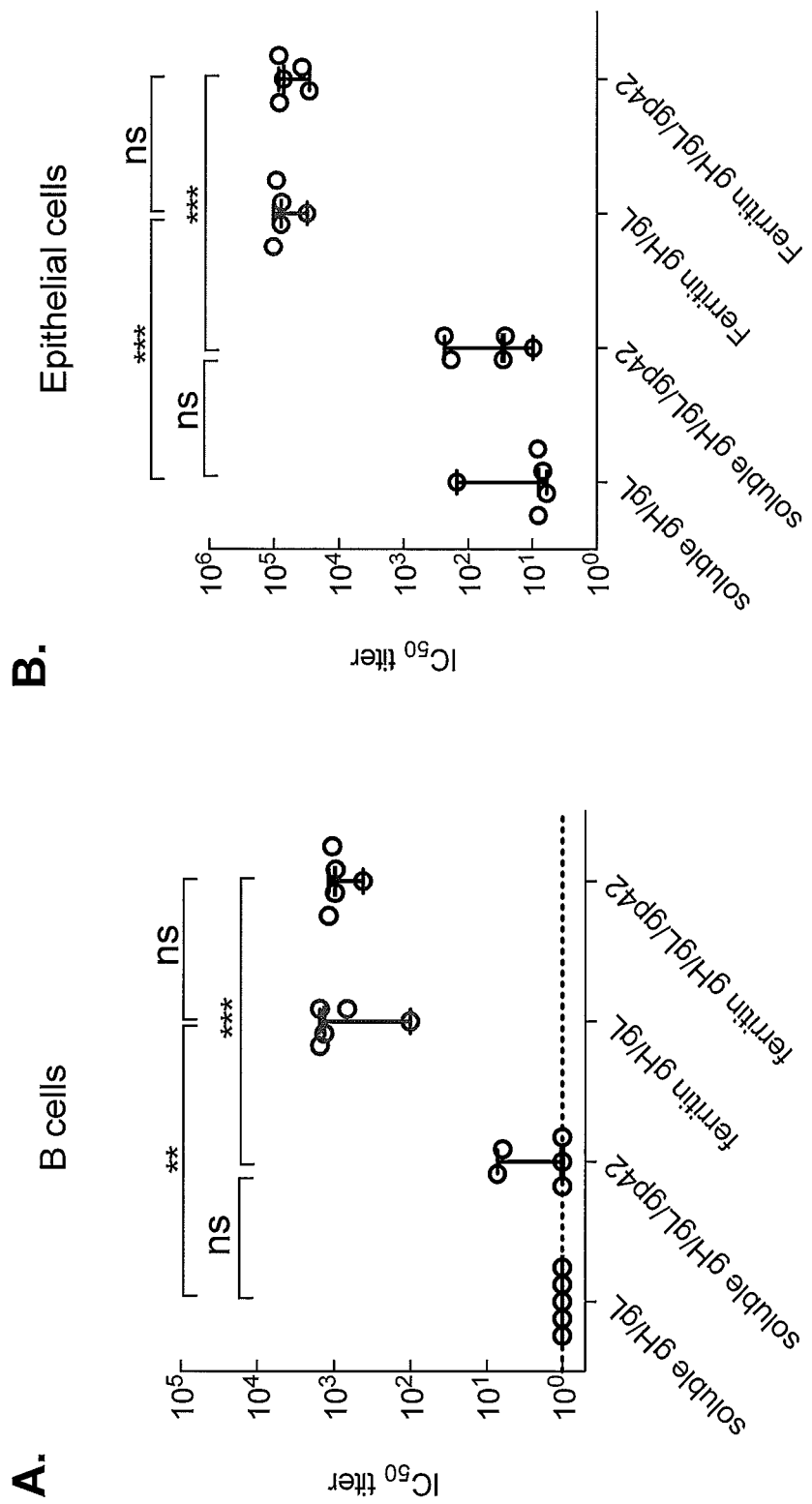

FIG. 16. Comparison of neutralization of soluble gH/gL, soluble gH/gL/gp42, ferritin-based gH/gL nanoparticle and ferritin-based gH/gL/gp42 nanoparticles in B cells (A) and epithelial cells (B). Groups of BALB/c mice (n=5) were immunized with 0.5 µg indicated proteins with a Ribi adjuvant at week 0 and 3. (A) The neutralization assay was based on infection of B cells with GFP reporter virus (Sashihara J., et al., Virology. 391, 249-256, 2009) and the titer is shown as the dilution of serum capable to inhibit virus infection by 50% ($IC_{50}$). (B) The neutralization of EBV infection of epithelial cells was performed by incubation of mouse sera serially diluted in a 2-fold steps with GFP reporter virus for 2 hours. The mixture was added to SVK-CR2 cells (an epithelial cell line that expresses CR2, a receptor for EBV) in a 96-well plate and incubated for 3 days at 37° C. Cells were washed with 1×PBS, trypsinized, and fixed in 2% paraformaldehyde in PBS.GFP positive cells were quantified and the titer is shown as the dilution of serum able to inhibit virus infection by 50% ($IC_{50}$). Each dot represents an individual mouse. Bar indicates the median with range. *, p<0.05; , p<0.01; *, p<0.001, ns, no significant difference.

Figure 17:
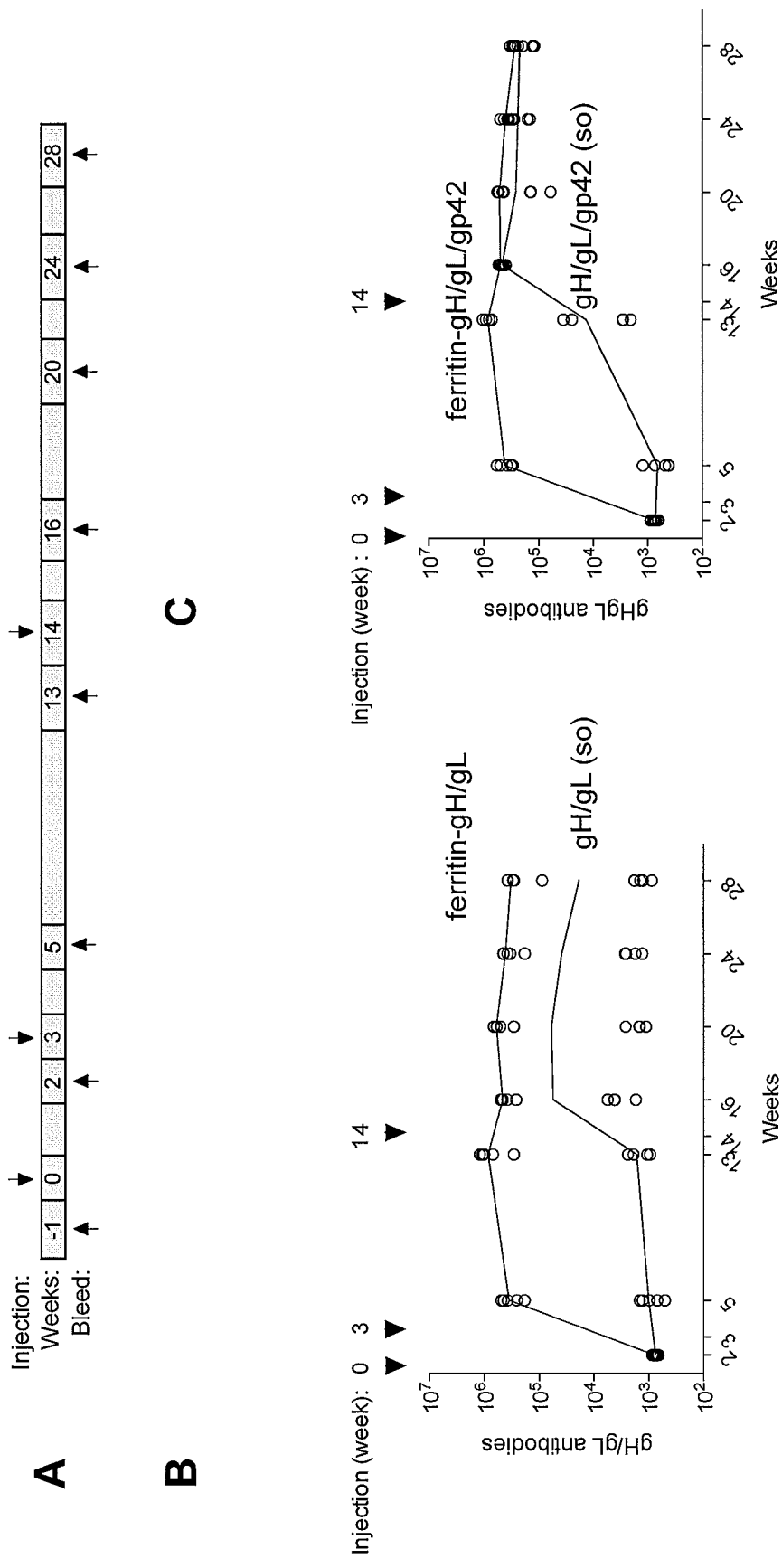

FIG. 17. (A) Immunization and sampling schedule. Comparison of kinetics of gH/gL antibody titers in sera from mice immunized with soluble gH/gL or gH/gL ferritin-based-nanoparticles (B) and soluble gH/gL/gp42 or gH/gL/gp42 ferritin-based-nanoparticles (C).

Figure 18:
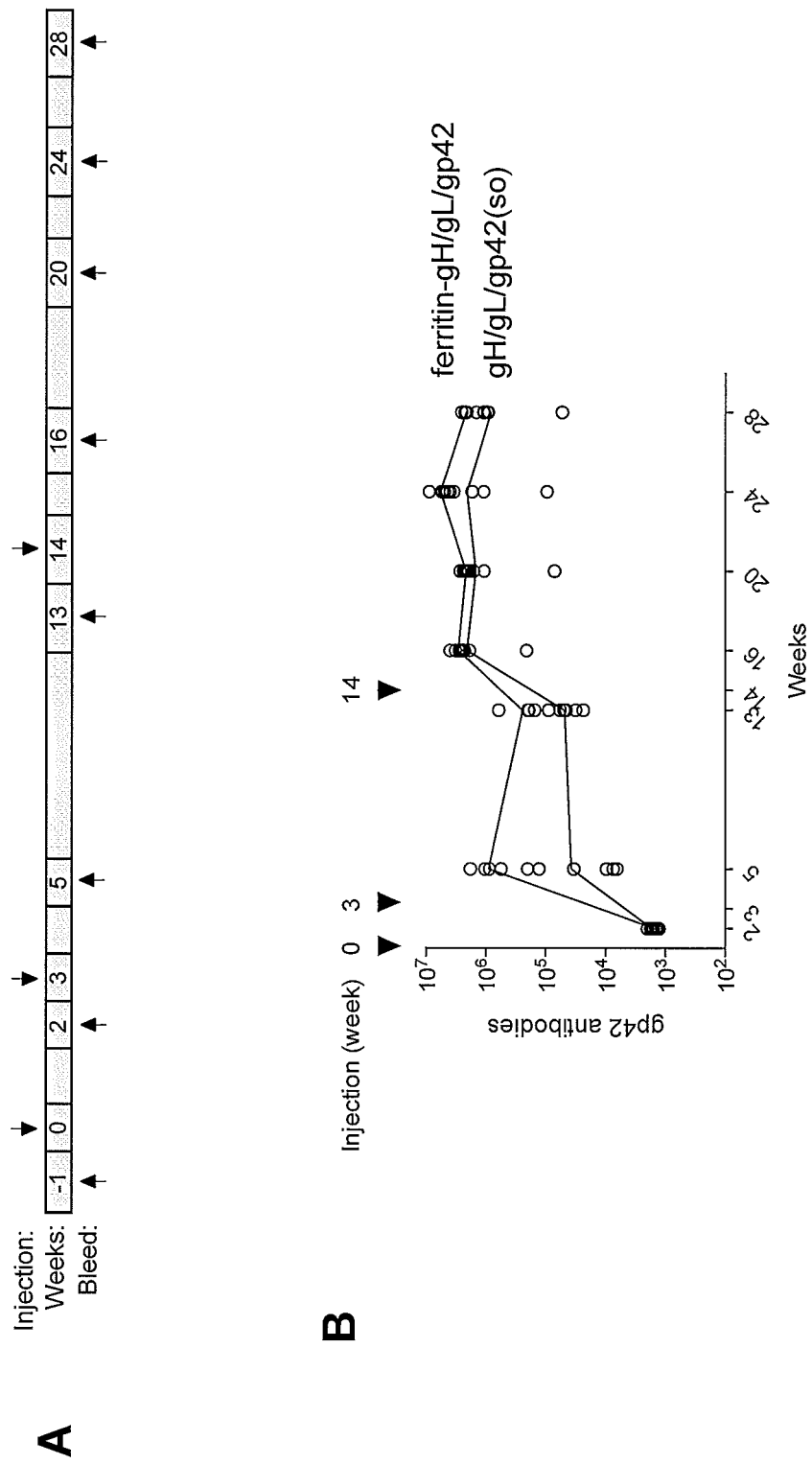

FIG. 18. (A) Immunization and sampling schedule. (B) Comparison of kinetics of gp42 antibody titers in sera from mice immunized with either soluble gH/gL/gp42 or gH/gL/gp42 ferritin-based-nanoparticles.

Figure 19:
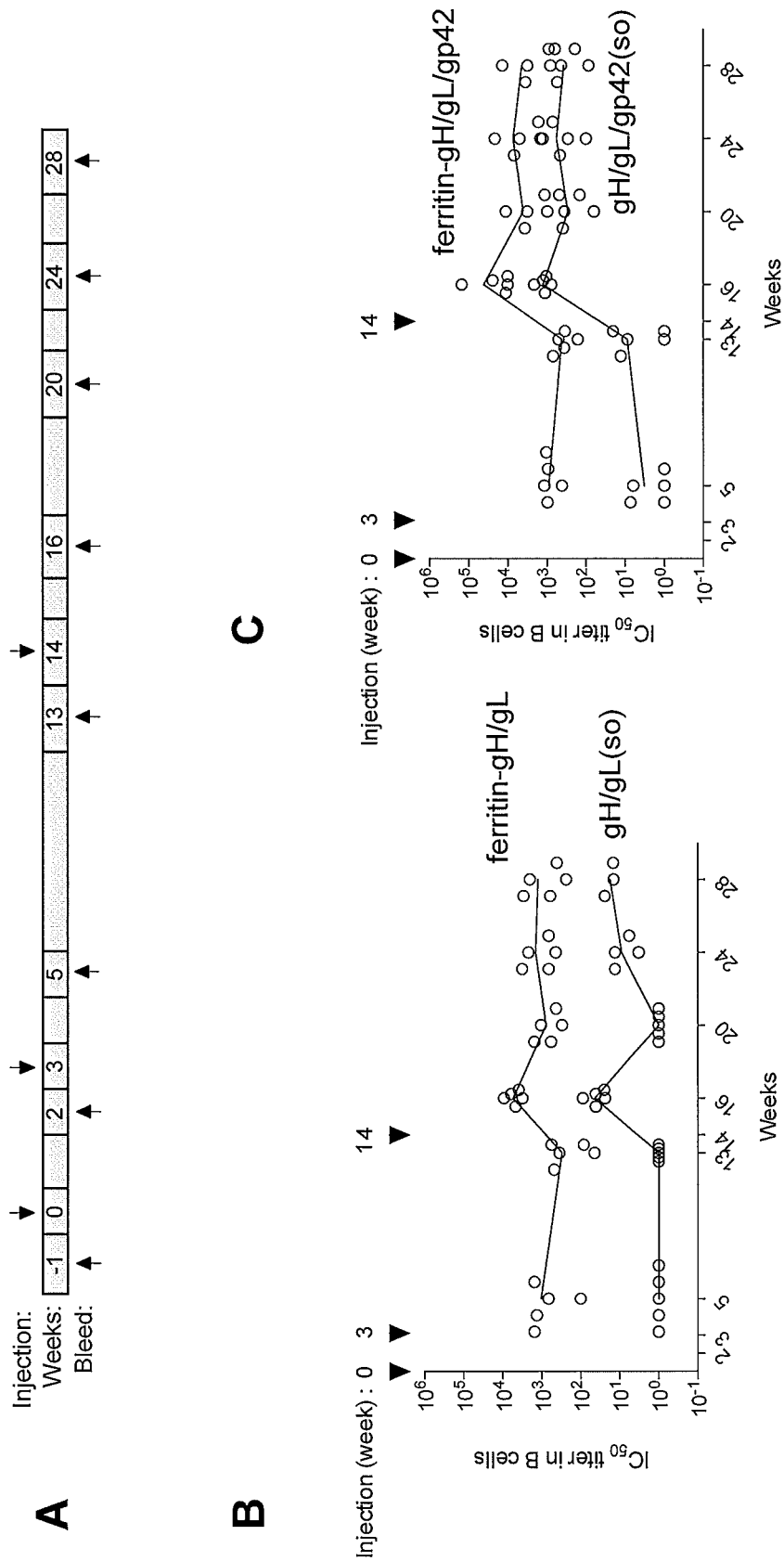

FIG. 19. (A) Immunization and sampling schedule. Comparison of kinetics of B cell neutralizing antibody titers in mice immunized with soluble gH/gL or gH/gL ferritin-based-nanoparticles (B) and soluble gH/gL/gp42 or gH/gL/gp42 ferritin-based-nanoparticles (C).

Figure 20:
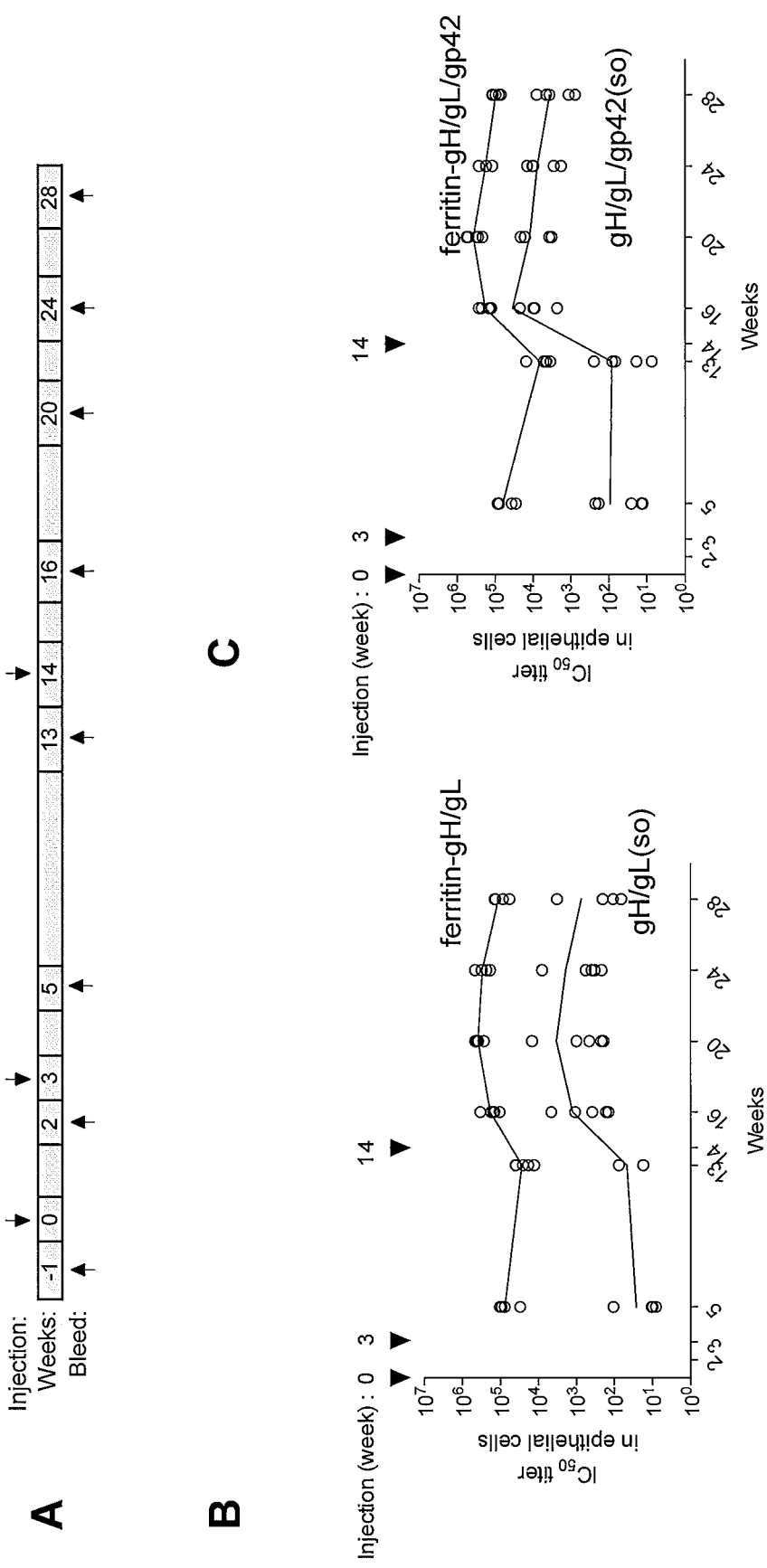

FIG. 20. (A) Immunization and sampling schedule. Comparison of kinetics of epithelial cell neutralizing antibody titers in mice immunized with soluble gH/gL or gH/gL ferritin-based-nanoparticles (B) and soluble gH/gL/gp42 or gH/gL/gp42 ferritin-based-nanoparticles (C).

Figure 21:
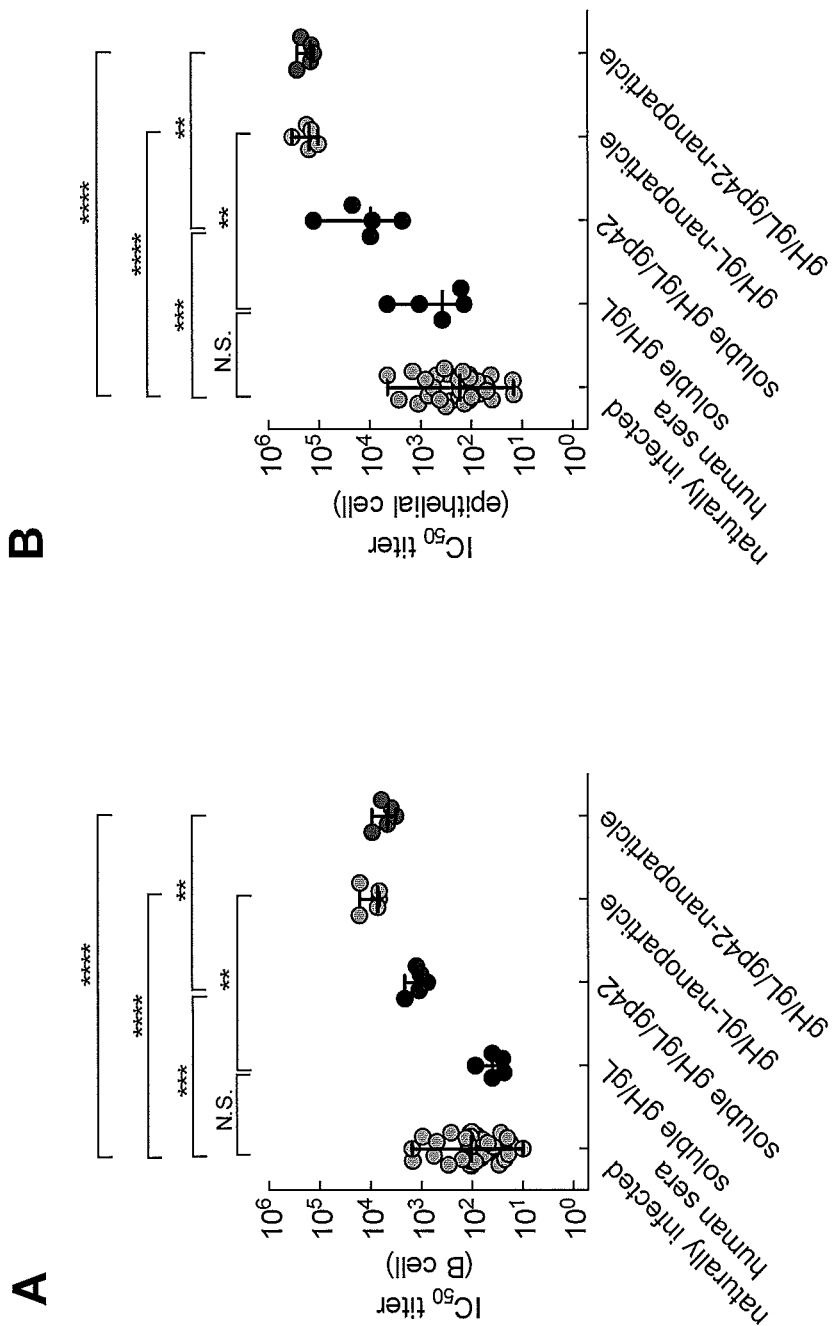

FIG. 21. (A) B cell neutralizing antibody and (B) epithelial cell neutralizing antibody titers after the 3rd dose in sera of mice immunized with soluble proteins or ferritin-based-nanoparticles compared to sera from naturally infected humans. Each dot represents one individual. The median titers with the range are plotted. N. S. indicates that the difference was not statistically significant. , p<0.01, *, p<0.001, and ****, p<0.0001.

Figure 22:
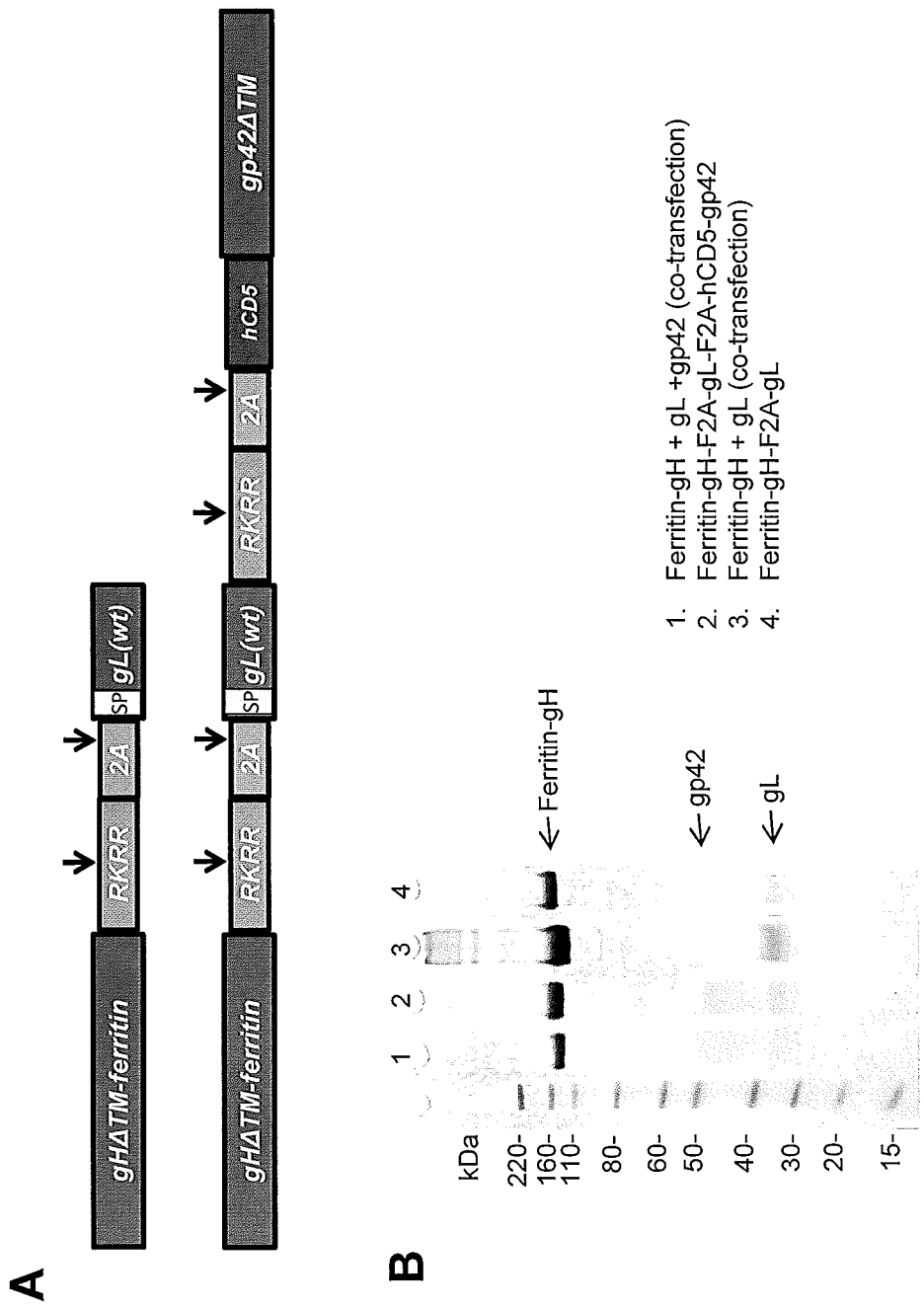

FIG. 22. (A) Design of single polypeptides expressing either gH/gL-nanoparticles or gH/gL/gp42-nanoparticles. (B) SDS-PAGE analysis of purified gH/gL nanoparticles and gH/gL/gp42 nanoparticles by size exclusion chromatography (B). Lanes show proteins purified from cells co-transfected with plasmids expressing individual proteins (cotransfection) or one plasmid expressing a single polypeptide that is spontaneously cleaved inside the cell.

Figure 23:
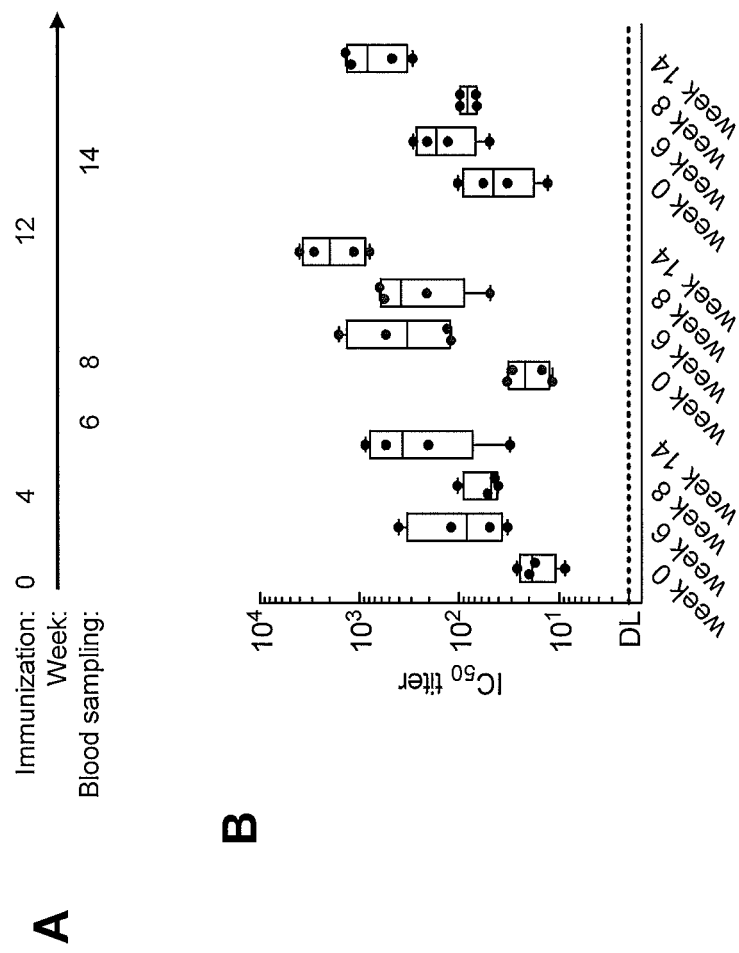

FIG. 23. Immunogenicity of EBV gp350-nanoparticles in cynomolgus monkeys. (A) Immunization schedule. (B) Titer of neutralizing virus in plasma from monkeys immunized with 50 µg of soluble gp350 ectodomain protein (left four bars), 25 µg of gp350 D123-ferritin (center four bars) or 25 µg of gp350 D123-encapsulin (right four bars) using the Sigma Adjuvant System.

Figure 24:
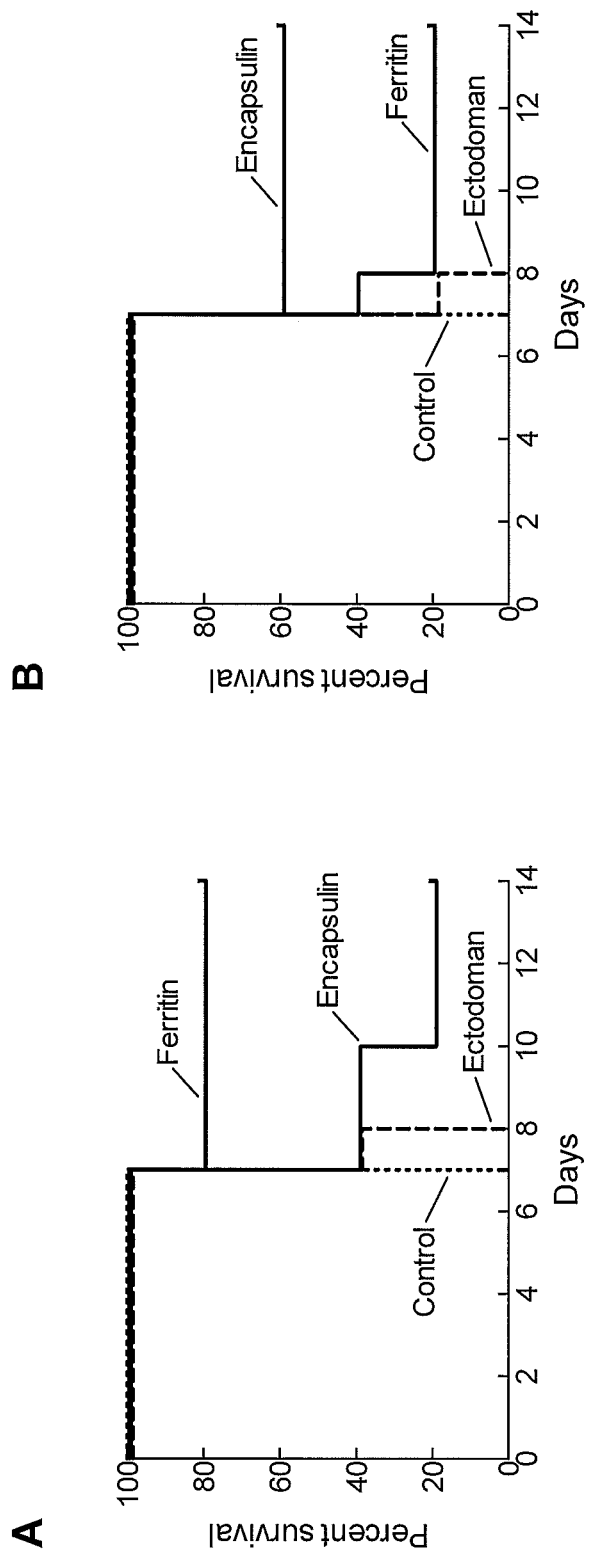

FIG. 24. Survival curve for EBV gp350 immunized mice after challenge with recombinant vaccinia virus expressing EBV gp350. Mice were either not immunized (control) or immunized 3 times with 0.5 ug (left) or 5.0 µg (right) of gp350 ectodomain, gp350 D123-ferritin, or gp350 D123-encapsulin. Five mice were immunized in each group.

Figure 25:
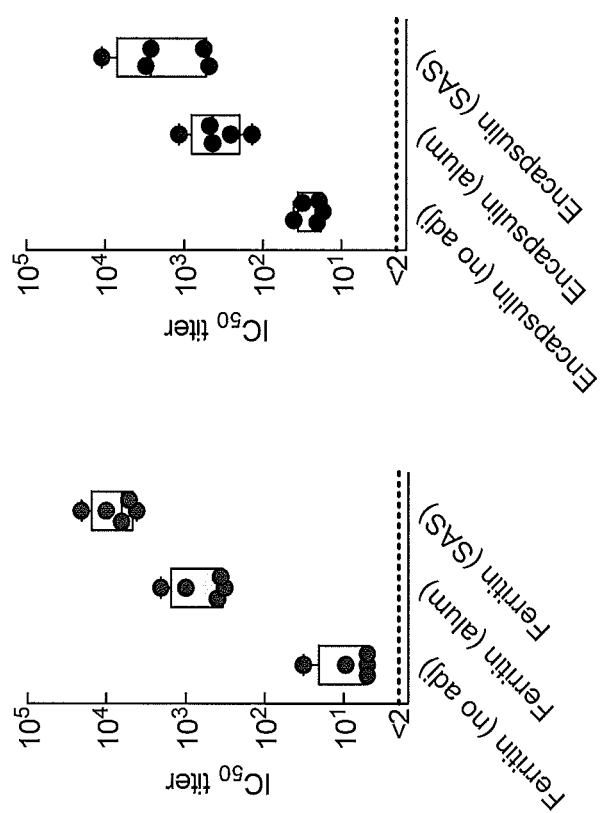

FIG. 25. Immunogenicity of EBV gp350-nanoparticles with no adjuvant, aluminum phosphate gel (alum), or Sigma Adjuvant System (SAS) adjuvant. Mice were immunized with 5 µg of gp350 D123-ferritin (left) or gp350 D123-encapsulin (right) at weeks 0, 4 and 16. Blood samples were collected 2 weeks after the final immunization and virus neutralization titers were measured.

DETAILED DESCRIPTION OF THE INVENTION

The present invention relates to a novel vaccine for Epstein-Barr virus (EBV). More specifically, the present invention relates to novel fusion proteins comprising EBV envelope proteins, wherein the fusion proteins self-assemble into nanoparticles that display immunogenic portions of the EBV envelope proteins on their surface. Such nanoparticles are useful for vaccinating individuals against EBV. Accordingly, the present invention also relates to fusion proteins for producing such nanoparticles and nucleic acid molecules encoding such proteins. Additionally, the present invention relates to, methods of producing nanoparticles of the present invention, and methods of using such nanoparticles to vaccinate individuals against EBV.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the claims.

It must be noted that as used herein and in the appended claims, the singular forms "a," "an," and "the" include plural referents unless the context clearly dictates otherwise. For example, a nucleic acid molecule refers to one or more nucleic acid molecules. As such, the terms "a", "an", "one or more" and "at least one" can be used interchangeably. Similarly the terms "comprising", "including" and "having" can be used interchangeably. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In addition to the above, unless specifically defined otherwise, the following terms and phrases, which are common to the various embodiments disclosed herein, are defined as follows:

As used herein, the term immunogenic refers to the ability of a specific protein, or a specific region thereof, to elicit an immune response to the specific protein, or to proteins comprising an amino acid sequence having a high degree of identity with the specific protein. According to the present invention, two proteins having a high degree of identity have amino acid sequences at least 80% identical, at least 85% identical, at least 87% identical, at least 90% identical, at least 92% identical, at least 94% identical, at least 96% identical, at least 98% identical or at least 99% identical.

As used herein, an immune response to a vaccine, or nanoparticle, of the present invention is the development in a subject of a humoral and/or a cellular immune response to an EBV envelope protein present in the vaccine. For purposes of the present invention, a "humoral immune response" refers to an immune response mediated by antibody molecules, including secretory (IgA) or IgG molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A cellular immune response also refers to the production of cytokines, chemokines and other such molecules produced by activated T-cells and/or other white blood cells, including those derived from CD4+ and CD8+T-cells.

Thus, an immunological response may be one that stimulates CTLs, and/or the production or activation of helper T-cells. The production of chemokines and/or cytokines may also be stimulated. The vaccine may also elicit an antibody-mediated immune response. Hence, an immunological response may include one or more of the following effects: the production of antibodies (e.g., IgA or IgG) by B-cells; and/or the activation of suppressor, cytotoxic, or helper T-cells and/or T-cells directed specifically to a protein present in the vaccine. These responses may serve to neutralize infectivity, and/or mediate antibody-complement, or antibody dependent cell cytotoxicity (ADCC) to provide protection to an immunized individual. Such responses can be determined using standard immunoassays and neutralization assays, well known in the art.

According to the present invention all nomenclature used to describe EBV, and components thereof, is that commonly used by those skilled in the art. Thus, EBV (or HHV-4) refers to all Epstein-Barr viruses including, but not limited to, EBV Type I, EBV Type II, EBV strain B95-8, EBV strain Cao and EBV strain RAJI. A TYPE of EBV refers to either a TYPE I EBV or a TYPE II EBV. Methods of classifying Epstein-Barr viruses are known to those skilled in the art.

As used herein, neutralizing antibodies are antibodies that prevent EBV from infecting a cell, completing one round of replication or establishing latency. As defined herein, one round of replication refers the life cycle of the virus, starting with attachment of the virus to a host cell and ending with budding of newly formed virus from the host cell. This life cycle includes, but is not limited to, the steps of attaching to a cell, entering a cell, production of viral proteins, formation of new viral particles and budding of viral particles from the host cell membrane.

As used herein, broadly neutralizing antibodies are antibodies that neutralize more than one type and/or strain of EBV. For example, broadly neutralizing antibodies elicited against an envelope protein from a Type I EBV may neutralize a Type II virus.

As used herein, an EBV envelope protein refers to a full-length EBV envelope protein or any portion thereof, which is capable of eliciting an immune response. An epitope of a full-length EBV envelope protein refers to a portion of such protein that can elicit a neutralizing antibody response against the homologous EBV strain, i.e., a strain from which the EBV envelope protein is derived. In some embodiments, such an epitope can also elicit a neutralizing antibody response against a heterologous strain of EBV, i.e., a strain having an envelope protein that is not identical to the envelope protein of the immunogen.

As used herein, a variant refers to a protein, or nucleic acid molecule, the sequence of which is similar, but not identical to, a reference sequence, wherein the activity of the variant protein (or the protein encoded by the variant nucleic acid molecule) is not significantly altered. These variations in sequence can be naturally occurring variations or they can be engineered through the use of genetic engineering technique know to those skilled in the art. Examples of such techniques are found in Sambrook J, Fritsch E F, Maniatis T et al., in Molecular Cloning—A Laboratory Manual, 2nd Edition, Cold Spring Harbor Laboratory Press, 1989, pp. 9.31-9.57), or in Current Protocols in Molecular Biology, John Wiley & Sons, N.Y. (1989), 6.3.1-6.3.6, both of which are incorporated herein by reference in their entirety.

With regard to variants, any type of alteration in the amino acid, or nucleic acid, sequence is permissible so long as the resulting variant protein retains the ability to elicit neutralizing antibodies against an Epstein-Barr virus. Examples of such variations include, but are not limited to, deletions, insertions, substitutions and combinations thereof. For example, with regard to proteins, it is well understood by those skilled in the art that one or more (e.g., 2, 3, 4, 5, 6, 7, 8, 9 or 10), amino acids can often be removed from the amino and/or carboxy terminal ends of a protein without significantly affecting the activity of that protein. Similarly, one or more (e.g., 2, 3, 4, 5, 6, 7, 8, 9 or 10) amino acids can often be inserted into a protein without significantly affecting the activity of the protein.

As noted, variant proteins of the present invention can contain amino acid substitutions relative to the proteins disclosed herein. Any amino acid substitution is permissible so long as the activity of the protein is not significantly affected. In this regard, it is appreciated in the art that amino acids can be classified into groups based on their physical properties. Examples of such groups include, but are not limited to, charged amino acids, uncharged amino acids, polar uncharged amino acids, and hydrophobic amino acids. Preferred variants that contain substitutions are those in which an amino acid is substituted with an amino acid from the same group. Such substitutions are referred to as conservative substitutions.

Naturally occurring residues may be divided into classes based on common side chain properties:
1) hydrophobic: Met, Ala, Val, Leu, Ile;
2) neutral hydrophilic: Asn, Gln, Cys, Ser, Thr;
3) acidic: Asp, Glu;
4) basic: His, Lys, Arg;
5) residues that influence chain orientation: Gly, Pro; and
6) aromatic: Trp, Tyr, Phe.

For example, non-conservative substitutions may involve the exchange of a member of one of these classes for a member from another class.

In making amino acid changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6);

histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is generally understood in the art (Kyte et al., 1982, J. Mol. Biol. 157:105-31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological invention, as in the present case. The greatest local average hydrophilicity of a protein, as governed by the hydrophilicity of its adjacent amino acids, correlates with its immunogenicity and antigenicity, i.e., with a biological property of the protein. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those within ±1 are particularly preferred, and those within ±0.5 are even more particularly preferred. One may also identify epitopes from primary amino acid sequences on the basis of hydrophilicity.

Desired amino acid substitutions (whether conservative or non-conservative) can be determined by those skilled in the art at the time such substitutions are desired. For example, amino acid substitutions can be used to identify important residues of the EBV envelope protein or the monomeric subunit protein, or to increase or decrease the immunogenicity, solubility or stability of the proteins described herein. Exemplary amino acid substitutions are shown below in Table 1.

TABLE 1

Amino Acid Substitutions

| Original Amino Acid | Exemplary Substitutions |
|---|---|
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala |
| Leu | Ile, Val, Met, Ala |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |

TABLE 1-continued

Amino Acid Substitutions

| Original Amino Acid | Exemplary Substitutions |
|---|---|
| Tyr | Trp, Phe, Thr, Ser |
| Val | Ile, Met, Leu, Phe, Ala |

As used herein, the phrase significantly affect a proteins activity refers to a decrease in the activity of a protein by at least 10%, at least 20%, at least 30%, at least 40% or at least 50%. With regard to the present invention, such an activity may be measured, for example, as the ability of a protein to elicit neutralizing antibodies against an EBV virus or to self-assemble into a nanoparticle. Such activity may be measured by measuring the titer of such antibodies against EBV, or by measuring the types or strains of virus neutralized by the elicited antibodies. Methods of determining antibody titers and methods of performing virus neutralization assays are known to those skilled in the art. In addition to the activities described above, variant EBV proteins may also be analyzed for their ability to bind receptors (e.g., complement receptor 2) or other proteins. For example, it is understood that EBV gH binds EBV gL to form dimers. Likewise, it is understood that EBV gH binds EBV gL and gp42 to form trimers. Thus, variant EBV proteins may be analyzed for their ability to bind to one another. Methods of measuring such activities are known to those skilled in the art.

As used herein, a fusion protein is a recombinant protein containing amino acid sequence from at least two unrelated proteins that have been joined together, via a peptide bond, to make a single protein. The unrelated amino acid sequences can be joined directly to each other or they can be joined using a linker sequence. As used herein, proteins are unrelated, if their amino acid sequences are not normally found joined together via a peptide bond in their natural environment(s) (e.g., inside a cell). For example, the amino acid sequences of monomeric subunits that make up ferritin, and the amino acid sequences of ENV envelope proteins are not normally found joined together via a peptide bond.

The terms individual, subject, and patient are well-recognized in the art, and are herein used interchangeably to refer to any human or non-human primate susceptible to infection with EBV. Examples include, but are not limited to, humans and other primates, including non-human primates such as chimpanzees and other apes and monkey species. The terms individual, subject, and patient by themselves, do not denote a particular age, sex, race, and the like. Thus, individuals of any age, whether male or female, are intended to be covered by the present disclosure and include, but are not limited to the elderly, adults, children, babies, infants, and toddlers. Likewise, the methods of the present invention can be applied to any race, including, for example, Caucasian (white), African-American (black), Native American, Native Hawaiian, Hispanic, Latino, Asian, and European. An infected subject is a subject that is known to have EBV in their body.

As used herein, the terms exposed, exposure, and the like, indicate the subject has come in contact with a person of animal that is known to be infected with EBV.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

According to the present invention, vaccines are provided that elicit a neutralizing immune response against Epstein-Barr virus envelope proteins. Some vaccines disclosed herein may elicit an immune response against the entire envelope protein, while others may elicit an immune response against a specific region or portion of an envelope protein. Moreover, the inventors have discovered that specific fusion proteins comprising portions of envelope protein are useful for eliciting an immune response against Epstein-Barr viruses. Each of these embodiments will now be disclosed in detail below.

The inventors have discovered that fusion of an EBV envelope (ENV) protein with a self-assembly (SA) protein, to produce an ENV-SA fusion protein, results in a vaccine that elicits a robust immune response to EBV virus. Such ENV-SA fusion proteins self-assemble into nanoparticles that display immunogenic portions of the EBV protein on their surface. These nanoparticles are useful for vaccinating individuals against EBV. Thus, one embodiment of the present invention is an ENV-SA fusion protein comprising a self-assembling subunit protein disclosed herein joined to an EBV envelope (ENV) protein disclosed herein, wherein the ENV-SA fusion protein is capable of self-assembling into nanoparticles.

According to the present invention, a self-assembling (SA) subunit protein of the present invention is a full length, monomeric polypeptide, or any portion thereof, which is capable of directing self-assembly of monomeric self-assembling subunit proteins into a nanoparticle. Examples of self-assembly proteins of the present invention include ferritin, encapsulin, sulfur oxygenase reductase (SOR), lumazine synthase (LS) and pyruvate dehydrogenase complex (PDC) dihydrolipoamide acetyltransferase (E2). Representative examples of such proteins are listed below in Table 2.

TABLE 2

| SEQ ID NO | Organism | Comments |
|---|---|---|
| | | FERRITIN |
| 1 | Helicobacter pylori | Coding sequence for ferritin monomeric subunit protein from H. pylori |
| 2 | Helicobacter pylori | Amino acid sequence encoded by SEQ ID NO: 1 |
| 3 | Helicobacter pylori | Complement of SEQ ID NO1 |
| 4 | Escherichia coli | Coding sequence for ferritin monomeric subunit protein from E. coli (gi 446839951_WP_000917207.1) |
| 5 | Escherichia coli | Amino acid sequence encoded by SEQ ID NO: 4 |
| 6 | Escherichia coli | Complement of SEQ ID NO4 |
| 7 | Rana catesbeiana | Coding sequence for bullfrog ferritin monomeric subunit protein (gi 13675 gb AAA49524.1) |
| 8 | Rana catesbeiana | Amino acid sequence encoded by SEQ ID NO: 7 |
| 9 | Rana catesbeiana | Complement of SEQ ID NO: 7 |
| | | FERRITIN PROTEINS |
| 10 | Artificial Sequence | Coding sequence for H. pylori-ferritin/bullfrog-ferritin fusion protein |
| 11 | Artificial Sequence | Amino acid sequence encoded by SEQ ID NO: 10 |
| 12 | Artificial Sequence | Complement of SEQ ID NO10 |
| 13 | Artificial Sequence | Coding sequence for E. coli-ferritin/bullfrog-ferritin fusion protein |
| 14 | Artificial Sequence | Amino acid sequence encoded by SEQ ID NO: 13 |
| 15 | Artificial Sequence | Complement of SEQ ID NO: 13 |
| | | OTHER SELF-ASSEMBING MONOMERIC SUBUNITS |
| 16 | Thermotoga maritime | Coding sequence for encapsulin protein |
| 17 | Thermotoga maritime | Amino acid sequence encoded by SEQ ID NO: 16 |

TABLE 2-continued

| SEQ ID NO | Organism | Comments |
|---|---|---|
| 18 | Thermotoga maritime | Complement of SEQ ID NO: 16 |
| 19 | Artificial Sequence | Coding sequence for Salmonella enteritis 03-33 protein (gi 390136278 pdb 3VCD) |
| 20 | Artificial Sequence | Amino acid sequence encoded by SEQ ID NO: 19 |
| 21 | Artificial Sequence | Complement of SEQ ID NO: 19 |
| 22 | Acidianus ambivalens | Coding sequence for sulfur oxygenase reductase protein from Acidianus ambivalens (gi 93279016 pdb 2CB2) |
| 23 | Acidianus ambivalens | Amino acid sequence encoded by SEQ ID NO: 22 |
| 24 | Acidianus ambivalens | Complement of SEQ ID NO: 22 |
| 25 | Aquifex aeolicus | Coding sequence for lumazine synthase protein from Aquifex aeolicus (gi 18159011 pdb1HQK) |
| 26 | Aquifex aeolicus | Amino acid sequence encoded by SEQ ID NO: 25 |
| 27 | Aquifex aeolicus | Complement of SEQ ID NO: 25 |
| 28 | Bacillus stearothermophilus | Coding sequence for dihydrolipoamide acetyltransferase (E2p) protein from Bacillus stearothermophilus (gi 4558102 pdb1B5S |
| 29 | Bacillus stearothermophilus | Amino acid sequence encoded by SEQ ID NO: 28 |
| 30 | Bacillus stearothermophilus | Complement of SEQ ID NO: 28 |
| | | EBV PROTEINS |
| 31 | Epstein Barr Virus | Coding sequence for EBV gp350 protein |
| 32 | Epstein Barr Virus | Amino acid sequence encoded by SEQ ID NO: 31 |
| 33 | Epstein Barr Virus | Complement of SEQ ID NO: 31 |
| 34 | Epstein Barr Virus | Coding sequence for EBV gp350 protein (2-860) ecto domain |
| 35 | Epstein Barr Virus | Amino acid sequence encoded by SEQ ID NO: 34 |
| 36 | Epstein Barr Virus | Complement of SEQ ID NO: 34 |
| 37 | Epstein Barr Virus | Coding sequence for EBV gp350 protein (2-470) RBD domain |
| 38 | Epstein Barr Virus | Amino acid sequence encoded by SEQ ID NO: 37 |
| 39 | Epstein Barr Virus | Complement of SEQ ID NO: 37 |
| 40 | Epstein Barr Virus | Coding sequence for EBV gp350 protein (4-153) Domain I |
| 41 | Epstein Barr Virus | Amino acid sequence encoded by SEQID NO: 40 |
| 42 | Epstein Barr Virus | Complement of SEQ ID NO: 40 |
| 43 | Epstein Barr Virus | Coding sequence for EBV gp350 protein (165-305) Domain II |
| 44 | Epstein Barr Virus | Amino acid sequence encoded by SEQ ID NO: 43 |
| 45 | Epstein Barr Virus | Complement of SEQ ID NO: 43 |
| 46 | Epstein Barr Virus | Coding sequence for EBV gp350 protein (317-426) Domain III |
| 47 | Epstein Barr Virus | Amino acid sequence encoded by SEQ ID NO: 46 |
| 48 | Epstein Barr Virus | Complement of SEQ ID NO: 46 |
| 49 | Epstein Barr Virus | Coding sequence for EBV gp350 protein (2-317) Domains I/II |
| 50 | Epstein Barr Virus | Amino acid sequence encoded by SEQ ID NO: 49 |
| 51 | Epstein Barr Virus | Complement of SEQ ID NO: 49 |
| 52 | Epstein Barr Virus | Coding sequence for EBV gp350 protein (2-425) Domains I/II/III |
| 53 | Epstein Barr Virus | Amino acid sequence encoded by SEQ ID NO: 52 |
| 54 | Epstein Barr Virus | Complement of SEQ ID NO: 52 |
| 55 | Epstein Barr Virus | Coding sequence for soluble EBV gp350 ectodomain protein |
| 56 | Epstein Barr Virus | Amino acid sequence encoded by SEQ ID NO: 55 |
| 57 | Epstein Barr Virus | Compliment of SEQ ID NO: 55 |
| 58 | Epstein Barr Virus | Coding sequence for soluble EBV gp350 Domains I/II/III |
| 59 | Epstein Barr Virus | Amino acid sequence encoded by SEQ ID NO: 58 |
| 60 | Epstein Barr Virus | Complement of SEQ ID NO: 58 |
| 61 | Epstein Barr Virus | Coding sequence for EBV gH protein |
| 62 | Epstein Barr Virus | Amino acid sequence encoded by SEQ ID NO: 61 |
| 63 | Epstein Barr Virus | Complement of SEQ ID NO: 61 |
| 64 | Epstein Barr Virus | Coding sequence for EBV gL protein |
| 65 | Epstein Barr Virus | Amino acid sequence encoded by SEQ ID NO: 64 |
| 66 | Epstein Barr Virus | Complement of SEQ ID NO: 64 |
| 67 | Epstein Barr Virus | Coding sequence for EBV gp42 protein |
| 68 | Epstein Barr Virus | Amino acid sequence encoded by SEQ ID NO: 67 |
| 69 | Epstein Barr Virus | Complement of SEQ ID NO: 67 |
| | | EBV FUSION PROTEINS |
| 70 | Artificial Sequence | Nucleic acid sequence encoding EBV gp350(2-860) ecto-ferritin (E. coli ferritin/bullfrog ferritin) fusion protein |
| 71 | Artificial Sequence | Amino acid sequence encoded by SEQ ID NO: 70 |
| 72 | Artificial Sequence | Complement of SEQ ID NO: 70 |

TABLE 2-continued

| SEQ ID NO | Organism | Comments |
|---|---|---|
| 73 | Artificial Sequence | Nucleic acid sequence encoding EBV gp350 (2-470) RBD-ferritin (*E. coli* ferritin/bullfrog ferritin)fusion protein |
| 74 | Artificial Sequence | Amino acid sequence encoded by SEQ ID NO: 73 |
| 75 | Artificial Sequence | Complement of SEQ ID NO: 73 |
| 76 | Artificial Sequence | Nucleic acid sequence encoding EBV gp350 (2-317) Domain I/II-ferritin (*E. coli* ferritin/bullfrog ferritin)fusion protein |
| 77 | Artificial Sequence | Amino acid sequence encoded by SEQ ID NO: 76 |
| 78 | Artificial Sequence | Complement of SEQ ID NO: 76 |
| 79 | Artificial Sequence | Nucleic acid sequence encoding EBV gp350 (2-425) Domain I/II/III-ferritin (*E. coli* ferritin/bullfrog ferritin)fusion protein |
| 80 | Artificial Sequence | Amino acid sequence encoded by SEQ ID NO: 79 |
| 81 | Artificial Sequence | Complement of SEQ ID NO: 79 |
| 82 | Artificial Sequence | Nucleic acid sequence encoding EBV gp350 (2-860) ecto-ferritin (*H. pylori* ferritin/bullfrog ferritin) fusion protein |
| 83 | Artificial Sequence | Amino acid sequence encoded by SEQ ID NO: 82 |
| 84 | Artificial Sequence | Complement of SEQ ID NO: 82 |
| 85 | Artificial Sequence | Nucleic acid sequence encoding EBV gp350(2-317) Domain VII- ferritin (*H. pylori* ferritin/bullfrog ferritin)fusion protein |
| 86 | Artificial Sequence | Amino acid sequence encoded by SEQ ID NO: 85 |
| 87 | Artificial Sequence | Complement of SEQ ID NO: 85 |
| 88 | Artificial Sequence | Nucleic acid sequence encoding EBV gp350 (2-425) Domain I/II/III- ferritin (*H. pylori* ferritin/bullfrog ferritin)fusion protein |
| 89 | Artificial Sequence | Amino acid sequence encoded by SEQ ID NO: 88 |
| 90 | Artificial Sequence | Complement of SEQ ID NO: 88 |
| 91 | Artificial Sequence | Nucleic acid sequence encoding EBV gp350 (2-470) RBD-ferritin (*H. pylori* ferritin/bullfrog ferritin)fusion protein |
| 92 | Artificial Sequence | Amino acid sequence encoded by SEQ ID NO: 91 |
| 93 | Artificial Sequence | Complement of SEQ ID NO: 91 |
| 94 | Artificial Sequence | Nucleic acid sequence encoding EBV gp350 (2-860) ecto-encapsulin fusion protein |
| 95 | Artificial Sequence | Amino acid sequence encoded by SEQ ID NO: 94 |
| 96 | Artificial Sequence | Complement of SEQ ID NO: 94 |
| 97 | Artificial Sequence | Nucleic acid sequence encoding EBV gp350 (2-470) RBD-encapsulin fusion protein |
| 98 | Artificial Sequence | Amino acid sequence encoded by SEQ ID NO: 97 |
| 99 | Artificial Sequence | Complement of SEQ ID NO: 97 |
| 100 | Artificial Sequence | Nucleic acid sequence encoding EBV gp350 (317) Domain I/II-encapsulin fusion protein |
| 101 | Artificial Sequence | Amino acid sequence encoded by SEQ ID NO: 100 |
| 102 | Artificial Sequence | Complement of SEQ ID NO: 100 |
| 103 | Artificial Sequence | Nucleic acid sequence encoding EBV gp350 (2-425)Domain I/II/III-encapsulin fusion protein |
| 104 | Artificial Sequence | Amino acid sequence encoded by SEQ ID NO: 103 |
| 105 | Artificial Sequence | Complement of SEQ ID NO: 103 |
| 106 | Artificial Sequence | Nucleic acid sequence of VRC 3421 |
| 107 | Artificial Sequence | Nucleic acid sequence of VRC 3422 |
| 108 | Artificial Sequence | Nucleic acid sequence of VRC 3423 |
| 109 | Artificial Sequence | Nucleic acid sequence of VRC 3424 |
| 110 | Artificial Sequence | Nucleic acid sequence of VRC 3425 |

TABLE 2-continued

| SEQ ID NO | Organism | Comments |
|---|---|---|
| 111 | Artificial Sequence | Nucleic acid sequence of VRC 3426 |
| 112 | Artificial Sequence | Nucleic acid sequence of VRC 3427 |
| 113 | Artificial Sequence | Nucleic acid sequence of VRC 3428 |
| 114 | Artificial Sequence | Nucleic acid sequence of VRC 3429 |
| 115 | Artificial Sequence | Nucleic acid sequence of VRC 3430 |
| 116 | Artificial Sequence | Nucleic acid sequence of VRC 3431 |
| 117 | Artificial Sequence | Nucleic acid sequence of VRC 3432 |
| 118 | Artificial Sequence | Nucleic acid sequence of VRC 3384 |
| 119 | Artificial Sequence | Nucleic acid sequence of VRC 3419 |
| 120 | Artificial Sequence | Nucleic acid sequence of VRC 3420 |
| 121 | Artificial Sequence | Nucleic acid sequence of VRC 3361 |
| 122 | Artificial Sequence | Nucleic acid sequence of VRC 3796 |
| 123 | Artificial Sequence | Nucleic acid sequence of VRC 3797 |
| 124 | Artificial Sequence | Nucleic acid sequence of VRC 2194 |
| 125 | Artificial Sequence | Nucleic acid sequence of VRC 2195 |
| 126 | Artificial Sequence | Nucleic acid sequence of VRC 2196 |
| 127 | Artificial Sequence | Nucleic acid sequence encoding gH-ferritin protein |
| 128 | Artificial Sequence | Protein encoded by SEQ ID NO: 127 |
| 129 | Artificial Sequence | Nucleic acid sequence encoding soluble gp42 protein |
| 130 | Artificial Sequence | Protein encoded by SEQ ID NO: 129 |
| 131 | Epstein Barr Virus | Nucleic acid sequence encoding gL protein |
| 132 | Epstein Barr Virus | Protein encoded by SEQ ID NO: 131 |
| 133 | Artificial Sequence | Nucleic acid sequence encoding encapsulin-gp42 |
| 134 | Artificial Sequence | Protein encoded by SEQ ID NO: 133 |
| 135 | Artificial Sequence | Nucleic acid sequence encoding soluble gH |
| 136 | Artificial Sequence | Protein encoded by SEQ ID NO: 135 |
| 137 | Picornvirus | Nucleic acid molecule encoding picornavirus 2A protease cleavage site |
| 138 | Picornavirus | Peptide encoded by SEQ ID NO: 137 (picornavirus 2A protease cleavage site) |
| 139 | Human | Nucleic acid sequence encoding human CD5 leader peptide sequence |
| 140 | Human | Amino acid sequence encoded by SEQ ID NO: 139 (human CD5 leader peptide sequence) |
| 141 | Artificial Sequence | Nucleic acid sequence encoding ferritin-gH-F2A-gL polyprotein |
| 142 | Artificial Sequence | Amino acid sequence encoded by SEQ ID NO: 141 (ferritin-gH-F2A-gL polyprotein) |
| 143 | Artificial Sequence | Nucleic acid sequence encoding ferritin-gH-F2A-gL-F2A-gp42 polyprotein |
| 144 | Artificial Sequence | Amino acid sequence encoded by SEQ ID NO: 143 (ferritin-gH-F2A-gL-F2A-gp42 polyprotein) |
| 145 | Artificial Sequence | Nucleic acid sequence encoding ferritin-gH fusion protein having SGGG linker |
| 146 | Artificial Sequence | Amino acid sequence encoded by SEQ ID NO: 145 (ferritin-gH fusion protein having SGGG linker) |

Thus one embodiment of the present invention is an ENV-SA fusion protein comprising a self-assembling subunit protein selected from the group consisting of ferritin, encapsulin, sulfur oxygenase reductase, lumazine synthase and dihydrolipoamide acetyltransferase (E2), joined to an EBV envelope (ENV) protein disclosed herein, wherein the ENV-SA fusion protein is capable of self-assembling into nanoparticles.

In one embodiment, the self-assembly protein is ferritin. Ferritin forms a spherical protein found in all animals, bacteria, and plants, that acts primarily to control the rate and location of polynuclear $Fe(III)_2O_3$ formation through the transportation of hydrated iron ions and protons to and from a mineralized core. The spherical form of ferritin is made up of monomeric subunit proteins (also referred to as monomeric ferritin subunits), which are polypeptides having a molecule weight of approximately 17-20 kDa. An example of the sequence of one such monomeric ferritin subunit is represented by SEQ ID NO:2. Each monomeric ferritin subunit has the topology of a helix bundle which includes a four antiparallel helix motif, with a fifth shorter helix (the c-terminal helix) lying roughly perpendicular to the long axis of the 4 helix bundle. According to convention, the helices are labeled 'A, B, C, and D & E' from the N-terminus respectively. The N-terminal sequence lies adjacent to the capsid three-fold axis and extends to the surface, while the E helices pack together at the four-fold axis with the C-terminus extending into the particle core. The consequence of this packing creates two pores on the capsid surface. It is expected that one or both of these pores represent the point by which the hydrated iron diffuses into and out of the capsid. Following production, these monomeric ferritin subunit proteins self-assemble into the spherical ferritin protein. Thus, the spherical form of ferritin comprises 24 monomeric, ferritin subunit proteins, and has a capsid-like structure having 432 symmetry.

According to the present invention, a monomeric ferritin subunit of the present invention is a full length, single polypeptide of a ferritin protein, or any portion thereof, which is capable of directing self-assembly of monomeric ferritin subunits into the spherical form of the protein. Amino acid sequences from monomeric ferritin subunits of any known ferritin protein can be used to produce fusion proteins of the present invention, so long as the monomeric ferritin subunit is capable of directing self-assembly of the fusion protein into a nanoparticle displaying an EBV ENV protein on its surface. In one embodiment, the monomeric subunit is from a ferritin protein selected from the group consisting of a bacterial ferritin protein, a plant ferritin protein, an algal ferritin protein, an insect ferritin protein, a fungal ferritin protein and a mammalian ferritin protein. In one embodiment, the ferritin protein is from *Helicobacter pylori*. In one embodiment, the ferritin protein is from *E. coli*. In one embodiment, the ferritin protein is bullfrog ferritin. In one embodiment, the ferritin protein comprises amino acid sequences from one or more ferritin proteins selected from the group consisting of *H. pylori* ferritin, *E. coli* ferritin and bullfrog ferritin. Amino acid sequences from representative ferritin proteins of the present invention are disclosed herein as SEQ ID NO:2 (*H. pylori* ferritin), SEQ ID NO:5 (*E. coli* ferritin), SEQ ID NO:8 (bullfrog ferritin), SEQ ID NO:11 (*H. pylori* ferritin-bullfrog ferritin fusion) and SEQ ID NO:14 (*E. coli* ferritin-bullfrog ferritin fusion).

In one embodiment, the self-assembly protein is encapsulin. According to the present invention, a monomeric encapsulin subunit of the present invention is a full length, single polypeptide of an encapsulin protein, or any portion thereof, which is capable of directing self-assembly of monomeric encapsulin subunits into a nanoparticle. Amino acid sequences from monomeric encapsulin subunits of any known encapsulin protein can be used to produce fusion proteins of the present invention, so long as the monomeric encapsulin subunit is capable of directing self-assembly of the fusion protein into a nanoparticle displaying an EBV ENV protein on its surface. The amino acid sequence of a representative encapsulin protein is disclosed herein as SEQ ID NO:17.

In one embodiment, the self-assembly protein is artificially designed *Salmonella* enteritis 03-33 subunit protein. According to the present invention, a monomeric 03-33 subunit of the present invention is a full length, single polypeptide of an 03-33 protein, or any portion thereof, which is capable of directing self-assembly of monomeric 03-33 subunits into a nanoparticle. Amino acid sequences from monomeric 03-33 subunits of any known 03-33 protein can be used to produce fusion proteins of the present invention, so long as the monomeric 03-33 subunit is capable of directing self-assembly of the fusion protein into a nanoparticle displaying an EBV ENV protein on its surface. The amino acid sequence of a representative 03-33 protein is disclosed herein as SEQ ID NO:20.

In one embodiment, the self-assembly protein is sulfur oxygenase reductase (SOR). According to the present invention, a monomeric SOR subunit of the present invention is a full length, single polypeptide of an SOR protein, or any portion thereof, which is capable of directing self-assembly of monomeric SOR subunits into a nanoparticle. Amino acid sequences from monomeric SOR subunits of any known SOR protein can be used to produce fusion proteins of the present invention, so long as the monomeric SOR subunit is capable of directing self-assembly of the fusion protein into a nanoparticle displaying an EBV ENV protein on its surface. The amino acid sequence of a representative SOR protein is disclosed herein as SEQ ID NO:23.

In one embodiment, the self-assembly protein is lumazine synthase (LS). According to the present invention, a monomeric LS subunit of the present invention is a full length, single polypeptide of an LS protein, or any portion thereof, which is capable of directing self-assembly of monomeric LS subunits into a nanoparticle. Amino acid sequences from monomeric LS subunits of any known LS protein can be used to produce fusion proteins of the present invention, so long as the monomeric LS subunit is capable of directing self-assembly of the fusion protein into a nanoparticle displaying an EBV ENV protein on its surface. The amino acid sequence of a representative LS protein is disclosed herein as SEQ ID NO:26.

In one embodiment, the self-assembly protein is pyruvate dehydrogenase complex (PDC) dihydrolipoamide acetyltransferase (E2p). According to the present invention, a monomeric E2p subunit of the present invention is a full length, single polypeptide of an E2p protein, or any portion thereof, which is capable of directing self-assembly of monomeric E2p subunits into a nanoparticle. Amino acid sequences from monomeric E2p subunits of any known E2p protein can be used to produce fusion proteins of the present invention, so long as the monomeric E2p subunit is capable of directing self-assembly of the fusion protein into a nanoparticle displaying an EBV ENV protein on its surface. The amino acid sequence of a representative E2p protein is disclosed herein as SEQ ID NO:29.

ENV-SA fusion proteins of the present invention need not comprise the full-length sequence of a monomeric subunit polypeptide of a self-assembly (SA) protein. Portions, or regions, of the monomeric SA subunit protein can be utilized so long as the portion comprises an amino acid sequence that directs self-assembly of the EBV-SA fusion protein into a nanoparticle. One example of such a portion is located between amino acids 5 and 167 of the *Helicobacter pylori* ferritin protein. More specific regions of the ferritin protein are described in Zhang, Y. Self-Assembly in the Ferritin Nano-Cage Protein Super Family. 2011, Int. J. Mol. Sci., 12, 5406-5421, which is incorporated herein by reference in its entirety.

One embodiment of the present invention is an ENV-SA fusion protein comprising an Epstein-Barr virus ENV protein of the present invention joined to at least 25 contiguous amino acids, at least 50 contiguous amino acids, at least 75 contiguous amino acids, at least 100 contiguous amino acids, or at least 150 contiguous amino acids from a protein selected from the group consisting of ferritin, encapsulin, sulfur oxygenase reductase, lumazine synthase and pyruvate dehydrogenase complex (PDC) dihydrolipoamide acetyltransferase (E2), wherein the ENV-SA fusion protein is capable of self-assembling into nanoparticles. One embodiment of the present invention is an ENV-SA fusion protein comprising an ENV protein of the present invention joined to at least 25 contiguous amino acids, at least 50 contiguous amino acids, at least 75 contiguous amino acids, at least 100 contiguous amino acids, or at least 150 contiguous amino acids from an amino acid sequence selected from the group consisting of SEQ ID NO:2, SEQ ID NO:5 SEQ ID NO:8, SEQ ID NO:11, SEQ ID NO:14, SEQ ID NO:17, SEQ ID NO:20, SEQ ID NO:23, SEQ ID NO:26 and SEQ ID NO:29, wherein the ENV-SA fusion protein is capable of self-assembling into nanoparticles. In one embodiment of the present, the ENV-SA fusion protein comprises an ENV-protein of the present invention joined to at least 25 contiguous amino acids, at least 50 contiguous amino acids, at least 75 contiguous amino acids, at least 100 contiguous amino acids, or at least 150 contiguous amino acids from amino acid residues 5-167 of SEQ ID NO:2, SEQ ID NO:5 or SEQ ID NO:8, wherein the ENV-SA fusion protein is capable of self-assembling into nanoparticles.

As has been previously discussed, it is well-known in the art that some variations can be made in the amino acid sequence of a protein without affecting the activity of that protein. Such variations include insertion of amino acid residues, deletions of amino acid residues, and substitutions of amino acid residues. Thus, in one embodiment, the sequence of a SA protein subunit is divergent enough from the sequence of a SA protein subunit found in nature, such that when the variant SA protein subunit is introduced into an animal, such as a mouse, it does not result in the production of antibodies that react with the natural SA protein. According to the present invention, such a monomeric subunit is referred to as immunogenically neutral. One embodiment of the present invention is an ENV-SA fusion protein comprising an ENV protein of the present invention joined to an amino acid sequence at least 80%, at least 85%, at least 90%, at least 95%, and at least 97% identical to the amino acid sequence of a monomeric SA protein subunit that is responsible for directing self-assembly of the monomeric ferritin subunits into a nanoparticle, wherein the ENV-SA fusion protein is capable of self-assembling into nanoparticles. In one embodiment, the ENV-SA fusion protein comprises a polypeptide sequence identical in sequence to a monomeric SA protein subunit selected from the group consisting of ferritin, encapsulin, sulfur oxygenase reductase, lumazine synthase and pyruvate dehydrogenase complex (PDC) dihydrolipoamide acetyltransferase (E2).

One embodiment of the present invention is an ENV-SA fusion protein comprising an ENV protein of the present invention joined to an amino acid sequence at least 80%, at least 85%, at least 90%, at least 95%, and at least 97% identical to the amino acid sequence of a monomeric SA protein subunit selected from the group consisting of ferritin, encapsulin, sulfur oxygenase reductase, lumazine synthase and pyruvate dehydrogenase complex (PDC) dihydrolipoamide acetyltransferase (E2), wherein the ENV-SA fusion protein is capable of self-assembling into nanoparticles. One embodiment of the present invention is an ENV-SA fusion protein comprising an ENV protein of the present invention joined to an amino acid sequence at least 80%, at least 85%, at least 90%, at least 95%, and at least 97% identical to a sequence selected from the group consisting of SEQ ID NO:2, SEQ ID NO:5 SEQ ID NO:8, SEQ ID NO:11, SEQ ID NO:14, SEQ ID NO:17, SEQ ID NO:20, SEQ ID NO:23, SEQ ID NO:26 and SEQ ID NO:29, wherein the ENV-SA fusion protein is capable of self-assembling into nanoparticles. One embodiment of the present invention is an ENV-SA fusion protein comprising an ENV protein of the present invention joined to an amino acid sequence at least 80%, at least 85%, at least 90%, at least 95%, and at least 97% identical to amino acid 5-167 from SEQ ID NO:2, SEQ ID NO:5 or SEQ ID NO:8, wherein the ENV-SA fusion protein is capable of self-assembling into nanoparticles.

In some embodiments, it may be useful to engineer mutations into the amino acid sequences of proteins of the present invention. For example, it may be useful to alter sites such as enzyme recognition sites or glycosylation sites in the monomeric ferritin subunit, the trimerization domain, or linker sequences, in order to give the fusion protein beneficial properties (e.g., stability, solubility, half-life, mask portions of the protein from immune surveillance). For example, it is known that the monomeric subunit of ferritin is not glycosylated naturally. However, it can be glycosylated if it is expressed as a secreted protein in mammalian or yeast cells. Thus, in one embodiment, potential N-linked glycosylation sites in the amino acid sequences from the monomeric ferritin subunit are mutated so that the mutated ferritin subunit sequences are no longer glycosylated at the mutated site.

According to the present invention, the EBV envelope protein portion of ENV-SA fusion proteins of the present invention can be from any EBV virus, so long as the ENV-SA fusion protein elicits an immune response against Epstein-Barr virus. Thus, one embodiment of the preset invention is an ENV-SA fusion protein comprising a self-assembly (SA) protein of the present invention joined to an amino acid sequence from an EBV envelope protein, wherein the ENV-SA fusion protein is capable of self-assembling into nanoparticles. One embodiment of the preset invention is an ENV-SA fusion protein comprising a self-assembly (SA) protein of the present invention joined to an amino acid sequence from a Type I EBV envelope protein, wherein the ENV-SA fusion protein is capable of self-assembling into nanoparticles. One embodiment of the preset invention is an ENV-SA fusion protein comprising a self-assembly (SA) protein of the present invention joined to an amino acid sequence from a Type II EBV envelope protein, wherein the ENV-SA fusion protein is capable of self-assembling into nanoparticles. One embodiment of the preset invention is an ENV-SA fusion protein comprising a SA protein of the present invention joined to an amino acid sequence from an EBV ENV protein listed in Table 2. One embodiment of the preset invention is an ENV-SA fusion protein comprising a SA protein of the present invention joined to an amino acid sequence from a protein selected from the group consisting of EBV gp350 protein, EBV gH protein, EBV gL protein and EBV gp42 protein. One embodiment of the present invention is an ENV-SA fusion protein comprising a SA protein of the present invention joined to an amino acid sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68 and SEQ ID NO:132.

Preferred ENV envelope proteins to use in constructing ENV-SA fusion proteins of the present invention are those that elicit an immune response against Epstein-Barr virus. Even more preferred EBV ENV proteins are those that are capable of eliciting antibodies to EBV. One embodiment of the present invention is an ENV-SA fusion protein that elicits antibodies to a Type I or Type II Epstein-Barr virus. One embodiment of the present invention is an ENV-SA fusion protein that elicits antibodies to an EBV ENV protein listed in Table 2. Preferred antibodies elicited by ENV-SA fusion proteins of the present invention are those that neutralize an Epstein-Barr virus. Thus, one embodiment of the present invention is an ENV-SA fusion protein that elicits neutralizing antibodies to a Type I or Type II EBV.

Neutralizing antibodies elicited by an ENV-SA fusion protein of the present invention can neutralize viral infections by affecting any step in the life cycle of the virus. Thus, in one embodiment of the present invention, an ENV-SA fusion protein elicits neutralizing antibodies that prevent EBV from attaching to the host cell. In one embodiment of the present invention, an ENV-SA fusion protein elicits neutralizing antibodies that prevent fusion of the viral envelope with the host cell membrane.

It will be understood by those skilled in the art that particularly useful ENV-SA proteins of the present invention are those comprising an immunogenic portion of an EBV envelope protein. Thus, one embodiment of the present invention is an ENV-SA fusion protein comprising a SA protein of the present invention joined to at least one immunogenic portion of an EBV ENV protein. One embodiment of the present invention is an ENV-SA protein comprising a SA protein of the present invention joined to at least one immunogenic portion of an ENV protein selected from the group consisting of EBV gp350 protein, EBV gH protein, EBV gL protein and EBV gp42 protein. One embodiment of the present invention is an ENV-SA protein comprising a SA protein of the present invention joined to at least one immunogenic portion of an ENV protein from the ENV proteins listed in Table 2. In one embodiment, an ENV-SA fusion protein comprising an immunogenic portion of an ENV protein elicits the production of neutralizing antibodies against EBV.

Immunogenic portions of proteins comprise epitopes, which are clusters of amino acid residues that are recognized by the immune system, thus eliciting an immune response. Such epitopes may consist of contiguous amino acids residues (i.e., amino acid residues that are adjacent to one another in the protein), or they may consist of non-contiguous amino acid residues (i.e., amino acid residues that are not adjacent one another in the protein) but which are in close special proximity in the finally folded protein. It is well understood by those skilled in the art that such epitopes require a minimum of six amino acid residues in order to be recognized by the immune system. Thus, one embodiment of the present invention is an ENV-SA fusion protein comprising an immunogenic portion from the ENV protein, wherein the immunogenic portion comprises at least one epitope.

It is known in the art that some variation in a protein sequence can be tolerated without significantly affecting the activity of the protein. Thus, one embodiment of the present invention is an ENV-SA fusion protein comprising a SA protein of the present invention joined to an amino acid sequence that is a variant of an ENV protein from a Type I or Type II Epstein-Barr virus. One embodiment of the present invention is an ENV-SA fusion protein comprising a ferritin protein of the present invention joined to an amino acid sequence at least about 80%, at least about 85%, at least about 90%, at least about 95%, at least about 97% or at least about 99% identical to the sequence of an ENV protein from a Type I or Type II Epstein-Barr virus, wherein the ENV-SA fusion protein elicits the production of neutralizing antibodies against EBV. One embodiment of the present invention is an ENV-SA fusion protein comprising an SA protein of the present invention joined to an amino acid sequence at least about 80%, at least about 85%, at least about 90%, at least about 95%, at least about 97% or at least about 99% identical to the sequence of an ENV protein from those listed in Table 2, wherein the ENV-SA fusion protein elicits the production of neutralizing antibodies against EBV. One embodiment of the present invention is an ENV-SA fusion protein comprising an SA protein of the present invention joined to an amino acid sequence at least about 80%, at least about 85%, at least about 90%, at least about 95%, at least about 97% or at least about 99% identical to the sequence of an ENV protein selected from the group consisting of consisting of EBV gp350 protein, EBV gH protein, EBV gL protein and EBV gp42 protein, wherein the ENV-SA fusion protein elicits the production of neutralizing antibodies against EBV. One embodiment of the present invention is an ENV-SA fusion protein comprising an SA protein of the present invention joined to amino acid sequence at least about 80%, at least about 85%, at least about 90%, at least about 95%, at least about 97% or at least about 99% identical to a sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132 and SEQ ID NO:136, wherein the ENV-SA fusion protein elicits the production of neutralizing antibodies against EBV. One embodiment of the present invention is an ENV-SA fusion protein comprising a SA protein of the present invention joined to amino acid sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132 and SEQ ID NO:136.

One embodiment of the present invention is an ENV-SA fusion protein comprising an amino acid sequence at least 80%, at least about 85%, at least about 90%, at least about 95%, at least about 97% or at least about 99% identical to a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:128, SEQ ID NO:130, SEQ ID NO:134 and SEQ ID NO:146. One embodiment of the present invention is an ENV-SA fusion protein comprising an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:128, SEQ ID NO:130, SEQ ID NO:134 and SEQ ID NO:146.

It is known in the art that the EBV ENV proteins have various regions, or domains, each possessing specific activities. For example, EBV gp350 has an ectodomain that extends out from the viral membrane and comprises the receptor binding domain (RBD). Thus, it will be understood by those skilled in the art that ENV-SA fusion proteins of the present invention need not comprise the entire sequence of the EBV ENV protein. Instead, an ENV-SA fusion protein can comprise only those portions, regions, domains, and the like, that contain the necessary activities for practicing the present invention. For example, an ENV-SA fusion protein may contain only those amino acid sequences from the ENV protein that contain antigenic sites, epitopes, immunodominant epitopes, and the like.

One embodiment of the present invention is an ENV-SA fusion protein comprising a SA protein of the present invention joined to at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from a protein from a Type I or Type II EBV, wherein the ENV-SA fusion protein elicits the production of neutralizing antibodies against EBV. One embodiment of the present invention is an ENV-SA fusion protein comprising a SA protein of the present invention joined to at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from an ENV protein from those listed in Table 2, wherein the ENV-SA fusion protein elicits the production of neutralizing antibodies against EBV. One embodiment of the present invention is an ENV-SA fusion protein comprising a SA protein of the present invention joined to at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from an ENV protein selected from the group consisting of consisting of EBV gp350 protein, EBV gH protein, EBV gL protein and EBV gp42 protein, wherein the ENV-SA fusion protein elicits the production of neutralizing antibodies against EBV. One embodiment of the present invention is an ENV-SA fusion protein comprising a SA protein of the present invention joined to at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from a protein consisting of a sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132 and SEQ ID NO:136.

One embodiment of the present invention is an ENV-SA fusion protein comprising a SA protein of the present invention joined to at least one domain from an EBV gp350 protein, wherein the domain is selected from the group consisting of an ectodomain, an RDB domain, Domain I, Domain II and Domain III. According to the present invention, an ectodomain of an EBV gp350 protein refers to the portion of the gp350 protein that lies outside its transmembrane domain. One embodiment of the present invention is an ENV-SA fusion protein comprising a SA protein of the present invention joined a sequence selected from the group consisting of SEQ ID NO:35, SEQ ID NO:38, SEQ ID NO:41, SEQ ID NO:44, SEQ ID NO:47, SEQ ID NO:50, SEQ ID NO:53, SEQ ID NO:55 and SEQ ID NO:58.

ENV-SA proteins of the present invention are constructed by joining a SA protein of the present invention with an ENV protein of the present invention. In some embodiments, joining of the various proteins and/or domains can be done such that the sequences are directly linked. In other embodiments, it may be necessary to employ linkers (also referred to as a spacer sequences) between the various proteins and/or domains so that the so that they are in the proper orientation. More specifically, linker sequence can be inserted so that the ENV protein is positioned in such a way to maintain the ability to elicit an immune response against EBV. Linker sequences of the present invention comprise amino acids. Preferable amino acids to use are those having small side chains and/or those which are not charged. Such amino acids are less likely to interfere with proper folding and activity of the fusion protein. Accordingly, preferred amino acids to use in linker sequences, either alone or in combination are serine, glycine and alanine. Examples of such linker sequences include, but are not limited to, SGG, SGGG, GSG, GG, NGTGGSG and iterations thereof. Amino acids can be added or subtracted as needed. Those skilled in the art are capable of determining appropriate linker sequences for proteins of the present invention.

In accordance with the invention, suitable portions of the ENV protein can be joined to the SA protein by fusion with the N-terminal sequence, as an endocapsid product by fusion with the C-terminus, or a combination thereof. In one embodiment, the ENV portion of the fusion protein is joined to the N-terminal sequence of the SA portion of the fusion protein. In one embodiment, the ENV portion of the fusion protein is joined to the C-terminal sequence of the SA portion of the fusion protein.

The present inventors have also discovered that the production of nanoparticles of the present invention can be facilitated by using constructs expressing a fusion protein comprising multiple EBV proteins. Thus, one embodiment of the present invention is an ENV-SA fusion protein comprising a self-assembly (SA) protein of the present invention joined to amino acid sequences from two or more EBV envelope (ENV) proteins, wherein the ENV-SA fusion protein is capable of self-assembling into nanoparticles. In one embodiment, the two or more EBV envelope proteins are from Type I and/or Type II EBV. In one embodiment, the amino acid sequences are from two or more ENV envelope proteins listed in Table 2. In one embodiment, the ENV-SA fusion protein comprises a self-assembly protein joined to immunogenic portions from two or more EBV envelope proteins. In one embodiment, the two or more EBV envelope proteins are selected from the group consisting of EBV gp350 protein, EBV gH protein, EBV gL protein and EBV gp42 protein. In one embodiment, the two or more envelope proteins comprise amino acid sequences selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68 and SEQ ID NO:132.

One embodiment of the present invention is an ENV-SA fusion protein comprising a self-assembly (SA) protein of the present invention joined to amino acid sequences from two or more an EBV envelope (ENV) proteins, wherein the ENV-SA fusion protein is capable of self-assembling into nanoparticles and wherein the two or more EBV envelope proteins are capable of eliciting antibodies to a Type I and/or Type II EBV. In one embodiment, the two or more envelope proteins are capable of eliciting antibodies to at least one EBV envelope protein listed in Table 2. In a preferred embodiment the ENV-SA fusion protein elicits neutralizing antibodies to a Type I and/or a Type II EBV.

One embodiment of the present invention is an ENV-SA fusion protein comprising a self-assembly (SA) protein of the present invention joined to amino acid sequences from two or more an EBV envelope (ENV) proteins, wherein the ENV-SA fusion protein is capable of self-assembling into nanoparticles, and wherein the amino acid sequence from each of the two or more EBV envelope proteins comprises an immunogenic portion of an EBV envelope protein. In one embodiment, at least one of the immunogenic portions is capable of eliciting antibodies to a Type I and/or Type II EBV. In a preferred embodiment, the antibodies are neutralizing antibodies. In one embodiment, the immunogenic portions are from an EBV envelope protein listed in Table 2. In one embodiment, the immunogenic portions are from an EBV envelope protein comprising an amino acid sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68 and SEQ ID NO:132.

One embodiment of the present invention is an ENV-SA fusion protein comprising a self-assembly (SA) protein of the present invention joined to amino acid sequences from two or more an EBV envelope (ENV) proteins, wherein the two or more EBV envelope proteins are variants of EBV envelope proteins from a Type I and/or Type II EBV, and wherein the ENV-SA fusion protein is capable of self-assembling into nanoparticles. In one embodiment, the two or more EBV envelope proteins comprise amino acid sequences at least about 80%, at least about 85%, at least about 90%, at least about 95%, at least about 97% or at least about 99% identical to the sequence of an EBV envelope protein from a Type I and/or a Type II EBV. In one embodiment, the two or more EBV envelope proteins comprise amino acid sequences at least about 80%, at least about 85%, at least about 90%, at least about 95%, at least about 97% or at least about 99% identical to the sequence of an EBV envelope protein selected from the group consisting of EBV gp350 protein, EBV gH protein, EBV gL protein and EBV gp42 protein. In one embodiment, the two or more EBV envelope proteins comprise amino acid sequences at least about 80%, at least about 85%, at least about 90%, at least about 95%, at least about 97% or at least about 99% identical to the sequence of an EBV envelope protein listed in Table 2. In one embodiment, the two or more EBV envelope proteins comprise amino acid sequences at least about 80%, at least about 85%, at least about 90%, at least about 95%, at least about 97% or at least about 99% identical to a sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68 and SEQ ID NO:132.

One embodiment of the present invention is an ENV-SA fusion protein comprising a self-assembly (SA) protein of the present invention joined to amino acid sequences from two or more EBV envelope (ENV) proteins, wherein each amino acid sequence from the two or more EBV envelope proteins is at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids in length, and wherein the ENV-SA fusion protein is capable of self-assembling into nanoparticles. In one embodiment, at least one of the amino acid sequences is capable of eliciting antibodies to a Type I and/or Type II EBV. In a preferred embodiment, the antibodies are neutralizing antibodies. In one embodiment, each amino acid sequence from the two or more EBV envelope proteins comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from an EBV envelope protein selected from the group consisting of EBV gH protein, EBV gL protein, EBV gp42 protein and EBV gp350 protein. In one embodiment, each amino acid sequence from the two or more EBV envelope proteins comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from an EBV envelope protein listed in Table 2. In one embodiment, each amino acid sequence from the two or more EBV envelope proteins comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from a protein having an amino acid sequence at least about 80%, at least about 85%, at least about 90%, at least about 95%, at least about 97% or at least about 99% identical to a sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68 and SEQ ID NO:132. In one embodiment, each amino acid sequence from the two or more EBV envelope proteins comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from a protein having an amino acid sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68 and SEQ ID NO:132.

In certain embodiments, sequences within the fusion protein are directly joined. In alternative embodiments, it is useful to employ linkers, spacers or other types of sequences in order to obtain desired results. Such sequences can be inserted between specific fusion elements in order to, for example, maintain stoichiometry (or molecular ratio) of the final proteins, maintain proper orientation of domains in the final fusion protein, to facilitate transport of the final protein within or out of a cell, or to allow cleavage of the final protein. Thus, examples of useful sequences to utilize include, but are not limited to, linker sequences, spacer sequences, binding sequences, cleavage sequences, leader sequences and secretion signal sequences. Examples of constructs utilizing such sequences are shown in FIG. 22. Thus, one embodiment of the present invention is a ENV-SA fusion protein comprising one or more sequences selected from the group consisting of spacer sequences, binding sequences, cleavage sequences, leader sequences and secretion signal sequences. In one embodiment, the ENV-SA fusion protein comprises one or more protease cleavage sequence. In one embodiment, the cleavage site is a self-cleavage site. In one embodiment, the cleavage sequence is a picornavirus protease cleavage sequence. In one embodiment, the cleavage sequence is a furin cleavage sequence (Arg-Lys-Arg-Arg). In one embodiment, the ENV-SA fusion protein comprises a sequence that directs secretion of the protein. In one embodiment, the fusion protein comprises a leader sequence from human CD5. In one embodiment, the fusion protein comprises one or more sequences selected from the group consisting of SEQ ID NO:138, SEQ ID NO:140, RKRR and functional variants thereof.

One embodiment of the present invention is a ENV-SA fusion protein comprising a self-assembly (SA) protein of the present invention joined to amino acid sequences from two or more EBV envelope (ENV) proteins, wherein the fusion protein comprises at least one cleavage site positioned such that cleavage, including self-cleavage, at the cleavage site results in a SA-gH fusion protein. In one embodiment, the SA-gH fusion protein is capable of forming a dimer with EBVgL. In one embodiment, the SA-gH fusion protein is capable of forming a trimer with EBV gL and EBV gp42. In one embodiment, the ENV-SA fusion protein comprises an EBV gH protein and one or more of the EBV gL and EBV gp42 protein. In one embodiment, the fusion protein comprises additional cleavage sites such that cleavage, including self-cleavage, of the fusion protein results in a SA-gH fusion protein and one or more of an EBV gL protein and EBV gp42 protein. One embodiment of the present invention is a fusion protein comprising an amino acid sequence at least about 80%, at least about 85%, at least about 90%, at least about 95%, at least about 97% or at least about 99% identical to a sequence selected from the group consisting of SEQ ID NO:142 and SEQ ID NO:144. One embodiment of the present invention is a fusion protein comprising SEQ ID NO:142 or SEQ ID NO:144.

Proteins of the present invention are encoded by nucleic acid molecules of the present invention. In addition, they are expressed by nucleic acid constructs of the present invention. As used herein a nucleic acid construct is a recombinant expression vector, i.e., a vector linked to a nucleic acid molecule encoding a protein such that the nucleic acid molecule can effect expression of the protein when the nucleic acid construct is administered to, for example, a subject or an organ, tissue or cell. The vector also enables transport of the nucleic acid molecule to a cell within an environment, such as, but not limited to, an organism, tissue, or cell culture. A nucleic acid construct of the present disclosure is produced by human intervention. The nucleic acid construct can be DNA, RNA or variants thereof. The vector can be a DNA plasmid, a viral vector, or other vector. In one embodiment, a vector can be a cytomegalovirus (CMV), retrovirus, adenovirus, adeno-associated virus, herpes virus, vaccinia virus, poliovirus, sindbis virus, or any other DNA or RNA virus vector. In one embodiment, a vector can be a pseudotyped lentiviral or retroviral vector. In one embodiment, a vector can be a DNA plasmid. In one embodiment, a vector can be a DNA plasmid comprising viral components and plasmid components to enable nucleic acid molecule delivery and expression. Methods for the construction of nucleic acid constructs of the present disclosure are well known. See, for example, *Molecular Cloning: a Laboratory Manual*, 3rd edition, Sambrook et al. 2001 Cold Spring Harbor Laboratory Press, and *Current Protocols in Molecular Biology*, Ausubel et al. eds., John Wiley & Sons, 1994. In one embodiment, the vector is a DNA plasmid, such as a CMV/R plasmid such as CMV/R or CMV/R 8 KB (also referred to herein as CMV/R 8 kb). Examples of CMV/R and CMV/R 8 kb are provided herein. CMV/R is also described in U.S. Pat. No. 7,094,598 B2, issued Aug. 22, 2006.

As used herein, a nucleic acid molecule comprises a nucleic acid sequence that encodes a SA monomeric subunit, an ENV protein, and/or an ENV-ferritin SA protein of the present invention. A nucleic acid molecule can be produced recombinantly, synthetically, or by a combination of recombinant and synthetic procedures. A nucleic acid molecule of the disclosure can have a wild-type nucleic acid sequence or a codon-modified nucleic acid sequence to, for example, incorporate codons better recognized by the human translation system. In one embodiment, a nucleic acid molecule can be genetically-engineered to introduce, or eliminate, codons encoding different amino acids, such as to introduce codons that encode an N-linked glycosylation site. Methods to produce nucleic acid molecules of the disclosure are known in the art, particularly once the nucleic acid sequence is know. It is to be appreciated that a nucleic acid construct can comprise one nucleic acid molecule or more than one nucleic acid molecule. It is also to be appreciated that a nucleic acid molecule can encode one protein or more than one protein.

Preferred nucleic acid molecules are those that encode a SA monomeric subunit, an ENV protein, and/or an ENV-SA fusion protein comprising a monomeric subunit of a SA protein joined to an EBV ENV protein. Thus, one embodiment of the present invention is a nucleic acid molecule comprising a nucleic acid sequence encoding a protein that comprises a monomeric subunit of a SA protein joined to an EBV ENV protein. In one embodiment, the monomeric subunit of an SA protein comprises an amino acid sequence at least 80%, at least 85%, at least 90%, at least 92%, at least 94%, at least 96%, at least 98% or at least 99% identical to a sequence selected from the group consisting of SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26 and SEQ ID NO:29. In one embodiment, the monomeric subunit comprises an amino acid sequence selected from the group consisting of SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26 and SEQ ID NO:29. In one embodiment the EBV ENV protein comprises an amino acid sequence at least 80%, at least 85%, at least 90%, at least 92%, at least 94%, at least 96%, at least 98% or at least 99% identical to a sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132 and SEQ ID NO:136. In one embodiment the EBV ENV protein comprises a sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132 and SEQ ID NO:136. In one embodiment the EBV ENV protein comprises at least 25 amino acids, at least 50 amino acids, at least 75 amino acids, at least 100 amino acids, at least 150 amino acids, or at least 200 amino acids from a sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132 and SEQ ID NO:136.

One embodiment of the present invention is a nucleic acid molecule comprising a nucleic sequence encoding a protein comprising an amino acid sequence at least 80%, at least 85%, at least 90%, at least 92%, at least 94%, at least 96%, at least 98% or at least 99% identical to a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:128, SEQ ID NO:130, SEQ ID NO:134 and SEQ ID NO:146. One embodiment of the present invention is a nucleic acid molecule comprising a nucleic sequence encoding an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:128, SEQ ID NO:130, SEQ ID NO:134 and SEQ ID NO:146.

Also embodied in the present invention are nucleic acid sequences that are variants of nucleic acid sequence encoding protein of the present invention. Such variants include nucleotide insertions, deletions, and substitutions, so long as they do not affect the ability of fusion proteins of the present invention to self-assemble into nanoparticles, or significantly affect the ability of the EBV envelope portion of fusion proteins to elicit an immune response to an Epstein-Barr virus. Thus, one embodiment of the present invention is a nucleic acid molecule encoding a fusion protein of the present invention, wherein the monomeric subunit of the SA protein is encoded by a nucleotide sequence at least 85%, at least 90%, at least 95%, or at least 97% identical to a nucleotide sequence selected from the group consisting of SEQ ID NO:1, SEQ ID NO:4, SEQ ID NO:7, SEQ ID NO:10, SEQ ID NO:13, SEQ ID NO:16, SEQ ID NO:19, SEQ ID NO:22, SEQ ID NO:2 and SEQ ID NO:28. One embodiment of the present invention is a nucleic acid molecule encoding an ENV-SA fusion protein of the present invention, wherein the ENV protein is encoded by a nucleotide sequence at least 85%, at least 90%, at least 95%, at least 97% identical or at least 99% identical to a nucleic acid sequence encoding an amino acid sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132 and SEQ ID NO:136.

One embodiment of the present invention is a nucleic acid molecule comprising a nucleic acid sequence at least about 80%, at least about 85%, at least about 90%, at least about 95%, at least about 97% or at least about 99% identical to a nucleic acid sequence selected from the group consisting of SEQ ID NO:10, SEQ ID NO:13 and SEQ ID NO:16. One embodiment of the present invention is a nucleic acid molecule comprising a nucleic acid sequence selected from the group consisting of SEQ ID NO:10, SEQ ID NO:13 and SEQ ID NO:16.

One embodiment of the present invention is a nucleic acid molecule comprising a nucleic acid sequence at least about 80%, at least about 85%, at least about 90%, at least about 95%, at least about 97% or at least about 99% identical to a nucleic acid sequence selected from the group consisting of SEQ ID NO:70, SEQ ID NO:73, SEQ ID NO:76, SEQ ID NO:79, SEQ ID NO:82, SEQ ID NO:85, SEQ ID NO:88 and SEQ ID NO:92. One embodiment of the present invention is a nucleic acid molecule comprising a nucleic acid sequence selected from the group consisting of SEQ ID NO:70, SEQ ID NO:73, SEQ ID NO:76, SEQ ID NO:79, SEQ ID NO:82, SEQ ID NO:85, SEQ ID NO:88, SEQ ID NO:91, SEQ ID NO:94, SEQ ID NO:97, SEQ ID NO:100, SEQ ID NO:103, SEQ ID NO:127, SEQ ID NO:129, SEQ ID NO:133 and SEQ ID NO:145.

One embodiment of the present invention is a nucleic acid molecule encoding an ENV-SA fusion protein comprising a self-assembly (SA) protein of the present invention joined to amino acid sequences from two or more an EBV envelope (ENV) proteins, wherein the ENV-SA fusion protein is capable of self-assembling into nanoparticles. In one embodiment, the two or more EBV envelope proteins are from Type I and/or Type II EBV. In one embodiment, the amino acid sequences are from two or more ENV envelope proteins listed in Table 2. In one embodiment, the ENV-SA fusion protein comprises a self-assembly protein joined to immunogenic portions from two or more EBV envelope proteins. In one embodiment, the two or more EBV envelope proteins are selected from the group consisting of EBV gp350 protein, EBV gH protein, EBV gL protein and EBV gp42 protein. In one embodiment, the two or more EBV envelope proteins comprise amino acid sequences selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68 and SEQ ID NO:132.

One embodiment of the present invention is nucleic acid molecule encoding a ENV-SA fusion protein comprising a self-assembly (SA) protein of the present invention joined to amino acid sequences from two or more an EBV envelope (ENV) proteins, wherein the ENV-SA fusion protein is capable of self-assembling into nanoparticles and wherein the two or more EBV envelope proteins are capable of eliciting antibodies to a Type I and/or Type II EBV. In one embodiment, the two or more EBV envelope proteins are capable of eliciting antibodies to at least one EBV envelope protein listed in Table 2. In a preferred embodiment the ENV-SA fusion protein elicits neutralizing antibodies to a Type I and/or a Type II EBV.

One embodiment of the present invention is a nucleic acid molecule encoding a ENV-SA fusion protein comprising a self-assembly (SA) protein of the present invention joined to amino acid sequences from two or more an EBV envelope (ENV) proteins, wherein the ENV-SA fusion protein is capable of self-assembling into nanoparticles, and wherein the amino acid sequence from each of the two or more EBV envelope proteins comprises an immunogenic portion of an EBV envelope protein. In one embodiment, at least one of the immunogenic portions is capable of eliciting antibodies to a Type I and/or Type II EBV. In a preferred embodiment, the antibodies are neutralizing antibodies. In one embodiment, the immunogenic portions are from an EBV envelope protein listed in Table 2. In one embodiment, the immunogenic portions are from an EBV envelope protein comprising an amino acid sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68 and SEQ ID NO:132.

One embodiment of the present invention is a nucleic acid molecule encoding a ENV-SA fusion protein comprising a self-assembly (SA) protein of the present invention joined to amino acid sequences from two or more EBV envelope (ENV) proteins, wherein the two or more EBV envelope proteins are variants of EBV envelope proteins from a Type I and/or Type II EBV, and wherein the ENV-SA fusion protein is capable of self-assembling into nanoparticles. In one embodiment, the two or more EBV envelope proteins comprise amino acid sequences at least about 80%, at least about 85%, at least about 90%, at least about 95%, at least about 97% or at least about 99% identical to the sequence of an EBV envelope protein from a Type I and/or a Type II EBV. In one embodiment, the two or more EBV envelope proteins comprise amino acid sequences at least about 80%, at least about 85%, at least about 90%, at least about 95%, at least about 97% or at least about 99% identical to the sequence of an EBV envelope protein selected from the group consisting of EBV gp350 protein, EBV gH protein, EBV gL protein and EBV gp42 protein. In one embodiment, the two or more EBV envelope proteins comprise amino acid sequences at least about 80%, at least about 85%, at least about 90%, at least about 95%, at least about 97% or at least about 99% identical to the sequence of an EBV envelope protein listed in Table 2. In one embodiment, the two or more EBV envelope proteins comprise amino acid sequences at least about 80%, at least about 85%, at least about 90%, at least about 95%, at least about 97% or at least about 99% identical to a sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68 and SEQ ID NO:132.

One embodiment of the present invention is a nucleic acid molecule encoding a ENV-SA fusion protein comprising a self-assembly (SA) protein of the present invention joined to amino acid sequences from two or more EBV envelope (ENV) proteins, wherein each amino acid sequence from the two or more EBV envelope proteins is at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids in length, and wherein the ENV-SA fusion protein is capable of self-assembling into nanoparticles. In one embodiment, at least one of the amino acid sequences is capable of eliciting antibodies to a Type I and/or Type II EBV. In a preferred embodiment, the antibodies are neutralizing antibodies. In one embodiment, each amino acid sequence from the two or more EBV envelope proteins comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from an EBV envelope protein selected from the group consisting of EBV gH protein, EBV gL protein, EBV gp42 protein and EBV gp350 protein. In one embodiment, each amino acid sequence from the two or more EBV envelope proteins comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from an EBV envelope protein listed in Table 2. In one embodiment, each amino acid sequence from the two or more EBV envelope proteins comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from a protein having an amino acid sequence at least about 80%, at least about 85%, at least about 90%, at least about 95%, at least about 97% or at least about 99% identical to a sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68 and SEQ ID NO:132. In one embodiment, each amino acid sequence from the two or more EBV envelope proteins comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from a protein having an amino acid sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68 and SEQ ID NO:132.

One embodiment of the present invention is a nucleic acid molecule comprising a nucleotide sequence at least about 80%, at least about 85%, at least about 90%, at least about 95%, at least about 97% or at least about 99% identical to a sequence selected from the group consisting of SEQ ID NO:141 and SEQ ID NO:143. One embodiment of the present invention is a nucleic acid molecule comprising SEQ ID NO:141 or SEQ ID NO:143.

Also encompassed by the present invention are expression systems for producing fusion proteins of the present invention. In one embodiment, nucleic acid molecules of the present invention are operationally linked to a promoter. As used herein, operationally linked means that proteins encoded by the linked nucleic acid molecules can be expressed when the linked promoter is activated. Promoters useful for practicing the present invention are known to those skilled in the art. One embodiment of the present invention is a recombinant cell comprising a nucleic acid molecule of the present invention. One embodiment of the present invention is a recombinant virus comprising a nucleic acid molecule of the present invention.

As indicated above, the recombinant production of the ENV-SA fusion proteins of the present invention can take place using any suitable conventional recombinant technology currently known in the field. For example, molecular cloning of a construct expressing a fusion protein, such as a SA protein of the present invention with a suitable protein such as a recombinant EBV ENV protein, can be carried out via expression in *E. coli*. The construct may then be transformed into protein expression cells, grown to suitable size, and induced to produce the fusion protein.

As has been described, because ENV-SA fusion proteins of the present invention comprise a monomeric self-assembly (SA) protein, they can self-assemble. According to the present invention, the supramolecule resulting from such self-assembly is referred to as an ENV-expressing, SA protein-based nanoparticle. For ease of discussion, the ENV-expressing, SA protein-based nanoparticle will simply be referred to as a, or the, nanoparticle (np). Nanoparticles of the present invention comprise fusion proteins comprising a SA monomeric subunit joined to an EBV ENV protein. Such nanoparticles display at least a portion of the ENV protein on their surface. In such a construction, the ENV protein is accessible to the immune system and thus can elicit an immune response. Thus, one embodiment of the present invention is a nanoparticle comprising an ENV-SA fusion protein, wherein the fusion protein comprises a monomeric SA subunit joined to an EBV ENV protein. In one embodiment, the nanoparticle is an octahedron. In one embodiment, the ENV protein is capable of eliciting neutralizing antibodies to EBV. In one embodiment, the monomeric SA subunit comprises at least 50 amino acids, at least 100 amino acids, or at least 150 amino acids from an amino acid sequence selected from the group consisting of SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26 and SEQ ID NO:29. In one embodiment, the monomeric SA subunit comprises an amino acid sequence at least 85%, at least 90%, at least 95%, at least 97% at least 99% identical to an amino acid sequence selected from the group consisting of SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26 and SEQ ID NO:29. In one embodiment, the monomeric SA subunit comprises an amino acid sequence selected from the group consisting of SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26 and SEQ ID NO:29.

In one embodiment, the ENV protein comprises at least one epitope from an EBV ENV protein listed in Table 2. In one embodiment, the ENV protein comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from an ENV protein listed in Table 2. In one embodiment, the ENV protein comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from a protein consisting of a sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132 and SEQ ID NO:136. In one embodiment, the ENV protein comprises a sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68.

In one embodiment, the ENV protein comprises an amino acid sequence at least 80%, at least 85%, at least 90%, at least 95%, at least 97%, at least 99% identical to the sequence of an ENV protein listed in Table 2. In one embodiment, the ENV protein comprises an amino acid sequence at least 80%, at least 85%, at least 90%, at least 95%, at least 97%, at least 99% identical to a protein sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132 and SEQ ID NO:136.

In one embodiment, the ENV-SA fusion protein comprises an amino acid sequence at least 80%, at least 85%, at least 90%, at least 95%, at least 97%, at least 99% identical to a protein sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:128, SEQ ID NO:130, SEQ ID NO:134 and SEQ ID NO:146. In one embodiment, the ENV-SA fusion protein comprises an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:128, SEQ ID NO:130, SEQ ID NO:134 and SEQ ID NO:146.

Nanoparticles of the present invention may comprise more than one type of fusion protein. That is, a nanoparticle of the present invention may comprise at least two types of fusion proteins, each of which comprises amino acid sequences from different EBV ENV proteins (e.g., gp350 and gH). Moreover, the different types of fusion proteins may comprise amino acid sequences from the same or different SA protein (i.e., ferritin and/or encapsulin). Furthermore, in addition to at least one ENV-SA fusion protein, nanoparticles of the present invention may comprise proteins that are not fused to a SA protein. For example, in addition to comprising an ENV-SA fusion protein (e.g., EBV gH-ferritin protein) a nanoparticle of the present invention may also comprise one or more proteins comprising an amino acid sequence from other EBV ENV proteins, or portions or variants thereof. Examples of such proteins include, but are not limited to gp350, gH, gL and gp42. Such additional one or more proteins may, but need not, form a complex with each other or with the ENV-SA fusion protein.

Because ENV-SA fusion proteins and nanoparticles of the present invention can elicit an immune response to an Epstein-Barr virus, they can be used as vaccines to protect individuals against infection by EBV. According to the present invention a vaccine can be an ENV-SA fusion protein, or a nanoparticle of the present invention. Thus, one embodiment of the present invention is a vaccine comprising an ENV-SA fusion protein or a nanoparticle of the present invention. Vaccines of the present invention can also contain other components such as adjuvants, buffers and the like. Although any adjuvant can be used, preferred embodiments can contain: chemical adjuvants such as aluminum phosphate, benzyalkonium chloride, ubenimex, and QS21; genetic adjuvants such as the IL-2 gene or fragments thereof, the granulocyte macrophage colony-stimulating factor (GM-CSF) gene or fragments thereof, the IL-18 gene or fragments thereof, the chemokine (C-C motif) ligand 21 (CCL21) gene or fragments thereof, the IL-6 gene or fragments thereof, CpG, LPS, TLR agonists, and other immune stimulatory genes; protein adjuvants such IL-2 or fragments thereof, the granulocyte macrophage colony-stimulating factor (GM-CSF) or fragments thereof, IL-18 or fragments thereof, the chemokine (C-C motif) ligand 21 (CCL21) or fragments thereof, IL-6 or fragments thereof, CpG, LPS, TLR agonists and other immune stimulatory cytokines or fragments thereof; lipid adjuvants such as cationic liposomes, N3 (cationic lipid), monophosphoryl lipid A (MPL1); other adjuvants including cholera toxin, enterotoxin, Fms-like tyrosine kinase-3 ligand (Flt-3L), bupivacaine, marcaine, and levamisole.

One embodiment of the disclosure is a SA protein-based nanoparticle vaccine that includes more than one EBV ENV protein. Such a vaccine can include a combination of different EBV envelope proteins, either in a single nanoparticle or as a mixture of nanoparticles, at least two of which have unique EBV ENV proteins. A multivalent vaccine can comprise as many EBV envelope proteins as necessary in order to result in production of the desired immune response. In one embodiment, the vaccine comprises ENV proteins from at least two different Types of EBV (bi-valent). In one embodiment, the vaccine comprises a ENV protein from at least three different Epstein-Barr viruses (tri-valent).

One embodiment of the present invention is a method to vaccinate an individual against EBV, the method comprising administering a nanoparticle to an individual such that an immune response against EBV is produced in the individual, wherein the nanoparticle comprises a monomeric subunit from an SA protein of the present invention joined to an EBV envelope protein of the present invention protein, and wherein the nanoparticle displays the EBV envelope on its surface. In one embodiment, the nanoparticle is a monovalent nanoparticle. In one embodiment, the nanoparticle is multivalent nanoparticle. Another embodiment of the present invention is a method to vaccinate an individual against infection with EBV, the method comprising:

a) obtaining a nanoparticle comprising monomeric subunits, wherein the monomeric subunits comprise an SA protein joined to an EBV ENV protein, and wherein the nanoparticle displays the EBV ENV protein on its surface; and, b) administering the nanoparticle to an individual such that an immune response against EBV is produced.

One embodiment of the present invention is a method to vaccinate an individual against EBV, the method comprising administering a vaccine of the embodiments to an individual such that an immune response against EBV is produced in the individual, wherein the vaccine comprises at least one nanoparticle comprising a monomeric subunit of an SA protein of the present invention joined to an EBV envelope protein of the present invention protein, and wherein the nanoparticle displays the EBV ENV protein on its surface. In one embodiment, the vaccine is a nanoparticle. In one embodiment, the vaccine is a monovalent vaccine. In one embodiment, the vaccine is multivalent vaccine. Another embodiment of the present invention is a method to vaccinate an individual against infection with EBV, the method comprising:

a) obtaining a vaccine comprising at least one nanoparticle comprising an ENV-SA fusion protein, wherein the fusion protein comprises an SA protein joined to an EBV ENV protein, and wherein the nanoparticle displays the EBV ENV on its surface; and, b) administering the vaccine to an individual such that an immune response against EBV is produced.

In one embodiment, the nanoparticle is a monovalent nanoparticle. In one embodiment, the nanoparticle is multivalent nanoparticle. In one embodiment, the nanoparticle is an octahedron. In one embodiment, the EBV ENV protein is capable of eliciting neutralizing antibodies to EBV. In one embodiment, the SA portion of the fusion protein comprise at least 50 amino acids, at least 100 amino acids, or at least 150 amino acids from an amino acid sequence selected from the group consisting of SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26 and SEQ ID NO:29. In one embodiment, the SA portion of the fusion protein comprises an amino acid sequence at least 85%, at least 90%, at least 95%, at least 97% at least 99% identical to an amino acid sequence selected from the group consisting of SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26 and SEQ ID NO:29. In one embodiment, the ENV portion of the fusion protein comprises at least one epitope from an ENV protein listed in Table 2. In one embodiment, the ENV portion of the fusion protein comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from an ENV listed in Table 2. In one embodiment, the ENV portion of the fusion protein comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from a protein consisting of a sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132 and SEQ ID NO:136. In one embodiment, the ENV portion of the fusion protein comprises an amino acid sequence at least 80%, at least 85%, at least 90%, at least 95%, at least 97%, at least 99% identical to the sequence of an ENV protein listed in Table 2. In one embodiment, the ENV portion of the fusion protein comprises an amino acid sequence at least 80%, at least 85%, at least 90%, at least 95%, at least 97%, at least 99% identical to a sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132 and SEQ ID NO:136. In one embodiment, the ENV-SA fusion protein comprises an amino acid sequence at least 80%, at least 85%, at least 90%, at least 95%, at least 97%, at least 99% identical to a protein sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:128, SEQ ID NO:130 and SEQ ID NO:134. In one embodiment, the ENV-SA fusion protein comprises an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:128, SEQ ID NO:130 and SEQ ID NO:134.

Vaccines of the present invention can be used to vaccinate individuals using a prime/boost protocol. Such a protocol is described in U.S. Patent Publication No. 20110177122, which is incorporated herein by reference in its entirety. In such a protocol, a first vaccine composition may be administered to the individual (prime) and then after a period of time, a second vaccine composition may be administered to the individual (boost). Administration of the boosting composition may be performed days, weeks or months after administration of the priming composition, preferably about 10 days, about two weeks, about three weeks, about 4 weeks, about 8 weeks, about 16 weeks, about 20 weeks, about 24 weeks, about 28 weeks, or about 32 weeks. In one embodiment, the boosting composition is formulated for administration about 1 week, about 2 weeks, about 3 weeks, about 4 weeks, about 5 weeks, about 6 weeks, about 7 weeks, about 8 weeks, about 9 weeks, about 16 weeks, about 20 weeks, about 24 weeks, about 28 weeks, or about 32 weeks after administration of the priming composition. In one embodiment, a second boosting composition (i.e., third vaccine composition) is administered at some period of time following administration of the first boosting composition. For example, a second boosting composition may be administered at a time about 8 weeks, about 9 weeks, about 10 weeks, about 12 weeks, about 16 weeks, about 20 weeks, about 24 weeks, about or 32 weeks after administration of the priming composition. In one embodiment, a second boosting composition is administered 6 months after administration of the priming composition. As used herein, and with specific regard to the timing of administration of a vaccine composition, the term about refers to a variation of no more than 10%. Thus for example, about 10 days specifies a time period of 9-11 days. Likewise, for example, about 6 months specifies a time period of 162-196 days.

The first and second vaccine compositions can be, but need not be, the same composition. Thus, in one embodiment of the present invention, the step of administering the vaccine comprises administering a first vaccine composition, and then at a later time, administering a second vaccine composition. In one embodiment, the first vaccine composition comprises a nanoparticle comprising an ENV-SA fusion protein of the present invention. In one embodiment, the first vaccine composition comprises a nanoparticle comprising EBV ENV protein. In one embodiment, the ENV of the first vaccine composition comprises an amino acid sequence at least about 80% identical, at least 85% identical, at least 90% identical, at least 95% identical, at least 97% identical or at least 99% identical to an amino acid sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132, SEQ ID NO:136 and SEQ ID NO:146. In one embodiment, the first vaccine composition comprises an ENV-SA fusion protein comprising an amino acid sequence at least 80% identical, at least 85% identical, at least 90% identical, at least 95% identical, at least 97% identical or at least 99% identical to a sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:130, SEQ ID NO:132, SEQ ID NO:136 and SEQ ID NO:146, wherein the nanoparticle elicits an immune response against EBV. In one embodiment, the first vaccine composition comprises an ENV-SA fusion protein comprising an amino acid sequence selected from the group consisting of SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68. In one embodiment, second vaccine composition comprises a nanoparticle comprising an ENV-SA fusion protein of the present invention. In one embodiment, the individual has been exposed to EBV. As used herein, the terms exposed, exposure, and the like, indicate the subject has come in contact with a person of animal that is known to be infected with an EBV. Vaccines of the present invention may be administered using techniques well known to those in the art. Techniques for formulation and administration may be found, for example, in "Remington's Pharmaceutical Sciences", 18$^{th}$ ed., 1990, Mack Publishing Co., Easton, PA Vaccines may be administered by means including, but not limited to, traditional syringes, needleless injection devices, or microprojectile bombardment gene guns. Suitable routes of administration include, but are not limited to, parenteral delivery, such as intramuscular, intradermal, subcutaneous, intramedullary injections, as well as, intrathecal, direct intraventricular, intravenous, intraperitoneal, intranasal, or intraocular injections, just to name a few. For injection, the compounds of one embodiment of the invention may be formulated in aqueous solutions, preferably in physiologically compatible buffers such as Hanks' solution, Ringer's solution, or physiological saline buffer.

In one embodiment, vaccines, or nanoparticles, of the present invention can be used to protect an individual against infection by heterologous EBV. That is, a vaccine made using an ENV protein from one Type of EBV is capable of protecting an individual against infection by a different Type of EBV. For example, a vaccine made using one or more ENV protein from Type I EBV, may be used to protect an individual against infection by a Type II EBV.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims.

The invention now being generally described will be more readily understood by reference to the following examples, which are included merely for the purposes of illustration of certain aspects of the embodiments of the present invention. The examples are not intended to limit the invention, as one of skill in the art would recognize from the above teachings and the following examples that other techniques and methods can satisfy the claims and can be employed without departing from the scope of the claimed invention.

EXAMPLES

Example 1. Design of EBV Surface Protein-Based Nanoparticles

This Example describes the construction of nanoparticles comprising EBV surface proteins and ferritin or encapsulin.

Two potential platforms were considered for construction of self-assembling nanoparticles capable of displaying antigens on their surface: ferritin (Cho, et al. J Mol Biol, 2009; Stillman, et al. J Mol Biol, 2001) and encapsulin (Sutter, et al. Nat Struct Mol Biol, 2008). Ferritin forms a 4-3-2 point octahedron consisting of 24 subunits while encapsulin forms a 5-3-2 point icosahedron (T=1) consisting of 60 identical subunits. Comparison of ferritin structures revealed that several ferritins including human light chain (Z. Wang, C. Li, M. Ellenburg, E. Soistman, J. Ruble, B. Wright, J. X. Ho, D. C. Carter, Structure of human ferritin L chain. *Acta Crystallogr D Biol Crystallogr* 62, 800-806 (2006)) (PDB: 2ffx) and bullfrog lower subunit (J. Trikha, E. C. Theil, N. M. Allewell, High resolution crystal structures of amphibian red-cell L ferritin: potential roles for structural plasticity and solvation in function. *J Mol Biol* 248, 949-967 (1995)) (PDB: lrcc) contain an N-terminal extension, which is not present in nonheme-type ferritins from *Helicobacter pylori* (K. J. Cho, H. J. Shin, J. H. Lee, K. J. Kim, S. S. Park, Y. Lee, C. Lee, S. S. Park, K. H. Kim, The crystal structure of ferritin from *Helicobacter pylori* reveals unusual conformational changes for iron uptake. J Mol Biol 390, 83-98 (2009)) (PDB: 3egm) or *Escherichia coli* (T. J. Stillman, P. D. Hempstead, P. J. Artymiuk, S. C. Andrews, A. J. Hudson, A. Treffry, J. R. Guest, P. M. Harrison, The high-resolution X-ray crystallographic structure of the ferritin (EcFtnA) of *Escherichia coli*; comparison with human H ferritin (HuHF) and the structures of the Fe(3+) and Zn(2+) derivatives. *J Mol Biol* 307, 587-603 (2001)) (PDB: leum). This N-terminal extension causes the most N-terminal residue to project radially from the assembled nanoparticle's center, and the termini to be evenly distributed on the surface of the ferritin particle. Thus, to test the idea that the N-terminal extension of bullfrog ferritin could be added to the bacterial counterpart to make its N-termini exposed and evenly distributed on the surface of the nanoparticle, a hybrid ferritin protein was constructed that combined sequence from *H. pylori* ferritin or *E. coli* ferritin with the N-terminal extension from bullfrog ferritin. The details of this construction are listed below.

Encapsulin has not been studied as a scaffold to present heterologous proteins on its surface. In contrast to ferritins, encapsulin has its C-termini exposed on the surface, thus providing a potential site at which to fuse exogeneous sequences. The C-termini of encapsulin are projected radially and are also located dispersedly around the 5-fold symmetry axes.

Figure 1:
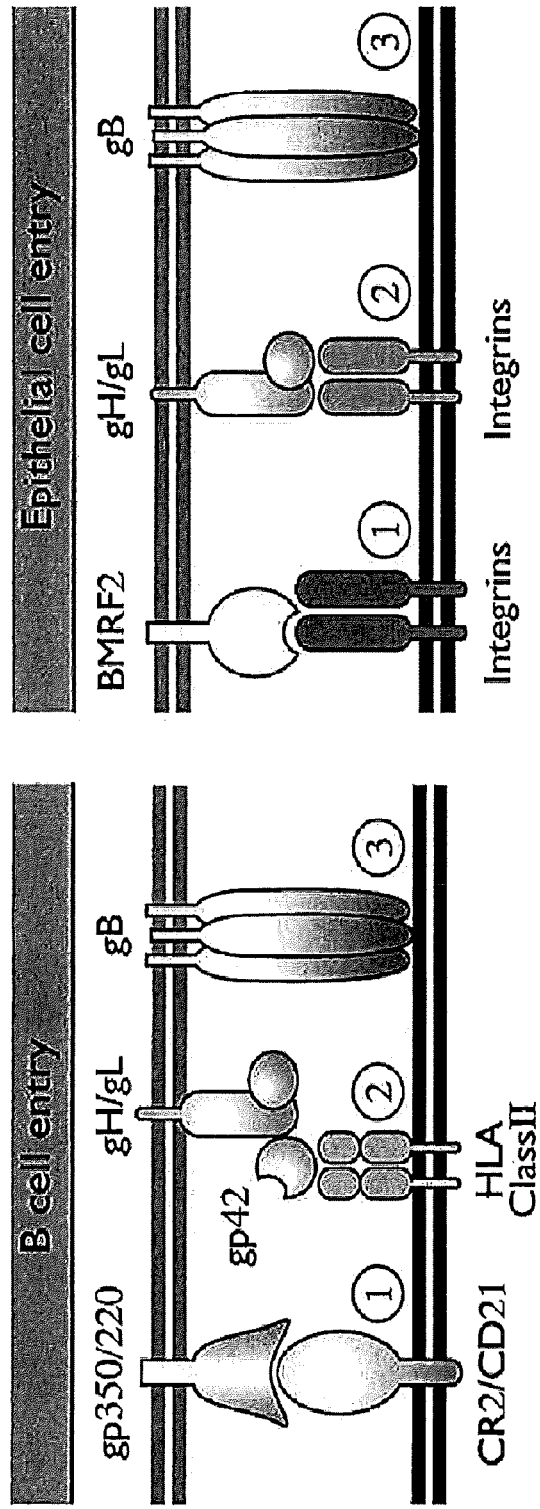
FIG. 1. Molecules essential for EBV infection of B cells and epithelial cells. Entry of EBV in B cells is initiated by attachment of EBV glycoprotein gp350 to its' cellular receptor CR2/CD21, followed by binding of viral glycoprotein gp42 (which also interacts with EBV gH/gL forming a trimer) to HLA class II. This triggers membrane fusion which is completed by glycoprotein gB. Entry of EBV into epithelial cells is thought to be initiated by binding of EBV BMRF2 to its cellular receptor integrins, followed by binding of gH/gL heterodimer to their cellular receptor integrins, and membrane fusion is subsequently triggered and completed by gB. (Figure from Longnecker R, Kieff E, and Cohen J I. Epstein-Barr virus. In: *Fields Virology* 2013).
Figure 2:
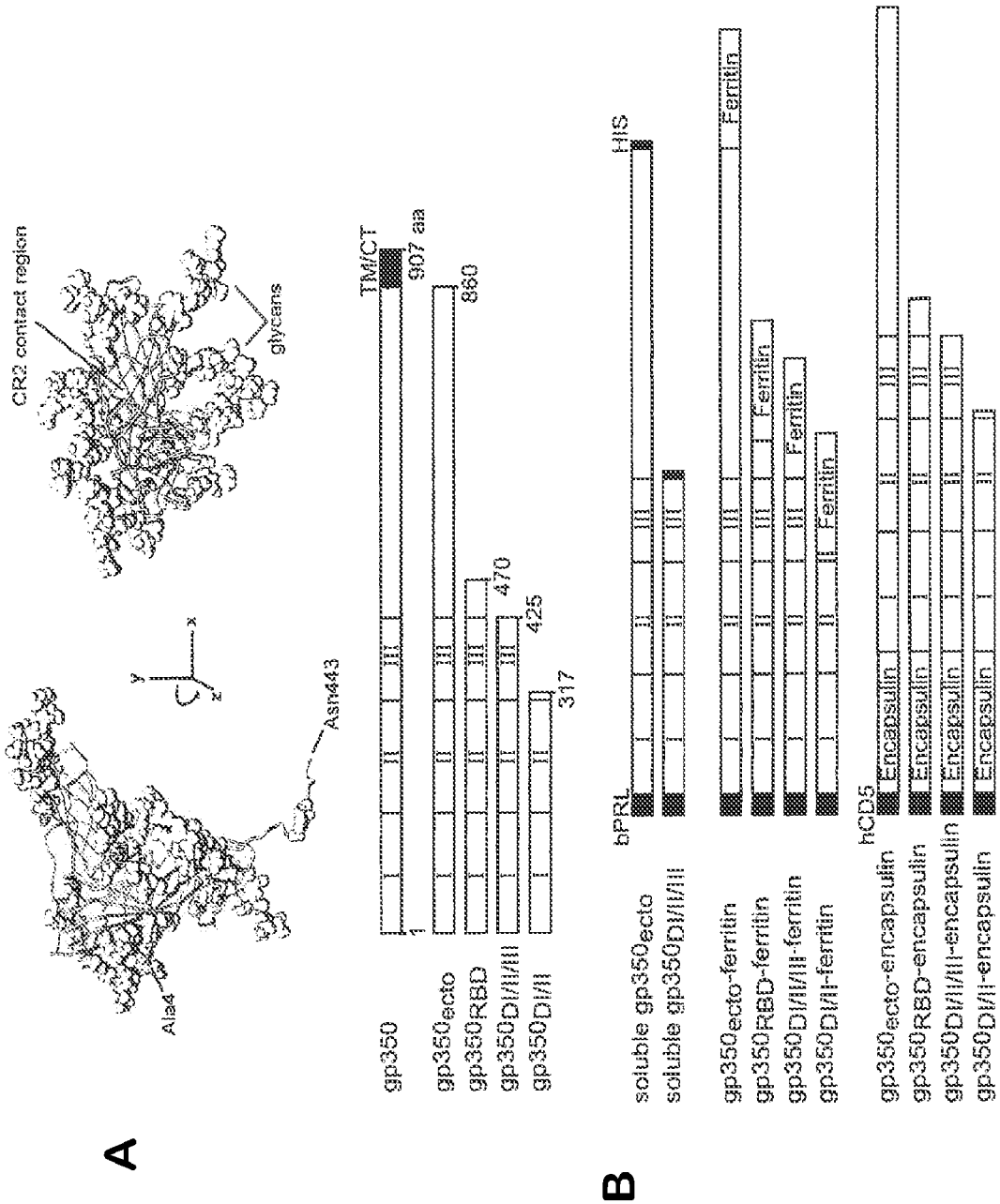
FIG. 2. Molecular design of truncated gp350 variants and gp350-based nanoparticles. (A) Molecular design of truncated gp350 containing CR2-binding site (CR2BS). Crystal structure of EBV gp350 receptor-binding domain (RBD) (PDB: 2h6o) is shown in surface representation (top). The N- and C-terminal residues in the crystal structures are indicated with amino acid number (B95-8 numbering) (left). Schematic representation of full length gp350 and its truncated variants (bottom). Gp350$_{ecto}$ is truncated by removing the transmembrane (TM) and cytoplasmic tail (CT). Gp350$_{RBD}$ is identical to the construct used for the crystallography study (Szakonyi, G., et al., *Nat Struct Mol Biol*. 13, 996-1001, 2006) and it contains intact domains I-III and an extended tail. Gp350$_{DI/II/III}$ and gp350$_{DI/II}$ are truncated further while retaining intact domains I-III and I-II, respectively. (B) Design of soluble monomeric gp350 and gp350-based nanoparticles. The soluble gp350 monomer constructs are made by genetically adding a modified bovine prolactin leader sequence (bPRL) and a poly histidine tag (HIS) at the N- and the C-terminus of gp350, respectively. The gp350-based ferritins are constructed by genetically fusing a bPRL sequence followed by gp350 variants to the N-terminus of ferritin (*Helicobacter pylori*-bullfrog hybrid (Hp) or *Escherichia coli*-bullfrog hybrid (Ec)) with a Ser-Gly linker between gp350 variants and ferritin. The gp350-based encapsulins are constructed by genetically fusing a human CD5 leader (hCD5) sequence and gp350 variants to the N- and the C-termini of encapsulin (*Thermotoga maritima*), respectively with a (Ser-Gly$_3$)$_2$ linker between gp350 variants and encapsulin. These fusion genes are then cloned into the mammalian expression vector (CMV8x/R). Soluble gp350$_{ecto}$ and gp350$_{DI/II/III}$ are designated as VRC 3796 and 3797, respectively. Gp350 variants fused with Ec ferritin, Hp ferritin and encapsulin are designated as VRC 3421-3424, 3425-3428 and 3429-3432, respectively.

Glycoprotein 350 (gp350) of Epstein-Barr virus (EBV) is the most abundant viral surface protein and is a major target of neutralizing antibodies in naturally infected individuals (Thorley-Lawson D A, Poodry C A. Identification and isolation of the main component (gp350-gp220) of Epstein-Barr virus responsible for generating neutralizing antibodies in vivo. J Virol. 1982; 43:730-736). Gp350 is a type I transmembrane protein comprising of 907 amino acids containing an ectodomain of 860 amino acids, a transmembrane domain and a cytoplasmic tail. To test the ability of gp350 to induce an immune response, truncation variants of gp350 were fused to ferritin or encapsulin without disturbing the self-assembly capability of the self-assembling protein (see FIG. 2). These fusion proteins were constructed by creating expression vectors encoding the fusion genes encoding the gp350 variants and either *H. pylori*-bullfrog (HpBf), *E. coli*-bullfrog (EcBf) or encapsulin. The details of this construction are given below.

A. Gene Synthesis and Vector Construction

All genes used in the study were optimized for mammalian codon usage. The gene encoding *Helicobacter pylori*-bullfrog hybrid ferritin was constructed by genetically fusing the N-terminus extension region (residues 2-9) of bullfrog (*Rana catesbeiana*) ferritin lower subunit (UniProtKB: P07797) to residues 3-167 of *H. pylori* nonheme ferritin (UniProtKB: Q9ZLI1. A point mutation was created at residue 8 (N8Q) of the bullfrog portion in order to abolish a potential N-linked glycosylation site. Similarly, point mutations were created at residue 7 (I7E) and 19 (N19Q) of the *H. pylori* ferritin in order to make a salt bridge with 6R of bullfrog N-terminus part and abolish a potential N-linked glycosylation site, respectively.

The gene encoding *Escherichia coli*-bullfrog hybrid ferritin was constructed similarly but without the N8Q mutation in the bullfrog N-terminus extension region and with *E. coli* ferritin-1 (UniProtKB: P0A998, residues 3-162 having a point mutation at residue 7 (I7E) to make a salt bridge with 6R of bullfrog N-terminus part). These constructs also contained extra SG residues at the end of *H. pylori* or *E. coli* ferritin for cloning purpose.

The gene encoding encapsulin was constructed by genetically fusing the human CD5 signal sequence to *Termotoga maritima* bacteriocin (also known as maritimacin or encapsulin, UniProtKB: Q9WZP2, residues 1-264).

The gene encoding Epstein-Barr virus strain B95-8 full-length gp350 (UniProtKB: P03200, residues 1-907) was synthesized and the gene fragments corresponding to ectodomain (residues 2-860), receptor-binding domain (RBD, residues 2-470), domains I, II and III ($D_{I/II/III}$ or $D_{123}$, residues 2-425) and domains I and II (residues 2-317) were amplified by polymerase chain reactions with appropriate primers. Amplified gene fragments were genetically fused to a modified bovine prolactin (bPRL) secretion signal sequence and the hybrid ferritin with a SG linker to give rise to the gp350-ferritin fusion genes.

Figure 3:
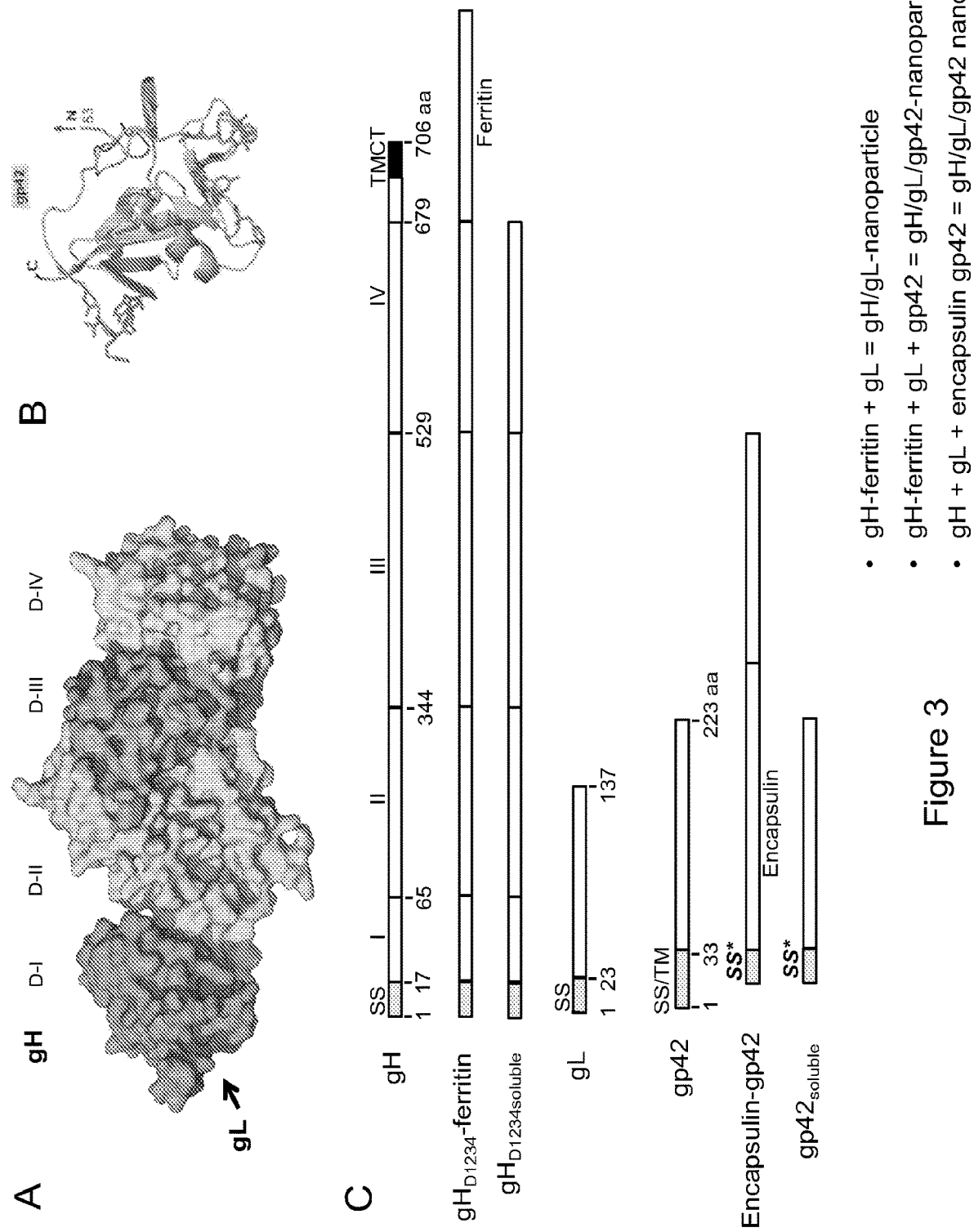
FIG. 3. Molecular structure and design of gH/gL ferritin-based, gH/gL/gp42 ferritin-based and gH/gL/gp42 encapsulin-based nanoparticles. (A) Crystal structure of EBV gH/gL heterodimer (PDB: 3PHF). (B) Ribbon diagram of EBV gp42 (PDB: 3FD4). (C) Schematic representation of full-length gH, gH$_{D1234}$-ferritin fusion protein, gH$_{D1234}$ soluble, full-length gL, full-length gp42, encapsulin-gp42 and gp42 soluble proteins. gH-ferritin fusion protein is generated by fusion of gH ectodomain (D$_{1234}$) to the N-terminus of ferritin (*Helicobacter pylori*-bullfrog hybrid (Hp)). Soluble gH is constructed by deletion of transmembrane domain and cytoplasmic tail. gH D$_{1234}$ is identical to the construct used for the crystallography study (Matsuura, H., et al. *Proc. Natl. Acad. Sci. U.S.A.* 107:22641-22646, 2010). EBV gL is the full-length wild type gL. The encapsulin-gp42 is constructed by fusing a human CD5 leader (hCD5) sequence to the N-termini of encapsulin (*Thermotoga maritima*), followed by (Ser-Gly$_3$)$_2$ linker, and followed by gp42 (with deletion of N-terminal amino acids 1-33). Soluble gp42 is constructed by fusing a human CD5 leader (hCD5) sequence to the N-terminus truncated gp42 in place of gp42 amino acids 1-33 which are deleted.

To construct the gp350-encapsulins fusion genes, amplified gene fragments were fused at the end of encapsulin gene with a $(SG_3)_2$ linker. To produce soluble gp350 ectodomain and $D_{123}$, the amplified gene fragments were fused with bPRL signal sequence and tagged with hexa-histidine at the end of the gp350 gene for purification purpose.

gH-ferritin was constructed by fusing the extracellular domain of gH (domains I, II, III, and IV) to the amino terminus of ferritin (FIG. 3).

Soluble gH was constructed by expressing the extracellular domain of gH (domains I, II, III, and IV) (FIG. 3).

Soluble gp42 was constructed by fusing a human CD5 leader (hCD5) sequence to the N-terminus truncated gp42 in place of gp42 amino acids 1-33.

The EBV gL protein used in this study is the fill-length, wild-type gL protein.

All gene constructs described above were cloned into CMV/R 8κb (VRC 8405) mammalian expression vectors for efficient expression.

B. Production and Purification of Recombinant Nanoparticles

FreeStyle 293-F or Expi293F cells (Life Technologies) were transiently transfected with the expression plasmids described in (A), either alone in or combination, using 293fectin or ExpiFectamine 293 transfection reagents, respectively (Life Technologies). For example, gp350 nanoparticles were made by transfecting individual gp350-ferritin or gp350-encapsulin constructs into recipient cells. gH/gL nanoparticles were made by co-transfecting plasmids expressing gH-ferritin and full length gL into cells, while gH/gL/gp42 nanoparticles were made by co-transfecting plasmids expressing gH-ferritin, full length gL, and soluble gp42 into cells. The cells were grown for 4 days after transfection, the culture supernatants harvested and the proteins or nanoparticles purified as described below.

Figure 4:
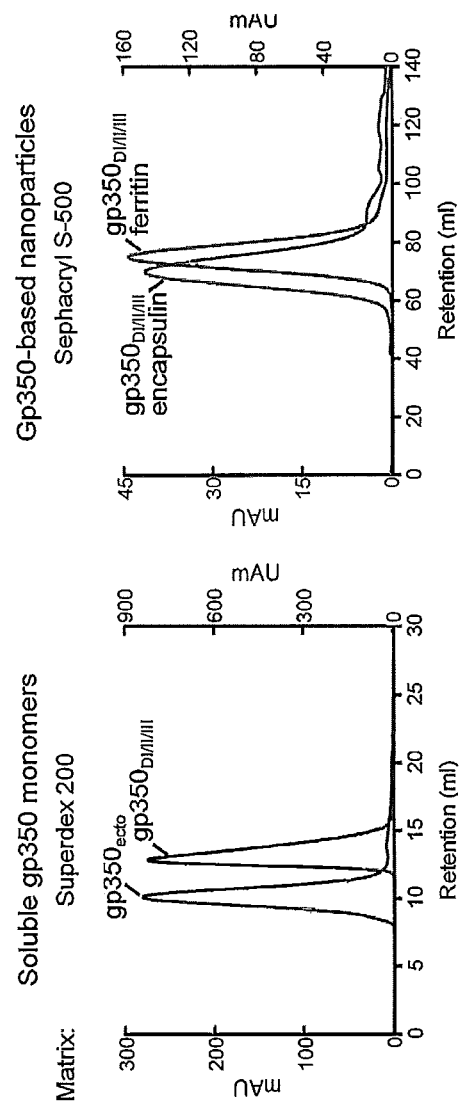
FIG. 4. Purification of truncated gp350 variants and gp350-based nanoparticles. (Left) Chromatograph resulting from size-exclusion chromatography (Superdex 200 10/300 GL) of immobilized metal ion (Ni$^{++}$) affinity chromatography purified, ferritin-based gp350 nanoparticles (gp350 ecto and gp350 DI/II/III) obtained from the supernatants of cells transfected with VRC 3796 and 3797 (Right) Chromatograph resulting from size-exclusion chromatography (Sephacryl S-500 16/60) of snowdrop lectin (*Galanthus nivalis*) affinity chromatography purified, encapsulin-based gp350 and ferritin-based gp350 nanoparticles obtained from the supernatants of cells transfected with VRC 3426 and 3430.
Figure 5:
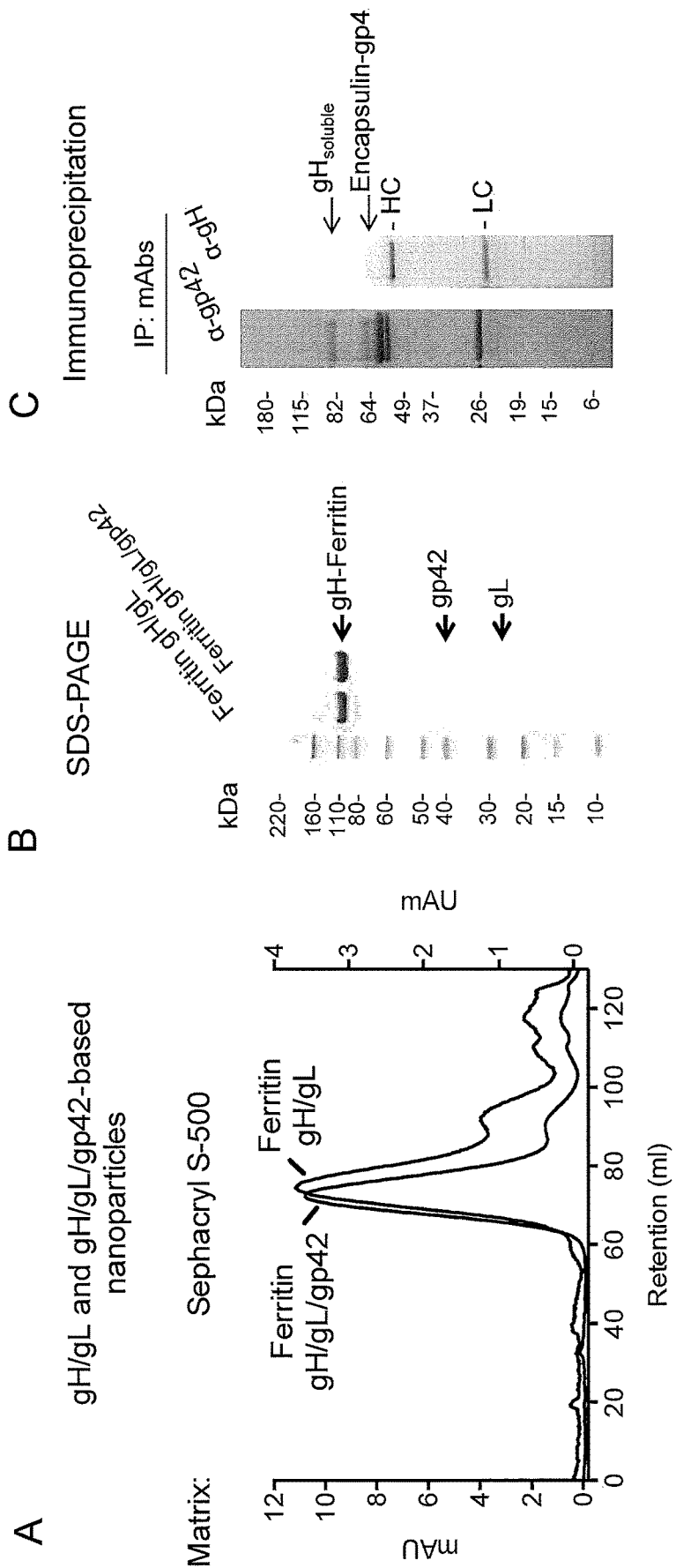
FIG. 5. Purification of gH/gL ferritin-based and gH/gL/gp42 ferritin-based nanoparticles. (A) Chromatograph resulting from size-exclusion chromatography (Sephacryl S-500 16/60 column) of snowdrop lectin (*Galanthus nivalis*) affinity chromatography purified, gH/gL and gH/gL/gp42 ferritin-based nanoparticles obtained from the supernatants of cells transfected with $gH_{D1234}$-ferritin and gL plasmids or $gH_{D1234}$-ferritin, gL, and soluble gp42 plasmids, respectively (B) Characterization of nanoparticles by SDS-PAGE. The bands corresponding to gH-ferritin, gp42, and gL are indicated. (C) Immunoprecipitation of gH/gL/gp42 encapsulin-based nanoparticle by mAbs. An anti-gp42 mAb (F2-1) and anti-gH/gL mAb (E1D1) were used to detect gH/gL/gp42 encapsulin-based nanoparticles. HC and LC denote antibody heavy and light chains, respectively.

Nanoparticles were purified using affinity and size-exclusion chromatography. Briefly, the cleared cell culture supernatants were concentrated using a 30 kDa molecular weight cut-off ultrafiltration unit (Pall) after which the buffer was replaced with PBS. The nanoparticles were then applied to a *Galanthus nivalis* agglutinin (GNA, snowdrop lectin) affinity column (EY Laboratories) and eluted using a solution of 1.0 M methyl α-D-mannopyranoside in PBS. The nanoparticles were further purified by size exclusion column chromatography using a HiPrep 16/60 Sephacryl S-500 HR column (GE Healthcare Life Sciences) in PBS and the peak fraction collected and used for further studies. The SEC chromatogram for the gp350-based nanoparticles is shown in FIG. 4 (right) while a SEC chromatogram for gH/gL-ferritin and gH/gL/gp42-ferritin nanoparticles is shown in FIG. 5A.

Soluble proteins were purified using ion affinity and SEC chromatography. Briefly, cleared cell culture supernatants were adjusted to 50 mM Tris, pH 8 and 500 mM NaCl, and applied to a metal ion affinity chromatography column containing Ni sepharose excel resin (GE Healthcare Life Sciences). After washing the column with buffer (50 mM Tris, 500 mM NaCl, 30 mM imidazole, pH 8.0), the proteins were eluted using elution buffer (50 mM Tris, 500 mM NaCl, 300 mM imidazole, pH 8.0). The proteins were then further purified by size exclusion column chromatography using a Superdex 200 10/300 GL or a Superose 6 10/300 GL column (GE Healthcare Life Sciences) in PBS and the peak fraction collected and used for further studies. A SEC chromatogram for soluble gp350 monomers is shown in FIG. 4 (left).

Figure 6:
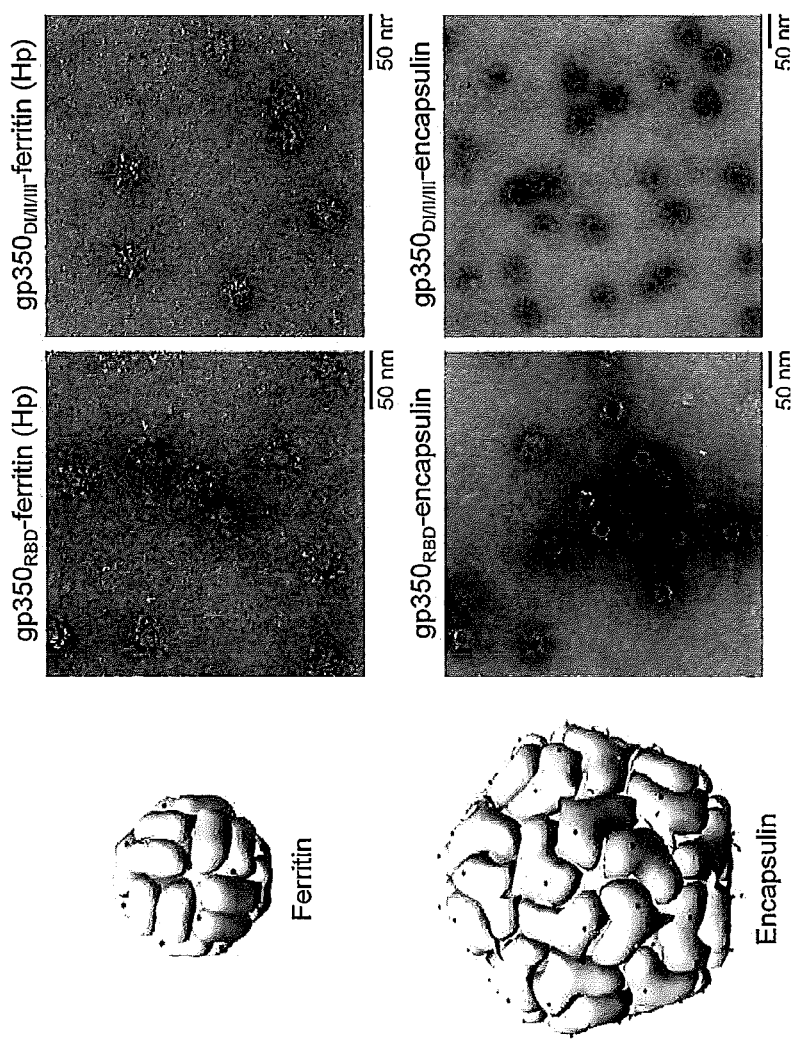
FIG. 6. Electron microscopic (EM) analyses of gp350-based nanoparticles. Assembled ferritin and encapsulin nanoparticles are shown (left). The sites of fusion (N-termini on ferritin and C-termini on encapsulin) are shown as black dots (24 sites on a ferritin and 60 sites on a encapsulin). Negative stain transmission EM pictures of gp350-based nanoparticles (middle and right), using Hp ferritin (top) and encapsulin (bottom) platforms. Gp350-based nanoparticles are derived from VRC 3426, 3427, 3430 and 3431.
Figure 7:
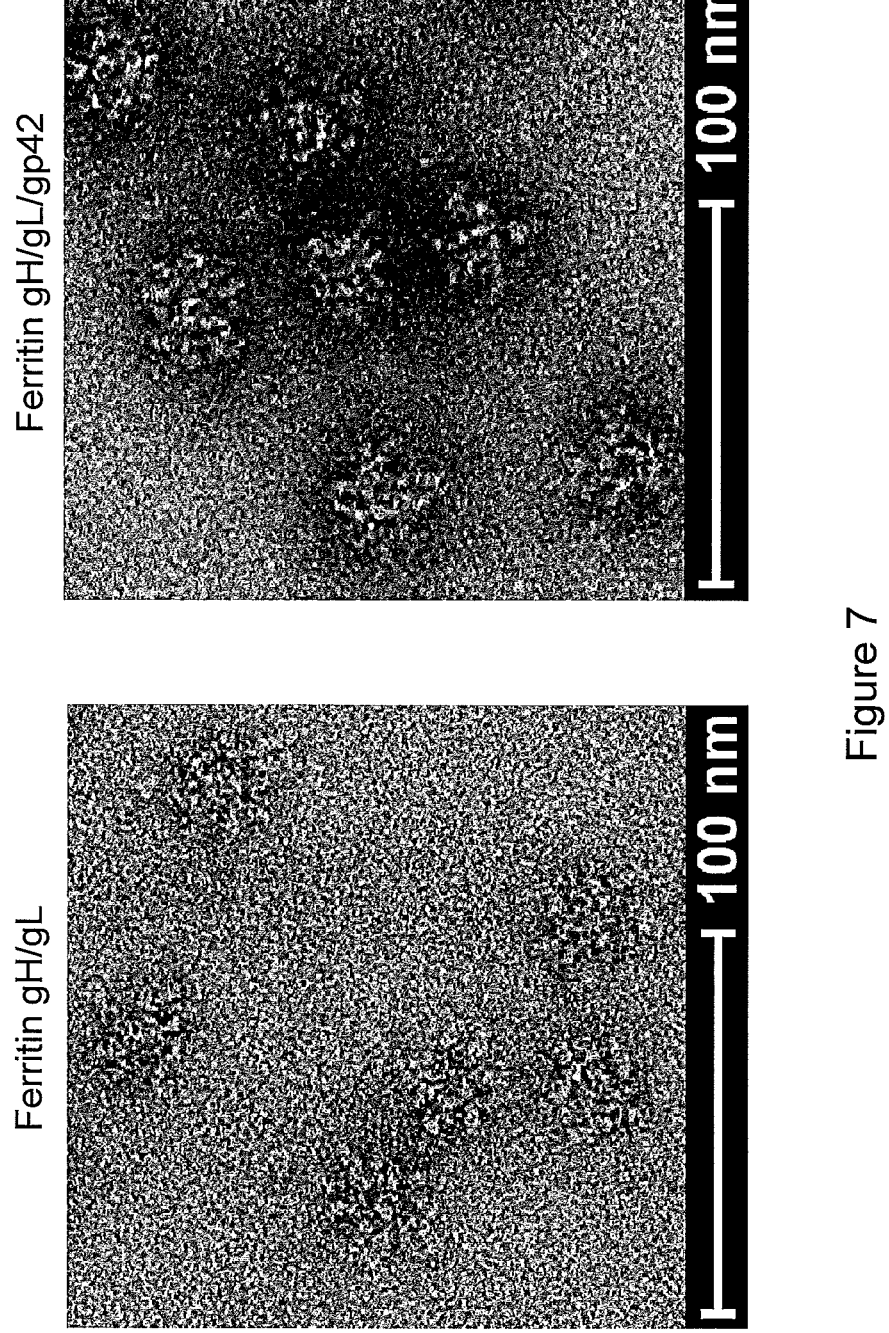
FIG. 7. Electron microscopic (EM) analysis of gH/gL ferritin and gH/gL/gp42 ferritin-based nanoparticles. Negative stain transmission EM images of gH/gL ferritin-based nanoparticles (left) and gH/gL/gp42 ferritin-based nanoparticles (right) are shown.

C. Characterization of EBV gp350-Based, gH/gL-Based, and gH/gL/gp42-Based Nanoparticles The purified nanoparticles were further examined by electron microscopic (EM) analysis. Briefly, for negative staining EM analysis, samples of about 50 µg ml$^{-1}$ were adsorbed to freshly glow-discharged carbon-coated grids, rinsed with PBS, and stained with 2% ammonium molybdate or 0.75% uranyl formate. Images were recorded on an FEI T20 microscope with a Eagle CCD camera. EM images of gp350-ferritin and gp350-encapsulin nanoparticles are shown in FIG. 6 while gH/gL ferritin-based nanoparticles and gH/gLgp42 ferritin-based nanoparticles are shown in FIG. 7, left and right, respectively. This analysis confirmed that the expressed proteins formed nanoparticles having globular protrusions from the spherical nanoparticle core.

Example 2. Antigenicity of gp350-Based Nanoparticles

To verify the antigenicity of the gp350-based nanoparticle, the reactivity of the nanoparticles was tested using the anti-gp350 monoclonal antibodies (mAbs) MAb 72A1 and MAb 2L10. MAb 72A1 recognizes the receptor-binding site of gp350, which mediates viral attachment to the host cell receptor, complement receptor 2 (CR2 or CD21). MAb 72A1 also potently neutralizes EBV (G. J. Hoffman, S. G. Lazarowitz, S. D. Hayward, Monoclonal antibody against a 250,000-dalton glycoprotein of Epstein-Barr virus identifies a membrane antigen and a neutralizing antigen. *Proc Natl Acad Sci USA* 77, 2979-2983 (1980), Sairenji T, Bertoni G, Medveczky M M, Medveczky P G, Nguyen Q V, Humphreys R E., Inhibition of Epstein-Barr virus (EBV) release from P3HR-1 and B95-8 cell lines by monoclonal antibodies to EBV membrane antigen gp350/220. J Virol. 1988 August; 62(8):2614-21). The CR2-binding site (CR2BS) is one of the sites of vulnerability on the virus and therefore an attractive target for vaccine development. MAb 2L10 is a non-neutralizing antibody and does not compete with 72A1 (J. Luka, R. C. Chase, G. R. Pearson, A sensitive enzyme-linked immunosorbent assay (ELISA) against the major EBV-associated antigens. I. Correlation between ELISA and immunofluorescence titers using purified antigens. *J Immunol Methods* 67, 145-156 (1984)). To test the reactivity of the expressed proteins and nanoparticles with these antibodies, 100 ul of purified nanoparticles or soluble gp350 protein (at 25 nM) were coated onto MaxiSorp plates (Nunc). To each well was then added anti-gp350 antibody (MAb 72A1 or MAb 2L10) or anti-influenza hemagglutinin (MAb C179). Following appropriate incubation and removal of the antibody, bound MAbs were detected using a peroxidase-conjugated, secondary antibody (anti-mouse IgG) (Southern Biotech).

Figure 8:
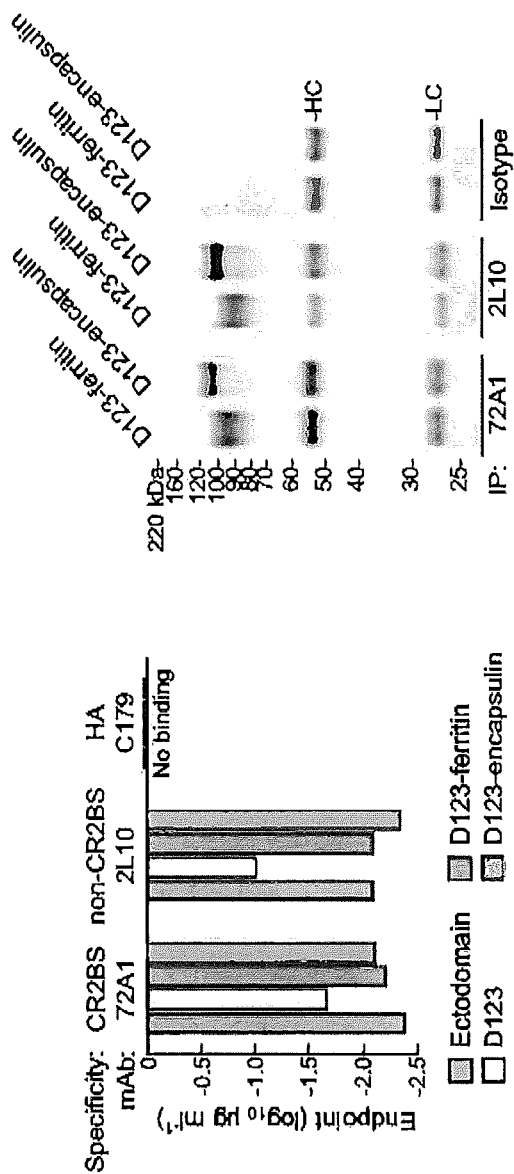
FIG. 8. Antigenic characterization of truncated gp350 variants and gp350-based nanoparticles. Binding properties of purified gp350 variants and gp350-based nanoparticles to anti-gp350 monoclonal antibodies (mAbs). Endpoint concentrations of binding mAbs were measured by ELISA (left). Immunoprecipitation of gp350-based nanoparticles by mAbs (right). A neutralizing anti-CR2BS mAb (72A1) and a non-neutralizing anti-gp350 (not specified, not anti-CR2BS) mAb (2L10) were used to detect gp350 variants and gp350-based nanoparticles. An anti-Influenza HA mAb (C179) was used as an isotype control. HC and LC denote antibody heavy and light chains, respectively. Soluble gp350 variants and gp350-based nanoparticles are derived from VRC 3796, 3797, 3426 and 3430.

The results of this study, which are shown in FIG. 8 (left), showed that both 72A1 and 2L10 mAbs recognized gp350-based nanoparticles as well as soluble gp350 ectodomain. In addition, both antibodies bound the soluble $D_{123}$ monomer to a lesser extent. Neither of the purified proteins bound the isotype control, MAb C179.

The antigenicity of the gp350-based nanoparticles was further confirmed by immunoprecipitation. Briefly, five micrograms of mAbs directed to gp350 CR2-binding site (72A1), gp350 non-CR2-binding site (2L10) or influenza hemagglutinin (C179) were incubated with purified nanoparticles (5 µg) at room temperature for 30 minutes. After incubation, pre-washed protein G Dynabeads (Life Technologies) were added to the reactions and incubated for another 30 minutes. PBS containing 0.01% Tween 20 was used as washing buffer. Immune complexes were then magnetically separated, washed and eluted in Lamini buffer containing reducing agent. A half volume of the reactions were then analyzed by SDS-PAGE. The results of this analysis are shown in FIG. 8 (right).

Example 3. Immune Response Induced by gp350-Based Nanoparticles

To evaluate the immunogenicity of the gp350-based nanoparticles, ten-week old mice were immunized at weeks 0 and 3 with 5.0 µg of both HpBf and EcBf ferritins and encapsulin nanoparticles expressing either gp350 RBD or $D_{123}$ on the surface in the presence of Sigma Adjuvant System (SAS, also known as Ribi). Immune sera were collected at 2 weeks after each immunization to analyze antibody response to gp350. Briefly, soluble gp350 ectodomain protein (2 µg ml$^{-1}$, 100 µl well$^{-1}$) were coated onto wells of a MaxiSorp plate (Nunc), after which to each well was added an aliquot of serially diluted immune sera. Following incubation and removal of the immune sera, to each well was added peroxidase-conjugated secondary antibody (anti-mouse IgG). Following incubation and removal of unbound secondary antibody, the wells were developed using a SureBlue chromogen (KPL) and the reaction was stopped by adding 0.5 M sulfuric acid. Absorbance at 450 nm was then measured by SpectraMax M2e (Molecular Devices). Endpoint titers were determined by calculating concentrations at the absorbance threshold (four times background) from the binding curve.

Figure 9:
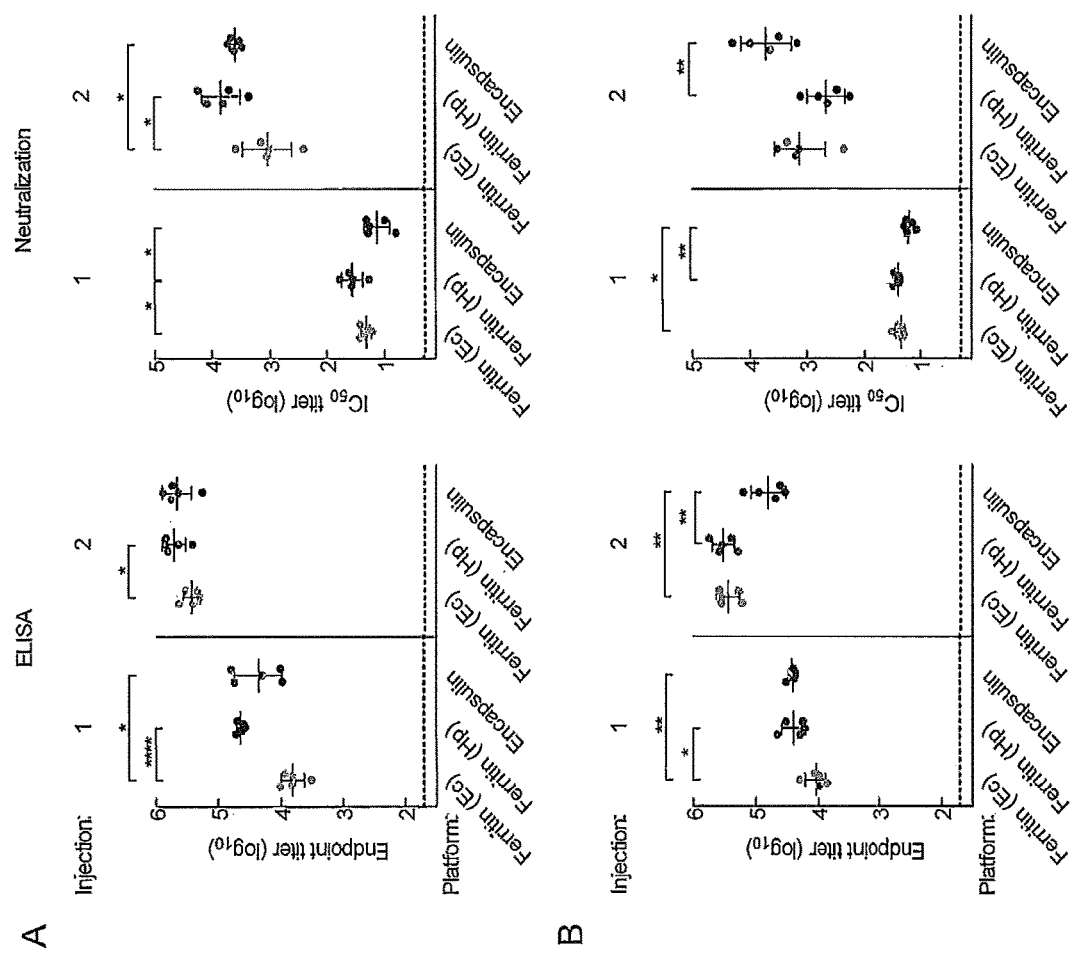
FIG. 9. Comparison of immunogenicity of different gp350-variants and nanoparticle platforms. Immunogenicity of gp350 $D_{123}$-based nanoparticles (A) and gp350 RBD-based nanoparticles (B). BALB/c mice (n=5) were immunized intramuscularly with 5 μg of indicated gp350-based nanoparticles mixed with a Ribi adjuvant at weeks 0 and 3. Immune sera were collected 2 weeks after the first (1) and the second (2) immunization. Immune sera were analyzed by measuring antibody binding titer against soluble $gp350_{ecto}$ by ELISA (left) and neutralizing titer (right). The endpoint titers of anti-$gp350_{ecto}$ are shown (left). The neutralization assay was based on the Raji B cell line and a GFP reporter virus (Sashihara J., et al., *Virology*. 391, 249-256, 2009) and the titer is shown as a dilution of serum needed to inhibit viral entry by 50% ($IC_{50}$). Each dot represents individual mouse. Bar indicates mean and s.d. *, p<0.05; , p<0.01; *, p<0.001; ****, p<0.0001. Gp350-based nanoparticles used for immunization are derived from VRC 3422, 3423, 3426, 3427, 3430 and 3431.

The results of this study, which are shown in FIG. 9, demonstrate that an antibody response to gp350 was detected in all gp350-based nanoparticle-immunized mice after a single dose at titers of ~$10^{3.9}$-$10^{4.9}$ and the titers were boosted about 10-fold by a second dose. Neutralizing antibody titers were also detected in all mice after a single dose although the titers were not high ($IC_{50}$<50). These titers were markedly boosted at ~100-fold by a second dose.

Example 4. Comparison of gp350-Based Nanoparticles and Soluble gp350 Protein

To compare immune responses elicited by the gp350-based nanoparticles to that of soluble gp350 proteins, ten-week old mice were immunized at weeks 0 and 3 with either soluble gp350 ectodomain or $D_{123}$ or $D_{123}$-nanoparticles at 5.0 and 0.5 µg in the presence of SAS as adjuvant. Immune sera were collected 2 weeks after the first (1) and the second (2) immunization and analyzed as described in Example 2 and 3.

Figure 10:
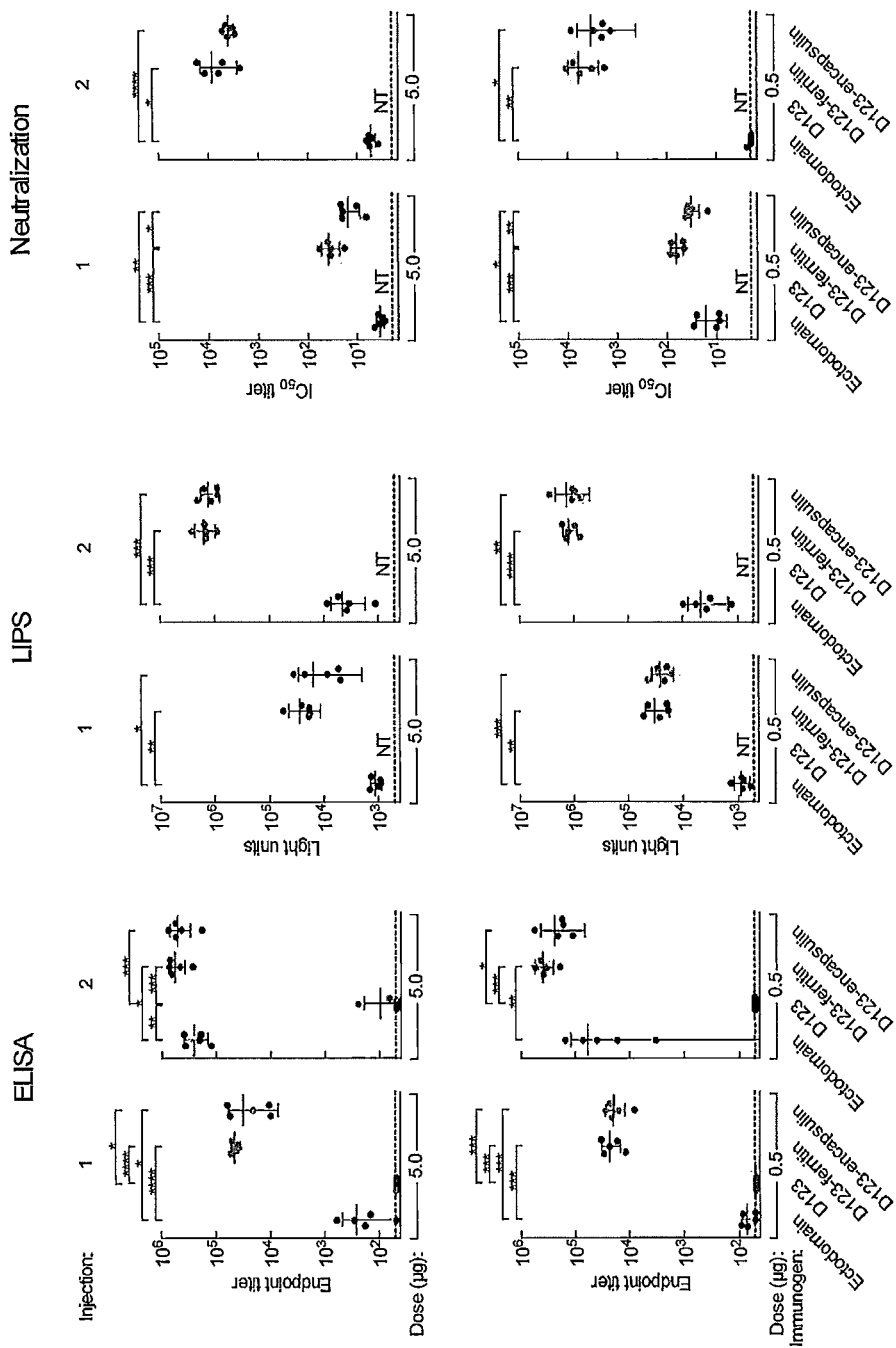
FIG. 10. Comparison of immunogenicity of soluble gp350 variants and gp350-based nanoparticle. Immune sera were analyzed by measuring anti-gp350 antibody binding titer by ELISA (left) and LIPS (center) assay and neutralization $IC_{50}$ titer (right). LIPS assay was performed as previously described (Sashihara J., et al., *Virology*. 391, 249-256, 2009). Each dot represents individual mouse. Bar indicates mean and s.d. *, p<0.05; , p<0.01; *, p<0.001; ****, p<0.0001. Gp350 variants and gp350-based nanoparticles used for immunization are derived from VRC 3796, 3797, 3426 and 3430.

The results of this study, which are shown in FIG. 10, show that at 2 weeks following the first immunization the $D_{123}$ nanoparticles elicited a higher antibody response than did either the soluble gp350 ectodomain or soluble $D_{123}$ protein (titers of 47,654±16,482 and 32,042±24907 for $D_{123}$-ferritin and $D_{123}$-encapsulin, respectively vs. 261±219 and <50 for gp350 ectodomain and $D_{123}$, respectively). However, following a second immunization, soluble gp350 ectodomain boosted ELISA titers dramatically to the titers at only ~2-3-fold lower than that of either $D_{123}$-ferritin- or $D_{123}$-encapsulin-immunized groups (261,116±116,301 vs. 567,764±188,536 or 499,128±211,748, respectively). Surprisingly, soluble gp350 $D_{123}$ failed to elicit antibody responses even after the second immunization (titers of 96±92) although the same $D_{123}$ displayed on ferritin and encapsulin was highly immunogenic. Because an earlier study (Sashihara, et al. Virology, 2009) demonstrated a strong correlation between titers measured in neutralization assay and immunoprecipitation-based assay (luciferase immunoprecipitation system, LIPS), the mouse immune sera was tested in an LIPS assay in addition to ELISA. For the LIPS assay, the fusion protein composed of gp350 and Remilla luciferase was incubated with sera and immunoprecipitated using protein A/G beads (Thermo Scientific) in 96-well filter bottom plates (Millipore). Luciferase activity of antibody-bound fusion proteins was then measured by adding coelenterazine substrate (Promega) and detecting by Centro LB 960 luminometer (Berthold Technologies).

These studies demonstrate that LIPS antibody titers in the sera of gp350 ectodomain-immunized mice were more than two logs lower than that of either $D_{123}$-ferritin- or $D_{123}$-encapsulin-nanoparticle-immunized mice ($10^{3.6\pm0.3}$ vs. $10^{6.2\pm0.2}$ or $10^{6.1\pm0.2}$, respectively) at 2 weeks after a second dose. To verify if the LIPS titers reflected neutralizing antibody titers, serum neutralizing antibody titers were determined by GFP-reporter assay (Sashihara, et al. Virology, 2009). Neutralization of EBV to B cells has been described previously (Sashihara, J., Burbelo, P. D., Savoldo, B., Pierson, T. C., Cohen, J. I., Human antibody titers to Epstein-Barr virus (EBV) gp350 correlate with neutralization of infectivity better than antibody titers to EBV gp42 using a rapid flow cytometry-based EBV neutralization assay. Virology 391, 249-256 (2009).) Briefly, immune sera were serially diluter in a 2-fold step and 25 ul of the diluted samples was incubated with B95-8/F virus for 2 hours. The mixture was added to Raji cells in the 96-well plate and incubated for 3 days at 37° C. (Raji cells were propagated in RPMI 1640 with complete supplements: 10% fetal bovine serum, 100 U/ml penicillin, 100 ug/ml streptomycin and 2 mM L-glutamine) Following incubation, cells were fixed in 2% paraformaldehyde in PBS and analyzed by Accuri C6 flow cytometer and BD CSampler software (BD Biosciences, San Jose, CA, USA) to quantify the percentage of infected ells based on GFP expression. Neutralization antibody titers were expressed as the concentration of serum antibody needed to inhibit viral entry by 50% (IC50) calculating with controls in the absence of virus (0% infection) or serum (100% infection).

Surprisingly, the differences in neutralizing antibody titers between the sera from soluble gp350 ectodomain-immunized mice and that from either $D_{123}$-ferritin- or $D_{123}$-encapsulin-immunized mice were ~1000-fold after a second dose (5±1 vs. 8,594±5944 or 3,939±874, respectively) and the titers in soluble gp350 ectodomain-immunized group were barely above the threshold of the assay ($IC_{50}<10$). Together, the results revealed that immunization using soluble gp350 ectodomain induced mostly non-neutralizing antibodies which were only detectable in ELISA. ELISA, LIPS and neutralizing antibody titers in mice immunized with 5.0 and 0.5 μg of $D_{123}$-ferritin and $D_{123}$-encapsulin were virtually the same (<2-fold differences), while there was a slight reduction in ELISA and neutralizing antibody titers in mice immunized with both soluble gp350 ectodomain (4.4-fold decrease in ELISA titers and no neutralizing antibody titers in group immunized with lower dose).

Example 5. Durability of Neutralizing Antibody Response in gp350-Based Nanoparticle-Immunized Animals To assess the kinetics of virus neutralizing antibody responses in the mice immunized in Example 4, the titers of neutralizing antibody were determined longitudinally for >6 months. At 2 months following the second immunization, the neutralizing titers in $D_{123}$-ferritin- and $D_{123}$-encapsulin-immunized animals at both 5.0 and 0.5 μg doses declined about one log to $10^{2.4}$-$10^{3.1}$, however, the titers remained at the same level for another month without further immunization. All mice then received a third dose at week 16 and their serum neutralizing antibody titers monitored.

Figure 12:
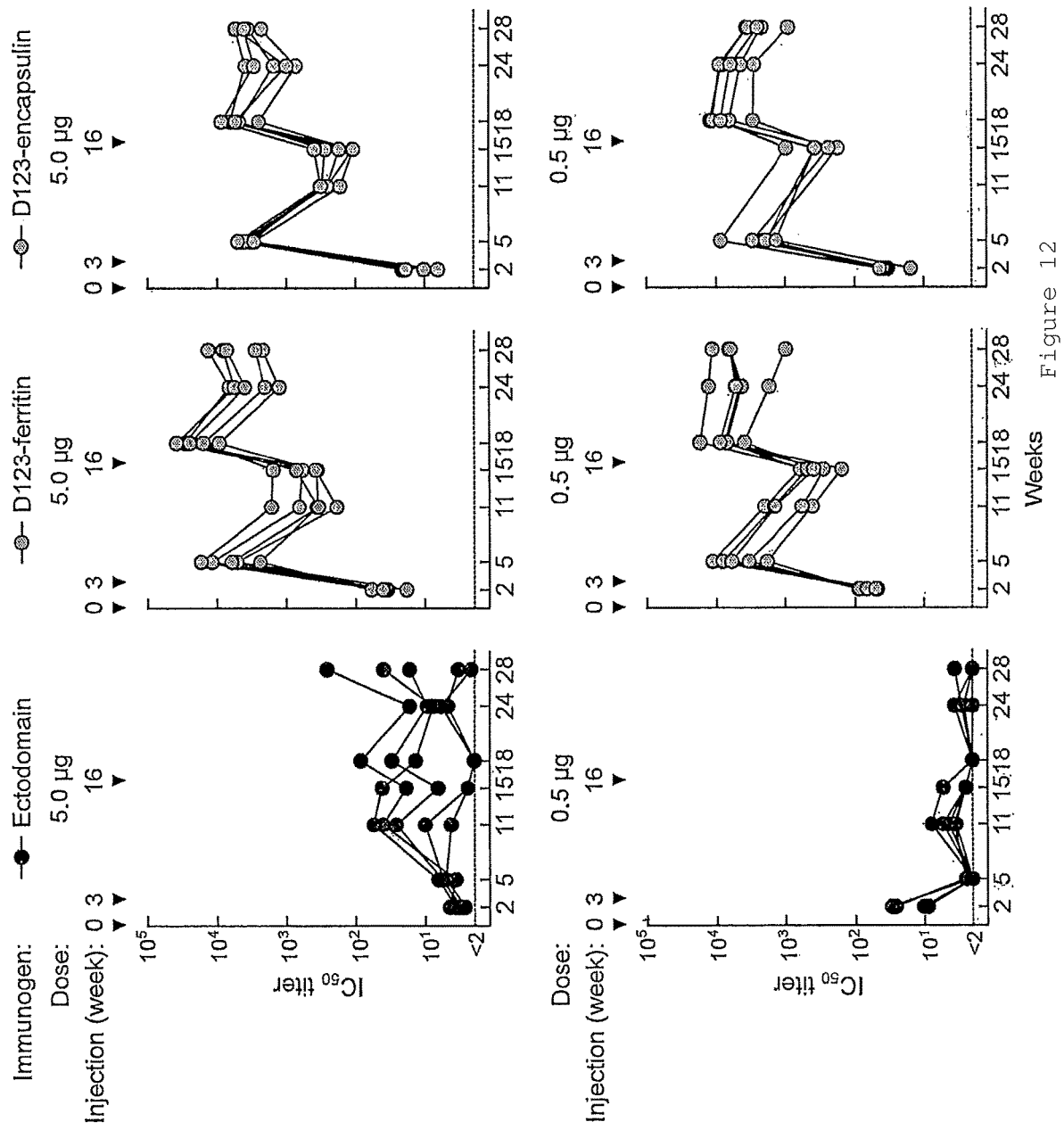
FIG. 12. Kinetics of serum neutralization titers after immunization with soluble gp350 and gp350 based nanoparticles. Groups of BALB/c mice (n=5) were immunized intramuscularly with 5 ug (upper panels) or 0.5 ug (lower panels) of soluble gp350 ectodomain (left), $D_{123}$-ferritin (center) or $D_{123}$-encapsulin (right) mixed with a Ribi adjuvant at weeks 0, 3, and 16. Immune sera were collected periodically after immunization and serum neutralization $IC_{50}$ titers were determined. gp350 ectodomain and gp350-based nanoparticles used for immunization are derived from VRC 3796, 3426 and 3430.

The results of this study are shown in FIG. 12. Expectedly, the titers were boosted by 33- and 26-fold in $D_{123}$-ferritin and $D_{123}$-encapsulin, respectively ($10^{4.3\pm0.2}$ and $10^{3.7\pm0.2}$, respectively), whereas the effect was not obvious in groups immunized with soluble gp350 ectodomain as measured at 2 weeks after the boost ($10^{1.0\pm0.7}$). The peak neutralizing antibody titers in $D_{123}$-ferritin were higher than that after the second immunization ($10^{3.8\pm0.3}$) and the titers did not wane as quickly as after the second immunization. The titers at 2 and 3 months after the third immunization were stable at $10^{3.3}$-$10^{3.8}$ in groups immunized with $D_{123}$-ferritin and $D_{123}$-encapsulin and that were 1.5-5.9 times lower than the peak and one log higher than the titers at the same time point after the second immunization. Similar kinetics and magnitudes of neutralizing antibody titers were observed when animals were immunized with a 10× smaller dosage (0.5 μg) of either gp350-based nanoparticles. However, at this dose the soluble gp350 ectodomain was unable to elicit any neutralizing antibody response.

Example 6. Characterization of Antibodies Elicited by Gp350-Based Nanoparticles

To determine the fine specificity of the antibodies elicited by either soluble gp350 ectodomain or gp350-based nanoparticles, a surface plasmon resonance (SPR)-based antibody competition assay was performed. This assay detects specific populations of antibodies in immune sera, the specificity of which is similar to that of a competing mAb. Briefly, the soluble gp350 ectodomain was immobilized on a sensor chip via amine coupling reaction. Before measuring the binding of the immune sera, 72A1, 2L10 or C179 was injected to the flow cell to saturate the sites where the mAb recognizes on the chip. Immune sera (taken 2 weeks after the second immunization with Ribi-adjuvanted 5 μg of immunogen) was then injected to the antibody-saturated flow cells and the binding kinetics of the serum antibodies were measured. The serum antibodies directed to the same epitope as 72A1 were not able to bind to the 72A1-saturated gp350 and therefore resulted in lower overall binding compared to that of C179-saturated gp350. All data were normalized with an isotype control (C179-saturated) and shown as fraction response. Inhibition of serum antibody to bind to gp350 by 72A1 or 2L10 (X) was calculated by an equation: X=100−{(maximum response unit of 72A1- or 2L10-saturated flow cell/maximum response unit of isotype antibody-saturated flow cell)×100}. Surprisingly, when the competitor antibody was CR2BS-directed mAb 72A1, 52±11 and 60±12% of total anti-gp350 antibodies in the immune sera elicited by $D_{123}$-ferritin and $D_{123}$-encapsulin, respectively, was competed, whereas only 5±4% of anti-gp350 antibodies in immune sera elicited by soluble gp350 ectodomain was blocked.

Figure 11:
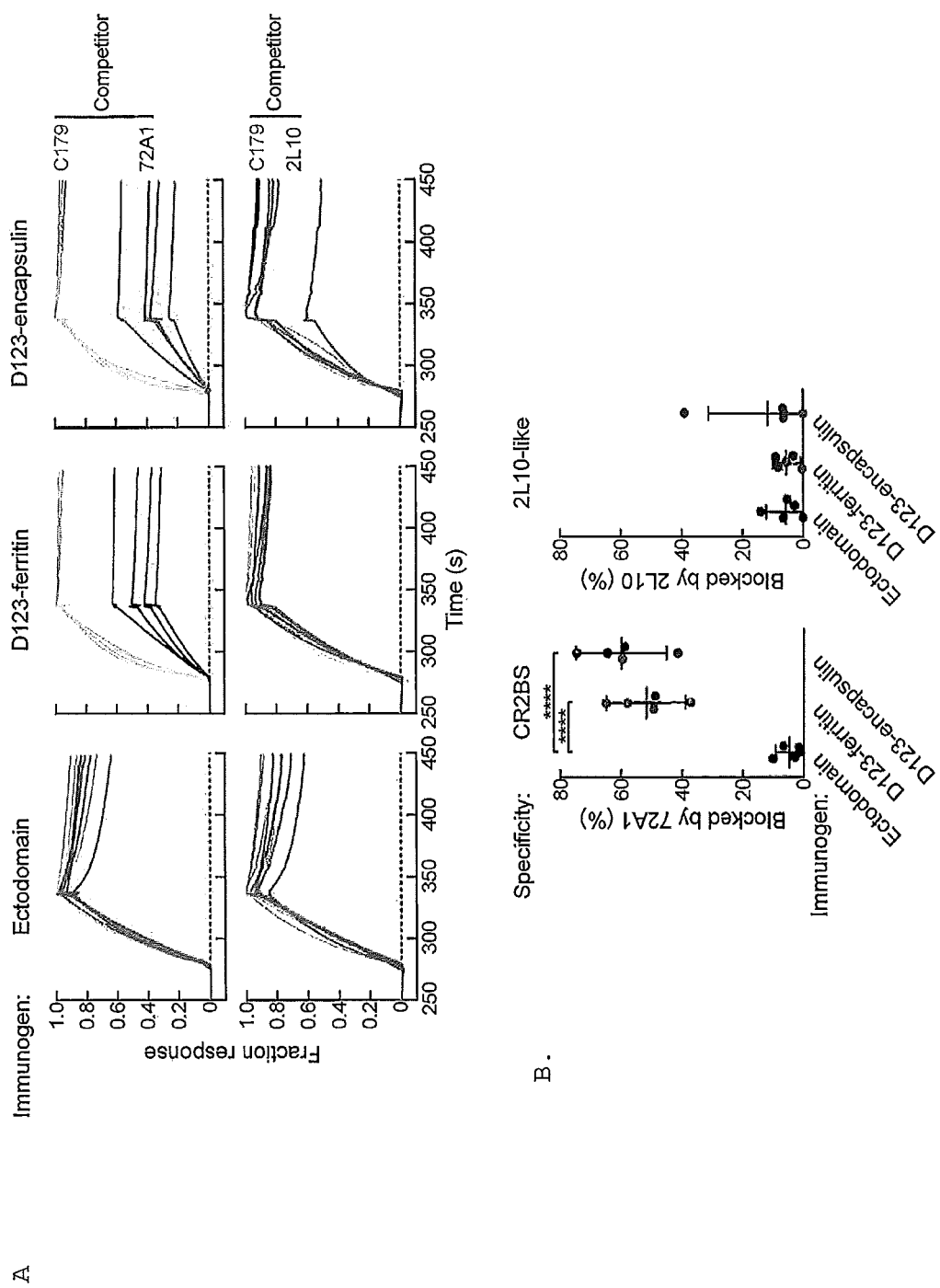
FIG. 11. Detection of CR2BS-directed antibodies in gp350-based nanoparticle-immune sera. (A) Surface plasmon resonance-based cross-competition assay of immune sera with an anti-CR2BS (72A1), an anti-gp350 (2L10, non-CR2BS directed) and an isotype control (C179, anti-influenza) mAbs. Each curve represents individual mouse. Cross-competition of immune sera by 72A1 (top) and 2L10 (bottom) were shown by different immunization groups. (B) Relative percentages of CR2BS-directed and 2L10-like antibodies in the immune sera. Each dot represents individual mouse and bar indicates mean and s.d. *, p<0.05; , p<0.01; *, p<0.001; ****, p<0.0001. Gp350 ectodomain and gp350-based nanoparticles used for immunization are derived from VRC 3796, 3426 and 3430.

The results of this analysis, which are shown in FIG. 11, demonstrate that the CR2BS on the gp350-based nanoparticles were indeed predominantly targeted by the antibody response and the same site on soluble gp350 ectodomain was not. Importantly, there was negligible fraction of anti-gp350 antibodies in these immune sera that was competed by a non-neutralizing, non-CR2BS-directed mAb 2L10 (6±5, 5±4 and 12±16% in soluble gp350 ectodomain, $D_{123}$- ferritin and $D_{123}$-encapsulin, respectively), suggesting the epitope recognized by 2L10 was not immunodominant in both soluble gp350 ectodomain and gp350-based nanoparticles.

Figure 13:
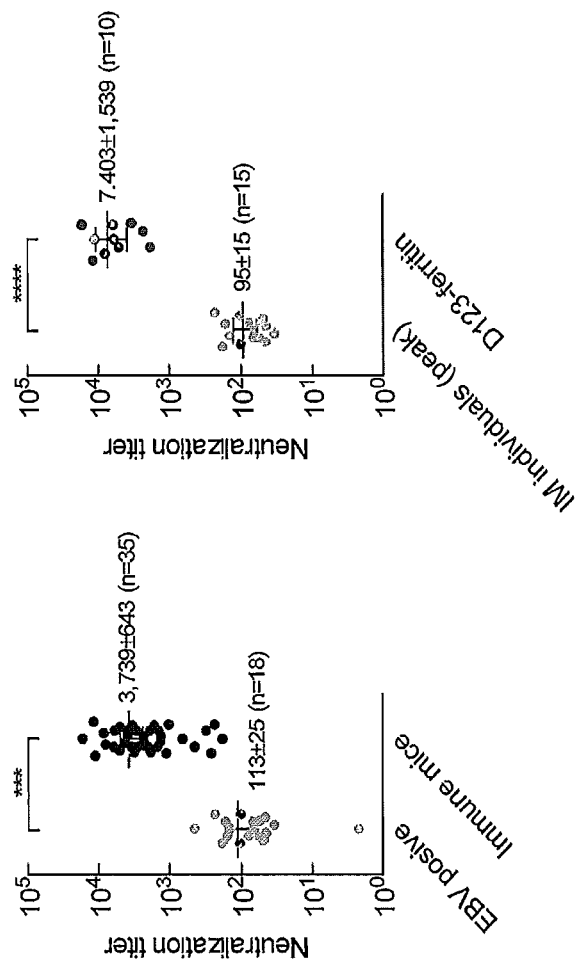
FIG. 13. Comparison of serum neutralization titers in EBV-positive human individuals and gp350-based nanoparticle-immunized mice. (left panel) Comparison of serum neutralization titer ($IC_{50}$) between a combination of EBV-seropositive individuals and persons with EBV-positive mononucleosis (n=18) and gp350-based nanoparticle-immunized mice (titers at 2 weeks after the second immunization, combined groups shown in FIGS. 9 and 10, n=35). (right panel) Comparison of serum neutralization titer ($IC_{50}$) between EBV-seropositive infectious mononucleosis human individuals (peak neutralization titers of each individual, n=15) and $D_{123}$-ferritin-immunized mice (titers at 2 weeks after the second immunization, combined groups shown in FIG. 6, n=10). Each dot represents individual serum sample and bar indicates mean and s.d. Gp350-based nanoparticles used for immunization are derived from VRC 3422, 3423, 3426, 3427, 3430 and 3431.
Figure 14:
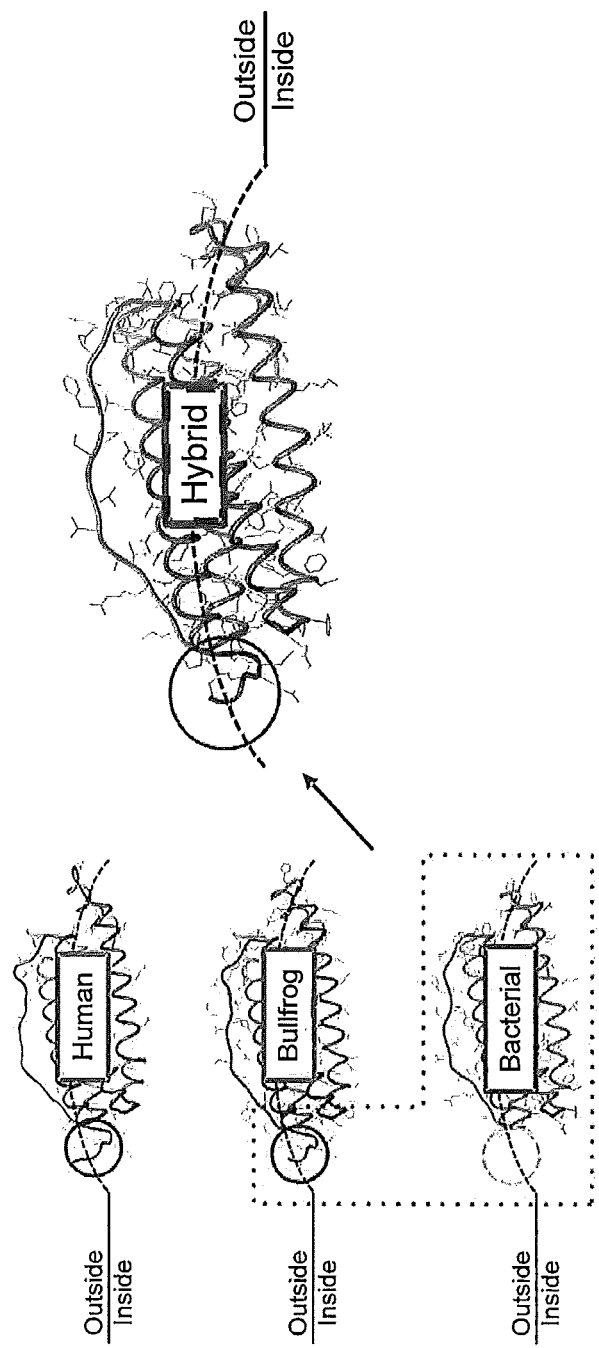
FIG. 14. Generation of bullfrog-*E. coli* and bullfrog-*H. pylori* hybrid ferritins. Crystal structure of ferritin subunit monomers of human (light chain), bullfrog (red cell lower subunit) and bacterial (*E. coli* non-heme ferritin, FtnA) are shown (left). The extended N-terminal parts (circled) in human and bullfrog ferritins are exposed on a surface of assembled ferritin nanoparticles and the corresponding region is missing in *E. coli* (and *H. pylori*) ferritin (circled with dashed line). To make hybrid ferritins the N-terminal extended part of bullfrog ferritin was transplanted to either *E. coli* or *H. pylori* ferritin. The plasmids encoding hybrid *E. coli*-bullfrog and *H. pylori*-bullfrog ferritins are designated as VRC 3384 and 3419, respectively.

Example 7. Comparison of Serum Neutralization Titers in EBV-Positive Human Individuals and gp350-Based Nanoparticle-Immunized Mice Sera from mice immunized in Examples 3 and 4 were obtained and serum neutralization titers determined. These titers were then compared to neutralization titers observed in humans naturally infected with EBV. FIG. 13. (left) shows a comparison of serum neutralization titer ($IC_{50}$) between a combination of EBV-seropositive individuals and persons with EBV-positive mononucleosis and gp350-based nanoparticle-immunized mice; (right) Comparison of serum neutralization titer ($IC_{50}$) between persons with EBV-positive infectious mononucleosis and $D_{123}$-ferritin-immunized mice.

Example 8. Antigenicity of gH/gL and gH/gL/gp42-Based Nanoparticles

The ability of purified nanoparticles to induce antibody production was tested in mice. Briefly, ten week old BALB/c mice (n=5) were injected intramuscularly with 0.5 ug of either soluble gH/gL, soluble gH/gL/gp42, ferritin-gH/gL or ferritin-gH/gL/gp42. A second round of injections was given three weeks later. At 5 weeks post-first injection, blood was drawn and antibody titers to gH, gL and gp42 were determined using a LIPS (luciferase immunoprecipitation assay) described by Sashihara, et al., Virology 391, 249-256, 2009.

Figure 15:
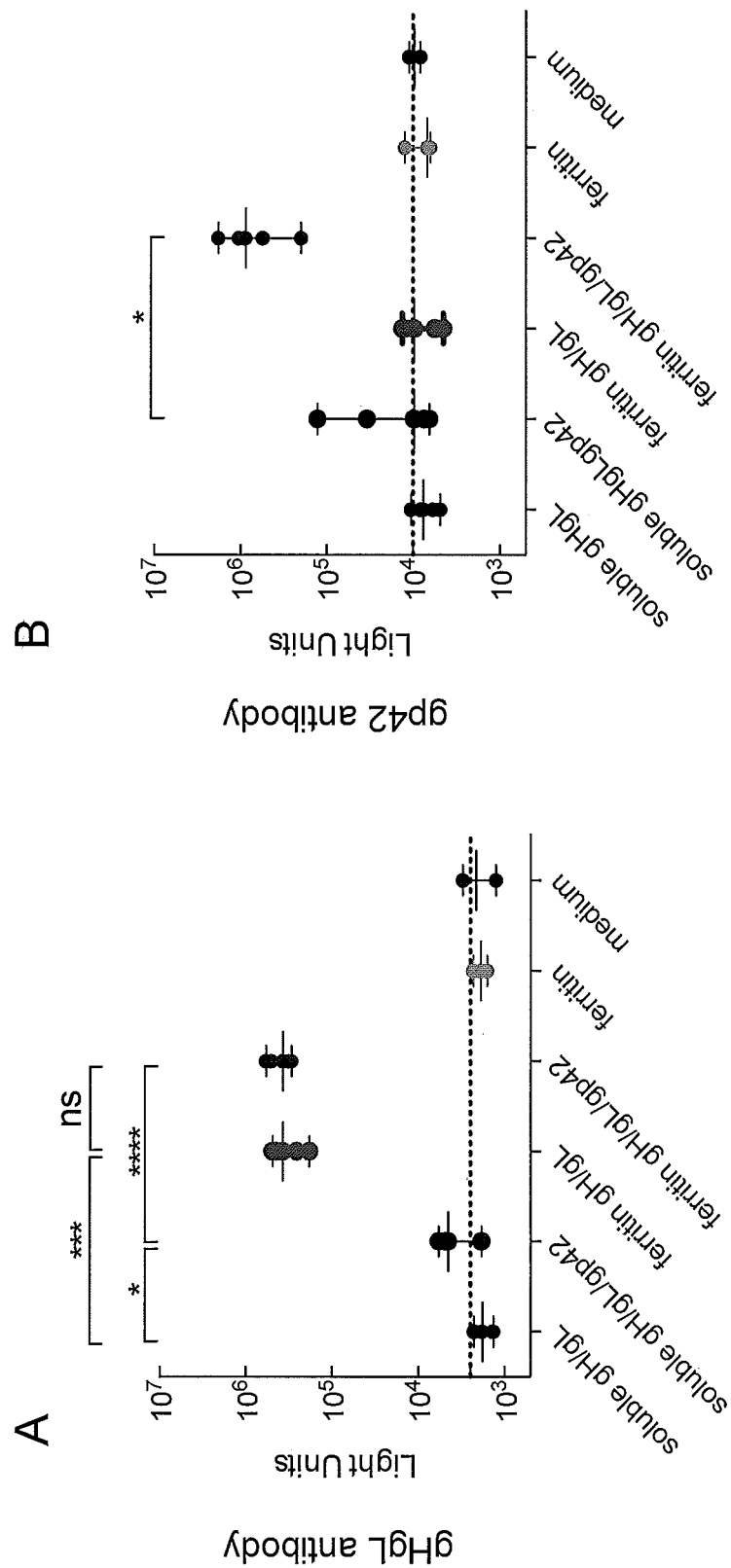
FIG. 15. Comparison of antibody titers of soluble gH/gL, soluble gH/gL/gp42, gH/gL ferritin-based nanoparticle and gH/gL/gp42 ferritin-based nanoparticles in immunized mouse sera. BALB/c mice (n=5) were immunized intramuscularly with 0.5 μg of the indicated proteins with a Ribi adjuvant at week 0 and 3. The antibody titers to gH/gL (A)

The result of this analysis, which is shown in FIG. 15, shows that ferritin-based gH/gL nanoparticles or ferritin-based gH/gL/gp42 nanoparticles induce levels of antibody to the gH/gL complex that are significantly higher than the levels induced by soluble gH or gL protein. Additionally, ferritin-based gH/gL/gp42 nanoparticles induce levels of antibodies to gp42 that are significantly higher than the levels induced by soluble gH/gL/gp42.

Example 9. Comparison of Neutralizing Antibody Induction

The ability of purified nanoparticles to induce neutralizing antibodies in mice was measured using a B-cell and epithelial cell neutralization assay. Briefly, ten week old BALB/c mice (n=5) were immunized as described in Example 8. At 2 weeks post-second injection, blood was drawn and the ability of the sera to inhibit infection of B-cells and epithelial cells by a recombinant reporter virus expressing GFP (Sashihara J., et al., Virology, 391, 249-256, 2009) was tested.

The results of this analysis, which is shown in FIG. 16, shows that ferritin-based gH/gL nanoparticles or ferritin-based gH/gL/gp42 nanoparticles induce levels of neutralizing antibodies to EBV that are significantly higher than the levels induced by soluble gH/gL protein or soluble gH/gL/gp42 protein.

Example 10. Comparison of Kinetics of gH/gL Antibody Titers in Sera from Mice Immunized with 0.5 µg Soluble gH/gL, gH/gL Nanoparticles, Soluble gH/gL/gp42, or gH/gL/gp42 Nanoparticles Ferritin-based nanoparticles and soluble proteins were prepared as described in Example 1. Balb/c mice (n=5) were then injected intramuscularly with 0.5 ug soluble gH/gL, soluble gH/gL/gp42, ferritin-gH/gL or ferritin-gH/gL/gp42 at weeks 0, 3 and 14. Blood was drawn at weeks 2, 5, 13, 16, 20, 24 and 28, and antibody titers to gH/gL were determined using a LIPS assay, as described by Sashihara, et al., Virology 391, 249-256, 2009. The results of this study, which are shown in FIG. 17, demonstrate that gH/gL antibody responses with gH/gL-nanoparticles are higher than soluble gH/gL protein and the antibody titers are sustained >12 weeks after the $3^{rd}$ dose. The results also demonstrate that gH/gL antibody titers in mice immunized with gH/gL/gp42-nanoparticles are higher than soluble gH/gL/gp42 after 2 doses, but comparable to soluble gH/gL/gp42 after 3 doses of vaccine. Finally, the result show that antibody titers are sustained >12 weeks after the $3^{rd}$ dose.

Example 11. Comparison of Kinetics of gp42 Antibody Titers in Sera from Mice Immunized with Soluble gH/gL/42 or gH/gL/gp42 Nanoparticles The production of nanoparticles and soluble proteins, and the immunization and blood draws were performed as described in Example 10. Antibody titers to gp42 were then determined by LIPS assay, as described by Sashihara, et al., Virology 391, 249-256, 2009. The results of this study, which are shown in FIG. 18, demonstrate that gp42 antibody titers in mice immunized with gH/gL/gp42-nanoparticles are higher than soluble gH/gL/gp42 after 2 doses, but comparable to soluble gH/gL/gp42 after 3 doses of vaccines. The results also show that gp42 antibody titers are sustained >12 weeks after the $3^{rd}$ dose.

Example 12. Comparison of Kinetics of B Cell Neutralizing Antibody Titers in Mice Immunized with Soluble gH/gL, gH/gL Nanoparticles, Soluble gH/gL/gp42, or gH/gL/gp42 Nanoparticles The production of nanoparticles and soluble proteins, and the immunization and blood draws were performed as described in Example 10. The ability of the mouse sera to neutralize EBV infection of B cells was then tested, as described in Example 9. The results of this study, which are shown in FIG. 19, demonstrate that B cell neutralizing antibody responses with gH/gL-nanoparticles or gH/gL/gp42-nanoparticles are higher than soluble gH/gL or gH/gL/gp42 proteins, respectively. The results also demonstrate that B cell neutralizing antibody titers are sustained >12 weeks after the 3rd dose.

Example 13. Comparison of Kinetics of Epithelial Cell Neutralizing Antibody Titers in Mice Immunized with Soluble gH/gL, gH/gL Nanoparticles, Soluble gH/gL/gp42, or gH/gL/gp42 Nanoparticles The production of nanoparticles and soluble proteins, and the immunization and blood draws were performed as described in Example 10. Epithelial cell neutralization assay were performed as described in Example 9. The results of this study, which are shown in FIG. 20, demonstrate that epithelial cell neutralizing antibody responses with gH/gL-nanoparticles or gH/gL/gp42-nanoparticles are higher than soluble gH/gL or gH/gL/gp42 proteins, respectively. The results also show that epithelial cell neutralizing antibody titers are sustained >12 weeks after the 3rd dose.

Example 14. B Cell and Epithelial Cell Neutralizing Antibody Titers after the 3$^{rd}$ Dose in Sera of Mice Immunized with Soluble Proteins or Nanoparticles Compared to Sera from Naturally Infected Humans The B cell neutralizing antibody titers obtained in Example 12 and the epithelial cell neutralizing antibody titers obtained in Example 13 were compared to neutralization titers observed in human sera from individuals naturally infected with EBV. FIG. 21 shows B cell neutralizing antibody titers (left) or epithelial cell neutralizing titers (right) in human sera compared to sera from mice immunized with soluble proteins or nanoparticles. This comparison shoes that B cell neutralizing antibody titers in mice immunized with nanoparticles are >20-fold higher than that in naturally infected humans, and that epithelial cell neutralizing antibody titers in mice immunized with nanoparticles are >100-fold higher than that in naturally infected humans.

Example 15. Generation of gH/gL-Nanoparticles or gH/gL/gp42-Nanoparticles from Single Polypeptides To facilitate manufacture of dimeric gH/gL-nanoparticle and trimeric gH/gL/gp42-nanoparticles for clinical studies, constructs were made that express a polyprotein capable of forming a nanoparticle containing multiple EBV proteins. Specifically, constructs were made that express either a ferritin-gH/gL polypeptide or a ferritin-gH/gL/gp42 polypeptide. Each of these polypeptides was designed to include furin and picornavirus 2A cleavage sites and so that they produce ferritin-based nanoparticles by self-cleavage. The polypeptides also comprise a leader peptide sequence from human CD5 protein, in order o facilitate secretion of the polyprotein from the cell. FIG. 22A illustrates the structure of two different polyproteins.

Nanoparticles were produced as described in Example 1. Briefly, proteins were purified from supernatant of cells co-transfected with multiple plasmids expressing individual proteins or cells transfected with plasmids expressing the gH/gL or gH/gL/gp42 polypeptide. Purification of nanoparticles by size exclusion chromatography was then performed as described in Example 1A. SDS-PAGE analysis of the purified gH/gL nanoparticles and gH/gL/gp42 nanoparticles (FIG. 22(B) shows that gH/gL-nanoparticles and gH/gL/gp42-nanoparticles can be produced by transient transfection of single plasmids that express a single polyprotein that is processed by self-cleavage.

Example 16. Immunogenicity of gp350 Nanoparticles in Non-Human Primates

To evaluate the ability of purified nanoparticles to induce neutralizing antibodies in a species closer to humans than mice, cynomolgus macaques (*Macaca fascicularis*) were immunized with gp350 nanoparticles. Briefly, twelve monkeys were divided into three groups and given 50 μg of gp350 ectodomain, or 25 μg of either gp350 $D_{123}$-ferritin or gp350 $D_{123}$-encapsulin with adjuvant (Sigma Adjuvant System) on weeks 0, 4 and 12. Blood was drawn prior to immunization and at weeks 6, 8 and 14, and neutralizing antibody titer determined. The results are shown in FIG. 23.

Cross reacting EBV neutralizing antibody was found in all of the monkeys prior to immunization ($IC_{50}$ titers from $10^{1.1}$ to $10^{2.0}$), which is unsurprising since cynomolgus monkeys are naturally infected with a lymphocryptovirus that shares homology with EBV. EBV neutralizing antibody titers were increased after two immunizations (week 6) in all groups and the titers were further boosted by a third dose (week 14). Neutralizing antibody titers in monkeys immunized with gp350 $D_{123}$-ferritin (center four bars) and $D_{123}$-encapsulin (right four bars) were $10^{3.3\pm0.3}$ and $10^{2.8\pm0.3}$, respectively, and were higher than that of soluble gp350-immunized monkeys ($10^{2.4\pm0.6}$) (left four bars). These results demonstrate the immunogenicity of gp350-based nanoparticles in a second species of animal.

Example 17. Protective Immunity Against Experimental Infection of Mice with Recombinant Vaccinia Virus Expressing EBV gp350

The ability of gp350 nanoparticle vaccines to protect mice from challenge with recombinant vaccinia virus expressing EBV gp350 was assessed by immunizing mice as described in Examples 4 and 5. Ten months after the final immunization, the mice were challenged with $10^6$ pfu of recombinant vaccinia virus expressing EBV gp350 by the intranasal route. Body weights and clinical symptoms were monitored daily.

The results of this study, which are shown in FIG. 24, demonstrate that mice immunized with gp350 $D_{123}$-ferritin and gp350 $D_{123}$-encapsulin were partially protected (up to 80% survival) against lethal challenge with vaccinia virus expressing gp350. In contrast, all non-immunized control mice and animals immunized with soluble gp350 ectodomain, with the exception of one, died as a result of the challenge virus infection. These results demonstrate that immunization with gp350-based nanoparticles provides partially protective immunity against challenge with recombinant vaccinia virus expressing gp350.

Example 18. Immunogenicity of Gp350 Nanoparticles in Aluminum Phosphate Gel Adjuvant The ability of purified nanoparticles to induce neutralizing antibodies in aluminum phosphate gel (alum) adjuvant, which is approved for use in humans, was tested in mice. Mice were divided into 6 groups; 3 groups received 5 μg of gp350 $D_{123}$-ferritin and 3 groups received $D_{123}$-encapsulin. The vaccines were given with no adjuvant, aluminum phosphate gel (alum) adjuvant, or Sigma Adjuvant System (SAS) at weeks 0, 4 and 16.

The results of this study, which are shown in FIG. 25, demonstrate that EBV neutralizing antibodies titers were higher in mice immunized with gp350 nanoparticles with adjuvant than in animals immunized with gp350 nanoparticles but without adjuvant. Animals that received gp350 $D_{123}$-ferritin (left) or gp350 $D_{123}$-encapsulin (right) vaccines in SAS adjuvant had about 10-time higher titers of EBV neutralizing antibody than animals that received the same vaccines in alum adjuvant. These results demonstrate that gp350 nanoparticle vaccine in alum adjuvant is capable of inducing EBV neutralizing antibody titers of $10^{2.6\pm0.3}$ to $10^{2.8\pm0.3}$, which are 5-8 times higher than the EBV neutralizing titers in naturally infected humans.

What is claimed:

1. A nucleic acid molecule encoding a recombinant protein, the recombinant protein comprising at least 25 contiguous amino acids from a monomeric subunit protein capable of self-assembling to form a nanoparticle, joined to at least one immunogenic portion from a first Epstein-Barr Virus (EBV) envelope protein is gp350,
   wherein the encoded recombinant protein comprises an amino acid sequence at least 80% identical to a sequence selected from the group consisting of SEQ ID NO:71, SEQ ID NO:74, SEQ ID NO:77 and SEQ ID NO:80.

* * * * *

SEQUENCE LISTING

<160> NUMBER OF SEQ ID NOS: 146

<210> SEQ ID NO 1
<211> LENGTH: 504
<212> TYPE: DNA
<213> ORGANISM: Helicobacter pylori

<400> SEQUENCE: 1

| | | |
|---|---|---|
| atgttatcaa aagacatcat taagttgcta acgaacaag tgaataagga aatgaactct | 60 |
| tccaacttgt atatgagcat gagttcatgg tgctataccc atagcttaga tggcgcgggg | 120 |
| cttttcttgt ttgaccatgc ggctgaagaa tacgagcatg ctaaaaagct tattatcttc | 180 |
| ttgaatgaaa acaatgtgcc tgtgcaattg accagcatca gcgcgcctga gcataagttt | 240 |
| gaaggtttga ctcaaatttt ccaaaaagcc tatgaacatg agcaacacat cagcgagtct | 300 |
| attaacaata tcgtagatca cgccataaaa agcaaagatc atgcgacttt caatttcttg | 360 |
| caatggtatg tggctgaaca gcatgaagaa gaagtgcttt tcaaggatat tttggataaa | 420 |
| attgagttga ttggtaatga aaaccatggc ttgtatttag ccgatcagta tgtcaaaggg | 480 |
| atcgctaaaa gcaggaaatc ttaa | 504 |

<210> SEQ ID NO 2
<211> LENGTH: 167
<212> TYPE: PRT
<213> ORGANISM: Helicobacter pylori

<400> SEQUENCE: 2

Met Leu Ser Lys Asp Ile Ile Lys Leu Leu Asn Glu Gln Val Asn Lys
1               5                   10                  15

Glu Met Asn Ser Ser Asn Leu Tyr Met Ser Met Ser Ser Trp Cys Tyr
            20                  25                  30

Thr His Ser Leu Asp Gly Ala Gly Leu Phe Leu Phe Asp His Ala Ala
        35                  40                  45

Glu Glu Tyr Glu His Ala Lys Lys Leu Ile Ile Phe Leu Asn Glu Asn
    50                  55                  60

Asn Val Pro Val Gln Leu Thr Ser Ile Ser Ala Pro Glu His Lys Phe
65                  70                  75                  80

Glu Gly Leu Thr Gln Ile Phe Gln Lys Ala Tyr Glu His Glu Gln His
                85                  90                  95

Ile Ser Glu Ser Ile Asn Asn Ile Val Asp His Ala Ile Lys Ser Lys
            100                 105                 110

Asp His Ala Thr Phe Asn Phe Leu Gln Trp Tyr Val Ala Glu Gln His
        115                 120                 125

Glu Glu Glu Val Leu Phe Lys Asp Ile Leu Asp Lys Val Glu Leu Ile
    130                 135                 140

Gly Asn Glu Asn His Gly Leu Tyr Leu Ala Asp Gln Tyr Val Lys Gly
145                 150                 155                 160

Ile Ala Lys Ser Arg Lys Ser
                165

<210> SEQ ID NO 3
<211> LENGTH: 504
<212> TYPE: DNA
<213> ORGANISM: Helicobacter pylori

<400> SEQUENCE: 3
ttaagatttc ctgcttttag cgatcccttt gacatactga tcggctaaat acaagccatg      60

-continued

```
gttttcatta ccaatcaact caattttatc caaaatatcc ttgaaaagca cttcttcttc    120
atgctgttca gccacatacc attgcaagaa attgaaagtc gcatgatctt tgctttttat    180
ggcgtgatct acgatattgt taatagactc gctgatgtgt tgctcatgtt cataggcttt    240
ttggaaaatt tgagtcaaac cttcaaactt atgctcaggc gcgctgatgc tggtcaattg    300
cacaggcaca ttgttttcat tcaagaagat aataagcttt ttagcatgct cgtattcttc    360
agccgcatgg tcaaacaaga aaagccccgc gccatctaag ctatgggtat agcaccatga    420
actcatgctc atatacaagt tggaagagtt catttcctta ttcacttgtt cgtttagcaa    480
cttaatgatg tcttttgata acat                                          504
```

<210> SEQ ID NO 4

<400> SEQUENCE: 4

000

<210> SEQ ID NO 5
<211> LENGTH: 165
<212> TYPE: PRT
<213> ORGANISM: Escherichia coli

<400> SEQUENCE: 5

```
Met Leu Lys Pro Glu Met Ile Glu Lys Leu Asn Glu Gln Met Asn Leu
1               5                   10                  15

Glu Leu Tyr Ser Ser Leu Leu Tyr Gln Gln Met Ser Ala Trp Cys Ser
            20                  25                  30

Tyr His Thr Phe Glu Gly Ala Ala Phe Leu Arg Arg His Ala Gln
        35                  40                  45

Glu Glu Met Thr His Met Gln Arg Leu Phe Asp Tyr Leu Thr Asp Thr
    50                  55                  60

Gly Asn Leu Pro Arg Ile Asn Thr Val Glu Ser Pro Phe Ala Glu Tyr
65                  70                  75                  80

Ser Ser Leu Asp Glu Leu Phe Gln Glu Thr Tyr Lys His Glu Gln Leu
                85                  90                  95

Ile Thr Gln Lys Ile Asn Glu Leu Ala His Ala Ala Met Thr Asn Gln
            100                 105                 110

Asp Tyr Pro Thr Phe Asn Phe Leu Gln Trp Tyr Val Ser Glu Gln His
        115                 120                 125

Glu Glu Glu Lys Leu Phe Lys Ser Ile Ile Asp Lys Leu Ser Leu Ala
    130                 135                 140

Gly Lys Ser Gly Glu Gly Leu Tyr Phe Ile Asp Lys Glu Leu Ser Thr
145                 150                 155                 160

Leu Asp Ala Gln Asn
                165
```

<210> SEQ ID NO 6

<400> SEQUENCE: 6

000

<210> SEQ ID NO 7

<400> SEQUENCE: 7

000

<210> SEQ ID NO 8
<211> LENGTH: 173
<212> TYPE: PRT
<213> ORGANISM: Rana catesbeiana

<400> SEQUENCE: 8

Met Glu Ser Gln Val Arg Gln Asn Phe His Gln Asp Cys Glu Ala Gly
1               5                   10                  15

Leu Asn Arg Thr Val Asn Leu Lys Phe His Ser Ser Tyr Val Tyr Leu
            20                  25                  30

Ser Met Ala Ser Tyr Phe Asn Arg Asp Asp Val Ala Leu Ser Asn Phe
        35                  40                  45

Ala Lys Phe Phe Arg Glu Arg Ser Glu Glu Lys Glu His Ala Glu
    50                  55                  60

Lys Leu Ile Glu Tyr Gln Asn Gln Arg Gly Gly Arg Val Phe Leu Gln
65                  70                  75                  80

Ser Val Glu Lys Pro Glu Arg Asp Asp Trp Ala Asn Gly Leu Glu Ala
                85                  90                  95

Leu Gln Thr Ala Leu Lys Leu Gln Lys Ser Val Asn Gln Ala Leu Leu
            100                 105                 110

Asp Leu His Ala Val Ala Ala Asp Lys Ser Asp Pro His Met Thr Asp
        115                 120                 125

Phe Leu Glu Ser Pro Tyr Leu Ser Glu Ser Val Glu Thr Ile Lys Lys
    130                 135                 140

Leu Gly Asp His Ile Thr Ser Leu Lys Lys Leu Trp Ser Ser His Pro
145                 150                 155                 160

Gly Met Ala Glu Tyr Leu Phe Asn Lys His Thr Leu Gly
                165                 170

<210> SEQ ID NO 9

<400> SEQUENCE: 9

000

<210> SEQ ID NO 10
<211> LENGTH: 531
<212> TYPE: DNA
<213> ORGANISM: Artificial Sequence
<220> FEATURE:
<223> OTHER INFORMATION: Synthetic

<400> SEQUENCE: 10
tccggagaga gccaggtgag gcagcagttc agcaaggaca tcgagaagct gctgaacgag      60
caggtgaaca aggagatgca gagcagcaac ctgtacatga gcatgagcag ctggtgctac     120
acccacagcc tggacggcgc cggcctgttc ctgttcgacc acgccgccga ggagtacgag     180
cacgccaaga agctgatcat cttcctgaac gagaacaacg tgcccgtgca gctgaccagc     240
atcagcgccc ccgagcacaa gttcgagggc ctgacccaga tcttccagaa ggcctacgag     300
cacgagcagc acatcagcga gagcatcaac aacatcgtgg accacgccat caagagcaag     360
gaccacgcca ccttcaactt cctgcagtgg tacgtggccg agcagcacga ggaggaggtg     420
ctgttcaagg acatcctgga caagatcgag ctgatcggca cgagaaccca cggcctgtac     480
ctggccgacc agtacgtgaa gggcatcgcc aagagcagga gagcggatc c               531

<210> SEQ ID NO 11
<211> LENGTH: 177
<212> TYPE: PRT

<213> ORGANISM: Artificial Sequence
<220> FEATURE:
<223> OTHER INFORMATION: Synthetic

<400> SEQUENCE: 11

```
Ser Gly Glu Ser Gln Val Arg Gln Gln Phe Ser Lys Asp Ile Glu Lys
1               5                   10                  15

Leu Leu Asn Glu Gln Val Asn Lys Glu Met Gln Ser Ser Asn Leu Tyr
            20                  25                  30

Met Ser Met Ser Ser Trp Cys Tyr Thr His Ser Leu Asp Gly Ala Gly
        35                  40                  45

Leu Phe Leu Phe Asp His Ala Ala Glu Tyr Glu His Ala Lys Lys
    50                  55                  60

Leu Ile Ile Phe Leu Asn Glu Asn Asn Val Pro Val Gln Leu Thr Ser
65                  70                  75                  80

Ile Ser Ala Pro Glu His Lys Phe Glu Gly Leu Thr Gln Ile Phe Gln
                85                  90                  95

Lys Ala Tyr Glu His Glu Gln His Ile Ser Glu Ser Ile Asn Asn Ile
                100                 105                 110

Val Asp His Ala Ile Lys Ser Lys Asp His Ala Thr Phe Asn Phe Leu
            115                 120                 125

Gln Trp Tyr Val Ala Glu Gln His Glu Glu Val Leu Phe Lys Asp
    130                 135                 140

Ile Leu Asp Lys Ile Glu Leu Ile Gly Asn Glu Asn His Gly Leu Tyr
145                 150                 155                 160

Leu Ala Asp Gln Tyr Val Lys Gly Ile Ala Lys Ser Arg Lys Ser Gly
                165                 170                 175

Ser
```

<210> SEQ ID NO 12
<211> LENGTH: 531
<212> TYPE: DNA
<213> ORGANISM: Artificial Sequence
<220> FEATURE:
<223> OTHER INFORMATION: Synthetic

<400> SEQUENCE: 12

```
ggatccgctc ttcctgctct tggcgatgcc cttcacgtac tggtcggcca ggtacaggcc    60
gtggttctcg ttgccgatca gctcgatctt gtccaggatg tccttgaaca gcacctcctc   120
ctcgtgctgc tcggccacgt accactgcag gaagttgaag gtggcgtggt ccttgctctt   180
gatggcgtgg tccacgatgt tgttgatgct ctcgctgatg tgctgctcgt gctcgtaggc   240
cttctggaag atctgggtca ggccctcgaa cttgtgctcg gggcgctga tgctggtcag   300 ctgcacgggc acgttgttct cgttcaggaa gatgatcagc ttcttggcgt gctcgtactc   360
ctcggcggcg tggtcgaaca ggaacaggcc ggcgccgtcc aggctgtggg tgtagcacca   420
gctgctcatg tcatgtaca ggttgctgct ctgcatctcc ttgttcacct gctcgttcag   480
cagcttctcg atgtccttgc tgaactgctg cctcacctgg ctctctccgg a            531
```

<210> SEQ ID NO 13
<211> LENGTH: 516
<212> TYPE: DNA
<213> ORGANISM: Artificial Sequence
<220> FEATURE:
<223> OTHER INFORMATION: Synthetic

<400> SEQUENCE: 13

```
tccggagaga gccaggtgag gcagaacttc aagcccgaga tggaggagaa gctgaacgag      60
cagatgaacc tggagctgta cagcagcctg ctgtaccagc agatgagcgc ctggtgcagc     120
taccacacct tcgagggcgc cgccgccttc ctgaggaggc acgcccagga ggagatgacc     180
cacatgcaga ggctgttcga ctacctgacc gacaccggca acctgcccag gatcaacacc     240
gtggagagcc ccttcgccga gtacagcagc ctggacgagc tgttccagga gacctacaag     300
cacgagcagc tgatcaccca gaagatcaac gagctggccc acgccgccat gaccaaccag     360
gactacccca ccttcaactt cctgcagtgg tacgtgagcg agcagcacga ggaggagaag     420
ctgttcaaga gcatcatcga caagctgagc ctggccggca gagcggcga gggcctgtac      480 ttcatcgaca aggagctgag caccctggac ggatcc                               516
```

<210> SEQ ID NO 14
<211> LENGTH: 172
<212> TYPE: PRT
<213> ORGANISM: Artificial Sequence
<220> FEATURE:
<223> OTHER INFORMATION: Synthetic

<400> SEQUENCE: 14

```
Ser Gly Glu Ser Gln Val Arg Gln Asn Phe Lys Pro Glu Met Glu Glu
1               5                   10                  15

Lys Leu Asn Glu Gln Met Asn Leu Glu Leu Tyr Ser Ser Leu Leu Tyr
            20                  25                  30

Gln Gln Met Ser Ala Trp Cys Ser Tyr His Thr Phe Glu Gly Ala Ala
        35                  40                  45

Ala Phe Leu Arg Arg His Ala Gln Glu Glu Met Thr His Met Gln Arg
    50                  55                  60

Leu Phe Asp Tyr Leu Thr Asp Thr Gly Asn Leu Pro Arg Ile Asn Thr
65                  70                  75                  80

Val Glu Ser Pro Phe Ala Glu Tyr Ser Ser Leu Asp Glu Leu Phe Gln
                85                  90                  95

Glu Thr Tyr Lys His Glu Gln Leu Ile Thr Gln Lys Ile Asn Glu Leu
            100                 105                 110

Ala His Ala Ala Met Thr Asn Gln Asp Tyr Pro Thr Phe Asn Phe Leu
        115                 120                 125

Gln Trp Tyr Val Ser Glu Gln His Glu Glu Lys Leu Phe Lys Ser
    130                 135                 140

Ile Ile Asp Lys Leu Ser Leu Ala Gly Lys Ser Gly Glu Gly Leu Tyr
145                 150                 155                 160

Phe Ile Asp Lys Glu Leu Ser Thr Leu Asp Gly Ser
                165                 170
```

<210> SEQ ID NO 15
<211> LENGTH: 516
<212> TYPE: DNA
<213> ORGANISM: Artificial Sequence
<220> FEATURE:
<223> OTHER INFORMATION: Synthetic

<400> SEQUENCE: 15

```
ggatccgtcc agggtgctca gctccttgtc gatgaagtac aggccctcgc cgctcttgcc      60
ggccaggctc agcttgtcga tgatgctctt gaacagcttc tcctcctcgt gctgctcgct    120
cacgtaccac tgcaggaagt tgaaggtggg gtagtcctgg ttggtcatgg cggcgtgggc    180
cagctcgttg atcttctggg tgatcagctg ctcgtgcttg taggtctcct ggaacagctc    240
```

-continued

```
gtccaggctg ctgtactcgg cgaaggggct ctccacggtg ttgatcctgg gcaggttgcc      300
ggtgtcggtc aggtagtcga acagcctctg catgtgggtc atctcctcct gggcgtgcct      360
cctcaggaag gcggcggcgc cctcgaaggt gtggtagctg caccaggcgc tcatctgctg      420
gtacagcagg ctgctgtaca gctccaggtt catctgctcg ttcagcttct cctccatctc      480
gggcttgaag ttctgcctca cctggctctc tccgga                                516
```

<210> SEQ ID NO 16
<211> LENGTH: 792
<212> TYPE: DNA
<213> ORGANISM: Thermotoga maritima

<400> SEQUENCE: 16

```
atggagttcc tgaagaggag cttcgcccct ctgaccgaga agcagtggca ggagatcgac       60
aacagggcca gggagatctt caagacccag ctgtacggca ggaagttcgt ggacgtggag      120
ggcccctacg gctgggagta cgccgcccac cccctgggcg aggtggaggt gctgagcgac      180
gagaacgagg tggtgaagtg gggcctgagg aagagcctgc ccctgatcga gctgagggcc      240
accttcaccc tggacctgtg ggagctggac aacctggaga gggcaagcc caacgtggac       300 ctgagcagcc tggaggagac cgtgaggaag gtggccgagt tcgaggacga ggtgatcttc      360
aggggctgcg agaagagcgg cgtgaagggc ctgctgagct tcgaggagag gaagatcgag      420
tgcggcagca cccccaagga cctgctggag gccatcgtga gggccctgag catcttcagc      480
aaggacggca tcgagggccc ctacaccctg gtgatcaaca ccgacaggtg gatcaacttc      540
ctgaaggagg aggccggcca ctaccccctg gagaagaggg tggaggagtg cctgaggggc      600
ggcaagatca tcaccacccc caggatcgag gacgccctgg tggtgagcga gagggcggc      660 gacttcaagc tgatcctggg ccaggacctg agcatcggct acgaggacag ggagaaggac      720
gccgtgaggc tgttcatcac cgagaccttc accttccagg tggtgaaccc cgaggccctg      780
atcctgctga ag                                                          792
```

<210> SEQ ID NO 17
<211> LENGTH: 264
<212> TYPE: PRT
<213> ORGANISM: Thermotoga maritima

<400> SEQUENCE: 17

```
Met Glu Phe Leu Lys Arg Ser Phe Ala Pro Leu Thr Glu Lys Gln Trp
1               5                   10                  15

Gln Glu Ile Asp Asn Arg Ala Arg Glu Ile Phe Lys Thr Gln Leu Tyr
            20                  25                  30

Gly Arg Lys Phe Val Asp Val Glu Gly Pro Tyr Gly Trp Glu Tyr Ala
        35                  40                  45

Ala His Pro Leu Gly Glu Val Glu Val Leu Ser Asp Glu Asn Glu Val
    50                  55                  60

Val Lys Trp Gly Leu Arg Lys Ser Leu Pro Leu Ile Glu Leu Arg Ala
65                  70                  75                  80

Thr Phe Thr Leu Asp Leu Trp Glu Leu Asp Asn Leu Glu Arg Gly Lys
                85                  90                  95

Pro Asn Val Asp Leu Ser Ser Leu Glu Glu Thr Val Arg Lys Val Ala
            100                 105                 110

Glu Phe Glu Asp Glu Val Ile Phe Arg Gly Cys Glu Lys Ser Gly Val
        115                 120                 125

Lys Gly Leu Leu Ser Phe Glu Glu Arg Lys Ile Glu Cys Gly Ser Thr
```

-continued

```
                130                 135                 140
Pro Lys Asp Leu Leu Glu Ala Ile Val Arg Ala Leu Ser Ile Phe Ser
145                 150                 155                 160

Lys Asp Gly Ile Glu Gly Pro Tyr Thr Leu Val Ile Asn Thr Asp Arg
                165                 170                 175

Trp Ile Asn Phe Leu Lys Glu Glu Ala Gly His Tyr Pro Leu Glu Lys
                180                 185                 190

Arg Val Glu Glu Cys Leu Arg Gly Gly Lys Ile Ile Thr Thr Pro Arg
            195                 200                 205

Ile Glu Asp Ala Leu Val Val Ser Glu Arg Gly Gly Asp Phe Lys Leu
        210                 215                 220

Ile Leu Gly Gln Asp Leu Ser Ile Gly Tyr Glu Asp Arg Glu Lys Asp
225                 230                 235                 240

Ala Val Arg Leu Phe Ile Thr Glu Thr Phe Thr Phe Gln Val Val Asn
                245                 250                 255

Pro Glu Ala Leu Ile Leu Leu Lys
            260
```

<210> SEQ ID NO 18
<211> LENGTH: 792
<212> TYPE: DNA
<213> ORGANISM: Thermotoga maritima

<400> SEQUENCE: 18

```
cttcagcagg atcagggcct cggggttcac cacctggaag gtgaaggtct cggtgatgaa      60
cagcctcacg gcgtccttct ccctgtcctc gtagccgatg ctcaggtcct ggcccaggat     120
cagcttgaag tcgccgcccc tctcgctcac caccagggcg tcctcgatcc tggggggtggt   180
gatgatcttg ccgcccctca ggcactcctc accctcttc tccagggggt agtggccggc      240
ctcctccttc aggaagttga tccacctgtc ggtgttgatc accagggtgt aggggccctc    300
gatgccgtcc ttgctgaaga tgctcagggc cctcacgatg gcctccagca ggtccttggg    360
ggtgctgccg cactcgatct tcctctcctc gaagctcagc aggcccttca cgccgctctt    420
ctcgcagccc ctgaagatca cctcgtcctc gaactcggcc accttcctca ggtctcctc    480
caggctgctc aggtccacgt tgggcttgcc cctctccagg ttgtccagct cccacaggtc    540
cagggtgaag gtggccctca gctcgatcag gggcaggctc ttcctcaggc cccacttcac    600
cacctcgttc tcgtcgctca gcacctccac ctcgcccagg gggtgggcgg cgtactccca    660
gccgtagggg ccctccacgt ccacgaactt cctgccgtac agctgggtct tgaagatctc    720
cctggccctg ttgtcgatct cctgccactg cttctcggtc agaggggcga agctcctctt    780
caggaactcc at                                                         792
```

<210> SEQ ID NO 19

<400> SEQUENCE: 19

000

<210> SEQ ID NO 20
<211> LENGTH: 192
<212> TYPE: PRT
<213> ORGANISM: Artificial Sequence
<220> FEATURE:
<223> OTHER INFORMATION: Synthetic

<400> SEQUENCE: 20

Met Ser Gln Ala Ile Gly Ile Leu Glu Leu Thr Ser Ile Ala Ala Gly
1               5                   10                  15

Met Glu Leu Gly Asp Ala Met Leu Lys Ser Ala Asn Val Asp Leu Leu
            20                  25                  30

Val Ser Lys Thr Ile Ser Pro Gly Lys Phe Leu Leu Met Leu Gly Gly
        35                  40                  45

Asp Ile Gly Ala Ile Gln Gln Ala Ile Glu Thr Gly Thr Ser Gln Ala
    50                  55                  60

Gly Glu Leu Leu Val Asp Ser Leu Val Leu Ala Asn Ile His Pro Ser
65              70                  75                  80

Val Leu Pro Ala Ile Ser Gly Leu Asn Ser Val Asp Lys Arg Gln Ala
                85                  90                  95

Val Gly Ile Val Glu Thr Trp Ser Val Ala Ala Cys Ile Ser Ala Ala
            100                 105                 110

Asp Arg Ala Val Lys Gly Ser Asn Val Thr Leu Val Arg Val His Met
        115                 120                 125

Ala Phe Gly Ile Gly Gly Lys Cys Tyr Met Val Ala Gly Asp Val
    130                 135                 140

Ser Asp Val Ala Leu Ala Val Thr Val Ala Ser Ser Ala Gly Ala
145             150                 155                 160

Tyr Gly Leu Leu Val Tyr Ala Ser Leu Ile Pro Arg Pro His Glu Ala
                165                 170                 175

Met Trp Arg Gln Met Val Glu Gly Leu Glu His His His His His His
            180                 185                 190

<210> SEQ ID NO 21

<400> SEQUENCE: 21

000

<210> SEQ ID NO 22

<400> SEQUENCE: 22

000

<210> SEQ ID NO 23
<211> LENGTH: 318
<212> TYPE: PRT
<213> ORGANISM: Acidianus ambivalens
<220> FEATURE:
<221> NAME/KEY: misc_feature
<222> LOCATION: (31)..(31)
<223> OTHER INFORMATION: Xaa can be any naturally occurring amino acid

<400> SEQUENCE: 23

Met Pro Lys Pro Tyr Val Ala Ile Asn Met Ala Glu Leu Lys Asn Glu
1               5                   10                  15

Pro Lys Thr Phe Glu Met Phe Ala Ser Val Gly Pro Lys Val Xaa Met
            20                  25                  30

Val Thr Ala Arg His Pro Gly Phe Val Gly Phe Gln Asn His Ile Gln
        35                  40                  45

Ile Gly Ile Leu Pro Phe Gly Asn Arg Tyr Gly Ala Lys Met Asp
    50                  55                  60

Met Thr Lys Glu Ser Ser Thr Val Arg Val Leu Gln Tyr Thr Phe Trp
65              70                  75                  80

Lys Asp Trp Lys Asp His Glu Glu Met His Arg Gln Asn Trp Ser Tyr
                85                  90                  95

```
Leu Phe Arg Leu Cys Tyr Ser Cys Ala Ser Gln Met Ile Trp Gly Pro
            100                 105                 110

Trp Glu Pro Ile Tyr Glu Ile Tyr Ala Asn Met Pro Ile Asn Thr
        115                 120                 125

Glu Met Thr Asp Phe Thr Ala Val Val Gly Lys Lys Phe Ala Glu Gly
    130                 135                 140

Lys Pro Leu Asp Ile Pro Val Ile Ser Gln Pro Tyr Gly Lys Arg Val
145                 150                 155                 160

Val Ala Phe Ala Glu His Ser Val Ile Pro Gly Lys Glu Lys Gln Phe
                165                 170                 175

Glu Asp Ala Ile Val Arg Thr Leu Glu Met Leu Lys Lys Ala Pro Gly
            180                 185                 190

Phe Leu Gly Ala Met Val Leu Lys Glu Ile Gly Val Ser Gly Ile Gly
        195                 200                 205

Ser Met Gln Phe Gly Ala Lys Gly Phe His Gln Val Leu Glu Asn Pro
    210                 215                 220

Gly Ser Leu Glu Pro Asp Pro Asn Asn Val Met Tyr Ser Val Pro Glu
225                 230                 235                 240

Ala Lys Asn Thr Pro Gln Gln Tyr Ile Val His Val Glu Trp Ala Asn
                245                 250                 255

Thr Asp Ala Leu Met Phe Gly Met Gly Arg Val Leu Leu Tyr Pro Glu
            260                 265                 270

Leu Arg Gln Val His Asp Glu Val Leu Asp Thr Leu Val Tyr Gly Pro
        275                 280                 285

Tyr Ile Arg Ile Leu Asn Pro Met Met Glu Gly Thr Phe Trp Arg Glu
    290                 295                 300

Tyr Leu Asn Glu Gln Ala Trp Arg His Pro Gln Phe Gly Gly
305                 310                 315

<210> SEQ ID NO 24

<400> SEQUENCE: 24

000

<210> SEQ ID NO 25

<400> SEQUENCE: 25

000

<210> SEQ ID NO 26
<211> LENGTH: 154
<212> TYPE: PRT
<213> ORGANISM: Aquifex pyrophilus

<400> SEQUENCE: 26

Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Cys Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80
```

```
Leu Ile Arg Gly Ala Thr Pro His Phe Asp Tyr Ile Ala Ser Glu Val
                85                  90                  95

Ser Lys Gly Leu Ala Asn Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Lys His Gly Asn Lys Gly Trp Glu Ala Ala Leu Ser Ala Ile
    130                 135                 140

Glu Met Ala Asn Leu Phe Lys Ser Leu Arg
145                 150
```

<210> SEQ ID NO 27

<400> SEQUENCE: 27

000

<210> SEQ ID NO 28

<400> SEQUENCE: 28

000

<210> SEQ ID NO 29
<211> LENGTH: 242
<212> TYPE: PRT
<213> ORGANISM: Bacillus stearothermophilus

<400> SEQUENCE: 29

```
Ala Ala Ala Lys Pro Ala Thr Thr Glu Gly Glu Phe Pro Glu Thr Arg
1               5                   10                  15

Glu Lys Met Ser Gly Ile Arg Arg Ala Ile Ala Lys Ala Met Val His
                20                  25                  30

Ser Lys His Thr Ala Pro His Val Thr Leu Met Asp Glu Ala Asp Val
            35                  40                  45

Thr Lys Leu Val Ala His Arg Lys Lys Phe Lys Ala Ile Ala Ala Glu
    50                  55                  60

Lys Gly Ile Lys Leu Thr Phe Leu Pro Tyr Val Val Lys Ala Leu Val
65                  70                  75                  80

Ser Ala Leu Arg Glu Tyr Pro Val Leu Asn Thr Ser Ile Asp Asp Glu
                85                  90                  95

Thr Glu Glu Ile Ile Gln Lys His Tyr Tyr Asn Ile Gly Ile Ala Ala
                100                 105                 110

Asp Thr Asp Arg Gly Leu Leu Val Pro Val Ile Lys His Ala Asp Arg
        115                 120                 125

Lys Pro Ile Phe Ala Leu Ala Gln Glu Ile Asn Glu Leu Ala Glu Lys
    130                 135                 140

Ala Arg Asp Gly Lys Leu Thr Pro Gly Glu Met Lys Gly Ala Ser Cys
145                 150                 155                 160

Thr Ile Thr Asn Ile Gly Ser Ala Gly Gly Gln Trp Phe Thr Pro Val
                165                 170                 175

Ile Asn His Pro Glu Val Ala Ile Leu Gly Ile Gly Arg Ile Ala Glu
                180                 185                 190

Lys Pro Ile Val Arg Asp Gly Glu Ile Val Ala Ala Pro Met Leu Ala
        195                 200                 205

Leu Ser Leu Ser Phe Asp His Arg Met Ile Asp Gly Ala Thr Ala Gln
    210                 215                 220
```

```
Lys Ala Leu Asn His Ile Lys Arg Leu Leu Ser Asp Pro Glu Leu Leu
225                 230                 235                 240

Leu Met

<210> SEQ ID NO 30

<400> SEQUENCE: 30

000

<210> SEQ ID NO 31
<211> LENGTH: 2721
<212> TYPE: DNA
<213> ORGANISM: Epstein Barr Virus

<400> SEQUENCE: 31
atggaagccg ccctgctggt gtgccagtac actattcaga gcctgattca tctgaccggg      60
gaggaccctg attttttcaa tgtggaaatc cctgagttcc cattttaccc cacctgcaac     120
gtctgtacag ccgacgtgaa cgtcaccatt aatttcgatg tgggcgggaa gaaacaccag     180
ctggacctgg attttggcca gctgacccca catacaaaag ccgtgtatca gcccagaggg     240
gctttcggag gcagcgagaa cgcaacaaat ctgtttctgc tggagctgct gggagcagga     300
gaactggctc tgaccatgag gtccaagaaa ctgcccatca atgtgaccac aggagaggaa     360
cagcaggtca gtctggaatc agtggacgtc tacttccagg atgtgtttgg caccatgtgg     420
tgccaccatg ccgagatgca gaatcctgtg tacctgatcc cgaaaccgt ccctatatt      480 aagtgggaca actgtaatag cactaacatt accgcagtgg tccgggcaca ggggctggac     540 gtgacccctgc cactgtcact gcccacaagc gcccaggata gcaacttctc cgtgaaaacc     600
gagatgctgg gaatgagat cgacattgaa tgcatcatga ggatggaga aattagccag     660 gtgctgcctg gcgataacaa gtttaatatc acctgttccg gctacgaatc tcacgtccca     720 agtggggaa tcctgacatc tactagtccc gtggccactc caattcccgg aaccggctac     780
gcttatagcc tgagactgac ccctaggcca gtctcacgct tcctgggcaa caatagcatt     840
ctgtacgtgt tttattccgg aaacggacca aaggcttctg gaggggacta ttgcatccag     900
agtaatattg tgttctcaga cgagatccca gccagccagg atatgccac taacactacc     960 gacattacct acgtgggcga taatgccact tattccgtgc ctatggtcac aagcgaagac    1020
gctaactccc caaatgtgac cgtcacagca ttctgggcct ggcccaacaa tactgagacc    1080
gattttaagt gcaaatggac actgacttca ggcaccccta cgggtgtga aaacatctct    1140 ggcgccttcg ctagtaatcg aacctttgat attacagtgt ccggcctggg gactgcccca    1200
aaaaccctga tcattacccg dacagctact aacgcaacaa ctaccacaca caagtgatc    1260 ttcagcaaag ctcccgagtc cactaccaca tctcctaccc tgaacactac cgggtttgcc    1320
gaccccaata caactaccgg actgcctagc tccacccatg tgccaacaaa cctgactgca    1380
ccagcatcca ccgacctac agtgtctact gccgatgtca ccagtcccac acctgccgga    1440
acaacttctg gcgctagtcc cgtgacccca tcacccagcc cttgggacaa tgggacagag    1500
agtaaggccc ctgatatgac ttctagtacc tcaccagtca ccacaccaac ccccaacgca    1560
acaagcccta ctccagccgt gactacccca acacctaatg ctaccagccc aacacccgca    1620
gtgacaactc ctacccccaaa cgccacttcc ccaaccctgg gaagacatc acccactagc    1680 gccgtgacca cacccacccc taatgctacc tctcctacac tggaaaaac ttccccaacc    1740
```

-continued

```
tctgcagtga ctaccccaac ccccaacgcc acaagcccca ctctgggcaa gaccagtcct   1800
acatcagctg tcacaactcc taccccaaat gcaactgggc caaccgtggg agagacatcc   1860
ccccaggcta acgcaacaaa tcacactctg ggaggcacca gtcccacacc tgtggtcacc   1920
tcacagccca agaacgccac aagcgctgtg accacaggcc agcataatat cacatcaagc   1980
tccacttcta gtatgagcct cgcccttca agcaacccag agacactgtc cccatctact   2040
agtgacaatt caaccagcca catgcctctg ctgacatctg cacatccaac tgggggagaa   2100
aacatcactc aggtcacccc cgcctccatt tctacccacc atgtgtccac atcctctcca   2160
gcaccccgac ctggaactac cagccaggca tccggaccag aaatagttc aaccagcaca   2220
aagcctggcg aggtgaacgt cacaaaaggg actcccctc agaatgctac ctcacctcag   2280
gcaccaagcg gccagaaaac agctgtgcct actgtcacct ccacaggcgg aaggcaaac   2340
tctacaactg gaggcaaaca caccacaggg catggagctc gcactagcac cgaaccaact   2400
accgactacg ggggagattc cacaactcca aggcccagat acaatgccac cacatatctg   2460
ccaccctcta ccagctccaa gctgcgaccc agatggacat tcactagtcc tccagtgact   2520
accgcacagg ctacagtgcc agtcccacct acttctcagc ctagattttc taacctgagt   2580
atgctggtgc tgcagtgggc aagcctggca gtcctgaccc tgctgctgct gctggtcatg   2640
gctgactgtg cattccggag aaacctgtcc acttcacaca cttacaccac ccccccttac   2700
gatgacgcag agacttatgt c                                             2721
```

<210> SEQ ID NO 32
<211> LENGTH: 907
<212> TYPE: PRT
<213> ORGANISM: Epstein Barr Virus

<400> SEQUENCE: 32

```
Met Glu Ala Ala Leu Leu Val Cys Gln Tyr Thr Ile Gln Ser Leu Ile
1               5                   10                  15

His Leu Thr Gly Glu Asp Pro Gly Phe Phe Asn Val Glu Ile Pro Glu
            20                  25                  30

Phe Pro Phe Tyr Pro Thr Cys Asn Val Cys Thr Ala Asp Val Asn Val
        35                  40                  45

Thr Ile Asn Phe Asp Val Gly Gly Lys Lys His Gln Leu Asp Leu Asp
    50                  55                  60

Phe Gly Gln Leu Thr Pro His Thr Lys Ala Val Tyr Gln Pro Arg Gly
65                  70                  75                  80

Ala Phe Gly Gly Ser Glu Asn Ala Thr Asn Leu Phe Leu Leu Glu Leu
                85                  90                  95

Leu Gly Ala Gly Glu Leu Ala Leu Thr Met Arg Ser Lys Lys Leu Pro
            100                 105                 110

Ile Asn Val Thr Thr Gly Glu Glu Gln Gln Val Ser Leu Glu Ser Val
        115                 120                 125

Asp Val Tyr Phe Gln Asp Val Phe Gly Thr Met Trp Cys His His Ala
    130                 135                 140

Glu Met Gln Asn Pro Val Tyr Leu Ile Pro Glu Thr Val Pro Tyr Ile
145                 150                 155                 160

Lys Trp Asp Asn Cys Asn Ser Thr Asn Ile Thr Ala Val Val Arg Ala
                165                 170                 175

Gln Gly Leu Asp Val Thr Leu Pro Leu Ser Leu Pro Thr Ser Ala Gln
            180                 185                 190

Asp Ser Asn Phe Ser Val Lys Thr Glu Met Leu Gly Asn Glu Ile Asp
```

-continued

```
            195                 200                 205
Ile Glu Cys Ile Met Glu Asp Gly Glu Ile Ser Gln Val Leu Pro Gly
210                 215                 220

Asp Asn Lys Phe Asn Ile Thr Cys Ser Gly Tyr Glu Ser His Val Pro
225                 230                 235                 240

Ser Gly Gly Ile Leu Thr Ser Thr Ser Pro Val Ala Thr Pro Ile Pro
                245                 250                 255

Gly Thr Gly Tyr Ala Tyr Ser Leu Arg Leu Thr Pro Arg Pro Val Ser
                260                 265                 270

Arg Phe Leu Gly Asn Asn Ser Ile Leu Tyr Val Phe Tyr Ser Gly Asn
                275                 280                 285

Gly Pro Lys Ala Ser Gly Gly Asp Tyr Cys Ile Gln Ser Asn Ile Val
290                 295                 300

Phe Ser Asp Glu Ile Pro Ala Ser Gln Asp Met Pro Thr Asn Thr Thr
305                 310                 315                 320

Asp Ile Thr Tyr Val Gly Asp Asn Ala Thr Tyr Ser Val Pro Met Val
                325                 330                 335

Thr Ser Glu Asp Ala Asn Ser Pro Asn Val Thr Val Thr Ala Phe Trp
                340                 345                 350

Ala Trp Pro Asn Asn Thr Glu Thr Asp Phe Lys Cys Lys Trp Thr Leu
                355                 360                 365

Thr Ser Gly Thr Pro Ser Gly Cys Glu Asn Ile Ser Gly Ala Phe Ala
370                 375                 380

Ser Asn Arg Thr Phe Asp Ile Thr Val Ser Gly Leu Gly Thr Ala Pro
385                 390                 395                 400

Lys Thr Leu Ile Ile Thr Arg Thr Ala Thr Asn Ala Thr Thr Thr Thr
                405                 410                 415

His Lys Val Ile Phe Ser Lys Ala Pro Glu Ser Thr Thr Ser Pro
                420                 425                 430

Thr Leu Asn Thr Thr Gly Phe Ala Asp Pro Asn Thr Thr Thr Gly Leu
                435                 440                 445

Pro Ser Ser Thr His Val Pro Thr Asn Leu Thr Ala Pro Ala Ser Thr
450                 455                 460

Gly Pro Thr Val Ser Thr Ala Asp Val Thr Ser Pro Thr Pro Ala Gly
465                 470                 475                 480

Thr Thr Ser Gly Ala Ser Pro Val Thr Pro Ser Pro Ser Pro Trp Asp
                485                 490                 495

Asn Gly Thr Glu Ser Lys Ala Pro Asp Met Thr Ser Ser Thr Ser Pro
                500                 505                 510

Val Thr Thr Pro Thr Pro Asn Ala Thr Ser Pro Thr Pro Ala Val Thr
                515                 520                 525

Thr Pro Thr Pro Asn Ala Thr Ser Pro Thr Pro Ala Val Thr Thr Pro
                530                 535                 540

Thr Pro Asn Ala Thr Ser Pro Thr Leu Gly Lys Thr Ser Pro Thr Ser
545                 550                 555                 560

Ala Val Thr Thr Pro Thr Pro Asn Ala Thr Ser Pro Thr Leu Gly Lys
                565                 570                 575

Thr Ser Pro Thr Ser Ala Val Thr Thr Pro Thr Pro Asn Ala Thr Ser
                580                 585                 590

Pro Thr Leu Gly Lys Thr Ser Pro Thr Ser Ala Val Thr Thr Pro Thr
                595                 600                 605

Pro Asn Ala Thr Gly Pro Thr Val Gly Glu Thr Ser Pro Gln Ala Asn
610                 615                 620
```

Ala Thr Asn His Thr Leu Gly Gly Thr Ser Pro Thr Pro Val Val Thr
625                 630                 635                 640

Ser Gln Pro Lys Asn Ala Thr Ser Ala Val Thr Thr Gly Gln His Asn
        645                 650                 655

Ile Thr Ser Ser Ser Thr Ser Ser Met Ser Leu Arg Pro Ser Ser Asn
            660                 665                 670

Pro Glu Thr Leu Ser Pro Ser Thr Ser Asp Asn Ser Thr Ser His Met
                675                 680                 685

Pro Leu Leu Thr Ser Ala His Pro Thr Gly Gly Glu Asn Ile Thr Gln
            690                 695                 700

Val Thr Pro Ala Ser Ile Ser Thr His His Val Ser Ser Ser Ser Pro
705                 710                 715                 720

Ala Pro Arg Pro Gly Thr Thr Ser Gln Ala Ser Gly Pro Gly Asn Ser
                725                 730                 735

Ser Thr Ser Thr Lys Pro Gly Glu Val Asn Val Thr Lys Gly Thr Pro
            740                 745                 750

Pro Gln Asn Ala Thr Ser Pro Gln Ala Pro Ser Gly Gln Lys Thr Ala
                755                 760                 765

Val Pro Thr Val Thr Ser Thr Gly Gly Lys Ala Asn Ser Thr Thr Gly
770                 775                 780

Gly Lys His Thr Thr Gly His Gly Ala Arg Thr Ser Thr Glu Pro Thr
785                 790                 795                 800

Thr Asp Tyr Gly Gly Asp Ser Thr Thr Pro Arg Pro Arg Tyr Asn Ala
                805                 810                 815

Thr Thr Tyr Leu Pro Pro Ser Thr Ser Ser Lys Leu Arg Pro Arg Trp
            820                 825                 830

Thr Phe Thr Ser Pro Pro Val Thr Thr Ala Gln Ala Thr Val Pro Val
            835                 840                 845

Pro Pro Thr Ser Gln Pro Arg Phe Ser Asn Leu Ser Met Leu Val Leu
            850                 855                 860

Gln Trp Ala Ser Leu Ala Val Leu Thr Leu Leu Leu Leu Leu Val Met
865                 870                 875                 880

Ala Asp Cys Ala Phe Arg Arg Asn Leu Ser Thr Ser His Thr Tyr Thr
                885                 890                 895

Thr Pro Pro Tyr Asp Asp Ala Glu Thr Tyr Val
            900                 905

<210> SEQ ID NO 33
<211> LENGTH: 2721
<212> TYPE: DNA
<213> ORGANISM: Epstein Barr Virus

<400> SEQUENCE: 33
gacataagtc tctgcgtcat cgtaaggggg ggtggtgtaa gtgtgtgaag tggacaggtt      60
tctccggaat gcacagtcag ccatgaccag cagcagcagc agggtcagga ctgccaggct     120
tgcccactgc agcaccagca tactcaggtt agaaaatcta ggctgagaag taggtgggac     180
tggcactgta gcctgtgcgg tagtcactgg aggactagtg aatgtccatc tgggtcgcag     240
cttggagctg gtagagggtg gcagatatgt ggtggcattg tatctgggcc ttggagttgt     300
ggaatctccc ccgtagtcgg tagttggttc ggtgctagtg cgagctccat gccctgtggt     360
gtgtttgcct ccagttgtag agtttgcctt cccgcctgtg gaggtgacag taggcacagc     420
tgttttctgg ccgcttggtg cctgaggtga ggtagcattc tgagggggag tcccttttgt     480

-continued

| | |
|---|---|
| gacgttcacc tcgccaggct tgtgctggt tgaactattt cctggtccgg atgcctggct | 540 |
| ggtagttcca ggtcgggtg ctggagagga tgtggacaca tggtgggtag aaatggaggc | 600 |
| gggggtgacc tgagtgatgt tttctccccc agttggatgt gcagatgtca gcagaggcat | 660 |
| gtggctggtt gaattgtcac tagtagatgg ggacagtgtc tctgggttgc ttgaagggcg | 720 |
| caggctcata ctagaagtgg agcttgatgt gatattatgc tggcctgtgg tcacagcgct | 780 |
| tgtggcgttc ttgggctgtg aggtgaccac aggtgtggga ctggtgcctc ccagagtgtg | 840 |
| atttgttgcg ttagcctggg gggatgtctc tcccacggtt ggcccagttg catttggggt | 900 |
| aggagttgtg acagctgatg taggactggt cttgcccaga gtgggcttg tggcgttggg | 960 |
| ggttgggta gtcactgcag aggttgggga agtttttccc agtgtaggag aggtagcatt | 1020 |
| aggggtggt gtggtcacgg cgctagtggg tgatgtcttc cccagggttg gggaagtggc | 1080 |
| gtttggggta ggagttgtca ctgcgggtgt tgggctggta gcattaggtg tggggtagt | 1140 |
| cacggctgga gtagggcttg ttgcgttggg ggttggtgtg gtgactggtg aggtactaga | 1200 |
| agtcatatca ggggccttac tctctgtccc attgtcccaa gggctgggtg atggggtcac | 1260 |
| gggactagcg ccagaagttg ttccggcagg tgtgggactg gtgacatcgg cagtagacac | 1320 |
| tgtaggtccg gtggatgctg gtgcagtcag gtttgttggc acatgggtgg agctaggcag | 1380 |
| tccggtagtt gtattgggt cggcaaaccc ggtagtgttc agggtaggag atgtggtagt | 1440 |
| ggactcggga gctttgctga agatcacttt tgtgtggta gttgttgcgt tagtagctgt | 1500 |
| ccgggtaatg atcagggttt ttggggcagt ccccaggccg gacactgtaa tatcaaaggt | 1560 |
| tcgattacta gcgaaggcgc cagagatgtt ttcacacccg ctaggggtgc ctgaagtcag | 1620 |
| tgtccatttg cacttaaaat cggtctcagt attgttgggc caggcccaga atgctgtgac | 1680 |
| ggtcacattt ggggagttag cgtcttcgct tgtgaccata ggcacggaat aagtggcatt | 1740 |
| atcgcccacg taggtaatgt cggtagtgtt agtgggcata tcctggctgg ctgggatctc | 1800 |
| gtctgagaac acaatattac tctggatgca atagtcccct ccagaagcct ttggtccgtt | 1860 |
| tccggaataa aacacgtaca gaatgctatt gttgcccagg aagcgtgaga ctggcctagg | 1920 |
| ggtcagtctc aggctataag cgtagccggt tccgggaatt ggagtggcca cgggactagt | 1980 |
| agatgtcagg attcccccac ttgggacgtg agattcgtag ccggaacagg tgatattaaa | 2040 |
| cttgttatcg ccaggcagca cctggctaat ttctccatcc tccatgatgc attcaatgtc | 2100 |
| gatctcattt cccagcatct cggttttcac ggagaagttg ctatcctggg cgcttgtggg | 2160 |
| cagtgacagt ggcagggtca cgtccagccc ctgtgcccgg accactgcgg taatgttagt | 2220 |
| gctattacag ttgtcccact taatataagg gacggtttcg gggatcaggt acacaggatt | 2280 |
| ctgcatctcg gcatggtggc accacatggt gccaaacaca tcctggaagt agacgtccac | 2340 |
| tgattccaga ctgacctgct gttcctctcc tgtggtcaca ttgatgggca gtttcttgga | 2400 |
| cctcatggtc agagccagtt ctcctgctcc cagcagctcc agcagaaaca gatttgttgc | 2460 |
| gttctcgctg cctccgaaag cccctctggg ctgatacacg gcttttgtat gtggggtcag | 2520 |
| ctggccaaaa tccaggtcca gctggtgttt cttcccgccc acatcgaaat taatggtgac | 2580 |
| gttcacgtcg gctgtacaga cgttgcaggt ggggtaaaat gggaactcag ggatttccac | 2640 |
| attgaaaaat ccagggtcct ccccggtcag atgaatcagg ctctgaatag tgtactggca | 2700 |
| caccagcagg gcggcttcca t | 2721 |

<210> SEQ ID NO 34
<211> LENGTH: 2577

<212> TYPE: DNA
<213> ORGANISM: Epstein Barr Virus

<400> SEQUENCE: 34

```
gaagccgccc tgctggtgtg ccagtacact attcagagcc tgattcatct gaccggggag      60
gaccctggat ttttcaatgt ggaaatccct gagttcccat tttacccccac ctgcaacgtc    120
tgtacagccg acgtgaacgt caccattaat ttcgatgtgg gcgggaagaa acaccagctg    180
gacctggatt ttggccagct gaccccacat acaaaagccg tgtatcagcc cagaggggct    240
ttcggaggca gcgagaacgc aacaaatctg tttctgctgg agctgctggg agcaggagaa    300
ctggctctga ccatgaggtc caagaaactg cccatcaatg tgaccacagg agaggaacag    360
caggtcagtc tggaatcagt ggacgtctac ttccaggatg tgtttggcac catgtggtgc    420
caccatgccg agatgcagaa tcctgtgtac ctgatcccg aaaccgtccc ttatattaag      480
tgggacaact gtaatagcac taacattacc gcagtggtcc gggcacaggg gctggacgtg    540
accctgccac tgtcactgcc cacaagcgcc caggatagca acttctccgt gaaaaccgag    600
atgctgggaa atgagatcga cattgaatgc atcatggagg atggagaaat tagccaggtg    660
ctgcctggcg ataacaagtt taatatcacc tgttccggct acgaatctca cgtcccaagt    720
gggggaatcc tgacatctac tagtcccgtg gccactccaa ttcccggaac cggctacgct    780
tatagcctga actgaccccc taggccagtc tcacgcttcc tgggcaacaa tagcattctg    840
tacgtgtttt attccggaaa cggaccaaag gcttctggag gggactattg catccagagt    900
aatattgtgt tctcagacga gatcccagcc agccaggata tgcccactaa cactaccgac    960
attacctacg tgggcgataa tgccacttat tccgtgccta tggtcacaag cgaagacgct   1020
aactcccccaa atgtgaccgt cacagcattc tgggcctggc caacaatac tgagaccgat   1080
tttaagtgca aatggacact gacttcaggc accctagcg ggtgtgaaaa catctctggc    1140
gccttcgcta gtaatcgaac cttt gatatt acagtgtccg gcctggggac tgccccaaaa   1200
accctgatca ttacccggac agctactaac gcaacaacta ccacacacaa agtgatcttc   1260
agcaaaagctc ccgagtccac taccacatct cctaccctga acactaccgg gtttgccgac   1320
cccaatacaa ctaccggact gcctagctcc acccatgtgc aacaaaacct gactgcacca   1380
gcatccaccg gacctacagt gtctactgcc gatgtcacca gtcccacacc tgccggaaca   1440
acttctggcg ctagtcccgt gaccccatca cccagccctt gggacaatgg gacagagagt   1500
aaggccctg atatgacttc tagtacctca ccagtcacca caccaacccc caacgcaaca   1560
agccctactc cagccgtgac taccccacaa cctaatgcta ccagcccaac acccgcagtg   1620
acaactccta ccccaaacgc cacttcccca accctgggga agacatcacc cactagcgcc   1680
gtgaccacac ccacccctaa tgctacctct cctacactgg gaaaaacttc cccaacctct   1740
gcagtgacta cccaccccc caacgccaca agccccactc tgggcaagac cagtcctaca   1800
tcagctgtca caactcctac cccaaaatgca actgggccaa ccgtgggaga catcccccc   1860
caggctaacg caacaaatca cactctggga ggcaccagtc ccacacctgt ggtcacctca   1920
cagcccaaga cgccacaag cgctgtgacc acaggccagc ataatatcac atcaagctcc   1980
acttctagta tgagcctgcg cccttcaagc aacccagaga cactgtcccc atctactagt   2040
gacaattcaa ccagccacat gcctctgctg acatctgcac atccaactgg gggagaaaac   2100
atcactcagg tcacccccgc ctccatttct acccaccatg tgtccacatc ctctccagca   2160
ccccgacctg gaactaccag ccaggcatcc ggaccaggaa atagttcaac cagcacaaag   2220
```

```
cctggcgagg tgaacgtcac aaaagggact cccctcaga atgctacctc acctcaggca    2280
ccaagcggcc agaaaacagc tgtgcctact gtcacctcca caggcgggaa ggcaaactct    2340
acaactggag gcaaacacac cacagggcat ggagctcgca ctagcaccga accaactacc    2400
gactacgggg gagattccac aactccaagg cccagataca atgccaccac atatctgcca    2460
ccctctacca gctccaagct gcgacccaga tggacattca ctagtcctcc agtgactacc    2520
gcacaggcta cagtgccagt cccacctact tctcagccta gatttctaa cctgagt        2577
```

<210> SEQ ID NO 35
<211> LENGTH: 859
<212> TYPE: PRT
<213> ORGANISM: Epstein Barr Virus

<400> SEQUENCE: 35

```
Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Gln Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Pro Tyr Ile Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
        195                 200                 205

Glu Cys Ile Met Glu Asp Gly Glu Ile Ser Gln Val Leu Pro Gly Asp
    210                 215                 220

Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
        275                 280                 285

Pro Lys Ala Ser Gly Gly Asp Tyr Cys Ile Gln Ser Asn Ile Val Phe
    290                 295                 300

Ser Asp Glu Ile Pro Ala Ser Gln Asp Met Pro Thr Asn Thr Thr Asp
305                 310                 315                 320
```

```
Ile Thr Tyr Val Gly Asp Asn Ala Thr Tyr Ser Val Pro Met Val Thr
            325                 330                 335

Ser Glu Asp Ala Asn Ser Pro Asn Val Thr Val Thr Ala Phe Trp Ala
            340                 345                 350

Trp Pro Asn Asn Thr Glu Thr Asp Phe Lys Cys Lys Trp Thr Leu Thr
            355                 360                 365

Ser Gly Thr Pro Ser Gly Cys Glu Asn Ile Ser Gly Ala Phe Ala Ser
            370                 375                 380

Asn Arg Thr Phe Asp Ile Thr Val Ser Gly Leu Gly Thr Ala Pro Lys
385                 390                 395                 400

Thr Leu Ile Ile Thr Arg Thr Ala Thr Asn Ala Thr Thr Thr His
            405                 410                 415

Lys Val Ile Phe Ser Lys Ala Pro Glu Ser Thr Thr Thr Ser Pro Thr
            420                 425                 430

Leu Asn Thr Thr Gly Phe Ala Asp Pro Asn Thr Thr Thr Gly Leu Pro
            435                 440                 445

Ser Ser Thr His Val Pro Thr Asn Leu Thr Ala Pro Ala Ser Thr Gly
            450                 455                 460

Pro Thr Val Ser Thr Ala Asp Val Thr Ser Pro Thr Pro Ala Gly Thr
465                 470                 475                 480

Thr Ser Gly Ala Ser Pro Val Thr Pro Ser Pro Ser Pro Trp Asp Asn
            485                 490                 495

Gly Thr Glu Ser Lys Ala Pro Asp Met Thr Ser Ser Thr Ser Pro Val
            500                 505                 510

Thr Thr Pro Thr Pro Asn Ala Thr Ser Pro Thr Pro Ala Val Thr Thr
            515                 520                 525

Pro Thr Pro Asn Ala Thr Ser Pro Thr Pro Ala Val Thr Thr Pro Thr
            530                 535                 540

Pro Asn Ala Thr Ser Pro Thr Leu Gly Lys Thr Ser Pro Thr Ser Ala
545                 550                 555                 560

Val Thr Thr Pro Thr Pro Asn Ala Thr Ser Pro Thr Leu Gly Lys Thr
            565                 570                 575

Ser Pro Thr Ser Ala Val Thr Thr Pro Thr Pro Asn Ala Thr Ser Pro
            580                 585                 590

Thr Leu Gly Lys Thr Ser Pro Thr Ser Ala Val Thr Thr Pro Thr Pro
            595                 600                 605

Asn Ala Thr Gly Pro Thr Val Gly Glu Thr Ser Pro Gln Ala Asn Ala
            610                 615                 620

Thr Asn His Thr Leu Gly Gly Thr Ser Pro Thr Pro Val Val Thr Ser
625                 630                 635                 640

Gln Pro Lys Asn Ala Thr Ser Ala Val Thr Thr Gly Gln His Asn Ile
            645                 650                 655

Thr Ser Ser Ser Thr Ser Ser Met Ser Leu Arg Pro Ser Ser Asn Pro
            660                 665                 670

Glu Thr Leu Ser Pro Ser Thr Ser Asp Asn Ser Thr Ser His Met Pro
            675                 680                 685

Leu Leu Thr Ser Ala His Pro Thr Gly Gly Glu Asn Ile Thr Gln Val
            690                 695                 700

Thr Pro Ala Ser Ile Ser Thr His His Val Ser Thr Ser Ser Pro Ala
705                 710                 715                 720

Pro Arg Pro Gly Thr Thr Ser Gln Ala Ser Gly Pro Gly Asn Ser Ser
            725                 730                 735
```

```
Thr Ser Thr Lys Pro Gly Glu Val Asn Val Thr Lys Gly Thr Pro Pro
            740                 745                 750

Gln Asn Ala Thr Ser Pro Gln Ala Pro Ser Gly Gln Lys Thr Ala Val
        755                 760                 765

Pro Thr Val Thr Ser Thr Gly Gly Lys Ala Asn Ser Thr Thr Gly Gly
    770                 775                 780

Lys His Thr Thr Gly His Gly Ala Arg Thr Ser Thr Glu Pro Thr Thr
785                 790                 795                 800

Asp Tyr Gly Gly Asp Ser Thr Thr Pro Arg Pro Arg Tyr Asn Ala Thr
                805                 810                 815

Thr Tyr Leu Pro Pro Ser Thr Ser Ser Lys Leu Arg Pro Arg Trp Thr
            820                 825                 830

Phe Thr Ser Pro Pro Val Thr Thr Ala Gln Ala Thr Val Pro Val Pro
835                 840                 845

Pro Thr Ser Gln Pro Arg Phe Ser Asn Leu Ser
    850                 855

<210> SEQ ID NO 36
<211> LENGTH: 2577
<212> TYPE: DNA
<213> ORGANISM: Epstein Barr Virus

<400> SEQUENCE: 36
```

| | |
|---|---|
| actcaggtta gaaaatctag gctgagaagt aggtgggact ggcactgtag cctgtgcggt | 60 |
| agtcactgga ggactagtga atgtccatct gggtcgcagc ttggagctgg tagagggtgg | 120 |
| cagatatgtg gtggcattgt atctgggcct tggagttgtg aatctcccc cgtagtcggt | 180 |
| agttggttcg gtgctagtgc gagctccatg ccctgtggtg tgtttgcctc cagttgtaga | 240 |
| gtttgccttc ccgcctgtgg aggtgacagt aggcacagct gttttctggc cgcttggtgc | 300 |
| ctgaggtgag gtagcattct gaggggagt ccctttttgtg acgttcacct cgccaggctt | 360 |
| tgtgctggtt gaactatttc ctggtccgga tgcctggctg gtagttccag gtcgggtgc | 420 |
| tggagaggat gtggacacat ggtgggtaga atggaggcg ggggtgaccct gagtgatgtt | 480 |
| ttctccccca gttggatgtg cagatgtcag cagaggcatg tggctggttg aattgtcact | 540 |
| agtagatggg gacagtgtct ctgggttgct tgaagggcgc aggctcatac tagaagtgga | 600 |
| gcttgatgtg atattatgct ggcctgtggt cacagcgctt gtggcgttct gggctgtga | 660 |
| ggtgaccaca ggtgtgggac tggtgcctcc cagagtgtga tttgttgcgt tagcctgggg | 720 |
| ggatgtctct cccacggttg gcccagttgc atttgggta ggagttgtga cagctgatgt | 780 |
| aggactggtc ttgcccagag tggggcttgt ggcgttgggg gttggggtag tcactgcaga | 840 |
| ggttggggaa gtttttccca gtgtaggaga ggtagcatta ggggtgggtg tggtcacggc | 900 |
| gctagtgggt gatgtcttcc ccaggggttgg ggaagtggcg tttggggtag gagttgtcac | 960 |
| tgcgggtgtt gggctggtag cattaggtgt gggggtagtc acggctggag tagggcttgt | 1020 |
| tgcgttgggg gttggtgtgg tgactggtga ggtactagaa gtcatatcag gggccttact | 1080 |
| ctctgtccca ttgtcccaag ggctgggtga tggggtcacg ggactagcgc cagaagttgt | 1140 |
| tccggcaggt gtgggactgg tgacatcggc agtagacact gtaggtccgg tggatgctgg | 1200 |
| tgcagtcagg tttgttggca catgggtgga gctaggcagt ccggtagttg tattggggtc | 1260 |
| ggcaaacccg gtagtgttca gggtaggaga tgtggtagtg gactcgggag ctttgctgaa | 1320 |
| gatcactttg tgtgtggtag ttgttgcgtt agtagctgtc cgggtaatga tcagggtttt | 1380 |
| tgggggcagtc cccaggccgg acactgtaat atcaaaggtt cgattactag cgaaggcgcc | 1440 |

```
agagatgttt tcacacccgc tagggggtgcc tgaagtcagt gtccatttgc acttaaaatc    1500
ggtctcagta ttgttgggcc aggcccagaa tgctgtgacg gtcacatttg gggagttagc    1560
gtcttcgctt gtgaccatag gcacggaata agtggcatta tcgcccacgt aggtaatgtc    1620
ggtagtgtta gtgggcatat cctggctggc tgggatctcg tctgagaaca caatattact    1680
ctggatgcaa tagtcccctc cagaagcctt tggtccgttt ccggaataaa acacgtacag    1740
aatgctattg ttgcccagga agcgtgagac tggcctaggg gtcagtctca ggctataagc    1800
gtagccggtt ccgggaattg gagtggccac gggactagta gatgtcagga ttcccccact    1860
tgggacgtga gattcgtagc cggaacaggt gatattaaac ttgttatcgc caggcagcac    1920
ctggctaatt tctccatcct ccatgatgca ttcaatgtcg atctcatttc ccagcatctc    1980
ggttttcacg gagaagttgc tatcctgggc gcttgtgggc agtgacagtg gcagggtcac    2040
gtccagcccc tgtgcccgga ccactgcggt aatgttagtg ctattacagt tgtcccactt    2100
aatataaggg acggtttcgg ggatcaggta cacaggattc tgcatctcgg catggtggca    2160
ccacatggtg ccaaacacat cctggaagta gacgtccact gattccagac tgacctgctg    2220
ttcctctcct gtggtcacat tgatgggcag tttcttggac ctcatggtca gagccagttc    2280
tcctgctccc agcagctcca gcagaaacag atttgttgcg ttctcgctgc ctccgaaagc    2340
ccctctgggc tgatacacgg cttttgtatg tggggtcagc tggccaaaat ccaggtccag    2400
ctggtgtttc ttcccgccca catcgaaatt aatggtgacg ttcacgtcgg ctgtacagac    2460
gttgcaggtg gggtaaaatg ggaactcagg gatttccaca ttgaaaaatc cagggtcctc    2520
cccggtcaga tgaatcaggc tctgaatagt gtactggcac accagcaggg cggcttc      2577

<210> SEQ ID NO 37
<211> LENGTH: 1407
<212> TYPE: DNA
<213> ORGANISM: Epstein Barr Virus

<400> SEQUENCE: 37
gaagccgccc tgctggtgtg ccagtacact attcagagcc tgattcatct gaccggggag      60
gaccctggat ttttcaatgt ggaaatccct gagttcccat tttaccccac ctgcaacgtc     120
tgtacagccg acgtgaacgt caccattaat ttcgatgtgg gcgggaagaa acaccagctg     180
gacctggatt ttggccagct gaccccacat acaaaagccg tgtatcagcc cagaggggct     240
ttcggaggca gcgagaacgc aacaaatctg tttctgctgg agctgctggg agcaggagaa     300
ctggctctga ccatgaggtc caagaaactg cccatcaatg tgaccacagg agaggaacag     360
caggtcagtc tggaatcagt ggacgtctac ttccaggatg tgtttggcac catgtggtgc     420
caccatgccg agatgcagaa tcctgtgtac ctgatccccg aaaccgtccc ttatattaag     480
tgggacaact gtaatagcac taacattacc gcagtggtcc gggcacaggg gctggacgtg     540
accctgccac tgtcactgcc cacaagcgcc aggatagca acttctccgt gaaaaccgag     600
atgctgggaa atgagatcga cattgaatgc atcatggagg atggagaaat tagccaggtg     660
ctgcctggcg ataacaagtt taatatcacc tgttccggct acgaatctca cgtcccaagt     720
gggggaatcc tgacatctac tagtcccgtg gccactccaa ttcccggaac cggctacgct     780
tatagcctga gactgacccc taggccagtc tcacgcttcc tgggcaacaa tagcattctg     840
tacgtgtttt attccggaaa cggaccaaag gcttctggag gggactattg catccagagt     900
aatattgtgt tctcagacga gatcccagcc agccaggata tgcccactaa cactaccgac     960
```

```
attacctacg tgggcgataa tgccacttat tccgtgccta tggtcacaag cgaagacgct   1020 aactcccccaa atgtgaccgt cacagcattc tgggcctggc ccaacaatac tgagaccgat   1080
tttaagtgca aatggacact gacttcaggc accctagcg gtgtgaaaa catctctggc      1140 gccttcgcta gtaatcgaac ctttgatatt acagtgtccg gctggggac tgccccaaaa     1200 accctgatca ttacccggac agctactaac gcaacaacta ccacacacaa agtgatcttc    1260
agcaaagctc ccgagtccac taccacatct cctaccctga acactaccgg gtttgccgac    1320
cccaatacaa ctaccggact gcctagctcc acccatgtgc caacaaacct gactgcacca    1380
gcatccaccg gacctacagt gtctact                                       1407
```

<210> SEQ ID NO 38
<211> LENGTH: 469
<212> TYPE: PRT
<213> ORGANISM: Epstein Barr Virus

<400> SEQUENCE: 38

```
Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Gln Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Pro Tyr Ile Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
        195                 200                 205

Glu Cys Ile Met Glu Asp Gly Glu Ile Ser Gln Val Leu Pro Gly Asp
    210                 215                 220

Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
        275                 280                 285

Pro Lys Ala Ser Gly Gly Asp Tyr Cys Ile Gln Ser Asn Ile Val Phe
```

```
            290                 295                 300
Ser Asp Glu Ile Pro Ala Ser Gln Asp Met Pro Thr Asn Thr Thr Asp
305                 310                 315                 320

Ile Thr Tyr Val Gly Asp Asn Ala Thr Tyr Ser Val Pro Met Val Thr
                325                 330                 335

Ser Glu Asp Ala Asn Ser Pro Asn Val Thr Val Thr Ala Phe Trp Ala
            340                 345                 350

Trp Pro Asn Asn Thr Glu Thr Asp Phe Lys Cys Lys Trp Thr Leu Thr
                355                 360                 365

Ser Gly Thr Pro Ser Gly Cys Glu Asn Ile Ser Gly Ala Phe Ala Ser
            370                 375                 380

Asn Arg Thr Phe Asp Ile Thr Val Ser Gly Leu Gly Thr Ala Pro Lys
385                 390                 395                 400

Thr Leu Ile Ile Thr Arg Thr Ala Thr Asn Ala Thr Thr Thr His
                405                 410                 415

Lys Val Ile Phe Ser Lys Ala Pro Glu Ser Thr Thr Thr Ser Pro Thr
            420                 425                 430

Leu Asn Thr Thr Gly Phe Ala Asp Pro Asn Thr Thr Gly Leu Pro
                435                 440                 445

Ser Ser Thr His Val Pro Thr Asn Leu Thr Ala Pro Ala Ser Thr Gly
            450                 455                 460

Pro Thr Val Ser Thr
465

<210> SEQ ID NO 39
<211> LENGTH: 1407
<212> TYPE: DNA
<213> ORGANISM: Epstein Barr Virus

<400> SEQUENCE: 39
agtagacact gtaggtccgg tggatgctgg tgcagtcagg tttgttggca catgggtgga    60
gctaggcagt ccggtagttg tattggggtc ggcaaacccg gtagtgttca gggtaggaga   120
tgtggtagtg gactcgggag ctttgctgaa gatcactttg tgtgtggtag ttgttgcgtt   180
agtagctgtc cgggtaatga tcagggtttt tggggcagtc cccaggccgg acactgtaat   240
atcaaaggtt cgattactag cgaaggcgcc agagatgttt tcacacccgc taggggtgcc   300
tgaagtcagt gtccatttgc acttaaaatc ggtctcagta ttgttgggcc aggcccagaa   360
tgctgtgacg tcacatttgg ggagttagc gtcttcgctt gtgaccatag cacggaata    420 agtggcatta tcgcccacgt aggtaatgtc ggtagtgtta gtgggcatat cctggctggc   480
tgggatctcg tctgagaaca caatattact ctggatgcaa tagtcccctc cagaagcctt   540
tggtccgttt ccgaataaaa acacgtacag aatgctattg ttgcccagga agcgtgagac   600
tggcctaggg gtcagtctca ggctataagc gtagccggtt ccgggaattg gagtggccac   660
gggactagta gatgtcagga ttcccccact tgggacgtga gattcgtagc cggaacaggt   720
gatattaaac ttgttatcgc caggcagcac ctggctaatt tctccatcct ccatgatgca   780
ttcaatgtcg atctcatttc ccagcatctc ggttttcacg gagaagttgc tatcctgggc   840
gcttgtgggc agtgacagtg gcagggtcac gtccagcccc tgtgcccgga ccactgcggt   900
aatgttagtg ctattacagt tgtcccactt aatataaggg acggtttcgg ggatcaggta   960
cacaggattc tgcatctcgg catggtggca ccacatggtg ccaaacacat cctggaagta  1020
gacgtccact gattccagac tgacctgctg ttcctctcct gtggtcacat tgatgggcag  1080
```

-continued

```
tttcttggac ctcatggtca gagccagttc tcctgctccc agcagctcca gcagaaacag   1140
atttgttgcg ttctcgctgc ctccgaaagc ccctctgggc tgatacacgg cttttgtatg   1200
tggggtcagc tggccaaaat ccaggtccag ctggtgtttc ttcccgccca catcgaaatt   1260
aatggtgacg ttcacgtcgg ctgtacagac gttgcaggtg gggtaaaatg ggaactcagg   1320
gatttccaca ttgaaaaatc cagggtcctc cccggtcaga tgaatcaggc tctgaatagt   1380
gtactggcac accagcaggg cggcttc                                        1407

<210> SEQ ID NO 40
<211> LENGTH: 450
<212> TYPE: DNA
<213> ORGANISM: Epstein Barr Virus

<400> SEQUENCE: 40
gccctgctgg tgtgccagta cactattcag agcctgattc atctgaccgg ggaggaccct     60
ggatttttca atgtggaaat ccctgagttc ccattttacc ccacctgcaa cgtctgtaca    120
gccgacgtga acgtcaccat taatttcgat gtgggcggga agaaacacca gctggacctg    180
gattttggcc agctgacccc acatacaaaa gccgtgtatc agcccagagg ggctttcgga    240
ggcagcgaga acgcaacaaa tctgtttctg ctggagctgc tgggagcagg agaactggct    300
ctgaccatga ggtccaagaa actgcccatc aatgtgacca caggagagga acagcaggtc    360
agtctggaat cagtggacgt ctacttccag gatgtgtttg gcaccatgtg gtgccaccat    420
gccgagatgc agaatcctgt gtacctgatc                                     450

<210> SEQ ID NO 41
<211> LENGTH: 150
<212> TYPE: PRT
<213> ORGANISM: Epstein Barr Virus

<400> SEQUENCE: 41

Ala Leu Leu Val Cys Gln Tyr Thr Ile Gln Ser Leu Ile His Leu Thr
1               5                   10                  15

Gly Glu Asp Pro Gly Phe Phe Asn Val Glu Ile Pro Glu Phe Pro Phe
            20                  25                  30

Tyr Pro Thr Cys Asn Val Cys Thr Ala Asp Val Asn Val Thr Ile Asn
        35                  40                  45

Phe Asp Val Gly Gly Lys Lys His Gln Leu Asp Leu Asp Phe Gly Gln
    50                  55                  60

Leu Thr Pro His Thr Lys Ala Val Tyr Gln Pro Arg Gly Ala Phe Gly
65                  70                  75                  80

Gly Ser Glu Asn Ala Thr Asn Leu Phe Leu Leu Glu Leu Leu Gly Ala
                85                  90                  95

Gly Glu Leu Ala Leu Thr Met Arg Ser Lys Lys Leu Pro Ile Asn Val
            100                 105                 110

Thr Thr Gly Glu Glu Gln Gln Val Ser Leu Glu Ser Val Asp Val Tyr
        115                 120                 125

Phe Gln Asp Val Phe Gly Thr Met Trp Cys His His Ala Glu Met Gln
    130                 135                 140

Asn Pro Val Tyr Leu Ile
145                 150

<210> SEQ ID NO 42
<211> LENGTH: 450
<212> TYPE: DNA
<213> ORGANISM: Epstein Barr Virus
```

<400> SEQUENCE: 42

```
gatcaggtac acaggattct gcatctcggc atggtggcac cacatggtgc aaacacatc    60
ctggaagtag acgtccactg attccagact gacctgctgt tcctctcctg tggtcacatt  120
gatgggcagt ttcttggacc tcatggtcag agccagttct cctgctccca gcagctccag  180
cagaaacaga tttgttgcgt tctcgctgcc tccgaaagcc cctctgggct gatacacggc  240
ttttgtatgt ggggtcagct ggccaaaatc caggtccagc tggtgtttct tcccgcccac  300
atcgaaatta atggtgacgt tcacgtcggc tgtacagacg ttgcaggtgg ggtaaaatgg  360
gaactcaggg atttccacat tgaaaaatcc agggtcctcc ccggtcagat gaatcaggct  420
ctgaatagtg tactggcaca ccagcagggc                                   450
```

<210> SEQ ID NO 43
<211> LENGTH: 423
<212> TYPE: DNA
<213> ORGANISM: Epstein Barr Virus

<400> SEQUENCE: 43

```
tgtaatagca ctaacattac cgcagtggtc cgggcacagg ggctggacgt gaccctgcca   60
ctgtcactgc ccacaagcgc ccaggatagc aacttctccg tgaaaaccga gatgctggga  120
aatgagatcg acattgaatg catcatggag gatggagaaa ttagccaggt gctgcctggc  180
gataacaagt ttaatatcac ctgttccggc tacgaatctc acgtcccaag tgggggaatc  240
ctgacatcta ctagtcccgt ggccactcca attcccggaa ccggctacgc ttatagcctg  300
agactgaccc ctaggccagt ctcacgcttc ctgggcaaca atagcattct gtacgtgttt  360
tattccggaa acggaccaaa ggcttctgga ggggactatt gcatccagag taatattgtg  420
ttc                                                                 423
```

<210> SEQ ID NO 44
<211> LENGTH: 141
<212> TYPE: PRT
<213> ORGANISM: Epstein Barr Virus

<400> SEQUENCE: 44

```
Cys Asn Ser Thr Asn Ile Thr Ala Val Val Arg Ala Gln Gly Leu Asp
1               5                   10                  15
Val Thr Leu Pro Leu Ser Leu Pro Thr Ser Ala Gln Asp Ser Asn Phe
            20                  25                  30
Ser Val Lys Thr Glu Met Leu Gly Asn Glu Ile Asp Ile Glu Cys Ile
        35                  40                  45
Met Glu Asp Gly Glu Ile Ser Gln Val Leu Pro Gly Asp Asn Lys Phe
    50                  55                  60
Asn Ile Thr Cys Ser Gly Tyr Glu Ser His Val Pro Ser Gly Gly Ile
65                  70                  75                  80
Leu Thr Ser Thr Ser Pro Val Ala Thr Pro Ile Pro Gly Thr Gly Tyr
                85                  90                  95
Ala Tyr Ser Leu Arg Leu Thr Pro Arg Pro Val Ser Arg Phe Leu Gly
            100                 105                 110
Asn Asn Ser Ile Leu Tyr Val Phe Tyr Ser Gly Asn Gly Pro Lys Ala
        115                 120                 125
Ser Gly Gly Asp Tyr Cys Ile Gln Ser Asn Ile Val Phe
    130                 135                 140
```

<210> SEQ ID NO 45
<211> LENGTH: 423
<212> TYPE: DNA
<213> ORGANISM: Epstein Barr Virus

<400> SEQUENCE: 45

```
gaacacaata ttactctgga tgcaatagtc ccctccagaa gcctttggtc cgtttccgga      60
ataaaacacg tacagaatgc tattgttgcc caggaagcgt gagactggcc tagggggtcag    120 tctcaggcta taagcgtagc cggttccggg aattggagtg ccacgggac tagtagatgt      180 caggattccc ccacttggga cgtgagattc gtagccggaa caggtgatat aaacttgtt     240 atcgccaggc agcacctggc taatttctcc atcctccatg atgcattcaa tgtcgatctc     300
atttcccagc atctcggttt tcacggagaa gttgctatcc tgggcgcttg tgggcagtga    360
cagtggcagg gtcacgtcca gccctgtgc ccggaccact gcggtaatgt tagtgctatt     420
aca                                                                  423
```

<210> SEQ ID NO 46
<211> LENGTH: 330
<212> TYPE: DNA
<213> ORGANISM: Epstein Barr Virus

<400> SEQUENCE: 46

```
actaacacta ccgacattac ctacgtgggc gataatgcca cttattccgt gcctatggtc     60
acaagcgaag acgctaactc cccaaatgtg accgtcacag cattctgggc ctggcccaac    120
aatactgaga ccgatttaa gtgcaaatgg acactgactt caggcaccc tagcgggtgt     180 gaaaacatct ctggcgcctt cgctagtaat cgaaccttg atattacagt gtccggcctg    240
gggactgccc caaaaaccct gatcattacc cggacagcta ctaacgcaac aactaccaca    300
cacaaagtga tcttcagcaa agctcccgag                                     330
```

<210> SEQ ID NO 47
<211> LENGTH: 110
<212> TYPE: PRT
<213> ORGANISM: Epstein Barr Virus

<400> SEQUENCE: 47

Thr Asn Thr Thr Asp Ile Thr Tyr Val Gly Asp Asn Ala Thr Tyr Ser
1               5                   10                  15

Val Pro Met Val Thr Ser Glu Asp Ala Asn Ser Pro Asn Val Thr Val
                20                  25                  30

Thr Ala Phe Trp Ala Trp Pro Asn Asn Thr Glu Thr Asp Phe Lys Cys
            35                  40                  45

Lys Trp Thr Leu Thr Ser Gly Thr Pro Ser Gly Cys Glu Asn Ile Ser
    50                  55                  60

Gly Ala Phe Ala Ser Asn Arg Thr Phe Asp Ile Thr Val Ser Gly Leu
65                  70                  75                  80

Gly Thr Ala Pro Lys Thr Leu Ile Ile Thr Arg Thr Ala Thr Asn Ala
                85                  90                  95

Thr Thr Thr Thr His Lys Val Ile Phe Ser Lys Ala Pro Glu
            100                 105                 110

<210> SEQ ID NO 48
<211> LENGTH: 330
<212> TYPE: DNA
<213> ORGANISM: Epstein Barr Virus

<400> SEQUENCE: 48

```
ctcgggagct tgctgaaga tcactttgtg tgtggtagtt gttgcgttag tagctgtccg        60
ggtaatgatc agggtttttg gggcagtccc caggccggac actgtaatat caaaggttcg       120
attactagcg aaggcgccag agatgttttc acaccgcta ggggtgcctg aagtcagtgt        180
ccatttgcac ttaaaatcgg tctcagtatt gttgggccag gcccagaatg ctgtgacggt       240
cacatttggg gagttagcgt cttcgcttgt gaccataggc acggaataag tggcattatc       300
gcccacgtag gtaatgtcgg tagtgttagt                                        330

<210> SEQ ID NO 49
<211> LENGTH: 948
<212> TYPE: DNA
<213> ORGANISM: Epstein Barr Virus

<400> SEQUENCE: 49
gaagccgccc tgctggtgtg ccagtacact attcagagcc tgattcatct gaccggggag        60
gaccctggat ttttcaatgt ggaaatccct gagttcccat tttaccccac ctgcaacgtc       120
tgtacagccg acgtgaacgt caccattaat ttcgatgtgg gcgggaagaa acaccagctg       180
gacctggatt ttggccagct gaccccacat acaaaagccg tgtatcagcc cagagggggct      240 ttcggaggca gcgagaacgc aacaaatctg tttctgctgg agctgctggg agcaggagaa       300
ctggctctga ccatgaggtc caagaaactg cccatcaatg tgaccacagg agaggaacag       360
caggtcagtc tggaatcagt ggacgtctac ttccaggatg tgtttggcac catgtggtgc       420
caccatgccg agatgcagaa tcctgtgtac ctgatccccg aaaccgtccc ttatattaag       480
tgggacaact gtaatagcac taacattacc gcagtggtcc gggcacaggg gctggacgtg       540
accctgccac tgtcactgcc cacaagcgcc caggatagca acttctccgt gaaaaccgag       600
atgctgggaa atgagatcga cattgaatgc atcatggagg atggagaaat tagccaggtg       660
ctgcctggcg ataacaagtt taatatcacc tgttccggct acgaatctca cgtcccaagt       720
gggggaatcc tgacatctac tagtcccgtg gccactccaa ttcccggaac cggctacgct       780
tatagcctga gactgacccc taggccagtc tcacgcttcc tgggcaacaa tagcattctg       840
tacgtgtttt attccggaaa cggaccaaag gcttctggag gggactattg catccagagt       900
aatattgtgt ctcagacgaa gatcccagcc agccaggata tgcccact                   948

<210> SEQ ID NO 50
<211> LENGTH: 316
<212> TYPE: PRT
<213> ORGANISM: Epstein Barr Virus

<400> SEQUENCE: 50

Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95
```

Gly Ala Gly Glu Leu Ala Leu Thr Met Arg Ser Lys Lys Leu Pro Ile
            100                 105                 110

Asn Val Thr Thr Gly Glu Glu Gln Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Pro Tyr Ile Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
        195                 200                 205

Glu Cys Ile Met Glu Asp Gly Glu Ile Ser Gln Val Leu Pro Gly Asp
    210                 215                 220

Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
        275                 280                 285

Pro Lys Ala Ser Gly Gly Asp Tyr Cys Ile Gln Ser Asn Ile Val Phe
    290                 295                 300

Ser Asp Glu Ile Pro Ala Ser Gln Asp Met Pro Thr
305                 310                 315

<210> SEQ ID NO 51
<211> LENGTH: 948
<212> TYPE: DNA
<213> ORGANISM: Epstein Barr Virus

<400> SEQUENCE: 51
agtgggcata tcctggctgg ctgggatctc gtctgagaac acaatattac tctggatgca      60
atagtcccct ccagaagcct ttggtccgtt tccggaataa acacgtaca gaatgctatt     120 gttgcccagg aagcgtgaga ctggcctagg ggtcagtctc aggctataag cgtagccggt     180
tccgggaatt ggagtggcca cgggactagt agatgtcagg attcccccac ttgggacgtg     240
agattcgtag ccggaacagg tgatattaaa cttgttatcg ccaggcagca cctggctaat     300
ttctccatcc tccatgatgc attcaatgtc gatctcattt cccagcatct cggttttcac     360
ggagaagttg ctatcctggg cgcttgtggg cagtgacagt ggcagggtca cgtccagccc     420
ctgtgcccgg accactgcgg taatgttagt gctattacag ttgtcccact aatataagg     480 gacggtttcg gggatcaggt acacaggatt ctgcatctcg gcatggtggc accacatggt     540
gccaaacaca tcctggaagt agacgtccac tgattccaga ctgacctgct gttcctctcc     600
tgtggtcaca ttgatgggca gtttcttgga cctcatggtc agagccagtt ctcctgctcc     660
cagcagctcc agcagaaaca gatttgttgc gttctcgctg cctccgaaag ccctctgggg     720
ctgatacacg gcttttgtat gtggggtcag ctggccaaaa tccaggtcca gctggtgttt     780 cttccccgccc acatcgaaat taatggtgac gttcacgtcg gctgtacaga cgttgcaggt     840
ggggtaaaat gggaactcag ggatttccac attgaaaaat ccagggtcct ccccggtcag     900

```
atgaatcagg ctctgaatag tgtactggca caccagcagg gcggcttc                948
```

<210> SEQ ID NO 52
<211> LENGTH: 1272
<212> TYPE: DNA
<213> ORGANISM: Epstein Barr Virus

<400> SEQUENCE: 52

```
gaagccgccc tgctggtgtg ccagtacact attcagagcc tgattcatct gaccggggag     60
gaccctggat ttttcaatgt ggaaatccct gagttcccat tttaccccac ctgcaacgtc    120
tgtacagccg acgtgaacgt caccattaat ttcgatgtgg gcgggaagaa acaccagctg    180
gacctggatt ttggccagct gaccccacat acaaaagccg tgtatcagcc cagaggggct    240
ttcggaggca gcgagaacgc aacaaatctg tttctgctgg agctgctggg agcaggagaa    300
ctggctctga ccatgaggtc caagaaactg cccatcaatg tgaccacagg agaggaacag    360
caggtcagtc tggaatcagt ggacgtctac ttccaggatg tgtttggcac catgtggtgc    420
caccatgccg agatgcagaa tcctgtgtac ctgatccccg aaaccgtccc ttatattaag    480
tgggacaact gtaatagcac taacattacc gcagtggtcc gggcacaggg gctggacgtg    540
accctgccac tgtcactgcc cacaagcgcc caggatagca acttctccgt gaaaaccgag    600
atgctgggaa atgagatcga cattgaatgc atcatggagg atggagaaat tagccaggtg    660
ctgcctggcg ataacaagtt taatatcacc tgttccggct acgaatctca cgtcccaagt    720
gggggaatcc tgcatctcta tagtcccgtg gccactccaa ttcccggaac cggctacgct    780
tatagcctga gactgacccc taggccagtc tcacgcttcc tgggcaacaa tagcattctg    840
tacgtgtttt attccggaaa cggaccaaag gcttctggag gggactattg catccagagt    900
aatattgtgt tctcagacga gatcccagcc agccaggata tgcccactaa cactaccgac    960
attacctacg tgggcgataa tgccacttat tccgtgccta tggtcacaag cgaagacgct   1020
aactccccaa atgtgaccgt cacagcattc tgggcctggc ccaacaatac tgagaccgat   1080
tttaagtgca atggacacct gacttcaggc accccctagcg ggtgtgaaaa catctctggc   1140
gccttcgcta gtaatcgaac ctttgatatt acagtgtccg gctgggac tgccccaaaa   1200
accctgatca ttacccggac agctactaac gcaacaacta ccacacacaa agtgatcttc   1260
agcaaagctc cc                                                      1272
```

<210> SEQ ID NO 53
<211> LENGTH: 424
<212> TYPE: PRT
<213> ORGANISM: Epstein Barr Virus

<400> SEQUENCE: 53

Glu Ala Ala Leu Leu Val Cys Gln Tyr Thr Ile Gln Ser Leu Ile His
1 5 10 15

Leu Thr Gly Glu Asp Pro Gly Phe Phe Asn Val Glu Ile Pro Glu Phe
20 25 30

Pro Phe Tyr Pro Thr Cys Asn Val Cys Thr Ala Asp Val Asn Val Thr
35 40 45

Ile Asn Phe Asp Val Gly Gly Lys Lys His Gln Leu Asp Leu Asp Phe
50 55 60

Gly Gln Leu Thr Pro His Thr Lys Ala Val Tyr Gln Pro Arg Gly Ala
65 70 75 80

Phe Gly Gly Ser Glu Asn Ala Thr Asn Leu Phe Leu Leu Glu Leu Leu 85                  90                  95
Gly Ala Gly Glu Leu Ala Leu Thr Met Arg Ser Lys Lys Leu Pro Ile
            100                 105                 110
Asn Val Thr Thr Gly Glu Glu Gln Gln Val Ser Leu Glu Ser Val Asp
            115                 120                 125
Val Tyr Phe Gln Asp Val Phe Gly Thr Met Trp Cys His His Ala Glu
            130                 135                 140
Met Gln Asn Pro Val Tyr Leu Ile Pro Glu Thr Val Pro Tyr Ile Lys
145                 150                 155                 160
Trp Asp Asn Cys Asn Ser Thr Asn Ile Thr Ala Val Arg Ala Gln
                165                 170                 175
Gly Leu Asp Val Thr Leu Pro Leu Ser Leu Pro Thr Ser Ala Gln Asp
            180                 185                 190
Ser Asn Phe Ser Val Lys Thr Glu Met Leu Gly Asn Glu Ile Asp Ile
            195                 200                 205
Glu Cys Ile Met Glu Asp Gly Glu Ile Ser Gln Val Leu Pro Gly Asp
    210                 215                 220
Asn Lys Phe Asn Ile Thr Cys Ser Gly Tyr Glu Ser His Val Pro Ser
225                 230                 235                 240
Gly Gly Ile Leu Thr Ser Thr Ser Pro Val Ala Thr Pro Ile Pro Gly
                245                 250                 255
Thr Gly Tyr Ala Tyr Ser Leu Arg Leu Thr Pro Arg Pro Val Ser Arg
            260                 265                 270
Phe Leu Gly Asn Asn Ser Ile Leu Tyr Val Phe Tyr Ser Gly Asn Gly
            275                 280                 285
Pro Lys Ala Ser Gly Gly Asp Tyr Cys Ile Gln Ser Asn Ile Val Phe
        290                 295                 300
Ser Asp Glu Ile Pro Ala Ser Gln Asp Met Pro Thr Asn Thr Thr Asp
305                 310                 315                 320
Ile Thr Tyr Val Gly Asp Asn Ala Thr Tyr Ser Val Pro Met Val Thr
                325                 330                 335
Ser Glu Asp Ala Asn Ser Pro Asn Val Thr Val Thr Ala Phe Trp Ala
            340                 345                 350
Trp Pro Asn Asn Thr Glu Thr Asp Phe Lys Cys Lys Trp Thr Leu Thr
            355                 360                 365
Ser Gly Thr Pro Ser Gly Cys Glu Asn Ile Ser Gly Ala Phe Ala Ser
        370                 375                 380
Asn Arg Thr Phe Asp Ile Thr Val Ser Gly Leu Gly Thr Ala Pro Lys
385                 390                 395                 400
Thr Leu Ile Ile Thr Arg Thr Ala Thr Asn Ala Thr Thr Thr His
                405                 410                 415
Lys Val Ile Phe Ser Lys Ala Pro
            420

<210> SEQ ID NO 54
<211> LENGTH: 1272
<212> TYPE: DNA
<213> ORGANISM: Epstein Barr Virus

<400> SEQUENCE: 54
gggagctttg ctgaagatca ctttgtgtgt ggtagttgtt gcgttagtag ctgtccgggt    60
aatgatcagg gttttggggg cagtccccag gccggacact gtaatatcaa aggttcgatt   120
actagcgaag gcgccagaga tgttttcaca cccgctaggg gtgcctgaag tcagtgtcca   180

| | | | |
|---|---|---|---|
| tttgcactta | aaatcggtct | cagtattgtt gggccaggcc | cagaatgctg tgacggtcac | 240 |
| atttggggag | ttagcgtctt | cgcttgtgac cataggcacg | gaataagtgg cattatcgcc | 300 |
| cacgtaggta | atgtcggtag | tgttagtggg catatcctgg | ctggctggga tctcgtctga | 360 |
| gaacacaata | ttactctgga | tgcaatagtc ccctccagaa | gcctttggtc cgtttccgga | 420 |
| ataaaacacg | tacagaatgc | tattgttgcc caggaagcgt | gagactggcc tagggGtcag | 480 |
| tctcaggcta | taagcgtagc | cggttccggg aattggagtg | gccacgggac tagtagatgt | 540 |
| caggattccc | ccacttggga | cgtgagattc gtagccggaa | caggtgatat taaacttgtt | 600 |
| atcgccaggc | agcacctggc | taatttctcc atcctccatg | atgcattcaa tgtcgatctc | 660 |
| atttcccagc | atctcggttt | tcacggagaa gttgctatcc | tgggcgcttg tgggcagtga | 720 |
| cagtggcagg | gtcacgtcca | gcccctgtgc ccggaccact | gcggtaatgt tagtgctatt | 780 |
| acagttgtcc | cacttaatat | aagggacggt ttcggggatc | aggtacacag gattctgcat | 840 |
| ctcggcatgg | tggcaccaca | tggtgccaaa cacatcctgg | aagtagacgt ccactgattc | 900 |
| cagactgacc | tgctgttcct | ctcctgtggt cacattgatg | ggcagtttct tggacctcat | 960 |
| ggtcagagcc | agttctcctg | ctcccagcag ctccagcaga | aacagatttg ttgcgttctc | 1020 |
| gctgcctccg | aaagcccctc | tgggctgata cacggcttt | gtatgtgggg tcagctggcc | 1080 |
| aaaatccagg | tccagctggt | gttcttccc gcccacatcg | aaattaatgg tgacgttcac | 1140 |
| gtcggctgta | cagacgttgc | aggtgggta aatgggaac | tcaggatttt ccacattgaa | 1200 |
| aaatccaggg | tcctccccgg | tcagatgaat caggctctga | atagtgtact ggcacaccag | 1260 |
| cagggcggct | tc | | | 1272 |

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61
<211> LENGTH: 2118
<212> TYPE: DNA
<213> ORGANISM: Epstein Barr Virus

<400> SEQUENCE: 61

| | | | | | |
|---|---|---|---|---|---|
| atgcagctcc | tgtgcgtgtt | ctgtctggtg | ctgctgtggg | aagtgggagc | cgcttctctg | 60 |
| agtgaggtga | agctgcacct | ggacattgaa | ggccacgcct | cccattacac | tatcccttgg | 120 |
| accgagctga | tggctaaagt | gccaggactg | tctcctgagg | ctctgtggcg | ggaagctaat | 180 |
| gtgaccgagg | atctggcctc | tatgctgaac | agatacaagc | tgatctataa | aaccagtggc | 240 |
| acactgggga | ttgctctggc | tgagccagtg | acatccccg | ccgtgtcaga | aggaagcatg | 300 |
| caggtggatg | ctagtaaggt | gcatccaggg | gtgattagcg | gactgaacag | cccagcttgc | 360 |
| atgctgagcg | ctcctctgga | gaaacagctc | ttctactata | tcggcaccat | gctgcctaat | 420 |
| acacggccac | acagctacgt | gttttatcag | ctcagatgtc | atctgtccta | cgtggccctg | 480 |
| tctattaacg | ggacaagtt | ccagtataca | ggagctatga | cttccaaatt | tctgatggga | 540 |
| acttacaagc | gggtgaccga | gaaaggcgat | gaacacgtgc | tgtctctggt | gttcgggaag | 600 |
| acaaaagacc | tgcccgatct | gagaggaccc | ttttcctacc | cttctctgac | tagtgcccag | 660 |
| tcaggcgact | atagcctggt | gatcgtgacc | acattcgtgc | actacgctaa | cttccataat | 720 |
| tattttgtgc | ccaatctgaa | ggatatgttt | tcccgggccg | tgaccatgac | agccgcttct | 780 |
| tacgctagat | atgtgctgca | gaagctggtg | ctgctggaga | tgaaaggcgg | gtgccgggag | 840 |
| cctgaactgg | acactgaaac | cctgactacc | atgttcgagg | tgtccgtggc | cttctttaaa | 900 |
| gtgggacacg | ctgtgggaga | gacaggaaac | ggatgcgtgg | acctgagatg | gctggccaag | 960 |
| agcttctttg | aactgaccgt | gctgaaagat | atcattggaa | tctgttacgg | cgccacagtg | 1020 |
| aaaggaatgc | agagctatgg | cctggagagg | ctggccgcta | tgctgatggc | caccgtgaag | 1080 |
| atggaggaac | tgggccacct | gacaactgag | aaacaggaat | acgctctgag | gctggctacc | 1140 |
| gtgggatacc | caaaggccgg | ggtgtattcc | ggactgattg | gaggcgccac | atctgtgctg | 1200 |
| ctgagtgctt | ataataggca | cccactgttc | cagcccctgc | atacagtgat | gcgcgagact | 1260 |
| ctgtttatcg | ggtctcatgt | ggtgctgcgg | gaactgagac | tgaatgtgac | cacacaggga | 1320 |
| cccaacctgg | ccctgtacca | gctcctgagt | actgccctgt | gctcagctct | ggagattgga | 1380 |
| gaagtgctga | ggggactggc | cctggggacc | gagtcaggac | tgttcagccc | ttgttatctg | 1440 |
| tcactgaggt | ttgacctgac | tcgcgataag | ctgctgagca | tggccccaca | ggaagctacc | 1500 |
| ctggaccagg | ccgctgtgag | caatgccgtg | gatggattcc | tgggcaggct | gtccctggag | 1560 |
| agggaagacc | gcgatgcctg | gcacctgcca | gcttacaagt | gcgtggaccg | cctggataaa | 1620 |
| gtgctgatga | tcattcccct | gatcaacgtg | accttcatca | ttagctccga | cagggaagtg | 1680 |
| agaggcagcg | ctctgtacga | agcttccact | acctatctgt | ctagttcact | gtttctgtca | 1740 |
| cctgtgatta | tgaataagtg | tagccaggga | gctgtggctg | gagagcccag | acagatccca | 1800 |
| aagattcaga | acttcacacg | cactcagaaa | agttgcatct | tctgtggctt | tgccctgctg | 1860 |
| tcatacgatg | agaagaagg | gctggagaca | actacctata | ttacatctca | ggaagtgcag | 1920 |
| aacagtatcc | tgagctccaa | ttacttcgac | tttgataacc | tgcacgtgca | ttatctgctg | 1980 |
| ctgacaacta | acggcaccgt | gatggagatc | gctggactgt | acgaggaaag | ggctcacgtg | 2040 |
| gtgctggcta | tcattctgta | tttcatcgcc | tttgctctgg | gcattttct | ggtgcataag | 2100 | atcgtgatgt tctttctg                                                    2118

<210> SEQ ID NO 62
<211> LENGTH: 706
<212> TYPE: PRT
<213> ORGANISM: Epstein Barr Virus

<400> SEQUENCE: 62

```
Met Gln Leu Leu Cys Val Phe Cys Leu Val Leu Leu Trp Glu Val Gly
1               5                   10                  15

Ala Ala Ser Leu Ser Glu Val Lys Leu His Leu Asp Ile Glu Gly His
                20                  25                  30

Ala Ser His Tyr Thr Ile Pro Trp Thr Glu Leu Met Ala Lys Val Pro
            35                  40                  45

Gly Leu Ser Pro Glu Ala Leu Trp Arg Glu Ala Asn Val Thr Glu Asp
    50                  55                  60

Leu Ala Ser Met Leu Asn Arg Tyr Lys Leu Ile Tyr Lys Thr Ser Gly
65                  70                  75                  80

Thr Leu Gly Ile Ala Leu Ala Glu Pro Val Asp Ile Pro Ala Val Ser
                85                  90                  95

Glu Gly Ser Met Gln Val Asp Ala Ser Lys Val His Pro Gly Val Ile
            100                 105                 110

Ser Gly Leu Asn Ser Pro Ala Cys Met Leu Ser Ala Pro Leu Glu Lys
        115                 120                 125

Gln Leu Phe Tyr Tyr Ile Gly Thr Met Leu Pro Asn Thr Arg Pro His
    130                 135                 140

Ser Tyr Val Phe Tyr Gln Leu Arg Cys His Leu Ser Tyr Val Ala Leu
145                 150                 155                 160

Ser Ile Asn Gly Asp Lys Phe Gln Tyr Thr Gly Ala Met Thr Ser Lys
                165                 170                 175

Phe Leu Met Gly Thr Tyr Lys Arg Val Thr Glu Lys Gly Asp Glu His
            180                 185                 190

Val Leu Ser Leu Val Phe Gly Lys Thr Lys Asp Leu Pro Asp Leu Arg
        195                 200                 205

Gly Pro Phe Ser Tyr Pro Ser Leu Thr Ser Ala Gln Ser Gly Asp Tyr
    210                 215                 220

Ser Leu Val Ile Val Thr Thr Phe Val His Tyr Ala Asn Phe His Asn
225                 230                 235                 240

Tyr Phe Val Pro Asn Leu Lys Asp Met Phe Ser Arg Ala Val Thr Met
                245                 250                 255

Thr Ala Ala Ser Tyr Ala Arg Tyr Val Leu Gln Lys Leu Val Leu Leu
            260                 265                 270

Glu Met Lys Gly Gly Cys Arg Glu Pro Glu Leu Asp Thr Glu Thr Leu
        275                 280                 285

Thr Thr Met Phe Glu Val Ser Val Ala Phe Phe Lys Val Gly His Ala
    290                 295                 300

Val Gly Glu Thr Gly Asn Gly Cys Val Asp Leu Arg Trp Leu Ala Lys
305                 310                 315                 320

Ser Phe Phe Glu Leu Thr Val Leu Lys Asp Ile Ile Gly Ile Cys Tyr
                325                 330                 335

Gly Ala Thr Val Lys Gly Met Gln Ser Tyr Gly Leu Glu Arg Leu Ala
            340                 345                 350

Ala Met Leu Met Ala Thr Val Lys Met Glu Glu Leu Gly His Leu Thr
        355                 360                 365
```

```
Thr Glu Lys Gln Glu Tyr Ala Leu Arg Leu Ala Thr Val Gly Tyr Pro
    370                 375                 380

Lys Ala Gly Val Tyr Ser Gly Leu Ile Gly Gly Ala Thr Ser Val Leu
385                 390                 395                 400

Leu Ser Ala Tyr Asn Arg His Pro Leu Phe Gln Pro Leu His Thr Val
                405                 410                 415

Met Arg Glu Thr Leu Phe Ile Gly Ser His Val Val Leu Arg Glu Leu
            420                 425                 430

Arg Leu Asn Val Thr Thr Gln Gly Pro Asn Leu Ala Leu Tyr Gln Leu
        435                 440                 445

Leu Ser Thr Ala Leu Cys Ser Ala Leu Glu Ile Gly Glu Val Leu Arg
450                 455                 460

Gly Leu Ala Leu Gly Thr Glu Ser Gly Leu Phe Ser Pro Cys Tyr Leu
465                 470                 475                 480

Ser Leu Arg Phe Asp Leu Thr Arg Asp Lys Leu Leu Ser Met Ala Pro
                485                 490                 495

Gln Glu Ala Thr Leu Asp Gln Ala Ala Val Ser Asn Ala Val Asp Gly
            500                 505                 510

Phe Leu Gly Arg Leu Ser Leu Glu Arg Glu Asp Arg Asp Ala Trp His
        515                 520                 525

Leu Pro Ala Tyr Lys Cys Val Asp Arg Leu Asp Lys Val Leu Met Ile
530                 535                 540

Ile Pro Leu Ile Asn Val Thr Phe Ile Ile Ser Ser Asp Arg Glu Val
545                 550                 555                 560

Arg Gly Ser Ala Leu Tyr Glu Ala Ser Thr Thr Tyr Leu Ser Ser Ser
                565                 570                 575

Leu Phe Leu Ser Pro Val Ile Met Asn Lys Cys Ser Gln Gly Ala Val
            580                 585                 590

Ala Gly Glu Pro Arg Gln Ile Pro Lys Ile Gln Asn Phe Thr Arg Thr
        595                 600                 605

Gln Lys Ser Cys Ile Phe Cys Gly Phe Ala Leu Leu Ser Tyr Asp Glu
610                 615                 620

Lys Glu Gly Leu Glu Thr Thr Thr Tyr Ile Thr Ser Gln Glu Val Gln
625                 630                 635                 640

Asn Ser Ile Leu Ser Ser Asn Tyr Phe Asp Phe Asp Asn Leu His Val
                645                 650                 655

His Tyr Leu Leu Leu Thr Thr Asn Gly Thr Val Met Glu Ile Ala Gly
            660                 665                 670

Leu Tyr Glu Glu Arg Ala His Val Val Leu Ala Ile Ile Leu Tyr Phe
        675                 680                 685

Ile Ala Phe Ala Leu Gly Ile Phe Leu Val His Lys Ile Val Met Phe
690                 695                 700

Phe Leu
705

<210> SEQ ID NO 63
<211> LENGTH: 2118
<212> TYPE: DNA
<213> ORGANISM: Epstein Barr Virus

<400> SEQUENCE: 63
cagaaagaac atcacgatct tatgcaccag aaaaatgccc agagcaaagg cgatgaaata      60
cagaatgata gccagcacca cgtgagccct ttcctcgtac agtccagcga tctccatcac     120
ggtgccgtta gttgtcagca gcagataatg cacgtgcagg ttatcaaagt cgaagtaatt     180
```

```
ggagctcagg atactgttct gcacttcctg agatgtaata taggtagttg tctccagccc      240
ttctttctca tcgtatgaca gcagggcaaa gccacagaag atgcaacttt tctgagtgcg      300
tgtgaagttc tgaatctttg ggatctgtct gggctctcca gccacagctc cctggctaca      360
cttattcata atcacaggtg acagaaacag tgaactagac agataggtag tggaagcttc      420
gtacagagcg ctgcctctca cttccctgtc ggagctaatg atgaaggtca cgttgatcag      480
gggaatgatc atcagcactt tatccaggcg gtccacgcac ttgtaagctg gcaggtgcca      540
ggcatcgcgg tcttccctct ccagggacag cctgcccagg aatccatcca cggcattgct      600
cacagcggcc tggtccaggg tagcttcctg tggggccatg ctcagcagct tatcgcgagt      660
caggtcaaac ctcagtgaca gataacaagg gctgaacagt cctgactcgg tccccagggc      720
cagtcccctc agcacttctc caatctccag agctgagcac agggcagtac tcaggagctg      780
gtacagggcc aggttgggtc cctgtgtggt cacattcagt ctcagttccc gcagcaccac      840
atgagacccg ataaacagag tctcgcgcat cactgtatgc aggggctgga acagtgggtg      900
cctattataa gcactcagca gcacagatgt ggcgcctcca atcagtccgg aatacacccc      960
ggcctttggg tatcccacgg tagccagcct cagagcgtat tcctgtttct cagttgtcag     1020
gtggcccagt cctccatctt tcacggtggc catcagcata gcggccagcc tctccaggcc     1080
atagctctgc attcctttca ctgtggcgcc gtaacagatt ccaatgatat ctttcagcac     1140
ggtcagttca agaagctct tggccagcca tctcaggtcc acgcatccgt ttcctgtctc      1200
tcccacagcg tgtcccactt taaagaaggc cacggacacc tcgaacatgg tagtcagggt     1260
ttcagtgtcc agttcaggct cccggcaccc gcctttcatc tccagcagca ccagcttctg     1320
cagcacatat ctagcgtaag aagcggctgt catggtcacg gcccgggaaa acatatcctt     1380
cagattgggc acaaaataat tatggaagtt agcgtagtgc acgaatgtgg tcacgatcac     1440
caggctatag tcgcctgact gggcactagt cagagaaggg taggaaaagg gtcctctcag     1500
atcgggcagg tcttttgtct tcccgaacac cagagacagc acgtgttcat cgcctttctc     1560
ggtcacccgc ttgtaagttc ccatcagaaa tttggaagtc atagctcctg tatactggaa     1620
cttgtccccg ttaatagaca gggccacgta ggacagatga catctgagct gataaaacac     1680
gtagctgtgt ggccgtgtat taggcagcat ggtgccgata tagtagaaga gctgtttctc     1740
cagaggagcg ctcagcatgc aagctgggct gttcagtccg ctaatcaccc ctggatgcac     1800
cttactagca tccacctgca tgcttccttc tgacacggcg gggatgtcca ctggctcagc     1860
cagagcaatc cccagtgtgc cactggtttt atagatcagc ttgtatctgt tcagcataga     1920
ggccagatcc tcggtcacat tagcttcccg ccacagagcc tcaggagaca gtcctggcac     1980
tttagccatc agctcggtcc aagggatagt gtaatgggag gcgtggcctt caatgtccag     2040
gtgcagcttc acctcactca gagaagcggc tcccacttcc cacagcagca ccagacagaa     2100
cacgcacagg agctgcat                                                   2118

<210> SEQ ID NO 64
<211> LENGTH: 411
<212> TYPE: DNA
<213> ORGANISM: Epstein Barr Virus

<400> SEQUENCE: 64
atgcgggccg tggggtgtt cctggctatc tgcctggtga ctattttgt gctgccaacc         60 tggggaaact gggcttaccc ttgctgtcac gtgacccagc tcagggccca gcatctgctg      120
```

```
gctctggaga acatcagcga catttatctg gtgtccaatc agacatgcga tgggttcagc      180
ctggcctccc tgaacagccc caagaacgga tctaatcagc tcgtgatctc ccggtgtgct      240
aacggcctga atgtcgtgag tttctttatc tcaattctga aaaggagctc ctctgctctg      300
acaggacacc tgagggagct gctgaccaca ctggaaactc tgtacggaag tttctcagtg      360
gaagacctgt ttggcgccaa cctgaatcgg tatgcttggc atagaggcgg g              411
```

<210> SEQ ID NO 65
<211> LENGTH: 137
<212> TYPE: PRT
<213> ORGANISM: Epstein Barr Virus

<400> SEQUENCE: 65

```
Met Arg Ala Val Gly Val Phe Leu Ala Ile Cys Leu Val Thr Ile Phe
1               5                   10                  15

Val Leu Pro Thr Trp Gly Asn Trp Ala Tyr Pro Cys Cys His Val Thr
            20                  25                  30

Gln Leu Arg Ala Gln His Leu Leu Ala Leu Glu Asn Ile Ser Asp Ile
        35                  40                  45

Tyr Leu Val Ser Asn Gln Thr Cys Asp Gly Phe Ser Leu Ala Ser Leu
    50                  55                  60

Asn Ser Pro Lys Asn Gly Ser Asn Gln Leu Val Ile Ser Arg Cys Ala
65                  70                  75                  80

Asn Gly Leu Asn Val Val Ser Phe Phe Ile Ser Ile Leu Lys Arg Ser
                85                  90                  95

Ser Ser Ala Leu Thr Gly His Leu Arg Glu Leu Leu Thr Thr Leu Glu
            100                 105                 110

Thr Leu Tyr Gly Ser Phe Ser Val Glu Asp Leu Phe Gly Ala Asn Leu
        115                 120                 125

Asn Arg Tyr Ala Trp His Arg Gly Gly
    130                 135
```

<210> SEQ ID NO 66
<211> LENGTH: 411
<212> TYPE: DNA
<213> ORGANISM: Epstein Barr Virus

<400> SEQUENCE: 66

```
cccgcctcta tgccaagcat accgattcag gttggcgcca acaggtcttc cactgagaa       60 acttccgtac agagtttcca gtgtggtcag cagctccctc aggtgtcctg tcagagcaga      120
ggagctcctt ttcagaattg agataaagaa actcacgaca ttcaggccgt agcacaccg       180 ggagatcacg agctgattag atccgttctt ggggctgttc agggaggcca ggctgaaccc      240
atcgcatgtc tgattggaca ccagataaat gtcgctgatg ttctccagag ccagcagatg      300
ctgggccctg agctgggtca cgtgacagca agggtaagcc cagtttcccc aggttggcag      360
cacaaaaata gtcaccaggc agatagccag gaacaccccc acggcccgca t               411
```

<210> SEQ ID NO 67
<211> LENGTH: 669
<212> TYPE: DNA
<213> ORGANISM: Epstein Barr Virus

<400> SEQUENCE: 67

```
atggtcagct tcaaacaagt gcgggtgccc ctgtttactg ccatcgctct ggtgattgtg       60
ctgctgctgg cctacttcct gccacctcgg gtcagaggag gaggaagagt ggccgctgcc      120
```

-continued

| | |
|---|---|
| gctatcacct gggtgccaaa acctaatgtg gaagtgtggc ctgtggaccc accacctcca | 180 |
| gtgaacttta ataagacagc cgagcaggaa tatggcgata agaagtgaa gctgcctcac | 240 |
| tggaccccaa cactgcatac attccaggtg ccacagaact acactaaagc taattgcact | 300 |
| tattgtaaca ccagggagta cacatttagt tataaggggt gctgtttcta ctttactaag | 360 |
| aaaaagcaca cctggaatgg atgcttccag gcctgtgctg aactgtatcc atgcacatac | 420 |
| ttttatggcc caactcccga catcctgccc gtggtgacca ggaacctgaa tgccattgag | 480 |
| tccctgtggg tgggagtgta cagggtggga gaaggcaact ggacctccct ggatggcggg | 540 |
| acattcaaag tgtaccagat ttttggctct cattgcactt atgtgtctaa gttcagtacc | 600 |
| gtgcccgtgt cacaccatga gtgtagcttt ctgaagcctt gcctgtgtgt gtctcagaga | 660 |
| agcaactcc | 669 |

<210> SEQ ID NO 68
<211> LENGTH: 223
<212> TYPE: PRT
<213> ORGANISM: Epstein Barr Virus

<400> SEQUENCE: 68

Met Val Ser Phe Lys Gln Val Arg Val Pro Leu Phe Thr Ala Ile Ala
1               5                   10                  15

Leu Val Ile Val Leu Leu Leu Ala Tyr Phe Leu Pro Pro Arg Val Arg
            20                  25                  30

Gly Gly Gly Arg Val Ala Ala Ala Ile Thr Trp Val Pro Lys Pro
        35                  40                  45

Asn Val Glu Val Trp Pro Val Asp Pro Pro Pro Val Asn Phe Asn
    50                  55                  60

Lys Thr Ala Glu Gln Glu Tyr Gly Asp Lys Glu Val Lys Leu Pro His
65                  70                  75                  80

Trp Thr Pro Thr Leu His Thr Phe Gln Val Pro Gln Asn Tyr Thr Lys
                85                  90                  95

Ala Asn Cys Thr Tyr Cys Asn Thr Arg Glu Tyr Thr Phe Ser Tyr Lys
            100                 105                 110

Gly Cys Cys Phe Tyr Phe Thr Lys Lys His Thr Trp Asn Gly Cys
        115                 120                 125

Phe Gln Ala Cys Ala Glu Leu Tyr Pro Cys Thr Tyr Phe Tyr Gly Pro
    130                 135                 140

Thr Pro Asp Ile Leu Pro Val Val Thr Arg Asn Leu Asn Ala Ile Glu
145                 150                 155                 160

Ser Leu Trp Val Gly Val Tyr Arg Val Gly Glu Gly Asn Trp Thr Ser
                165                 170                 175

Leu Asp Gly Gly Thr Phe Lys Val Tyr Gln Ile Phe Gly Ser His Cys
            180                 185                 190

Thr Tyr Val Ser Lys Phe Ser Thr Val Pro Val Ser His His Glu Cys
        195                 200                 205

Ser Phe Leu Lys Pro Cys Leu Cys Val Ser Gln Arg Ser Asn Ser
    210                 215                 220

<210> SEQ ID NO 69
<211> LENGTH: 669
<212> TYPE: DNA
<213> ORGANISM: Epstein Barr Virus

<400> SEQUENCE: 69

| | |
|---|---|
| ggagttgctt ctctgagaca cacacaggca aggcttcaga aagctacact catggtgtga | 60 |

| | |
|---|---|
| cacgggcacg gtactgaact tagacacata agtgcaatga gagccaaaaa tctggtacac | 120 |
| tttgaatgtc ccgccatcca gggaggtcca gttgccttct cccaccctgt acactcccac | 180 |
| ccacagggac tcaatggcat tcaggttcct ggtcaccacg ggcaggatgt cgggagttgg | 240 |
| gccataaaag tatgtgcatg gatacagttc agcacaggcc tggaagcatc cattccaggt | 300 |
| gtgcttttc ttagtaaagt agaaacagca cccttataa ctaaatgtgt actccctggt | 360 |
| gttacaataa gtgcaattag ctttagtgta gttctgtggc acctggaatg tatgcagtgt | 420 |
| tggggtccag tgaggcagct tcacttcttt atcgccatat tcctgctcgg ctgtcttatt | 480 |
| aaagttcact ggaggtggtg ggtccacagg ccacacttcc acattaggtt ttggcaccca | 540 |
| ggtgatagcg gcagcggcca ctcttcctcc tcctctgacc cgaggtggca ggaagtaggc | 600 |
| cagcagcagc acaatcacca gagcgatggc agtaaacagg ggcacccgca cttgtttgaa | 660 |
| gctgaccat | 669 |

<210> SEQ ID NO 70
<211> LENGTH: 3093
<212> TYPE: DNA
<213> ORGANISM: Artificial Sequence
<220> FEATURE:
<223> OTHER INFORMATION: Synthetic

<400> SEQUENCE: 70

| | |
|---|---|
| gaagccgccc tgctggtgtg ccagtacact attcagagcc tgattcatct gaccggggag | 60 |
| gaccctggat ttttcaatgt ggaaatccct gagttcccat tttaccccac ctgcaacgtc | 120 |
| tgtacagccg acgtgaacgt caccattaat ttcgatgtgg gcgggaagaa acaccagctg | 180 |
| gacctggatt ttggccagct gaccccacat acaaaagccg tgtatcagcc cagaggggct | 240 |
| ttcggaggca gcgagaacgc aacaaatctg tttctgctgg agctgctggg agcaggagaa | 300 |
| ctggctctga ccatgaggtc caagaaactg cccatcaatg tgaccacagg agaggaacag | 360 |
| caggtcagtc tggaatcagt ggacgtctac ttccaggatg tgtttggcac catgtggtgc | 420 |
| caccatgccg agatgcagaa tcctgtgtac ctgatccccg aaaccgtccc ttatattaag | 480 |
| tgggacaact gtaatagcac taacattacc gcagtggtcc gggcacaggg gctggacgtg | 540 |
| accctgccac tgtcactgcc cacaagcgcc caggatagca acttctccgt gaaaaccgag | 600 |
| atgctgggaa atgagatcga cattgaatgc atcatggagg atgagaaat tagccaggtg | 660 |
| ctgcctggcg ataacaagtt taatatcacc tgttccggct acgaatctca cgtcccaagt | 720 |
| gggggaatcc tgcatctac tagtcccgtg gccactccaa ttcccggaac cggctacgct | 780 |
| tatagcctga gactgacccc taggccagtc tcacgcttcc tgggcaacaa tagcattctg | 840 |
| tacgtgtttt attccggaaa cggaccaaag gcttctggag gggactattg catccagagt | 900 |
| aatattgtgt tctcagacga gatcccagcc agccaggata tgcccactaa cactaccgac | 960 |
| attacctacg tgggcgataa tgccacttat tccgtgccta tggtcacaag cgaagacgct | 1020 |
| aactccccaa atgtgaccgt cacagcattc tgggcctggc ccaacaatac tgagaccgat | 1080 |
| tttaagtgca atggacact gacttcaggc acccctagcg ggtgtgaaaa catctctggc | 1140 |
| gccttcgcta gtaatcgaac ctttgatatt acagtgtccg gcctggggac tgccccaaaa | 1200 |
| accctgatca ttacccggac agctactaac gcaacaacta ccacacacaa agtgatcttc | 1260 |
| agcaaagctc ccgagtccac taccacatct cctaccctga acactaccgg gtttgccgac | 1320 |
| cccaatacaa ctaccggact gcctagctcc acccatgtgc caacaaacct gactgcacca | 1380 |

```
gcatccaccg gacctacagt gtctactgcc gatgtcacca gtcccacacc tgccggaaca    1440
acttctggcg ctagtcccgt gaccccatca cccagccctt gggacaatgg gacagagagt    1500
aaggccctg atatgacttc tagtacctca ccagtcacca caccaacccc caacgcaaca    1560
agccctactc cagccgtgac tacccccaca cctaatgcta ccagcccaac accgcagtg    1620
acaactccta ccccaaacgc cacttcccca accctgggga agacatcacc cactagcgcc    1680
gtgaccacac ccaccctaa tgctacctct cctacactgg gaaaaacttc cccaacctct    1740
gcagtgacta ccccaacccc caacgccaca gccccactc tgggcaagac cagtcctaca    1800
tcagctgtca caactcctac cccaaatgca actgggccaa ccgtgggaga cacatccccc    1860
caggctaacg caacaaatca cactctggga ggcaccagtc ccacacctgt ggtcacctca    1920
cagcccaaga cgccacaag cgctgtgacc acaggccagc ataatatcac atcaagctcc    1980
acttctagta tgagcctgcg cccttcaagc aacccagaga cactgtcccc atctactagt    2040
gacaattcaa ccagccacat gcctctgctg acatctgcac atccaactgg gggagaaaac    2100
atcactcagg tcaccccgc ctccatttct acccaccatg tgtccacatc ctctccagca    2160
ccccgacctg aactaccag ccaggcatcc ggaccaggaa atagttcaac cagcacaaag    2220
cctggcgagg tgaacgtcac aaaagggact ccccctcaga atgctacctc acctcaggca    2280
ccaagcggcc agaaaacagc tgtgcctact gtcacctcca caggcgggaa ggcaaactct    2340
acaactggag gcaaacacac cacagggcat ggagctcgca ctagcaccga accaactacc    2400
gactacgggg gagattccac aactccaagg cccagataca atgccaccac atatctgcca    2460
ccctctacca gctccaagct gcgacccaga tggacattca ctagtcctcc agtgactacc    2520
gcacaggcta cagtgccagt cccacctact tctcagccta gattttctaa cctgagttcc    2580
ggagagagcc aggtgaggca gaacttcaag cccgagatgg aggagaagct gaacgagcag    2640
atgaacctgg agctgtacag cagcctgctg taccagcaga tgagcgcctg gtgcagctac    2700
cacaccttcg agggcgccgc cgccttcctg aggaggcacg cccaggagga gatgacccac    2760
atgcagaggc tgttcgacta cctgaccgac accggcaacc tgcccaggat caacaccgtg    2820
gagagccct cgccgagta cagcagcctg acgagctgt tccaggagac ctacaagcac    2880
gagcagctga tcacccagaa gatcaacgag ctggcccacg ccgccatgac caaccaggac    2940
tacccccacct tcaacttcct gcagtggtac gtgagcgagc agcacgagga ggagaagctg    3000
ttcaagagca tcatcgacaa gctgagcctg gccggcaaga gcggcgaggg cctgtacttc    3060
atcgacaagg agctgagcac cctggacgga tcc                                 3093
```

<210> SEQ ID NO 71
<211> LENGTH: 1031
<212> TYPE: PRT
<213> ORGANISM: Artificial Sequence
<220> FEATURE:
<223> OTHER INFORMATION: Synthetic

<400> SEQUENCE: 71

Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

```
Gly Gln Leu Thr Pro His Thr Lys Ala Val Tyr Gln Pro Arg Gly Ala
 65                  70                  75                  80

Phe Gly Gly Ser Glu Asn Ala Thr Asn Leu Phe Leu Glu Leu Leu
             85                  90                  95

Gly Ala Gly Glu Leu Ala Leu Thr Met Arg Ser Lys Lys Leu Pro Ile
            100                 105                 110

Asn Val Thr Thr Gly Glu Glu Gln Gln Val Ser Leu Glu Ser Val Asp
            115                 120                 125

Val Tyr Phe Gln Asp Val Phe Gly Thr Met Trp Cys His His Ala Glu
130                 135                 140

Met Gln Asn Pro Val Tyr Leu Ile Pro Glu Thr Val Pro Tyr Ile Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
        195                 200                 205

Glu Cys Ile Met Glu Asp Gly Glu Ile Ser Gln Val Leu Pro Gly Asp
210                 215                 220

Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
        275                 280                 285

Pro Lys Ala Ser Gly Gly Asp Tyr Cys Ile Gln Ser Asn Ile Val Phe
    290                 295                 300

Ser Asp Glu Ile Pro Ala Ser Gln Asp Met Pro Thr Asn Thr Thr Asp
305                 310                 315                 320

Ile Thr Tyr Val Gly Asp Asn Ala Thr Tyr Ser Val Pro Met Val Thr
                325                 330                 335

Ser Glu Asp Ala Asn Ser Pro Asn Val Thr Val Thr Ala Phe Trp Ala
            340                 345                 350

Trp Pro Asn Asn Thr Glu Thr Asp Phe Lys Cys Lys Trp Thr Leu Thr
        355                 360                 365

Ser Gly Thr Pro Ser Gly Cys Glu Asn Ile Ser Gly Ala Phe Ala Ser
    370                 375                 380

Asn Arg Thr Phe Asp Ile Thr Val Ser Gly Leu Gly Thr Ala Pro Lys
385                 390                 395                 400

Thr Leu Ile Ile Thr Arg Thr Ala Thr Asn Ala Thr Thr Thr His
                405                 410                 415

Lys Val Ile Phe Ser Lys Ala Pro Glu Ser Thr Thr Ser Pro Thr
            420                 425                 430

Leu Asn Thr Thr Gly Phe Ala Asp Pro Asn Thr Thr Gly Leu Pro
        435                 440                 445

Ser Ser Thr His Val Pro Thr Asn Leu Thr Ala Pro Ala Ser Thr Gly
    450                 455                 460

Pro Thr Val Ser Thr Ala Asp Val Thr Ser Pro Thr Pro Ala Gly Thr
465                 470                 475                 480
```

-continued

```
Thr Ser Gly Ala Ser Pro Val Thr Pro Ser Pro Ser Pro Trp Asp Asn
                485                 490                 495
Gly Thr Glu Ser Lys Ala Pro Asp Met Thr Ser Ser Thr Ser Pro Val
            500                 505                 510
Thr Thr Pro Thr Pro Asn Ala Thr Ser Pro Thr Pro Ala Val Thr Thr
        515                 520                 525
Pro Thr Pro Asn Ala Thr Ser Pro Thr Pro Ala Val Thr Thr Pro Thr
    530                 535                 540
Pro Asn Ala Thr Ser Pro Thr Leu Gly Lys Thr Ser Pro Thr Ser Ala
545                 550                 555                 560
Val Thr Thr Pro Thr Pro Asn Ala Thr Ser Pro Thr Leu Gly Lys Thr
                565                 570                 575
Ser Pro Thr Ser Ala Val Thr Thr Pro Thr Pro Asn Ala Thr Ser Pro
            580                 585                 590
Thr Leu Gly Lys Thr Ser Pro Thr Ser Ala Val Thr Thr Pro Thr Pro
        595                 600                 605
Asn Ala Thr Gly Pro Thr Val Gly Glu Thr Ser Pro Gln Ala Asn Ala
    610                 615                 620
Thr Asn His Thr Leu Gly Gly Thr Ser Pro Thr Pro Val Val Thr Ser
625                 630                 635                 640
Gln Pro Lys Asn Ala Thr Ser Ala Val Thr Thr Gly Gln His Asn Ile
                645                 650                 655
Thr Ser Ser Ser Thr Ser Ser Met Ser Leu Arg Pro Ser Ser Asn Pro
            660                 665                 670
Glu Thr Leu Ser Pro Ser Thr Ser Asp Asn Ser Thr Ser His Met Pro
        675                 680                 685
Leu Leu Thr Ser Ala His Pro Thr Gly Gly Glu Asn Ile Thr Gln Val
    690                 695                 700
Thr Pro Ala Ser Ile Ser Thr His His Val Ser Thr Ser Ser Pro Ala
705                 710                 715                 720
Pro Arg Pro Gly Thr Thr Ser Gln Ala Ser Gly Pro Gly Asn Ser Ser
                725                 730                 735
Thr Ser Thr Lys Pro Gly Glu Val Asn Val Thr Lys Gly Thr Pro Pro
            740                 745                 750
Gln Asn Ala Thr Ser Pro Gln Ala Pro Ser Gly Gln Lys Thr Ala Val
        755                 760                 765
Pro Thr Val Thr Ser Thr Gly Gly Lys Ala Asn Ser Thr Thr Gly Gly
    770                 775                 780
Lys His Thr Thr Gly His Gly Ala Arg Thr Ser Thr Glu Pro Thr Thr
785                 790                 795                 800
Asp Tyr Gly Gly Asp Ser Thr Thr Pro Arg Pro Arg Tyr Asn Ala Thr
                805                 810                 815
Thr Tyr Leu Pro Pro Ser Thr Ser Ser Lys Leu Arg Pro Arg Trp Thr
            820                 825                 830
Phe Thr Ser Pro Pro Val Thr Thr Ala Gln Ala Thr Val Pro Val Pro
        835                 840                 845
Pro Thr Ser Gln Pro Arg Phe Ser Asn Leu Ser Ser Gly Glu Ser Gln
    850                 855                 860
Val Arg Gln Asn Phe Lys Pro Glu Met Glu Lys Leu Asn Glu Gln
865                 870                 875                 880
Met Asn Leu Glu Leu Tyr Ser Ser Leu Leu Tyr Gln Gln Met Ser Ala
                885                 890                 895
Trp Cys Ser Tyr His Thr Phe Glu Gly Ala Ala Ala Phe Leu Arg Arg
```

```
                900             905             910
        His Ala Gln Glu Glu Met Thr His Met Gln Arg Leu Phe Asp Tyr Leu
                915                 920                 925

Thr Asp Thr Gly Asn Leu Pro Arg Ile Asn Thr Val Glu Ser Pro Phe
                930                 935                 940

Ala Glu Tyr Ser Ser Leu Asp Glu Leu Phe Gln Thr Tyr Lys His
        945                 950                 955                 960

Glu Gln Leu Ile Thr Gln Lys Ile Asn Glu Leu Ala His Ala Ala Met
                965                 970                 975

Thr Asn Gln Asp Tyr Pro Thr Phe Asn Phe Leu Gln Trp Tyr Val Ser
                980                 985                 990

Glu Gln His Glu Glu Lys Leu Phe Lys Ser Ile Ile Asp Lys Leu
                995                 1000                1005

Ser Leu Ala Gly Lys Ser Gly Glu Gly Leu Tyr Phe Ile Asp Lys
                1010                1015                1020

Glu Leu Ser Thr Leu Asp Gly Ser
                1025                1030

<210> SEQ ID NO 72
<211> LENGTH: 3093
<212> TYPE: DNA
<213> ORGANISM: Artificial Sequence
<220> FEATURE:
<223> OTHER INFORMATION: Synthetic

<400> SEQUENCE: 72
ggatccgtcc agggtgctca gctccttgtc gatgaagtac aggccctcgc cgctcttgcc      60
ggccaggctc agcttgtcga tgatgctctt gaacagcttc tcctcctcgt gctgctcgct     120
cacgtaccac tgcaggaagt tgaaggtggg gtagtcctgg ttggtcatgg cggcgtgggc     180
cagctcgttg atcttctggg tgatcagctg ctcgtgcttg taggtctcct ggaacagctc     240
gtccaggctg ctgtactcgg cgaaggggct ctccacggtg ttgatcctgg caggttgcc      300 ggtgtcggtc aggtagtcga acagcctctg catgtgggtc atctcctcct gggcgtgcct     360
cctcaggaag gcggcggcgc cctcgaaggt gtggtagctg caccaggcgc tcatctgctg     420
gtacagcagg ctgctgtaca gctccaggtt catctgctcg ttcagcttct cctccatctc     480
gggcttgaag ttctgcctca cctggctctc tccggaactc aggttagaaa atctaggctg     540
agaagtaggt gggactggca ctgtagcctg tgcggtagtc actggaggac tagtgaatgt     600
ccatctgggt cgcagcttgg agctggtaga gggtggcaga tatgtggtgg cattgtatct     660
gggccttgga gttgtggaat ctcccccgta gtcggtagtt ggttcggtgc tagtgcgagc     720
tccatgccct gtggtgtgtt tgcctccagt tgtagagttt gccttcccgc ctgtggaggt     780
gacagtaggc acagctgttt tctggccgct tggtgcctga ggtgaggtag cattctgagg     840
gggagtccct tttgtgacgt tcacctcgcc aggctttgtg ctggttgaac tatttcctgg     900
tccggatgcc tggctggtag ttccaggtcg gggtgctgga gaggatgtgg acacatggtg     960
ggtagaaatg gaggcggggg tgacctgagt gatgttttct cccccagttg gatgtgcaga    1020
tgtcagcaga ggcatgtggc tggttgaatt gtcactagta gatggggaca gtgtctctgg    1080
gttgcttgaa gggcgcaggc tcatactaga agtggagctt gatgtgatat tatgctggcc    1140
tgtggtcaca gcgcttgtgg cgttcttggg ctgtgaggtg accacaggtg tgggactggt    1200
gcctcccaga gtgtgatttg ttgcgttagc ctgggggat gtctctccca cggttggccc    1260
agttgcattt ggggtaggag ttgtgacagc tgatgtagga ctggtcttgc ccagagtggg    1320
```

```
gcttgtggcg ttgggggttg gggtagtcac tgcagaggtt ggggaagttt ttcccagtgt      1380
aggagaggta gcattagggg tgggtgtggt cacggcgcta gtgggtgatg tcttccccag      1440
ggttggggaa gtggcgtttg gggtaggagt tgtcactgcg ggtgttgggc tggtagcatt      1500
aggtgtgggg gtagtcacgg ctggagtagg gcttgttgcg ttgggggttg gtgtggtgac      1560
tggtgaggta ctagaagtca tatcaggggc cttactctct gtcccattgt cccaagggct      1620
gggtgatggg gtcacgggac tagcgccaga agttgttccg gcaggtgtgg gactggtgac      1680
atcggcagta gacactgtag gtccggtgga tgctggtgca gtcaggtttg ttggcacatg      1740
ggtggagcta ggcagtccgg tagttgtatt ggggtcggca acccggtag tgttcagggt      1800 aggagatgtg gtagtggact cgggagcttt gctgaagatc actttgtgtg tggtagttgt      1860
tgcgttagta gctgtccggg taatgatcag ggttttttggg gcagtcccca ggccggacac      1920
tgtaatatca aaggttcgat tactagcgaa ggcgccagag atgttttcac acccgctagg      1980
ggtgcctgaa gtcagtgtcc atttgcactt aaaatcggtc tcagtattgt tgggccaggc      2040
ccagaatgct gtgacggtca catttgggga gttagcgtct tcgcttgtga ccataggcac      2100
ggaataagtg gcattatcgc ccacgtaggt aatgtcggta gtgttagtgg gcatatcctg      2160
gctggctggg atctcgtctg agaacacaat attactctgg atgcaatagt cccctccaga      2220
agcctttggt ccgtttccgg aataaaacac gtacagaatg ctattgttgc ccaggaagcg      2280
tgagactggc ctaggggtca gtctcaggct ataagcgtag ccggttccgg gaattggagt      2340
ggccacggga ctagtagatg tcaggattcc cccacttggg acgtgagatt cgtagccgga      2400
acaggtgata ttaaacttgt tatcgccagg cagcacctgg ctaatttctc catcctccat      2460
gatgcattca atgtcgatct catttcccag catctcggtt ttcacggaga agttgctatc      2520
ctgggcgctt gtgggcagtg acagtggcag ggtcacgtcc agccctgtg cccggaccac      2580 tgcggtaatg ttagtgctat tacagttgtc ccacttaata taagggacgg tttcggggat      2640
caggtacaca ggattctgca tctcggcatg gtggcaccac atggtgccaa acacatcctg      2700
gaagtagacg tccactgatt ccagactgac ctgctgttcc tctcctgtgg tcacattgat      2760
gggcagtttc ttggacctca tggtcagagc cagttctcct gctcccagca gctccagcag      2820
aaacagattt gttgcgttct cgctgcctcc gaaagcccct ctgggctgat acacggcttt      2880
tgtatgtggg gtcagctggc caaaatccag gtccagctgg tgtttcttcc cgcccacatc      2940
gaaattaatg gtgacgttca cgtcggctgt acagacgttg caggtggggt aaaatgggaa      3000
ctcagggatt tccacattga aaaatccagg gtcctccccg gtcagatgaa tcaggctctg      3060
aatagtgtac tggcacacca gcagggcggc ttc                                  3093
```

<210> SEQ ID NO 73
<211> LENGTH: 1923
<212> TYPE: DNA
<213> ORGANISM: Artificial Sequence
<220> FEATURE:
<223> OTHER INFORMATION: Synthetic

<400> SEQUENCE: 73

```
gaagccgccc tgctggtgtg ccagtacact attcagagcc tgattcatct gaccggggag        60
gaccctggat ttttcaatgt ggaaatccct gagttcccat tttaccccac ctgcaacgtc       120
tgtacagccg acgtgaacgt caccattaat ttcgatgtgg gcgggaagaa acaccagctg       180
gacctggatt ttggccagct gacccccacat acaaaagccg tgtatcagcc cagaggggct       240
```

```
ttcggaggca gcgagaacgc aacaaatctg tttctgctgg agctgctggg agcaggagaa    300
ctggctctga ccatgaggtc caagaaactg cccatcaatg tgaccacagg agaggaacag    360
caggtcagtc tggaatcagt ggacgtctac ttccaggatg tgtttggcac catgtggtgc    420
caccatgccg agatgcagaa tcctgtgtac ctgatcccccg aaaccgtccc ttatattaag    480
tgggacaact gtaatagcac taacattacc gcagtggtcc gggcacaggg gctggacgtg    540
accctgccac tgtcactgcc cacaagcgcc caggatagca acttctccgt gaaaaccgag    600
atgctgggaa atgagatcga cattgaatgc atcatggagg atggagaaat tagccaggtg    660
ctgcctggcg ataacaagtt taatatcacc tgttccggct acgaatctca cgtcccaagt    720
gggggaatcc tgacatctac tagtcccgtg gccactccaa ttcccggaac cggctacgct    780
tatagcctga gactgacccc taggccagtc tcacgcttcc tgggcaacaa tagcattctg    840
tacgtgtttt attccggaaa cggaccaaag gcttctggag gggactattg catccagagt    900
aatattgtgt tctcagacga gatcccagcc agccaggata tgcccactaa cactaccgac    960
attacctacg tgggcgataa tgccacttat tccgtgccta tggtcacaag cgaagacgct   1020 aactcccccaa atgtgaccgt cacagcattc tgggcctggc ccaacaatac tgagaccgat   1080
tttaagtgca aatggacact gacttcaggc accccctagcg ggtgtgaaaa catctctggc   1140
gccttcgcta gtaatcgaac ctttgatatt acagtgtccg gcctggggac tgccccaaaa   1200
accctgatca ttacccggac agctactaac gcaacaacta ccacacacaa agtgatcttc   1260
agcaaagctc ccgagtccac taccacatct cctaccctga acactaccgg gtttgccgac   1320
cccaatacaa ctaccggact gcctagctcc acccatgtgc caacaaacct gactgcacca   1380
gcatccaccg gacctacagt gtctacttcc ggagagagcc aggtgaggca gaacttcaag   1440
cccgagatgg aggagaagct gaacgagcag atgaacctgg agctgtacag cagcctgctg   1500
taccagcaga tgagcgcctg gtgcagctac cacaccttcg agggcgccgc cgccttcctg   1560
aggaggcacg cccaggagga gatgacccac atgcagaggc tgttcgacta cctgaccgac   1620
accggcaacc tgcccaggat caacaccgtg agagcccct cgccgagta cagcagcctg   1680 gacgagctgt ccaggagac ctacaagcac gagcagctga tcacccagaa gatcaacgag   1740
ctggcccacg ccgccatgac caaccaggac taccccacct tcaacttcct gcagtggtac   1800
gtgagcgagc agcacgagga ggagaagctg ttcaagagca tcgacaa gctgagcctg   1860 gccggcaaga gcggcgaggg cctgtacttc atcgacaagg agctgagcac cctggacgga   1920
tcc                                                                 1923
```

<210> SEQ ID NO 74
<211> LENGTH: 641
<212> TYPE: PRT
<213> ORGANISM: Artificial Sequence
<220> FEATURE:
<223> OTHER INFORMATION: Synthetic

<400> SEQUENCE: 74

```
Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60
```

```
Gly Gln Leu Thr Pro His Thr Lys Ala Val Tyr Gln Pro Arg Gly Ala
 65                  70                  75                  80

Phe Gly Gly Ser Glu Asn Ala Thr Asn Leu Phe Leu Glu Leu Leu
                 85                  90                  95

Gly Ala Gly Glu Leu Ala Leu Thr Met Arg Ser Lys Lys Leu Pro Ile
                100                 105                 110

Asn Val Thr Thr Gly Glu Glu Gln Gln Val Ser Leu Glu Ser Val Asp
                115                 120                 125

Val Tyr Phe Gln Asp Val Phe Gly Thr Met Trp Cys His His Ala Glu
130                 135                 140

Met Gln Asn Pro Val Tyr Leu Ile Pro Glu Thr Val Pro Tyr Ile Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
                180                 185                 190

Ser Asn Phe Ser Val Lys Thr Glu Met Leu Gly Asn Glu Ile Asp Ile
                195                 200                 205

Glu Cys Ile Met Glu Asp Gly Glu Ile Ser Gln Val Leu Pro Gly Asp
210                 215                 220

Asn Lys Phe Asn Ile Thr Cys Ser Gly Tyr Glu Ser His Val Pro Ser
225                 230                 235                 240

Gly Gly Ile Leu Thr Ser Thr Pro Val Ala Thr Pro Ile Pro Gly
                245                 250                 255

Thr Gly Tyr Ala Tyr Ser Leu Arg Leu Thr Pro Arg Pro Val Ser Arg
                260                 265                 270

Phe Leu Gly Asn Asn Ser Ile Leu Tyr Val Phe Tyr Ser Gly Asn Gly
                275                 280                 285

Pro Lys Ala Ser Gly Gly Asp Tyr Cys Ile Gln Ser Asn Ile Val Phe
                290                 295                 300

Ser Asp Glu Ile Pro Ala Ser Gln Asp Met Pro Thr Asn Thr Thr Asp
305                 310                 315                 320

Ile Thr Tyr Val Gly Asp Asn Ala Thr Tyr Ser Val Pro Met Val Thr
                325                 330                 335

Ser Glu Asp Ala Asn Ser Pro Asn Val Thr Val Thr Ala Phe Trp Ala
                340                 345                 350

Trp Pro Asn Asn Thr Glu Thr Asp Phe Lys Cys Lys Trp Thr Leu Thr
                355                 360                 365

Ser Gly Thr Pro Ser Gly Cys Glu Asn Ile Ser Gly Ala Phe Ala Ser
                370                 375                 380

Asn Arg Thr Phe Asp Ile Thr Val Ser Gly Leu Gly Thr Ala Pro Lys
385                 390                 395                 400

Thr Leu Ile Ile Thr Arg Thr Ala Thr Asn Ala Thr Thr Thr His
                405                 410                 415

Lys Val Ile Phe Ser Lys Ala Pro Glu Ser Thr Thr Ser Pro Thr
                420                 425                 430

Leu Asn Thr Thr Gly Phe Ala Asp Pro Asn Thr Thr Gly Leu Pro
                435                 440                 445

Ser Ser Thr His Val Pro Thr Asn Leu Thr Ala Pro Ala Ser Thr Gly
                450                 455                 460

Pro Thr Val Ser Thr Ser Gly Glu Ser Gln Val Arg Gln Asn Phe Lys
465                 470                 475                 480
```

```
Pro Glu Met Glu Glu Lys Leu Asn Glu Gln Met Asn Leu Glu Leu Tyr
            485                 490                 495

Ser Ser Leu Leu Tyr Gln Gln Met Ser Ala Trp Cys Ser Tyr His Thr
        500                 505                 510

Phe Glu Gly Ala Ala Ala Phe Leu Arg Arg His Ala Gln Glu Glu Met
        515                 520                 525

Thr His Met Gln Arg Leu Phe Asp Tyr Leu Thr Asp Thr Gly Asn Leu
    530                 535                 540

Pro Arg Ile Asn Thr Val Glu Ser Pro Phe Ala Glu Tyr Ser Ser Leu
545                 550                 555                 560

Asp Glu Leu Phe Gln Glu Thr Tyr Lys His Glu Gln Leu Ile Thr Gln
                565                 570                 575

Lys Ile Asn Glu Leu Ala His Ala Ala Met Thr Asn Gln Asp Tyr Pro
            580                 585                 590

Thr Phe Asn Phe Leu Gln Trp Tyr Val Ser Glu Gln His Glu Glu Glu
        595                 600                 605

Lys Leu Phe Lys Ser Ile Ile Asp Lys Leu Ser Leu Ala Gly Lys Ser
    610                 615                 620

Gly Glu Gly Leu Tyr Phe Ile Asp Lys Glu Leu Ser Thr Leu Asp Gly
625                 630                 635                 640

Ser
```

<210> SEQ ID NO 75
<211> LENGTH: 1923
<212> TYPE: DNA
<213> ORGANISM: Artificial Sequence
<220> FEATURE:
<223> OTHER INFORMATION: Synthetic

<400> SEQUENCE: 75

```
ggatccgtcc agggtgctca gctccttgtc gatgaagtac aggccctcgc cgctcttgcc      60
ggccaggctc agcttgtcga tgatgctctt gaacagcttc tcctcctcgt gctgctcgct     120
cacgtaccac tgcaggaagt tgaaggtggg gtagtcctgg ttggtcatgg cggcgtgggc     180
cagctcgttg atcttctggg tgatcagctg ctcgtgcttg taggtctcct ggaacagctc     240
gtccaggctg ctgtactcgg cgaaggggct ctccacggtg ttgatcctgg gcaggttgcc     300
ggtgtcggtc aggtagtcga acagcctctg catgtgggtc atctcctcct gggcgtgcct     360
cctcaggaag gcggcggcgc cctcgaaggt gtggtagctg caccaggcgc tcatctgctg     420
gtacagcagg ctgctgtaca gctccaggtt catctgctcg ttcagcttct cctccatctc     480
gggcttgaag ttctgcctca cctggctctc tccggaagta gacactgtag gtccggtgga     540
tgctggtgca gtcaggtttg ttggcacatg ggtggagcta ggcagtccgg tagttgtatt     600
ggggtcggca aacccggtag tgttcagggt aggagatgtg gtagtggact cgggagcttt     660
gctgaagatc actttgtgtg tggtagttgt tgcgttagta gctgtccggg taatgatcag     720
ggttttggg gcagtcccca ggccggacac tgtaatatca aaggttcgat tactagcgaa     780
ggcgccagag atgttttcac acccgctagg ggtgcctgaa gtcagtgtcc atttgcactt     840
aaaatcggtc tcagtattgt tgggccaggc cagaatgct gtgacggtca catttgggga     900
gttagcgtct tcgcttgtga ccataggcac ggaataagtg gcattatcgc ccacgtaggt     960
aatgtcggta gtgttagtgg gcatatcctg gctggctggg atctcgtctg agaacacaat    1020
attactctgg atgcaaatagt cccctccaga agcctttggt ccgttccgg aataaaacac    1080
gtacagaatg ctattgttgc ccaggaagcg tgagactggc ctaggggtca gtctcaggct    1140
```

```
ataagcgtag ccggttccgg gaattggagt ggccacggga ctagtagatg tcaggattcc   1200
cccacttggg acgtgagatt cgtagccgga acaggtgata ttaaacttgt tatcgccagg   1260
cagcacctgg ctaatttctc catcctccat gatgcattca atgtcgatct catttcccag   1320
catctcggtt ttcacggaga agttgctatc ctgggcgctt gtgggcagtg acagtggcag   1380
ggtcacgtcc agccctgtg cccggaccac tgcggtaatg ttagtgctat tacagttgtc    1440
ccacttaata taagggacgg tttcggggat caggtacaca ggattctgca tctcggcatg   1500
gtggcaccac atggtgccaa acacatcctg gaagtagacg tccactgatt ccagactgac   1560
ctgctgttcc tctcctgtgg tcacattgat gggcagtttc ttggacctca tggtcagagc   1620
cagttctcct gctcccagca gctccagcag aaacagattt gttgcgttct cgctgcctcc   1680
gaaagcccct ctgggctgat acacggcttt tgtatgtggg gtcagctggc caaaatccag   1740
gtccagctgg tgtttcttcc cgcccacatc gaaattaatg gtgacgttca cgtcggctgt   1800
acagacgttg caggtggggt aaaatgggaa ctcagggatt tccacattga aaaatccagg   1860
gtcctccccg gtcagatgaa tcaggctctg aatagtgtac tggcacacca gcagggcggc   1920
ttc                                                                1923

<210> SEQ ID NO 76
<211> LENGTH: 1464
<212> TYPE: DNA
<213> ORGANISM: Artificial Sequence
<220> FEATURE:
<223> OTHER INFORMATION: Synthetic

<400> SEQUENCE: 76
gaagccgccc tgctggtgtg ccagtacact attcagagcc tgattcatct gaccggggag     60
gaccctggat ttttcaatgt ggaaatccct gagttcccat tttaccccac ctgcaacgtc    120
tgtacagccg acgtgaacgt caccattaat ttcgatgtgg gcgggaagaa acaccagctg    180
gacctggatt ttggccagct gaccccacat acaaaagccg tgtatcagcc cagagggggct  240 ttcggaggca gcgagaacgc aacaaatctg tttctgctgg agctgctggg agcaggagaa    300
ctggctctga ccatgaggtc caagaaactg cccatcaatg tgaccacagg agaggaacag    360
caggtcagtc tggaatcagt ggacgtctac ttccaggatg tgtttggcac catgtggtgc    420
caccatgccg agatgcagaa tcctgtgtac ctgatccccg aaaccgtccc ttatattaag    480
tgggacaact gtaatagcac taacattacc gcagtggtcc gggcacaggg gctggacgtg   540
accctgccac tgtcactgcc cacaagcgcc caggatagca acttctccgt gaaaaccgag    600
atgctgggaa atgagatcga cattgaatgc atcatggagg atggagaaat tagccaggtg    660
ctgcctggcg ataacaagtt taatatcacc tgttccggct acgaatctca cgtcccaagt    720
gggggaatcc tgacatctac tagtcccgtg ccactccaa ttcccggaac cggctacgct     780
tatagcctga actgaccccc taggccagtc tcacgcttcc tgggcaacaa tagcattctg    840
tacgtgtttt attccggaaa cggaccaaag gcttctggag gggactattg catccagagt    900
aatattgtgt tctcagacga gatcccagcc agccaggata tgcccacttc cggagagagc    960
caggtgaggc agaacttcaa gcccgagatg gaggagaagc tgaacgagca gatgaacctg    1020
gagctgtaca gcagcctgct gtaccagcag atgagcgcct ggtgcagcta ccacaccttc   1080
gagggcgccg ccgccttcct gaggaggcac gcccaggagg agatgaccca catgcagagg    1140
ctgttcgact acctgaccga caccggcaac ctgcccagga tcaacaccgt ggagagcccc    1200
```

-continued

```
ttcgccgagt acagcagcct ggacgagctg ttccaggaga cctacaagca cgagcagctg   1260
atcacccaga agatcaacga gctggcccac gccgccatga ccaaccagga ctacccacc   1320 ttcaacttcc tgcagtggta cgtgagcgag cagcacgagg aggagaagct gttcaagagc   1380
atcatcgaca agctgagcct ggccggcaag agcggcgagg gcctgtactt catcgacaag   1440
gagctgagca ccctggacgg atcc                                         1464
```

<210> SEQ ID NO 77
<211> LENGTH: 488
<212> TYPE: PRT
<213> ORGANISM: Artificial Sequence
<220> FEATURE:
<223> OTHER INFORMATION: Synthetic

<400> SEQUENCE: 77

```
Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Val Ser Leu Glu Ser Val Asp
            115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Pro Tyr Ile Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
            195                 200                 205

Glu Cys Ile Met Glu Asp Gly Glu Ile Ser Gln Val Leu Pro Gly Asp
    210                 215                 220

Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
            275                 280                 285

Pro Lys Ala Ser Gly Gly Asp Tyr Cys Ile Gln Ser Asn Ile Val Phe
    290                 295                 300

Ser Asp Glu Ile Pro Ala Ser Gln Asp Met Pro Thr Ser Gly Glu Ser
305                 310                 315                 320
```

Gln Val Arg Gln Asn Phe Lys Pro Glu Met Glu Lys Leu Asn Glu
              325                 330                 335

Gln Met Asn Leu Glu Leu Tyr Ser Ser Leu Leu Tyr Gln Gln Met Ser
              340                 345                 350

Ala Trp Cys Ser Tyr His Thr Phe Glu Gly Ala Ala Phe Leu Arg
              355                 360                 365

Arg His Ala Gln Glu Glu Met Thr His Met Gln Arg Leu Phe Asp Tyr
        370                 375                 380

Leu Thr Asp Thr Gly Asn Leu Pro Arg Ile Asn Thr Val Glu Ser Pro
385                 390                 395                 400

Phe Ala Glu Tyr Ser Ser Leu Asp Glu Leu Phe Gln Gly Thr Tyr Lys
              405                 410                 415

His Glu Gln Leu Ile Thr Gln Lys Ile Asn Glu Leu Ala His Ala Ala
              420                 425                 430

Met Thr Asn Gln Asp Tyr Pro Thr Phe Asn Phe Leu Gln Trp Tyr Val
              435                 440                 445

Ser Glu Gln His Glu Glu Lys Leu Phe Lys Ser Ile Ile Asp Lys
              450                 455                 460

Leu Ser Leu Ala Gly Lys Ser Gly Glu Gly Leu Tyr Phe Ile Asp Lys
465                 470                 475                 480

Glu Leu Ser Thr Leu Asp Gly Ser
              485

<210> SEQ ID NO 78
<211> LENGTH: 1464
<212> TYPE: DNA
<213> ORGANISM: Artificial Sequence
<220> FEATURE:
<223> OTHER INFORMATION: Synthetic

<400> SEQUENCE: 78
ggatccgtcc agggtgctca gctccttgtc gatgaagtac aggccctcgc cgctcttgcc      60
ggccaggctc agcttgtcga tgatgctctt gaacagcttc tcctcctcgt gctgctcgct     120
cacgtaccac tgcaggaagt tgaaggtggg gtagtcctgg ttggtcatgg cggcgtgggc     180
cagctcgttg atcttctggg tgatcagctg ctcgtgcttg taggtctcct ggaacagctc     240
gtccaggctc tgtactcggc gaaggggct ctccacggtg ttgatcctgg caggttgcc      300 ggtgtcggtc aggtagtcga acagcctctg catgtgggtc atctcctcct gggcgtgcct     360
cctcaggaag gcggcggcgc cctcgaaggt gtggtagctg caccaggcgc tcatctgctg     420
gtacagcagg ctgctgtaca gctccaggtt catctgctcg ttcagcttct cctccatctc     480
gggcttgaag ttctgcctca cctggctctc tccggaagtg gcatatcct ggctggctgg      540 gatctcgtct gagaacacaa tattactctg gatgcaatag tcccctccag aagcctttgg     600
tccgtttccg gaataaaaca cgtacagaat gctattgttg cccaggaagc gtgagactgg     660 cctagggtc agtctcaggc tataagcgta gccggttccg ggaattggag tggccacggg     720
actagtagat gtcaggattc ccccacttgg gacgtgagat tcgtagccgg aacaggtgat     780
attaaacttg ttatcgccag gcagcacctg gctaatttct ccatcctcca tgatgcattc     840
aatgtcgatc tcatttccca gcatctcggt tttcacggag aagttgctat cctgggcgct     900
tgtgggcagt gacagtggca gggtcacgtc cagcccctgt gccggacca ctgcggtaat       960 gttagtgcta ttcagttgt cccacttaat ataaggacg tttcggggga tcaggtacac      1020
aggattctgc atctcggcat ggtggcacca catggtgcca acacatcct ggaagtagac     1080

| | |
|---|---|
| gtccactgat tccagactga cctgctgttc ctctcctgtg gtcacattga tgggcagttt | 1140 |
| cttggacctc atggtcagag ccagttctcc tgctcccagc agctccagca gaaacagatt | 1200 |
| tgttgcgttc tcgctgcctc cgaaagcccc tctgggctga tacacggctt ttgtatgtgg | 1260 |
| ggtcagctgg ccaaaatcca ggtccagctg gtgtttcttc ccgcccacat cgaaattaat | 1320 |
| ggtgacgttc acgtcggctg tacagacgtt gcaggtgggg taaaatggga actcagggat | 1380 |
| ttccacattg aaaaatccag ggtcctcccc ggtcagatga atcaggctct gaatagtgta | 1440 |
| ctggcacacc agcagggcgg cttc | 1464 |

<210> SEQ ID NO 79
<211> LENGTH: 1788
<212> TYPE: DNA
<213> ORGANISM: Artificial Sequence
<220> FEATURE:
<223> OTHER INFORMATION: Synthetic

<400> SEQUENCE: 79

| | |
|---|---|
| gaagccgccc tgctggtgtg ccagtacact attcagagcc tgattcatct gaccggggag | 60 |
| gaccctggat ttttcaatgt ggaaatccct gagttcccat tttaccccac ctgcaacgtc | 120 |
| tgtacagccg acgtgaacgt caccattaat ttcgatgtgg gcgggaagaa acaccagctg | 180 |
| gacctggatt ttggccagct gaccccacat acaaaagccg tgtatcagcc cagaggggct | 240 |
| ttcggaggca gcgagaacgc aacaaatctg tttctgctgg agctgctggg agcaggagaa | 300 |
| ctggctctga ccatgaggtc caagaaactg cccatcaatg tgaccacagg agaggaacag | 360 |
| caggtcagtc tggaatcagt ggacgtctac ttccaggatg tgtttggcac catgtggtgc | 420 |
| caccatgccg agatgcagaa tcctgtgtac ctgatcccg aaaccgtccc ttatattaag | 480 |
| tgggacaact gtaatagcac taacattacc gcagtggtcc gggcacaggg gctggacgtg | 540 |
| accctgccac tgtcactgcc cacaagcgcc caggatagca acttctccgt gaaaaccgag | 600 |
| atgctgggaa atgagatcga cattgaatgc atcatggagg atggagaaat tagccaggtg | 660 |
| ctgcctggcg ataacaagtt taatatcacc tgttccggct acgaatctca cgtcccaagt | 720 |
| gggggaatcc tgacatctac tagtcccgtg gccactccaa ttcccggaac cggctacgct | 780 |
| tatagcctga gactgacccc taggccagtc tcacgcttcc tgggcaacaa tagcattctg | 840 |
| tacgtgtttt attccggaaa cggaccaaag gcttctggag gggactattg catccagagt | 900 |
| aatattgtgt ctcagacgga gatcccagcc agccaggata tgcccactaa cactaccgac | 960 |
| attacctacg tgggcgataa tgccacttat tccgtgccta tggtcacaag cgaagacgct | 1020 |
| aactccccaa atgtgaccgt cacagcattc tgggcctggc caacaatac tgagaccgat | 1080 |
| tttaagtgca aatggacact gacttcaggc acccctagcg ggtgtgaaaa catctctggc | 1140 |
| gccttcgcta gtaatcgaac ctttgatatt acagtgtccg gcctggggac tgccccaaaa | 1200 |
| accctgatca ttacccggac agctactaac gcaacaacta ccacacacaa agtgatcttc | 1260 |
| agcaaagctc cctccggaga gagccaggtg aggcagaact tcaagcccga gatggaggag | 1320 |
| aagctgaacg agcagatgaa cctggagctg tacagcagcc tgctgtacca gcagatgagc | 1380 |
| gcctggtgca gctaccacac cttcgagggc ccgccgcct tcctgaggag gcacgcccag | 1440 |
| gaggagatga cccacatgca gaggctgttc gactacctga ccgacaccgg caacctgccc | 1500 |
| aggatcaaca ccgtgggaga ccccttcgcc gagtacagca gcctggacga gctgttccag | 1560 |
| gagacctaca gcacgagca gctgatcacc cagaagatca acgagctggc ccacgccgcc | 1620 |

```
atgaccaacc aggactaccc caccttcaac ttcctgcagt ggtacgtgag cgagcagcac    1680
gaggaggaga agctgttcaa gagcatcatc gacaagctga gcctggccgg caagagcggc    1740
gagggcctgt acttcatcga caaggagctg agcaccctgg acggatcc                 1788
```

<210> SEQ ID NO 80
<211> LENGTH: 596
<212> TYPE: PRT
<213> ORGANISM: Artificial Sequence
<220> FEATURE:
<223> OTHER INFORMATION: Synthetic

<400> SEQUENCE: 80

```
Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Gln Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Pro Tyr Ile Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
        195                 200                 205

Glu Cys Ile Met Glu Asp Gly Glu Ile Ser Gln Val Leu Pro Gly Asp
    210                 215                 220

Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
        275                 280                 285

Pro Lys Ala Ser Gly Gly Asp Tyr Cys Ile Gln Ser Asn Ile Val Phe
    290                 295                 300

Ser Asp Glu Ile Pro Ala Ser Gln Asp Met Pro Thr Asn Thr Thr Asp
305                 310                 315                 320

Ile Thr Tyr Val Gly Asp Asn Ala Thr Tyr Ser Val Pro Met Val Thr
                325                 330                 335
```

Ser Glu Asp Ala Asn Ser Pro Asn Val Thr Val Thr Ala Phe Trp Ala
                340                 345                 350

Trp Pro Asn Asn Thr Glu Thr Asp Phe Lys Cys Lys Trp Thr Leu Thr
            355                 360                 365

Ser Gly Thr Pro Ser Gly Cys Glu Asn Ile Ser Gly Ala Phe Ala Ser
        370                 375                 380

Asn Arg Thr Phe Asp Ile Thr Val Ser Gly Leu Gly Thr Ala Pro Lys
385                 390                 395                 400

Thr Leu Ile Ile Thr Arg Thr Ala Thr Asn Ala Thr Thr Thr His
                405                 410                 415

Lys Val Ile Phe Ser Lys Ala Pro Ser Gly Glu Ser Gln Val Arg Gln
                420                 425                 430

Asn Phe Lys Pro Glu Met Glu Glu Lys Leu Asn Glu Gln Met Asn Leu
            435                 440                 445

Glu Leu Tyr Ser Ser Leu Leu Tyr Gln Gln Met Ser Ala Trp Cys Ser
        450                 455                 460

Tyr His Thr Phe Glu Gly Ala Ala Ala Phe Leu Arg Arg His Ala Gln
465                 470                 475                 480

Glu Glu Met Thr His Met Gln Arg Leu Phe Asp Tyr Leu Thr Asp Thr
                485                 490                 495

Gly Asn Leu Pro Arg Ile Asn Thr Val Glu Ser Pro Phe Ala Glu Tyr
                500                 505                 510

Ser Ser Leu Asp Glu Leu Phe Gln Glu Thr Tyr Lys His Glu Gln Leu
        515                 520                 525

Ile Thr Gln Lys Ile Asn Glu Leu Ala His Ala Met Thr Asn Gln
    530                 535                 540

Asp Tyr Pro Thr Phe Asn Phe Leu Gln Trp Tyr Val Ser Glu Gln His
545                 550                 555                 560

Glu Glu Glu Lys Leu Phe Lys Ser Ile Ile Asp Lys Leu Ser Leu Ala
                565                 570                 575

Gly Lys Ser Gly Glu Gly Leu Tyr Phe Ile Asp Lys Glu Leu Ser Thr
            580                 585                 590

Leu Asp Gly Ser
        595

<210> SEQ ID NO 81
<211> LENGTH: 1788
<212> TYPE: DNA
<213> ORGANISM: Artificial Sequence
<220> FEATURE:
<223> OTHER INFORMATION: Synthetic

<400> SEQUENCE: 81
ggatccgtcc agggtgctca gctccttgtc gatgaagtac aggccctcgc cgctcttgcc      60
ggccaggctc agcttgtcga tgatgctctt gaacagcttc tcctcctcgt gctgctcgct     120
cacgtaccac tgcaggaagt tgaaggtggg tagtcctgg ttggtcatgg cggcgtgggc     180
cagctcgttg atcttctggg tgatcagctg ctcgtgcttg taggtctcct ggaacagctc     240
gtccaggctg ctgtactcgg cgaaggggct ctccacggtg ttgatcctgg caggttgcc     300 ggtgtcggtc aggtagtcga acagcctctg catgtgggtc atctcctcct gggcgtgcct     360
cctcaggaag cggcggcgc cctcgaaggt gtggtagctg caccaggcgc tcatctgctg     420
gtacagcagg ctgctgtaca gctccaggtt catctgctcg ttcagcttct cctccatctc     480
gggcttgaag ttctgcctca cctggctctc tccggaggga gctttgctga agatcacttt     540

```
gtgtgtggta gttgttgcgt tagtagctgt ccgggtaatg atcagggttt ttggggcagt      600
ccccaggccg gacactgtaa tatcaaaggt tcgattacta gcgaaggcgc cagagatgtt      660
ttcacacccg ctagggggtgc ctgaagtcag tgtccatttg cacttaaaat cggtctcagt    720
attgttgggc caggcccaga atgctgtgac ggtcacattt ggggagttag cgtcttcgct     780
tgtgaccata ggcacggaat aagtggcatt atcgcccacg taggtaatgt cggtagtgtt     840
agtgggcata tcctggctgg ctgggatctc gtctgagaac acaatattac tctggatgca     900
atagtcccct ccagaagcct tggtccgtt tccggaataa acacgtaca gaatgctatt       960 gttgcccagg aagcgtgaga ctggcctagg ggtcagtctc aggctataag cgtagccggt    1020
tccgggaatt ggagtggcca cgggactagt agatgtcagg attcccccac ttgggacgtg    1080
agattcgtag ccggaacagg tgatattaaa cttgttatcg ccaggcagca cctggctaat   1140
ttctccatcc tccatgatgc attcaatgtc gatctcattt cccagcatct cggttttcac    1200
ggagaagttg ctatcctggg cgcttgtggg cagtgacagt ggcagggtca cgtccagccc    1260
ctgtgcccgg accactgcgg taatgttagt gctattacag ttgtcccact taatataagg    1320
gacggtttcg gggatcaggt acacaggatt ctgcatctcg gcatggtggc accacatggt   1380
gccaaacaca tcctggaagt agacgtccac tgattccaga ctgacctgct gttcctctcc    1440
tgtggtcaca ttgatgggca gtttcttgga cctcatggtc agagccagtt ctcctgctcc   1500
cagcagctcc agcagaaaca gatttgttgc gttctcgctg cctccgaaag ccctctgggg   1560
ctgatacacg gcttttgtat gtgggtcag ctggccaaaa tccaggtcca gctggtgttt   1620
cttcccgccc acatcgaaat taatggtgac gttcacgtcg gctgtacaga cgttgcaggt    1680
ggggtaaaat gggaactcag ggatttccac attgaaaaat ccagggtcct ccccggtcag   1740
atgaatcagg ctctgaatag tgtactggca caccagcagg gcggcttc                 1788

<210> SEQ ID NO 82
<211> LENGTH: 3108
<212> TYPE: DNA
<213> ORGANISM: Artificial Sequence
<220> FEATURE:
<223> OTHER INFORMATION: Synthetic

<400> SEQUENCE: 82
gaagccgccc tgctggtgtg ccagtacact attcagagcc tgattcatct gaccggggag       60
gaccctggat ttttcaatgt ggaaatccct gagttcccat tttaccccac ctgcaacgtc      120
tgtacagccg acgtgaacgt caccattaat ttcgatgtgg gcgggaagaa acaccagctg      180
gacctggatt ttggccagct gaccccacat acaaaagccg tgtatcagcc cagaggggct     240
ttcggaggca gcgagaacgc aacaaatctg tttctgctgg agctgctggg agcaggagaa      300
ctggctctga ccatgaggtc caagaaactg cccatcaatg tgaccacagg agaggaacag      360
caggtcagtc tggaatcagt ggacgtctac ttccaggatg tgtttggcac catgtggtgc      420
caccatgccg agatgcagaa tcctgtgtac ctgatccccg aaaccgtccc ttatattaag     480
tgggacaact gtaatagcac taacattacc gcagtggtcc gggcacaggg gctggacgtg    540
accctgccac tgtcactgcc cacaagcgcc caggatagca acttctccgt gaaaaccgag    600
atgctgggaa atgagatcga cattgaatgc atcatggagg atggagaaat tagccaggtg   660
ctgcctggcg ataacaagtt taatatcacc tgttccggct acgaatctca cgtcccaagt    720
gggggaatcc tgcatctac tagtcccgtg ccactccaa ttcccggaac cggctacgct      780
tatagcctga gactgacccc taggccagtc tcacgcttcc tgggcaacaa tagcattctg     840
```

```
tacgtgtttt attccggaaa cggaccaaag gcttctggag gggactattg catccagagt    900
aatattgtgt tctcagacga gatcccagcc agccaggata tgcccactaa cactaccgac    960
attacctacg tgggcgataa tgccacttat tccgtgccta tggtcacaag cgaagacgct   1020
aactccccaa atgtgaccgt cacagcattc tgggcctggc ccaacaatac tgagaccgat   1080
tttaagtgca aatggacact gacttcaggc accectagcg ggtgtgaaaa catctctggc   1140
gccttcgcta gtaatcgaac ctttgatatt acagtgtccg gcctgggac tgccccaaaa    1200
accctgatca ttacccggac agctactaac gcaacaacta ccacacacaa agtgatcttc   1260
agcaaagctc ccgagtccac taccacatct cctaccctga acactaccgg gtttgccgac   1320
cccaatacaa ctaccggact gcctagctcc acccatgtgc aacaaacct gactgcacca    1380
gcatccaccg gacctacagt gtctactgcc gatgtcacca gtcccacacc tgccggaaca   1440
acttctggcg ctagtcccgt gaccccatca cccagccctt gggacaatgg gacagagagt   1500
aaggcccctg atatgacttc tagtacctca ccagtcacca caccaacccc caacgcaaca   1560
agccctactc cagccgtgac tacccccaca cctaatgcta ccagcccaac accogcagtg   1620
acaactccta ccccaaaacgc cacttcccca accctgggga agacatcacc cactagcgcc   1680
gtgaccacac ccaccectaa tgctacctct cctacactgg gaaaaacttc cccaacctct   1740
gcagtgacta ccccaacccc caacgccaca agccccactc tgggcaagac cagtcctaca   1800
tcagctgtca aactcctac cccaaatgca actgggccaa ccgtgggaga gacatccccc   1860
caggctaacg caacaaatca cactctggga ggcaccagtc ccacacctgt ggtcacctca   1920
cagcccaaga acgccacaag cgctgtgacc acaggccagc ataatatcac atcaagctcc   1980
acttctagta tgagcctgcg cccttcaagc aacccagaga cactgtcccc atctactagt   2040
gacaattcaa ccagccacat gcctctgctg acatctgcac atccaactgg gggagaaaac   2100
atcactcagg tcaccccccgc ctccatttct acccaccatg tgtccacatc ctctccagca   2160
ccccgacctg gaactaccag ccaggcatcc ggaccaggaa atagttcaac cagcacaaag   2220
cctggcgagg tgaacgtcac aaaagggact cccectcaga atgctacctc acctcaggca   2280
ccaagcggcc agaaaacagc tgtgcctact gtcacctcca caggcgggaa ggcaaactct   2340
acaactggag gcaaacacac cacagggcat ggagctcgca ctagcaccga accaactacc   2400
gactacgggg gagattccac aactccaagg cccagataca atgccaccac atatctgcca   2460
ccctctacca gctccaagct gcgacccaga tggacattca ctagtcctcc agtgactacc   2520
gcacaggcta cagtgccagt cccacctact tctcagccta gatttttctaa cctgagttcc   2580
ggagagagcc aggtgaggca gcagttcagc aaggacatcg agaagctgct gaacgagcag   2640
gtgaacaagg agatgcagag cagcaacctg tacatgagca tgagcagctg gtgctacacc   2700
cacagcctgg acggcgccgg cctgttcctg ttcgaccacg ccgccgagga gtacgagcac   2760
gccaagaagc tgatcatctt cctgaacgag aacaacgtgc ccgtgcagct gaccagcatc   2820
agcgccccccg agcacaagtt cgagggcctg acccagatct tccagaaggc ctacgagcac   2880
gagcagcaca tcagcgagag catcaacaac atcgtggacc acgccatcaa gagcaaggac   2940
cacgccacct tcaacttcct gcagtggtac gtggccgagc agcacgagga ggaggtgctg   3000
ttcaaggaca tcctggacaa gatcgagctg atcggcaacg agaaccacgg cctgtacctg   3060
gccgaccagt acgtgaaggg catcgccaag agcaggaaga gcggatcc                3108
```

<210> SEQ ID NO 83

<211> LENGTH: 1036
<212> TYPE: PRT
<213> ORGANISM: Artificial Sequence
<220> FEATURE:
<223> OTHER INFORMATION: Synthetic

<400> SEQUENCE: 83

```
Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Gln Val Ser Leu Glu Ser Val Asp
        115                 120                 125

Val Tyr Phe Gln Asp Val Phe Gly Thr Met Trp Cys His His Ala Glu
130                 135                 140

Met Gln Asn Pro Val Tyr Leu Ile Pro Glu Thr Val Pro Tyr Ile Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
        195                 200                 205

Glu Cys Ile Met Glu Asp Gly Glu Ile Ser Gln Val Leu Pro Gly Asp
210                 215                 220

Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
        275                 280                 285

Pro Lys Ala Ser Gly Gly Asp Tyr Cys Ile Gln Ser Asn Ile Val Phe
290                 295                 300

Ser Asp Glu Ile Pro Ala Ser Gln Asp Met Pro Thr Asn Thr Thr Asp
305                 310                 315                 320

Ile Thr Tyr Val Gly Asp Asn Ala Thr Tyr Ser Val Pro Met Val Thr
                325                 330                 335

Ser Glu Asp Ala Asn Ser Pro Asn Val Thr Val Thr Ala Phe Trp Ala
            340                 345                 350

Trp Pro Asn Asn Thr Glu Thr Asp Phe Lys Cys Lys Trp Thr Leu Thr
        355                 360                 365

Ser Gly Thr Pro Ser Gly Cys Glu Asn Ile Ser Gly Ala Phe Ala Ser
370                 375                 380
```

```
Asn Arg Thr Phe Asp Ile Thr Val Ser Gly Leu Gly Thr Ala Pro Lys
385                 390                 395                 400

Thr Leu Ile Ile Thr Arg Thr Ala Thr Asn Ala Thr Thr Thr Thr His
            405                 410                 415

Lys Val Ile Phe Ser Lys Ala Pro Glu Ser Thr Thr Thr Ser Pro Thr
        420                 425                 430

Leu Asn Thr Thr Gly Phe Ala Asp Pro Asn Thr Thr Thr Gly Leu Pro
        435                 440                 445

Ser Ser Thr His Val Pro Thr Asn Leu Thr Ala Pro Ala Ser Thr Gly
    450                 455                 460

Pro Thr Val Ser Thr Ala Asp Val Thr Ser Pro Thr Pro Ala Gly Thr
465                 470                 475                 480

Thr Ser Gly Ala Ser Pro Val Thr Pro Ser Pro Ser Pro Trp Asp Asn
                485                 490                 495

Gly Thr Glu Ser Lys Ala Pro Asp Met Thr Ser Thr Ser Pro Val
                500                 505                 510

Thr Thr Pro Thr Pro Asn Ala Thr Ser Pro Thr Pro Ala Val Thr Thr
            515                 520                 525

Pro Thr Pro Asn Ala Thr Ser Pro Thr Pro Ala Val Thr Thr Pro Thr
            530                 535                 540

Pro Asn Ala Thr Ser Pro Thr Leu Gly Lys Thr Ser Pro Thr Ser Ala
545                 550                 555                 560

Val Thr Thr Pro Thr Pro Asn Ala Thr Ser Pro Thr Leu Gly Lys Thr
                565                 570                 575

Ser Pro Thr Ser Ala Val Thr Thr Pro Thr Pro Asn Ala Thr Ser Pro
            580                 585                 590

Thr Leu Gly Lys Thr Ser Pro Thr Ser Ala Val Thr Thr Pro Thr Pro
            595                 600                 605

Asn Ala Thr Gly Pro Thr Val Gly Glu Thr Ser Pro Gln Ala Asn Ala
            610                 615                 620

Thr Asn His Thr Leu Gly Gly Thr Ser Pro Thr Pro Val Val Thr Ser
625                 630                 635                 640

Gln Pro Lys Asn Ala Thr Ser Ala Val Thr Thr Gly Gln His Asn Ile
                645                 650                 655

Thr Ser Ser Ser Thr Ser Ser Met Ser Leu Arg Pro Ser Ser Asn Pro
            660                 665                 670

Glu Thr Leu Ser Pro Ser Thr Ser Asp Asn Ser Thr Ser His Met Pro
            675                 680                 685

Leu Leu Thr Ser Ala His Pro Thr Gly Gly Glu Asn Ile Thr Gln Val
            690                 695                 700

Thr Pro Ala Ser Ile Ser Thr His His Val Ser Thr Ser Ser Pro Ala
705                 710                 715                 720

Pro Arg Pro Gly Thr Thr Ser Gln Ala Ser Gly Pro Gly Asn Ser Ser
                725                 730                 735

Thr Ser Thr Lys Pro Gly Glu Val Asn Val Thr Lys Gly Thr Pro Pro
            740                 745                 750

Gln Asn Ala Thr Ser Pro Gln Ala Pro Ser Gly Gln Lys Thr Ala Val
            755                 760                 765

Pro Thr Val Thr Ser Thr Gly Gly Lys Ala Asn Ser Thr Thr Gly Gly
            770                 775                 780

Lys His Thr Thr Gly His Gly Ala Arg Thr Ser Thr Glu Pro Thr Thr
785                 790                 795                 800
```

```
Asp Tyr Gly Gly Asp Ser Thr Thr Pro Arg Pro Arg Tyr Asn Ala Thr
                805                 810                 815

Thr Tyr Leu Pro Pro Ser Thr Ser Ser Lys Leu Arg Pro Arg Trp Thr
            820                 825                 830

Phe Thr Ser Pro Pro Val Thr Thr Ala Gln Ala Thr Val Pro Val Pro
            835                 840                 845

Pro Thr Ser Gln Pro Arg Phe Ser Asn Leu Ser Ser Gly Glu Ser Gln
850                 855                 860

Val Arg Gln Gln Phe Ser Lys Asp Ile Glu Lys Leu Leu Asn Glu Gln
865                 870                 875                 880

Val Asn Lys Glu Met Gln Ser Ser Asn Leu Tyr Met Ser Met Ser Ser
                885                 890                 895

Trp Cys Tyr Thr His Ser Leu Asp Gly Ala Gly Leu Phe Leu Phe Asp
                900                 905                 910

His Ala Ala Glu Glu Tyr Glu His Ala Lys Lys Leu Ile Ile Phe Leu
            915                 920                 925

Asn Glu Asn Asn Val Pro Val Gln Leu Thr Ser Ile Ser Ala Pro Glu
    930                 935                 940

His Lys Phe Glu Gly Leu Thr Gln Ile Phe Gln Lys Ala Tyr Glu His
945                 950                 955                 960

Glu Gln His Ile Ser Glu Ser Ile Asn Asn Ile Val Asp His Ala Ile
                965                 970                 975

Lys Ser Lys Asp His Ala Thr Phe Asn Phe Leu Gln Trp Tyr Val Ala
            980                 985                 990

Glu Gln His Glu Glu Val Leu Phe Lys Asp Ile Leu Asp Lys Ile
            995                 1000                1005

Glu Leu Ile Gly Asn Glu Asn His Gly Leu Tyr Leu Ala Asp Gln
    1010                1015                1020

Tyr Val Lys Gly Ile Ala Lys Ser Arg Lys Ser Gly Ser
    1025                1030                1035

<210> SEQ ID NO 84
<211> LENGTH: 3108
<212> TYPE: DNA
<213> ORGANISM: Artificial Sequence
<220> FEATURE:
<223> OTHER INFORMATION: Synthetic

<400> SEQUENCE: 84
ggatccgctc ttcctgctct tggcgatgcc cttcacgtac tggtcggcca ggtacaggcc      60
gtggttctcg ttgccgatca gctcgatctt gtccaggatg tccttgaaca gcacctcctc     120
ctcgtgctgc tcggccacgt accactgcag gaagttgaag gtggcgtggt ccttgctctt     180
gatggcgtgg tccacgatgt tgttgatgct ctcgctgatg tgctgctcgt gctcgtaggc     240
cttctggaag atctgggtca ggccctcgaa cttgtgctcg ggggcgctga tgctggtcag     300
ctgcacgggc acgttgttct cgttcaggaa gatgatcagc ttcttggcgt gctcgtactc     360
ctcggcggcg tggtcgaaca ggaacaggcc ggcgccgtcc aggctgtggg tgtagcacca     420
gctgctcatg ctcatgtaca ggttgctgct ctgcatctcc ttgttcacct gctcgttcag     480
cagcttctcg atgtccttgc tgaactgctg cctcacctgg ctctctccgg aactcaggtt     540
agaaaatcta ggctgagaag taggtgggac tggcactgta gcctgtgcgg tagtcactgg     600
aggactagta atgtccatc tgggtcgcag cttggagctg gtagagggtg gcagatatgt     660
ggtggcattg tatctgggcc ttggagttgt ggaatctccc ccgtagtcgg tagttggttc     720
```

```
ggtgctagtg cgagctccat gccctgtggt gtgtttgcct ccagttgtag agtttgcctt    780
cccgcctgtg gaggtgacag taggcacagc tgttttctgg ccgcttggtg cctgaggtga    840
ggtagcattc tgagggggag tccctttttgt dacgttcacc tcgccaggct tgtgctggt    900
tgaactattt cctggtccgg atgcctggct ggtagttcca ggtcgggtg ctggagagga     960
tgtggacaca tggtgggtag aaatggaggc gggggtgacc tgagtgatgt tttctccccc   1020
agttggatgt gcagatgtca gcagaggcat gtggctggtt gaattgtcac tagtagatgg   1080
ggacagtgtc tctgggttgc ttgaagggcg caggctcata ctagaagtgg agcttgatgt   1140
gatattatgc tggcctgtgg tcacagcgct tgtggcgttc ttgggctgtg aggtgaccac   1200
aggtgtggga ctggtgcctc ccagagtgtg atttgttgcg ttagcctggg gggatgtctc   1260
tcccacggtt ggcccagttg catttggggt aggagttgtg acagctgatg taggactggt   1320
cttgcccaga gtgggcttg tggcgttggg ggttgggta gtcactgcag aggttgggga    1380
agttttccc agtgtaggag aggtagcatt aggggtgggt gtggtcacgg cgctagtggg    1440
tgatgtcttc cccaggggttg gggaagtggc gtttgggta ggagttgtca ctgcgggtgt   1500
tgggctggta gcattaggtg tgggggtagt cacggctgga gtagggcttg ttgcgttggg   1560
ggttggtgtg gtgactggtg aggtactaga agtcatatca ggggccttac tctctgtccc   1620
attgtcccaa gggctgggtg atggggtcac gggactagcg ccagaagttg ttccggcagg   1680
tgtgggactg gtgacatcgg cagtagacac tgtaggtccg gtggatgctg gtgcagtcag   1740
gtttgttggc acatgggtgg agctaggcag tccggtagtt gtattggggt cggcaaaccc   1800
ggtagtgttc agggtaggag atgtggtagt ggactcggga gctttgctga agatcacttt   1860
gtgtgtggta gttgttgcgt tagtagctgt ccgggtaatg atcagggttt ttggggcagt   1920
ccccaggccg gacactgtaa tatcaaaggt tcgattacta gcgaaggcgc cagagatgtt   1980
ttcacacccg ctagggtgc ctgaagtcag tgtccatttg cacttaaaat cggtctcagt    2040
attgttgggc caggcccaga atgctgtgac ggtcacattt ggggagttag cgtcttcgct   2100
tgtgaccata ggcacggaat aagtggcatt atcgcccacg taggtaatgt cggtagtgtt   2160
agtgggcata tcctggctgg ctgggatctc gtctgagaac acaatattac tctggatgca   2220
atagtcccct ccagaagcct ttggtccgtt tccggaataa aacacgtaca gaatgctatt   2280
gttgcccaga aagcgtgaga ctggcctagg ggtcagtctc aggctataag cgtagccggt   2340
tccgggaatt ggagtggcca cgggactagt agatgtcagg attccccac ttgggacgtg    2400
agattcgtag ccggaacagg tgatattaaa cttgttatcg ccaggcagca cctggctaat   2460
ttctccatcc tccatgatgc attcaatgtc gatctcattt cccagcatct cggttttcac   2520
ggagaagttg ctatcctggg cgcttgtggg cagtgacagt ggcagggtca cgtccagccc   2580
ctgtgcccgg accactgcgg taatgttagt gctattacag ttgtcccact aatataagg    2640
gacggtttcg gggatcaggt acacaggatt ctgcatctcg gcatggtggc accacatggt   2700
gccaaacaca tcctggaagt agacgtccac tgattccaga ctgacctgct gttcctctcc   2760
tgtggtcaca ttgatgggca gtttcttgga cctcatggtc agagccagtt ctcctgctcc   2820
cagcagctcc agcagaaaca gatttgttgc gttctcgctg cctccgaaag cccctctggg   2880
ctgatacacg gcttttgtat gtggggtcag ctggccaaaa tccaggtcca gctggtgttt   2940
cttcccgccc acatcgaaat taatggtgac gttcacgtcg gctgtacaga cgttgcaggt   3000
ggggtaaaat gggaactcag ggatttccac attgaaaaat ccaggtcct ccccggtcag    3060
atgaatcagg ctctgaatag tgtactggca caccagcagg gcggcttc              3108
```

<210> SEQ ID NO 85
<211> LENGTH: 1479
<212> TYPE: DNA
<213> ORGANISM: Artificial Sequence
<220> FEATURE:
<223> OTHER INFORMATION: Synthetic

<400> SEQUENCE: 85

| | | | | | |
|---|---|---|---|---|---|
| gaagccgccc | tgctggtgtg | ccagtacact | attcagagcc | tgattcatct | gaccggggag | 60 |
| gaccctggat | ttttcaatgt | ggaaatccct | gagttcccat | tttaccccac | ctgcaacgtc | 120 |
| tgtacagccg | acgtgaacgt | caccattaat | ttcgatgtgg | gcgggaagaa | acaccagctg | 180 |
| gacctggatt | ttggccagct | gaccccacat | acaaaagccg | tgtatcagcc | cagaggggct | 240 |
| ttcggaggca | gcgagaacgc | aacaaatctg | tttctgctgg | agctgctggg | agcaggagaa | 300 |
| ctggctctga | ccatgaggtc | caagaaactg | cccatcaatg | tgaccacagg | agaggaacag | 360 |
| caggtcagtc | tggaatcagt | ggacgtctac | ttccaggatg | tgtttggcac | catgtggtgc | 420 |
| caccatgccg | agatgcagaa | tcctgtgtac | ctgatccccg | aaaccgtccc | ttatattaag | 480 |
| tgggacaact | gtaatagcac | taacattacc | gcagtggtcc | gggcacaggg | gctggacgtg | 540 |
| accctgccac | tgtcactgcc | cacaagcgcc | caggatagca | acttctccgt | gaaaaccgag | 600 |
| atgctgggaa | atgagatcga | cattgaatgc | atcatggagg | atggagaaat | tagccaggtg | 660 |
| ctgcctggcg | ataacaagtt | taatatcacc | tgttccggct | acgaatctca | cgtcccaagt | 720 |
| gggggaatcc | tgacatctac | tagtcccgtg | gccactccaa | ttcccggaac | cggctacgct | 780 |
| tatagcctga | gactgacccc | taggccagtc | tcacgcttcc | tgggcaacaa | tagcattctg | 840 |
| tacgtgtttt | attccggaaa | cggaccaaag | gcttctggag | gggactattg | catccagagt | 900 |
| aatattgtgt | ctcagacga | gatcccagcc | agccaggata | tgcccacttc | cggagagagc | 960 |
| caggtgaggc | agcagttcag | caaggacatc | gagaagctgc | tgaacgagca | ggtgaacaag | 1020 |
| gagatgcaga | gcagcaacct | gtacatgagc | atgagcagct | ggtgctacac | ccacagcctg | 1080 |
| gacggcgccg | gcctgttcct | gttcgaccac | gccgccgagg | agtacgagca | cgccaagaag | 1140 |
| ctgatcatct | tcctgaacga | gaacaacgtg | cccgtgcagc | tgaccagcat | cagcgccccc | 1200 |
| gagcacaagt | tcgagggcct | gacccagatc | ttccagaagg | cctacgagca | cgagcagcac | 1260 |
| atcagcgaga | gcatcaacaa | catcgtggac | acgccatca | agagcaagga | ccacgccacc | 1320 |
| ttcaacttcc | tgcagtggta | cgtggccgag | cagcacgagg | aggaggtgct | gttcaaggac | 1380 |
| atcctggaca | gatcgagct | gatcggcaac | gagaaccacg | gcctgtacct | ggccgaccag | 1440 |
| tacgtgaagg | gcatcgccaa | gagcaggaag | agcggatcc | | | 1479 |

<210> SEQ ID NO 86
<211> LENGTH: 493
<212> TYPE: PRT
<213> ORGANISM: Artificial Sequence
<220> FEATURE:
<223> OTHER INFORMATION: Synthetic

<400> SEQUENCE: 86

Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

-continued

```
Ile Asn Phe Asp Val Gly Gly Lys Lys His Gln Leu Asp Leu Asp Phe
 50                  55                  60

Gly Gln Leu Thr Pro His Thr Lys Ala Val Tyr Gln Pro Arg Gly Ala
 65                  70                  75                  80

Phe Gly Gly Ser Glu Asn Ala Thr Asn Leu Phe Leu Leu Glu Leu Leu
                 85                  90                  95

Gly Ala Gly Glu Leu Ala Leu Thr Met Arg Ser Lys Lys Leu Pro Ile
                100                 105                 110

Asn Val Thr Thr Gly Glu Gln Gln Val Ser Leu Glu Ser Val Asp
                115                 120                 125

Val Tyr Phe Gln Asp Val Phe Gly Thr Met Trp Cys His His Ala Glu
 130                 135                 140

Met Gln Asn Pro Val Tyr Leu Ile Pro Glu Thr Val Pro Tyr Ile Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
                180                 185                 190

Ser Asn Phe Ser Val Lys Thr Glu Met Leu Gly Asn Glu Ile Asp Ile
195                 200                 205

Glu Cys Ile Met Glu Asp Gly Glu Ile Ser Gln Val Leu Pro Gly Asp
210                 215                 220

Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
                260                 265                 270

Phe Leu Gly Asn Asn Ser Ile Leu Tyr Val Phe Tyr Ser Gly Asn Gly
                275                 280                 285

Pro Lys Ala Ser Gly Gly Asp Tyr Cys Ile Gln Ser Asn Ile Val Phe
                290                 295                 300

Ser Asp Glu Ile Pro Ala Ser Gln Asp Met Pro Thr Ser Gly Glu Ser
305                 310                 315                 320

Gln Val Arg Gln Gln Phe Ser Lys Asp Ile Glu Lys Leu Leu Asn Glu
                325                 330                 335

Gln Val Asn Lys Glu Met Gln Ser Ser Asn Leu Tyr Met Ser Met Ser
                340                 345                 350

Ser Trp Cys Tyr Thr His Ser Leu Asp Gly Ala Gly Leu Phe Leu Phe
                355                 360                 365

Asp His Ala Ala Glu Glu Tyr Glu His Ala Lys Lys Leu Ile Ile Phe
370                 375                 380

Leu Asn Glu Asn Asn Val Pro Val Gln Leu Thr Ser Ile Ser Ala Pro
385                 390                 395                 400

Glu His Lys Phe Glu Gly Leu Thr Gln Ile Phe Gln Lys Ala Tyr Glu
                405                 410                 415

His Glu Gln His Ile Ser Glu Ser Ile Asn Asn Ile Val Asp His Ala
                420                 425                 430

Ile Lys Ser Lys Asp His Ala Thr Phe Asn Phe Leu Gln Trp Tyr Val
                435                 440                 445

Ala Glu Gln His Glu Glu Val Leu Phe Lys Asp Ile Leu Asp Lys
450                 455                 460
```

Ile Glu Leu Ile Gly Asn Glu Asn His Gly Leu Tyr Leu Ala Asp Gln
465                 470                 475                 480

Tyr Val Lys Gly Ile Ala Lys Ser Arg Lys Ser Gly Ser
                485                 490

<210> SEQ ID NO 87
<211> LENGTH: 1479
<212> TYPE: DNA
<213> ORGANISM: Artificial Sequence
<220> FEATURE:
<223> OTHER INFORMATION: Synthetic

<400> SEQUENCE: 87

| | | |
|---|---|---|
| ggatccgctc ttcctgctct tggcgatgcc cttcacgtac tggtcggcca ggtacaggcc | 60 |
| gtggttctcg ttgccgatca gctcgatctt gtccaggatg tccttgaaca gcacctcctc | 120 |
| ctcgtgctgc tcggccacgt accactgcag gaagttgaag gtggcgtggt ccttgctctt | 180 |
| gatggcgtgg tccacgatgt tgttgatgct ctcgctgatg tgctgctcgt gctcgtaggc | 240 |
| cttctggaag atctgggtca ggccctcgaa cttgtgctcg ggggcgctga tgctggtcag | 300 |
| ctgcacgggc acgttgttct cgttcaggaa gatgatcagc ttcttggcgt gctcgtactc | 360 |
| ctcggcggcg tggtcgaaca ggaacaggcc ggcgccgtcc aggctgtggg tgtagcacca | 420 |
| gctgctcatg ctcatgtaca ggttgctgct ctgcatctcc ttgttcacct gctcgttcag | 480 |
| cagcttctcg atgtccttgc tgaactgctg cctcacctgg ctctctccgg aagtgggcat | 540 |
| atcctggctg gctgggatct cgtctgagaa cacaatatta ctctggatgc aatagtcccc | 600 |
| tccagaagcc tttggtccgt ttccggaata aacacgtac agaatgctat tgttgcccag | 660 |
| gaagcgtgag actggcctag gggtcagtct caggctataa gcgtagccgg ttccgggaat | 720 |
| tggagtggcc acgggactag tagatgtcag gattccccca cttgggacgt gagattcgta | 780 |
| gccggaacag gtgatattaa acttgttatc gccaggcagc acctggctaa tttctccatc | 840 |
| ctccatgatg cattcaatgt cgatctcatt tcccagcatc tcggttttca cggagaagtt | 900 |
| gctatcctgg gcgcttgtgg gcagtgacag tggcagggtc acgtccagcc cctgtgcccg | 960 |
| gaccactgcg gtaatgttag tgctattaca gttgtcccac ttaatataag ggacggtttc | 1020 |
| ggggatcagg tacacaggat tctgcatctc ggcatggtgg caccacatgg tgccaaacac | 1080 |
| atcctggaag tagacgtcca ctgattccag actgacctgc tgttcctctc ctgtggtcac | 1140 |
| attgatgggc agtttcttgg acctcatggt cagagccagt tctcctgctc ccagcagctc | 1200 |
| cagcagaaac agatttgttg cgttctcgct gcctccgaaa gccctctgg ctgatacac | 1260 |
| ggcttttgta tgtggggtca gctggccaaa atccaggtcc agctggtgtt tcttcccgcc | 1320 |
| cacatcgaaa ttaatggtga cgttcacgtc ggctgtacag acgttgcagg tggggtaaaa | 1380 |
| tgggaactca gggatttcca cattgaaaaa tccagggtcc tccccggtca gatgaatcag | 1440 |
| gctctgaata gtgtactggc acaccagcag ggcggcttc | 1479 |

<210> SEQ ID NO 88
<211> LENGTH: 1803
<212> TYPE: DNA
<213> ORGANISM: Artificial Sequence
<220> FEATURE:
<223> OTHER INFORMATION: Synthetic

<400> SEQUENCE: 88

| | | |
|---|---|---|
| gaagccgccc tgctggtgtg ccagtacact attcagagcc tgattcatct gaccggggag | 60 |
| gaccctggat ttttcaatgt ggaaatccct gagttcccat tttaccccac ctgcaacgtc | 120 |

-continued

```
tgtacagccg acgtgaacgt caccattaat ttcgatgtgg gcgggaagaa acaccagctg      180
gacctggatt ttggccagct gaccccacat acaaaagccg tgtatcagcc cagagggggct    240
ttcggaggca gcgagaacgc aacaaatctg tttctgctgg agctgctggg agcaggagaa    300
ctggctctga ccatgaggtc caagaaactg cccatcaatg tgaccacagg agaggaacag    360
caggtcagtc tggaatcagt ggacgtctac ttccaggatg tgtttggcac catgtggtgc    420
caccatgccg agatgcagaa tcctgtgtac ctgatccccg aaaccgtccc ttatattaag    480
tgggacaact gtaatagcac taacattacc gcagtggtcc gggcacaggg gctggacgtg    540
accctgccac tgtcactgcc cacaagcgcc caggatagca acttctccgt gaaaaccgag    600
atgctgggaa atgagatcga cattgaatgc atcatggagg atggagaaat tagccaggtg    660
ctgcctggcg ataacaagtt taatatcacc tgttccggct acgaatctca cgtcccaagt    720
gggggaatcc tgacatctac tagtcccgtg ccactccaa ttcccggaac cggctacgct     780
tatagcctga gactgacccc taggccagtc tcacgcttcc tgggcaacaa tagcattctg    840
tacgtgtttt attccggaaa cggaccaaag gcttctggag gggactattg catccagagt    900
aatattgtgt ctcagacga gatcccagcc agccaggata tgcccactaa cactaccgac    960
attacctacg tgggcgataa tgccacttat tccgtgccta tggtcacaag cgaagacgct    1020
aactccccaa atgtgaccgt cacagcattc tgggcctggc caacaatac tgagaccgat    1080
tttaagtgca aatggacact gacttcaggc accctagcg ggtgtgaaaa catctctggc    1140
gccttcgcta gtaatcgaac ctttgatatt acagtgtccg gcctggggac tgccccaaaa    1200
accctgatca ttacccggac agctactaac gcaacaacta ccacacacaa agtgatcttc    1260
agcaaagctc cctccggaga gagccaggtg aggcagcagt tcagcaagga catcgagaag    1320
ctgctgaacg agcaggtgaa caaggagatg cagagcagca acctgtacat gagcatgagc    1380
agctggtgct acacccacag cctggacggc gccggcctgt tcctgttcga ccacgccgcc    1440
gaggagtacg agcacgccaa gaagctgatc atcttcctga cgagaacaa cgtgcccgtg    1500
cagctgacca gcatcagcgc ccccgagcac aagttcgagg gcctgaccca gatcttccag    1560
aaggcctacg agcacgagca gcacatcagc gagagcatca acaacatcgt ggaccacgcc    1620
atcaagagca aggaccacgc caccttcaac ttcctgcagt ggtacgtggc cgagcagcac    1680
gaggaggagg tgctgttcaa ggacatcctg acaagatcg agctgatcgg caacgagaac    1740
cacggcctgt acctggccga ccagtacgtg aagggcatcg ccaagagcag gaagagcgga    1800
tcc                                                                  1803
```

<210> SEQ ID NO 89
<211> LENGTH: 601
<212> TYPE: PRT
<213> ORGANISM: Artificial Sequence
<220> FEATURE:
<223> OTHER INFORMATION: Synthetic

<400> SEQUENCE: 89

Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe

```
            50                  55                  60
Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Glu Leu Leu
                85                  90                  95

Gly Ala Gly Glu Leu Ala Leu Thr Met Arg Ser Lys Lys Leu Pro Ile
                100                 105                 110

Asn Val Thr Thr Gly Glu Glu Gln Val Ser Leu Glu Ser Val Asp
                115                 120                 125

Val Tyr Phe Gln Asp Val Phe Gly Thr Met Trp Cys His His Ala Glu
        130                 135                 140

Met Gln Asn Pro Val Tyr Leu Ile Pro Glu Thr Val Pro Tyr Ile Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
                180                 185                 190

Ser Asn Phe Ser Val Lys Thr Glu Met Leu Gly Asn Glu Ile Asp Ile
                195                 200                 205

Glu Cys Ile Met Glu Asp Gly Glu Ile Ser Gln Val Leu Pro Gly Asp
                210                 215                 220

Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
                260                 265                 270

Phe Leu Gly Asn Asn Ser Ile Leu Tyr Val Phe Tyr Ser Gly Asn Gly
                275                 280                 285

Pro Lys Ala Ser Gly Gly Asp Tyr Cys Ile Gln Ser Asn Ile Val Phe
                290                 295                 300

Ser Asp Glu Ile Pro Ala Ser Gln Asp Met Pro Thr Asn Thr Thr Asp
305                 310                 315                 320

Ile Thr Tyr Val Gly Asp Asn Ala Thr Tyr Ser Val Pro Met Val Thr
                325                 330                 335

Ser Glu Asp Ala Asn Ser Pro Asn Val Thr Val Thr Ala Phe Trp Ala
                340                 345                 350

Trp Pro Asn Asn Thr Glu Thr Asp Phe Lys Cys Lys Trp Thr Leu Thr
                355                 360                 365

Ser Gly Thr Pro Ser Gly Cys Glu Asn Ile Ser Gly Ala Phe Ala Ser
                370                 375                 380

Asn Arg Thr Phe Asp Ile Thr Val Ser Gly Leu Gly Thr Ala Pro Lys
385                 390                 395                 400

Thr Leu Ile Ile Thr Arg Thr Ala Thr Asn Ala Thr Thr Thr His
                405                 410                 415

Lys Val Ile Phe Ser Lys Ala Pro Ser Gly Glu Ser Gln Val Arg Gln
                420                 425                 430

Gln Phe Ser Lys Asp Ile Glu Lys Leu Leu Asn Glu Gln Val Asn Lys
                435                 440                 445

Glu Met Gln Ser Ser Asn Leu Tyr Met Ser Met Ser Ser Trp Cys Tyr
                450                 455                 460

Thr His Ser Leu Asp Gly Ala Gly Leu Phe Leu Phe Asp His Ala Ala
465                 470                 475                 480
```

Glu Glu Tyr Glu His Ala Lys Lys Leu Ile Ile Phe Leu Asn Glu Asn
                485                 490                 495

Asn Val Pro Val Gln Leu Thr Ser Ile Ser Ala Pro Glu His Lys Phe
            500                 505                 510

Glu Gly Leu Thr Gln Ile Phe Gln Lys Ala Tyr Glu His Glu Gln His
        515                 520                 525

Ile Ser Glu Ser Ile Asn Asn Ile Val Asp His Ala Ile Lys Ser Lys
    530                 535                 540

Asp His Ala Thr Phe Asn Phe Leu Gln Trp Tyr Val Ala Glu Gln His
545                 550                 555                 560

Glu Glu Glu Val Leu Phe Lys Asp Ile Leu Asp Lys Ile Glu Leu Ile
                565                 570                 575

Gly Asn Glu Asn His Gly Leu Tyr Leu Ala Asp Gln Tyr Val Lys Gly
            580                 585                 590

Ile Ala Lys Ser Arg Lys Ser Gly Ser
        595                 600

<210> SEQ ID NO 90
<211> LENGTH: 1803
<212> TYPE: DNA
<213> ORGANISM: Artificial Sequence
<220> FEATURE:
<223> OTHER INFORMATION: Synthetic

<400> SEQUENCE: 90

| | | | | | |
|---|---|---|---|---|---|
| ggatccgctc | ttcctgctct | tggcgatgcc | cttcacgtac | tggtcggcca | ggtacaggcc | 60 |
| gtggttctcg | ttgccgatca | gctcgatctt | gtccaggatg | tccttgaaca | gcacctcctc | 120 |
| ctcgtgctgc | tcggccacgt | accactgcag | gaagttgaag | gtggcgtggt | ccttgctctt | 180 |
| gatggcgtgg | tccacgatgt | tgttgatgct | ctcgctgatg | tgctgctcgt | gctcgtaggc | 240 |
| cttctggaag | atctgggtca | ggccctcgaa | cttgtgctcg | ggggcgctga | tgctggtcag | 300 |
| ctgcacgggc | acgttgttct | cgttcaggaa | gatgatcagc | ttcttggcgt | gctcgtactc | 360 |
| ctcggcggcg | tggtcgaaca | ggaacaggcc | ggcgccgtcc | aggctgtggg | tgtagcacca | 420 |
| gctgctcatg | ctcatgtaca | ggttgctgct | ctgcatctcc | ttgttcacct | gctcgttcag | 480 |
| cagcttctcg | atgtccttgc | tgaactgctg | cctcacctgg | ctctctccgg | agggagcttt | 540 |
| gctgaagatc | actttgtgtg | tggtagttgt | tgcgttagta | gctgtccggg | taatgatcag | 600 |
| ggttttggg | gcagtcccca | ggccggacac | tgtaatatca | aggttcgat | tactagcgaa | 660 |
| ggcgccagag | atgttttcac | acccgctagg | ggtgcctgaa | gtcagtgtcc | atttgcactt | 720 |
| aaaatcggtc | tcagtattgt | tgggccaggc | ccagaatgct | gtgacggtca | catttgggga | 780 |
| gttagcgtct | tcgcttgtga | ccataggcac | ggaataagtg | gcattatcgc | ccacgtaggt | 840 |
| aatgtcggta | gtgttagtgg | gcatatcctg | gctggctggg | atctcgtctg | agaacacaat | 900 |
| attactctgg | atgcaaatagt | cccctccaga | agcctttggt | ccgtttccgg | aataaaacac | 960 |
| gtacagaatg | ctattgttgc | ccaggaagcg | tgagactggc | ctaggggtca | gtctcaggct | 1020 |
| ataagcgtag | ccggttccgg | gaattggagt | ggccacggga | ctagtagatg | tcaggattcc | 1080 |
| cccacttggg | acgtgagatt | cgtagccgga | acaggtgata | ttaaacttgt | tatcgccagg | 1140 |
| cagcacctgg | ctaatttctc | catcctccat | gatgcattca | atgtcgatct | catttcccag | 1200 |
| catctcggtt | ttcacggaga | agttgctatc | ctgggcgctt | gtgggcagtg | acagtggcag | 1260 |
| ggtcacgtcc | agcccctgtg | cccggaccac | tgcggtaatg | ttagtgctat | tacagttgtc | 1320 |

| | |
|---|---:|
| ccacttaata taagggacgg tttcggggat caggtacaca ggattctgca tctcggcatg | 1380 |
| gtggcaccac atggtgccaa acacatcctg gaagtagacg tccactgatt ccagactgac | 1440 |
| ctgctgttcc tctcctgtgg tcacattgat gggcagtttc ttggacctca tggtcagagc | 1500 |
| cagttctcct gctcccagca gctccagcag aaacagattt gttgcgttct cgctgcctcc | 1560 |
| gaaagcccct ctgggctgat acacggcttt tgtatgtggg gtcagctggc caaaatccag | 1620 |
| gtccagctgg tgtttcttcc cgcccacatc gaaattaatg gtgacgttca cgtcggctgt | 1680 |
| acagacgttg caggtggggt aaaatgggaa ctcagggatt tccacattga aaatccagg | 1740 |
| gtcctccccg gtcagatgaa tcaggctctg aatagtgtac tggcacacca gcagggcggc | 1800 |
| ttc | 1803 |

<210> SEQ ID NO 91
<211> LENGTH: 1938
<212> TYPE: DNA
<213> ORGANISM: Artificial Sequence
<220> FEATURE:
<223> OTHER INFORMATION: Synthetic

<400> SEQUENCE: 91

| | |
|---|---:|
| gaagccgccc tgctggtgtg ccagtacact attcagagcc tgattcatct gaccggggag | 60 |
| gaccctggat ttttcaatgt ggaaatccct gagttcccat tttaccccac ctgcaacgtc | 120 |
| tgtacagccg acgtgaacgt caccattaat ttcgatgtgg gcgggaagaa acaccagctg | 180 |
| gacctggatt ttggccagct gaccccacat acaaaagccg tgtatcagcc cagaggggct | 240 |
| ttcggaggca gcgagaacgc aacaaatctg tttctgctgg agctgctggg agcaggagaa | 300 |
| ctggctctga ccatgaggtc caagaaactg cccatcaatg tgaccacagg agaggaacag | 360 |
| caggtcagtc tggaatcagt ggacgtctac ttccaggatg tgtttggcac catgtggtgc | 420 |
| caccatgccg agatgcagaa tcctgtgtac ctgatccccg aaaccgtccc ttatattaag | 480 |
| tgggacaact gtaatagcac taacattacc gcagtggtcc gggcacaggg gctgacgtg | 540 |
| accctgccac tgtcactgcc cacaagcgcc caggatagca acttctccgt gaaaaccgag | 600 |
| atgctgggaa atgagatcga cattgaatgc atcatggagg atggagaaat tagccaggtg | 660 |
| ctgcctggcg ataacaagtt taatatcacc tgttccggct acgaatctca cgtcccaagt | 720 |
| gggggaatcc tgcatctac tagtcccgtg gccactccaa ttcccggaac cggctacgct | 780 |
| tatagcctga gactgacccc taggccagtc tcacgcttcc tgggcaacaa tagcattctg | 840 |
| tacgtgtttt attccggaaa cggaccaaag gcttctggag gggactattg catccagagt | 900 |
| aatattgtgt tctcagacga gatcccagcc agccaggata tgcccactaa cactaccgac | 960 |
| attacctacg tgggcgataa tgccacttat tccgtgccta tggtcacaag cgaagacgct | 1020 |
| aactccccaa atgtgaccgt cacagcattc tgggcctggc caacaatac tgagaccgat | 1080 |
| tttaagtgca aatggacact gacttcaggc accctagcg ggtgtgaaaa catctctggc | 1140 |
| gccttcgcta gtaatcgaac ctttgatatt acagtgtccg gctggggac tgccccaaaa | 1200 |
| accctgatca ttacccggac agctactaac gcaacaacta ccacacacaa agtgatcttc | 1260 |
| agcaaagctc ccgagtccac taccacatct cctaccctga acactaccgg gtttgccgac | 1320 |
| cccaatacaa ctaccggact gcctagctcc acccatgtgc aacaaacct gactgcacca | 1380 |
| gcatccaccg gacctacagt gtctacttcc ggagagagcc aggtgaggca gcagttcagc | 1440 |
| aaggacatcg agaagctgct gaacgagcag gtgaacaagg agatgcagag cagcaacctg | 1500 |
| tacatgagca tgagcagctg gtgctacacc cacagcctgg acggcgccgg cctgttcctg | 1560 |

```
ttcgaccacg ccgccgagga gtacgagcac gccaagaagc tgatcatctt cctgaacgag   1620
aacaacgtgc ccgtgcagct gaccagcatc agcgcccccg agcacaagtt cgagggcctg   1680
acccagatct tccagaaggc ctacgagcac gagcagcaca tcagcgagag catcaacaac   1740
atcgtggacc acgccatcaa gagcaaggac cacgccacct tcaacttcct gcagtggtac   1800
gtggccgagc agcacgagga ggaggtgctg ttcaaggaca tcctggacaa gatcgagctg   1860
atcggcaacg agaaccacgg cctgtacctg gccgaccagt acgtgaaggg catcgccaag   1920
agcaggaaga gcggatcc                                                 1938
```

<210> SEQ ID NO 92
<211> LENGTH: 646
<212> TYPE: PRT
<213> ORGANISM: Artificial Sequence
<220> FEATURE:
<223> OTHER INFORMATION: Synthetic

<400> SEQUENCE: 92

```
Glu Ala Ala Leu Leu Val Cys Gln Tyr Thr Ile Gln Ser Leu Ile His
1               5                   10                  15

Leu Thr Gly Glu Asp Pro Gly Phe Phe Asn Val Glu Ile Pro Glu Phe
            20                  25                  30

Pro Phe Tyr Pro Thr Cys Asn Val Cys Thr Ala Asp Val Asn Val Thr
        35                  40                  45

Ile Asn Phe Asp Val Gly Gly Lys Lys His Gln Leu Asp Leu Asp Phe
    50                  55                  60

Gly Gln Leu Thr Pro His Thr Lys Ala Val Tyr Gln Pro Arg Gly Ala
65                  70                  75                  80

Phe Gly Gly Ser Glu Asn Ala Thr Asn Leu Phe Leu Leu Glu Leu Leu
                85                  90                  95

Gly Ala Gly Glu Leu Ala Leu Thr Met Arg Ser Lys Lys Leu Pro Ile
            100                 105                 110

Asn Val Thr Thr Gly Glu Glu Gln Gln Val Ser Leu Glu Ser Val Asp
        115                 120                 125

Val Tyr Phe Gln Asp Val Phe Gly Thr Met Trp Cys His His Ala Glu
    130                 135                 140

Met Gln Asn Pro Val Tyr Leu Ile Pro Glu Thr Val Pro Tyr Ile Lys
145                 150                 155                 160

Trp Asp Asn Cys Asn Ser Thr Asn Ile Thr Ala Val Val Arg Ala Gln
                165                 170                 175

Gly Leu Asp Val Thr Leu Pro Leu Ser Leu Pro Thr Ser Ala Gln Asp
            180                 185                 190

Ser Asn Phe Ser Val Lys Thr Glu Met Leu Gly Asn Glu Ile Asp Ile
        195                 200                 205

Glu Cys Ile Met Glu Asp Gly Glu Ile Ser Gln Val Leu Pro Gly Asp
    210                 215                 220

Asn Lys Phe Asn Ile Thr Cys Ser Gly Tyr Glu Ser His Val Pro Ser
225                 230                 235                 240

Gly Gly Ile Leu Thr Ser Thr Ser Pro Val Ala Thr Pro Ile Pro Gly
                245                 250                 255

Thr Gly Tyr Ala Tyr Ser Leu Arg Leu Thr Pro Arg Pro Val Ser Arg
            260                 265                 270

Phe Leu Gly Asn Asn Ser Ile Leu Tyr Val Phe Tyr Ser Gly Asn Gly
        275                 280                 285
```

-continued

```
Pro Lys Ala Ser Gly Gly Asp Tyr Cys Ile Gln Ser Asn Ile Val Phe
    290                 295                 300

Ser Asp Glu Ile Pro Ala Ser Gln Asp Met Pro Thr Asn Thr Thr Asp
305                 310                 315                 320

Ile Thr Tyr Val Gly Asp Asn Ala Thr Tyr Ser Val Pro Met Val Thr
                325                 330                 335

Ser Glu Asp Ala Asn Ser Pro Asn Val Thr Val Thr Ala Phe Trp Ala
            340                 345                 350

Trp Pro Asn Asn Thr Glu Thr Asp Phe Lys Cys Lys Trp Thr Leu Thr
        355                 360                 365

Ser Gly Thr Pro Ser Gly Cys Glu Asn Ile Ser Gly Ala Phe Ala Ser
    370                 375                 380

Asn Arg Thr Phe Asp Ile Thr Val Ser Gly Leu Gly Thr Ala Pro Lys
385                 390                 395                 400

Thr Leu Ile Ile Thr Arg Thr Ala Thr Asn Ala Thr Thr Thr His
                405                 410                 415

Lys Val Ile Phe Ser Lys Ala Pro Glu Ser Thr Thr Thr Ser Pro Thr
            420                 425                 430

Leu Asn Thr Thr Gly Phe Ala Asp Pro Asn Thr Thr Thr Gly Leu Pro
        435                 440                 445

Ser Ser Thr His Val Pro Thr Asn Leu Thr Ala Pro Ala Ser Thr Gly
    450                 455                 460

Pro Thr Val Ser Thr Ser Gly Glu Ser Gln Val Arg Gln Gln Phe Ser
465                 470                 475                 480

Lys Asp Ile Glu Lys Leu Leu Asn Glu Gln Val Asn Lys Glu Met Gln
                485                 490                 495

Ser Ser Asn Leu Tyr Met Ser Met Ser Ser Trp Cys Tyr Thr His Ser
            500                 505                 510

Leu Asp Gly Ala Gly Leu Phe Leu Phe Asp His Ala Ala Glu Glu Tyr
        515                 520                 525

Glu His Ala Lys Lys Leu Ile Ile Phe Leu Asn Glu Asn Asn Val Pro
    530                 535                 540

Val Gln Leu Thr Ser Ile Ser Ala Pro Glu His Lys Phe Glu Gly Leu
545                 550                 555                 560

Thr Gln Ile Phe Gln Lys Ala Tyr Glu His Glu Gln His Ile Ser Glu
                565                 570                 575

Ser Ile Asn Asn Ile Val Asp His Ala Ile Lys Ser Lys Asp His Ala
            580                 585                 590

Thr Phe Asn Phe Leu Gln Trp Tyr Val Ala Glu Gln His Glu Glu Glu
        595                 600                 605

Val Leu Phe Lys Asp Ile Leu Asp Lys Ile Glu Leu Ile Gly Asn Glu
    610                 615                 620

Asn His Gly Leu Tyr Leu Ala Asp Gln Tyr Val Lys Gly Ile Ala Lys
625                 630                 635                 640

Ser Arg Lys Ser Gly Ser
                645
```

<210> SEQ ID NO 93
<211> LENGTH: 1938
<212> TYPE: DNA
<213> ORGANISM: Artificial Sequence
<220> FEATURE:
<223> OTHER INFORMATION: Synthetic

<400> SEQUENCE: 93

| | |
|---|---:|
| ggatccgctc ttcctgctct tggcgatgcc cttcacgtac tggtcggcca ggtacaggcc | 60 |
| gtggttctcg ttgccgatca gctcgatctt gtccaggatg tccttgaaca gcacctcctc | 120 |
| ctcgtgctgc tcggccacgt accactgcag gaagttgaag gtggcgtggt ccttgctctt | 180 |
| gatggcgtgg tccacgatgt tgttgatgct ctcgctgatg tgctgctcgt gctcgtaggc | 240 |
| cttctggaag atctgggtca ggccctcgaa cttgtgctcg ggggcgctga tgctggtcag | 300 |
| ctgcacgggc acgttgttct cgttcaggaa gatgatcagc ttcttggcgt gctcgtactc | 360 |
| ctcggcggcg tggtcgaaca ggaacaggcc ggcgccgtcc aggctgtggg tgtagcacca | 420 |
| gctgctcatg ctcatgtaca ggttgctgct ctgcatctcc ttgttcacct gctcgttcag | 480 |
| cagcttctcg atgtccttgc tgaactgctg cctcacctgg ctctctccgg aagtagacac | 540 |
| tgtaggtccg gtggatgctg gtgcagtcag gtttgttggc acatgggtgg agctaggcag | 600 |
| tccggtagtt gtattggggt cggcaaaccc ggtagtgttc agggtaggag atgtggtagt | 660 |
| ggactcggga gctttgctga agatcacttt gtgtgtggta gttgttgcgt tagtagctgt | 720 |
| ccgggtaatg atcagggttt tgggggcagt ccccaggccg acactgtaa tatcaaaggt | 780 |
| tcgattacta gcgaaggcgc cagagatgtt ttcacacccg ctaggggtgc ctgaagtcag | 840 |
| tgtccatttg cacttaaaat cggtctcagt attgttgggc caggcccaga atgctgtgac | 900 |
| ggtcacattt ggggagttag cgtcttcgct tgtgaccata ggcacggaat aagtggcatt | 960 |
| atcgcccacg taggtaatgt cggtagtgtt agtgggcata tcctggctgg ctgggatctc | 1020 |
| gtctgagaac acaatattac tctggatgca atagtcccct ccagaagcct ttggtccgtt | 1080 |
| tccggaataa aacacgtaca gaatgctatt gttgcccagg aagcgtgaga ctggcctagg | 1140 |
| ggtcagtctc aggctataag cgtagccggt tccgggaatt ggagtggcca cgggactagt | 1200 |
| agatgtcagg attcccccac ttgggacgtg agattcgtag ccggaacagg tgatattaaa | 1260 |
| cttgttatcg ccaggcagca cctggctaat ttctccatcc tccatgatgc attcaatgtc | 1320 |
| gatctcattt cccagcatct cggttttcac ggagaagttg ctatcctggg cgcttgtggg | 1380 |
| cagtgacagt ggcagggtca cgtccagccc ctgtgcccgg accactgcgg taatgttagt | 1440 |
| gctattacag ttgtcccact taatataagg gacggtttcg gggatcaggt acacaggatt | 1500 |
| ctgcatctcg gcatggtggc accacatggt gccaaacaca tcctggaagt agacgtccac | 1560 |
| tgattccaga ctgacctgct gttcctctcc tgtggtcaca ttgatgggca gtttcttgga | 1620 |
| cctcatggtc agagccagtt ctcctgctcc cagcagctcc agcagaaaca gatttgttgc | 1680 |
| gttctcgctg cctccgaaag cccctctggg ctgatacacg gcttttgtat gtggggtcag | 1740 |
| ctggccaaaa tccaggtcca gctggtgttt cttcccgccc acatcgaaat taatggtgac | 1800 |
| gttcacgtcg gctgtacaga cgttgcaggt ggggtaaaat gggaactcag ggatttccac | 1860 |
| attgaaaaat ccagggtcct ccccggtcag atgaatcagg ctctgaatag tgtactggca | 1920 |
| caccagcagg gcggcttc | 1938 |

<210> SEQ ID NO 94
<211> LENGTH: 3393
<212> TYPE: DNA
<213> ORGANISM: Artificial Sequence
<220> FEATURE:
<223> OTHER INFORMATION: Synthetic

<400> SEQUENCE: 94

| | |
|---|---:|
| atggagttcc tgaagaggag cttcgcccct ctgaccgaga agcagtggca ggagatcgac | 60 |
| aacagggcca gggagatctt caagacccag ctgtacggca ggaagttcgt ggacgtggag | 120 |

```
ggcccctacg gctgggagta cgccgcccac cccctgggcg aggtggaggt gctgagcgac    180
gagaacgagg tggtgaagtg gggcctgagg aagagcctgc ccctgatcga gctgagggcc    240
accttcaccc tggacctgtg ggagctggac aacctggaga ggggcaagcc caacgtggac    300
ctgagcagcc tggaggagac cgtgaggaag gtggccgagt tcgaggacga ggtgatcttc    360
aggggctgcg agaagagcgg cgtgaagggc ctgctgagct tcgaggagag gaagatcgag    420
tgcggcagca cccccaagga cctgctggag gccatcgtga gggccctgag catcttcagc    480
aaggacggca tcgagggccc ctacaccctg gtgatcaaca ccgacaggtg gatcaacttc    540
ctgaaggagg aggccggcca ctacccctg gagaagaggg tggaggagtg cctgaggggc    600
ggcaagatca tcaccacccc caggatcgag gacgccctgg tggtgagcga gagggcggc    660 gacttcaagc tgatcctggg ccaggacctg agcatcggct acgaggacag ggagaaggac    720
gccgtgaggc tgttcatcac cgagaccttc accttccagg tggtgaaccc cgaggccctg    780
atcctgctga gtccggagg cggatctggc ggaggcgaag ccgccctgct ggtgtgccag    840
tacactattc agagcctgat tcatctgacc ggggaggacc ctggattttt caatgtggaa    900
atccctgagt tcccattta ccccacctgc aacgtctgta cagccgacgt gaacgtcacc    960
attaatttcg atgtgggcgg gaagaaacac cagctggacc tggattttgg ccagctgacc   1020
ccacatacaa aagccgtgta tcagcccaga ggggctttcg gaggcagcga gaacgcaaca   1080
aatctgtttc tgctggagct gctgggagca ggagaactgg ctctgaccat gaggtccaag   1140
aaactgccca tcaatgtgac cacaggagag gaacagcagg tcagtctgga atcagtggac   1200
gtctacttcc aggatgtgtt tggcaccatg tggtgccacc atgccgagat gcagaatcct   1260
gtgtacctga tccccgaaac cgtcccttat attaagtggg acaactgtaa tagcactaac   1320
attaccgcag tggtccgggc acagggctg gacgtgaccc tgccactgtc actgcccaca   1380
agcgcccagg atagcaactt ctccgtgaaa accgagatgc tgggaaatga gatcgacatt   1440
gaatgcatca tggaggatgg agaaattagc caggtgctgc ctggcgataa caagtttaat   1500 atccctgtt ccggctacga atctcacgtc ccaagtgggg gaatcctgac atctactagt   1560
cccgtggcca ctccaattcc cggaaccggc tacgcttata gcctgagact gaccccctagg   1620 ccagtctcac gcttcctggg caacaatagc attctgtacg tgttttattc cggaaacgga   1680
ccaaaggctt ctgagggga ctattgcatc cagagtaata ttgtgttctc agacgagatc   1740
ccagccagcc aggatatgcc cactaacact accgacatta cctacgtggg cgataatgcc   1800
acttattccg tgcctatggt cacaagcgaa gacgctaact ccccaaatgt gaccgtcaca   1860
gcattctggg cctggcccaa caatactgag accgatttta gtgcaaatg gacactgact   1920 tcaggcaccc ctagcgggtg tgaaaacatc tctggcgcct tcgctagtaa tcgaaccttt   1980
gatattacag tgtccggcct ggggactgcc ccaaaaaccc tgatcattac ccggacagct   2040
actaacgcaa caactaccac acacaaagtg atcttcagca aagctcccga gtccactacc   2100
acatctccta ccctgaacac taccgggttt gccgacccca atacaactac cggactgcct   2160
agctccaccc atgtgccaac aaacctgact gcaccagcat ccaccggacc tacagtgtct   2220
actgccgatg tcaccagtcc cacacctgcc ggaacaactt ctggcgctag tcccgtgacc   2280
ccatcaccca gcccttggga caatgggaca gagagtaagg ccctgatat gacttctagt   2340 acctcaccag tcaccacacc aacccccaac gcaacaagcc ctactccagc cgtgactacc   2400
cccacaccta atgctaccag cccaacaccc gcagtgacaa ctcctacccc aaacgccact   2460
```

```
tccccaaccc tggggaagac atcacccact agcgccgtga ccacacccac ccctaatgct   2520
acctctccta cactgggaaa aacttcccca acctctgcag tgactacccc aaccccccaac   2580 gccacaagcc ccactctggg caagaccagt cctacatcag ctgtcacaac tcctacccca   2640
aatgcaactg ggccaaccgt gggagagaca tcccccagg ctaacgcaac aaatcacact    2700
ctgggaggca ccagtcccac acctgtggtc acctcacagc ccaagaacgc cacaagcgct   2760
gtgaccacag gccagcataa tatcacatca agctccactt ctagtatgag cctgcgccct   2820
tcaagcaacc cagagacact gtccccatct actagtgaca attcaaccag ccacatgcct   2880
ctgctgacat ctgcacatcc aactgggga gaaaacatca ctcaggtcac ccccgcctcc    2940
atttctaccc accatgtgtc cacatcctct ccagcacccc gacctggaac taccagccag   3000
gcatccggac caggaaatag ttcaaccagc acaaagcctg gcgaggtgaa cgtcacaaaa   3060
gggactcccc ctcagaatgc tacctcacct caggcaccaa gcggccagaa aacagctgtg   3120
cctactgtca cctccacagg cgggaaggca aactctacaa ctggaggcaa acacaccaca   3180
gggcatggag ctcgcactag caccgaacca actaccgact acgggggaga ttccacaact   3240
ccaaggccca gatacaatgc caccacatat ctgccaccct ctaccagctc caagctgcga   3300
cccagatgga cattcactag tcctccagtg actaccgcac aggctacagt gccagtccca   3360
cctacttctc agcctagatt ttctaacctg agt                                3393

<210> SEQ ID NO 95
<211> LENGTH: 1131
<212> TYPE: PRT
<213> ORGANISM: Artificial Sequence
<220> FEATURE:
<223> OTHER INFORMATION: Synthetic

<400> SEQUENCE: 95

Met Glu Phe Leu Lys Arg Ser Phe Ala Pro Leu Thr Glu Lys Gln Trp
1               5                   10                  15

Gln Glu Ile Asp Asn Arg Ala Arg Glu Ile Phe Lys Thr Gln Leu Tyr
                20                  25                  30

Gly Arg Lys Phe Val Asp Val Glu Gly Pro Tyr Gly Trp Glu Tyr Ala
            35                  40                  45

Ala His Pro Leu Gly Glu Val Glu Val Leu Ser Asp Glu Asn Glu Val
        50                  55                  60

Val Lys Trp Gly Leu Arg Lys Ser Leu Pro Leu Ile Glu Leu Arg Ala
65                  70                  75                  80

Thr Phe Thr Leu Asp Leu Trp Glu Leu Asp Asn Leu Glu Arg Gly Lys
                85                  90                  95

Pro Asn Val Asp Leu Ser Ser Leu Glu Glu Thr Val Arg Lys Val Ala
            100                 105                 110

Glu Phe Glu Asp Glu Val Ile Phe Arg Gly Cys Glu Lys Ser Gly Val
        115                 120                 125

Lys Gly Leu Leu Ser Phe Glu Glu Arg Lys Ile Glu Cys Gly Ser Thr
    130                 135                 140

Pro Lys Asp Leu Leu Glu Ala Ile Val Arg Ala Leu Ser Ile Phe Ser
145                 150                 155                 160

Lys Asp Gly Ile Glu Gly Pro Tyr Thr Leu Val Ile Asn Thr Asp Arg
                165                 170                 175

Trp Ile Asn Phe Leu Lys Glu Glu Ala Gly His Tyr Pro Leu Glu Lys
            180                 185                 190

Arg Val Glu Glu Cys Leu Arg Gly Gly Lys Ile Ile Thr Thr Pro Arg
```

-continued

```
            195                 200                 205
Ile Glu Asp Ala Leu Val Val Ser Glu Arg Gly Gly Asp Phe Lys Leu
210                 215                 220

Ile Leu Gly Gln Asp Leu Ser Ile Gly Tyr Glu Asp Arg Glu Lys Asp
225                 230                 235                 240

Ala Val Arg Leu Phe Ile Thr Glu Thr Phe Thr Phe Gln Val Val Asn
                245                 250                 255

Pro Glu Ala Leu Ile Leu Leu Lys Ser Gly Gly Ser Gly Gly Gly
                260                 265                 270

Glu Ala Ala Leu Leu Val Cys Gln Tyr Thr Ile Gln Ser Leu Ile His
                275                 280                 285

Leu Thr Gly Glu Asp Pro Gly Phe Phe Asn Val Glu Ile Pro Glu Phe
                290                 295                 300

Pro Phe Tyr Pro Thr Cys Asn Val Cys Thr Ala Asp Val Asn Val Thr
305                 310                 315                 320

Ile Asn Phe Asp Val Gly Gly Lys Lys His Gln Leu Asp Leu Asp Phe
                    325                 330                 335

Gly Gln Leu Thr Pro His Thr Lys Ala Val Tyr Gln Pro Arg Gly Ala
                340                 345                 350

Phe Gly Gly Ser Glu Asn Ala Thr Asn Leu Phe Leu Leu Glu Leu Leu
                355                 360                 365

Gly Ala Gly Glu Leu Ala Leu Thr Met Arg Ser Lys Lys Leu Pro Ile
370                 375                 380

Asn Val Thr Thr Gly Glu Gln Gln Val Ser Leu Glu Ser Val Asp
385                 390                 395                 400

Val Tyr Phe Gln Asp Val Phe Gly Thr Met Trp Cys His His Ala Glu
                    405                 410                 415

Met Gln Asn Pro Val Tyr Leu Ile Pro Glu Thr Val Pro Tyr Ile Lys
                420                 425                 430

Trp Asp Asn Cys Asn Ser Thr Asn Ile Thr Ala Val Val Arg Ala Gln
                435                 440                 445

Gly Leu Asp Val Thr Leu Pro Leu Ser Leu Pro Thr Ser Ala Gln Asp
450                 455                 460

Ser Asn Phe Ser Val Lys Thr Glu Met Leu Gly Asn Glu Ile Asp Ile
465                 470                 475                 480

Glu Cys Ile Met Glu Asp Gly Glu Ile Ser Gln Val Leu Pro Gly Asp
                485                 490                 495

Asn Lys Phe Asn Ile Thr Cys Ser Gly Tyr Glu Ser His Val Pro Ser
                500                 505                 510

Gly Gly Ile Leu Thr Ser Thr Ser Pro Val Ala Thr Pro Ile Pro Gly
                515                 520                 525

Thr Gly Tyr Ala Tyr Ser Leu Arg Leu Thr Pro Arg Pro Val Ser Arg
                530                 535                 540

Phe Leu Gly Asn Asn Ser Ile Leu Tyr Val Phe Tyr Ser Gly Asn Gly
545                 550                 555                 560

Pro Lys Ala Ser Gly Gly Asp Tyr Cys Ile Gln Ser Asn Ile Val Phe
                565                 570                 575

Ser Asp Glu Ile Pro Ala Ser Gln Asp Met Pro Thr Asn Thr Thr Asp
                580                 585                 590

Ile Thr Tyr Val Gly Asp Asn Ala Thr Tyr Ser Val Pro Met Val Thr
                595                 600                 605

Ser Glu Asp Ala Asn Ser Pro Asn Val Thr Val Thr Ala Phe Trp Ala
610                 615                 620
```

Trp Pro Asn Asn Thr Glu Thr Asp Phe Lys Cys Lys Trp Thr Leu Thr
625                 630                 635                 640

Ser Gly Thr Pro Ser Gly Cys Glu Asn Ile Ser Gly Ala Phe Ala Ser
            645                 650                 655

Asn Arg Thr Phe Asp Ile Thr Val Ser Gly Leu Gly Thr Ala Pro Lys
        660                 665                 670

Thr Leu Ile Ile Thr Arg Thr Ala Thr Asn Ala Thr Thr Thr Thr His
    675                 680                 685

Lys Val Ile Phe Ser Lys Ala Pro Glu Ser Thr Thr Thr Ser Pro Thr
690                 695                 700

Leu Asn Thr Thr Gly Phe Ala Asp Pro Asn Thr Thr Gly Leu Pro
705                 710                 715                 720

Ser Ser Thr His Val Pro Thr Asn Leu Thr Ala Pro Ala Ser Thr Gly
                725                 730                 735

Pro Thr Val Ser Thr Ala Asp Val Thr Ser Pro Thr Pro Ala Gly Thr
            740                 745                 750

Thr Ser Gly Ala Ser Pro Val Thr Pro Ser Pro Ser Pro Trp Asp Asn
        755                 760                 765

Gly Thr Glu Ser Lys Ala Pro Asp Met Thr Ser Ser Ser Pro Val
    770                 775                 780

Thr Thr Pro Thr Pro Asn Ala Thr Ser Pro Thr Pro Ala Val Thr Thr
785                 790                 795                 800

Pro Thr Pro Asn Ala Thr Ser Pro Thr Pro Ala Val Thr Thr Pro Thr
                805                 810                 815

Pro Asn Ala Thr Ser Pro Thr Leu Gly Lys Thr Ser Pro Thr Ser Ala
            820                 825                 830

Val Thr Thr Pro Thr Pro Asn Ala Thr Ser Pro Thr Leu Gly Lys Thr
        835                 840                 845

Ser Pro Thr Ser Ala Val Thr Thr Pro Thr Pro Asn Ala Thr Ser Pro
850                 855                 860

Thr Leu Gly Lys Thr Ser Pro Thr Ser Ala Val Thr Thr Pro Thr Pro
865                 870                 875                 880

Asn Ala Thr Gly Pro Thr Val Gly Glu Thr Ser Pro Gln Ala Asn Ala
                885                 890                 895

Thr Asn His Thr Leu Gly Gly Thr Ser Pro Thr Pro Val Val Thr Ser
            900                 905                 910

Gln Pro Lys Asn Ala Thr Ser Ala Val Thr Thr Gly Gln His Asn Ile
        915                 920                 925

Thr Ser Ser Ser Thr Ser Ser Met Ser Leu Arg Pro Ser Ser Asn Pro
    930                 935                 940

Glu Thr Leu Ser Pro Ser Thr Ser Asp Asn Ser Thr His Met Pro
945                 950                 955                 960

Leu Leu Thr Ser Ala His Pro Thr Gly Gly Glu Asn Ile Thr Gln Val
                965                 970                 975

Thr Pro Ala Ser Ile Ser Thr His His Val Ser Thr Ser Ser Pro Ala
            980                 985                 990

Pro Arg Pro Gly Thr Thr Ser Gln Ala Ser Gly Pro Gly Asn Ser Ser
        995                 1000                1005

Thr Ser Thr Lys Pro Gly Glu Val Asn Val Thr Lys Gly Thr Pro
    1010                1015                1020

Pro Gln Asn Ala Thr Ser Pro Gln Ala Pro Ser Gly Gln Lys Thr
    1025                1030                1035

| Ala | Val | Pro | Thr | Val | Thr | Ser | Thr | Gly | Gly | Lys | Ala | Asn | Ser | Thr |
| | 1040 | | | | | 1045 | | | | 1050 | | | | |

| Thr | Gly | Gly | Lys | His | Thr | Thr | Gly | His | Gly | Ala | Arg | Thr | Ser | Thr |
| 1055 | | | | | 1060 | | | | | 1065 | | | | |

| Glu | Pro | Thr | Thr | Asp | Tyr | Gly | Gly | Asp | Ser | Thr | Thr | Pro | Arg | Pro |
| | 1070 | | | | | 1075 | | | | | 1080 | | | |

| Arg | Tyr | Asn | Ala | Thr | Thr | Tyr | Leu | Pro | Pro | Ser | Thr | Ser | Ser | Lys |
| | 1085 | | | | | 1090 | | | | | 1095 | | | |

| Leu | Arg | Pro | Arg | Trp | Thr | Phe | Thr | Ser | Pro | Pro | Val | Thr | Thr | Ala |
| | 1100 | | | | | 1105 | | | | | 1110 | | | |

| Gln | Ala | Thr | Val | Pro | Val | Pro | Pro | Thr | Ser | Gln | Pro | Arg | Phe | Ser |
| | 1115 | | | | | 1120 | | | | | 1125 | | | |

Asn Leu Ser
1130

<210> SEQ ID NO 96
<211> LENGTH: 3393
<212> TYPE: DNA
<213> ORGANISM: Artificial Sequence
<220> FEATURE:
<223> OTHER INFORMATION: Synthetic

<400> SEQUENCE: 96

```
actcaggtta gaaaatctag gctgagaagt aggtgggact ggcactgtag cctgtgcggt      60
agtcactgga ggactagtga atgtccatct gggtcgcagc ttggagctgg tagagggtgg     120
cagatatgtg gtggcattgt atctgggcct tggagttgtg aatctcccc cgtagtcggt      180
agttggttcg gtgctagtgc gagctccatg ccctgtggtg tgtttgcctc cagttgtaga     240
gtttgccttc ccgcctgtgg aggtgacagt aggcacagct gttttctggc cgcttggtgc     300
ctgaggtgag gtagcattct gaggggagt ccctttgtg acgttcacct cgccaggctt      360
tgtgctggtt gaactatttc ctggtccgga tgcctggctg gtagttccag gtcgggtgc       420
tggagaggat gtggacacat ggtgggtaga atggaggcg ggggtgaccct gagtgatgtt     480
ttctccccca gttggatgtg cagatgtcag cagaggcatg tggctggttg aattgtcact      540
agtagatggg gacagtgtct ctgggttgct tgaagggcgc aggctcatac tagaagtgga     600
gcttgatgtg atattatgct ggcctgtggt cacagcgctt gtggcgttct tgggctgtga     660
ggtgaccaca ggtgtgggac tggtgcctcc cagagtgtga tttgttgcgt tagcctgggg    720
ggatgtctct cccacggttg gcccagttgc atttgggta ggagttgtga cagctgatgt      780
aggactggtc ttgcccagag tgggcgttgt ggcgttgggg gttggggtag tcactgcaga    840
ggttggggaa gttttttccca gtgtaggaga ggtagcatta ggggtgggtg tggtcacggc    900
gctagtgggg gatgtcttcc ccaggggtgg ggaagtggcg tttggggtag gagttgtcac    960
tgcgggtgtt gggctggtag cattaggtgt ggggtagtc acggctggag tagggcttgt    1020
tgcgttgggg gttggtgtgg tgactggtga ggtactagaa gtcatatcag gggccttact    1080
ctctgtccca ttgtcccaag ggctgggtga tggggtcacg ggactagcgc cagaagttgt     1140
tccggcaggt gtgggactgg tgacatcggc agtagacact gtaggtccgg tggatgctgg    1200
tgcagtcagg tttgttggca catggtgga gctaggcagt ccggtagttg tattgggtc     1260
ggcaaacccg gtagtgttca gggtaggaga tgtggtagtg gactcgggag ctttgctgaa    1320
gatcactttg tgtgtggtag ttgttgcgtt agtagctgtc cgggtaatga tcagggtttt    1380
tgggggcagtc cccaggccgg acactgtaat atcaaaggtt cgattactag cgaaggcgcc    1440
```

| | |
|---|---|
| agagatgttt tcacacccgc taggggtgcc tgaagtcagt gtccatttgc acttaaaatc | 1500 |
| ggtctcagta ttgttgggcc aggcccagaa tgctgtgacg gtcacatttg gggagttagc | 1560 |
| gtcttcgctt gtgaccatag gcacggaata agtggcatta tcgcccacgt aggtaatgtc | 1620 |
| ggtagtgtta gtgggcatat cctggctggc tgggatctcg tctgagaaca caatattact | 1680 |
| ctggatgcaa tagtcccctc cagaagcctt tggtccgttt ccggaataaa acacgtacag | 1740 |
| aatgctattg ttgcccagga agcgtgagac tggcctaggg gtcagtctca ggctataagc | 1800 |
| gtagccggtt ccgggaattg gagtggccac gggactagta gatgtcagga ttcccccact | 1860 |
| tgggacgtga gattcgtagc cggaacaggt gatattaaac ttgttatcgc caggcagcac | 1920 |
| ctggctaatt tctccatcct ccatgatgca ttcaatgtcg atctcatttc ccagcatctc | 1980 |
| ggttttcacg gagaagttgc tatcctgggc gcttgtgggc agtgacagtg gcagggtcac | 2040 |
| gtccagcccc tgtgcccgga ccactgcggt aatgttagtg ctattacagt tgtcccactt | 2100 |
| aatataaggg acggtttcgg ggatcaggta cacaggattc tgcatctcgg catggtggca | 2160 |
| ccacatggtg ccaaacacat cctggaagta gacgtccact gattccagac tgacctgctg | 2220 |
| ttcctctcct gtggtcacat tgatgggcag tttcttggac ctcatggtca gagccagttc | 2280 |
| tcctgctccc agcagctcca gcagaaacag atttgttgcg ttctcgctgc ctccgaaagc | 2340 |
| ccctctgggc tgatacacgg cttttgtatg tggggtcagc tggccaaaat ccaggtccag | 2400 |
| ctggtgtttc ttcccgccca catcgaaatt aatggtgacg ttcacgtcgg ctgtacagac | 2460 |
| gttgcaggtg gggtaaaatg ggaactcagg gatttccaca ttgaaaaatc cagggtcctc | 2520 |
| cccggtcaga tgaatcaggc tctgaatagt gtactggcac accagcaggg cggcttcgcc | 2580 |
| tccgccagat ccgcctccgg acttcagcag gatcagggcc tcggggttca ccacctggaa | 2640 |
| ggtgaaggtc tcggtgatga acagcctcac ggcgtccttc tccctgtcct cgtagccgat | 2700 |
| gctcaggtcc tggcccagga tcagcttgaa gtcgccgccc ctctcgctca ccaccagggc | 2760 |
| gtcctcgatc ctgggggtgg tgatgatctt gccgcccctc aggcactcct ccaccctctt | 2820 |
| ctccaggggg tagtggccgg cctcctcctt caggaagttg atccacctgt cggtgttgat | 2880 |
| caccagggtg taggggccct cgatgccgtc cttgctgaag atgctcaggg ccctcacgat | 2940 |
| ggcctccagc aggtccttgg gggtgctgcc gcactcgatc ttcctctcct cgaagctcag | 3000 |
| caggcccttc acgccgctct tctcgcagcc cctgaagatc acctcgtcct cgaactcggc | 3060 |
| caccttcctc acggtctcct ccaggctgct caggtccacg ttgggcttgc ccctctccag | 3120 |
| gttgtccagc tcccacaggt ccagggtgaa ggtggccctc agctcgatca ggggcaggct | 3180 |
| cttcctcagg ccccacttca ccacctcgtt ctcgtcgctc agcacctcca cctcgcccag | 3240 |
| ggggtgggcg cgtactccc agccgtaggg gccctccacg tccacgaact tcctgccgta | 3300 |
| cagctgggtc ttgaagatct ccctggccct gttgtcgatc tcctgccact gcttctcggt | 3360 |
| cagaggggcg aagctcctct tcaggaactc cat | 3393 |

<210> SEQ ID NO 97
<211> LENGTH: 2223
<212> TYPE: DNA
<213> ORGANISM: Artificial Sequence
<220> FEATURE:
<223> OTHER INFORMATION: Synthetic

<400> SEQUENCE: 97

| | |
|---|---|
| atggagttcc tgaagaggag cttcgcccct ctgaccgaga agcagtggca ggagatcgac | 60 |
| aacagggcca gggagatctt caagacccag ctgtacggca ggaagttcgt ggacgtggag | 120 |

-continued

```
ggcccctacg gctgggagta cgccgcccac cccctgggcg aggtggaggt gctgagcgac      180
gagaacgagg tggtgaagtg gggcctgagg aagagcctgc ccctgatcga gctgagggcc      240
accttcaccc tggacctgtg ggagctggac aacctggaga ggggcaagcc caacgtggac      300
ctgagcagcc tggaggagac cgtgaggaag gtggccgagt cgaggacgca ggtgatcttc      360
aggggctgcg agaagagcgg cgtgaagggc ctgctgagct tcgaggagag gaagatcgag      420
tgcggcagca cccccaagga cctgctggag gccatcgtga gggccctgag catcttcagc      480
aaggacggca tcgagggccc ctacaccctg gtgatcaaca ccgacaggtg gatcaacttc      540
ctgaaggagg aggccggcca ctaccccctg gagaagaggg tggaggagtg cctgaggggc      600
ggcaagatca tcaccacccc caggatcgag gacgccctgg tggtgagcga gaggggcggc      660
gacttcaagc tgatcctggg ccaggacctg agcatcggct acgaggacag ggagaaggac      720
gccgtgaggc tgttcatcac cgagaccttc accttccagg tggtgaaccc cgaggccctg      780
atcctgctga gtccggagg cggatctggc ggaggcgaag ccgccctgct ggtgtgccag      840
tacactattc agagcctgat tcatctgacc ggggaggacc ctggattttt caatgtggaa      900
atccctgagt tcccatttta ccccacctgc aacgtctgta cagccgacgt gaacgtcacc      960
attaatttcg atgtgggcgg gaagaaacac cagctggacc tggattttgg ccagctgacc     1020
ccacatacaa aagccgtgta tcagcccaga ggggctttcg gaggcagcga gaacgcaaca     1080
aatctgtttc tgctggagct gctgggagca ggagaactgg ctctgaccat gaggtccaag     1140
aaactgccca tcaatgtgac cacaggagag gaacagcagg tcagtctgga atcagtggac     1200
gtctacttcc aggatgtgtt tggcaccatg tggtgccacc atgccgagat gcagaatcct     1260
gtgtacctga tccccgaaac cgtcccttat attaagtggg acaactgtaa tagcactaac     1320
attaccgcag tggtccgggc acaggggctg gacgtgaccc tgccactgtc actgcccaca     1380
agcgcccagg atagcaactt ctccgtgaaa accgagatgc tgggaaatga gatcgacatt     1440
gaatgcatca tggaggatgg agaaattagc caggtgctgc ctggcgataa caagtttaat     1500 atccctgtt ccggctacga atctcacgtc ccaagtgggg gaatcctgac atctactagt     1560
cccgtggcca ctccaattcc cggaaccggc tacgcttata gcctgagact gacccctagg     1620
ccagtctcac gcttcctggg caacaatagc attctgtacg tgttttattc cggaaacgga     1680
ccaaaggctt ctgagggga ctattgcatc cagagtaata ttgtgttctc agacgagatc     1740
ccagccagcc aggatatgcc cactaacact accgacatta cctacgtggg cgataatgcc     1800
acttattccg tgcctatggt cacaagcgaa gacgctaact ccccaaatgt gaccgtcaca     1860
gcattctggg cctggcccaa caatactgag accgatttta gtgcaaatg gacactgact     1920 tcaggcaccc ctagcgggtg tgaaaacatc tctggcgcct cgctagtaa tcgaaccttt     1980 gatattacag tgtccggcct ggggactgcc ccaaaaaccc tgatcattac ccggacagct     2040
actaacgcaa caactaccac acacaaagtg atcttcagca agctcccga gtccactacc     2100 acatctccta ccctgaacac taccgggttt gccgacccca atacaactac cggactgcct     2160
agctccaccc atgtgccaac aaacctgact gcaccagcat ccaccggacc tacagtgtct     2220
act                                                                     2223
```

<210> SEQ ID NO 98
<211> LENGTH: 741
<212> TYPE: PRT
<213> ORGANISM: Artificial Sequence
<220> FEATURE:

-continued

<223> OTHER INFORMATION: Synthetic

<400> SEQUENCE: 98

```
Met Glu Phe Leu Lys Arg Ser Phe Ala Pro Leu Thr Glu Lys Gln Trp
1               5                   10                  15
Gln Glu Ile Asp Asn Arg Ala Arg Glu Ile Phe Lys Thr Gln Leu Tyr
            20                  25                  30
Gly Arg Lys Phe Val Asp Val Glu Gly Pro Tyr Gly Trp Glu Tyr Ala
        35                  40                  45
Ala His Pro Leu Gly Glu Val Glu Val Leu Ser Asp Glu Asn Glu Val
    50                  55                  60
Val Lys Trp Gly Leu Arg Lys Ser Leu Pro Leu Ile Glu Leu Arg Ala
65                  70                  75                  80
Thr Phe Thr Leu Asp Leu Trp Glu Leu Asp Asn Leu Glu Arg Gly Lys
                85                  90                  95
Pro Asn Val Asp Leu Ser Ser Leu Glu Glu Thr Val Arg Lys Val Ala
            100                 105                 110
Glu Phe Glu Asp Glu Val Ile Phe Arg Gly Cys Glu Lys Ser Gly Val
        115                 120                 125
Lys Gly Leu Leu Ser Phe Glu Glu Arg Lys Ile Glu Cys Gly Ser Thr
    130                 135                 140
Pro Lys Asp Leu Leu Glu Ala Ile Val Arg Ala Leu Ser Ile Phe Ser
145                 150                 155                 160
Lys Asp Gly Ile Glu Gly Pro Tyr Thr Leu Val Ile Asn Thr Asp Arg
                165                 170                 175
Trp Ile Asn Phe Leu Lys Glu Glu Ala Gly His Tyr Pro Leu Glu Lys
            180                 185                 190
Arg Val Glu Glu Cys Leu Arg Gly Gly Lys Ile Ile Thr Thr Pro Arg
        195                 200                 205
Ile Glu Asp Ala Leu Val Val Ser Glu Arg Gly Gly Asp Phe Lys Leu
    210                 215                 220
Ile Leu Gly Gln Asp Leu Ser Ile Gly Tyr Glu Asp Arg Glu Lys Asp
225                 230                 235                 240
Ala Val Arg Leu Phe Ile Thr Glu Thr Phe Thr Phe Gln Val Val Asn
                245                 250                 255
Pro Glu Ala Leu Ile Leu Leu Lys Ser Gly Gly Ser Gly Gly Gly
            260                 265                 270
Glu Ala Ala Leu Leu Val Cys Gln Tyr Thr Ile Gln Ser Leu Ile His
        275                 280                 285
Leu Thr Gly Glu Asp Pro Gly Phe Phe Asn Val Glu Ile Pro Glu Phe
    290                 295                 300
Pro Phe Tyr Pro Thr Cys Asn Val Cys Thr Ala Asp Val Asn Val Thr
305                 310                 315                 320
Ile Asn Phe Asp Val Gly Gly Lys Lys His Gln Leu Asp Leu Asp Phe
                325                 330                 335
Gly Gln Leu Thr Pro His Thr Lys Ala Val Tyr Gln Pro Arg Gly Ala
            340                 345                 350
Phe Gly Gly Ser Glu Asn Ala Thr Asn Leu Phe Leu Leu Glu Leu Leu
        355                 360                 365
Gly Ala Gly Glu Leu Ala Leu Thr Met Arg Ser Lys Lys Leu Pro Ile
    370                 375                 380
Asn Val Thr Thr Gly Glu Glu Gln Gln Val Ser Leu Glu Ser Val Asp
385                 390                 395                 400
```

```
Val Tyr Phe Gln Asp Val Phe Gly Thr Met Trp Cys His His Ala Glu
                405                 410                 415

Met Gln Asn Pro Val Tyr Leu Ile Pro Glu Thr Val Pro Tyr Ile Lys
            420                 425                 430

Trp Asp Asn Cys Asn Ser Thr Asn Ile Thr Ala Val Val Arg Ala Gln
        435                 440                 445

Gly Leu Asp Val Thr Leu Pro Leu Ser Leu Pro Thr Ser Ala Gln Asp
    450                 455                 460

Ser Asn Phe Ser Val Lys Thr Glu Met Leu Gly Asn Glu Ile Asp Ile
465                 470                 475                 480

Glu Cys Ile Met Glu Asp Gly Glu Ile Ser Gln Val Leu Pro Gly Asp
                485                 490                 495

Asn Lys Phe Asn Ile Thr Cys Ser Gly Tyr Glu Ser His Val Pro Ser
            500                 505                 510

Gly Gly Ile Leu Thr Ser Thr Ser Pro Val Ala Thr Pro Ile Pro Gly
        515                 520                 525

Thr Gly Tyr Ala Tyr Ser Leu Arg Leu Thr Pro Arg Pro Val Ser Arg
    530                 535                 540

Phe Leu Gly Asn Asn Ser Ile Leu Tyr Val Phe Tyr Ser Gly Asn Gly
545                 550                 555                 560

Pro Lys Ala Ser Gly Gly Asp Tyr Cys Ile Gln Ser Asn Ile Val Phe
                565                 570                 575

Ser Asp Glu Ile Pro Ala Ser Gln Asp Met Pro Thr Asn Thr Thr Asp
            580                 585                 590

Ile Thr Tyr Val Gly Asp Asn Ala Thr Tyr Ser Val Pro Met Val Thr
        595                 600                 605

Ser Glu Asp Ala Asn Ser Pro Asn Val Thr Val Thr Ala Phe Trp Ala
    610                 615                 620

Trp Pro Asn Asn Thr Glu Thr Asp Phe Lys Cys Lys Trp Thr Leu Thr
625                 630                 635                 640

Ser Gly Thr Pro Ser Gly Cys Glu Asn Ile Ser Gly Ala Phe Ala Ser
                645                 650                 655

Asn Arg Thr Phe Asp Ile Thr Val Ser Gly Leu Gly Thr Ala Pro Lys
            660                 665                 670

Thr Leu Ile Ile Thr Arg Thr Ala Thr Asn Ala Thr Thr Thr Thr His
        675                 680                 685

Lys Val Ile Phe Ser Lys Ala Pro Glu Ser Thr Thr Thr Ser Pro Thr
    690                 695                 700

Leu Asn Thr Thr Gly Phe Ala Asp Pro Asn Thr Thr Thr Gly Leu Pro
705                 710                 715                 720

Ser Ser Thr His Val Pro Thr Asn Leu Thr Ala Pro Ala Ser Thr Gly
                725                 730                 735

Pro Thr Val Ser Thr
            740

<210> SEQ ID NO 99

<400> SEQUENCE: 99

000

<210> SEQ ID NO 100
<211> LENGTH: 1764
<212> TYPE: DNA
<213> ORGANISM: Artificial Sequence
<220> FEATURE:
```

<223> OTHER INFORMATION: Synthetic

<400> SEQUENCE: 100

```
atggagttcc tgaagaggag cttcgcccct ctgaccgaga agcagtggca ggagatcgac      60
aacagggcca gggagatctt caagacccag ctgtacggca ggaagttcgt ggacgtggag     120
ggcccctacg gctgggagta cgccgcccac cccctgggcg aggtggaggt gctgagcgac     180
gagaacgagg tggtgaagtg gggcctgagg aagagcctgc ccctgatcga gctgagggcc     240
accttcaccc tggacctgtg ggagctggac aacctggaga ggggcaagcc caacgtggac     300
ctgagcagcc tggaggagac cgtgaggaag gtggccgagt cgaggacgga ggtgatcttc     360
aggggctgcg agaagagcgg cgtgaagggc ctgctgagct cgaggagag gaagatcgag      420
tgcggcagca cccccaagga cctgctggag gccatcgtga gggccctgag catcttcagc     480
aaggacggca tcgagggccc ctacaccctg gtgatcaaca ccgacaggtg gatcaacttc     540
ctgaaggagg aggccggcca ctaccccctg gagaagaggg tggaggagtg cctgaggggc     600
ggcaagatca tcaccacccc caggatcgag gacgccctgg tggtgagcga gggggcggc     660
gacttcaagc tgatcctggg ccaggacctg agcatcggct acgaggacag ggagaaggac     720
gccgtgaggc tgttcatcac cgagaccttc accttccagg tggtgaaccc cgaggccctg     780
atcctgctga gtccggagg cggatctggc ggaggcgaag ccgccctgct ggtgtgccag     840
tacactattc agagcctgat tcatctgacc ggggaggacc ctggatttt caatgtggaa     900
atccctgagt tcccattta ccccacctgc aacgtctgta cagccgacgt gaacgtcacc     960
attaatttcg atgtgggcgg aagaaacac cagctgacc tggattttgg ccagctgacc    1020
ccacatacaa aagccgtgta tcagcccaga ggggctttcg gaggcagcga aacgcaaca    1080
aatctgtttc tgctggagct gctgggagca ggagaactgg ctctgaccat gaggtccaag    1140
aaactgccca tcaatgtgac cacaggagag aacagcagg tcagtctgga atcagtggac    1200
gtctacttcc aggatgtgtt tggcaccatg tggtgccacc atgccgagat gcagaatcct    1260
gtgtacctga tccccgaaac cgtcccttat attaagtggg acaactgtaa tagcactaac    1320
attaccgcag tggtccgggc acaggggctg acgtgaccc tgccactgtc actgcccaca    1380
agcgcccagg atagcaactt ctccgtgaaa accgagatgc tgggaaatga gatcgacatt    1440
gaatgcatca tggaggatgg agaaattagc caggtgctgc ctggcgataa caagtttaat    1500
atcacctgtt ccggctacga atctcacgtc ccaagtgggg gaatcctgac atctactagt    1560
cccgtggcca ctccaattcc cggaaccggc tacgcttata gcctgagact gaccccctagg   1620
ccagtctcac gcttcctggg caacaatagc attctgtacg tgttttattc cggaaacgga   1680
ccaaaggctt ctgagggga ctattgcatc cagagtaata ttgtgttctc agacgagatc    1740
ccagccagcc aggatatgcc cact                                           1764
```

<210> SEQ ID NO 101
<211> LENGTH: 588
<212> TYPE: PRT
<213> ORGANISM: Artificial Sequence
<220> FEATURE:
<223> OTHER INFORMATION: Synthetic

<400> SEQUENCE: 101

```
Met Glu Phe Leu Lys Arg Ser Phe Ala Pro Leu Thr Glu Lys Gln Trp
 1               5                  10                  15

Gln Glu Ile Asp Asn Arg Ala Arg Glu Ile Phe Lys Thr Gln Leu Tyr
            20                  25                  30
```

```
Gly Arg Lys Phe Val Asp Val Glu Gly Pro Tyr Gly Trp Glu Tyr Ala
        35                  40                  45

Ala His Pro Leu Gly Glu Val Glu Val Leu Ser Asp Glu Asn Glu Val
    50                  55                  60

Val Lys Trp Gly Leu Arg Lys Ser Leu Pro Leu Ile Glu Leu Arg Ala
65                  70                  75                  80

Thr Phe Thr Leu Asp Leu Trp Glu Leu Asp Asn Leu Glu Arg Gly Lys
                85                  90                  95

Pro Asn Val Asp Leu Ser Ser Leu Glu Glu Thr Val Arg Lys Val Ala
                100                 105                 110

Glu Phe Glu Asp Glu Val Ile Phe Arg Gly Cys Glu Lys Ser Gly Val
                115                 120                 125

Lys Gly Leu Leu Ser Phe Glu Glu Arg Lys Ile Glu Cys Gly Ser Thr
                130                 135                 140

Pro Lys Asp Leu Leu Glu Ala Ile Val Arg Ala Leu Ser Ile Phe Ser
145                 150                 155                 160

Lys Asp Gly Ile Glu Gly Pro Tyr Thr Leu Val Ile Asn Thr Asp Arg
                165                 170                 175

Trp Ile Asn Phe Leu Lys Glu Glu Ala Gly His Tyr Pro Leu Glu Lys
                180                 185                 190

Arg Val Glu Glu Cys Leu Arg Gly Gly Lys Ile Ile Thr Thr Pro Arg
                195                 200                 205

Ile Glu Asp Ala Leu Val Val Ser Glu Arg Gly Gly Asp Phe Lys Leu
                210                 215                 220

Ile Leu Gly Gln Asp Leu Ser Ile Gly Tyr Glu Asp Arg Glu Lys Asp
225                 230                 235                 240

Ala Val Arg Leu Phe Ile Thr Glu Thr Phe Thr Phe Gln Val Val Asn
                245                 250                 255

Pro Glu Ala Leu Ile Leu Leu Lys Ser Gly Gly Ser Gly Gly Gly
                260                 265                 270

Glu Ala Ala Leu Leu Val Cys Gln Tyr Thr Ile Gln Ser Leu Ile His
                275                 280                 285

Leu Thr Gly Glu Asp Pro Gly Phe Phe Asn Val Glu Ile Pro Glu Phe
                290                 295                 300

Pro Phe Tyr Pro Thr Cys Asn Val Cys Thr Ala Asp Val Asn Val Thr
305                 310                 315                 320

Ile Asn Phe Asp Val Gly Gly Lys Lys His Gln Leu Asp Leu Asp Phe
                325                 330                 335

Gly Gln Leu Thr Pro His Thr Lys Ala Val Tyr Gln Pro Arg Gly Ala
                340                 345                 350

Phe Gly Gly Ser Glu Asn Ala Thr Asn Leu Phe Leu Leu Glu Leu Leu
                355                 360                 365

Gly Ala Gly Glu Leu Ala Leu Thr Met Arg Ser Lys Lys Leu Pro Ile
                370                 375                 380

Asn Val Thr Thr Gly Glu Glu Gln Gln Val Ser Leu Glu Ser Val Asp
385                 390                 395                 400

Val Tyr Phe Gln Asp Val Phe Gly Thr Met Trp Cys His His Ala Glu
                405                 410                 415

Met Gln Asn Pro Val Tyr Leu Ile Pro Glu Thr Val Pro Tyr Ile Lys
                420                 425                 430

Trp Asp Asn Cys Asn Ser Thr Asn Ile Thr Ala Val Val Arg Ala Gln
                435                 440                 445
```

Gly Leu Asp Val Thr Leu Pro Leu Ser Leu Pro Thr Ser Ala Gln Asp
            450                 455                 460

Ser Asn Phe Ser Val Lys Thr Glu Met Leu Gly Asn Glu Ile Asp Ile
465                 470                 475                 480

Glu Cys Ile Met Glu Asp Gly Glu Ile Ser Gln Val Leu Pro Gly Asp
                485                 490                 495

Asn Lys Phe Asn Ile Thr Cys Ser Gly Tyr Glu Ser His Val Pro Ser
            500                 505                 510

Gly Gly Ile Leu Thr Ser Thr Ser Pro Val Ala Thr Pro Ile Pro Gly
            515                 520                 525

Thr Gly Tyr Ala Tyr Ser Leu Arg Leu Thr Pro Arg Pro Val Ser Arg
530                 535                 540

Phe Leu Gly Asn Asn Ser Ile Leu Tyr Val Phe Tyr Ser Gly Asn Gly
545                 550                 555                 560

Pro Lys Ala Ser Gly Gly Asp Tyr Cys Ile Gln Ser Asn Ile Val Phe
                565                 570                 575

Ser Asp Glu Ile Pro Ala Ser Gln Asp Met Pro Thr
            580                 585

<210> SEQ ID NO 102
<211> LENGTH: 1764
<212> TYPE: DNA
<213> ORGANISM: Artificial Sequence
<220> FEATURE:
<223> OTHER INFORMATION: Synthetic

<400> SEQUENCE: 102
agtgggcata tcctggctgg ctgggatctc gtctgagaac acaatattac tctggatgca      60
atagtcccct ccagaagcct ttggtccgtt tccggaataa acacgtaca gaatgctatt      120 gttgcccagg aagcgtgaga ctggcctagg ggtcagtctc aggctataag cgtagccggt     180
tccgggaatt ggagtggcca cggactagta gatgtcagg attcccccac ttgggacgtg      240
agattcgtag ccggaacagg tgatattaaa cttgttatcg ccaggcagca cctggctaat     300
ttctccatcc tccatgatgc attcaatgtc gatctcattt cccagcatct cggttttcac     360
ggagaagttg ctatcctggg cgcttgtggg cagtgacagt ggcagggtca cgtccagccc     420
ctgtgcccgg accactgcgg taatgttagt gctattacag ttgtcccact taatataagg     480
gacggtttcg gggatcaggt acacaggatt ctgcatctcg gcatggtggc accacatggt     540
gccaaacaca tcctggaagt agacgtccac tgattccaga ctgacctgct gttcctctcc     600
tgtggtcaca ttgatgggca gtttcttgga cctcatggtc agagccagtt ctcctgctcc     660
cagcagctcc agcagaaaca gatttgttgc gttctcgctg cctccgaaag ccctctggg      720 ctgatacacg gcttttgtat gtgggtcag ctggccaaaa tccaggtcca gctggtgttt     780
cttcccgccc acatcgaaat taatggtgac gttcacgtcg gctgtacaga cgttgcaggt     840 gggtaaaat gggaactcag gatttccac attgaaaaat ccaggtcct ccccggtcag       900 atgaatcagg ctctgaatag tgtactggca caccagcagg gcggcttcgc ctccgccaga     960
tccgcctccg gacttcagca ggatcagggc ctcggggttc accacctgga aggtgaaggt    1020
ctcggtgatg aacagcctca cggcgtcctt ctccctgtcc tcgtagccga tgctcaggtc    1080
ctggcccagg atcagcttga agtcgccgcc cctctcgctc accaccaggg cgtcctcgat    1140
cctgggggtg gtgatgatct tgccgcccct caggcactcc tccaccctct tctccagggg   1200
gtagtggccg gcctcctcct tcaggaagtt gatccacctg tcggtgttga tcaccagggt   1260

| | |
|---|---|
| gtaggggccc tcgatgccgt ccttgctgaa gatgctcagg gccctcacga tggcctccag | 1320 |
| caggtccttg ggggtgctgc cgcactcgat cttcctctcc tcgaagctca gcaggccctt | 1380 |
| cacgccgctc ttctcgcagc ccctgaagat cacctcgtcc tcgaactcgg ccaccttcct | 1440 |
| cacggtctcc tccaggctgc tcaggtccac gttgggcttg ccctctcca ggttgtccag | 1500 |
| ctcccacagg tccagggtga aggtggccct cagctcgatc aggggcaggc tcttcctcag | 1560 |
| gccccacttc accacctcgt tctcgtcgct cagcacctcc acctcgccca ggggtgggc | 1620 |
| ggcgtactcc cagccgtagg ggccctccac gtccacgaac ttcctgccgt acagctgggt | 1680 |
| cttgaagatc tccctggccc tgttgtcgat ctcctgccac tgcttctcgg tcagggggc | 1740 |
| gaagctcctc ttcaggaact ccat | 1764 |

<210> SEQ ID NO 103
<211> LENGTH: 2088
<212> TYPE: DNA
<213> ORGANISM: Artificial Sequence
<220> FEATURE:
<223> OTHER INFORMATION: Synthetic

<400> SEQUENCE: 103

| | |
|---|---|
| atggagttcc tgaagaggag cttcgcccct ctgaccgaga agcagtggca ggagatcgac | 60 |
| aacagggcca gggagatctt caagacccag ctgtacggca ggaagttcgt ggacgtggag | 120 |
| ggccctacg ctgggagta cgccgccac ccctgggcg aggtggaggt gctgagcgac | 180 |
| gagaacgagg tggtgaagtg gggcctgagg aagagcctgc ccctgatcga gctgagggcc | 240 |
| accttcaccc tggacctgtg ggagctggac aacctgagga ggggcaagcc caacgtggac | 300 |
| ctgagcagcc tggaggagac cgtgaggaag gtggccgagt cgaggacga ggtgatcttc | 360 |
| aggggctgcg agaagagcgg cgtgaagggc ctgctgagct cgaggagag gaagatcgag | 420 |
| tgcggcagca cccccaagga cctgctggag gccatcgtga gggccctgag catcttcagc | 480 |
| aaggacggca tcgagggccc ctacacccctg gtgatcaaca ccgacaggtg gatcaacttc | 540 |
| ctgaaggagg aggccggcca ctacccctg gagaagaggg tggaggagtg cctgaggggc | 600 |
| ggcaagatca tcaccacccc caggatcgag gacgccctgg tggtgagcga gaggggcggc | 660 |
| gacttcaagc tgatcctggg ccaggacctg agcatcggct acgaggacag ggagaaggac | 720 |
| gccgtgaggc tgttcatcac cgagaccttc accttccagg tggtgaaccc cgaggccctg | 780 |
| atcctgctga agtccggagg cggatctggc ggaggcgaag ccgccctgct ggtgtgccag | 840 |
| tacactattc agagcctgat tcatctgacc ggggaggacc ctggattttt caatgtggaa | 900 |
| atccctgagt tccattttta ccccacctgc aacgtctgta cagccgacgt gaacgtcacc | 960 |
| attaatttcg atgtgggcgg gaagaaacac cagctggacc tggattttgg ccagctgacc | 1020 |
| ccacatacaa aagccgtgta tcagcccaga ggggctttcg gaggcagcga gaacgcaaca | 1080 |
| aatctgtttc tgctggagct gctgggagca ggagaactgg ctctgaccat gaggtccaag | 1140 |
| aaactgccca tcaatgtgac cacaggagag gaacagcagg tcagtctgga atcagtggac | 1200 |
| gtctacttcc aggatgtgtt tggcaccatg tggtgccacc atgccgagat gcagaatcct | 1260 |
| gtgtacctga tccccgaaac cgtcccttat attaagtggg acaactgtaa tagcactaac | 1320 |
| attaccgcag tggtccgggc acaggggctg gacgtgaccc tgccactgtc actgcccaca | 1380 |
| agcgcccagg atagcaactt ctccgtgaaa accgagatgc tgggaaatga gatcgacatt | 1440 |
| gaatgcatca tggaggatgg agaaattagc caggtgctgc ctggcgataa caagtttaat | 1500 |
| atcacctgtt ccggctacga atctcacgtc ccaagtgggg gaatcctgac atctactagt | 1560 |

-continued

```
cccgtggcca ctccaattcc cggaaccggc tacgcttata gcctgagact gaccctagg    1620 ccagtctcac gcttcctggg caacaatagc attctgtacg tgttttattc cggaaacgga    1680
ccaaaggctt ctggagggga ctattgcatc cagagtaata ttgtgttctc agacgagatc    1740
ccagccagcc aggatatgcc cactaacact accgacatta cctacgtggg cgataatgcc    1800
acttattccg tgcctatggt cacaagcgaa gacgctaact ccccaaatgt gaccgtcaca    1860
gcattctggg cctggcccaa caatactgag accgatttta gtgcaaatg acactgact    1920 tcaggcaccc ctagcgggtg tgaaaacatc tctggcgcct tcgctagtaa tcgaaccttt    1980
gatattacag tgtccggcct ggggactgcc ccaaaaaccc tgatcattac ccggacagct    2040
actaacgcaa caactaccac acacaaagtg atcttcagca aagctccc                 2088
```

<210> SEQ ID NO 104
<211> LENGTH: 696
<212> TYPE: PRT
<213> ORGANISM: Artificial Sequence
<220> FEATURE:
<223> OTHER INFORMATION: Synthetic

<400> SEQUENCE: 104

```
Met Glu Phe Leu Lys Arg Ser Phe Ala Pro Leu Thr Glu Lys Gln Trp
1               5                   10                  15

Gln Glu Ile Asp Asn Arg Ala Arg Glu Ile Phe Lys Thr Gln Leu Tyr
            20                  25                  30

Gly Arg Lys Phe Val Asp Val Glu Gly Pro Tyr Gly Trp Glu Tyr Ala
        35                  40                  45

Ala His Pro Leu Gly Glu Val Glu Val Leu Ser Asp Glu Asn Glu Val
    50                  55                  60

Val Lys Trp Gly Leu Arg Lys Ser Leu Pro Leu Ile Glu Leu Arg Ala
65                  70                  75                  80

Thr Phe Thr Leu Asp Leu Trp Glu Leu Asp Asn Leu Glu Arg Gly Lys
                85                  90                  95

Pro Asn Val Asp Leu Ser Ser Leu Glu Glu Thr Val Arg Lys Val Ala
            100                 105                 110

Glu Phe Glu Asp Glu Val Ile Phe Arg Gly Cys Glu Lys Ser Gly Val
        115                 120                 125

Lys Gly Leu Leu Ser Phe Glu Glu Arg Lys Ile Glu Cys Gly Ser Thr
    130                 135                 140

Pro Lys Asp Leu Leu Glu Ala Ile Val Arg Ala Leu Ser Ile Phe Ser
145                 150                 155                 160

Lys Asp Gly Ile Glu Gly Pro Tyr Thr Leu Val Ile Asn Thr Asp Arg
                165                 170                 175

Trp Ile Asn Phe Leu Lys Glu Glu Ala Gly His Tyr Pro Leu Glu Lys
            180                 185                 190

Arg Val Glu Glu Cys Leu Arg Gly Gly Lys Ile Thr Thr Pro Arg
        195                 200                 205

Ile Glu Asp Ala Leu Val Val Ser Glu Arg Gly Gly Asp Phe Lys Leu
    210                 215                 220

Ile Leu Gly Gln Asp Leu Ser Ile Gly Tyr Glu Asp Arg Glu Lys Asp
225                 230                 235                 240

Ala Val Arg Leu Phe Ile Thr Glu Thr Phe Thr Phe Gln Val Val Asn
                245                 250                 255

Pro Glu Ala Leu Ile Leu Leu Lys Ser Gly Gly Ser Gly Gly Gly
            260                 265                 270
```

```
Glu Ala Ala Leu Leu Val Cys Gln Tyr Thr Ile Gln Ser Leu Ile His
            275                 280                 285

Leu Thr Gly Glu Asp Pro Gly Phe Phe Asn Val Glu Ile Pro Glu Phe
290                 295                 300

Pro Phe Tyr Pro Thr Cys Asn Val Cys Thr Ala Asp Val Asn Val Thr
305                 310                 315                 320

Ile Asn Phe Asp Val Gly Gly Lys Lys His Gln Leu Asp Leu Asp Phe
                325                 330                 335

Gly Gln Leu Thr Pro His Thr Lys Ala Val Tyr Gln Pro Arg Gly Ala
            340                 345                 350

Phe Gly Gly Ser Glu Asn Ala Thr Asn Leu Phe Leu Leu Glu Leu Leu
            355                 360                 365

Gly Ala Gly Glu Leu Ala Leu Thr Met Arg Ser Lys Lys Leu Pro Ile
370                 375                 380

Asn Val Thr Thr Gly Glu Glu Gln Val Ser Leu Glu Ser Val Asp
385                 390                 395                 400

Val Tyr Phe Gln Asp Val Phe Gly Thr Met Trp Cys His His Ala Glu
                405                 410                 415

Met Gln Asn Pro Val Tyr Leu Ile Pro Glu Thr Val Pro Tyr Ile Lys
            420                 425                 430

Trp Asp Asn Cys Asn Ser Thr Asn Ile Thr Ala Val Val Arg Ala Gln
            435                 440                 445

Gly Leu Asp Val Thr Leu Pro Leu Ser Leu Pro Thr Ser Ala Gln Asp
            450                 455                 460

Ser Asn Phe Ser Val Lys Thr Glu Met Leu Gly Asn Glu Ile Asp Ile
465                 470                 475                 480

Glu Cys Ile Met Glu Asp Gly Glu Ile Ser Gln Val Leu Pro Gly Asp
                485                 490                 495

Asn Lys Phe Asn Ile Thr Cys Ser Gly Tyr Glu Ser His Val Pro Ser
            500                 505                 510

Gly Gly Ile Leu Thr Ser Thr Ser Pro Val Ala Thr Pro Ile Pro Gly
            515                 520                 525

Thr Gly Tyr Ala Tyr Ser Leu Arg Leu Thr Pro Arg Pro Val Ser Arg
            530                 535                 540

Phe Leu Gly Asn Asn Ser Ile Leu Tyr Val Phe Tyr Ser Gly Asn Gly
545                 550                 555                 560

Pro Lys Ala Ser Gly Gly Asp Tyr Cys Ile Gln Ser Asn Ile Val Phe
                565                 570                 575

Ser Asp Glu Ile Pro Ala Ser Gln Asp Met Pro Thr Asn Thr Thr Asp
            580                 585                 590

Ile Thr Tyr Val Gly Asp Asn Ala Thr Tyr Ser Val Pro Met Val Thr
            595                 600                 605

Ser Glu Asp Ala Asn Ser Pro Asn Val Thr Val Thr Ala Phe Trp Ala
610                 615                 620

Trp Pro Asn Asn Thr Glu Thr Asp Phe Lys Cys Lys Trp Thr Leu Thr
625                 630                 635                 640

Ser Gly Thr Pro Ser Gly Cys Glu Asn Ile Ser Gly Ala Phe Ala Ser
                645                 650                 655

Asn Arg Thr Phe Asp Ile Thr Val Ser Gly Leu Gly Thr Ala Pro Lys
            660                 665                 670

Thr Leu Ile Ile Thr Arg Thr Ala Thr Asn Ala Thr Thr Thr His
            675                 680                 685
```

Lys Val Ile Phe Ser Lys Ala Pro
    690             695

<210> SEQ ID NO 105
<211> LENGTH: 2088
<212> TYPE: DNA
<213> ORGANISM: Artificial Sequence
<220> FEATURE:
<223> OTHER INFORMATION: Synthetic

<400> SEQUENCE: 105

| | | | | | |
|---|---|---|---|---|---|
| gggagctttg | ctgaagatca | ctttgtgtgt | ggtagttgtt | gcgttagtag | ctgtccgggt | 60 |
| aatgatcagg | gttttggggg | cagtccccag | gccggacact | gtaatatcaa | aggttcgatt | 120 |
| actagcgaag | gcgccagaga | tgttttcaca | cccgctaggg | gtgcctgaag | tcagtgtcca | 180 |
| tttgcactta | aaatcggtct | cagtattgtt | gggccaggcc | cagaatgctg | tgacggtcac | 240 |
| atttggggag | ttagcgtctt | cgcttgtgac | cataggcacg | gaataagtgg | cattatcgcc | 300 |
| cacgtaggta | atgtcggtag | tgttagtggg | catatcctgg | ctggctggga | tctcgtctga | 360 |
| gaacacaata | ttactctgga | tgcaatagtc | ccctccagaa | gcctttggtc | cgtttccgga | 420 |
| ataaaacacg | tacagaatgc | tattgttgcc | caggaagcgt | gagactggcc | taggggtcag | 480 |
| tctcaggcta | aagcgtagc | cggttccggg | aattggagtg | gccacgggac | tagtagatgt | 540 |
| caggattccc | ccacttggga | cgtgagattc | gtagccggaa | caggtgatat | taaacttgtt | 600 |
| atcgccaggc | agcacctggc | taatttctcc | atcctccatg | atgcattcaa | tgtcgatctc | 660 |
| atttcccagc | atctcggttt | tcacggagaa | gttgctatcc | tgggcgcttg | tgggcagtga | 720 |
| cagtggcagg | gtcacgtcca | gcccctgtgc | ccggaccact | gcggtaatgt | tagtgctatt | 780 |
| acagttgtcc | cacttaatat | aagggacggt | ttcggggatc | aggtacacag | gattctgcat | 840 |
| ctcggcatgg | tggcaccaca | tggtgccaaa | cacatcctgg | aagtagacgt | ccactgattc | 900 |
| cagactgacc | tgctgttcct | ctcctgtggt | cacattgatg | ggcagtttct | tggacctcat | 960 |
| ggtcagagcc | agttctcctg | ctcccagcag | ctccagcaga | aacagatttg | ttgcgttctc | 1020 |
| gctgcctccg | aaagcccctc | tgggctgata | cacggctttt | gtatgtgggg | tcagctggcc | 1080 |
| aaaatccagg | tccagctggt | gtttcttccc | gcccacatcc | aaattaatgg | tgacgttcac | 1140 |
| gtcggctgta | cagacgttgc | aggtgggggta | aatgggaac | tcaggatttt | ccacattgaa | 1200 |
| aaatccaggg | tcctccccgg | tcagatgaat | caggctctga | atagtgtact | ggcacaccag | 1260 |
| cagggcggct | tcgcctccgc | cagatccgcc | tccggacttc | agcaggatca | gggcctcggg | 1320 |
| gttcaccacc | tggaaggtga | aggtctcggt | gatgaacagc | ctcacggcgt | ccttctccct | 1380 |
| gtcctcgtag | ccgatgctca | ggtcctggcc | caggatcagc | ttgaagtcgc | cgccctctc | 1440 |
| gctcaccacc | agggcgtcct | cgatcctggg | ggtggtgatg | atcttgccgc | ccctcaggca | 1500 |
| ctcctccacc | ctcttctcca | gggggtagtg | gccggcctcc | tccttcagga | agttgatcca | 1560 |
| cctgtcggtg | ttgatcacca | gggtgtaggg | gccctcgatg | ccgtccttgc | tgaagatgct | 1620 |
| cagggccctc | acgatggcct | ccagcaggtc | cttggggtg | ctgccgcact | cgatcttcct | 1680 |
| ctcctcgaag | ctcagcaggc | ccttcacgcc | gctcttctcg | cagcccctga | agatcacctc | 1740 |
| gtcctcgaac | tcggccacct | tcctcacggt | tcctccagg | ctgctcaggt | ccacgttggg | 1800 |
| cttgccccctc | tccaggttgt | ccagctccca | caggtccagg | gtgaaggtgg | ccctcagctc | 1860 |
| gatcaggggc | aggctcttcc | tcaggcccca | cttcaccacc | tcgttctcgt | cgctcagcac | 1920 |
| ctccacctcg | cccaggggggt | gggcggcgta | ctcccagccg | taggggccct | ccacgtccac | 1980 |

```
gaacttcctg ccgtacagct gggtcttgaa gatctccctg gccctgttgt cgatctcctg    2040
ccactgcttc tcggtcagag gggcgaagct cctcttcagg aactccat               2088

<210> SEQ ID NO 106
<211> LENGTH: 6005
<212> TYPE: DNA
<213> ORGANISM: Artificial Sequence
<220> FEATURE:
<223> OTHER INFORMATION: Synthetic

<400> SEQUENCE: 106
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
gggaacttcc atagcccata tatggagttc cgcgttacat aacttacggg aatttccaaa    420
cctggctgac cgcccaacga ccccccgccca ttgacgtcaa taatgacgta tgttcccata    480
gtaacgccaa tagggaactt ccattgacgt caatgggtgg agtatttacg gtaaactgcc    540
cacttgggaa tttccaagtg tatcatatgc caagtacgcc ccctattgac gtcaatgacg    600
ggaacttcca taagcttgca ttatgcccag tacatgacct tatgggaatt cctacttgg     660 cagtacatct acgtattagt catcgctatt accatggtga tgcggttttg gcagtacatc    720
aatgggcgtg gatagcggtt tgactcacgg gaacttccaa gtctccaccc cattgacgtc    780
aatgggagtt tgttttgact caccaaaatc aacgggaatt cccaaaatgt cgtaacaact    840
ccgccccatt gacgcaaatg gcggtaggc gtgtacggtg ggaggtctat ataagcagag    900
ctcgtttagt gaaccgtcag atcgcctgga gacgccatcc acgctgtttt gacctccata    960
gaagacaccg ggaccgatcc agcctccatc ggctcgcatc tctccttcac gcgcccgccg   1020
ccctacctga ggccgccatc cacgccggtt gagtcgcgtt ctgccgcctc ccgcctgtgg   1080
tgcctcctga actgcgtccg ccgtctaggt aagtttaaag ctcaggtcga ccgggcct     1140 ttgtccggcg ctcccttgga gcctacctag actcagccgg ctctccacgc tttgcctgac   1200
cctgcttgct caactctagt aacggtgga gggcagtgta gtctgagcag tactcgttgc    1260
tgccgcgcgc gccaccagac ataatagctg acagactaac agactgttcc tttccatggg   1320
tcttttctgc agtcaccgtc gtcgacacgt gtgatcagat atcgcggccg ctctagagat   1380
atcgccacca tggacagcaa gggcagcagc cagaagggca gcagactgct gctgctgctg   1440
gtggtgagca acctgctgct gcctcagggc gtgctagccg aagccgccct gctggtgtgc   1500
cagtacacta ttcagagcct gattcatctg accggggagg accctggatt tttcaatgtg   1560
gaaatccctg agttcccatt ttaccccacc tgcaacgtct gtacagccga cgtgaacgtc   1620
accattaatt tcgatgtggg cgggaagaaa caccagctgg acctggattt tggccagctg   1680
accccacata caaaagccgt gtatcagccc agaggggctt tcgaggcag cgagaacgca   1740 acaaatctgt ttctgctgga gctgctggga gcaggagaac tggctctgac catgaggtcc   1800
aagaaactgc ccatcaatgt gaccacagga gaggaacagc aggtcagtct ggaatcagtg   1860
gacgtctact tccaggatgt gtttggcacc atgtggtgcc accatgccga gatgcagaat   1920
cctgtgtacc tgatccccga aaccgtccct tatattaagt gggacaactg taatagcact   1980
```

```
aacattaccg cagtggtccg ggcacagggg ctggacgtga ccctgccact gtcactgccc    2040
acaagcgccc aggatagcaa cttctccgtg aaaaccgaga tgctgggaaa tgagatcgac    2100
attgaatgca tcatggagga tggagaaatt agccaggtgc tgcctggcga taacaagttt    2160
aatatcacct gttccggcta cgaatctcac gtcccaagtg ggggaatcct gacatctact    2220
agtcccgtgg ccactccaat tcccggaacc ggctacgctt atagcctgag actgacccct    2280
aggccagtct cacgcttcct gggcaacaat agcattctgt acgtgtttta ttccggaaac    2340
ggaccaaagg cttctggagg ggactattgc atccagagta atattgtgtt ctcagacgag    2400
atcccagcca gccaggatat gcccacttcc ggagagagcc aggtgaggca gaacttcaag    2460
cccgagatgg aggagaagct gaacgagcag atgaacctgg agctgtacag cagcctgctg    2520
taccagcaga tgagcgcctg gtgcagctac cacaccttcg agggcgccgc cgccttcctg    2580
aggaggcacg cccaggagga gatgacccac atgcagaggc tgttcgacta cctgaccgac    2640
accggcaacc tgcccaggat caacaccgtg gagagcccct cgccgagta cagcagcctg    2700
gacgagctgt ccaggagac ctacaagcac gagcagctga tcacccagaa gatcaacgag    2760
ctggcccacg ccgccatgac caaccaggac taccccacct tcaacttcct gcagtggtac    2820
gtgagcgagc agcacgagga ggagaagctg ttcaagagca tcatcgacaa gctgagcctg    2880
gccggcaaga gcgcgagggg cctgtacttc atcgacaagg agctgagcac cctggacgga    2940
tcctagcatc atcatcatca ttagtctgga agggcgaatt gatccagatc tgctgtgcct    3000
tctagttgcc agccatctgt tgtttgcccc tcccccgtgc cttccttgac cctggaaggt    3060
gccactccca ctgtcctttc ctaataaaat gaggaaattg catcgcattg tctgagtagg    3120
tgtcattcta ttctgggggg tggggtgggg caggacagca aggggagga ttgggaagac    3180
aatagcaggc atgctgggga tgcggtgggc tctatgggta cccaggtgct gaagaattga    3240
cccggttcct cctgggccag aaagaagcag gcacatcccc ttctctgtga cacaccctgt    3300
ccacgcccct ggttcttagt tccagcccca ctcataggac actcatagct caggagggct    3360
ccgccttcaa tcccaccgc taaagtactt ggagcggtct ctccctccct catcagccca    3420
ccaaaccaaa cctagcctcc aagagtggga agaaattaaa gcaagatagg ctattaagtg    3480
cagagggaga gaaatgcct ccaacatgtg aggaagtaat gagagaaatc atagaatttt    3540
aaggccatga tttaaggcca tcatggcctt aatcttccgc ttcctcgctc actgactcgc    3600
tgcgctcggt cgttcggctg cggcgagcgg tatcagctca ctcaaaggcg gtaatacggt    3660
tatccacaga atcaggggat aacgcaggaa agaacatgtg agcaaaaggc cagcaaaagg    3720
ccaggaaccg taaaaaggcc gcgttgctgg cgttttccca taggctccgc cccctgacg    3780
agcatcacaa aaatcgacgc tcaagtcaga ggtggcgaaa cccgacagga ctataaagat    3840
accaggcgtt ccccctgga agctccctcg tgcgctctcc tgttccgacc ctgccgctta    3900
ccggatacct gtccgccttt ctcccttcgg aagcgtggc gctttctcat agctcacgct    3960
gtaggtatct cagttcggtg taggtcgttc gctccaagct gggctgtgtg cacgaacccc    4020
ccgttcagcc cgaccgctgc gccttatccg gtaactatcg tcttgagtcc aacccggtaa    4080
gacacgactt atcgccactg gcagcagcca ctggtaacag gattagcaga gcgaggtatg    4140
taggcggtgc tacagagttc ttgaagtggt ggcctaacta cggctacact agaagaacag    4200
tatttggtat ctgcgctctg ctgaagccag ttaccttcgg aaaaagagtt ggtagctctt    4260
gatccggcaa acaaaccacc gctggtagcg gtggttttt tgtttgcaag cagcagatta    4320
```

```
cgcgcagaaa aaaaggatct caagaagatc ctttgatctt ttctacgggg tctgacgctc    4380
agtggaacga aaactcacgt taagggattt tggtcatgag attatcaaaa aggatcttca    4440
cctagatcct tttaaattaa aaatgaagtt ttaaatcaat ctaaagtata tatgagtaaa    4500
cttggtctga cagttaccaa tgcttaatca gtgaggcacc tatctcagcg atctgtctat    4560
ttcgttcatc catagttgcc tgactcgggg ggggggggcg ctgaggtctg cctcgtgaag    4620
aaggtgttgc tgactcatac caggcctgaa tcgccccatc atccagccag aaagtgaggg    4680
agccacggtt gatgagagct tgttgtagg tggaccagtt ggtgattttg aacttttgct     4740
ttgccacgga acgtctgcg ttgtcggaa gatgcgtgat ctgatccttc aactcagcaa      4800
aagttcgatt tattcaacaa agccgccgtc ccgtcaagtc agcgtaatgc tctgccagtg    4860
ttacaaccaa ttaaccaatt ctgattagaa aaactcatcg agcatcaaat gaaactgcaa    4920
tttattcata tcaggattat caataccata tttttgaaaa agccgtttct gtaatgaagg    4980
agaaaactca ccgaggcagt tccataggat ggcaagatcc tggtatcggt ctgcgattcc    5040
gactcgtcca acatcaatac aacctattaa tttcccctcg tcaaaaataa ggttatcaag    5100
tgagaaatca ccatgagtga cgactgaatc cggtgagaat ggcaaaagct tatgcatttc    5160
tttccagact tgttcaacag gccagccatt acgctcgtca tcaaaatcac tcgcatcaac    5220
caaaccgtta ttcattcgtg attgcgcctg agcgagacga atacgcgat cgctgttaaa     5280 aggacaatta caaacaggaa tcgaatgcaa ccggcgcagg aacactgcca gcgcatcaac    5340
aatattttca cctgaatcag gatattcttc taatacctgg aatgctgttt tcccggggat    5400
cgcagtggtg agtaaccatg catcatcagg agtacggata aaatgcttga tggtcggaag    5460
aggcataaat tccgtcagcc agtttagtct gaccatctca tctgtaacat cattggcaac    5520
gctacctttg ccatgtttca gaaacaactc tggcgcatcg gcttcccat acaatcgata     5580 gattgtcgca cctgattgcc cgacattatc gcgagcccat ttatacccat ataaatcagc    5640
atccatgttg gaatttaatc gcggcctcga gcaagacgtt tccgttgaa tatggctcat     5700 aacaccccctt gtattactgt ttatgtaagc agacagtttt attgttcatg atgatatatt    5760
tttatcttgt gcaatgtaac atcagagatt ttgagacaca acgtggcttt cccccccccc    5820
ccattattga agcatttatc agggttattg tctcatgagc ggatacatat ttgaatgtat    5880
ttagaaaaat aaacaaatag gggttccgcg cacatttccc cgaaaagtgc cacctgacgt    5940
ctaagaaacc attattatca tgacattaac ctataaaaat aggcgtatca cgaggccctt    6000
tcgtc                                                                6005
```

<210> SEQ ID NO 107
<211> LENGTH: 6329
<212> TYPE: DNA
<213> ORGANISM: Artificial Sequence
<220> FEATURE:
<223> OTHER INFORMATION: Synthetic

<400> SEQUENCE: 107

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc     180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
```

```
gggaacttcc atagcccata tatggagttc gcgttacat aacttacggg aatttccaaa    420
cctggctgac cgcccaacga cccccgccca ttgacgtcaa taatgacgta tgttcccata    480
gtaacgccaa tagggaactt ccattgacgt caatgggtgg agtatttacg gtaaactgcc    540
cacttgggaa tttccaagtg tatcatatgc caagtacgcc ccctattgac gtcaatgacg    600
ggaacttcca taagcttgca ttatgcccag tacatgacct tatgggaatt tcctacttgg    660
cagtacatct acgtattagt catcgctatt accatggtga tgcggttttg gcagtacatc    720
aatgggcgtg gatagcggtt tgactcacgg gaacttccaa gtctccaccc cattgacgtc    780
aatgggagtt tgttttgact caccaaaatc aacgggaatt cccaaaatgt cgtaacaact    840 ccgcccatt gacgcaaatg gcggtaggc gtgtacggtg ggaggtctat ataagcagag    900
ctcgtttagt gaaccgtcag atcgcctgga cgccatcc acgctgtttt gacctccata    960
gaagacaccg ggaccgatcc agcctccatc ggctcgcatc tctccttcac gcgcccgccg   1020
ccctacctga ggccgccatc cacgccggtt gagtcgcgtt ctgccgcctc cgcctgtgg    1080 tgcctcctga actgcgtccg ccgtctaggt aagtttaaag ctcaggtcga gaccgggcct   1140
ttgtccggcg ctcccttgga gcctacctag actcagccgg ctctccacgc tttgcctgac   1200
cctgcttgct caactctagt taacggtgga gggcagtgta gtctgagcag tactcgttgc   1260
tgccgcgcgc gccaccagac ataatagctg acagactaac agactgttcc tttccatggg   1320
tcttttctgc agtcaccgtc gtcgacacgt gtgatcagat atcgcggccg ctctagagat   1380
atcgccacca tggacagcaa gggcagcagc cagaagggca gcagactgct gctgctgctg   1440
gtggtgagca acctgctgct gcctcagggc gtgctagccg aagccgccct gctggtgtgc   1500
cagtacacta ttcagagcct gattcatctg accggggagg accctggatt tttcaatgtg   1560
gaaatccctg agttcccatt ttaccccacc tgcaacgtct gtacagccga cgtgaacgtc   1620
accattaatt tcgatgtggg cgggaagaaa caccagctgg acctggattt tggccagctg   1680
accccacata caaaagccgt gtatcagccc agaggggctt tcggaggcag cgagaacgca   1740
acaaatctgt ttctgctgga gctgctggga gcaggagaac tggctctgac catgaggtcc   1800
aagaaactgc ccatcaatgt gaccacagga gaggaacagc aggtcagtct ggaatcagtg   1860
gacgtctact tccaggatgt gtttggcacc atgtggtgcc accatgccga gatgcagaat   1920
cctgtgtacc tgatccccga aaccgtccct tatattaagt gggacaactg taatagcact   1980
aacattaccg cagtggtccg ggcacagggg ctggacgtga ccctgccact gtcactgccc   2040
acaagcgccc aggatagcaa cttctccgtg aaaaccgaga tgctgggaaa tgagatcgac   2100
attgaatgca tcatggagga tggagaaatt agccaggtgc tgcctggcga taacaagttt   2160
aatatcacct gttccggcta cgaatctcac gtcccaagtg ggggaatcct gacatctact   2220
agtcccgtgg ccactccaat tcccggaacc ggctacgctt atagcctgag actgaccct    2280 aggccagtct cacgcttcct gggcaacaat agcattctgt acgtgtttta ttccggaaac   2340
ggaccaaagg cttctggagg ggactattgc atccagagta atattgtgtt ctcagacgag   2400
atcccagcca ccaggatat gcccactaac actaccgaca ttacctacgt gggcgataat   2460
gccacttatt ccgtgcctat ggtcacaagc gaagacgcta actcccccaaa tgtgaccgtc   2520 acagcattct gggcctggcc caacaatact gagaccgatt ttaagtgcaa atggacactg   2580
acttcaggca cccctagcgg gtgtgaaaac atctctggcg ccttcgctag taatcgaacc   2640
tttgatatta cagtgtccgg cctggggact gccccaaaaa ccctgatcat tacccggaca   2700
```

```
gctactaacg caacaactac cacacacaaa gtgatcttca gcaaagctcc ctccggagag    2760
agccaggtga ggcagaactt caagcccgag atggaggaga agctgaacga gcagatgaac    2820
ctggagctgt acagcagcct gctgtaccag cagatgagcg cctggtgcag ctaccacacc    2880
ttcgagggcg ccgccgcctt cctgaggagg cacgcccagg aggagatgac ccacatgcag    2940
aggctgttcg actacctgac cgacaccggc aacctgccca ggatcaacac cgtggagagc    3000
cccttcgccg agtacagcag cctggacgag ctgttccagg agacctacaa gcacgagcag    3060
ctgatcaccc agaagatcaa cgagctggcc cacgccgcca tgaccaacca ggactacccc    3120
accttcaact tcctgcagtg gtacgtgagc gagcagcacg aggaggagaa gctgttcaag    3180
agcatcatcg acaagctgag cctggccggc aagagcggcg agggcctgta cttcatcgac    3240
aaggagctga gcaccctgga cggatcctag catcatcatc atcattagtc tggaagggcg    3300
aattgatcca gatctgctgt gccttctagt tgccagccat ctgttgtttg cccctccccc    3360
gtgccttcct tgaccctgga aggtgccact cccactgtcc tttcctaata aaatgaggaa    3420
attgcatcgc attgtctgag taggtgtcat tctattctgg ggggtggggt ggggcaggac    3480
agcaaggggg aggattggga agacaatagc aggcatgctg gggatgcggt gggctctatg    3540
ggtacccagg tgctgaagaa ttgacccggt tcctcctggg ccagaaagaa gcaggcacat    3600
cccccttctct gtgacacacc ctgtccacgc ccctggttct tagttccagc cccactcata    3660
ggacactcat agctcaggag ggctccgcct tcaatcccac ccgctaaagt acttggagcg    3720
gtctctccct ccctcatcag cccaccaaac caaacctagc ctccaagagt gggaagaaat    3780
taaagcaaga taggctatta agtgcagagg gagagaaaat gcctccaaca tgtgaggaag    3840
taatgagaga aatcatagaa ttttaaggcc atgatttaag gccatcatgg ccttaatctt    3900
ccgcttcctc gctcactgac tcgctgcgct cggtcgttcg gctgcggcga gcggtatcag    3960
ctcactcaaa ggcggtaata cggttatcca cagaatcagg ggataacgca ggaaagaaca    4020
tgtgagcaaa aggccagcaa aaggccagga accgtaaaaa ggccgcgttg ctggcgtttt    4080
tccataggct ccgcccccct gacgagcatc acaaaaatcg acgctcaagt cagaggtggc    4140
gaaacccgac aggactataa agataccagg cgtttccccc tggaagctcc ctcgtgcgct    4200
ctcctgttcc gaccctgccg cttaccggat acctgtccgc ctttctccct tcgggaagcg    4260
tggcgctttc tcatagctca cgctgtaggt atctcagttc ggtgtaggtc gttcgctcca    4320
agctgggctg tgtgcacgaa ccccccgttc agcccgaccg ctgcgcctta tccggtaact    4380
atcgtcttga gtccaacccg gtaagacacg acttatcgcc actggcagca gccactggta    4440
acaggattag cagagcgagg tatgtaggcg gtgctacaga gttcttgaag tggtggccta    4500
actacggcta cactagaaga acagtatttg gtatctgcgc tctgctgaag ccagttacct    4560
tcggaaaaag agttggtagc tcttgatccg gcaaacaaac caccgctggt agcggtggtt    4620
tttttgtttg caagcagcag attacgcgca gaaaaaaagg atctcaagaa gatcctttga    4680
tcttttctac ggggtctgac gctcagtgga acgaaaactc acgttaaggg attttggtca    4740
tgagattatc aaaaaggatc ttcacctaga tccttttaaa ttaaaaatga agttttaaat    4800
caatctaaag tatatatgag taaacttggt ctgacagtta ccaatgctta atcagtgagg    4860
cacctatctc agcgatctgt ctatttcgtt catccatagt tgcctgactc ggggggggggg    4920
ggcgctgagg tctgcctcgt gaagaaggtg ttgctgactc ataccaggcc tgaatcgccc    4980
catcatccag ccagaaagtg agggagccac ggttgatgag agctttgttg taggtggacc    5040
agttggtgat tttgaacttt tgctttgcca cggaacggtc tgcgttgtcg ggaagatgcg    5100
```

```
tgatctgatc cttcaactca gcaaaagttc gatttattca acaaagccgc cgtcccgtca    5160
agtcagcgta atgctctgcc agtgttacaa ccaattaacc aattctgatt agaaaaactc    5220
atcgagcatc aaatgaaact gcaatttatt catatcagga ttatcaatac catattttg     5280 aaaaagccgt ttctgtaatg aaggagaaaa ctcaccgagg cagttccata ggatggcaag    5340
atcctggtat cggtctgcga ttccgactcg tccaacatca atacaaccta ttaatttccc    5400
ctcgtcaaaa ataaggttat caagtgagaa atcaccatga gtgacgactg aatccggtga    5460
gaatggcaaa agcttatgca tttctttcca gacttgttca acaggccagc cattacgctc    5520
gtcatcaaaa tcactcgcat caaccaaacc gttattcatt cgtgattgcg cctgagcgag    5580
acgaaatacg cgatcgctgt taaaaggaca attacaaaca ggaatcgaat gcaaccggcg    5640
caggaacact gccagcgcat caacaatatt ttcacctgaa tcaggatatt cttctaatac    5700
ctggaatgct gttttcccgg ggatcgcagt ggtgagtaac catgcatcat caggagtacg    5760
gataaaatgc ttgatggtcg gaagaggcat aaattccgtc agccagttta gtctgaccat    5820
ctcatctgta acatcattgg caacgctacc tttgccatgt ttcagaaaca actctggcgc    5880
atcgggcttc ccatacaatc gatagattgt cgcacctgat tgcccgacat tatcgcgagc    5940
ccatttatac ccatataaat cagcatccat gttggaattt aatcgcggcc tcgagcaaga    6000
cgtttcccgt tgaatatggc tcataacacc ccttgtatta ctgtttatgt aagcagacag    6060
ttttattgtt catgatgata tatttttatc ttgtgcaatg taacatcaga gattttgaga    6120
cacaacgtgg ctttcccccc cccccatta ttgaagcatt tatcagggtt attgtctcat    6180
gagcggatac atatttgaat gtatttagaa aaataaacaa atagggggttc cgcgcacatt    6240 tccccgaaaa gtgccacctg acgtctaaga aaccattatt atcatgacat taacctataa    6300
aaataggcgt atcacgaggc cctttcgtc                                      6329
```

<210> SEQ ID NO 108
<211> LENGTH: 6464
<212> TYPE: DNA
<213> ORGANISM: Artificial Sequence
<220> FEATURE:
<223> OTHER INFORMATION: Synthetic

<400> SEQUENCE: 108

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc     180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
gggaacttcc atagcccata tatggagttc cgcgttacat aacttacggg aatttccaaa    420
cctggctgac cgcccaacga cccccgccca ttgacgtcaa taatgacgta tgttcccata    480
gtaacgccaa tagggaactt ccattgacgt caatgggtgg agtatttacg gtaaactgcc    540
cacttgggaa tttccaagtg tatcatatgc caagtacgcc ccctattgac gtcaatgacg    600
ggaacttcca taagcttgca ttatgcccag tacatgacct tatgggaatt tcctacttgg    660
cagtacatct acgtattagt catcgctatt accatggtga tgcggttttg gcagtacatc    720
aatgggcgtg atagcggttt tgactcacgg gaacttccaa gtctccaccc cattgacgtc    780
```

```
aatgggagtt tgttttgact caccaaaatc aacgggaatt cccaaaatgt cgtaacaact    840
ccgccccatt gacgcaaatg ggcggtaggc gtgtacggtg ggaggtctat ataagcagag    900
ctcgtttagt gaaccgtcag atcgcctgga gacgccatcc acgctgtttt gacctccata    960
gaagacaccg ggaccgatcc agcctccatc ggctcgcatc tctccttcac gcgcccgccg   1020
ccctacctga ggccgccatc cacgccggtt gagtcgcgtt ctgccgcctc ccgcctgtgg   1080
tgcctcctga actgcgtccg ccgtctaggt aagtttaaag ctcaggtcga gacagggcct   1140
ttgtccggcg ctcccttgga gcctacctag actcagccgg ctctccacgc tttgcctgac   1200
cctgcttgct caactctagt taacggtgga gggcagtgta gtctgagcag tactcgttgc   1260
tgccgcgcgc gccaccagac ataatagctg acagactaac agactgttcc tttccatggg   1320
tcttttctgc agtcaccgtc gtcgacacgt gtgatcagat atcgcggccg ctctagagat   1380
atcgccacca tggacagcaa gggcagcagc cagaagggca gcagactgct gctgctgctg   1440
gtggtgagca acctgctgct gcctcagggc gtgctagccg aagccgccct gctggtgtgc   1500
cagtacacta ttcagagcct gattcatctg accggggagg accctggatt tttcaatgtg   1560
gaaatccctg agttcccatt ttaccccacc tgcaacgtct gtacagccga cgtgaacgtc   1620
accattaatt tcgatgtggg cgggaagaaa caccagctgg acctggattt tggccagctg   1680
accccacata caaaagccgt gtatcagccc agaggggctt tcggaggcag cgagaacgca   1740
acaaatctgt ttctgctgga gctgctggga gcaggagaac tggctctgac catgaggtcc   1800
aagaaactgc ccatcaatgt gaccacagga gaggaacagc aggtcagtct ggaatcagtg   1860
gacgtctact tccaggatgt gtttggcacc atgtggtgcc accatgccga gatgcagaat   1920
cctgtgtacc tgatccccga aaccgtccct tatattaagt gggacaactg taatagcact   1980
aacattaccg cagtggtccg ggcacagggg ctggacgtga ccctgccact gtcactgccc   2040
acaagcgccc aggatagcaa cttctccgtg aaaaccgaga tgctgggaaa tgagatcgac   2100
attgaatgca tcatggagga tggagaaatt agccaggtgc tgcctggcga taacaagttt   2160
aatatcacct gttccggcta cgaatctcac gtcccaagtg ggggaatcct gacatctact   2220
agtcccgtgg ccactccaat tcccggaacc ggctacgctt atagcctgag actgaccact   2280
aggccagtct cacgcttcct gggcaacaat agcattctgt acgtgtttta ttccggaaac   2340
ggaccaaagg cttctggagg ggactattgc atccagagta atattgtgtt ctcagacgag   2400
atcccagcca gccaggatat gcccactaac actaccgaca ttacctacgt gggcgataat   2460
gccacttatt ccgtgcctat ggtcacaagc gaagacgcta actcccccaaa tgtgaccgtc   2520
acagcattct gggcctggcc caacaatact gagaccgatt ttaagtgcaa atggacactg   2580
acttcaggca cccctagcgg gtgtgaaaac atctctggcg ccttcgctag taatcgaacc   2640
tttgatatta cagtgtccgg cctggggact gccccaaaaa ccctgatcat acccggaca   2700
gctactaacg caacaactac cacacacaaa gtgatcttca gcaaagctcc cgagtccact   2760
accacatctc ctaccctgaa cactaccggg tttgccgacc ccaatacaac taccggactg   2820
cctagctcca cccatgtgcc aacaaacctg actgcaccag catccaccgg acctacagtg   2880
tctacttccg agagagccca ggtgaggcag aacttcaagc ccgagatgga ggagaagctg   2940
aacgagcaga tgaacctgga gctgtacagc agcctgctgt accagcagat gagcgcctgg   3000
tgcagctacc acaccttcga gggcgccgcc gccttcctga ggaggcacgc ccaggaggag   3060
atgacccaca tgcagaggct gttcgactac ctgaccgaca ccggcaacct gcccaggatc   3120
aacaccgtgg agagcccctt cgccgagtac agcagcctgg acgagctgtt ccaggagacc   3180
```

| | |
|---|---|
| tacaagcacg agcagctgat cacccagaag atcaacgagc tggcccacgc cgccatgacc | 3240 |
| aaccaggact accccacctt caacttcctg cagtggtacg tgagcgagca gcacgaggag | 3300 |
| gagaagctgt tcaagagcat catcgacaag ctgagcctgg ccggcaagag cggcgagggc | 3360 |
| ctgtacttca tcgacaagga gctgagcacc ctggacggat cctagcatca tcatcatcat | 3420 |
| tagtctggaa gggcgaattg atccagatct gctgtgcctt ctagttgcca gccatctgtt | 3480 |
| gtttgcccct cccccgtgcc ttccttgacc ctggaaggtg ccactcccac tgtcctttcc | 3540 |
| taataaaatg aggaaattgc atcgcattgt ctgagtaggt gtcattctat tctgggggt | 3600 |
| ggggtggggc aggacagcaa gggggaggat tgggaagaca atagcaggca tgctggggat | 3660 |
| gcggtgggct ctatgggtac ccaggtgctg aagaattgac ccggttcctc ctgggccaga | 3720 |
| aagaagcagg cacatcccct tctctgtgac acaccctgtc cacgccctg gttcttagtt | 3780 |
| ccagccccac tcataggaca ctcatagctc aggagggctc cgccttcaat cccacccgct | 3840 |
| aaagtacttg gagcggtctc tccctccctc atcagcccac caaaccaaac ctagcctcca | 3900 |
| agagtgggaa gaaattaaag caagataggc tattaagtgc agagggagag aaaatgcctc | 3960 |
| caacatgtga ggaagtaatg agagaaatca tagaattta aggccatgat ttaaggccat | 4020 |
| catggcctta atcttccgct tcctcgctca ctgactcgct gcgctcggtc gttcggctgc | 4080 |
| ggcgagcggt atcagctcac tcaaaggcgg taatacggtt atccacagaa tcaggggata | 4140 |
| acgcaggaaa gaacatgtga gcaaaaggcc agcaaaaggc caggaaccgt aaaaaggccg | 4200 |
| cgttgctggc gtttttccat aggctccgcc cccctgacga gcatcacaaa aatcgacgct | 4260 |
| caagtcagag gtggcgaaac ccgacaggac tataaagata ccaggcgttt cccctggaa | 4320 |
| gctcctcgt gcgctctcct gttccgaccc tgccgcttac cggatacctg tccgcctttc | 4380 |
| tcccttcggg aagcgtggcg ctttctcata gctcacgctg taggtatctc agttcggtgt | 4440 |
| aggtcgttcg ctccaagctg ggctgtgtgc acgaaccccc cgttcagccc gaccgctgcg | 4500 |
| ccttatccgg taactatcgt cttgagtcca acccggtaag acacgactta tcgccactgg | 4560 |
| cagcagccac tggtaacagg attagcagag cgaggtatgt aggcggtgct acagagttct | 4620 |
| tgaagtggtg gcctaactac ggctacacta gaagaacagt atttggtatc tgcgctctgc | 4680 |
| tgaagccagt taccttcgga aaagagttg gtagctcttg atccggcaaa caaaccaccg | 4740 |
| ctggtagcgg tggtttttt gtttgcaagc agcagattac gcgcagaaaa aaggatctc | 4800 |
| aagaagatcc tttgatcttt tctacggggt ctgacgctca gtggaacgaa aactcacgtt | 4860 |
| aagggatttt ggtcatgaga ttatcaaaaa ggatcttcac ctagatcctt ttaaattaaa | 4920 |
| aatgaagttt taaatcaatc taaagtatat atgagtaaac ttggtctgac agttaccaat | 4980 |
| gcttaatcag tgaggcacct atctcagcga tctgtctatt tcgttcatcc atagttgcct | 5040 |
| gactcggggg gggggggcgc tgaggtctgc ctcgtgaaga aggtgttgct gactcatacc | 5100 |
| aggcctgaat cgccccatca tccagccaga aagtgaggga gccacggttg atgagagctt | 5160 |
| tgttgtaggt ggaccagttg gtgattttga acttttgctt tgccacggaa cggtctgcgt | 5220 |
| tgtcgggaag atgcgtgatc tgatccttca actcagcaaa agttcgattt attcaacaaa | 5280 |
| gccgccgtcc cgtcaagtca gcgtaatgct ctgccagtgt tacaaccaat taaccaattc | 5340 |
| tgattagaaa aactcatcga gcatcaaatg aaactgcaat ttattcatat caggattatc | 5400 |
| aataccatat ttttgaaaaa gccgtttctg taatgaagga gaaaactcac cgaggcagtt | 5460 |
| ccataggatg gcaagatcct ggtatcggtc tgcgattccg actcgtccaa catcaataca | 5520 |

| | |
|---|---|
| acctattaat ttcccctcgt caaaaataag gttatcaagt gagaaatcac catgagtgac | 5580 |
| gactgaatcc ggtgagaatg gcaaaagctt atgcatttct ttccagactt gttcaacagg | 5640 |
| ccagccatta cgctcgtcat caaaatcact cgcatcaacc aaaccgttat tcattcgtga | 5700 |
| ttgcgcctga gcgagacgaa atacgcgatc gctgttaaaa ggacaattac aaacaggaat | 5760 |
| cgaatgcaac cggcgcagga acactgccag cgcatcaaca atattttcac ctgaatcagg | 5820 |
| atattcttct aatacctgga atgctgtttt cccggggatc gcagtggtga gtaaccatgc | 5880 |
| atcatcagga gtacggataa aatgcttgat ggtcggaaga ggcataaatt ccgtcagcca | 5940 |
| gtttagtctg accatctcat ctgtaacatc attggcaacg ctacctttgc catgtttcag | 6000 |
| aaacaactct ggcgcatcgg gcttcccata caatcgatag attgtcgcac ctgattgccc | 6060 |
| gacattatcg cgagcccatt tacccccata taaatcagca tccatgttgg aatttaatcg | 6120 |
| cggcctcgag caagacgttt cccgttgaat atggctcata cacccccttg tattactgtt | 6180 |
| tatgtaagca gacagtttta ttgttcatga tgatatattt ttatcttgtg caatgtaaca | 6240 |
| tcagagattt tgagacacaa cgtggctttc cccccccccc cattattgaa gcatttatca | 6300 |
| gggttattgt ctcatgagcg gatacatatt tgaatgtatt tagaaaaata aacaaatagg | 6360 |
| ggttccgcgc acatttcccc gaaaagtgcc acctgacgtc taagaaacca ttattatcat | 6420 |
| gacattaacc tataaaaata ggcgtatcac gaggcccttt cgtc | 6464 |

<210> SEQ ID NO 109
<211> LENGTH: 7634
<212> TYPE: DNA
<213> ORGANISM: Artificial Sequence
<220> FEATURE:
<223> OTHER INFORMATION: Synthetic

<400> SEQUENCE: 109

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| gggaacttcc atagcccata tatggagttc cgcgttacat aacttacggg aatttccaaa | 420 |
| cctggctgac cgcccaacga ccccgcccca ttgacgtcaa taatgacgta tgttcccata | 480 |
| gtaacgccaa tagggaactt ccattgacgt caatgggtgg agtatttacg gtaaactgcc | 540 |
| cacttgggaa tttccaagtg tatcatatgc caagtacgcc ccctattgac gtcaatgacg | 600 |
| ggaacttcca taagcttgca ttatgcccag tacatgacct tatgggaatt cctacttgg | 660 |
| cagtacatct acgtattagt catcgctatt accatggtga tgcggttttg gcagtacatc | 720 |
| aatgggcgtg atagcggttt tgactcacgg gaacttccaa gtctccaccc cattgacgtc | 780 |
| aatgggagtt tgttttgact caccaaaatc aacgggaatt cccaaaatgt cgtaacaact | 840 |
| ccgccccatt gacgcaaatg ggcggtaggc gtgtacggtg ggaggtctat ataagcagag | 900 |
| ctcgtttagt gaaccgtcag atcgcctgga gacgccatcc acgctgtttt gacctccata | 960 |
| gaagacaccg ggaccgatcc agcctccatc ggctcgcatc tctccttcac gcgcccgccg | 1020 |
| ccctacctga ggccgccatc cacgccggtt gagtcgcgtt ctgccgcctc ccgcctgtgg | 1080 |
| tgcctcctga actgcgtccg ccgtctaggt aagtttaaag ctcaggtcga accgggcct | 1140 |

```
ttgtccggcg ctcccttgga gcctacctag actcagccgg ctctccacgc tttgcctgac   1200
cctgcttgct caactctagt taacggtgga gggcagtgta gtctgagcag tactcgttgc   1260
tgccgcgcgc gccaccagac ataatagctg acagactaac agactgttcc tttccatggg   1320
tcttttctgc agtcaccgtc gtcgacacgt gtgatcagat atcgcggccg ctctagagat   1380
atcgccacca tggacagcaa gggcagcagc cagaagggca gcagactgct gctgctgctg   1440
gtggtgagca acctgctgct gcctcagggc gtgctagccg aagccgccct gctggtgtgc   1500
cagtacacta ttcagagcct gattcatctg accggggagg accctggatt tttcaatgtg   1560
gaaatccctg agttcccatt ttaccccacc tgcaacgtct gtacagccga cgtgaacgtc   1620
accattaatt tcgatgtggg cgggaagaaa caccagctgg acctggattt tggccagctg   1680
accccacata caaaagccgt gtatcagccc agagggggctt cggaggcag cgagaacgca   1740 acaaatctgt ttctgctgga gctgctggga gcaggagaac tggctctgac catgaggtcc   1800
aagaaactgc ccatcaatgt gaccacagga gaggaacagc aggtcagtct ggaatcagtg   1860
gacgtctact tccaggatgt gtttggcacc atgtggtgcc accatgccga gatgcagaat   1920
cctgtgtacc tgatccccga aaccgtccct tatattaagt gggacaactg taatagcact   1980
aacattaccg cagtggtccg ggcacagggg ctggacgtga ccctgccact gtcactgccc   2040
acaagcgccc aggatagcaa cttctccgtg aaaaccgaga tgctgggaaa tgagatcgac   2100
attgaatgca tcatggagga tggagaaatt agccaggtgc tgcctggcga taacaagttt   2160
aatatcacct gttccggcta cgaatctcac gtcccaagtg ggggaatcct gacatctact   2220
agtcccgtgg ccactccaat tcccggaacc ggctacgctt atagcctgag actgacccct   2280
aggccagtct cacgcttcct gggcaacaat agcattctgt acgtgtttta ttccggaaac   2340
ggaccaaagg cttctggagg ggactattgc atccagtaa atattgtgtt ctcagacgag   2400
atcccagcca gcaggatat gcccactaac actaccgaca ttacctacgt gggcgataat   2460
gccacttatt ccgtgcctat ggtcacaagc gaagacgcta actccccaaa tgtgaccgtc   2520
acagcattct gggcctggcc caacaatact gagaccgatt ttaagtgcaa atggacactg   2580
acttcaggca ccccctagcgg gtgtgaaaac atctctggcg ccttcgctag taatcgaacc   2640
tttgatatta cagtgtccgg cctggggact gccccaaaaa ccctgatcat tacccggaca   2700
gctactaacg caacaactac cacacacaaa gtgatcttca gcaaagctcc cgagtccact   2760
accacatctc ctaccctgaa cactaccggg tttgccgacc ccaatacaac taccggactg   2820
cctagctcca cccatgtgcc aacaaacctg actgcaccag catccaccgg acctacagtg   2880
tctactgccg atgtcaccag tcccacacct gccggaacaa cttctggcgc tagtcccgtg   2940
accccatcac ccagcccttg gacaatggg acagagagta aggcccctga tatgacttct   3000
agtacctcac cagtcaccac accaaccccc aacgcaacaa gccctactcc agccgtgact   3060 accccacac ctaatgctac cagcccaaca cccgcagtga caactcctac cccaaacgcc   3120
acttccccaa ccctggggaa gacatcaccc actagcgccg tgaccacacc caccccctaat   3180 gctacctctc ctacactggg aaaaacttcc ccaacctctg cagtgactac cccaaccccc   3240
aacgccacaa gccccactct gggcaagacc agtcctacat cagctgtcac aactcctacc   3300
ccaaatgcaa ctgggccaac cgtgggagag acatccccc aggctaacgc aacaaatcac   3360
actctgggag gcaccagtcc cacacctgtg gtcacctcac agcccaagaa cgccacaagc   3420
gctgtgacca caggccagca taatatcaca tcaagctcca cttctagtat gagcctgcgc   3480
```

```
ccttcaagca acccagagac actgtcccca tctactagtg acaattcaac cagccacatg    3540
cctctgctga catctgcaca tccaactggg ggagaaaaca tcactcaggt caccccccgcc   3600
tccatttcta cccaccatgt gtccacatcc tctccagcac cccgacctgg aactaccagc    3660
caggcatccg gaccaggaaa tagttcaacc agcacaaagc ctggcgaggt gaacgtcaca    3720
aaagggactc cccctcagaa tgctacctca cctcaggcac caagcggcca gaaaacagct    3780
gtgcctactg tcacctccac aggcgggaag gcaaactcta caactggagg caaacacacc    3840
acagggcatg gagctcgcac tagcaccgaa ccaactaccg actacggggg agattccaca    3900
actccaaggc ccagatacaa tgccaccaca tatctgccac cctctaccag ctccaagctg    3960
cgacccagat ggacattcac tagtcctcca gtgactaccg cacaggctac agtgccagtc    4020
ccacctactt ctcagcctag attttctaac ctgagttccg gagagagcca ggtgaggcag    4080
aacttcaagc ccgagatgga ggagaagctg aacgagcaga tgaacctgga gctgtacagc    4140
agcctgctgt accagcagat gagcgcctgg tgcagctacc acaccttcga gggcgccgcc    4200
gccttcctga ggaggcacgc ccaggaggag atgacccaca tgcagaggct gttcgactac    4260
ctgaccgaca ccggcaacct gcccaggatc aacaccgtgg agagccccctt cgccgagtac    4320
agcagcctgg acgagctgtt ccaggagacc tacaagcacg agcagctgat cacccagaag    4380
atcaacgagc tggcccacgc cgccatgacc aaccaggact accccacctt caacttcctg    4440
cagtggtacg tgagcgagca gcacgaggag gagaagctgt tcaagagcat catcgacaag    4500
ctgagcctgg ccggcaagag cggcgagggc ctgtacttca tcgacaagga gctgagcacc    4560
ctggacggat cctagcatca tcatcatcat tagtctggaa gggcgaattg atccagatct    4620
gctgtgcctt ctagttgcca gccatctgtt gtttgcccct ccccgtgcc ttccttgacc     4680
ctggaaggtg ccactcccac tgtccttttcc taataaaatg aggaaattgc atcgcattgt    4740
ctgagtaggt gtcattctat tctgggggt ggggtggggc aggacagcaa gggggaggat     4800
tgggaagaca atagcaggca tgctggggat gcggtgggct ctatgggtac ccaggtgctg    4860
aagaattgac ccggttcctc ctgggccaga aagaagcagg cacatcccct tctctgtgac    4920
acaccctgtc cacgccccctg gttcttagtt ccagccccac tcataggaca ctcatagctc    4980
aggagggctc cgccttcaat cccacccgct aaagtacttg gagcggtctc tccctccctc    5040
atcagcccac caaaccaaac ctagcctcca agagtgggaa gaaattaaag caagataggc    5100
tattaagtgc agagggagag aaaatgcctc caacatgtga ggaagtaatg agagaaatca    5160
tagaatttta aggccatgat ttaaggccat catggcctta atcttccgct tcctcgctca    5220
ctgactcgct gcgctcggtc gttcggctgc ggcgagcggt atcagctcac tcaaaggcgg    5280
taatacggtt atccacagaa tcaggggata cgcaggaaa gaacatgtga gcaaaaggcc    5340
agcaaaaggc caggaaccgt aaaaaggccg cgttgctggc gtttttccat aggctccgcc    5400
cccctgacga gcatcacaaa aatcgacgct caagtcagag gtggcgaaac ccgacaggac    5460
tataaagata ccaggcgttt ccccctggaa gctccctcgt gcgctctcct gttccgaccc    5520
tgccgcttac cggatacctg tccgcctttc tcccttcggg aagcgtggcg ctttctcata    5580
gctcacgctg taggtatctc agttcggtgt aggtcgttcg ctccaagctg ggctgtgtgc    5640
acgaacccccc cgttcagccc gaccgctgcg ccttatccgg taactatcgt cttgagtcca    5700
acccggtaag acacgactta tcgccactgg cagcagccac tggtaacagg attagcagag    5760
cgaggtatgt aggcggtgct acagagttct tgaagtggtg gcctaactac ggctacacta    5820
gaagaacagt atttggtatc tgcgctctgc tgaagccagt taccttcgga aaaagagttg    5880
```

```
gtagctcttg atccggcaaa caaaccaccg ctggtagcgg tggttttttt gtttgcaagc    5940
agcagattac gcgcagaaaa aaaggatctc aagaagatcc tttgatcttt tctacggggt    6000
ctgacgctca gtggaacgaa aactcacgtt aagggatttt ggtcatgaga ttatcaaaaa    6060
ggatcttcac ctagatcctt ttaaattaaa aatgaagttt taaatcaatc taaagtatat    6120
atgagtaaac ttggtctgac agttaccaat gcttaatcag tgaggcacct atctcagcga    6180
tctgtctatt tcgttcatcc atagttgcct gactcggggg ggggggggcgc tgaggtctgc    6240 ctcgtgaaga aggtgttgct gactcatacc aggcctgaat cgccccatca tccagccaga    6300
aagtgaggga gccacggttg atgagagctt tgttgtaggt ggaccagttg gtgattttga    6360
acttttgctt tgccacggaa cggtctgcgt tgtcgggaag atgcgtgatc tgatccttca    6420
actcagcaaa agttcgattt attcaacaaa gccgccgtcc cgtcaagtca gcgtaatgct    6480
ctgccagtgt tacaaccaat taaccaattc tgattagaaa aactcatcga gcatcaaatg    6540
aaactgcaat ttattcatat caggattatc aataccatat ttttgaaaaa gccgtttctg    6600
taatgaagga gaaaactcac cgaggcagtt ccataggatg caagatcct ggtatcggtc    6660 tgcgattccg actcgtccaa catcaataca acctattaat ttcccctcgt caaaataag    6720 gttatcaagt gagaaatcac catgagtgac gactgaatcc ggtgagaatg gcaaaagctt    6780
atgcatttct ttccagactt gttcaacagg ccagccatta cgctcgtcat caaaatcact    6840
cgcatcaacc aaaccgttat tcattcgtga ttgcgcctga gcgagacgaa atacgcgatc    6900
gctgttaaaa ggacaattac aaacaggaat cgaatgcaac cggcgcagga acactgccag    6960
cgcatcaaca atattttcac ctgaatcagg atattcttct aatacctgga atgctgtttt    7020
cccggggatc gcagtggtga gtaaccatgc atcatcagga gtacggataa aatgcttgat    7080
ggtcggaaga ggcataaatt ccgtcagcca gtttagtctg accatctcat ctgtaacatc    7140
attggcaacg ctacctttgc catgtttcag aaacaactct ggcgcatcgg gcttcccata    7200
caatcgatag attgtcgcac ctgattgccc gacattatcg cgagcccatt tatacccata    7260
taaatcagca tccatgttgg aatttaatcg cggcctcgag caagacgttt cccgttgaat    7320
atggctcata acacccccttg tattactgtt tatgtaagca gacagttta ttgttcatga    7380 tgatatattt ttatcttgtg caatgtaaca tcagagattt tgagacacaa cgtggctttc    7440
cccccccccc cattattgaa gcatttatca gggttattgt ctcatgagcg gatacatatt    7500
tgaatgtatt tagaaaaata aacaaatagg ggttccgcgc acatttcccc gaaaagtgcc    7560
acctgacgtc taagaaacca ttattatcat gacattaacc tataaaaata ggcgtatcac    7620
gaggcccttt cgtc                                                      7634
```

<210> SEQ ID NO 110
<211> LENGTH: 6020
<212> TYPE: DNA
<213> ORGANISM: Artificial Sequence
<220> FEATURE:
<223> OTHER INFORMATION: Synthetic

<400> SEQUENCE: 110

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcagattgg     240
```

```
ctattggcca ttgcatacgt tgtatccata tcataatatg tacatttata ttggctcatg    300
tccaacatta ccgccatgtt gacattgatt attgactagt tattaatagt aatcaattac    360
gggaacttcc atagcccata tatggagttc cgcgttacat aacttacggg aatttccaaa    420
cctggctgac cgcccaacga cccccgccca ttgacgtcaa taatgacgta tgttcccata    480
gtaacgccaa tagggaactt ccattgacgt caatgggtgg agtatttacg gtaaactgcc    540
cacttgggaa tttccaagtg tatcatatgc caagtacgcc ccctattgac gtcaatgacg    600 ggacttcca taagcttgca ttatgcccag tacatgacct tatgggaatt cctacttgg     660 cagtacatct acgtattagt catcgctatt accatggtga tgcggttttg gcagtacatc    720
aatgggcgtg atagcggttt gactcacgg gaacttccaa gtctcaccc cattgacgtc      780 aatgggagtt tgttttgact caccaaaatc aacgggaatt cccaaaatgt cgtaacaact    840 ccgcccatt gacgcaaatg ggcggtaggc gtgtacggtg ggaggtctat ataagcagag     900
ctcgtttagt gaaccgtcag atcgcctgga gacgccatcc acgctgtttt gacctccata    960
gaagacaccg ggaccgatcc agcctccatc ggctcgcatc tctccttcac gcgcccgccg   1020
ccctacctga ggccgccatc cacgccggtt gagtcgcgtt ctgccgcctc ccgcctgtgg   1080
tgcctcctga actgcgtccg ccgtctaggt aagtttaaag ctcaggtcga gacccgggcct  1140 ttgtccggcg ctcccttgga gcctacctag actcagccgg ctctccacgc tttgcctgac   1200
cctgcttgct caactctagt taacggtgga gggcagtgta gtctgagcag tactcgttgc   1260
tgccgcgcgc gccaccagac ataatagctg acagactaac agactgttcc tttccatggg   1320
tcttttctgc agtcaccgtc gtcgacacgt gtgatcagat atcgcggccg ctctagagat   1380
atcgccacca tggacagcaa gggcagcagc cagaagggca gcagactgct gctgctgctg   1440
gtggtgagca acctgctgct gcctcagggc gtgctagccg aagccgccct gctggtgtgc   1500
cagtacacta ttcagagcct gattcatctg accggggagg accctggatt tttcaatgtg   1560
gaaatccctg agttcccatt ttaccccacc tgcaacgtct gtacagccga cgtgaacgtc   1620
accattaatt tcgatgtggg cgggaagaaa caccagctgg acctggattt tggccagctg   1680
accccacata caaaagccgt gtatcagccc agagggggctt tcggaggcag cgagaacgca   1740
acaaatctgt ttctgctgga gctgctggga gcaggagaac tggctctgac catgaggtcc   1800
aagaaactgc ccatcaatgt gaccacagga gaggaacagc aggtcagtct ggaatcagtg   1860
gacgtctact tccaggatgt gtttggcacc atgtggtgcc accatgccga gatgcagaat   1920
cctgtgtacc tgatccccga aaccgtccct tatattaagt gggacaactg taatagcact   1980
aacattaccg cagtggtccg ggcacagggg ctggacgtga ccctgccact gtcactgccc   2040
acaagcgccc aggatagcaa cttctccgtg aaaaccgaga tgctgggaaa tgagatcgac   2100
attgaatgca tcatggagga tggagaaatt agccaggtgc tgcctggcga taacaagttt   2160
aatatcacct gttccggcta cgaatctcac gtcccaagtg ggggaatcct gacatctact   2220
agtcccgtgg ccactccaat tcccggaacc ggctacgctt atagcctgag actgacccct   2280
aggccagtct cacgcttcct gggcaacaat agcattctgt acgtgtttta ttccggaaac   2340
ggaccaaagg cttctggagg ggactattgc atccagtaca tattgtgtt ctcagacgag    2400 atcccagcca gccaggatat gcccacttcc ggagagagcc aggtgaggca gcagttcagc   2460
aaggacatcg agaagctgct gaacgagcag gtgaacaagg agatgcagag cagcaacctg   2520
tacatgagca tgagcagctg gtgctacacc cacagcctgg acggcgccgg cctgttcctg   2580
ttcgaccacg ccgccgagga gtacgagcac gccaagaagc tgatcatctt cctgaacgag   2640
```

```
aacaacgtgc cgtgcagct gaccagcatc agcgccccg agcacaagtt cgagggcctg    2700
acccagatct tccagaaggc ctacgagcac gagcagcaca tcagcgagag catcaacaac    2760
atcgtggacc acgccatcaa gagcaaggac cacgccacct tcaacttcct gcagtggtac    2820
gtggccgagc agcacgagga ggaggtgctg ttcaaggaca tcctggacaa gatcgagctg    2880
atcggcaacg agaaccacgg cctgtacctg gccgaccagt acgtgaaggg catcgccaag    2940
agcaggaaga gcggatccta gcatcatcat catcattagt ctggaagggc gaattgatcc    3000
agatctgctg tgccttctag ttgccagcca tctgttgttt gcccctcccc cgtgccttcc    3060
ttgaccctgg aaggtgccac tcccactgtc ctttcctaat aaaatgagga aattgcatcg    3120
cattgtctga gtaggtgtca ttctattctg ggggtgggg tggggcagga cagcaagggg    3180
gaggattggg aagacaatag caggcatgct gggatgcgg tgggctctat ggtacccag    3240 gtgctgaaga attgacccgg ttcctcctgg gccagaaaga agcaggcaca tccccttctc    3300
tgtgacacac cctgtccacg cccctggttc ttagttccag ccccactcat aggacactca    3360
tagctcagga gggctccgcc ttcaatccca cccgctaaag tacttggagc ggtctctccc    3420
tccctcatca gccaccaaa ccaaacctag cctccaagag tgggaagaaa ttaaagcaag    3480
ataggctatt aagtgcagag ggagagaaaa tgcctccaac atgtgaggaa gtaatgagag    3540
aaatcataga atttttaaggc catgatttaa ggccatcatg ccttaatct tccgcttcct    3600 cgctcactga ctcgctgcgc tcggtcgttc ggctgcggcg agcggtatca gctcactcaa    3660
aggcggtaat acggttatcc acagaatcag gggataacgc aggaaagaac atgtgagcaa    3720
aaggccagca aaaggccagg aaccgtaaaa aggccgcgtt gctggcgttt ttccataggc    3780
tccgcccccc tgacgagcat cacaaaaatc gacgctcaag tcagaggtgg cgaaacccga    3840
caggactata aagataccag gcgtttcccc ctggaagctc cctcgtgcgc tctcctgttc    3900
cgaccctgcc gcttaccgga tacctgtccg ccttctccc ttcgggaagc gtggcgcttt    3960
ctcatagctc acgctgtagg tatctcagtt cggtgtaggt cgttcgctcc aagctgggct    4020
gtgtgcacga accccccgtt cagcccgacc gctgcgcctt atccggtaac tatcgtcttg    4080
agtccaaccc ggtaagacac gacttatcgc cactggcagc agccactggt aacaggatta    4140
gcagagcgag gtatgtaggc ggtgctacag agttcttgaa gtggtggcct aactacggct    4200
acactagaag aacagtattt ggtatctgcg ctctgctgaa gccagttacc ttcggaaaaa    4260
gagttggtag ctcttgatcc ggcaaacaaa ccaccgctgg tagcggtggt ttttttgttt    4320
gcaagcagca gattacgcgc agaaaaaaag gatctcaaga agatcctttg atcttttcta    4380
cggggtctga cgctcagtgg aacgaaaact cacgttaagg gattttggtc atgagattat    4440
caaaaaggat cttcacctag atcctttta attaaaaatg aagttttaaa tcaatctaaa    4500
gtatatatga gtaaacttgg tctgacagtt accaatgctt aatcagtgag gcacctatct    4560
cagcgatctg tctatttcgt tcatccatag ttgcctgact cggggggggg gggcgctgag    4620
gtctgcctcg tgaagaaggt gttgctgact cataccaggc ctgaatcgcc ccatcatcca    4680
gccagaaagt gagggagcca cggttgatga gagctttgtt gtaggtggac cagttggtga    4740
ttttgaactt ttgctttgcc acggaacggt ctgcgttgtc gggaagatgc gtgatctgat    4800
ccttcaactc agcaaaagtt cgatttattc aacaaagccg ccgtccgtc aagtcagcgt    4860 aatgctctgc cagtgttaca accaattaac caattctgat tagaaaaact catcgagcat    4920
caaatgaaac tgcaattat tcatatcagg attatcaata ccatatttt gaaaaagccg    4980
```

```
tttctgtaat gaaggagaaa actcaccgag gcagttccat aggatggcaa gatcctggta    5040
tcggtctgcg attccgactc gtccaacatc aatacaacct attaatttcc cctcgtcaaa    5100
aataaggtta tcaagtgaga atcaccatg agtgacgact gaatccggtg agaatggcaa     5160
aagcttatgc atttctttcc agacttgttc aacaggccag ccattacgct cgtcatcaaa    5220
atcactcgca tcaaccaaac cgttattcat tcgtgattgc gcctgagcga gacgaaatac    5280
gcgatcgctg ttaaaaggac aattacaaac aggaatcgaa tgcaaccggc gcaggaacac    5340
tgccagcgca tcaacaatat tttcacctga atcaggatat tcttctaata cctggaatgc    5400
tgttttcccg gggatcgcag tggtgagtaa ccatgcatca tcaggagtac ggataaaatg    5460
cttgatggtc ggaagaggca taaattccgt cagccagttt agtctgacca tctcatctgt    5520
aacatcattg gcaacgctac ctttgccatg tttcagaaac aactctggcg catcgggctt    5580
cccatacaat cgatagattg tcgcacctga ttgcccgaca ttatcgcgag cccatttata    5640
cccatataaa tcagcatcca tgttggaatt taatcgcggc ctcgagcaag acgtttcccg    5700
ttgaatatgg ctcataacac cccttgtatt actgtttatg taagcagaca gttttattgt    5760
tcatgatgat atattttat cttgtgcaat gtaacatcag attttgag acacaacgtg        5820 gctttcccccc cccccccatt attgaagcat ttatcagggt tattgtctca tgagcggata    5880
catatttgaa tgtatttaga aaaataaaca ataggggtt ccgcgcacat ttccccgaaa      5940
agtgccacct gacgtctaag aaaccattat tatcatgaca ttaacctata aaaataggcg    6000
tatcacgagg ccctttcgtc                                                6020
```

<210> SEQ ID NO 111
<211> LENGTH: 6344
<212> TYPE: DNA
<213> ORGANISM: Artificial Sequence
<220> FEATURE:
<223> OTHER INFORMATION: Synthetic

<400> SEQUENCE: 111

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
gggaacttcc atagcccata tatggagttc cgcgttacat aacttacggg aatttccaaa    420
cctggctgac cgcccaacga ccccccgccca ttgacgtcaa taatgacgta tgttcccata    480
gtaacgccaa tagggaactt ccattgacgt caatgggtgg agtatttacg gtaaactgcc    540
cacttgggaa tttccaagtg tatcatatgc caagtacgcc ccctattgac gtcaatgacg    600
ggaacttcca taagcttgca ttatgcccag tacatgacct tatgggaatt tcctacttgg    660
cagtacatct acgtattagt catcgctatt accatggtga tgcggttttg gcagtacatc    720
aatgggcgtg atagcggtt tgactcacgg gaacttccaa gtctccaccc cattgacgtc    780
aatgggagtt tgttttgact caccaaaatc aacgggaatt cccaaaatgt cgtaacaact    840
ccgccccatt gacgcaaatg gcggtaggc gtgtacggtg ggaggtctat ataagcagag    900
ctcgtttagt gaaccgtcag atcgcctgga gacgccatcc acgctgtttt gacctccata    960
gaagacaccg ggaccgatcc agcctccatc ggctcgcatc tctccttcac gcgcccgccg    1020
```

```
ccctacctga ggccgccatc cacgccggtt gagtcgcgtt ctgccgcctc ccgcctgtgg    1080
tgcctcctga actgcgtccg ccgtctaggt aagtttaaag ctcaggtcga gacccgggcct   1140 ttgtccggcg ctcccttgga gcctacctag actcagccgg ctctccacgc tttgcctgac    1200
cctgcttgct caactctagt taacggtgga gggcagtgta gtctgagcag tactcgttgc    1260
tgccgcgcgc gccaccagac ataatagctg acagactaac agactgttcc tttccatggg    1320
tcttttctgc agtcaccgtc gtcgacacgt gtgatcagat atcgcggccg ctctagagat    1380
atcgccacca tggacagcaa gggcagcagc cagaagggca gcagactgct gctgctgctg    1440
gtggtgagca acctgctgct gcctcagggc gtgctagccg aagccgccct gctggtgtgc    1500
cagtacacta ttcagagcct gattcatctg accggggagg accctggatt tttcaatgtg    1560
gaaatccctg agttcccatt ttaccccacc tgcaacgtct gtacagccga cgtgaacgtc    1620
accattaatt tcgatgtggg cgggaagaaa caccagctgg acctggattt tggccagctg    1680
accccacata caaaagccgt gtatcagccc agagggggctt tcggaggcag cgagaacgca    1740
acaaatctgt ttctgctgga gctgctggga gcaggagaac tggctctgac catgaggtcc    1800
aagaaactgc ccatcaatgt gaccacagga gaggaacagc aggtcagtct ggaatcagtg    1860
gacgtctact tccaggatgt gtttggcacc atgtggtgcc accatgccga gatgcagaat    1920
cctgtgtacc tgatccccga aaccgtccct tatattaagt gggacaactg taatagcact    1980
aacattaccg cagtggtccg ggcacagggg ctggacgtga ccctgccact gtcactgccc    2040
acaagcgccc aggatagcaa cttctccgtg aaaaccgaga tgctgggaaa tgagatcgac    2100
attgaatgca tcatggagga tggagaaatt agccaggtgc tgcctggcga taacaagttt    2160
aatatcacct gttccggcta cgaatctcac gtcccaagtg ggggaatcct gacatctact    2220
agtcccgtgg ccactccaat tcccggaacc ggctacgctt atagcctgag actgaccct    2280 aggccagtct cacgcttcct gggcaacaat agcattctgt acgtgttta ttccggaaac    2340 ggaccaaagg cttctggagg ggactattgc atccagagta atattgtgtt ctcagacgag    2400
atcccagcca gcaggatat gcccactaac actaccgaca ttacctacgt gggcgataat    2460
gccacttatt ccgtgcctat ggtcacaagc gaagacgcta actccccaaa tgtgaccgtc    2520
acagcattct gggcctggcc caacaatact gagaccgatt ttaagtgcaa atggacactg    2580
acttcaggca ccccctagcgg gtgtgaaaac atctctggcg ccttcgctag taatcgaacc    2640
tttgatatta cagtgtccgg cctggggact gccccaaaaa ccctgatcat tacccggaca    2700
gctactaacg caacaactac cacacacaaa gtgatcttca gcaaagctcc ctccggagag    2760
agccaggtga ggcagcagtt cagcaaggac atcgagaagc tgctgaacga gcaggtgaac    2820
aaggagatgc agagcagcaa cctgtacatg agcatgagca gctggtgcta cacccacagc    2880
ctggacggcg ccggcctgtt cctgttcgac cacgccgccg aggagtacga gcacgccaag    2940
aagctgatca tcttcctgaa cgagaacaac gtgcccgtgc agctgaccag catcagcgcc    3000
cccgagcaca gttcgaggg cctgacccag atcttccaga aggcctacga gcacgagcag    3060
cacatcagcg agagcatcaa caacatcgtg gaccacgcca tcaagagcaa ggaccacgcc    3120
accttcaact tcctgcagtg gtacgtggcc gagcagcacg aggaggaggt gctgttcaag    3180
gacatcctgg acaagatcga gctgatcggc aacgagaacc acggcctgta cctggccgac    3240
cagtacgtga agggcatcgc caagagcagg aagagcggat cctagcatca tcatcatcat    3300
tagtctggaa gggcgaattg atccagatct gctgtgcctt ctagttgcca gccatctgtt    3360
```

```
gtttgcccct ccccgtgcc ttccttgacc ctggaaggtg ccactcccac tgtcctttcc    3420
taataaaatg aggaaattgc atcgcattgt ctgagtaggt gtcattctat tctgggggt    3480
ggggtggggc aggacagcaa gggggaggat tgggaagaca atagcaggca tgctggggat    3540
gcggtgggct ctatgggtac ccaggtgctg aagaattgac ccggttcctc ctgggccaga    3600
aagaagcagg cacatcccct tctctgtgac acaccctgtc cacgcccctg gttcttagtt    3660
ccagccccac tcataggaca ctcatagctc aggagggctc cgccttcaat cccacccgct    3720
aaagtacttg gagcggtctc tccctccctc atcagcccac caaaccaaac ctagcctcca    3780
agagtgggaa gaaattaaag caagataggc tattaagtgc agagggagag aaaatgcctc    3840
caacatgtga ggaagtaatg agagaaatca tagaatttta aggccatgat ttaaggccat    3900
catggcctta atcttccgct tcctcgctca ctgactcgct gcgctcggtc gttcggctgc    3960
ggcgagcggt atcagctcac tcaaaggcgg taatacggtt atccacagaa tcaggggata    4020
acgcaggaaa gaacatgtga gcaaaaggcc agcaaaaggc caggaaccgt aaaaaggccg    4080
cgttgctggc gtttttccat aggctccgcc cccctgacga gcatcacaaa aatcgacgct    4140
caagtcagag gtggcgaaac ccgacaggac tataaagata ccaggcgttt ccccctggaa    4200
gctccctcgt gcgctctcct gttccgaccc tgccgcttac cggatacctg tccgcctttc    4260
tcccttcggg aagcgtggcg ctttctcata gctcacgctg taggtatctc agttcggtgt    4320
aggtcgttcg ctccaagctg ggctgtgtgc acgaaccccc cgttcagccc gaccgctgcg    4380
ccttatccgg taactatcgt cttgagtcca acccggtaag acacgactta tcgccactgg    4440
cagcagccac tggtaacagg attagcagag cgaggtatgt aggcggtgct acagagttct    4500
tgaagtggtg gcctaactac ggctacacta agaacagt atttggtatc tgcgctctgc    4560
tgaagccagt taccttcgga aaaagagttg gtagctcttg atccggcaaa caaaccaccg    4620
ctggtagcgg tggttttttt gtttgcaagc agcagattac gcgcagaaaa aaggatctc    4680
aagaagatcc tttgatcttt tctacggggt ctgacgctca gtggaacgaa aactcacgtt    4740
aagggatttt ggtcatgaga ttatcaaaaa ggatcttcac ctagatcctt ttaaattaaa    4800
aatgaagttt taaatcaatc taaagtatat atgagtaaac ttggtctgac agttaccaat    4860
gcttaatcag tgaggcacct atctcagcga tctgtctatt tcgttcatcc atagttgcct    4920
gactcggggg gggggggcgc tgaggtctgc ctcgtgaaga aggtgttgct gactcatacc    4980
aggcctgaat cgccccatca tccagccaga aagtgaggga gccacggttg atgagagctt    5040
tgttgtaggt ggaccagttg gtgattttga acttttgctt tgccacggaa cggtctgcgt    5100
tgtcgggaag atgcgtgatc tgatccttca actcagcaaa agttcgattt attcaacaaa    5160
gccgccgtcc cgtcaagtca gcgtaatgct ctgccagtgt tacaaccaat taaccaattc    5220
tgattagaaa aactcatcga gcatcaaatg aaactgcaat ttattcatat caggattatc    5280
aataccatat ttttgaaaaa gccgtttctg taatgaagga gaaaactcac cgaggcagtt    5340
ccataggatg caagatcct ggtatcggtc tgcgattccg actcgtccaa catcaataca    5400
acctattaat ttcccctcgt caaaaataag gttatcaagt gagaaatcac catgagtgac    5460
gactgaatcc ggtgagaatg gcaaaagctt atgcatttct ttccagactt gttcaacagg    5520
ccagccatta cgctcgtcat caaaatcact cgcatcaacc aaaccgttat tcattcgtga    5580
ttgcgcctga gcgagacgaa atacgcgatc gctgttaaaa ggacaattac aaacaggaat    5640
cgaatgcaac cggcgcagga acactgccag cgcatcaaca atattttcac ctgaatcagg    5700
atattcttct aatacctgga atgctgtttt cccggggatc gcagtggtga gtaaccatgc    5760
```

| | |
|---|---|
| atcatcagga gtacggataa aatgcttgat ggtcggaaga ggcataaatt ccgtcagcca | 5820 |
| gtttagtctg accatctcat ctgtaacatc attggcaacg ctacctttgc catgtttcag | 5880 |
| aaacaactct ggcgcatcgg gcttcccata caatcgatag attgtcgcac ctgattgccc | 5940 |
| gacattatcg cgagcccatt tatacccata taaatcagca tccatgttgg aatttaatcg | 6000 |
| cggcctcgag caagacgttt cccgttgaat atggctcata acacccctty tattactgtt | 6060 |
| tatgtaagca dacagtttta ttgttcatga tgatatattt ttatcttgtg caatgtaaca | 6120 |
| tcagagattt tgagacacaa cgtggctttc cccccccccc cattattgaa gcatttatca | 6180 |
| gggttattgt ctcatgagcg gatacatatt tgaatgtatt tagaaaaata aacaaatagg | 6240 |
| ggttccgcgc acatttcccc gaaaagtgcc acctgacgtc taagaaacca ttattatcat | 6300 |
| gacattaacc tataaaaata ggcgtatcac gaggccctt cgtc | 6344 |

<210> SEQ ID NO 112
<211> LENGTH: 6479
<212> TYPE: DNA
<213> ORGANISM: Artificial Sequence
<220> FEATURE:
<223> OTHER INFORMATION: Synthetic

<400> SEQUENCE: 112

| | |
|---|---|
| tcgcgcgttt cggtgatgac ggtgaaaacc tctgacacat gcagctcccg gagacggtca | 60 |
| cagcttgtct gtaagcggat gccggagca gacaagcccg tcagggcgcg tcagcgggtg | 120 |
| ttggcgggtg tcgggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| gggaacttcc atagcccata tatggagttc cgcgttacat aacttacggg aatttccaaa | 420 |
| cctggctgac cgcccaacga cccccgccca ttgacgtcaa taatgacgta tgttcccata | 480 |
| gtaacgccaa tagggaactt ccattgacgt caatgggtgg agtatttacg gtaaactgcc | 540 |
| cacttgggaa tttccaagtg tatcatatgc caagtacgcc ccctattgac gtcaatgacg | 600 |
| ggaacttcca taagcttgca ttatgcccag tacatgacct tatgggaatt tcctacttgg | 660 |
| cagtacatct acgtattagt catcgctatt accatggtga tgcggttttg gcagtacatc | 720 |
| aatgggcgtg gatagcggtt tgactcacgg gaacttccaa gtctccaccc cattgacgtc | 780 |
| aatgggagtt tgttttgact caccaaaatc aacgggaatt cccaaaatgt cgtaacaact | 840 |
| ccgccccatt gacgcaaatg ggcggtaggc gtgtacggtg ggaggtctat ataagcagag | 900 |
| ctcgtttagt gaaccgtcag atcgcctgga dacgccatcc acgctgtttt gacctccata | 960 |
| gaagacaccg ggaccgatcc agcctccatc ggctcgcatc tctccttcac gcgcccgccg | 1020 |
| ccctacctga ggccgccatc cacgccggtt gagtcgcgtt ctgccgcctc ccgcctgtgg | 1080 |
| tgcctcctga actgcgtccg ccgtctaggt aagtttaaag ctcaggtcga accgggcct | 1140 |
| ttgtccggcg ctcccttgga gcctacctag actcagccgg ctctccacgc tttgcctgac | 1200 |
| cctgcttgct caactctagt taacggtgga gggcagtgta gtctgagcag tactcgttgc | 1260 |
| tgccgcgcgc gccaccagac ataatagctg acagactaac agactgttcc tttccatggg | 1320 |
| tcttttctgc agtcaccgtc gtcgacacgt gtgatcagat atcgcggccg ctctagagat | 1380 |
| atcgccacca tggacagcaa gggcagcagc cagaagggca gcagactgct gctgctgctg | 1440 |

```
gtggtgagca acctgctgct gcctcagggc gtgctagccg aagccgccct gctggtgtgc   1500
cagtacacta ttcagagcct gattcatctg accggggagg accctggatt tttcaatgtg   1560
gaaatccctg agttcccatt ttaccccacc tgcaacgtct gtacagccga cgtgaacgtc   1620
accattaatt tcgatgtggg cgggaagaaa caccagctgg acctggattt tggccagctg   1680
accccacata caaaagccgt gtatcagccc agagggggctt tcggaggcag cgagaacgca   1740
acaaatctgt ttctgctgga gctgctggga caggagaac tggctctgac catgaggtcc   1800
aagaaactgc ccatcaatgt gaccacagga gaggaacagc aggtcagtct ggaatcagtg   1860
gacgtctact tccaggatgt gtttggcacc atgtggtgcc accatgccga gatgcagaat   1920
cctgtgtacc tgatccccga aaccgtccct tatattaagt gggacaactg taatagcact   1980
aacattaccg cagtggtccg ggcacagggg ctggacgtga ccctgccact gtcactgccc   2040
acaagcgccc aggatagcaa cttctccgtg aaaaccgaga tgctgggaaa tgagatcgac   2100
attgaatgca tcatggagga tggagaaatt agccaggtgc tgcctggcga taacaagttt   2160
aatatcacct gttccggcta cgaatctcac gtcccaagtg ggggaatcct gacatctact   2220
agtcccgtgg ccactccaat tcccggaacc ggctacgctt atagcctgag actgacccct   2280
aggccagtct cacgcttcct gggcaacaat agcattctgt acgtgtttta ttccggaaac   2340
ggaccaaagg cttctggagg ggactattgc atccagagta atattgtgtt ctcagacgag   2400
atcccagcca gccaggatat gcccactaac actaccgaca ttacctacgt gggcgataat   2460
gccacttatt ccgtgcctat ggtcacaagc gaagacgcta actccccaaa tgtgaccgtc   2520
acagcattct gggcctggcc caacaatact gagaccgatt ttaagtgcaa atggacactg   2580
acttcaggca cccctagcgg gtgtgaaaac atctctggcg ccttcgctag taatcgaacc   2640
tttgatatta cagtgtccgg cctggggact gccccaaaaa ccctgatcat tacccggaca   2700
gctactaacg caacaactac cacacacaaa gtgatcttca gcaaagctcc cgagtccact   2760
accacatctc ctaccctgaa cactaccggg tttgccgacc ccaatacaac taccggactg   2820
cctagctcca cccatgtgcc aacaaacctg actgcaccag catccaccgg acctacagtg   2880
tctacttccg gagagagcca ggtgaggcag cagttcagca aggacatcga gaagctgctg   2940
aacgagcagg tgaacaagga gatgcagagc agcaacctgt acatgagcat gagcagctgg   3000
tgctacaccc acagcctgga cggcgccggc ctgttcctgt cgaccacgc cgccgaggag   3060 tacgagcacg ccaagaagct gatcatcttc ctgaacgaga caacgtgcc cgtgcagctg   3120 accagcatca gcgcccccga gcacaagttc gagggcctga cccagatctt ccagaaggcc   3180
tacgagcacg agcagcacat cagcgagagc atcaacaaca tcgtggacca cgccatcaag   3240
agcaaggacc acgccacctt caacttcctg cagtggtacg tggccgagca gcacgaggag   3300
gaggtgctgt tcaaggacat cctggacaag atcgagctga tcggcaacga gaaccacggc   3360
ctgtacctgg ccgaccagta cgtgaagggc atcgccaaga gcaggaagag cggatcctag   3420
catcatcatc atcattagtc tggaagggcg aattgatcca gatctgctgt gccttctagt   3480
tgccagccat ctgttgtttg cccctccccc gtgccttcct tgaccctgga aggtgccact   3540
cccactgtcc tttcctaata aaatgaggaa attgcatcgc attgtctgag taggtgtcat   3600
tctattctgg ggggtggggt ggggcaggac agcaaggggg aggattggga agacaatagc   3660
aggcatgctg gggatgcggt gggctctatg gtacccagg tgctgaagaa ttgacccggt   3720
tcctcctggg ccagaaagaa gcaggcacat ccccttctct gtgacacacc ctgtccacgc   3780
ccctggttct tagttccagc cccactcata ggacactcat agctcaggag ggctccgcct   3840
```

```
tcaatcccac ccgctaaagt acttggagcg gtctctccct ccctcatcag cccaccaaac    3900
caaacctagc ctccaagagt gggaagaaat taaagcaaga taggctatta agtgcagagg    3960
gagagaaaat gcctccaaca tgtgaggaag taatgagaga aatcatagaa ttttaaggcc    4020
atgatttaag gccatcatgg ccttaatctt ccgcttcctc gctcactgac tcgctgcgct    4080
cggtcgttcg gctgcggcga gcggtatcag ctcactcaaa ggcggtaata cggttatcca    4140
cagaatcagg ggataacgca ggaaagaaca tgtgagcaaa aggccagcaa aaggccagga    4200
accgtaaaaa ggccgcgttg ctggcgtttt tccataggct ccgcccccct gacgagcatc    4260
acaaaaatcg acgctcaagt cagaggtggc gaaacccgac aggactataa agataccagg    4320
cgtttccccc tggaagctcc ctcgtgcgct ctcctgttcc gaccctgccg cttaccggat    4380
acctgtccgc ctttctccct tcgggaagcg tggcgctttc tcatagctca cgctgtaggt    4440
atctcagttc ggtgtaggtc gttcgctcca agctgggctg tgtgcacgaa ccccccgttc    4500
agcccgaccg ctgcgcctta tccggtaact atcgtcttga gtccaacccg gtaagacacg    4560
acttatcgcc actggcagca gccactggta acaggattag cagagcgagg tatgtaggcg    4620
gtgctacaga gttcttgaag tggtggccta actacggcta cactagaaga acagtatttg    4680
gtatctgcgc tctgctgaag ccagttacct tcggaaaaag agttggtagc tcttgatccg    4740
gcaaacaaac caccgctggt agcggtggtt ttttgtttg caagcagcag attacgcgca    4800
gaaaaaaagg atctcaagaa gatcctttga tcttttctac ggggtctgac gctcagtgga    4860
acgaaaactc acgttaaggg attttggtca tgagattatc aaaaaggatc ttcacctaga    4920
tccttttaaa ttaaaaatga agttttaaat caatctaaag tatatatgag taaacttggt    4980
ctgacagtta ccaatgctta atcagtgagg cacctatctc agcgatctgt ctatttcgtt    5040
catccatagt tgcctgactc ccccggggggg ggcgctgagg tctgcctcgt gaagaaggtg    5100
ttgctgactc ataccaggcc tgaatcgccc catcatccag ccagaaagtg agggagccac    5160
ggttgatgag agctttgttg taggtggacc agttggtgat tttgaacttt tgctttgcca    5220
cggaacggtc tgcgttgtcg ggaagatgcg tgatctgatc cttcaactca gcaaagttc    5280
gatttattca acaaagccgc cgtcccgtca agtcagcgta atgctctgcc agtgttacaa    5340
ccaattaacc aattctgatt agaaaaactc atcgagcatc aaatgaaact gcaatttatt    5400
catatcagga ttatcaatac catatttttg aaaaagccgt ttctgtaatg aaggagaaaa    5460
ctcaccgagg cagttccata ggatggcaag atcctggtat cggtctgcga ttccgactcg    5520
tccaacatca atacaaccta ttaatttccc ctcgtcaaaa ataaggttat caagtgagaa    5580
atcaccatga gtgacgactg aatccggtga gaatggcaaa agcttatgca tttctttcca    5640
gacttgttca acaggccagc cattacgctc gtcatcaaaa tcactcgcat caaccaaacc    5700
gttattcatt cgtgattgcg cctgagcgag acgaaatacg cgatcgctgt taaaaggaca    5760
attacaaaca ggaatcgaat gcaaccggcg caggaacact gccagcgcat caacaatatt    5820
ttcacctgaa tcaggatatt cttctaatac ctggaatgct gttttcccgg ggatcgcagt    5880
ggtgagtaac catgcatcat caggagtacg ataaaatgc ttgatggtcg gaagaggcat    5940
aaattccgtc agccagttta gtctgaccat ctcatctgta acatcattgg caacgctacc    6000
tttgccatgt ttcagaaaca actctggcgc atcgggcttc ccatacaatc gatagattgt    6060
cgcacctgat tgcccgacat tatcgcgagc ccatttatac ccatataaat cagcatccat    6120
gttggaattt aatcgcggcc tcgagcaaga cgtttcccgt tgaatatggc tcataacacc    6180
```

| | |
|---|---|
| ccttgtatta ctgtttatgt aagcagacag ttttattgtt catgatgata tattttatc | 6240 |
| ttgtgcaatg taacatcaga gattttgaga cacaacgtgg cttttccccc cccccatta | 6300 |
| ttgaagcatt tatcagggtt attgtctcat gagcggatac atatttgaat gtatttagaa | 6360 |
| aaataaacaa ataggggttc cgcgcacatt tccccgaaaa gtgccacctg acgtctaaga | 6420 |
| aaccattatt atcatgacat taacctataa aaataggcgt atcacgaggc cctttcgtc | 6479 |

<210> SEQ ID NO 113
<211> LENGTH: 7649
<212> TYPE: DNA
<213> ORGANISM: Artificial Sequence
<220> FEATURE:
<223> OTHER INFORMATION: Synthetic

<400> SEQUENCE: 113

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| gggaacttcc atagcccata tatggagttc gcgttacat aacttacggg aatttccaaa | 420 |
| cctggctgac cgcccaacga ccccccgccca ttgacgtcaa taatgacgta tgttcccata | 480 |
| gtaacgccaa tagggaactt ccattgacgt caatgggtgg agtatttacg gtaaactgcc | 540 |
| cacttgggaa tttccaagtg tatcatatgc caagtacgcc ccctattgac gtcaatgacg | 600 |
| ggaacttcca taagcttgca ttatgcccag tacatgacct tatgggaatt tcctacttgg | 660 |
| cagtacatct acgtattagt catcgctatt accatggtga tgcggttttg gcagtacatc | 720 |
| aatgggcgtg gatagcggtt tgactcacgg gaacttccaa gtctccaccc cattgacgtc | 780 |
| aatgggagtt tgttttgact caccaaaatc aacgggaatt cccaaaatgt cgtaacaact | 840 |
| ccgccccatt gacgcaaatg ggcggtaggc gtgtacggtg gaggtctat ataagcagag | 900 |
| ctcgtttagt gaaccgtcag atcgcctgga gacgccatcc acgctgtttt gacctccata | 960 |
| gaagacaccg ggaccgatcc agcctccatc ggctcgcatc tctccttcac gcgcccgccg | 1020 |
| ccctacctga ggccgccatc cacgccggtt gagtcgcgtt ctgccgcctc ccgcctgtgg | 1080 |
| tgcctcctga actgcgtccg ccgtctaggt aagtttaaag ctcaggtcga ccgggcct | 1140 |
| ttgtccggcg ctcccttgga gcctacctag actcagccgg ctctccacgc tttgcctgac | 1200 |
| cctgcttgct caactctagt taacggtgga gggcagtgta gtctgagcag tactcgttgc | 1260 |
| tgccgcgcgc gccaccagac ataatagctg acagactaac agactgttcc tttccatggg | 1320 |
| tcttttctgc agtcaccgtc gtcgacacgt gtgatcagat atcgcggccg ctctagagat | 1380 |
| atcgccacca tggacagcaa gggcagcagc cagaagggca gcagctgct gctgctgctg | 1440 |
| gtggtgagca acctgctgct gcctcagggc gtgctagccg aagccgccct gctggtgtgc | 1500 |
| cagtacacta ttcagagcct gattcatctg accggggagg accctggatt tttcaatgtg | 1560 |
| gaaatccctg agttcccatt ttaccccacc tgcaacgtct gtacagccga cgtgaacgtc | 1620 |
| accattaatt tcgatgtggg cgggaagaaa caccagctgg acctggattt tggccagctg | 1680 |
| accccacata caaaagccgt gtatcagccc agaggggctt tcggaggcag cgagaacgca | 1740 |
| acaaatctgt ttctgctgga gctgctggga gcaggagaac tggctctgac catgaggtcc | 1800 |

```
aagaaactgc ccatcaatgt gaccacagga gaggaacagc aggtcagtct ggaatcagtg   1860
gacgtctact tccaggatgt gtttggcacc atgtggtgcc accatgccga gatgcagaat   1920
cctgtgtacc tgatccccga aaccgtccct tatattaagt gggacaactg taatagcact   1980
aacattaccg cagtggtccg ggcacagggg ctggacgtga ccctgccact gtcactgccc   2040
acaagcgccc aggatagcaa cttctccgtg aaaaccgaga tgctgggaaa tgagatcgac   2100
attgaatgca tcatggagga tggagaaatt agccaggtgc tgcctggcga taacaagttt   2160
aatatcacct gttccggcta cgaatctcac gtcccaagtg ggggaatcct gacatctact   2220
agtcccgtgg ccactccaat tcccggaacc ggctacgctt atagcctgag actgacccct   2280
aggccagtct cacgcttcct gggcaacaat agcattctgt acgtgtttta ttccggaaac   2340
ggaccaaagg cttctggagg ggactattgc atccagagta atattgtgtt ctcagacgag   2400
atcccagcca gccaggatat gcccactaac actaccgaca ttacctacgt gggcgataat   2460
gccacttatt ccgtgcctat ggtcacaagc gaagacgcta actccccaaa tgtgaccgtc   2520
acagcattct gggcctggcc caacaatact gagaccgatt ttaagtgcaa atggacactg   2580
acttcaggca cccctagcgg gtgtgaaaac atctctggcg ccttcgctag taatcgaacc   2640
tttgatatta cagtgtccgg cctggggact gccccaaaaa ccctgatcat tacccggaca   2700
gctactaacg caacaactac cacacacaaa gtgatcttca gcaaagctcc cgagtccact   2760
accacatctc taccctgaa cactaccggg tttgccgacc caatacaac taccggactg   2820 cctagctcca cccatgtgcc aacaaacctg actgcaccag catccaccgg acctacagtg   2880
tctactgccg atgtcaccag tcccacacct gccggaacaa cttctggcgc tagtcccgtg   2940
accccatcac ccagcccttg ggacaatggg acagagagta aggcccctga tatgacttct   3000
agtacctcac cagtcaccac accaaccccc aacgcaacaa gccctactcc agccgtgact   3060
acccccacac ctaatgctac cagcccaaca cccgcagtga caactcctac cccaaacgcc   3120
acttccccaa ccctggggaa gacatcaccc actagcgccg tgaccacacc caccctaat   3180 gctacctctc ctacactggg aaaaacttcc ccaacctctg cagtgactac cccaaccccc   3240
aacgccacaa gccccactct gggcaagacc agtcctacat cagctgtcac aactcctacc   3300
ccaaatgcaa ctgggccaac cgtgggagag acatccccc aggctaacgc aacaaatcac   3360
actctgggag gcaccagtcc cacacctgtg gtcacctcac agcccaagaa cgccacaagc   3420
gctgtgacca caggccagca taatatcaca tcaagctcca cttctagtat gagcctgcgc   3480
ccttcaagca acccagagac actgtcccca tctactagtg acaattcaac cagccacatg   3540
cctctgctga catctgcaca tccaactggg ggagaaaaca tcactcaggt caccccgcc   3600 tccatttcta cccaccatgt gtccacatcc tctccagcac cccgacctgg aactaccagc   3660
caggcatccg gaccaggaaa tagttcaacc agcacaaagc ctggcgaggt gaacgtcaca   3720
aaagggactc cccctcagaa tgctacctca cctcaggcac caagcggcca gaaaacagct   3780
gtgcctactg tcacctccac aggcgggaag gcaaactcta caactggagg caaacacacc   3840
acagggcatg gagctcgcac tagcaccgaa ccaactaccg actacggggg agattccaca   3900
actccaaggc ccagatacaa tgccaccaca tatctgccac cctctaccag ctccaagctg   3960
cgacccagat ggacattcac tagtcctcca gtgactaccg cacaggctac agtgccagtc   4020
ccacctactt ctcagcctag attttctaac ctgagttccg gagagagcca ggtgaggcag   4080
cagttcagca aggacatcga gaagctgctg aacgagcagg tgaacaagga gatgcagagc   4140
```

```
agcaacctgt acatgagcat gagcagctgg tgctacaccc acagcctgga cggcgccggc      4200
ctgttcctgt tcgaccacgc cgccgaggag tacgagcacg ccaagaagct gatcatcttc      4260
ctgaacgaga acaacgtgcc cgtgcagctg accagcatca gcgcccccga gcacaagttc      4320
gagggcctga cccagatctt ccagaaggcc tacgagcacg agcagcacat cagcgagagc      4380
atcaacaaca tcgtggacca cgccatcaag agcaaggacc acgccacctt caacttcctg      4440
cagtggtacg tggccgagca gcacgaggag gaggtgctgt tcaaggacat cctggacaag      4500
atcgagctga tcggcaacga gaaccacggc ctgtacctgg ccgaccagta cgtgaagggc      4560
atcgccaaga gcaggaagag cggatcctag catcatcatc atcattagtc tggaagggcg      4620
aattgatcca gatctgctgt gccttctagt tgccagccat ctgttgtttg ccctccccc      4680 gtgccttcct tgaccctgga aggtgccact cccactgtcc tttcctaata aaatgaggaa      4740
attgcatcgc attgtctgag taggtgtcat tctattctgg ggggtggggt ggggcaggac      4800
agcaaggggg aggattggga agacaatagc aggcatgctg gggatgcggt gggctctatg      4860
ggtacccagg tgctgaagaa ttgacccggt tcctcctggg ccagaaagaa gcaggcacat      4920 cccttctct gtgacacacc ctgtccacgc ccctggttct tagttccagc cccactcata      4980
ggacactcat agctcaggag ggctccgcct tcaatcccac ccgctaaagt acttggagcg      5040
gtctctccct ccctcatcag cccaccaaac caaacctagc ctccaagagt gggaagaaat      5100
taaagcaaga taggctatta agtgcagagg gagagaaaat gcctccaaca tgtgaggaag      5160
taatgagaga aatcatagaa ttttaaggcc atgatttaag gccatcatgg ccttaatctt      5220
ccgcttcctc gctcactgac tcgctgcgct cggtcgttcg gctgcggcga gcggtatcag      5280
ctcactcaaa ggcggtaata cggttatcca cagaatcagg ggataacgca ggaaagaaca      5340
tgtgagcaaa aggccagcaa aaggccagga accgtaaaaa ggccgcgttg ctggcgtttt      5400
tccataggct ccgcccccct gacgagcatc acaaaaatcg acgctcaagt cagaggtggc      5460
gaaacccgac aggactataa agataccagg cgtttccccc tggaagctcc ctcgtgcgct      5520
ctcctgttcc gaccctgccg cttaccggat acctgtccgc ctttctccct tcgggaagcg      5580
tggcgctttc tcatagctca cgctgtaggt atctcagttc ggtgtaggtc gttcgctcca      5640
agctgggctg tgtgcacgaa ccccccgttc agcccgaccg ctgcgcctta tccggtaact      5700
atcgtcttga gtccaacccg gtaagacacg acttatcgcc actggcagca gccactggta      5760
acaggattag cagagcgagg tatgtaggcg gtgctacaga gttcttgaag tggtggccta      5820
actacggcta cactagaaga acagtatttg gtatctgcgc tctgctgaag ccagttacct      5880
tcggaaaaag agttggtagc tcttgatccg gcaaacaaac caccgctggt agcggtggtt      5940 ttttttgtttg caagcagcag attacgcgca gaaaaaaagg atctcaagaa gatcctttga      6000
tcttttctac ggggtctgac gctcagtgga acgaaaactc acgttaaggg attttggtca      6060
tgagattatc aaaaaggatc ttcacctaga tccttttaaa ttaaaaatga agttttaaat      6120
caatctaaag tatatatgag taaacttggt ctgacagtta ccaatgctta atcagtgagg      6180
cacctatctc agcgatctgt ctatttcgtt catccatagt tgcctgactc gggggggggg      6240
ggcgctgagg tctgcctcgt gaagaaggtg ttgctgactc ataccaggcc tgaatcgccc      6300
catcatccag ccagaaagtg agggagccac ggttgatgag agctttgttg taggtggacc      6360
agttggtgat tttgaacttt tgcttttgcca cggaacggtc tgcgttgtcg gaagatgcg      6420 tgatctgatc cttcaactca gcaaaagttc gatttattca acaaagccgc cgtcccgtca      6480
agtcagcgta atgctctgcc agtgttacaa ccaattaacc aattctgatt agaaaaactc      6540
```

```
atcgagcatc aaatgaaact gcaatttatt catatcagga ttatcaatac catatttttg    6600
aaaaagccgt ttctgtaatg aaggagaaaa ctcaccgagg cagttccata ggatggcaag    6660
atcctggtat cggtctgcga ttccgactcg tccaacatca atacaaccta ttaatttccc    6720
ctcgtcaaaa ataaggttat caagtgagaa atcaccatga gtgacgactg aatccggtga    6780
gaatggcaaa agcttatgca tttctttcca gacttgttca acaggccagc cattacgctc    6840
gtcatcaaaa tcactcgcat caaccaaacc gttattcatt cgtgattgcg cctgagcgag    6900
acgaaatacg cgatcgctgt taaaaggaca attacaaaca ggaatcgaat gcaaccggcg    6960
caggaacact gccagcgcat caacaatatt ttcacctgaa tcaggatatt cttctaatac    7020
ctggaatgct gttttcccgg ggatcgcagt ggtgagtaac catgcatcat caggagtacg    7080
gataaaatgc ttgatggtcg gaagaggcat aaattccgtc agccagttta gtctgaccat    7140
ctcatctgta acatcattgg caacgctacc tttgccatgt ttcagaaaca actctggcgc    7200
atcgggcttc ccatacaatc gatagattgt cgcacctgat tgcccgacat tatcgcgagc    7260
ccatttatac ccatataaat cagcatccat gttggaattt aatcgcggcc tcgagcaaga    7320
cgtttcccgt tgaatatggc tcataacacc ccttgtatta ctgtttatgt aagcagacag    7380
ttttattgtt catgatgata tatttttatc ttgtgcaatg taacatcaga gattttgaga    7440
cacaacgtgg ctttcccccc cccccatta ttgaagcatt tatcagggtt attgtctcat    7500
gagcggatac atatttgaat gtatttagaa aaataaacaa atagggttc cgcgcacatt    7560 tccccgaaaa gtgccacctg acgtctaaga aaccattatt atcatgacat taacctataa    7620
aaataggcgt atcacgaggc cctttcgtc                                     7649
```

<210> SEQ ID NO 114
<211> LENGTH: 6291
<212> TYPE: DNA
<213> ORGANISM: Artificial Sequence
<220> FEATURE:
<223> OTHER INFORMATION: Synthetic

<400> SEQUENCE: 114

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
gggaacttcc atagcccata tatggagttc cgcgttacat aacttacggg aatttccaaa    420
cctggctgac cgcccaacga cccccgccca ttgacgtcaa taatgacgta tgttcccata    480
gtaacgccaa tagggaactt ccattgacgt caatgggtgg agtatttacg gtaaactgcc    540
cacttgggaa tttccaagtg tatcatatgc caagtacgcc ccctattgac gtcaatgacg    600
ggaacttcca taagcttgca ttatgcccag tacatgacct tatgggaatt tcctacttgg    660
cagtacatct acgtattagt catcgctatt accatggtga tgcggttttg gcagtacatc    720
aatgggcgtg atagcggttt tgactcacgg gaacttccaa gtctccaccc cattgacgtc    780
aatgggagtt tgttttgact caccaaaatc aacgggaatt cccaaaatgt cgtaacaact    840
ccgccccatt gacgcaaatg gcggtaggc gtgtacggtg ggaggtctat ataagcagag    900
```

```
ctcgtttagt gaaccgtcag atcgcctgga gacgccatcc acgctgtttt gacctccata    960
gaagacaccg ggaccgatcc agcctccatc ggctcgcatc tctccttcac gcgcccgccg   1020
ccctacctga ggccgccatc cacgccggtt gagtcgcgtt ctgccgcctc ccgcctgtgg   1080
tgcctcctga actgcgtccg ccgtctaggt aagtttaaag ctcaggtcga gacccgggcct  1140
ttgtccggcg ctcccttgga gcctacctag actcagccgg ctctccacgc tttgcctgac   1200
cctgcttgct caactctagt taacggtgga gggcagtgta gtctgagcag tactcgttgc   1260
tgccgcgcgc gccaccagac ataatagctg acagactaac agactgttcc tttccatggg   1320
tcttttctgc agtcaccgtc gtcgacacgt gtgatcagat atcgcggccg ctctagacac   1380
catgcccatg ggcagcctgc agcccctggc caccctgtac ctgctgggca tgctggtggc   1440
tagcgtgctg gccatggagt tcctgaagag gagcttcgcc cctctgaccg agaagcagtg   1500
gcaggagatc gacaacaggg ccaggagat cttcaagacc cagctgtacg gcaggaagtt   1560
cgtggacgtg gagggcccct acggctggga gtacgccgcc cacccctgg gcgaggtgga   1620
ggtgctgagc gacgagaacg aggtggtgaa gtggggcctg aggaagagcc tgccctgat    1680
cgagctgagg gccaccttca ccctggacct gtgggagctg gacaacctgg agagggcaa    1740
gcccaacgtg gacctgagca gcctggagga gaccgtgagg aaggtggccg agttcgagga   1800
cgaggtgatc ttcaggggct gcgagaagag cggcgtgaag ggcctgctga gcttcgagga   1860
gaggaagatc gagtgcggca gcaccccaa ggacctgctg gaggccatcg tgagggccct    1920
gagcatcttc agcaaggacg gcatcgaggg cccctacacc ctggtgatca acaccgacag   1980
gtggatcaac ttcctgaagg aggaggccgg ccactacccc ctggagaaga gggtggagga   2040
gtgcctgagg ggcggcaaga tcatcaccac ccccaggatc gaggacgccc tggtggtgag   2100
cgagaggggc ggcgacttca gctgatcct gggccaggac ctgagcatcg gctacgagga    2160
cagggagaag gacgccgtga ggctgttcat caccgagacc ttcaccttcc aggtggtgaa   2220
ccccgaggcc ctgatcctgc tgaagtccgg aggcggatct ggcggaggcg aagccgccct   2280
gctggtgtgc cagtacacta ttcagagcct gattcatctg accggggagg accctggatt   2340
tttcaatgtg gaaatccctg agttcccatt ttaccccacc tgcaacgtct gtacagccga   2400
cgtgaacgtc accattaatt tcgatgtggg cgggaagaaa caccagctgg acctggattt   2460
tggccagctg acccccacata caaaagccgt gtatcagccc agaggggctt tcggaggcag   2520
cgagaacgca acaaatctgt ttctgctgga gctgctggga gcaggagaac tggctctgac   2580
catgaggtcc aagaaactgc ccatcaatgt gaccacagga gaggaacagc aggtcagtct   2640
ggaatcagtg gacgtctact tccaggatgt gtttggcacc atgtggtgcc accatgccga   2700
gatgcagaat cctgtgtacc tgatccccga aaccgtccct tatattaagt gggacaactg   2760
taatagcact aacattaccg cagtggtccg ggcacagggg ctggacgtga ccctgccact   2820
gtcactgccc acaagcgccc aggatagcaa cttctccgtg aaaaccgaga tgctgggaaa   2880
tgagatcgac attgaatgca tcatggagga tggagaaatt agccaggtgc tgcctggcga   2940
taacaagttt aatatcaccc tgttccggcta cgaatctcac gtcccaagtg ggggaatcct   3000
gacatctact agtcccgtgg ccactccaat tcccggaacc ggctacgctt atagcctgag   3060
actgacccct aggccagtct cacgcttcct gggcaacaat agcattctgt acgtgtttta   3120
ttccggaaac ggaccaaagg cttctggagg ggactattgc atccagagta atattgtgtt   3180
ctcagacgag atcccagcca gccaggatat gcccacttga tgaggatccc atcatcatca   3240
tcatcattag tctggaaggg cgaattgatc cagatctgct gtgccttcta gttgccagcc   3300
```

```
atctgttgtt tgcccctccc ccgtgccttc cttgaccctg gaaggtgcca ctcccactgt    3360
cctttcctaa taaaatgagg aaattgcatc gcattgtctg agtaggtgtc attctattct    3420
ggggggtggg gtggggcagg acagcaaggg ggaggattgg gaagacaata gcaggcatgc    3480
tggggatgcg gtgggctcta tgggtaccca ggtgctgaag aattgacccg gttcctcctg    3540
ggccagaaag aagcaggcac atccccttct ctgtgacaca ccctgtccac gcccctggtt    3600
cttagttcca gccccactca taggacactc atagctcagg agggctccgc cttcaatccc    3660
acccgctaaa gtacttggag cggtctctcc ctccctcatc agcccaccaa accaaaccta    3720
gcctccaaga gtgggaagaa attaaagcaa gataggctat taagtgcaga gggagagaaa    3780
atgcctccaa catgtgagga agtaatgaga gaaatcatag aattttaagg ccatgattta    3840
aggccatcat ggccttaatc ttccgcttcc tcgctcactg actcgctgcg ctcggtcgtt    3900
cggctgcggc gagcggtatc agctcactca aaggcggtaa tacggttatc cacagaatca    3960
ggggataacg caggaaagaa catgtgagca aaaggccagc aaaaggccag gaaccgtaaa    4020
aaggccgcgt tgctggcgtt ttttccatagg ctccgccccc ctgacgagca tcacaaaaat    4080
cgacgctcaa gtcagaggtg gcgaaacccg acaggactat aaagatacca ggcgtttccc    4140
cctggaagct ccctcgtgcg ctctcctgtt ccgaccctgc cgcttaccgg atacctgtcc    4200
gcctttctcc cttcgggaag cgtggcgctt tctcatagct cacgctgtag gtatctcagt    4260
tcggtgtagg tcgttcgctc caagctgggc tgtgtgcacg aaccccccgt tcagcccgac    4320
cgctgcgcct tatccggtaa ctatcgtctt gagtccaacc cggtaagaca cgacttatcg    4380
ccactggcag cagccactgg taacaggatt agcagagcga ggtatgtagg cggtgctaca    4440
gagttcttga agtggtggcc taactacggc tacactagaa gaacagtatt tggtatctgc    4500
gctctgctga agccagttac cttcggaaaa agagttggta gctcttgatc cggcaaacaa    4560
accaccgctg gtagcggtgg tttttttgtt tgcaagcagc agattacgcg cagaaaaaaa    4620
ggatctcaag aagatccttt gatcttttct acggggtctg acgctcagtg gaacgaaaac    4680
tcacgttaag ggattttggt catgagatta tcaaaaagga tcttcaccta gatcctttta    4740
aattaaaaat gaagttttaa atcaatctaa agtatatatg agtaaacttg gtctgacagt    4800
taccaatgct taatcagtga ggcacctatc tcagcgatct gtctatttcg ttcatccata    4860
gttgcctgac tcggggggggg ggggcgctga ggtctgcctc gtgaagaagg tgttgctgac    4920
tcataccagg cctgaatcgc cccatcatcc agccagaaag tgagggagcc acggttgatg    4980
agagctttgt tgtaggtgga ccagttggtg attttgaact tttgctttgc cacggaacgg    5040
tctgcgttgt cgggaagatg cgtgatctga tccttcaact cagcaaaagt tcgatttatt    5100
caacaaagcc gccgtcccgt caagtcagcg taatgctctg ccagtgttac aaccaattaa    5160
ccaattctga ttagaaaaac tcatcgagca tcaaatgaaa ctgcaattta ttcatatcag    5220
gattatcaat accatatttt tgaaaaagcc gtttctgtaa tgaaggagaa actcaccga    5280 ggcagttcca taggatggca agatcctggt atcggtctgc gattccgact cgtccaacat    5340
caatacaacc tattaatttc ccctcgtcaa aaataaggtt atcaagtgag aaatcaccat    5400
gagtgacgac tgaatccggt gagaatggca aaagcttatg catttctttc cagacttgtt    5460
caacaggcca gccattacgc tcgtcatcaa aatcactcgc atcaaccaaa ccgttattca    5520
ttcgtgattg cgcctgagcg agacgaaata cgcgatcgct gttaaaagga caattacaaa    5580
caggaatcga atgcaaccgg cgcaggaaca ctgccagcgc atcaacaata ttttcacctg    5640
```

```
aatcaggata ttcttctaat acctggaatg ctgttttccc ggggatcgca gtggtgagta    5700
accatgcatc atcaggagta cggataaaat gcttgatggt cggaagaggc ataaattccg    5760
tcagccagtt tagtctgacc atctcatctg taacatcatt ggcaacgcta cctttgccat    5820
gtttcagaaa caactctggc gcatcgggct tcccatacaa tcgatagatt gtcgcacctg    5880
attgcccgac attatcgcga gcccatttat acccatataa atcagcatcc atgttggaat    5940
ttaatcgcgg cctcgagcaa gacgtttccc gttgaatatg gctcataaca ccccttgtat    6000
tactgtttat gtaagcagac agttttattg ttcatgatga tatattttta tcttgtgcaa    6060
tgtaacatca gagattttga gacacaacgt ggctttcccc ccccccccat tattgaagca    6120
tttatcaggg ttattgtctc atgagcggat acatatttga atgtatttag aaaaataaac    6180 aaatagggt tccgcgcaca tttccccgaa aagtgccacc tgacgtctaa gaaaccatta    6240
ttatcatgac attaacctat aaaaataggc gtatcacgag gccctttcgt c             6291
```

<210> SEQ ID NO 115
<211> LENGTH: 6615
<212> TYPE: DNA
<213> ORGANISM: Artificial Sequence
<220> FEATURE:
<223> OTHER INFORMATION: Synthetic

<400> SEQUENCE: 115

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
gggaacttcc atagcccata tatggagttc cgcgttacat aacttacggg aatttccaaa     420
cctggctgac cgcccaacga ccccccgccca ttgacgtcaa taatgacgta tgttcccata     480
gtaacgccaa tagggaactt ccattgacgt caatgggtgg agtatttacg gtaaactgcc     540
cacttgggaa tttccaagtg tatcatatgc caagtacgcc ccctattgac gtcaatgacg     600
ggaacttcca taagcttgca ttatgcccag tacatgacct tatgggaatt tcctacttgg     660
cagtacatct acgtattagt catcgctatt accatggtga tgcggttttg gcagtacatc     720
aatgggcgtg atagcggtt tgactcacgg gaacttccaa gtctccaccc cattgacgtc     780
aatgggagtt tgttttgact caccaaaatc aacgggaatt cccaaaatgt cgtaacaact     840
ccgccccatt gacgcaaatg ggcggtaggc gtgtacggtg gaggtctat ataagcagag      900 ctcgtttagt gaaccgtcag atcgcctgga gacgccatcc acgctgtttt gacctccata     960
gaagacaccg ggaccgatcc agcctccatc ggctcgcatc tctccttcac gcgcccgccg    1020
ccctacctga ggccgccatc cacgccggtt gagtcgcgtt ctgccgcctc ccgcctgtgg    1080
tgcctcctga actgcgtccg ccgtctaggt aagtttaaag ctcaggtcga accgggcct     1140 ttgtccggcg ctcccttgga gcctacctag actcagccgg ctctccacgc tttgcctgac    1200
cctgcttgct caactctagt taacggtgga gggcagtgta gtctgagcag tactcgttgc    1260 tgccggcgc gccaccagac ataatagctg acagactaac agactgttcc tttccatggg    1320
tcttttctgc agtcaccgtc gtcgacacgt gtgatcagat atcgcggccg ctctagacac    1380
catgcccatg ggcagcctgc agcccctggc caccctgtac ctgctgggca tgctggtggc    1440
```

```
tagcgtgctg gccatggagt tcctgaagag gagcttcgcc cctctgaccg agaagcagtg    1500
gcaggagatc gacaacaggg ccagggagat cttcaagacc cagctgtacg gcaggaagtt    1560
cgtggacgtg gagggcccct acggctggga gtacgccgcc cacccctgg gcgaggtgga     1620
ggtgctgagc gacgagaacg aggtggtgaa gtggggcctg aggaagagcc tgcccctgat    1680
cgagctgagg gccaccttca ccctggacct gtgggagctg acaacctgg agaggggcaa     1740
gcccaacgtg gacctgagca gcctggagga ccgtgaggg aagtggccg agttcgagga      1800
cgaggtgatc ttcaggggct gcgagaagag cggcgtgaag ggcctgctga gcttcgagga    1860
gaggaagatc gagtgcggca gcacccccaa ggacctgctg gaggccatcg tgagggccct    1920
gagcatcttc agcaaggacg gcatcgaggg cccctacacc ctggtgatca acaccgacag    1980
gtggatcaac ttcctgaagg aggaggccgg ccactacccc ctggagaaga gggtggagga   2040
gtgcctgagg ggcggcaaga tcatcaccac ccccaggatc gaggacgccc tggtggtgag   2100
cgagaggggc ggcgacttca gctgatcct gggccaggac ctgagcatcg gctacgagga    2160
cagggagaag gacgccgtga ggctgttcat caccgagacc ttcaccttcc aggtggtgaa   2220
ccccgaggcc ctgatcctgc tgaagtccgg aggcggatct ggcggaggcg aagccgccct   2280
gctggtgtgc cagtacacta ttcagagcct gattcatctg accggggagg accctggatt   2340
tttcaatgtg gaaatccctg agttcccatt ttacccccacc tgcaacgtct gtacagccga  2400
cgtgaacgtc accattaatt tcgatgtggg cgggaagaaa caccagctgg acctggattt   2460
tggccagctg accccacata caaaagccgt gtatcagccc agaggggctt tcggaggcag   2520
cgagaacgca acaaatctgt ttctgctgga gctgctggga gcaggagaac tggctctgac   2580
catgaggtcc aagaaactgc ccatcaatgt gaccacagga gaggaacagc aggtcagtct   2640
ggaatcagtg gacgtctact ccaggatgt gtttggcacc atgtggtgcc accatgccga    2700
gatgcagaat cctgtgtacc tgatccccga aaccgtccct tatattaagt gggacaactg   2760
taatagcact aacattaccg cagtggtccg ggcacagggg ctggacgtga ccctgccact   2820
gtcactgccc acaagcgccc aggatagcaa cttctccgtg aaaaccgaga tgctgggaaa   2880
tgagatcgac attgaatgca tcatggagga tggagaaatt agccaggtgc tgcctggcga   2940
taacaagttt aatatcacct gttccggcta cgaatctcac gtcccaagtg ggggaatcct   3000
gacatctact agtcccgtgg ccactccaat tcccggaacc ggctacgctt atagcctgag   3060
actgaccccct aggccagtct cacgcttcct gggcaacaat agcattctgt acgtgtttta   3120
ttccggaaac ggaccaaagg cttctggagg ggactattgc atccagagta atattgtgtt   3180
ctcagacgag atcccagcca gcaggatat gcccactaac actaccgaca ttacctacgt    3240
gggcgataat gccacttatt ccgtgcctat ggtcacaagc gaagacgcta actcccaaa    3300
tgtgaccgtc acagcattct gggcctggcc caacaatact gagaccgatt ttaagtgcaa   3360
atggacactg acttcaggca ccccccagcgg gtgtgaaaac atctctggcg ccttcgctag   3420
taatcgaacc tttgatatta cagtgtccgg cctggggact gccccaaaaa ccctgatcat   3480
tacccggaca gctactaacg caacaactac cacacaaaa gtgatcttca gcaaagctcc   3540
ctgatgagga tccatcatc atcatcatca ttagtctgga agggcgaatt gatccagatc   3600
tgctgtgcct tctagttgcc agccatctgt tgtttgcccc tcccccgtgc cttccttgac   3660
cctggaaggt gccactccca ctgtccttc ctaataaaat gaggaaattg catcgcattg    3720
tctgagtagg tgtcattcta ttctgggggg tggggtgggg caggacagca aggggagga   3780
```

```
ttgggaagac aatagcaggc atgctgggga tgcggtgggc tctatgggta cccaggtgct    3840
gaagaattga cccggttcct cctgggccag aaagaagcag gcacatcccc ttctctgtga    3900
cacaccctgt ccacgcccct ggttcttagt tccagcccca ctcataggac actcatagct    3960
caggagggct ccgccttcaa tcccaccccgc taaagtactt ggagcggtct ctccctccct    4020
catcagccca ccaaaccaaa cctagcctcc aagagtggga agaaattaaa gcaagatagg    4080
ctattaagtg cagagggaga gaaaatgcct ccaacatgtg aggaagtaat gagagaaatc    4140
atagaatttt aaggccatga tttaaggcca tcatggcctt aatcttccgc ttcctcgctc    4200
actgactcgc tgcgctcggt cgttcggctg cggcgagcgg tatcagctca ctcaaaggcg    4260
gtaatacggt tatccacaga atcaggggat aacgcaggaa agaacatgtg agcaaaaggc    4320
cagcaaaagg ccaggaaccg taaaaaggcc gcgttgctgg cgttttttcca taggctccgc    4380 ccccctgacg agcatcacaa aaatcgacgc tcaagtcaga ggtggcgaaa cccgacagga    4440
ctataaagat accaggcgtt tccccctgga agctccctcg tgcgctctcc tgttccgacc    4500
ctgccgctta ccggatacct gtccgccttt ctcccttcgg gaagcgtggc gctttctcat    4560
agctcacgct gtaggtatct cagttcggtg taggtcgttc gctccaagct gggctgtgtg    4620
cacgaacccc ccgttcagcc cgaccgctgc gccttatccg gtaactatcg tcttgagtcc    4680
aacccggtaa gacacgactt atcgccactg gcagcagcca ctggtaacag gattagcaga    4740
gcgaggtatg taggcggtgc tacagagttc ttgaagtggt ggcctaacta cggctacact    4800
agaagaacag tatttggtat ctgcgctctg ctgaagccag ttaccttcgg aaaaagagtt    4860
ggtagctctt gatccggcaa acaaaccacc gctggtagcg tggtttttt tgtttgcaag    4920 cagcagatta cgcgcagaaa aaaggatct caagaagatc ctttgatctt ttctacgggg    4980
tctgacgctc agtggaacga aaactcacgt taagggattt tggtcatgag attatcaaaa    5040
aggatcttca cctagatcct tttaaattaa aaatgaagtt ttaaatcaat ctaaagtata    5100
tatgagtaaa cttggtctga cagttaccaa tgcttaatca gtgaggcacc tatctcagcg    5160
atctgtctat ttcgttcatc catagttgcc tgactcgggg gggggggcg ctgaggtctg    5220 cctcgtgaag aaggtgttgc tgactcatac caggcctgaa tcgccccatc atccagccag    5280
aaagtgaggg agccacggtt gatgagagct tgttgtagg tggaccagtt ggtgattttg    5340
aacttttgct ttgccacgga acggtctgcg ttgtcgggaa gatgcgtgat ctgatccttc    5400
aactcagcaa aagttcgatt tattcaacaa agccgccgtc ccgtcaagtc agcgtaatgc    5460
tctgccagtg ttacaaccaa ttaaccaatt ctgattagaa aaactcatcg agcatcaaat    5520
gaaactgcaa tttattcata tcaggattat caataccata ttttttgaaaa agccgtttct    5580 gtaatgaagg agaaaactca ccgaggcagt tccataggat ggcaagatcc tggtatcggt    5640
ctgcgattcc gactcgtcca acatcaatac aacctattaa tttcccctcg tcaaaaataa    5700
ggttatcaag tgagaaatca ccatgagtga cgactgaatc cggtgagaat ggcaaaagct    5760
tatgcatttc tttccagact tgttcaacag gccagccatt acgctcgtca tcaaaatcac    5820
tcgcatcaac caaaccgtta ttcattcgtg attgcgcctg agcgagacga atacgcgat    5880 cgctgttaaa aggacaatta caaacaggaa tcgaatgcaa ccggcgcagg aacactgcca    5940
gcgcatcaac aatattttca cctgaatcag gatattcttc taatacctgg aatgctgttt    6000
tcccggggat cgcagtggtg agtaaccatg catcatcagg agtacggata aaatgcttga    6060
tggtcggaag aggcataaat tccgtcagcc agtttagtct gaccatctca tctgtaacat    6120
cattggcaac gctacctttg ccatgtttca gaaacaactc tggcgcatcg gcttcccat    6180
```

```
acaatcgata gattgtcgca cctgattgcc cgacattatc gcgagcccat ttatacccat    6240
ataaatcagc atccatgttg gaatttaatc gcggcctcga gcaagacgtt tcccgttgaa    6300
tatggctcat aacaccccctt gtattactgt ttatgtaagc agacagtttt attgttcatg   6360
atgatatatt tttatcttgt gcaatgtaac atcagagatt ttgagacaca acgtggcttt    6420 ccccccccc ccattattga agcatttatc agggttattg tctcatgagc ggatacatat     6480
ttgaatgtat ttagaaaaat aaacaaatag gggttccgcg cacatttccc cgaaaagtgc    6540
cacctgacgt ctaagaaacc attattatca tgacattaac ctataaaaat aggcgtatca    6600
cgaggccctt tcgtc                                                     6615

<210> SEQ ID NO 116
<211> LENGTH: 6750
<212> TYPE: DNA
<213> ORGANISM: Artificial Sequence
<220> FEATURE:
<223> OTHER INFORMATION: Synthetic

<400> SEQUENCE: 116
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
gggaacttcc atagcccata tatggagttc cgcgttacat aacttacggg aatttccaaa     420
cctggctgac cgcccaacga cccccgccca ttgacgtcaa taatgacgta tgttcccata     480
gtaacgccaa tagggaactt ccattgacgt caatgggtgg agtatttacg gtaaactgcc     540
cacttgggaa tttccaagtg tatcatatgc caagtacgcc ccctattgac gtcaatgacg     600
ggaacttcca taagcttgca ttatgcccag tacatgacct tatgggaatt tcctacttgg     660
cagtacatct acgtattagt catcgctatt accatggtga tgcggttttg gcagtacatc     720
aatgggcgtg gatagcggtt tgactcacgg gaacttccaa gtctccaccc cattgacgtc     780
aatgggagtt tgttttgact caccaaaatc aacgggaatt cccaaaatgt cgtaacaact     840
ccgccccatt gacgcaaatg ggcggtaggc gtgtacggtg ggaggtctat ataagcagag     900
ctcgtttagt gaaccgtcag atcgcctgga dacgccatcc acgctgtttt gacctccata     960
gaagacaccg ggaccgatcc agcctccatc ggctcgcatc tctccttcac gcgcccgccg    1020
ccctacctga ggccgccatc cacgccggtt gagtcgcgtt ctgccgcctc ccgcctgtgg    1080
tgcctcctga actgcgtccg ccgtctaggt aagtttaaag ctcaggtcga ccgggcct     1140 ttgtccggcg ctcccttgga gcctacctag actcagccgg ctctcacgc tttgcctgac     1200 cctgcttgct caactctagt taacggtgga gggcagtgta gtctgagcag tactcgttgc    1260
tgccgcgcgc gccaccagac ataatagctg acagactaac agactgttcc tttccatggg    1320
tcttttctgc agtcaccgtc gtcgacacgt gtgatcagat atcgcggccg ctctagacac    1380
catgcccatg gcagcctgc agcccctggc caccctgtac ctgctgggca tgctggtggc    1440
tagcgtgctg gccatggagt tcctgaagag gagcttcgcc cctctgaccg agaagcagtg    1500
gcaggagatc gacaacaggg ccaggcagat cttcaagacc cagctgtacg gcaggaagtt    1560
```

```
cgtggacgtg gagggcccct acggctggga gtacgccgcc cacccctgg gcgaggtgga      1620 ggtgctgagc gacgagaacg aggtggtgaa gtggggcctg aggaagagcc tgccctgat      1680 cgagctgagg gccaccttca ccctggacct gtgggagctg gacaacctgg agaggggcaa     1740
gcccaacgtg gacctgagca gcctggagga gaccgtgagg aaggtggccg agttcgagga     1800
cgaggtgatc ttcaggggct gcgagaagag cggcgtgaag ggcctgctga gcttcgagga     1860
gaggaagatc gagtgcggca gcaccccaa ggacctgctg gaggccatcg tgagggccct      1920
gagcatcttc agcaaggacg gcatcgaggg cccctacacc ctggtgatca caccgacag      1980 gtggatcaac ttcctgaagg aggaggccgg ccactacccc ctggagaaga gggtggagga    2040
gtgcctgagg ggcggcaaga tcatcaccac ccccaggatc gaggacgccc tggtggtgag    2100
cgagaggggc ggcgacttca gctgatcct gggccaggac ctgagcatcg gctacgagga     2160
cagggagaag gacgccgtga ggctgttcat caccgagacc ttcaccttcc aggtggtgaa    2220
ccccgaggcc ctgatcctgc tgaagtccgg aggcggatct ggcggaggcg aagccgccct    2280
gctggtgtgc cagtacacta ttcagagcct gattcatctg accggggagg accctggatt    2340
tttcaatgtg gaaatccctg agttcccatt ttaccccacc tgcaacgtct gtacagccga    2400
cgtgaacgtc accattaatt tcgatgtggg cgggaagaaa caccagctgg acctggattt    2460
tggccagctg accccacata caaaagccgt gtatcagccc agaggggctt cggaggcag     2520 cgagaacgca caaatctgt ttctgctgga gctgctggga gcaggagaac tggctctgac     2580
catgaggtcc aagaaactgc ccatcaatgt gaccacagga gaggaacagc aggtcagtct    2640
ggaatcagtg gacgtctact tccaggatgt gtttggcacc atgtggtgcc accatgccga    2700
gatgcagaat cctgtgtacc tgatccccga aaccgtccct tatattaagt gggacaactg    2760
taatagcact aacattaccg cagtggtccg ggcacagggg ctggacgtga ccctgccact    2820
gtcactgccc acaagcgccc aggatagcaa cttctccgtg aaaaccgaga tgctgggaaa    2880
tgagatcgac attgaatgca tcatggagga tggagaaatt agccaggtgc tgcctggcga    2940
taacaagttt aatatcacct gttccggcta cgaatctcac gtcccaagtg ggggaatcct    3000
gacatctact agtcccgtgg ccactccaat tcccggaacc ggctacgctt atagcctgag    3060 actgaccccct aggccagtct cacgcttcct gggcaacaat agcattctgt acgtgtttta    3120
ttccggaaac ggaccaaagg cttctggagg ggactattgc atccagagta atattgtgtt    3180
ctcagacgag atcccagcca gccaggatat gcccactaac actaccgaca ttacctacgt    3240
gggcgataat gccacttatt ccgtgcctat ggtcacaagc gaagacgcta actccccaaa    3300
tgtgaccgtc acagcattct gggcctggcc caacaatact gagaccgatt ttaagtgcaa    3360
atggacactg acttcaggca ccctagcgg gtgtgaaaac atctctggcg ccttcgctag    3420
taatcgaacc tttgatatta cagtgtccgg cctggggact gccccaaaaa ccctgatcat    3480
tacccggaca gctactaacg caacaactac cacacacaaa gtgatcttca gcaaagctcc    3540
cgagtccact accacatctc ctaccctgaa cactaccggg tttgccgacc ccaatacaac    3600
taccggactg cctagctcca cccatgtgcc aacaaacctg actgcaccag catccaccgg    3660
acctacagtg tctacttgat gaggatccca tcatcatcat catcattagt ctggaagggc    3720
gaattgatcc agatctgctg tgccttctag ttgccagcca tctgttgttt gcccctcccc    3780
cgtgccttcc ttgaccctgg aaggtgccac tcccactgtc ctttcctaat aaaatgagga    3840
aattgcatcg cattgtctga gtaggtgtca ttctattctg gggggtgggg tgggcagga    3900 cagcaagggg gaggattggg aagacaatag caggcatgct ggggatgcgg tggctctat    3960
```

```
gggtacccag gtgctgaaga attgacccgg ttcctcctgg gccagaaaga agcaggcaca    4020
tccccttctc tgtgacacac cctgtccacg cccctggttc ttagttccag ccccactcat    4080
aggacactca tagctcagga gggctccgcc ttcaatccca cccgctaaag tacttggagc    4140
ggtctctccc tccctcatca gcccaccaaa ccaaacctag cctccaagag tgggaagaaa    4200
ttaaagcaag ataggctatt aagtgcagag ggagagaaaa tgcctccaac atgtgaggaa    4260
gtaatgagag aaatcataga attttaaggc catgatttaa ggccatcatg gccttaatct    4320
tccgcttcct cgctcactga ctcgctgcgc tcggtcgttc ggctgcggcg agcggtatca    4380
gctcactcaa aggcggtaat acggttatcc acagaatcag gggataacgc aggaaagaac    4440
atgtgagcaa aaggccagca aaaggccagg aaccgtaaaa aggccgcgtt gctggcgttt    4500
ttccataggc tccgcccccc tgacgagcat cacaaaaatc gacgctcaag tcagaggtgg    4560
cgaaacccga caggactata agataccagg cgtttccccc tggaagctcc ctcgtgcgc    4620 tctcctgttc cgaccctgcc gcttaccgga tacctgtccg cctttctccc ttcgggaagc    4680
gtggcgcttt ctcatagctc acgctgtagg tatctcagtt cggtgtaggt cgttcgctcc    4740
aagctgggct gtgtgcacga accccccgtt cagcccgacc gctgcgcctt atccggtaac    4800
tatcgtcttg agtccaaccc ggtaagacac gacttatcgc cactggcagc agccactggt    4860
aacaggatta gcagagcgag gtatgtaggc ggtgctacag agttcttgaa gtggtggcct    4920
aactacggct acactagaag aacagtattt ggtatctgcg ctctgctgaa gccagttacc    4980
ttcggaaaaa gagttggtag ctcttgatcc ggcaaacaaa ccaccgctgg tagcggtggt    5040
ttttttgttt gcaagcagca gattacgcgc agaaaaaaag gatctcaaga agatcctttg    5100
atcttttcta cggggtctga cgctcagtgg aacgaaaact cacgttaagg gattttggtc    5160
atgagattat caaaaaggat cttcacctag atccttttaa attaaaaatg aagttttaaa    5220
tcaatctaaa gtatatatga gtaaacttgg tctgacagtt accaatgctt aatcagtgag    5280
gcacctatct cagcgatctg tctatttcgt tcatccatag ttgcctgact cggggggggg    5340
gggcgctgag gtctgcctcg tgaagaaggt gttgctgact cataccaggc ctgaatcgcc    5400
ccatcatcca gccagaaagt gagggagcca cggttgatga gagctttgtt gtaggtggac    5460
cagttggtga ttttgaactt ttgctttgcc acggaacggt ctgcgttgtc gggaagatgc    5520
gtgatctgat ccttcaactc agcaaaagtt cgatttattc aacaaagccg ccgtcccgtc    5580
aagtcagcgt aatgctctgc cagtgttaca accaattaac caattctgat tagaaaaact    5640
catcgagcat caaatgaaac tgcaatttat tcatatcagg attatcaata ccatatttt    5700 gaaaaagccg tttctgtaat gaaggagaaa actcaccgag gcagttccat aggatggcaa    5760
gatcctggta tcggtctgcg attccgactc gtccaacatc aatacaacct attaatttcc    5820
cctcgtcaaa aataaggtta tcaagtgaga aatcaccatg agtgacgact gaatccggtg    5880
agaatggcaa aagcttatgc atttctttcc agacttgttc aacaggccag ccattacgct    5940
cgtcatcaaa atcactcgca tcaaccaaac cgttattcat tcgtgattgc gcctgagcga    6000
gacgaaatac gcgatcgctg ttaaaaggac aattacaaac aggaatcgaa tgcaaccggc    6060
gcaggaacac tgccagcgca tcaacaatat tttcacctga atcaggatat tcttctaata    6120
cctggaatgc tgttttcccg gggatcgcag tggtgagtaa ccatgcatca tcaggagtac    6180
ggataaaatg cttgatggtc ggaagaggca taaattccgt cagccagttt agtctgacca    6240
tctcatctgt aacatcattg gcaacgctac ctttgccatg tttcagaaac aactctggcg    6300
```

| | |
|---|---:|
| catcgggctt cccatacaat cgatagattg tcgcacctga ttgcccgaca ttatcgcgag | 6360 |
| cccatttata cccatataaa tcagcatcca tgttggaatt taatcgcggc ctcgagcaag | 6420 |
| acgtttcccg ttgaatatgg ctcataacac cccttgtatt actgtttatg taagcagaca | 6480 |
| gttttattgt tcatgatgat atattttat cttgtgcaat gtaacatcag agattttgag | 6540 |
| acacaacgtg gctttccccc ccccccatt attgaagcat ttatcagggt tattgtctca | 6600 |
| tgagcggata catatttgaa tgtatttaga aaaataaaca aataggggtt ccgcgcacat | 6660 |
| ttccccgaaa agtgccacct gacgtctaag aaaccattat tatcatgaca ttaacctata | 6720 |
| aaaataggcg tatcacgagg ccctttcgtc | 6750 |

<210> SEQ ID NO 117
<211> LENGTH: 7920
<212> TYPE: DNA
<213> ORGANISM: Artificial Sequence
<220> FEATURE:
<223> OTHER INFORMATION: Synthetic

<400> SEQUENCE: 117

| | |
|---|---:|
| tcgcgcgttt cggtgatgac ggtgaaaacc tctgacacat gcagctcccg gagacggtca | 60 |
| cagcttgtct gtaagcggat gccgggagca gacaagcccg tcaggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggaacttcc atagcccata tatggagttc cgcgttacat aacttacggg aatttccaaa | 420 |
| cctggctgac cgcccaacga ccccgccca ttgacgtcaa taatgacgta tgttcccata | 480 |
| gtaacgccaa tagggaactt ccattgacgt caatgggtgg agtatttacg gtaaactgcc | 540 |
| cacttgggaa tttccaagtg tatcatatgc caagtacgcc ccctattgac gtcaatgacg | 600 |
| ggaacttcca taagcttgca ttatgcccag tacatgacct tatgggaatt tcctacttgg | 660 |
| cagtacatct acgtattagt catcgctatt accatggtga tgcggttttg gcagtacatc | 720 |
| aatgggcgtg atagcggtt tgactcacgg gaacttccaa gtctccaccc cattgacgtc | 780 |
| aatgggagtt gttttgact caccaaaatc aacgggaatt cccaaaatgt cgtaacaact | 840 |
| ccgccccatt gacgcaaatg ggcggtaggc gtgtacggtg ggaggtctat ataagcagag | 900 |
| ctcgtttagt gaaccgtcag atcgcctgga gacgccatcc acgctgtttt gacctccata | 960 |
| gaagacaccg ggaccgatcc agcctccatc ggctcgcatc tctccttcac gcgcccgccg | 1020 |
| ccctacctga ggccgccatc cacgccggtt gagtcgcgtt ctgccgcctc ccgcctgtgg | 1080 |
| tgcctcctga actgcgtccg ccgtctaggt aagtttaaag ctcaggtcga gaccgggcct | 1140 |
| ttgtccggcg ctcccttgga gcctacctag actcagccgg ctctccacgc tttgcctgac | 1200 |
| cctgcttgct caactctagt taacggtgga gggcagtgta gtctgagcag tactcgttgc | 1260 |
| tgccgcgcgc gccaccagac ataatagctg acagactaac agactgttcc tttccatggg | 1320 |
| tcttttctgc agtcaccgtc gtcgacacgt gtgatcagat atcgcggccg ctctagacac | 1380 |
| catgcccatg ggcagcctgc agcccctggc caccctgtac ctgctgggca tgctggtggc | 1440 |
| tagcgtgctg gccatggagt tcctgaagag gagcttcgcc cctctgaccg agaagcagtg | 1500 |
| gcaggagatc gacaacaggg ccaggagat cttcaagacc cagctgtacg gcaggaagtt | 1560 |
| cgtggacgtg gagggcccct acggctggga gtacgccgcc cacccctggg cgaggtgga | 1620 |

-continued

```
ggtgctgagc gacgagaacg aggtggtgaa gtggggcctg aggaagagcc tgccctgat   1680 cgagctgagg gccaccttca ccctggacct gtgggagctg acaacctgg agaggggcaa    1740 gcccaacgtg gacctgagca gcctggagga accgtgagg aaggtggccg agttcgagga    1800
cgaggtgatc ttcaggggct gcgagaagag cggcgtgaag ggcctgctga gcttcgagga   1860
gaggaagatc gagtgcggca gcaccccaa ggacctgctg gaggccatcg tgagggccct    1920
gagcatcttc agcaaggacg gcatcgaggg cccctacacc ctggtgatca acaccgacag   1980
gtggatcaac ttcctgaagg aggaggccgg ccactacccc ctggagaaga gggtggagga   2040
gtgcctgagg ggcggcaaga tcatcaccac ccccaggatc gaggacgccc tggtggtgag   2100 cgagagggc ggcgacttca agctgatcct gggccaggac ctgagcatcg gctacgagga    2160
cagggagaag gacgccgtga ggctgttcat caccgagacc ttcaccttcc aggtggtgaa   2220
ccccgaggcc ctgatcctgc tgaagtccgg aggcggatct ggcggaggcg aagccgccct   2280
gctggtgtgc cagtcactga ttcagagcct gattcatctg accggggagg accctggatt   2340
tttcaatgtg gaaatccctg agttcccatt ttaccccacc tgcaacgtct gtacagccga   2400
cgtgaacgtc accattaatt tcgatgtggg cgggaagaaa caccagctgg acctggattt   2460
tggccagctg accccacata caaaagccgt gtatcagccc agaggggctt tcggaggcag   2520
cgagaacgca caaatctgt ttctgctgga gctgctggga gcaggagaac tggctctgac    2580
catgaggtcc aagaaactgc ccatcaatgt gaccacagga gaggaacagc aggtcagtct   2640
ggaatcagtg gacgtctact tccaggatgt gtttggcacc atgtggtgcc accatgccga   2700
gatgcagaat cctgtgtacc tgatccccga aaccgtccct tatattaagt gggacaactg   2760
taatagcact aacattaccg cagtggtccg ggcacagggg ctggacgtga ccctgccact   2820
gtcactgccc acaagcgccc aggatagcaa cttctccgtg aaaaccgaga tgctgggaaa   2880
tgagatcgac attgaatgca tcatggagga tggagaaatt agccaggtgc tgcctggcga   2940
taacaagttt aatatcacct gttccggcta cgaatctcac gtcccaagtg ggggaatcct   3000
gacatctact agtcccgtgg ccactccaat tccggaacc ggctacgctt atagcctgag    3060 actgaccect aggccagtct cacgcttcct gggcaacaat agcattctgt acgtgtttta   3120
ttccggaaac ggaccaaagg cttctggagg ggactattgc atccagagta atattgtgtt   3180
ctcagacgag atcccagcca gccaggatat gcccactaac actaccgaca ttacctacgt   3240
gggcgataat gccacttatt ccgtgcctat ggtcacaagc gaagacgcta actccccaaa   3300
tgtgaccgtc acagcattct gggcctggcc caacaatact gagaccgatt ttaagtgcaa   3360
atggacactg acttcaggca ccctagcgg gtgtgaaaac atctctggcg ccttcgctag    3420
taatcgaacc tttgatatta cagtgtccgg cctggggact gccccaaaaa ccctgatcat   3480
tacccggaca gctactaacg caacaactac cacacaaa gtgatcttca gcaaagctcc     3540
cgagtccact accacatctc ctaccctgaa cactaccggg tttgccgacc caatacaac    3600 taccggactg cctagctcca cccatgtgcc aacaaacctg actgcaccag catccaccgg   3660
acctacagtg tctactgccg atgtcaccag tcccacacct gccggaacaa cttctggcgc   3720
tagtcccgtg accccatcac ccagcccttg ggacaatggg acagagagta aggccccga    3780 tatgacttct agtacctcac cagtcaccac accaaccccc aacgcaacaa gccctactcc   3840
agccgtgact accccacac ctaatgctac cagcccaaca cccgcagtga caactcctac    3900
cccaaacgcc acttccccaa ccctggggaa gacatcaccc actagcgccg tgaccacacc   3960
```

```
caccccctaat gctacctctc ctacactggg aaaaacttcc ccaacctctg cagtgactac    4020
cccaaccccc aacgccacaa gccccactct gggcaagacc agtcctacat cagctgtcac    4080
aactcctacc ccaaatgcaa ctgggccaac cgtgggagag acatccccc aggctaacgc     4140 aacaaatcac actctgggag gcaccagtcc cacacctgtg gtcacctcac agcccaagaa    4200
cgccacaagc gctgtgacca caggccagca taatatcaca tcaagctcca cttctagtat    4260
gagcctgcgc ccttcaagca acccagagac actgtcccca tctactagtg acaattcaac    4320
cagccacatg cctctgctga catctgcaca tccaactggg ggagaaaaca tcactcaggt    4380 caccccccgcc tccatttcta cccaccatgt gtccacatcc tctccagcac ccgacctgg    4440 aactaccagc caggcatccg gaccaggaaa tagttcaacc agcacaaagc ctggcgaggt    4500
gaacgtcaca aaagggactc cccctcagaa tgctacctca cctcaggcac caagcggcca    4560
gaaaacagct gtgcctactg tcacctccac aggcgggaag gcaaactcta caactggagg    4620
caaacacacc acagggcatg gagctcgcac tagcaccgaa ccaactaccg actacggggg    4680
agattccaca actccaaggc ccagatacaa tgccaccaca tatctgccac cctctaccag    4740
ctccaagctg cgacccagat ggacattcac tagtcctcca gtgactaccg cacaggctac    4800
agtgccagtc ccacctactt ctcagcctag attttctaac ctgagttgat gaggatccca    4860
tcatcatcat catcattagt ctggaagggc gaattgatcc agatctgctg tgccttctag    4920
ttgccagcca tctgttgttt gccctcccc cgtgccttcc ttgaccctgg aaggtgccac     4980
tcccactgtc ctttcctaat aaaatgagga aattgcatcg cattgtctga gtaggtgtca    5040
ttctattctg gggggtgggg tggggcagga cagcaagggg gaggattggg aagacaatag    5100
caggcatgct ggggatgcgg tgggctctat gggtacccag gtgctgaaga attgacccgg    5160
ttcctcctgg gccagaaaga agcaggcaca tccccttctc tgtgacacac cctgtccacg    5220
cccctggttc ttagttccag ccccactcat aggacactca tagctcagga gggctccgcc    5280
ttcaatccca cccgctaaag tacttggagc ggtctctccc tccctcatca gcccaccaaa    5340
ccaaacctag cctccaagag tgggaagaaa ttaaagcaag ataggctatt aagtgcagag    5400
ggagagaaaa tgcctccaac atgtgaggaa gtaatgagag aaatcataga atttaaggc    5460 catgatttaa ggccatcatg gccttaatct tccgcttcct cgctcactga ctcgctgcgc    5520
tcggtcgttc ggctgcggcg agcggtatca gctcactcaa aggcggtaat acggttatcc    5580
acagaatcag gggataacgc aggaaagaac atgtgagcaa aaggccagca aaaggccagg    5640
aaccgtaaaa aggccgcgtt gctggcgttt ttccataggc tccgccccc tgacgagcat    5700 cacaaaaatc gacgctcaag tcagaggtgg cgaaacccga caggactata agataccag    5760 gcgtttcccc ctggaagctc cctcgtgcgc tctcctgttc cgaccctgcc gcttaccgga    5820
tacctgtccg cctttctccc ttcgggaagc gtggcgcttt ctcatagctc acgctgtagg    5880
tatctcagtt cggtgtaggt cgttcgctcc aagctgggct gtgtgcacga accccccgtt    5940
cagcccgacc gctgcgcctt atccggtaac tatcgtcttg agtccaaccc ggtaagacac    6000
gacttatcgc cactggcagc agccactggt aacaggatta gcagagcgag gtatgtaggc    6060
ggtgctacag agttcttgaa gtggtggcct aactacggct acactagaag aacagtattt    6120
ggtatctgcg ctctgctgaa gccagttacc ttcggaaaaa gagttggtag ctcttgatcc    6180
ggcaaacaaa ccaccgctgg tagcggtggt ttttttgttt gcaagcagca gattacgcgc    6240
agaaaaaaag gatctcaaga agatcctttg atcttttcta cggggtctga cgctcagtgg    6300
aacgaaaact cacgttaagg gattttggtc atgagattat caaaaaggat cttcacctag    6360
```

```
atccttttaa attaaaaatg aagttttaaa tcaatctaaa gtatatatga gtaaacttgg    6420
tctgacagtt accaatgctt aatcagtgag gcacctatct cagcgatctg tctatttcgt    6480
tcatccatag ttgcctgact cggggggggg gggcgctgag gtctgcctcg tgaagaaggt    6540
gttgctgact cataccaggc ctgaatcgcc ccatcatcca gccagaaagt gagggagcca    6600
cggttgatga gagctttgtt gtaggtggac cagttggtga ttttgaactt ttgctttgcc    6660
acggaacggt ctgcgttgtc gggaagatgc gtgatctgat ccttcaactc agcaaaagtt    6720
cgatttattc aacaaagccg ccgtcccgtc aagtcagcgt aatgctctgc cagtgttaca    6780
accaattaac caattctgat tagaaaaact catcgagcat caaatgaaac tgcaatttat    6840
tcatatcagg attatcaata ccatatttt gaaaaagccg tttctgtaat gaaggagaaa     6900
actcaccgag gcagttccat aggatggcaa gatcctggta tcggtctgcg attccgactc    6960
gtccaacatc aatacaacct attaatttcc cctcgtcaaa aataaggtta tcaagtgaga    7020
aatcaccatg agtgacgact gaatccggtg agaatggcaa aagcttatgc atttctttcc    7080
agacttgttc aacaggccag ccattacgct cgtcatcaaa atcactcgca tcaaccaaac    7140
cgttattcat tcgtgattgc gcctgagcga cgaaatac gcgatcgctg ttaaaaggac      7200
aattacaaac aggaatcgaa tgcaaccggc gcaggaacac tgccagcgca tcaacaatat   7260
tttcacctga atcaggatat tcttctaata cctggaatgc tgttttcccg gggatcgcag    7320
tggtgagtaa ccatgcatca tcaggagtac ggataaaatg cttgatggtc ggaagaggca    7380
taaattccgt cagccagttt agtctgacca tctcatctgt aacatcattg gcaacgctac    7440
ctttgccatg tttcagaaac aactctggcg catcgggctt cccatacaat cgatagattg    7500
tcgcacctga ttgcccgaca ttatcgcgag cccatttata cccatataaa tcagcatcca    7560
tgttggaatt taatcgcggc ctcgagcaag acgtttcccg ttgaatatgg ctcataacac    7620
cccttgtatt actgtttatg taagcagaca gttttattgt tcatgatgat atatttttat    7680
cttgtgcaat gtaacatcag agattttgag acacaacgtg gctttccccc cccccccatt    7740
attgaagcat ttatcagggt tattgtctca tgagcggata catatttgaa tgtatttaga    7800
aaaataaaca aataggggtt ccgcgcacat ttccccgaaa agtgccacct gacgtctaag    7860
aaaccattat tatcatgaca ttaacctata aaaataggcg tatcacgagg cccttttcgtc   7920
```

<210> SEQ ID NO 118
<211> LENGTH: 5031
<212> TYPE: DNA
<213> ORGANISM: Artificial Sequence
<220> FEATURE:
<223> OTHER INFORMATION: Synthetic

<400> SEQUENCE: 118

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
gggaacttcc atagcccata tatggagttc cgcgttacat aacttacggg aatttccaaa    420
cctggctgac cgcccaacga ccccccgccca ttgacgtcaa taatgacgta tgttcccata     480
```

```
gtaacgccaa tagggaactt ccattgacgt caatgggtgg agtatttacg gtaaactgcc    540
cacttgggaa tttccaagtg tatcatatgc caagtacgcc ccctattgac gtcaatgacg    600
ggaacttcca taagcttgca ttatgcccag tacatgacct tatgggaatt tcctacttgg    660
cagtacatct acgtattagt catcgctatt accatggtga tgcggttttg gcagtacatc    720
aatgggcgtg gatagcggtt tgactcacgg gaacttccaa gtctccaccc cattgacgtc    780
aatgggagtt tgttttgact caccaaaatc aacgggattt cccaaaatgt cgtaacaact    840
ccgcccattg acgcaaatgg gcggtaggcg tgtacggtgg gaggtctat ataagcagag     900
ctcgtttagt gaaccgtcag atcgcctgga cgccatcc acgctgtttt gacctccata      960
gaagacaccg ggaccgatcc agcctccatc ggctcgcatc tctccttcac gcgcccgccg   1020
ccctacctga gccgccatc cacgccggtt gagtcgcgtt ctgccgcctc cgcctgtgg    1080
tgcctcctga actgcgtccg ccgtctaggt aagtttaaag ctcaggtcga gaccgggcct   1140
ttgtccggcg ctcccttgga gcctacctag actcagccgg ctctccacgc tttgcctgac   1200
cctgcttgct caactctagt taacggtgga gggcagtgta gtctgagcag tactcgttgc   1260
tgccgcgcgc gccaccagac ataatagctg acagactaac agactgttcc tttccatggg   1320
tcttttctgc agtcaccgtc gtcgacacgt gtgatcagat atcgcggccg ctctagacac   1380
catgcccatg gcagcctgc agcccctggc caccctgtac ctgctgggca tgctggtggc   1440
tagcgtgctg gcctccggag agagccaggt gaggcagaac ttcaagcccg agatggagga   1500
gaagctgaac gagcagatga acctggagct gtacagcagc ctgctgtacc agcagatgag   1560
cgcctggtgc agctaccaca ccttcgaggg cgccgccgcc ttcctgagga ggcacgccca   1620
ggaggagatg acccacatgc agaggctgtt cgactacctg accgacaccg gcaacctgcc   1680
caggatcaac accgtggaga gcccttcgc cgagtacagc agcctggacg agctgttcca   1740
ggagacctac aagcacgagc agctgatcac ccagaagatc aacgagctgg cccacgccgc   1800
catgaccaac caggactacc ccaccttcaa cttcctgcag tggtacgtga gcagcagca   1860
cgaggaggag aagctgttca gagcatcat cgacaagctg agcctggccg gcaagagcgg   1920
cgagggcctg tacttcatcg acaaggagct gagcaccctg gacggatcct agcatcatca   1980
tcatcattag tctggaaggg cgaattgatc cagatctgct gtgccttcta gttgccagcc   2040
atctgttgtt tgcccctccc ccgtgccttc cttgaccctg gaaggtgcca ctcccactgt   2100
cctttcctaa taaaatgagg aaattgcatc gcattgtctg agtaggtgtc attctattct   2160
ggggggtggg gtggggcagg acagcaaggg ggaggattgg gaagacaata gcaggcatgc   2220
tggggatgcg gtgggctcta tgggtaccca ggtgctgaag aattgacccg gttcctcctg   2280
ggccagaaag aagcaggcac atccccttct ctgtgacaca ccctgtccac gcccctggtt   2340
cttagttcca gccccactca taggacactc atagctcagg agggctccgc cttcaatccc   2400
acccgctaaa gtacttggag cggtctctcc ctccctcatc agcccaccaa accaaaccta   2460
gcctccaaga gtgggaagaa attaaagcaa gataggctat taagtgcaga gggagagaaa   2520
atgcctccaa catgtgagga agtaatgaga gaaatcatag aattttaagg ccatgattta   2580
aggccatcat ggccttaatc ttccgcttcc tcgctcactg actcgctgcg ctcggtcgtt   2640
cggctgcggc gagcggtatc agctcactca aaggcggtaa tacggttatc cacagaatca   2700
ggggataacg caggaaagaa catgtgagca aaaggccagc aaaaggccag gaaccgtaaa   2760
aaggccgcgt tgctggcgtt tttccatagg ctccgccccc ctgacgagca tcacaaaaat   2820
cgacgctcaa gtcagaggtg gcgaaacccg acaggactat aaagatacca ggcgtttccc   2880
```

```
cctggaagct ccctcgtgcg ctctcctgtt ccgaccctgc cgcttaccgg atacctgtcc    2940
gcctttctcc cttcgggaag cgtggcgctt tctcatagct cacgctgtag gtatctcagt    3000
tcggtgtagg tcgttcgctc caagctgggc tgtgtgcacg aacccccgt tcagcccgac    3060 cgctgcgcct tatccggtaa ctatcgtctt gagtccaacc cggtaagaca cgacttatcg    3120
ccactggcag cagccactgg taacaggatt agcagagcga ggtatgtagg cggtgctaca    3180
gagttcttga agtggtggcc taactacggc tacactagaa gaacagtatt tggtatctgc    3240
gctctgctga agccagttac cttcggaaaa agagttggta gctcttgatc cggcaaacaa    3300
accaccgctg gtagcggtgg tttttttgtt tgcaagcagc agattacgcg cagaaaaaaa    3360
ggatctcaag aagatccttt gatcttttct acggggtctg acgctcagtg gaacgaaaac    3420
tcacgttaag ggattttggt catgagatta tcaaaaagga tcttcaccta gatccttta    3480 aattaaaaat gaagttttaa atcaatctaa agtatatatg agtaaacttg gtctgacagt    3540
taccaatgct taatcagtga ggcacctatc tcagcgatct gtctatttcg ttcatccata    3600
gttgcctgac tcggggggg ggggcgctga ggtctgcctc gtgaagaagg tgttgctgac    3660
tcataccagg cctgaatcgc cccatcatcc agccagaaag tgagggagcc acggttgatg    3720
agagctttgt tgtaggtgga ccagttggtg attttgaact tttgctttgc cacggaacgg    3780
tctgcgttgt cgggaagatg cgtgatctga tccttcaact cagcaaaagt tcgatttatt    3840
caacaaagcc gccgtcccgt caagtcagcg taatgctctg ccagtgttac aaccaattaa    3900
ccaattctga ttagaaaaac tcatcgagca tcaaatgaaa ctgcaattta ttcatatcag    3960
gattatcaat accatatttt tgaaaagcc gtttctgtaa tgaaggagaa aactcaccga    4020
ggcagttcca taggatggca agatcctggt atcggtctgc gattccgact cgtccaacat    4080
caatacaacc tattaatttc ccctcgtcaa aaataaggtt atcaagtgag aaatcaccat    4140
gagtgacgac tgaatccggt gagaatggca aaagcttatg catttctttc cagacttgtt    4200
caacaggcca gccattacgc tcgtcatcaa aatcactcgc atcaaccaaa ccgttattca    4260
ttcgtgattg cgcctgagcg agacgaaata cgcgatcgct gttaaaagga caattacaaa    4320
caggaatcga atgcaaccgg cgcaggaaca ctgccagcgc atcaacaata ttttcacctg    4380
aatcaggata ttcttctaat acctggaatg ctgttttccc ggggatcgca gtggtgagta    4440
accatgcatc atcaggagta cggataaaat gcttgatggt cggaagaggc ataaattccg    4500
tcagccagtt tagtctgacc atctcatctg taacatcatt ggcaacgcta cctttgccat    4560
gtttcagaaa caactctggc gcatcgggct tcccatacaa tcgatagatt gtcgcacctg    4620
attgcccgac attatcgcga gcccatttat acccatataa atcagcatcc atgttggaat    4680
ttaatcgcgg cctcgagcaa gacgtttccc gttgaatatg gctcataaca cccttgtat    4740 tactgtttat gtaagcagac agttttattg ttcatgatga tatattttta tcttgtgcaa    4800
tgtaacatca gagattttga gacacaacgt ggctttcccc cccccccat tattgaagca    4860 tttatcaggg ttattgtctc atgagcggat acatatttga atgtatttag aaaaataaac    4920
aaataggggt tccgcgcaca tttccccgaa aagtgccacc tgacgtctaa gaaaccatta    4980
ttatcatgac attaacctat aaaaataggc gtatcacgag gccctttcgt c            5031
```

<210> SEQ ID NO 119
<211> LENGTH: 5046
<212> TYPE: DNA
<213> ORGANISM: Artificial Sequence
<220> FEATURE:

-continued

<223> OTHER INFORMATION: Synthetic

<400> SEQUENCE: 119

```
tcgcgcgttt cggtgatgac ggtgaaaacc tctgacacat gcagctcccg gagacggtca    60
cagcttgtct gtaagcggat gccgggagca gacaagcccg tcaggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
gggaacttcc atagcccata tatggagttc cgcgttacat aacttacggg aatttccaaa    420
cctggctgac cgcccaacga ccccgccca ttgacgtcaa taatgacgta tgttcccata    480
gtaacgccaa tagggaactt ccattgacgt caatgggtgg agtatttacg gtaaactgcc    540
cacttgggaa tttccaagtg tatcatatgc caagtacgcc ccctattgac gtcaatgacg    600
ggaacttcca taagcttgca ttatgcccag tacatgacct tatgggaatt tcctacttgg    660
cagtacatct acgtattagt catcgctatt accatggtga tgcggttttg gcagtacatc    720
aatgggcgtg gatagcggtt tgactcacgg gaacttccaa gtctccaccc cattgacgtc    780
aatgggagtt tgttttgact caccaaaatc aacgggaatt cccaaaatgt cgtaacaact    840
ccgccccatt gacgcaaatg ggcggtaggc gtgtacggtg gaggtctat ataagcagag    900
ctcgtttagt gaaccgtcag atcgcctgga gacgccatcc acgctgtttt gacctccata    960
gaagacaccg ggaccgatcc agcctccatc ggctcgcatc tctccttcac gcgcccgccg    1020
ccctacctga ggccgccatc cacgccggtt gagtcgcgtt ctgccgcctc ccgcctgtgg    1080
tgcctcctga actgcgtccg ccgtctaggt aagtttaaag ctcaggtcga gaccgggcct    1140
ttgtccggcg ctcccttgga gcctacctag actcagccgg ctctccacgc tttgcctgac    1200
cctgcttgct caactctagt taacggtgga gggcagtgta gtctgagcag tactcgttgc    1260
tgccgcgcgc gccaccagac ataatagctg acagactaac agactgttcc tttccatggg    1320
tcttttctgc agtcaccgtc gtcgacacgt gtgatcagat atcgcggccg ctctagacac    1380
catgcccatg ggcagcctgc agcccctggc caccctgtac ctgctgggca tgctggtggc    1440
tagcgtgctg gcctccggag agagccaggt gaggcagcag ttcagcaagg acatcgagaa    1500
gctgctgaac gagcaggtga caaggagat gcagagcagc aacctgtaca tgagcatgag    1560
cagctggtgc tacacccaca gcctggacgg cgccggcctg ttcctgttcg accacgccgc    1620
cgaggagtac gagcacgcca agaagctgat catcttcctg aacgagaaca cgtgcccgt    1680
gcagctgacc agcatcagcg cccccgagca caagttcgag ggcctgaccc agatcttcca    1740
gaaggcctac gagcacgagc agcacatcag cgagagcatc aacaacatcg tggaccacgc    1800
catcaagagc aaggaccacg ccaccttcaa cttcctgcag tggtacgtgg ccgagcagca    1860
cgaggaggag gtgctgttca aggacatcct ggacaagatc gagctgatcg caacgagaa    1920
ccacggcctg tacctggccg accagtacgt gaagggcatc gccaagagca ggaagagcgg    1980
atcctagcat catcatcatc attagtctgg aagggcgaat tgatccagat ctgctgtgcc    2040
ttctagttgc cagccatctg ttgtttgccc ctccccgtg ccttccttga ccctggaagg    2100
tgccactccc actgtcctt cctaataaaa tgaggaaatt gcatcgcatt gtctgagtag    2160
gtgtcattct attctggggg gtggggtggg gcaggacagc aagggggagg attgggaaga    2220
caatagcagg catgctgggg atgcggtggg ctctatgggt acccaggtgc tgaagaattg    2280
```

```
acccggttcc tcctgggcca gaaagaagca ggcacatccc cttctctgtg acacaccctg   2340
tccacgcccc tggttcttag ttccagcccc actcatagga cactcatagc tcaggagggc   2400
tccgccttca atcccacccg ctaaagtact tggagcggtc tctccctccc tcatcagccc   2460
accaaaccaa acctagcctc aagagtgggg aagaaattaa agcaagatag gctattaagt   2520
gcagagggag agaaaatgcc tccaacatgt gaggaagtaa tgagagaaat catagaattt   2580
taaggccatg atttaaggcc atcatggcct taatcttccg cttcctcgct cactgactcg   2640
ctgcgctcgg tcgttcggct gcggcgagcg gtatcagctc actcaaaggc ggtaatacgg   2700
ttatccacag aatcagggga taacgcagga agaacatgt  gagcaaaagg ccagcaaaag   2760
gccaggaacc gtaaaaaggc cgcgttgctg gcgttttcc  ataggctccg cccccctgac   2820
gagcatcaca aaaatcgacg ctcaagtcag aggtggcgaa acccgacagg actataaaga   2880
taccaggcgt ttccccctgg aagctccctc gtgcgctctc ctgttccgac cctgccgctt   2940
accggatacc tgtccgcctt tctcccttcg ggaagcgtgg cgctttctca tagctcacgc   3000
tgtaggtatc tcagttcggt gtaggtcgtt cgctccaagc tgggctgtgt gcacgaaccc   3060
cccgttcagc ccgaccgctg cgccttatcc ggtaactatc gtcttgagtc caacccggta   3120
agacacgact tatcgccact ggcagcagcc actggtaaca ggattagcag agcgaggtat   3180
gtaggcggtg ctacagagtt cttgaagtgg tggcctaact acggctacac tagaagaaca   3240
gtatttggta tctgcgctct gctgaagcca gttaccttcg gaaaaagagt tggtagctct   3300
tgatccggca aacaaaccac cgctggtagc ggtggttttt ttgtttgcaa gcagcagatt   3360
acgcgcagaa aaaaggatc  tcaagaagat cctttgatct tttctacggg gtctgacgct   3420
cagtggaacg aaaactcacg ttaagggatt ttggtcatga gattatcaaa aaggatcttc   3480
acctagatcc ttttaaatta aaaatgaagt tttaaatcaa tctaaagtat atatgagtaa   3540
acttggtctg acagttacca atgcttaatc agtgaggcac ctatctcagc gatctgtcta   3600
tttcgttcat ccatagttgc ctgactcggg ggggggggc  gctgaggtct gcctcgtgaa   3660
gaaggtgttg ctgactcata ccaggcctga atcgccccat catccagcca gaaagtgagg   3720
gagccacggt tgatgagagc tttgttgtag gtggaccagt tggtgatttt gaacttttgc   3780
tttgccacgg aacggtctgc gttgtcggga agatgcgtga tctgatcctt caactcagca   3840
aaagttcgat ttattcaaca aagccgccgt cccgtcaagt cagcgtaatg ctctgccagt   3900
gttacaacca attaaccaat tctgattaga aaaactcatc gagcatcaaa tgaaactgca   3960
atttattcat atcaggatta tcaataccat attttgaaa  aagccgtttc tgtaatgaag   4020
gagaaaactc accgaggcag ttccatagga tggcaagatc ctggtatcgg tctgcgattc   4080
cgactcgtcc aacatcaata caacctatta atttcccctc gtcaaaaata aggttatcaa   4140
gtgagaaatc accatgagtg acgactgaat ccggtgagaa tggcaaaagc ttatgcattt   4200
ctttccagac ttgttcaaca ggccagccat tacgctcgtc atcaaaatca ctcgcatcaa   4260
ccaaaccgtt attcattcgt gattgcgcct gagcgagacg aaatacgcga tcgctgttaa   4320
aaggacaatt acaaacagga atcgaatgca accggcgcag gaacactgcc agcgcatcaa   4380
caatattttc acctgaatca ggatattctt ctaatacctg gaatgctgtt ttcccgggga   4440
tcgcagtggt gagtaaccat gcatcatcag gagtacggat aaaatgcttg atggtcggaa   4500
gaggcataaa ttccgtcagc cagtttagtc tgaccatctc atctgtaaca tcattggcaa   4560 cgctacccttt gccatgtttc agaaacaact ctggcgcatc gggcttccca tacaatcgat   4620
```

```
agattgtcgc acctgattgc ccgacattat cgcgagccca tttatacccca tataaatcag    4680 catccatgtt ggaatttaat cgcggcctcg agcaagacgt ttcccgttga atatggctca    4740
taacacccct tgtattactg tttatgtaag cagacagttt tattgttcat gatgatatat    4800
ttttatcttg tgcaatgtaa catcagagat tttgagacac aacgtggctt tccccccccc    4860
cccattattg aagcatttat cagggttatt gtctcatgag cggatacata tttgaatgta    4920
tttagaaaaa taaacaaata ggggttccgc gcacatttcc ccgaaaagtg ccacctgacg    4980
tctaagaaac cattattatc atgacattaa cctataaaaa taggcgtatc acgaggccct    5040
ttcgtc                                                                5046
```

<210> SEQ ID NO 120
<211> LENGTH: 5322
<212> TYPE: DNA
<213> ORGANISM: Artificial Sequence
<220> FEATURE:
<223> OTHER INFORMATION: Synthetic

<400> SEQUENCE: 120

```
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg     120 ttggcgggtg tcgggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
gggaacttcc atagcccata tatggagttc cgcgttacat aacttacggg aatttccaaa     420
cctggctgac cgcccaacga cccccgccca ttgacgtcaa taatgacgta tgttcccata     480
gtaacgccaa tagggaactt ccattgacgt caatgggtgg agtatttacg gtaaactgcc     540
cacttgggaa tttccaagtg tatcatatgc caagtacgcc ccctattgac gtcaatgacg     600
ggaacttcca taagcttgca ttatgcccag tacatgacct tatgggaatt tcctacttgg     660
cagtacatct acgtattagt catcgctatt accatggtga tgcggttttg gcagtacatc     720
aatgggcgtg atagcggttt gactcacgg gaacttccaa gtctccaccc cattgacgtc     780
aatgggagtt gtttttgact caccaaaatc aacgggaatt cccaaaatgt cgtaacaact     840
ccgccccatt gacgcaaatg ggcggtaggc gtgtacggtg ggaggtctat ataagcagag     900
ctcgtttagt gaaccgtcag atcgcctgga gacgccatcc acgctgtttt gacctccata     960
gaagacaccg ggaccgatcc agcctccatc ggctcgcatc tctccttcac gcgcccgccg    1020
ccctacctga ggccgccatc cacgccggtt gagtcgcgtt ctgccgcctc ccgcctgtgg    1080
tgcctcctga actgcgtccg ccgtctaggt aagtttaaag ctcaggtcga accgggcct    1140 ttgtccggcg ctcccttgga gcctacctag actcagccgg ctctccacgc tttgcctgac    1200
cctgcttgct caactctagt taacggtgga gggcagtgta gtctgagcag tactcgttgc    1260
tgccgcgcgc gccaccagac ataatagctg acagactaac agactgttcc tttccatggg    1320
tcttttctgc agtcaccgtc gtcgacacgt gtgatcagat atcgcggccg ctctagacac    1380
catgcccatg ggcagcctgc agcccctggc caccctgtac ctgctgggca tgctggtggc    1440
tagcgtgctg gccatggagt tcctgaagag gagcttcgcc cctctgaccg agaagcagtg    1500
gcaggagatc gacaacaggg ccaggagatt ttcaagacc cagctgtacg gcaggaagtt    1560
cgtggacgtg gagggcccct acggctggga gtacgccgcc cacccctgg gcgaggtgga    1620
```

```
ggtgctgagc gacgagaacg aggtggtgaa gtggggcctg aggaagagcc tgccctgat   1680
cgagctgagg gccaccttca ccctggacct gtgggagctg acaacctgg agaggggcaa   1740
gcccaacgtg gacctgagca gcctggagga gaccgtgagg aaggtggccg agttcgagga   1800
cgaggtgatc ttcagggggct gcgagaagag cggcgtgaag ggcctgctga gcttcgagga   1860
gaggaagatc gagtgcggca gcacccccaa ggacctgctg gaggccatcg tgagggccct   1920
gagcatcttc agcaaggacg gcatcgaggg cccctacacc ctggtgatca acaccgacag   1980
gtggatcaac ttcctgaagg aggaggccgg ccactacccc ctggagaaga gggtggagga   2040
gtgcctgagg ggcggcaaga tcatcaccac ccccaggatc gaggacgccc tggtggtgag   2100
cgagaggggc ggcgacttca agctgatcct gggccaggac ctgagcatcg gctacgagga   2160
cagggagaag gacgccgtga ggctgttcat caccgagacc ttcaccttcc aggtggtgaa   2220
ccccgaggcc ctgatcctgc tgaagtccgg aggcggatcc catcatcatc atcatcatta   2280
gtctggaagg gcgaattgat ccagatctgc tgtgccttct agttgccagc catctgttgt   2340
ttgcccctcc ccgtgccttc cttgaccct ggaaggtgcc actcccactg tcctttccta   2400
ataaaatgag gaaattgcat cgcattgtct gagtaggtgt cattctattc tggggggtgg   2460
ggtggggcag gacagcaagg gggaggattg ggaagacaat agcaggcatg ctggggatgc   2520
ggtgggctct atgggtaccc aggtgctgaa gaattgaccc ggttcctcct gggccagaaa   2580
gaagcaggca catccccttc tctgtgacac accctgtcca cgccctggt tcttagttcc   2640
agccccactc ataggacact catagctcag gagggctccg ccttcaatcc cacccgctaa   2700
agtacttgga gcggtctctc cctccctcat cagcccacca aaccaaacct agcctccaag   2760
agtgggaaga aattaaagca agataggcta ttaagtgcag agggagagaa aatgcctcca   2820
acatgtgagg aagtaatgag agaaatcata gaattttaag gccatgattt aaggccatca   2880
tggccttaat cttccgcttc ctcgctcact gactcgctgc gctcggtcgt tcggctgcgg   2940
cgagcggtat cagctcactc aaaggcggta atacggttat ccacagaatc aggggataac   3000
gcaggaaaga acatgtgagc aaaaggccag caaaaggcca ggaaccgtaa aaaggccgcg   3060
ttgctggcgt ttttccatag gctccgcccc cctgacgagc atcacaaaaa tcgacgctca   3120
agtcagaggt ggcgaaaccc gacaggacta taaagatacc aggcgtttcc ccctggaagc   3180
tccctcgtgc gctctcctgt tccgaccctg ccgcttaccg gatacctgtc cgcctttctc   3240
ccttcgggaa gcgtggcgct ttctcatagc tcacgctgta ggtatctcag ttcggtgtag   3300
gtcgttcgct ccaagctggg ctgtgtgcac gaaccccccg ttcagcccga ccgctgcgcc   3360
ttatccggta actatcgtct tgagtccaac ccggtaagac acgacttatc gccactggca   3420
gcagccactg gtaacaggat tagcagagcg aggtatgtag cggtgctac agagttcttg   3480
aagtggtggc ctaactacgg ctacactaga agaacagtat ttggtatctg cgctctgctg   3540
aagccagtta ccttcggaaa aagagttggt agctcttgat ccggcaaaca aaccaccgct   3600
ggtagcggtg gttttttgt ttgcaagcag cagattacgc gcagaaaaaa aggatctcaa   3660
gaagatcctt tgatctttc tacggggtct gacgctcagt ggaacgaaaa ctcacgttaa   3720
gggattttgg tcatgagatt atcaaaaagg atcttcacct agatcctttt aaattaaaaa   3780
tgaagtttta aatcaatcta agtatatat gagtaaactt ggtctgacag ttaccaatgc   3840
ttaatcagtg aggcacctat ctcagcgatc tgtctatttc gttcatccat agttgcctga   3900
ctcgggggggg ggggcgctg aggtctgcct cgtgaagaag gtgttgctga ctcataccag   3960
```

| | |
|---|---|
| gcctgaatcg cccatcatc cagccagaaa gtgagggagc cacggttgat gagagctttg | 4020 |
| ttgtaggtgg accagttggt gattttgaac ttttgctttg ccacggaacg gtctgcgttg | 4080 |
| tcgggaagat gcgtgatctg atccttcaac tcagcaaaag ttcgatttat tcaacaaagc | 4140 |
| cgccgtcccg tcaagtcagc gtaatgctct gccagtgtta caaccaatta accaattctg | 4200 |
| attagaaaaa ctcatcgagc atcaaatgaa actgcaattt attcatatca ggattatcaa | 4260 |
| taccatattt ttgaaaaagc cgtttctgta atgaaggaga aaactcaccg aggcagttcc | 4320 |
| ataggatggc aagatcctgg tatcggtctg cgattccgac tcgtccaaca tcaatacaac | 4380 |
| ctattaattt ccctcgtca aaaataaggt tatcaagtga aaatcacca tgagtgacga | 4440 |
| ctgaatccgg tgagaatggc aaaagcttat gcatttcttt ccagacttgt tcaacaggcc | 4500 |
| agccattacg ctcgtcatca aaatcactcg catcaaccaa accgttattc attcgtgatt | 4560 |
| gcgcctgagc gagacgaaat acgcgatcgc tgttaaaagg acaattacaa acaggaatcg | 4620 |
| aatgcaaccg cgcaggaac actgccagca tcaacaat attttcacct gaatcaggat | 4680 |
| attcttctaa tacctggaat gctgttttcc cggggatcgc agtggtgagt aaccatgcat | 4740 |
| catcaggagt acgataaaa tgcttgatgg tcggaagagg cataaattcc gtcagccagt | 4800 |
| ttagtctgac catctcatct gtaacatcat ggcaacgct acctttgcca tgtttcagaa | 4860 |
| acaactctgg cgcatcgggc ttcccataca atcgatagat tgtcgcacct gattgcccga | 4920 |
| cattatcgcg agcccattta tacccatata atcagcatc catgttggaa tttaatcgcg | 4980 |
| gcctcgagca agacgtttcc cgttgaatat ggctcataac accccttgta ttactgttta | 5040 |
| tgtaagcaga cagttttatt gttcatgatg atatattttt atcttgtgca atgtaacatc | 5100 |
| agagattttg agacacaacg tggctttccc ccccccccca ttattgaagc atttatcagg | 5160 |
| gttattgtct catgagcgga tacatatttg aatgtattta gaaaataaa caaatagggg | 5220 |
| ttccgcgcac atttccccga aaagtgccac ctgacgtcta agaaaccatt attatcatga | 5280 |
| cattaaccta taaaaatagg cgtatcacga ggccctttcg tc | 5322 |

<210> SEQ ID NO 121
<211> LENGTH: 7135
<212> TYPE: DNA
<213> ORGANISM: Artificial Sequence
<220> FEATURE:
<223> OTHER INFORMATION: Synthetic

<400> SEQUENCE: 121

| | |
|---|---|
| tcgcgcgttt cggtgatgac ggtgaaaacc tctgacacat gcagctcccg gagacggtca | 60 |
| cagcttgtct gtaagcggat gccggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca acgacccccg cccattgacg tcaataatga cgtatgttcc | 480 |
| catagtaacg ccaatagga ctttccattg acgtcaatgg gtggagtatt tacggtaaac | 540 |
| tgcccacttg gcagtacatc aagtgtatca tatgccaagt acgccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |

```
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgctctagac   1380
accatggaag ccgccctgct ggtgtgccag tacactattc agagcctgat tcatctgacc   1440
ggggaggacc ctggattttt caatgtggaa atccctgagt tcccatttta ccccacctgc   1500
aacgtctgta cagccgacgt gaacgtcacc attaatttcg atgtgggcgg gaagaaacac   1560
cagctggacc tggattttgg ccagctgacc ccacatacaa aagccgtgta tcagcccaga   1620
ggggctttcg gaggcagcga gaacgcaaca aatctgtttc tgctggagct gctgggagca   1680
ggagaactgg ctctgaccat gaggtccaag aaactgccca tcaatgtgac cacaggagag   1740
gaacagcagg tcagtctgga atcagtggac gtctacttcc aggatgtgtt tggcaccatg   1800
tggtgccacc atgccgagat gcagaatcct gtgtacctga tccccgaaac cgtcccttat   1860
attaagtggg acaactgtaa tagcactaac attaccgcag tggtccgggc acaggggctg   1920
gacgtgaccc tgccactgtc actgcccaca agcgcccagg atagcaactt ctccgtgaaa   1980
accgagatgc tgggaaatga gatcgacatt gaatgcatca tggaggatgg agaaattagc   2040
caggtgctgc ctggcgataa caagtttaat atcacctgtt ccggctacga atctcacgtc   2100
ccaagtgggg gaatcctgac atctactagt cccgtggcca ctccaattcc cggaaccggc   2160
tacgcttata gcctgagact gacccctagg ccagtctcac gcttcctggg caacaatagc   2220
attctgtacg tgttttattc cggaaacgga ccaaaggctt ctggagggga ctattgcatc   2280
cagagtaata ttgtgttctc agacgagatc ccagccagcc aggatatgcc cactaacact   2340
accgacatta cctacgtggg cgataatgcc acttattccg tgcctatggt cacaagcgaa   2400
gacgctaact ccccaaatgt gaccgtcaca gcattctggg cctggcccaa caatactgag   2460
accgatttta gtgcaaatg gacactgact tcaggcaccc ctagcgggtg tgaaaacatc   2520
tctggcgcct tcgctagtaa tcgaaccttt gatattacag tgtccggcct ggggactgcc   2580
ccaaaaaccc tgatcattac ccggacagct actaacgcaa caactaccac acacaaagtg   2640
atcttcagca aagctcccga gtccactacc acatctccta ccctgaacac taccgggttt   2700
gccgacccca atacaactac cggactgcct agctccaccc atgtgccaac aaacctgact   2760
gcaccagcat ccaccggacc tacagtgtct actgccgatg tcaccagtcc cacacctgcc   2820
ggaacaactt ctgcgctag tcccgtgacc ccatcaccca gccttggga caatgggaca   2880
gagagtaagg cccctgatat gacttctagt acctcaccag tcaccacacc aaccccaac   2940
gcaacaagcc ctactccagc cgtgactacc cccacaccta tgctaccag cccaacaccc   3000
gcagtgacaa ctcctacccc aaacgccact tccccaaccc tggggaagac atcacccact   3060
```

```
agcgccgtga ccacacccac ccctaatgct acctctccta cactgggaaa aacttcccca    3120
acctctgcag tgactacccc aaccccccaac gccacaagcc ccactctggg caagaccagt    3180
cctacatcag ctgtcacaac tcctacccca aatgcaactg ggccaaccgt gggagagaca    3240
tccccccagg ctaacgcaac aaatcacact ctgggaggca ccagtcccac acctgtggtc    3300
acctcacagc ccaagaacgc cacaagcgct gtgaccacag gccagcataa tatcacatca    3360
agctccactt ctagtatgag cctgcgccct tcaagcaacc cagagacact gtccccatct    3420
actagtgaca attcaaccag ccacatgcct ctgctgacat ctgcacatcc aactggggga    3480
gaaaacatca ctcaggtcac ccccgcctcc atttctaccc accatgtgtc cacatcctct    3540
ccagcacccc gacctggaac taccagccag gcatccggac caggaaatag ttcaaccagc    3600
acaaagcctg gcgaggtgaa cgtcacaaaa gggactcccc ctcagaatgc tacctcacct    3660
caggcaccaa gcggccagaa aacagctgtg cctactgtca cctccacagg cgggaaggca    3720
aactctacaa ctggaggcaa acacaccaca gggcatggag ctcgcactag caccgaacca    3780
actaccgact acgggggaga ttccacaact ccaaggccca gatacaatgc caccacatat    3840
ctgccaccct ctaccagctc caagctgcga cccagatgga cattcactag tcctccagtg    3900
actaccgcac aggctacagt gccagtccca cctacttctc agcctagatt ttctaacctg    3960
agtatgctgg tgctgcagtg ggcaagcctg gcagtcctga ccctgctgct gctgctggtc    4020
atggctgact gtgcattccg gagaaacctg tccacttcac acacttacac cacccccccct    4080 tacgatgacg cagagactta tgtctgatag gatccagatc tgctgtgcct tctagttgcc    4140
agccatctgt tgtttgcccc tccccgtgc cttccttgac cctggaaggt gccactccca    4200 ctgtccttc ctaataaaat gaggaaattg catcgcattg tctgagtagg tgtcattcta    4260
ttctgggggg tggggtgggg caggacagca aggggggagga ttgggaagac aatagcaggc    4320
atgctgggga tgcggtgggc tctatgggta cccaggtgct gaagaattga cccggttcct    4380
cctgggccag aaagaagcag gcacatcccc ttctctgtga cacaccctgt ccacgcccct    4440
ggttcttagt tccagcccca ctcataggac actcatagct caggagggct ccgccttcaa    4500
tcccacccgc taaagtactt ggagcggtct ctccctccct catcagccca ccaaaccaaa    4560
cctagcctcc aagagtggga agaaattaaa gcaagatagg ctattaagtg cagagggaga    4620
gaaaatgcct ccaacatgtg aggaagtaat gagagaaatc atagaatttt aaggccatga    4680
tttaaggcca tcatggcctt aatcttccgc ttcctcgctc actgactcgc tgcgctcggt    4740
cgttcggctg cggcgagcgg tatcagctca ctcaaaggcg gtaatacggt tatccacaga    4800 atcagggat aacgcaggaa agaacatgtg agcaaaaggc cagcaaaagg ccaggaaccg    4860
taaaaaggcc gcgttgctgg cgttttttcca taggctccgc cccctgacg agcatcacaa    4920 aaatcgacgc tcaagtcaga ggtggcgaaa cccgacagga ctataaagat accaggcgtt    4980
tccccctgga agctccctcg tgcgctctcc tgttccgacc ctgccgctta ccggatacct    5040
gtccgccttt ctcccttcgg gaagcgtggc gctttctcat agctcacgct gtaggtatct    5100
cagttcggtg taggtcgttc gctccaagct gggctgtgtg cacgaacccc ccgttcagcc    5160
cgaccgctgc gccttatccg gtaactatcg tcttgagtcc aacccggtaa gacacgactt    5220
atcgccactg gcagcagcca ctggtaacag gattagcaga gcgaggtatg taggcggtgc    5280
tacagagttc ttgaagtggt ggcctaacta cggctacact agaagaacag tatttggtat    5340
ctgcgctctg ctgaagccag ttaccttcgg aaaaagagtt ggtagctctt gatccggcaa    5400
acaaaccacc gctggtagcg gtggtttttt tgtttgcaag cagcagatta cgcgcagaaa    5460
```

```
aaaaggatct caagaagatc ctttgatctt ttctacgggg tctgacgctc agtggaacga    5520
aaactcacgt taagggattt tggtcatgag attatcaaaa aggatcttca cctagatcct    5580
tttaaattaa aaatgaagtt ttaaatcaat ctaaagtata tatgagtaaa cttggtctga    5640
cagttaccaa tgcttaatca gtgaggcacc tatctcagcg atctgtctat ttcgttcatc    5700
catagttgcc tgactcgggg ggggggggcg ctgaggtctg cctcgtgaag aaggtgttgc    5760
tgactcatac caggcctgaa tcgccccatc atccagccag aaagtgaggg agccacggtt    5820
gatgagagct tgttgtaggt ggaccagttt ggtgattttg aacttttgct tgccacggag    5880
acggtctgcg ttgtcgggaa gatgcgtgat ctgatccttc aactcagcaa aagttcgatt    5940
tattcaacaa agccgccgtc ccgtcaagtc agcgtaatgc tctgccagtg ttacaaccaa    6000
ttaaccaatt ctgattagaa aaactcatcg agcatcaaat gaaactgcaa tttattcata    6060
tcaggattat caataccata tttttgaaaa agccgtttct gtaatgaagg agaaaactca    6120
ccgaggcagt tccataggat ggcaagatcc tggtatcggt ctgcgattcc gactcgtcca    6180
acatcaatac aacctattaa tttcccctcg tcaaaaataa ggttatcaag tgagaaatca    6240
ccatgagtga cgactgaatc cggtgagaat ggcaaaagct tatgcatttc tttccagact    6300
tgttcaacag gccagccatt acgctcgtca tcaaaatcac tcgcatcaac caaaccgtta    6360
ttcattcgtg attgcgcctg agcgagacga atacgcgat cgctgttaaa aggacaatta    6420
caaacaggaa tcgaatgcaa ccggcgcagg aacactgcca gcgcatcaac aatattttca    6480
cctgaatcag gatattcttc taatacctgg aatgctgttt tcccggggat cgcagtggtg    6540
agtaaccatg catcatcagg agtacggata aaatgcttga tggtcggaag aggcataaat    6600
tccgtcagcc agtttagtct gaccatctca tctgtaacat cattggcaac gctacctttg    6660
ccatgtttca gaaacaactc tggcgcatcg gcttcccat acaatcgata gattgtcgca    6720
cctgattgcc cgacattatc gcgagcccat ttatacccat ataaatcagc atccatgttg    6780
gaatttaatc gcggcctcga gcaagacgtt tcccgttgaa tatggctcat aacaccccnt    6840
gtattactgt ttatgtaagc agacagtttt attgttcatg atgatatatt tttatcttgt    6900
gcaatgtaac atcagagatt tgagacaca acgtggcttt cccccccccc ccattattga    6960
agcatttatc agggttattg tctcatgagc ggatacatat ttgaatgtat ttagaaaaat    7020
aaacaaatag gggttccgcg cacatttccc cgaaaagtgc cacctgacgt ctaagaaacc    7080
attattatca tgacattaac ctataaaaat aggcgtatca cgaggccctt tcgtc         7135
```

<210> SEQ ID NO 122
<211> LENGTH: 7148
<212> TYPE: DNA
<213> ORGANISM: Artificial Sequence
<220> FEATURE:
<223> OTHER INFORMATION: Synthetic

<400> SEQUENCE: 122

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
```

```
gggaacttcc atagcccata tatggagttc cgcgttacat aacttacggg aatttccaaa    420
cctggctgac cgcccaacga cccccgccca ttgacgtcaa taatgacgta tgttcccata    480
gtaacgccaa tagggaactt ccattgacgt caatgggtgg agtatttacg gtaaactgcc    540
cacttgggaa tttccaagtg tatcatatgc caagtacgcc ccctattgac gtcaatgacg    600
ggaacttcca taagcttgca ttatgcccag tacatgacct tatgggaatt tcctacttgg    660
cagtacatct acgtattagt catcgctatt accatggtga tgcggttttg gcagtacatc    720
aatgggcgtg gatagcggtt tgactcacgg gaacttccaa gtctccaccc cattgacgtc    780
aatgggagtt tgttttgact caccaaaatc aacgggaatt cccaaaatgt cgtaacaact    840 ccgcccatt gacgcaaatg ggcggtaggc gtgtacggtg ggaggtctat ataagcagag    900
ctcgtttagt gaaccgtcag atcgcctgga gacgccatcc acgctgtttt gacctccata    960
gaagacaccg ggaccgatcc agcctccatc ggctcgcatc tctccttcac gcgcccgccg   1020
ccctacctga gccgccatc cacgccggtt gagtcgcgtt ctgccgcctc ccgcctgtgg   1080
tgcctcctga actgcgtccg ccgtctaggt aagtttaaag ctcaggtcga gaccgggcct   1140
ttgtccggcg ctcccttgga gcctacctag actcagccgg ctctccacgc tttgcctgac   1200
cctgcttgct caactctagt taacggtgga gggcagtgta gtctgagcag tactcgttgc   1260
tgccgcgcgc gccaccagac ataatagctg acagactaac agactgttcc tttccatggg   1320
tcttttctgc agtcaccgtc gtcgacacgt gtgatcagat atcgcggccg ctctagagat   1380
atcgccacca tggacagcaa gggcagcagc cagaagggca gcagactgct gctgctgctg   1440
gtggtgagca acctgctgct gcctcagggc gtgctagccg aagccgccct gctggtgtgc   1500
cagtacacta ttcagagcct gattcatctg accggggagg accctggatt tttcaatgtg   1560
gaaatccctg agttcccatt ttaccccacc tgcaacgtct gtacagccga cgtgaacgtc   1620
accattaatt tcgatgtggg cgggaagaaa caccagctgg acctggattt tggccagctg   1680
accccacata caaaagccgt gtatcagccc agagggggctt tcggaggcag cgagaacgca   1740
acaaatctgt ttctgctgga gctgctggga gcaggagaac tggctctgac catgaggtcc   1800
aagaaactgc ccatcaatgt gaccacagga gaggaacagc aggtcagtct ggaatcagtg   1860
gacgtctact tccaggatgt gtttggcacc atgtggtgcc accatgccga gatgcagaat   1920
cctgtgtacc tgatccccga aaccgtccct tatattaagt gggacaactg taatagcact   1980
aacattaccg cagtggtccg ggcacagggg ctggacgtga ccctgccact gtcactgccc   2040
acaagcgccc aggatagcaa cttctccgtg aaaaccgaga tgctgggaaa tgagatcgac   2100
attgaatgca tcatggagga tggagaaatt agccaggtgc tgcctggcga taacaagttt   2160
aatatcacct gttccggcta cgaatctcac gtcccaagtg ggggaatcct gacatctact   2220
agtcccgtgg ccactccaat tcccggaacc ggctacgctt atagcctgag actgacccct   2280
aggccagtct cacgcttcct gggcaacaat agcattctgt acgtgtttta ttccggaaac   2340
ggaccaaagg cttctggagg ggactattgc atccagtaa atattgtgtt ctcagacgag   2400
atcccagcca gccaggatat gcccactaac actaccgaca ttacctacgt gggcgataat   2460
gccacttatt ccgtgcctat ggtcacaagc gaagacgcta actccccaaa tgtgaccgtc   2520
acagcattct gggcctggcc caacaatact gagaccgatt ttaagtgcaa atggacactg   2580
acttcaggca ccccctagcgg gtgtgaaaac atctctggcg ccttcgctag taatcgaacc   2640
tttgatatta cagtgtccgg cctggggact gccccaaaaa ccctgatcat tacccggaca   2700
gctactaacg caacaactac cacacacaaa gtgatcttca gcaaagctcc cgagtccact   2760
```

```
accacatctc ctaccctgaa cactaccggg tttgccgacc ccaatacaac taccggactg    2820
cctagctcca cccatgtgcc aacaaacctg actgcaccag catccaccgg acctacagtg    2880
tctactgccg atgtcaccag tcccacacct gccggaacaa cttctggcgc tagtcccgtg    2940
accccatcac ccagcccttg ggacaatggg acagagagta aggcccctga tatgacttct    3000
agtacctcac cagtcaccac accaacccccc aacgcaacaa gccctactcc agccgtgact    3060
acccccacac ctaatgctac cagcccaaca cccgcagtga caactcctac cccaaacgcc    3120
acttccccaa ccctggggaa gacatcaccc actagcgccg tgaccacacc caccccctaat   3180 gctacctctc ctacactggg aaaaacttcc ccaacctctg cagtgactac cccaaccccc    3240
aacgccacaa gccccactct gggcaagacc agtcctacat cagctgtcac aactcctacc    3300
ccaaatgcaa ctgggccaac cgtgggagag acatccccccc aggctaacgc aacaaatcac   3360
actctgggag gcaccagtcc cacacctgtg gtcacctcac agcccaagaa cgccacaagc    3420
gctgtgacca caggccagca taatatcaca tcaagctcca cttctagtat gagcctgcgc    3480
ccttcaagca acccagagac actgtcccca tctactagtg acaattcaac cagccacatg    3540
cctctgctga catctgcaca tccaactggg ggagaaaaca tcactcaggt cacccccgcc    3600
tccatttcta cccaccatgt gtccacatcc tctccagcac cccgacctgg aactaccagc    3660
caggcatccg gaccaggaaa tagttcaacc agcacaaagc ctggcgaggt gaacgtcaca    3720
aaagggactc cccctcagaa tgctacctca cctcaggcac caagcggcca gaaaacagct    3780
gtgcctactg tcacctccac aggcgggaag gcaaactcta caactggagg caaacacacc    3840
acagggcatg gagctcgcac tagcaccgaa ccaactaccg actacggggg agattccaca    3900
actccaaggc ccagatacaa tgccaccaca tatctgccac cctctaccag ctccaagctg    3960
cgacccagat ggacattcac tagtcctcca gtgactaccg cacaggctac agtgccagtc    4020
ccacctactt ctcagcctag attttctaac ctgagtcacc accaccacca ccactgatga    4080
ggatcctagc atcatcatca tcattagtct ggaagggcga attgatccag atctgctgtg    4140
ccttctagtt gccagccatc tgttgtttgc ccctcccccg tgccttcctt gaccctggaa    4200
ggtgccactc ccactgtcct ttcctaataa aatgaggaaa ttgcatcgca ttgtctgagt    4260
aggtgtcatt ctattctggg gggtggggtg gggcaggaca gcaaggggga ggattgggaa    4320
gacaatagca ggcatgctgg ggatgcggtg ggctctatgg gtacccaggt gctgaagaat    4380
tgacccggtt cctcctgggc cagaaagaag caggcacatc cccttctctg tgacacaccc    4440
tgtccacgcc cctggttctt agttccagcc ccactcatag gacactcata gctcaggagg    4500
gctccgcctt caatcccacc cgctaaagta cttggagcgg tctctccctc cctcatcagc    4560
ccaccaaacc aaacctagcc tccaagagtg ggaagaaatt aaagcaagat aggctattaa    4620
gtgcagaggg agagaaaatg cctccaacat gtgaggaagt aatgagagaa atcatagaat    4680
tttaaggcca tgatttaagg ccatcatggc cttaatcttc cgcttcctcg ctcactgact    4740
cgctgcgctc ggtcgttcgg ctgcggcgag cggtatcagc tcactcaaag gcggtaatac    4800
ggttatccac agaatcaggg gataacgcag gaaagaacat gtgagcaaaa ggccagcaaa    4860
aggccaggaa ccgtaaaaag gccgcgttgc tggcgttttt ccataggctc cgcccccctg    4920
acgagcatca caaaaatcga cgctcaagtc agaggtggcg aaacccgaca ggactataaa    4980
gataccaggc gtttccccct ggaagctccc tcgtgcgctc tcctgttccg accctgccgc    5040
ttaccggata cctgtccgcc tttctccctt cgggaagcgt ggcgctttct catagctcac    5100
```

```
gctgtaggta tctcagttcg gtgtaggtcg ttcgctccaa gctgggctgt gtgcacgaac    5160
cccccgttca gcccgaccgc tgcgccttat ccggtaacta tcgtcttgag tccaacccgg    5220
taagacacga cttatcgcca ctggcagcag ccactggtaa caggattagc agagcgaggt    5280
atgtaggcgg tgctacagag ttcttgaagt ggtggcctaa ctacggctac actagaagaa    5340
cagtatttgg tatctgcgct ctgctgaagc cagttacctt cggaaaaaga gttggtagct    5400
cttgatccgg caaacaaacc accgctggta gcggtggttt ttttgtttgc aagcagcaga    5460
ttacgcgcag aaaaaaagga tctcaagaag atcctttgat cttttctacg ggtctgacg    5520 ctcagtggaa cgaaaactca cgttaaggga ttttggtcat gagattatca aaaggatct    5580 tcacctagat ccttttaaat taaaatgaa gttttaaatc aatctaaagt atatatgagt    5640
aaacttggtc tgacagttac caatgcttaa tcagtgaggc acctatctca gcgatctgtc    5700
tatttcgttc atccatagtt gcctgactcg ggggggggg gcgctgaggt ctgcctcgtg    5760
aagaaggtgt tgctgactca taccaggcct gaatcgcccc atcatccagc cagaaagtga    5820
gggagccacg gttgatgaga ctttgttgt aggtggacca gttggtgatt ttgaactttt    5880
gctttgccac ggaacggtct gcgttgtcgg aagatgcgt gatctgatcc ttcaactcag    5940
caaaagttcg atttattcaa caaagccgcc gtcccgtcaa gtcagcgtaa tgctctgcca    6000
gtgttacaac caattaacca attctgatta gaaaaactca tcgagcatca atgaaactg    6060 caattattc atatcaggat tatcaatacc atattttga aaaagccgtt tctgtaatga    6120
aggagaaaac tcaccgaggc agttccatag gatggcaaga tcctggtatc ggtctgcgat    6180
tccgactcgt ccaacatcaa tacaacctat aatttcccc tcgtcaaaaa taaggttatc    6240
aagtgagaaa tcaccatgag tgacgactga atccggtgag aatggcaaaa gcttatgcat    6300
ttctttccag acttgttcaa caggccagcc attacgctcg tcatcaaaat cactcgcatc    6360
aaccaaaccg ttattcattc gtgattgcgc ctgagcgaga cgaaatacgc gatcgctgtt    6420
aaaaggacaa ttacaaacag gaatcgaatg caaccggcgc aggaacactg ccagcgcatc    6480
aacaatattt tcacctgaat caggatattc ttctaatacc tggaatgctg ttttcccggg    6540
gatcgcagtg gtgagtaacc atgcatcatc aggagtacgg ataaaatgct tgatggtcgg    6600
aagaggcata aattccgtca gccagtttag tctgaccatc tcatctgtaa catcattggc    6660
aacgctacct ttgccatgtt tcagaaacaa ctctggcgca tcgggcttcc catacaatcg    6720
atagattgtc gcacctgatt gcccgacatt atcgcgagcc catttatacc catataaatc    6780
agcatccatg ttggaattta atcgcggcct cgagcaagac gtttcccgtt gaatatggct    6840
cataacaccc cttgtattac tgtttatgta agcagacagt tttattgttc atgatgatat    6900
atttttatct tgtgcaatgt aacatcgag attttgagac acaacgtggc tttccccccc    6960
cccccattat tgaagcattt atcagggtta ttgtctcatg agcggataca tatttgaatg    7020
tatttagaaa aataaacaaa taggggttcc gcgcacattt ccccgaaaag tgccacctga    7080
cgtctaagaa accattatta tcatgacatt aacctataaa aataggcgta tcacgaggcc    7140
ctttcgtc                                                             7148

<210> SEQ ID NO 123
<211> LENGTH: 5843
<212> TYPE: DNA
<213> ORGANISM: Artificial Sequence
<220> FEATURE:
<223> OTHER INFORMATION: Synthetic

<400> SEQUENCE: 123
```

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
gggaacttcc atagcccata tatggagttc cgcgttacat aacttacggg aatttccaaa     420
cctggctgac cgcccaacga cccccgccca ttgacgtcaa taatgacgta tgttcccata     480
gtaacgccaa tagggaactt ccattgacgt caatgggtgg agtatttacg gtaaactgcc     540
cacttgggaa tttccaagtg tatcatatgc caagtacgcc ccctattgac gtcaatgacg     600
ggaacttcca taagcttgca ttatgcccag tacatgacct tatgggaatt cctacttgg      660 cagtacatct acgtattagt catcgctatt accatggtga tgcggttttg gcagtacatc     720
aatgggcgtg gatagcggtt tgactcacgg gaacttccaa gtctccaccc cattgacgtc     780
aatgggagtt gtttttgact caccaaaatc aacgggaatt cccaaaatgt cgtaacaact     840
ccgccccatt gacgcaaatg gcggtaggcg tgtacggtg ggaggtctat ataagcagag     900
ctcgtttagt gaaccgtcag atcgcctgga gacgccatcc acgctgtttt gacctccata     960
gaagacaccg ggaccgatcc agcctccatc ggctcgcatc tctccttcac gcgcccgccg    1020
ccctacctga gccgccatc cacgccggtt gagtcgcgtt ctgccgcctc ccgcctgtgg     1080
tgcctcctga actgcgtccg ccgtctaggt aagtttaaag ctcaggtcga gaccgggcct    1140
ttgtccggcg ctcccttgga gcctacctag actcagccgg ctctccacgc tttgcctgac    1200
cctgcttgct caactctagt taacggtgga gggcagtgta gtctgagcag tactcgttgc    1260
tgccgcgcgc gccaccagac ataatagctg acagactaac agactgttcc tttccatggg    1320
tcttttctgc agtcaccgtc gtcgacacgt gtgatcagat atcgcggccg ctctagagat    1380
atcgccacca tggacagcaa gggcagcagc cagaagggca gcagactgct gctgctgctg    1440
gtggtgagca acctgctgct gcctcagggc gtgctagccg aagccgccct gctggtgtgc    1500
cagtacacta ttcagagcct gattcatctg accggggagg accctggatt tttcaatgtg    1560
gaaatccctg agttcccatt ttaccccacc tgcaacgtct gtacagccga cgtgaacgtc    1620
accattaatt tcgatgtggg cgggaagaaa caccagctgg acctggattt tggccagctg    1680
accccacata caaaagccgt gtatcagccc agaggggctt tcggaggcag cgagaacgca    1740
acaaatctgt ttctgctgga gctgctggga gcaggagaac tggctctgac catgaggtcc    1800
aagaaactgc ccatcaatgt gaccacagga gaggaacagg aggtcagtct ggaatcagtg    1860
gacgtctact tccaggatgt gtttggcacc atgtggtgcc accatgccga gatgcagaat    1920
cctgtgtacc tgatccccga aaccgtccct tatattaagt gggacaactg taatagcact    1980
aacattaccg cagtggtccg ggcacagggg ctggacgtga ccctgccact gtcactgccc    2040
acaagcgccc aggatagcaa cttctccgtg aaaaccgaga tgctgggaaa tgagatcgac    2100
attgaatgca tcatggagga tggagaaatt agccaggtgc tgcctggcga taacaagttt    2160
aatatcacct gttccggcta cgaatctcac gtcccaagtg ggggaatcct gacatctact    2220
agtcccgtgg ccactccaat tcccggaacc ggctacgctt atagcctgag actgacccct    2280
aggccagtct cacgcttcct gggcaacaat agcattctgt acgtgtttta ttccggaaac    2340
```

```
ggaccaaagg cttctggagg ggactattgc atccagagta atattgtgtt ctcagacgag    2400
atcccagcca gccaggatat gcccactaac actaccgaca ttacctacgt gggcgataat    2460
gccacttatt ccgtgcctat ggtcacaagc gaagacgcta actccccaaa tgtgaccgtc    2520
acagcattct gggcctggcc caacaatact gagaccgatt ttaagtgcaa atggacactg    2580
acttcaggca cccctagcgg gtgtgaaaac atctctggcg ccttcgctag taatcgaacc    2640
tttgatatta cagtgtccgg cctggggact gccccaaaaa ccctgatcat tacccggaca    2700
gctactaacg caacaactac cacacacaaa gtgatcttca gcaaagctcc ccaccaccac    2760
caccaccact gatgaggatc ctagcatcat catcatcatt agtctggaag gcgaattga    2820 tccagatctg ctgtgccttc tagttgccag ccatctgttg tttgcccctc cccgtgcct    2880 tccttgaccc tggaaggtgc cactcccact gtccttccct aataaaatga ggaaattgca    2940
tcgcattgtc tgagtaggtg tcattctatt ctggggggtg gggtggggca ggacagcaag    3000
ggggaggatt gggaagacaa tagcaggcat gctgggatg cggtgggctc tatgggtacc    3060
caggtgctga agaattgacc cggttcctcc tgggccagaa agaagcaggc catccccctt    3120
ctctgtgaca caccctgtcc acgcccctgg ttcttagttc cagccccact cataggacac    3180
tcatagctca ggagggctcc gccttcaatc ccacccgcta agtacttggg agcggtctct    3240
ccctccctca tcagcccacc aaaccaaacc tagcctccaa gagtgggaag aaattaaagc    3300
aagataggct attaagtgca gagggagaga aaatgcctcc aacatgtgag gaagtaatga    3360
gagaaatcat agaattttaa ggccatgatt taaggccatc atggccttaa tcttccgctt    3420
cctcgctcac tgactcgctg cgctcggtcg ttcggctgcg gcgagcggta tcagctcact    3480
caaaggcggt aatacggtta tccacagaat caggggataa cgcaggaaag aacatgtgag    3540
caaaaggcca gcaaaggcc aggaaccgta aaaaggccgc gttgctggcg ttttccata    3600 ggctccgccc ccctgacgag catcacaaaa atcgacgctc aagtcagagg tggcgaaacc    3660
cgacaggact ataaagatac caggcgtttc ccccctggaag ctccctcgtg cgctctcctg    3720
ttccgaccct gccgcttacc ggatacctgt ccgcctttct cccttcggga agcgtggcgc    3780
tttctcatag ctcacgctgt aggtatctca gttcggtgta ggtcgttcgc tccaagctgg    3840
gctgtgtgca cgaacccccc gttcagcccg accgctgcgc cttatccggt aactatcgtc    3900
ttgagtccaa cccggtaaga cacgacttat cgccactggc agcagccact ggtaacagga    3960
ttagcagagc gaggtatgta ggcggtgcta cagagttctt gaagtggtgg cctaactacg    4020
gctacactag aagaacagta tttggtatct gcgctctgct gaagccagtt accttcggaa    4080
aaagagttgg tagctcttga tccggcaaac aaaccaccgc tggtagcggt ggttttttttg    4140 tttgcaagca gcagattacg cgcagaaaaa aaggatctca agaagatcct ttgatctttt    4200
ctacggggtc tgacgctcag tggaacgaaa actcacgtta agggattttg gtcatgagat    4260
tatcaaaaag gatcttcacc tagatccttt taaattaaaa atgaagtttt aaatcaatct    4320
aaagtatata tgagtaaact tggtctgaca gttaccaatg cttaatcagt gaggcaccta    4380
tctcagcgat ctgtctattt cgttcatcca tagttgcctg actcggggg ggggggcgct    4440 gaggtctgcc tcgtgaagaa ggtgttgctg actcatacca ggcctgaatc gccccatcat    4500
ccagccagaa agtgagggag ccacggttga tgagagcttt gttgtaggtg gaccagttgg    4560
tgattttgaa cttttgcttt gccacggaac ggtctgcgtt gtcggaaga tgcgtgatct    4620 gatccttcaa ctcagcaaaa gttcgattta ttcaacaaag ccgccgtccc gtcaagtcag    4680
cgtaatgctc tgccagtgtt acaaccaatt aaccaattct gattagaaaa actcatcgag    4740
```

```
catcaaatga aactgcaatt tattcatatc aggattatca ataccatatt tttgaaaaag    4800
ccgtttctgt aatgaaggag aaaactcacc gaggcagttc cataggatgg caagatcctg    4860
gtatcggtct gcgattccga ctcgtccaac atcaatacaa cctattaatt tcccctcgtc    4920
aaaaataagg ttatcaagtg agaaatcacc atgagtgacg actgaatccg gtgagaatgg    4980
caaaagctta tgcatttctt ccagacttgt tcaacaggc cagccattac gctcgtcatc    5040
aaaatcactc gcatcaacca aaccgttatt cattcgtgat gcgcctgag cgagacgaaa    5100 tacgcgatcg ctgttaaaag gacaattaca acaggaatc gaatgcaacc ggcgcaggaa    5160
cactgccagc gcatcaacaa tattttcacc tgaatcagga tattcttcta atacctggaa    5220
tgctgttttc ccggggatcg cagtggtgag taaccatgca tcatcaggag tacggataaa    5280
atgcttgatg gtcggaagag gcataaaattc cgtcagccag tttagtctga ccatctcatc    5340
tgtaacatca ttggcaacgc tacctttgcc atgtttcaga acaactctg gcgcatcggg    5400 cttcccatac aatcgataga ttgtcgcacc tgattgcccg acattatcgc gagcccattt    5460 atcccatat aaatcagcat ccatgttgga atttaatcgc ggcctcgagc aagacgtttc    5520
ccgttgaata tggctcataa cacccttgt attactgttt atgtaagcag acagttttat    5580
tgttcatgat gatatatttt tatcttgtgc aatgtaacat cagagatttt gagacacaac    5640
gtggctttcc cccccccc attattgaag catttatcag ggttattgtc tcatgagcgg    5700
atacatattt gaatgtattt agaaaaataa acaaatagg gttccgcgca catttccccg    5760
aaaagtgcca cctgacgtct aagaaaccat tattatcatg acattaaccct ataaaaatag    5820 gcgtatcacg aggccctttc gtc                                          5843
```

<210> SEQ ID NO 124
<211> LENGTH: 6533
<212> TYPE: DNA
<213> ORGANISM: Artificial Sequence
<220> FEATURE:
<223> OTHER INFORMATION: Synthetic

<400> SEQUENCE: 124

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgccccta ttgacgtcaa    600 tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
```

```
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgcttctaga   1380
caccatgcag ctcctgtgcg tgttctgtct ggtgctgctg tgggaagtgg agccgcttc    1440
tctgagtgag gtgaagctgc acctggacat tgaaggccac gcctcccatt acactatccc   1500
ttggaccgag ctgatggcta aagtgccagg actgtctcct gaggctctgt ggcgggaagc   1560
taatgtgacc gaggatctgg cctctatgct gaacagatac aagctgatct ataaaaccag   1620
tggcacactg gggattgctc tggctgagcc agtggacatc cccgccgtgt cagaaggaag   1680
catgcaggtg gatgctagta aggtgcatcc aggggtgatt agcggactga acagcccagc   1740
ttgcatgctg agcgctcctc tggagaaaca gctcttctac tatatcggca ccatgctgcc   1800
taatacacgg ccacacagct acgtgtttta tcagctcaga tgtcatctgt cctacgtggc   1860
cctgtctatt aacggggaca agttccagta tacaggagct atgacttcca aatttctgat   1920
gggaacttac aagcgggtga ccgagaaagg cgatgaacac gtgctgtctc tggtgttcgg   1980
gaagacaaaa gacctgcccg atctgagagg accctttttcc tacccttctc tgactagtgc   2040
ccagtcaggc gactatagcc tggtgatcgt gaccacattc gtgcactacg ctaacttcca   2100
taattatttt gtgcccaatc tgaaggatat gttttcccgg gccgtgacca tgacagccgc   2160
ttcttacgct agatatgtgc tgcagaagct ggtgctgctg gagatgaaag gcgggtgccg   2220
ggagcctgaa ctggacactg aaaccctgac taccatgttc gaggtgtccg tggccttctt   2280
taaagtggga cacgctgtgg gagagacagg aaacggatgc gtggacctga atggctggc    2340
caagagcttc tttgaactga ccgtgctgaa agatatcatt ggaatctgtt acggcgccac   2400
agtgaaagga atgcagagct atggcctgga gaggctggcc gctatgctga tggccaccgt   2460
gaagatggag gaactgggcc acctgacaac tgagaaacag gaatacgctc tgaggctggc   2520
taccgtggga tacccaaagg ccggggtgta ttccggactg attggaggcg ccacatctgt   2580
gctgctgagt gcttataata ggcacccact gttccagccc ctgcatacag tgatgcgcga   2640
gactctgttt atcgggtctc atgtggtgct gcgggaactg agactgaatg tgaccacaca   2700
gggacccaac ctggccctgt accagctcct gagtactgcc ctgtgctcag ctctggagat   2760
tggagaagtg ctgaggggac tggccctggg gaccgagtca ggactgttca gcccttgtta   2820
tctgtcactg aggtttgacc tgactcgcga taagctgctg agcatggccc cacaggaagc   2880
taccctggac caggccgctg tgagcaatgc cgtggatgga ttcctgggca ggctgtccct   2940
ggagagggaa gaccgcgatg cctggcacct gccagcttac aagtgcgtgg accgcctgga   3000
taaagtgctg atgatcattc ccctgatcaa cgtgaccttc atcattagct ccgacaggga   3060
agtgagaggc agcgctctgt acgaagcttc cactacctat ctgtctagtt cactgtttct   3120
gtcacctgtg attatgaata agtgtagcca gggagctgtg gctggagagc ccagacagat   3180
cccaaagatt cagaacttca cacgcactca gaaaagttgc atcttctgtg gctttgccct   3240
gctgtcatac gatgagaaag aagggctgga gacaactacc tatattacat ctcaggaagt   3300
```

```
gcagaacagt atcctgagct ccaattactt cgactttgat aacctgcacg tgcattatct   3360
gctgctgaca actaacggca ccgtgatgga gatcgctgga ctgtacgagg aaagggctca   3420
cgtggtgctg gctatcattc tgtatttcat cgcctttgct ctgggcattt ttctggtgca   3480
taagatcgtg atgttctttc tgtgatagga tccagatctg ctgtgccttc tagttgccag   3540
ccatctgttg tttgcccctc ccccgtgcct tccttgaccc tggaaggtgc cactcccact   3600
gtcctttcct aataaaatga ggaaattgca tcgcattgtc tgagtaggtg tcattctatt   3660
ctggggggtg gggtggggca ggacagcaag ggggaggatt gggaagacaa tagcaggcat   3720
gctgggggatg cggtgggctc tatgggtacc caggtgctga agaattgacc cggttcctcc   3780
tgggccagaa agaagcaggc acatcccctt ctctgtgaca caccctgtcc acgccctgg    3840
ttcttagttc cagccccact cataggacac tcatagctca ggagggctcc gccttcaatc   3900
ccaccogcta agtacttgg agcggtctct ccctcctca tcagcccacc aaaccaaacc     3960
tagcctccaa gagtgggaag aaattaaagc aagataggct attaagtgca gagggagaga   4020
aaatgcctcc aacatgtgag gaagtaatga gagaaatcat agaattttaa ggccatgatt   4080
taaggccatc atggccttaa tcttccgctt cctcgctcac tgactcgctg cgctcggtcg   4140
ttcggctgcg gcgagcggta tcagctcact caaaggcggt aatacggtta ccacagaat    4200
caggggataa cgcaggaaag aacatgtgag caaaaggcca gcaaaaggcc aggaaccgta   4260
aaaaggccgc gttgctggcg tttttccata ggctccgccc cctgacgag catcacaaaa    4320
atcgacgctc aagtcagagg tggcgaaacc cgacaggact ataaagatac caggcgtttc   4380
ccctggaag ctccctcgtg cgctctcctg ttccgaccct gccgcttacc ggatacctgt    4440
ccgcctttct cccttcggga agcgtggcgc tttctcatag ctcacgctgt aggtatctca   4500
gttcggtgta ggtcgttcgc tccaagctgg gctgtgtgca cgaacccccc gttcagcccg   4560
accgctgcgc cttatccggt aactatcgtc ttgagtccaa cccggtaaga cacgacttat   4620
cgccactggc agcagccact ggtaacagga ttagcagagc gaggtatgta ggcggtgcta   4680
cagagttctt gaagtggtgg cctaactacg gctacactag aagaacagta tttggtatct   4740
gcgctctgct gaagccagtt accttcggaa aaagagttgg tagctcttga tccggcaaac   4800
aaaccaccgc tggtagcggt ggtttttttg tttgcaagca gcagattacg cgcagaaaaa   4860
aaggatctca agaagatcct ttgatctttt ctacggggtc tgacgctcag tggaacgaaa   4920
actcacgtta agggattttg gtcatgagat tatcaaaaag gatcttcacc tagatccttt   4980
taaattaaaa atgaagtttt aaatcaatct aaagtatata tgagtaaact ggtctgaca    5040
gttaccaatg cttaatcagt gaggcaccta tctcagcgat ctgtctattt cgttcatcca   5100
tagttgccta actcgggggg ggggggcgct gaggtctgcc tcgtgaagaa ggtgttgctg   5160
actcatacca ggcctgaatc gccccatcat ccagccagaa agtgagggag ccacggttga   5220
tgagagcttt gttgtaggtg gaccagttgg tgattttgaa cttttgcttt gccacggaac   5280
ggtctgcgtt gtcgggaaga tgcgtgatct gatccttcaa ctcagcaaaa gttcgattta   5340
ttcaacaaag ccgccgtccc gtcaagtcag cgtaatgctc tgccagtgtt acaaccaatt   5400
aaccaattct gattagaaaa actcatcgag catcaaatga actgcaatt tattcatatc     5460
aggattatca ataccatatt tttgaaaaag ccgtttctgt aatgaaggag aaaactcacc   5520
gaggcagttc cataggatgg caagatcctg gtatcggtct gcgattccga ctcgtccaac   5580
atcaatacaa cctattaatt tcccctcgtc aaaaataagg ttatcaagtg agaaatcacc   5640
```

| | |
|---|---|
| atgagtgacg actgaatccg gtgagaatgg caaaagctta tgcatttctt tccagacttg | 5700 |
| ttcaacaggc cagccattac gctcgtcatc aaaatcactc gcatcaacca aaccgttatt | 5760 |
| cattcgtgat tgcgcctgag cgagacgaaa tacgcgatcg ctgttaaaag gacaattaca | 5820 |
| aacaggaatc gaatgcaacc ggcgcaggaa cactgccagc gcatcaacaa tattttcacc | 5880 |
| tgaatcagga tattcttcta atacctggaa tgctgttttc ccggggatcg cagtggtgag | 5940 |
| taaccatgca tcatcaggag tacgataaaa atgcttgatg gtcggaagag gcataaattc | 6000 |
| cgtcagccag tttagtctga ccatctcatc tgtaacatca ttggcaacgc tacctttgcc | 6060 |
| atgtttcaga aacaactctg gcgcatcggg cttcccatac aatcgataga ttgtcgcacc | 6120 |
| tgattgcccg acattatcgc gagcccattt atacccatat aaatcagcat ccatgttgga | 6180 |
| atttaatcgc ggcctcgagc aagacgtttc ccgttgaata tggctcataa cacccccttgt | 6240 |
| attactgttt atgtaagcag acagttttat tgttcatgat gatatatttt tatcttgtgc | 6300 |
| aatgtaacat cagagatttt gagacacaac gtggctttcc ccccccccc attattgaag | 6360 |
| catttatcag ggttattgtc tcatgagcgg atacatattt gaatgtattt agaaaaataa | 6420 |
| acaaataggg gttccgcgca catttccccg aaaagtgcca cctgacgtct aagaaaccat | 6480 |
| tattatcatg acattaacct ataaaaatag gcgtatcacg aggccctttc gtc | 6533 |

<210> SEQ ID NO 125
<211> LENGTH: 4826
<212> TYPE: DNA
<213> ORGANISM: Artificial Sequence
<220> FEATURE:
<223> OTHER INFORMATION: Synthetic

<400> SEQUENCE: 125

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca acgacccccg cccattgacg tcaataatga cgtatgttcc | 480 |
| catagtaacg ccaatagga cttccattg acgtcaatgg gtggagtatt tacggtaaac | 540 |
| tgcccacttg gcagtacatc aagtgtatca tatgccaagt acgcccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |
| ctccgcccca ttgacgcaaa tgggcggtag gcgtgtacgg tgggaggtct atataagcag | 900 |
| agctcgttta gtgaaccgtc agatcgcctg gagacgccat ccacgctgtt ttgacctcca | 960 |
| tagaagacac cgggaccgat ccagcctcca tcggctcgca tctctccttc acgcgcccgc | 1020 |
| cgccctacct gaggccgcca tccacgccgg ttgagtcgcg ttctgccgcc tcccgcctgt | 1080 |
| ggtgcctcct gaactgcgtc cgccgtctag gtaagtttaa agctcaggtc gagaccgggc | 1140 |
| ctttgtccgg cgctcccttg gagcctacct agactcagcc ggctctccac gctttgcctg | 1200 |

```
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgcttctaga   1380
caccatgcgg gccgtggggg tgttcctggc tatctgcctg gtgactattt ttgtgctgcc   1440
aacctgggga aactgggctt acccttgctg tcacgtgacc cagctcaggg cccagcatct   1500
gctggctctg gagaacatca gcgacattta tctggtgtcc aatcagacat gcatgggtt    1560
cagcctggcc tccctgaaca gccccaagaa cggatctaat cagctcgtga tctcccggtg   1620
tgctaacggc ctgaatgtcg tgagtttctt tatctcaatt ctgaaaagga gctcctctgc   1680
tctgacagga cacctgaggg agctgctgac cacactggaa actctgtacg aagtttctc    1740
agtggaagac ctgtttggcg ccaacctgaa tcggtatgct tggcatagag gcgggtgata   1800
ggatccagat ctgctgtgcc ttctagttgc cagccatctg ttgtttgccc ctccccgtg    1860
ccttccttga ccctggaagg tgccactccc actgtccttt cctaataaaa tgaggaaatt   1920
gcatcgcatt gtctgagtag gtgtcattct attctggggg gtggggtggg gcaggacagc   1980
aaggggggagg attgggaaga caatagcagg catgctgggg atgcggtggg ctctatgggt   2040
acccaggtgc tgaagaattg acccggttcc tcctgggcca gaaagaagca ggcacatccc   2100
cttctctgtg acacccctg tccacgcccc tggttcttag ttccagcccc actcatagga    2160
cactcatagc tcaggagggc tccgccttca atcccacccg ctaaagtact tggagcggtc   2220
tctccctccc tcatcagccc accaaaccaa acctagcctc caagagtggg aagaaattaa   2280
agcaagatag gctattaagt gcagagggag agaaaatgcc tccaacatgt gaggaagtaa   2340
tgagagaaat catagaattt taaggccatg atttaaggcc atcatggcct taatcttccg   2400
cttcctcgct cactgactcg ctgcgctcgg tcgttcggct gcggcgagcg gtatcagctc   2460
actcaaaggc ggtaatacgg ttatccacag aatcagggga taacgcagga agaacatgt    2520
gagcaaaagg ccagcaaaag gccaggaacc gtaaaaaggc cgcgttgctg gcgttttcc    2580
ataggctccg ccccccctgac gagcatcaca aaaatcgacg ctcaagtcag aggtggcgaa   2640
acccgacagg actataaaga taccaggcgt ttccccctgg aagctccctc gtgcgctctc   2700
ctgttccgac cctgccgctt accggatacc tgtccgcctt ctcccttcg ggaagcgtgg    2760
cgctttctca tagctcacgc tgtaggtatc tcagttcggt gtaggtcgtt cgctccaagc   2820
tgggctgtgt gcacgaaccc cccgttcagc ccgaccgctg cgccttatcc ggtaactatc   2880
gtcttgagtc caacccggta agacacgact tatcgccact ggcagcagcc actggtaaca   2940
ggattagcag agcgaggtat gtaggcggtg ctacagagtt cttgaagtgg tggcctaact   3000
acggctacac tagaagaaca gtatttggta tctgcgctct gctgaagcca gttaccttcg   3060
gaaaaagagt tggtagctct tgatccggca aacaaaccac cgctggtagc ggtggttttt   3120
ttgtttgcaa gcagcagatt acgcgcagaa aaaaaggatc tcaagaagat cctttgatct   3180
tttctacggg gtctgacgct cagtggaacg aaaactcacg ttaagggatt ttggtcatga   3240
gattatcaaa aaggatcttc acctagatcc ttttaaatta aaaatgaagt tttaaatcaa   3300
tctaaagtat atatgagtaa acttggtctg acagttacca atgcttaatc agtgaggcac   3360
ctatctcagc gatctgtcta tttcgttcat ccatagttgc ctgactcggg ggggggggc    3420
gctgaggtct gcctcgtgaa gaaggtgttg ctgactcata ccaggcctga atcgccccat   3480
catccagcca gaaagtgagg gagccacggt tgatgagagc tttgttgtag gtggaccagt   3540
```

```
tggtgatttt gaactttttgc tttgccacgg aacggtctgc gttgtcggga agatgcgtga    3600
tctgatcctt caactcagca aaagttcgat ttattcaaca aagccgccgt cccgtcaagt    3660
cagcgtaatg ctctgccagt gttacaacca attaaccaat tctgattaga aaaactcatc    3720
gagcatcaaa tgaaactgca atttattcat atcaggatta tcaataccat atttttgaaa    3780
aagccgtttc tgtaatgaag gagaaaactc accgaggcag ttccatagga tggcaagatc    3840
ctggtatcgg tctgcgattc cgactcgtcc aacatcaata caacctatta atttcccctc    3900
gtcaaaaata aggttatcaa gtgagaaatc accatgagtg acgactgaat ccggtgagaa    3960
tggcaaaagc ttatgcattt cttttccagac ttgttcaaca ggccagccat tacgctcgtc    4020
atcaaaatca ctcgcatcaa ccaaaccgtt attcattcgt gattgcgcct gagcgagacg    4080
aaatacgcga tcgctgttaa aaggacaatt acaaacagga tcgaatgca accggcgcag    4140 gaacactgcc agcgcatcaa caatattttc acctgaatca ggatattctt ctaatacctg    4200
gaatgctgtt ttcccgggga tcgcagtggt gagtaaccat gcatcatcag gagtacggat    4260
aaaatgcttg atggtcggaa gaggcataaa ttccgtcagc cagtttagtc tgaccatctc    4320
atctgtaaca tcattggcaa cgctacctttt gccatgtttc agaaacaact ctggcgcatc    4380
gggcttccca tacaatcgat agattgtcgc acctgattgc ccgacattat cgcgagccca    4440 tttatacccca tataaatcag catccatgtt ggaatttaat cgcggcctcg agcaagacgt    4500
ttcccgttga atatggctca taacaccct tgtattactg tttatgtaag cagacagttt    4560
tattgttcat gatgatatat ttttatcttg tgcaatgtaa catcagagat tttgagacac    4620
aacgtggctt tcccccccc cccattattg aagcatttat cagggttatt gtctcatgag    4680
cggatacata tttgaatgta tttagaaaaa taaacaaata ggggttccgc gcacatttcc    4740
ccgaaaagtg ccacctgacg tctaagaaac cattattatc atgacattaa cctataaaaa    4800
taggcgtatc acgaggccct ttcgtc                                         4826
```

<210> SEQ ID NO 126  
<211> LENGTH: 5084  
<212> TYPE: DNA  
<213> ORGANISM: Artificial Sequence  
<220> FEATURE:  
<223> OTHER INFORMATION: Synthetic

<400> SEQUENCE: 126

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaatagggda cttttccattg acgtcaatgg gtggagtatt tacgtaaac     540 tgcccacttg gcagtacatc aagtgtatca tatgccaagt acgccccta ttgacgtcaa     600 tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
```

-continued

| | |
|---|---|
| cgtcaatggg agtttgtttt ggcaccaaaa tcaacgggac tttccaaaat gtcgtaacaa | 840 |
| ctccgcccca ttgacgcaaa tgggcggtag gcgtgtacgg tgggaggtct atataagcag | 900 |
| agctcgttta gtgaaccgtc agatcgcctg gagacgccat ccacgctgtt ttgacctcca | 960 |
| tagaagacac cgggaccgat ccagcctcca tcggctcgca tctctccttc acgcgcccgc | 1020 |
| cgccctacct gaggccgcca tccacgccgg ttgagtcgcg ttctgccgcc tcccgcctgt | 1080 |
| ggtgcctcct gaactgcgtc cgccgtctag gtaagtttaa agctcaggtc gagaccgggc | 1140 |
| ctttgtccgg cgctcccttg gagcctacct agactcagcc ggctctccac gctttgcctg | 1200 |
| accctgcttg ctcaactcta gttaacggtg gagggcagtg tagtctgagc agtactcgtt | 1260 |
| gctgccgcgc gcgccaccag acataatagc tgacagacta acagactgtt cctttccatg | 1320 |
| ggtcttttct gcagtcaccg tcgtcgacac gtgtgatcag atatcgcggc cgcttctaga | 1380 |
| caccatggtc agcttcaaac aagtgcgggt gccctgtttt actgccatcg ctctggtgat | 1440 |
| tgtgctgctg ctggcctact tcctgccacc tcgggtcaga ggaggaggaa gagtggccgc | 1500 |
| tgccgctatc acctgggtgc aaaacctaa tgtggaagtg tggcctgtgg acccaccacc | 1560 |
| tccagtgaac tttaataaga cagccgagca ggaatatggc gataaagaag tgaagctgcc | 1620 |
| tcactggacc ccaacactgc atacattcca ggtgccacag aactacacta aagctaattg | 1680 |
| cacttattgt aacaccaggg agtacacatt tagttataag gggtgctgtt tctactttac | 1740 |
| taagaaaaag cacacctgga atggatgctt ccaggcctgt gctgaactgt atccatgcac | 1800 |
| atacttttat ggcccaactc ccgacatcct gcccgtggtg accaggaacc tgaatgccat | 1860 |
| tgagtccctg tgggtgggag tgtacagggt gggagaaggc aactggacct ccctggatgg | 1920 |
| cgggacattc aaagtgtacc agattttggg ctctcattgc acttatgtgt ctaagttcag | 1980 |
| taccgtgccc gtgtcacacc atgagtgtag ctttctgaag ccttgcctgt gtgtgtctca | 2040 |
| gagaagcaac tcctgatagg atccagatct gctgtgcctt ctagttgcca gccatctgtt | 2100 |
| gtttgcccct ccccgtgcc ttccttgacc ctggaaggtg ccactccac tgtcctttcc | 2160 |
| taataaaatg aggaaattgc atcgcattgt ctgagtaggt gtcattctat tctgggggt | 2220 |
| ggggtggggc aggacagcaa gggggaggat tgggaagaca atagcaggca tgctgggat | 2280 |
| gcggtgggct ctatgggtac ccaggtgctg aagaattgac ccggttcctc ctgggccaga | 2340 |
| aagaagcagg cacatcccct tctctgtgac acccctgtc cacgccctg gttcttagtt | 2400 |
| ccagccccac tcataggaca ctcatagctc aggagggctc cgccttcaat cccacccgct | 2460 |
| aaagtacttg gagcggtctc tccctccctc atcagcccac caaaccaaac ctagcctcca | 2520 |
| agagtgggaa gaaattaaag caagataggc tattaagtgc agagggagag aaaatgcctc | 2580 |
| caacatgtga ggaagtaatg agagaaatca tagaatttta aggccatgat ttaaggccat | 2640 |
| catggcctta atcttccgct tcctcgctca ctgactcgct gcgctcggtc gttcggctgc | 2700 |
| ggcgagcggt atcagctcac tcaaaggcgg taatacggtt atccacagaa tcaggggata | 2760 |
| acgcaggaaa gaacatgtga gcaaaaggcc agcaaaggc caggaaccgt aaaaaggccg | 2820 |
| cgttgctggc gtttttccat aggctccgcc cccctgacga gcatcacaaa aatcgacgct | 2880 |
| caagtcagag gtggcgaaac ccgacaggac tataaagata ccaggcgttt ccccctggaa | 2940 |
| gctccctcgt gcgctctcct gttccgaccc tgccgcttac cggatacctg tccgcctttc | 3000 |
| tcccttcggg aagcgtggcg ctttctcata gctcacgctg taggtatctc agttcggtgt | 3060 |
| aggtcgttcg ctccaagctg ggctgtgtgc acgaaccccc cgttcagccc gaccgctgcg | 3120 |

| ccttatccgg taactatcgt cttgagtcca acccggtaag acacgactta tcgccactgg | 3180 |
| cagcagccac tggtaacagg attagcagag cgaggtatgt aggcggtgct acagagttct | 3240 |
| tgaagtggtg gcctaactac ggctacacta aagaacagt atttggtatc tgcgctctgc | 3300 |
| tgaagccagt taccttcgga aaaagagttg gtagctcttg atccggcaaa caaaccaccg | 3360 |
| ctggtagcgg tggttttttt gtttgcaagc agcagattac gcgcagaaaa aaggatctc | 3420 |
| aagaagatcc tttgatcttt tctacggggt ctgacgctca gtggaacgaa aactcacgtt | 3480 |
| aagggatttt ggtcatgaga ttatcaaaaa ggatcttcac ctagatcctt ttaaattaaa | 3540 |
| aatgaagttt taaatcaatc taaagtatat atgagtaaac ttggtctgac agttaccaat | 3600 |
| gcttaatcag tgaggcacct atctcagcga tctgtctatt tcgttcatcc atagttgcct | 3660 |
| gactcggggg gggggggcgc tgaggtctgc ctcgtgaaga aggtgttgct gactcatacc | 3720 |
| aggcctgaat cgccccatca tccagccaga aagtgaggga gccacggttg atgagagctt | 3780 |
| tgttgtaggt ggaccagttg gtgattttga acttttgctt tgccacggaa cggtctgcgt | 3840 |
| tgtcgggaag atgcgtgatc tgatccttca actcagcaaa agttcgattt attcaacaaa | 3900 |
| gccgccgtcc cgtcaagtca gcgtaatgct ctgccagtgt acaaccaat taaccaattc | 3960 |
| tgattagaaa aactcatcga gcatcaaatg aaactgcaat ttattcatat caggattatc | 4020 |
| aataccatat ttttgaaaaa gccgtttctg taatgaagga gaaaactcac cgaggcagtt | 4080 |
| ccataggatg caagatcct ggtatcggtc tgcgattccg actcgtccaa catcaataca | 4140 |
| acctattaat ttcccctcgt caaaaataag gttatcaagt gagaaatcac catgagtgac | 4200 |
| gactgaatcc ggtgagaatg gcaaaagctt atgcatttct ttccagactt gttcaacagg | 4260 |
| ccagccatta cgctcgtcat caaaatcact cgcatcaacc aaaccgttat tcattcgtga | 4320 |
| ttgcgcctga gcgagacgaa atacgcgatc gctgttaaaa ggacaattac aaacaggaat | 4380 |
| cgaatgcaac cggcgcagga acactgccag cgcatcaaca atattttcac ctgaatcagg | 4440 |
| atattcttct aatacctgga atgctgtttt cccggggatc gcagtggtga gtaaccatgc | 4500 |
| atcatcagga gtacggataa aatgcttgat ggtcggaaga ggcataaatt ccgtcagcca | 4560 |
| gtttagtctg accatctcat ctgtaacatc attggcaacg ctacctttgc catgtttcag | 4620 |
| aaacaactct ggcgcatcgg gcttcccata caatcgatag attgtcgcac ctgattgccc | 4680 |
| gacattatcg cgagcccatt tatacccata taaatcagca tccatgttgg aatttaatcg | 4740 |
| cggcctcgag caagacgttt cccgttgaat atggctcata cacccccttg tattactgtt | 4800 |
| tatgtaagca gacagttta ttgttcatga tgatatattt ttatcttgtg caatgtaaca | 4860 |
| tcagagattt tgagacacaa cgtggctttc ccccccccc cattattgaa gcatttatca | 4920 |
| gggttattgt ctcatgagcg gatacatatt tgaatgtatt tagaaaaata acaaataggg | 4980 |
| ggttccgcgc acatttcccc gaaaagtgcc acctgacgtc taagaaacca ttattatcat | 5040 |
| gacattaacc tataaaaata ggcgtatcac gaggcccttt cgtc | 5084 |

<210> SEQ ID NO 127
<211> LENGTH: 2580
<212> TYPE: DNA
<213> ORGANISM: Artificial Sequence
<220> FEATURE:
<223> OTHER INFORMATION: Synthetic

<400> SEQUENCE: 127

| atgcagctcc tgtgcgtgtt ctgtctggtg ctgctgtggg aagtgggagc cgcttctctg | 60 |
| agtgaggtga agctgcacct ggacattgaa ggccacgcct cccattacac tatcccttgg | 120 |

-continued

```
accgagctga tggctaaagt gccaggactg tctcctgagg ctctgtggcg ggaagctaat      180
gtgaccgagg atctggcctc tatgctgaac agatacaagc tgatctataa aaccagtggc      240
acactgggga ttgctctggc tgagccagtg acatccccg ccgtgtcaga aggaagcatg       300
caggtggatg ctagtaaggt gcatccaggg gtgattagcg gactgaacag cccagcttgc      360
atgctgagcg ctcctctgga gaaacagctc ttctactata tcggcaccat gctgcctaat      420
acacggccac acagctacgt gttttatcag ctcagatgtc atctgtccta cgtgccctg      480 tctattaacg gggacaagtt ccagtataca ggagctatga cttccaaatt tctgatggga     540
acttacaagc gggtgaccga gaaaggcgat gaacacgtgc tgtctctggt gttcgggaag     600
acaaaagacc tgcccgatct gagaggaccc ttttcctacc cttctctgac tagtgcccag     660
tcaggcgact atagcctggt gatcgtgacc acattcgtgc actacgctaa cttccataat     720
tattttgtgc ccaatctgaa ggatatgttt tcccgggccg tgaccatgac agccgcttct     780
tacgctagat atgtgctgca gaagctggtg ctgctggaga tgaaaggcgg gtgccgggag    840
cctgaactgg acactgaaac cctgactacc atgttcgagg tgtccgtggc cttctttaaa    900
gtgggacacg ctgtgggaga gacaggaaac ggatgcgtgg acctgagatg gctggccaag    960
agcttctttg aactgaccgt gctgaaagat atcattggaa tctgttacgg cgccacagtg    1020
aaaggaatgc agagctatgg cctggagagg ctggccgcta tgctgatggc caccgtgaag    1080
atggaggaac tgggccacct gacaactgag aaacaggaat acgctctgag gctggctacc    1140
gtgggatacc caaaggccgg ggtgtattcc ggactgattg gaggcgccac atctgtgctg    1200
ctgagtgctt ataataggca cccactgttc cagcccctgc atacagtgat gcgcgagact    1260
ctgtttatcg ggtctcatgt ggtgctgcgg gaactgagac tgaatgtgac cacacaggga    1320
cccaacctgg ccctgtacca gctcctgagt actgccctgt gctcagctct ggagattgga    1380
gaagtgctga ggggactggc cctggggacc gagtcaggac tgttcagccc ttgttatctg    1440
tcactgaggt ttgacctgac tcgcgataag ctgctgagca tggccccaca ggaagctacc    1500
ctggaccagg ccgctgtgag caatgccgtg gatggattcc tgggcaggct gtccctggag    1560
agggaagacc gcgatgcctg gcacctgcca gcttacaagt gcgtggaccg cctggataaa    1620
gtgctgatga tcattcccct gatcaacgtg accttcatca ttagctccga cagggaagtg    1680
agaggcagcg ctctgtacga agcttccact acctatctgt ctagttcact gtttctgtca    1740
cctgtgatta tgaataagtg tagccaggga gctgtggctg agagcccag acagatccca    1800 aagattcaga acttcacacg cactcagaaa agttgcatct tctgtggctt tgccctgctg    1860
tcatacgatg agaagaagg gctggagaca actacctata ttacatctca ggaagtgcag    1920
aacagtatcc tgagctccaa ttacttcgac tttgataacc tgcacgtgca ttatctgctg    1980
ctgacaacta acggcaccgt gatggagatc gctggactgt acgaggaaag ggctcactct    2040
ggcggctccg agagagcca ggtgaggcag cagttcagca aggacatcga gaagctgctg    2100
aacgagcagg tgaacaagga gatgcagagc agcaacctgt acatgagcat gagcagctgg    2160
tgctacaccc acagcctgga cggcgccggc ctgttcctgt cgaccacgc cgccgaggag    2220 tacgagcacg ccaagaagct gatcatcttc ctgaacgaga caacgtgcc cgtgcagctg    2280 accagcatca gcgcccccga gcacaagttc gagggcctga cccagatctt ccagaaggcc    2340
tacgagcacg agcagcacat cagcgagagc atcaacaaca tcgtggacca cgccatcaag    2400
agcaaggacc acgccacctt caacttcctg cagtggtacg tggccgagca gcacgaggag    2460
```

```
gaggtgctgt tcaaggacat cctggacaag atcgagctga tcggcaacga gaaccacggc    2520
ctgtacctgg ccgaccagta cgtgaagggc atcgccaaga gcaggaagag cggatcctag    2580

<210> SEQ ID NO 128
<211> LENGTH: 859
<212> TYPE: PRT
<213> ORGANISM: Artificial Sequence
<220> FEATURE:
<223> OTHER INFORMATION: Synthetic

<400> SEQUENCE: 128

Met Gln Leu Leu Cys Val Phe Cys Leu Val Leu Leu Trp Glu Val Gly
1               5                   10                  15

Ala Ala Ser Leu Ser Glu Val Lys Leu His Leu Asp Ile Glu Gly His
            20                  25                  30

Ala Ser His Tyr Thr Ile Pro Trp Thr Glu Leu Met Ala Lys Val Pro
        35                  40                  45

Gly Leu Ser Pro Glu Ala Leu Trp Arg Glu Ala Asn Val Thr Glu Asp
    50                  55                  60

Leu Ala Ser Met Leu Asn Arg Tyr Lys Leu Ile Tyr Lys Thr Ser Gly
65                  70                  75                  80

Thr Leu Gly Ile Ala Leu Ala Glu Pro Val Asp Ile Pro Ala Val Ser
                85                  90                  95

Glu Gly Ser Met Gln Val Asp Ala Ser Lys Val His Pro Gly Val Ile
            100                 105                 110

Ser Gly Leu Asn Ser Pro Ala Cys Met Leu Ser Ala Pro Leu Glu Lys
        115                 120                 125

Gln Leu Phe Tyr Tyr Ile Gly Thr Met Leu Pro Asn Thr Arg Pro His
    130                 135                 140

Ser Tyr Val Phe Tyr Gln Leu Arg Cys His Leu Ser Tyr Val Ala Leu
145                 150                 155                 160

Ser Ile Asn Gly Asp Lys Phe Gln Tyr Thr Gly Ala Met Thr Ser Lys
                165                 170                 175

Phe Leu Met Gly Thr Tyr Lys Arg Val Thr Glu Lys Gly Asp Glu His
            180                 185                 190

Val Leu Ser Leu Val Phe Gly Lys Thr Lys Asp Leu Pro Asp Leu Arg
        195                 200                 205

Gly Pro Phe Ser Tyr Pro Ser Leu Thr Ser Ala Gln Ser Gly Asp Tyr
    210                 215                 220

Ser Leu Val Ile Val Thr Thr Phe Val His Tyr Ala Asn Phe His Asn
225                 230                 235                 240

Tyr Phe Val Pro Asn Leu Lys Asp Met Phe Ser Arg Ala Val Thr Met
                245                 250                 255

Thr Ala Ala Ser Tyr Ala Arg Tyr Val Leu Gln Lys Leu Val Leu Leu
            260                 265                 270

Glu Met Lys Gly Gly Cys Arg Glu Pro Glu Leu Asp Thr Glu Thr Leu
        275                 280                 285

Thr Thr Met Phe Glu Val Ser Val Ala Phe Phe Lys Val Gly His Ala
    290                 295                 300

Val Gly Glu Thr Gly Asn Gly Cys Val Asp Leu Arg Trp Leu Ala Lys
305                 310                 315                 320

Ser Phe Phe Glu Leu Thr Val Leu Lys Asp Ile Ile Gly Ile Cys Tyr
                325                 330                 335

Gly Ala Thr Val Lys Gly Met Gln Ser Tyr Gly Leu Glu Arg Leu Ala
            340                 345                 350
```

```
Ala Met Leu Met Ala Thr Val Lys Met Glu Glu Leu Gly His Leu Thr
            355                 360                 365

Thr Glu Lys Gln Glu Tyr Ala Leu Arg Leu Ala Thr Val Gly Tyr Pro
    370                 375                 380

Lys Ala Gly Val Tyr Ser Gly Leu Ile Gly Gly Ala Thr Ser Val Leu
385                 390                 395                 400

Leu Ser Ala Tyr Asn Arg His Pro Leu Phe Gln Pro Leu His Thr Val
                405                 410                 415

Met Arg Glu Thr Leu Phe Ile Gly Ser His Val Val Leu Arg Glu Leu
            420                 425                 430

Arg Leu Asn Val Thr Thr Gln Gly Pro Asn Leu Ala Leu Tyr Gln Leu
            435                 440                 445

Leu Ser Thr Ala Leu Cys Ser Ala Leu Glu Ile Gly Glu Val Leu Arg
            450                 455                 460

Gly Leu Ala Leu Gly Thr Glu Ser Gly Leu Phe Ser Pro Cys Tyr Leu
465                 470                 475                 480

Ser Leu Arg Phe Asp Leu Thr Arg Asp Lys Leu Leu Ser Met Ala Pro
                485                 490                 495

Gln Glu Ala Thr Leu Asp Gln Ala Ala Val Ser Asn Ala Val Asp Gly
            500                 505                 510

Phe Leu Gly Arg Leu Ser Leu Glu Arg Glu Asp Arg Asp Ala Trp His
            515                 520                 525

Leu Pro Ala Tyr Lys Cys Val Asp Arg Leu Asp Lys Val Leu Met Ile
            530                 535                 540

Ile Pro Leu Ile Asn Val Thr Phe Ile Ile Ser Ser Asp Arg Glu Val
545                 550                 555                 560

Arg Gly Ser Ala Leu Tyr Glu Ala Ser Thr Thr Tyr Leu Ser Ser Ser
                565                 570                 575

Leu Phe Leu Ser Pro Val Ile Met Asn Lys Cys Ser Gln Gly Ala Val
            580                 585                 590

Ala Gly Glu Pro Arg Gln Ile Pro Lys Ile Gln Asn Phe Thr Arg Thr
            595                 600                 605

Gln Lys Ser Cys Ile Phe Cys Gly Phe Ala Leu Leu Ser Tyr Asp Glu
            610                 615                 620

Lys Glu Gly Leu Glu Thr Thr Thr Tyr Ile Thr Ser Gln Glu Val Gln
625                 630                 635                 640

Asn Ser Ile Leu Ser Ser Asn Tyr Phe Asp Phe Asp Asn Leu His Val
                645                 650                 655

His Tyr Leu Leu Leu Thr Thr Asn Gly Thr Val Met Glu Ile Ala Gly
            660                 665                 670

Leu Tyr Glu Glu Arg Ala His Ser Gly Gly Ser Gly Glu Ser Gln Val
            675                 680                 685

Arg Gln Gln Phe Ser Lys Asp Ile Glu Lys Leu Leu Asn Glu Gln Val
    690                 695                 700

Asn Lys Glu Met Gln Ser Ser Asn Leu Tyr Met Ser Met Ser Ser Trp
705                 710                 715                 720

Cys Tyr Thr His Ser Leu Asp Gly Ala Gly Leu Phe Leu Phe Asp His
                725                 730                 735

Ala Ala Glu Glu Tyr Glu His Ala Lys Lys Leu Ile Ile Phe Leu Asn
            740                 745                 750

Glu Asn Asn Val Pro Val Gln Leu Thr Ser Ile Ser Ala Pro Glu His
            755                 760                 765
```

Lys Phe Glu Gly Leu Thr Gln Ile Phe Gln Lys Ala Tyr Glu His Glu
770                 775                 780

Gln His Ile Ser Glu Ser Ile Asn Asn Ile Val Asp His Ala Ile Lys
785                 790                 795                 800

Ser Lys Asp His Ala Thr Phe Asn Phe Leu Gln Trp Tyr Val Ala Glu
                805                 810                 815

Gln His Glu Glu Val Leu Phe Lys Asp Ile Leu Asp Lys Ile Glu
            820                 825                 830

Leu Ile Gly Asn Glu Asn His Gly Leu Tyr Leu Ala Asp Gln Tyr Val
            835                 840                 845

Lys Gly Ile Ala Lys Ser Arg Lys Ser Gly Ser
    850                 855

<210> SEQ ID NO 129
<211> LENGTH: 645
<212> TYPE: DNA
<213> ORGANISM: Artificial Sequence
<220> FEATURE:
<223> OTHER INFORMATION: Synthetic

<400> SEQUENCE: 129
atgcccatgg gcagcctgca gcccctggcc accctgtacc tgctgggcat gctggtggct      60
agcgtgctgg ccggaggaag agtggccgct gccgctatca cctgggtgcc aaaacctaat     120
gtggaagtgt ggcctgtgga cccaccacct ccagtgaact ttaataagac agccgagcag     180
gaatatggcg ataaagaagt gaagctgcct cactggaccc caacactgca tacattccag     240
gtgccacaga actacactaa agctaattgc acttattgta acaccaggga gtacacattt     300
agttataagg ggtgctgttt ctactttact aagaaaaagc acacctggaa tggatgcttc     360
caggcctgtg ctgaactgta tccatgcaca tactttatgt gcccaactcc cgacatcctg     420
cccgtggtga ccaggaacct gaatgccatt gagtccctgt gggtgggagt gtacagggtg     480
ggagaaggca actggacctc cctggatggc gggacattca agtgtaccag gattttggc      540 tctcattgca cttatgtgtc taagttcagt accgtgcccg tgtcacacca tgagtgtagc     600
tttctgaagc cttgcctgtg tgtgtctcag agaagcaact cctga                     645

<210> SEQ ID NO 130
<211> LENGTH: 214
<212> TYPE: PRT
<213> ORGANISM: Artificial Sequence
<220> FEATURE:
<223> OTHER INFORMATION: Synthetic

<400> SEQUENCE: 130

Met Pro Met Gly Ser Leu Gln Pro Leu Ala Thr Leu Tyr Leu Leu Gly
1               5                   10                  15

Met Leu Val Ala Ser Val Leu Ala Gly Gly Arg Val Ala Ala Ala Ala
            20                  25                  30

Ile Thr Trp Val Pro Lys Pro Asn Val Glu Val Trp Pro Val Asp Pro
        35                  40                  45

Pro Pro Pro Val Asn Phe Asn Lys Thr Ala Glu Gln Glu Tyr Gly Asp
    50                  55                  60

Lys Glu Val Lys Leu Pro His Trp Thr Pro Thr Leu His Thr Phe Gln
65                  70                  75                  80

Val Pro Gln Asn Tyr Thr Lys Ala Asn Cys Thr Tyr Cys Asn Thr Arg
                85                  90                  95

Glu Tyr Thr Phe Ser Tyr Lys Gly Cys Cys Phe Tyr Phe Thr Lys Lys

|  |  |  | 100 |  |  |  | 105 |  |  |  | 110 |  |  |
|---|---|---|---|---|---|---|---|---|---|---|---|---|---|
| Lys | His | Thr | Trp | Asn | Gly | Cys | Phe | Gln | Ala | Cys | Ala | Glu | Leu | Tyr | Pro |
|  |  |  | 115 |  |  |  | 120 |  |  |  | 125 |  |  |

Cys Thr Tyr Phe Tyr Gly Pro Thr Pro Asp Ile Leu Pro Val Val Thr
    130            135          140

Arg Asn Leu Asn Ala Ile Glu Ser Leu Trp Val Gly Val Tyr Arg Val
145            150            155            160

Gly Glu Gly Asn Trp Thr Ser Leu Asp Gly Gly Thr Phe Lys Val Tyr
          165            170            175

Gln Ile Phe Gly Ser His Cys Thr Tyr Val Ser Lys Phe Ser Thr Val
        180            185            190

Pro Val Ser His His Glu Cys Ser Phe Leu Lys Pro Cys Leu Cys Val
        195            200            205

Ser Gln Arg Ser Asn Ser
    210

<210> SEQ ID NO 131
<211> LENGTH: 414
<212> TYPE: DNA
<213> ORGANISM: Epstein Barr Virus

<400> SEQUENCE: 131

| atgcgggccg | tggggtgtt | cctggctatc | tgcctggtga | ctattttgt | gctgccaacc | 60 |
| tggggaaact | gggcttaccc | ttgctgtcac | gtgacccagc | tcagggccca | gcatctgctg | 120 |
| gctctggaga | acatcagcga | catttatctg | gtgtccaatc | agacatgcga | tgggttcagc | 180 |
| ctggcctccc | tgaacagccc | caagaacgga | tctaatcagc | tcgtgatctc | ccggtgtgct | 240 |
| aacggcctga | atgtcgtgag | tttctttatc | tcaattctga | aaggagctc | ctctgctctg | 300 |
| acaggacacc | tgagggagct | gctgaccaca | ctggaaactc | tgtacggaag | tttctcagtg | 360 |
| gaagacctgt | ttggcgccaa | cctgaatcgg | tatgcttggc | atagaggcgg | gtga | 414 |

<210> SEQ ID NO 132
<211> LENGTH: 137
<212> TYPE: PRT
<213> ORGANISM: Epstein Barr Virus

<400> SEQUENCE: 132

Met Arg Ala Val Gly Val Phe Leu Ala Ile Cys Leu Val Thr Ile Phe
1            5                10              15

Val Leu Pro Thr Trp Gly Asn Trp Ala Tyr Pro Cys Cys His Val Thr
        20            25            30

Gln Leu Arg Ala Gln His Leu Leu Ala Leu Glu Asn Ile Ser Asp Ile
          35            40            45

Tyr Leu Val Ser Asn Gln Thr Cys Asp Gly Phe Ser Leu Ala Ser Leu
    50            55            60

Asn Ser Pro Lys Asn Gly Ser Asn Gln Leu Val Ile Ser Arg Cys Ala
65            70            75            80

Asn Gly Leu Asn Val Val Ser Phe Phe Ile Ser Ile Leu Lys Arg Ser
        85            90            95

Ser Ser Ala Leu Thr Gly His Leu Arg Glu Leu Leu Thr Thr Leu Glu
          100           105          110

Thr Leu Tyr Gly Ser Phe Ser Val Glu Asp Leu Phe Gly Ala Asn Leu
        115           120          125

Asn Arg Tyr Ala Trp His Arg Gly Gly
        130           135

<210> SEQ ID NO 133
<211> LENGTH: 1458
<212> TYPE: DNA
<213> ORGANISM: Artificial Sequence
<220> FEATURE:
<223> OTHER INFORMATION: Synthetic

<400> SEQUENCE: 133

```
atgcccatgg gcagcctgca gcccctggcc accctgtacc tgctgggcat gctggtggct    60
agcatggagt tcctgaagag gagcttcgcc cctctgaccg agaagcagtg gcaggagatc   120
gacaacaggg ccagggagat cttcaagacc cagctgtacg caggaagtt cgtggacgtg   180
gagggcccct acggctggga gtacgccgcc accccctgg gcgaggtgga ggtgctgagc   240
gacgagaacg aggtggtgaa gtggggcctg aggaagagcc tgcccctgat cgagctgagg   300
gccaccttca ccctggacct gtgggagctg acaacctgg agggggcaa gcccaacgtg   360
gacctgagca gcctggagga gaccgtgagg aaggtggccg agttcgagga cgaggtgatc   420
ttcaggggct gcgagaagag cggcgtgaag ggcctgctga gcttcgagga gaggaagatc   480
gagtgcggca gcacccccaa ggacctgctg gaggccatcg tgagggccct gagcatcttc   540
agcaaggacg gcatcgaggg ccccta cacc ctggtgatca acaccgacag gtggatcaac   600
ttcctgaagg aggaggccgg ccactacccc ctggagaaga gggtggagga gtgcctgagg   660
ggcggcaaga tcatcaccac ccccaggatc gaggacgccc tggtggtgag cgagaggggc   720
ggcgacttca gctgatcct gggccaggac ctgagcatcg gctacgagga cagggagaag   780
gacgccgtga ggctgttcat caccgagacc ttcaccttcc aggtggtgaa ccccgaggcc   840
ctgatcctgc tgaagtccgg atctggcggc ggtagcggcg gtggcggagg aagagtggcc   900
gctgccgcta tcacctgggt gccaaaacct aatgtggaag tgtggcctgt ggacccacca   960
cctccagtga actttaataa gacagccgag caggaatatg cgataaaga agtgaagctg  1020
cctcactgga ccccaacact gcatacattc caggtgccac agaactacac taaagctaat  1080
tgcacttatt gtaacaccag ggagtacaca tttagttata agggtgctg tttctacttt  1140
actaagaaaa agcacacctg gaatggatgc ttccaggcct gtgctgaact gtatccatgc  1200
acatactttt atggcccaac tcccgacatc ctgcccgtgg tgaccaggaa cctgaatgcc  1260
attgagtccc tgtgggtggg agtgtacagg gtgggagaag caactggac ctcccctggat  1320
ggcgggacat tcaaagtgta ccagattttt ggctctcatt gcacttatgt gtctaagttc  1380
agtaccgtgc ccgtgtcaca ccatgagtgt agctttctga gccttgcct gtgtgtgtct  1440
cagagaagca actcctga                                                 1458
```

<210> SEQ ID NO 134
<211> LENGTH: 485
<212> TYPE: PRT
<213> ORGANISM: Artificial Sequence
<220> FEATURE:
<223> OTHER INFORMATION: Synthetic

<400> SEQUENCE: 134

```
Met Pro Met Gly Ser Leu Gln Pro Leu Ala Thr Leu Tyr Leu Leu Gly
1               5                   10                  15

Met Leu Val Ala Ser Met Glu Phe Leu Lys Arg Ser Phe Ala Pro Leu
            20                  25                  30

Thr Glu Lys Gln Trp Gln Glu Ile Asp Asn Arg Ala Arg Glu Ile Phe
        35                  40                  45
```

-continued

```
Lys Thr Gln Leu Tyr Gly Arg Lys Phe Val Asp Val Glu Gly Pro Tyr
     50                  55                  60

Gly Trp Glu Tyr Ala Ala His Pro Leu Gly Glu Val Glu Val Leu Ser
 65                  70                  75                  80

Asp Glu Asn Glu Val Val Lys Trp Gly Leu Arg Lys Ser Leu Pro Leu
                     85                  90                  95

Ile Glu Leu Arg Ala Thr Phe Thr Leu Asp Leu Trp Glu Leu Asp Asn
                100                 105                 110

Leu Glu Arg Gly Lys Pro Asn Val Asp Leu Ser Ser Leu Glu Glu Thr
            115                 120                 125

Val Arg Lys Val Ala Glu Phe Glu Asp Glu Val Ile Phe Arg Gly Cys
        130                 135                 140

Glu Lys Ser Gly Val Lys Gly Leu Leu Ser Phe Glu Glu Arg Lys Ile
145                 150                 155                 160

Glu Cys Gly Ser Thr Pro Lys Asp Leu Leu Glu Ala Ile Val Arg Ala
                165                 170                 175

Leu Ser Ile Phe Ser Lys Asp Gly Ile Glu Gly Pro Tyr Thr Leu Val
                180                 185                 190

Ile Asn Thr Asp Arg Trp Ile Asn Phe Leu Lys Glu Glu Ala Gly His
            195                 200                 205

Tyr Pro Leu Glu Lys Arg Val Glu Glu Cys Leu Arg Gly Gly Lys Ile
        210                 215                 220

Ile Thr Thr Pro Arg Ile Glu Asp Ala Leu Val Val Ser Glu Arg Gly
225                 230                 235                 240

Gly Asp Phe Lys Leu Ile Leu Gly Gln Asp Leu Ser Ile Gly Tyr Glu
                245                 250                 255

Asp Arg Glu Lys Asp Ala Val Arg Leu Phe Ile Thr Glu Thr Phe Thr
            260                 265                 270

Phe Gln Val Val Asn Pro Glu Ala Leu Ile Leu Leu Lys Ser Gly Ser
        275                 280                 285

Gly Gly Gly Ser Gly Gly Gly Gly Arg Val Ala Ala Ala Ala Ala Ile
290                 295                 300

Thr Trp Val Pro Lys Pro Asn Val Glu Val Trp Pro Val Asp Pro Pro
305                 310                 315                 320

Pro Pro Val Asn Phe Asn Lys Thr Ala Glu Gln Glu Tyr Gly Asp Lys
                325                 330                 335

Glu Val Lys Leu Pro His Trp Thr Pro Thr Leu His Thr Phe Gln Val
            340                 345                 350

Pro Gln Asn Tyr Thr Lys Ala Asn Cys Thr Tyr Cys Asn Thr Arg Glu
        355                 360                 365

Tyr Thr Phe Ser Tyr Lys Gly Cys Cys Phe Tyr Phe Thr Lys Lys Lys
    370                 375                 380

His Thr Trp Asn Gly Cys Phe Gln Ala Cys Ala Glu Leu Tyr Pro Cys
385                 390                 395                 400

Thr Tyr Phe Tyr Gly Pro Thr Pro Asp Ile Leu Pro Val Val Thr Arg
                405                 410                 415

Asn Leu Asn Ala Ile Glu Ser Leu Trp Val Gly Val Tyr Arg Val Gly
            420                 425                 430

Glu Gly Asn Trp Thr Ser Leu Asp Gly Gly Thr Phe Lys Val Tyr Gln
        435                 440                 445

Ile Phe Gly Ser His Cys Thr Tyr Val Ser Lys Phe Ser Thr Val Pro
    450                 455                 460
```

Val Ser His His Glu Cys Ser Phe Leu Lys Pro Cys Leu Cys Val Ser
465                 470                 475                 480

Gln Arg Ser Asn Ser
            485

<210> SEQ ID NO 135
<211> LENGTH: 2040
<212> TYPE: DNA
<213> ORGANISM: Artificial Sequence
<220> FEATURE:
<223> OTHER INFORMATION: Synthetic

<400> SEQUENCE: 135

| | | | | |
|---|---|---|---|---|
| atgcagctcc | tgtgcgtgtt | ctgtctggtg | ctgctgtggg | aagtgggagc cgcttctctg | 60 |
| agtgaggtga | agctgcacct | ggacattgaa | ggccacgcct | cccattacac tatcccttgg | 120 |
| accgagctga | tggctaaagt | gccaggactg | tctcctgagg | ctctgtggcg ggaagctaat | 180 |
| gtgaccgagg | atctggcctc | tatgctgaac | agatacaagc | tgatctataa aaccagtggc | 240 |
| acactgggga | ttgctctggc | tgagccagtg | acatccccg | ccgtgtcaga aggaagcatg | 300 |
| caggtggatg | ctagtaaggt | gcatccaggg | gtgattagcg | gactgaacag cccagcttgc | 360 |
| atgctgagcg | ctcctctgga | gaaacagctc | ttctactata | tcggcaccat gctgcctaat | 420 |
| acacggccac | acagctacgt | gttttatcag | ctcagatgtc | atctgtccta cgtggccctg | 480 |
| tctattaacg | gggacaagtt | ccagtataca | ggagctatga | cttccaaatt tctgatggga | 540 |
| acttacaagc | gggtgaccga | gaaaggcgat | gaacacgtgc | tgtctctggt gttcgggaag | 600 |
| acaaaagacc | tgcccgatct | gagaggaccc | ttttcctacc | cttctctgac tagtgcccag | 660 |
| tcaggcgact | atagcctggt | gatcgtgacc | acattcgtgc | actacgctaa cttccataat | 720 |
| tattttgtgc | ccaatctgaa | ggatatgttt | tcccggccg | tgaccatgac agccgcttct | 780 |
| tacgctagat | atgtgctgca | gaagctggtg | ctgctggaga | tgaaaggcgg gtgccgggag | 840 |
| cctgaactgg | acactgaaac | cctgactacc | atgttcgagg | tgtccgtggc cttctttaaa | 900 |
| gtgggacacg | ctgtgggaga | gacaggaaac | ggatgcgtgg | acctgagatg gctggccaag | 960 |
| agcttctttg | aactgaccgt | gctgaaagat | atcattggaa | tctgttacgg cgccacagtg | 1020 |
| aaaggaatgc | agagctatgg | cctggagagg | ctggccgcta | tgctgatggc caccgtgaag | 1080 |
| atggaggaac | tgggccacct | gacaactgag | aaacaggaat | acgctctgag gctggctacc | 1140 |
| gtgggatacc | caaaggccgg | ggtgtattcc | ggactgattg | gaggcgccac atctgtgctg | 1200 |
| ctgagtgctt | ataataggca | cccactgttc | cagcccctgc | atacagtgat gcgcgagact | 1260 |
| ctgtttatcg | ggtctcatgt | ggtgctgcgg | gaactgagac | tgaatgtgac cacacaggga | 1320 |
| cccaacctgg | ccctgtacca | gctcctgagt | actgccctgt | gctcagctct ggagattgga | 1380 |
| gaagtgctga | ggggactggc | cctggggacc | gagtcaggac | tgttcagccc ttgttatctg | 1440 |
| tcactgaggt | ttgacctgac | tcgcgataag | ctgctgagca | tggccccaca ggaagctacc | 1500 |
| ctggaccagc | ccgctgtgag | caatgccgtg | gatggattcc | tgggcaggct gtccctggag | 1560 |
| agggaagacc | gcgatgcctg | gcacctgcca | gcttacaagt | gcgtggaccg cctggataaa | 1620 |
| gtgctgatga | tcattcccct | gatcaacgtg | accttcatca | ttagctccga cagggaagtg | 1680 |
| agaggcagcg | ctctgtacga | agcttccact | acctatctgt | ctagttcact gtttctgtca | 1740 |
| cctgtgatta | tgaataagtg | tagccaggga | gctgtggctg | gagagcccag acagatccca | 1800 |
| aagattcaga | acttcacacg | cactcagaaa | agttgcatct | tctgtggctt tgccctgctg | 1860 |
| tcatacgatg | agaaagaagg | gctggagaca | actacctata | ttacatctca ggaagtgcag | 1920 |

```
aacagtatcc tgagctccaa ttacttcgac tttgataacc tgcacgtgca ttatctgctg   1980
ctgacaacta acggcaccgt gatggagatc gctggactgt acgaggaaag ggctcactga   2040
```

<210> SEQ ID NO 136
<211> LENGTH: 679
<212> TYPE: PRT
<213> ORGANISM: Artificial Sequence
<220> FEATURE:
<223> OTHER INFORMATION: Synthetic

<400> SEQUENCE: 136

```
Met Gln Leu Leu Cys Val Phe Cys Leu Val Leu Leu Trp Glu Val Gly
1               5                   10                  15

Ala Ala Ser Leu Ser Glu Val Lys Leu His Leu Asp Ile Glu Gly His
            20                  25                  30

Ala Ser His Tyr Thr Ile Pro Trp Thr Glu Leu Met Ala Lys Val Pro
        35                  40                  45

Gly Leu Ser Pro Glu Ala Leu Trp Arg Glu Ala Asn Val Thr Glu Asp
    50                  55                  60

Leu Ala Ser Met Leu Asn Arg Tyr Lys Leu Ile Tyr Lys Thr Ser Gly
65                  70                  75                  80

Thr Leu Gly Ile Ala Leu Ala Glu Pro Val Asp Ile Pro Ala Val Ser
                85                  90                  95

Glu Gly Ser Met Gln Val Asp Ala Ser Lys Val His Pro Gly Val Ile
            100                 105                 110

Ser Gly Leu Asn Ser Pro Ala Cys Met Leu Ser Ala Pro Leu Glu Lys
        115                 120                 125

Gln Leu Phe Tyr Tyr Ile Gly Thr Met Leu Pro Asn Thr Arg Pro His
    130                 135                 140

Ser Tyr Val Phe Tyr Gln Leu Arg Cys His Leu Ser Tyr Val Ala Leu
145                 150                 155                 160

Ser Ile Asn Gly Asp Lys Phe Gln Tyr Thr Gly Ala Met Thr Ser Lys
                165                 170                 175

Phe Leu Met Gly Thr Tyr Lys Arg Val Thr Glu Lys Gly Asp Glu His
            180                 185                 190

Val Leu Ser Leu Val Phe Gly Lys Thr Lys Asp Leu Pro Asp Leu Arg
        195                 200                 205

Gly Pro Phe Ser Tyr Pro Ser Leu Thr Ser Ala Gln Ser Gly Asp Tyr
    210                 215                 220

Ser Leu Val Ile Val Thr Thr Phe Val His Tyr Ala Asn Phe His Asn
225                 230                 235                 240

Tyr Phe Val Pro Asn Leu Lys Asp Met Phe Ser Arg Ala Val Thr Met
                245                 250                 255

Thr Ala Ala Ser Tyr Ala Arg Tyr Val Leu Gln Lys Leu Val Leu Leu
            260                 265                 270

Glu Met Lys Gly Gly Cys Arg Glu Pro Glu Leu Asp Thr Glu Thr Leu
        275                 280                 285

Thr Thr Met Phe Glu Val Ser Val Ala Phe Phe Lys Val Gly His Ala
    290                 295                 300

Val Gly Glu Thr Gly Asn Gly Cys Val Asp Leu Arg Trp Leu Ala Lys
305                 310                 315                 320

Ser Phe Phe Glu Leu Thr Val Leu Lys Asp Ile Ile Gly Ile Cys Tyr
                325                 330                 335

Gly Ala Thr Val Lys Gly Met Gln Ser Tyr Gly Leu Glu Arg Leu Ala
```

```
              340                 345                 350
Ala Met Leu Met Ala Thr Val Lys Met Glu Glu Leu Gly His Leu Thr
            355                 360                 365

Thr Glu Lys Gln Glu Tyr Ala Leu Arg Leu Ala Thr Val Gly Tyr Pro
        370                 375                 380

Lys Ala Gly Val Tyr Ser Gly Leu Ile Gly Ala Thr Ser Val Leu
385                 390                 395                 400

Leu Ser Ala Tyr Asn Arg His Pro Leu Phe Gln Pro Leu His Thr Val
                405                 410                 415

Met Arg Glu Thr Leu Phe Ile Gly Ser His Val Val Leu Arg Glu Leu
            420                 425                 430

Arg Leu Asn Val Thr Thr Gln Gly Pro Asn Leu Ala Leu Tyr Gln Leu
        435                 440                 445

Leu Ser Thr Ala Leu Cys Ser Ala Leu Glu Ile Gly Glu Val Leu Arg
    450                 455                 460

Gly Leu Ala Leu Gly Thr Glu Ser Gly Leu Phe Ser Pro Cys Tyr Leu
465                 470                 475                 480

Ser Leu Arg Phe Asp Leu Thr Arg Asp Lys Leu Leu Ser Met Ala Pro
                485                 490                 495

Gln Glu Ala Thr Leu Asp Gln Ala Ala Val Ser Asn Ala Val Asp Gly
            500                 505                 510

Phe Leu Gly Arg Leu Ser Leu Glu Arg Glu Asp Arg Asp Ala Trp His
        515                 520                 525

Leu Pro Ala Tyr Lys Cys Val Asp Arg Leu Asp Lys Val Leu Met Ile
    530                 535                 540

Ile Pro Leu Ile Asn Val Thr Phe Ile Ile Ser Ser Asp Arg Glu Val
545                 550                 555                 560

Arg Gly Ser Ala Leu Tyr Glu Ala Ser Thr Thr Tyr Leu Ser Ser Ser
                565                 570                 575

Leu Phe Leu Ser Pro Val Ile Met Asn Lys Cys Ser Gln Gly Ala Val
            580                 585                 590

Ala Gly Glu Pro Arg Gln Ile Pro Lys Ile Gln Asn Phe Thr Arg Thr
        595                 600                 605

Gln Lys Ser Cys Ile Phe Cys Gly Phe Ala Leu Leu Ser Tyr Asp Glu
    610                 615                 620

Lys Glu Gly Leu Glu Thr Thr Tyr Ile Thr Ser Gln Glu Val Gln
625                 630                 635                 640

Asn Ser Ile Leu Ser Ser Asn Tyr Phe Asp Phe Asp Asn Leu His Val
                645                 650                 655

His Tyr Leu Leu Leu Thr Thr Asn Gly Thr Val Met Glu Ile Ala Gly
            660                 665                 670

Leu Tyr Glu Glu Arg Ala His
        675

<210> SEQ ID NO 137
<211> LENGTH: 84
<212> TYPE: DNA
<213> ORGANISM: Picornavirus

<400> SEQUENCE: 137
agcgggtccg gagctccagt gaaacagacc ctgaactttg acctgctgaa gctggcaggg      60
gatgtggaga gcaatcctgg ccca                                            84

<210> SEQ ID NO 138
```

```
<211> LENGTH: 28
<212> TYPE: PRT
<213> ORGANISM: Picornavirus

<400> SEQUENCE: 138

Ser Gly Ser Gly Ala Pro Val Lys Gln Thr Leu Asn Phe Asp Leu Leu
1               5                   10                  15

Lys Leu Ala Gly Asp Val Glu Ser Asn Pro Gly Pro
            20                  25

<210> SEQ ID NO 139
<211> LENGTH: 72
<212> TYPE: DNA
<213> ORGANISM: Homo sapiens

<400> SEQUENCE: 139
atgccaatgg gcagcctgca gccactggca actctgtacc tgctgggaat gctggtggca      60
tccgtcctgg ca                                                         72

<210> SEQ ID NO 140
<211> LENGTH: 24
<212> TYPE: PRT
<213> ORGANISM: Homo sapiens

<400> SEQUENCE: 140

Met Pro Met Gly Ser Leu Gln Pro Leu Ala Thr Leu Tyr Leu Leu Gly
1               5                   10                  15

Met Leu Val Ala Ser Val Leu Ala
            20

<210> SEQ ID NO 141
<211> LENGTH: 3087
<212> TYPE: DNA
<213> ORGANISM: Artificial Sequence
<220> FEATURE:
<223> OTHER INFORMATION: NAM encoding ferritin-gH-F2A-gL

<400> SEQUENCE: 141
atgcagctgc tgtgtgtgtt ctgtctggtc ctgctgtggg aagtcggagc cgcctctctg      60
agcgaagtga aactgcacct ggatattgaa gggcacgcct tcattacac catcccttgg      120 acagagctga tggctaaggt gcctggactg agtccagaag ctctgtgccg cgaggcaaac      180
gtgaccgaag acctggcctc catgctgaat cgatacaaac tgatctacaa gacatctggg      240
actctgggaa tcgccctggc tgaacccgtg acattcctg ctgtcagtga gggctcaatg      300
caggtggatg caagcaaagt gcacccagga gtcatctctg gcctgaacag tcccgcctgc      360
atgctgtccg ctcctctgga aagcagctg ttctactata ttgggacaat gctgccaaac      420
actagacccc acagctacgt gttttatcag ctgaggtgtc atctgagcta cgtcgcactg      480
tccatcaatg agacaaaatt ccagtatact ggcgccatga cctctaagtt tctgatggga      540
acctacaaaa gggtgacaga aagggcgat gagcacgtgc tgagcctggt cttcggcaaa      600
accaaggacc tgcccgatct gcgcgggcct tttagctacc atccctgac atctgcccag      660 agtggcgact atagcctggt catcgtcacc acattcgtgc actacgctaa cttccataat      720
tattttgtcc ctaacctgaa ggatatgttt ccagggcag tgactatgac cgccgcttct      780
tacgcccgct atgtgctgca gaaactggtc ctgctggaga tgaagggagg atgccgagaa      840
ccagagctgg acacagaaac tctgactacc atgttcgagg tgtccgtcgc tttctttaaa      900
gtggggcacg cagtcggaga aacaggcaat gggtgcgtgg acctgagatg gctggccaaa      960
```

```
agcttctttg agctgaccgt gctgaaggat atcattggca tctgttacgg ggctacagtc   1020
aagggcatgc agtcctatgg gctggagcgg ctggcagcca tgctgatggc caccgtgaaa   1080
atggaggaac tgggacacct gacaactgaa aagcaggagt acgccctgag actggctact   1140
gtgggctacc caaaggccgg agtctatagc ggactgatcg gaggagcaac ctcagtgctg   1200
ctgagcgctt ataaccgaca ccccctgttc cagcctctgc atactgtgat gcgggaaacc   1260
ctgtttattg gctcccatgt ggtcctgcga gagctgcggc tgaacgtgac cacacagggg   1320
cccaatctgg ctctgtacca gctgctgtct acagcactgt gcagtgccct ggaaatcgga   1380
gaggtgctga ggggactggc actgggaact gaatccggac tgttctctcc ctgttatctg   1440
agtctgaggt ttgacctgac tcgcgataag ctgctgtcaa tggctcctca ggaggcaacc   1500
ctggaccagg ctgcagtgtc aaacgcagtc gatggcttcc tgggacgact gagcctggaa   1560
agagaggaca gggatgcatg gcacctgcct gcctacaaat gcgtggacag actggataag   1620
gtcctgatga tcattccact gatcaatgtg accttcatca ttagctccga ccgagaagtc   1680
cgaggctccg cactgtacga ggcttctact acctatctgt ctagttcact gtttctgtca   1740
cccgtgatca tgaacaaatg tagccaggga gcagtcgcag agagccacg acagatcccc    1800 aaaattcaga atttcacccg aacacagaag tcttgcattt tctgtggatt tgccctgctg   1860
agttacgatg aaaaggaggg cctggaaaca actacctata tcacaagtca ggaggtgcag   1920
aattcaattc tgagctccaa ctacttcgac tttgataatc tgcacgtgca ttatctgctg   1980
ctgacaacta cgggaccgt catggaaatc gcaggactgt acgaggaaag agcacactca    2040
ggaggaagcg gagagtccca ggtgaggcag cagttctcta aagacattga aagctgctg    2100 aacgaacaag tgaataagga gatgcagtct agtaacctgt acatgagtat gtcaagctgg   2160 tgctatacccc actcactgga cggagcaggc ctgttcctgt tgatcacgc cgctgaggaa   2220 tacgaacatg ccaagaaact gatcattttt ctgaacgaga acaacgtgcc tgtccagctg   2280
acatcaatca gcgctccaga acataaattc gagggcctga ctcagatctt tcagaaggca   2340
tacgaacacg agcagcatat ttccgaatct atcaacaata ttgtggacca cgccatcaag   2400
agcaaggatc atgcaacctt caatttctg cagtggtacg tggccgagca gcacgaggaa    2460
gaggtcctgt tcaaagacat cctggataag atcgaactga ttggaaacga gaatcatggc   2520
ctgtacctgg ccgatcagta tgtgaaaggc attgctaaat ctcgaaagag tgggtcacgg   2580
aagcgaagaa gcgggtccgg agctccagtg aaacagaccc tgaactttga cctgctgaag   2640
ctggcagggg atgtggagag caatcctggc ccaatgaggg ccgtggggt cttcctggct    2700 atctgtctgg tgaccatttt tgtcctgcca acatgggaa actgggccta cccatgctgt    2760
cacgtgaccc agctgcgagc tcagcatctg ctggcactgg agaacatcag cgacatctac   2820
ctggtgagca atcagacatg cgatgggttc tctctggcca gtctgaattc acctaaaaac   2880
ggatctaatc agctggtcat cagtaggtgt gctaacggcc tgaatgtggt cagtttcttt   2940
atctcaattc tgaagcggtc ctctagtgcc ctgacaggcc acctgagaga actgctgacc   3000
acactggaga ctctgtacgg gtctttcagt gtggaggacc tgtttggagc aaacctgaat   3060
cgctatgcat ggcatcgagg aggatga                                      3087
```

<210> SEQ ID NO 142
<211> LENGTH: 1028
<212> TYPE: PRT
<213> ORGANISM: Artificial Sequence
<220> FEATURE:

<223> OTHER INFORMATION: Protein encoded by SEQ ID NO:141 (ferritin-gH-F2A-gL)

<400> SEQUENCE: 142

| | | | | | | | | | | | | | | |
|---|---|---|---|---|---|---|---|---|---|---|---|---|---|---|
| Met | Gln | Leu | Leu | Cys | Val | Phe | Cys | Leu | Val | Leu | Leu | Trp | Glu | Val | Gly |
| 1 | | | | 5 | | | | | 10 | | | | | 15 | |
| Ala | Ala | Ser | Leu | Ser | Glu | Val | Lys | Leu | His | Leu | Asp | Ile | Glu | Gly | His |
| | | | 20 | | | | | 25 | | | | | 30 | | |
| Ala | Ser | His | Tyr | Thr | Ile | Pro | Trp | Thr | Glu | Leu | Met | Ala | Lys | Val | Pro |
| | | 35 | | | | | 40 | | | | | 45 | | | |
| Gly | Leu | Ser | Pro | Glu | Ala | Leu | Trp | Arg | Glu | Ala | Asn | Val | Thr | Glu | Asp |
| | 50 | | | | | 55 | | | | | 60 | | | | |
| Leu | Ala | Ser | Met | Leu | Asn | Arg | Tyr | Lys | Leu | Ile | Tyr | Lys | Thr | Ser | Gly |
| 65 | | | | | 70 | | | | | 75 | | | | | 80 |
| Thr | Leu | Gly | Ile | Ala | Leu | Ala | Glu | Pro | Val | Asp | Ile | Pro | Ala | Val | Ser |
| | | | | 85 | | | | | 90 | | | | | 95 | |
| Glu | Gly | Ser | Met | Gln | Val | Asp | Ala | Ser | Lys | Val | His | Pro | Gly | Val | Ile |
| | | | 100 | | | | | 105 | | | | | 110 | | |
| Ser | Gly | Leu | Asn | Ser | Pro | Ala | Cys | Met | Leu | Ser | Ala | Pro | Leu | Glu | Lys |
| | | 115 | | | | | 120 | | | | | 125 | | | |
| Gln | Leu | Phe | Tyr | Tyr | Ile | Gly | Thr | Met | Leu | Pro | Asn | Thr | Arg | Pro | His |
| | 130 | | | | | 135 | | | | | 140 | | | | |
| Ser | Tyr | Val | Phe | Tyr | Gln | Leu | Arg | Cys | His | Leu | Ser | Tyr | Val | Ala | Leu |
| 145 | | | | | 150 | | | | | 155 | | | | | 160 |
| Ser | Ile | Asn | Gly | Asp | Lys | Phe | Gln | Tyr | Thr | Gly | Ala | Met | Thr | Ser | Lys |
| | | | | 165 | | | | | 170 | | | | | 175 | |
| Phe | Leu | Met | Gly | Thr | Tyr | Lys | Arg | Val | Thr | Glu | Lys | Gly | Asp | Glu | His |
| | | | 180 | | | | | 185 | | | | | 190 | | |
| Val | Leu | Ser | Leu | Val | Phe | Gly | Lys | Thr | Lys | Asp | Leu | Pro | Asp | Leu | Arg |
| | | 195 | | | | | 200 | | | | | 205 | | | |
| Gly | Pro | Phe | Ser | Tyr | Pro | Ser | Leu | Thr | Ser | Ala | Gln | Ser | Gly | Asp | Tyr |
| | 210 | | | | | 215 | | | | | 220 | | | | |
| Ser | Leu | Val | Ile | Val | Thr | Thr | Phe | Val | His | Tyr | Ala | Asn | Phe | His | Asn |
| 225 | | | | | 230 | | | | | 235 | | | | | 240 |
| Tyr | Phe | Val | Pro | Asn | Leu | Lys | Asp | Met | Phe | Ser | Arg | Ala | Val | Thr | Met |
| | | | | 245 | | | | | 250 | | | | | 255 | |
| Thr | Ala | Ala | Ser | Tyr | Ala | Arg | Tyr | Val | Leu | Gln | Lys | Leu | Val | Leu | Leu |
| | | | 260 | | | | | 265 | | | | | 270 | | |
| Glu | Met | Lys | Gly | Gly | Cys | Arg | Glu | Pro | Glu | Leu | Asp | Thr | Glu | Thr | Leu |
| | | 275 | | | | | 280 | | | | | 285 | | | |
| Thr | Thr | Met | Phe | Glu | Val | Ser | Val | Ala | Phe | Phe | Lys | Val | Gly | His | Ala |
| | 290 | | | | | 295 | | | | | 300 | | | | |
| Val | Gly | Glu | Thr | Gly | Asn | Gly | Cys | Val | Asp | Leu | Arg | Trp | Leu | Ala | Lys |
| 305 | | | | | 310 | | | | | 315 | | | | | 320 |
| Ser | Phe | Phe | Glu | Leu | Thr | Val | Leu | Lys | Asp | Ile | Ile | Gly | Ile | Cys | Tyr |
| | | | | 325 | | | | | 330 | | | | | 335 | |
| Gly | Ala | Thr | Val | Lys | Gly | Met | Gln | Ser | Tyr | Gly | Leu | Glu | Arg | Leu | Ala |
| | | | 340 | | | | | 345 | | | | | 350 | | |
| Ala | Met | Leu | Met | Ala | Thr | Val | Lys | Met | Glu | Glu | Leu | Gly | His | Leu | Thr |
| | | 355 | | | | | 360 | | | | | 365 | | | |
| Thr | Glu | Lys | Gln | Glu | Tyr | Ala | Leu | Arg | Leu | Ala | Thr | Val | Gly | Tyr | Pro |
| | 370 | | | | | 375 | | | | | 380 | | | | |
| Lys | Ala | Gly | Val | Tyr | Ser | Gly | Leu | Ile | Gly | Gly | Ala | Thr | Ser | Val | Leu |
| 385 | | | | | 390 | | | | | 395 | | | | | 400 |

```
Leu Ser Ala Tyr Asn Arg His Pro Leu Phe Gln Pro Leu His Thr Val
                405                 410                 415

Met Arg Glu Thr Leu Phe Ile Gly Ser His Val Val Leu Arg Glu Leu
            420                 425                 430

Arg Leu Asn Val Thr Thr Gln Gly Pro Asn Leu Ala Leu Tyr Gln Leu
            435                 440                 445

Leu Ser Thr Ala Leu Cys Ser Ala Leu Glu Ile Gly Glu Val Leu Arg
        450                 455                 460

Gly Leu Ala Leu Gly Thr Glu Ser Gly Leu Phe Ser Pro Cys Tyr Leu
465                 470                 475                 480

Ser Leu Arg Phe Asp Leu Thr Arg Asp Lys Leu Leu Ser Met Ala Pro
                485                 490                 495

Gln Glu Ala Thr Leu Asp Gln Ala Ala Val Ser Asn Ala Val Asp Gly
            500                 505                 510

Phe Leu Gly Arg Leu Ser Leu Glu Arg Glu Asp Arg Asp Ala Trp His
            515                 520                 525

Leu Pro Ala Tyr Lys Cys Val Asp Arg Leu Asp Lys Val Leu Met Ile
        530                 535                 540

Ile Pro Leu Ile Asn Val Thr Phe Ile Ile Ser Ser Asp Arg Glu Val
545                 550                 555                 560

Arg Gly Ser Ala Leu Tyr Glu Ala Ser Thr Thr Tyr Leu Ser Ser Ser
                565                 570                 575

Leu Phe Leu Ser Pro Val Ile Met Asn Lys Cys Ser Gln Gly Ala Val
            580                 585                 590

Ala Gly Glu Pro Arg Gln Ile Pro Lys Ile Gln Asn Phe Thr Arg Thr
            595                 600                 605

Gln Lys Ser Cys Ile Phe Cys Gly Phe Ala Leu Leu Ser Tyr Asp Glu
        610                 615                 620

Lys Glu Gly Leu Glu Thr Thr Thr Tyr Ile Thr Ser Gln Glu Val Gln
625                 630                 635                 640

Asn Ser Ile Leu Ser Ser Asn Tyr Phe Asp Phe Asp Asn Leu His Val
                645                 650                 655

His Tyr Leu Leu Leu Thr Thr Asn Gly Thr Val Met Glu Ile Ala Gly
            660                 665                 670

Leu Tyr Glu Glu Arg Ala His Ser Gly Gly Ser Gly Glu Ser Gln Val
            675                 680                 685

Arg Gln Gln Phe Ser Lys Asp Ile Glu Lys Leu Leu Asn Glu Gln Val
        690                 695                 700

Asn Lys Glu Met Gln Ser Ser Asn Leu Tyr Met Ser Met Ser Ser Trp
705                 710                 715                 720

Cys Tyr Thr His Ser Leu Asp Gly Ala Gly Leu Phe Leu Phe Asp His
                725                 730                 735

Ala Ala Glu Glu Tyr Glu His Ala Lys Lys Leu Ile Ile Phe Leu Asn
            740                 745                 750

Glu Asn Asn Val Pro Val Gln Leu Thr Ser Ile Ser Ala Pro Glu His
            755                 760                 765

Lys Phe Glu Gly Leu Thr Gln Ile Phe Gln Lys Ala Tyr Glu His Glu
        770                 775                 780

Gln His Ile Ser Glu Ser Ile Asn Asn Ile Val Asp His Ala Ile Lys
785                 790                 795                 800

Ser Lys Asp His Ala Thr Phe Asn Phe Leu Gln Trp Tyr Val Ala Glu
                805                 810                 815
```

Gln His Glu Glu Val Leu Phe Lys Asp Ile Leu Asp Lys Ile Glu
            820                 825                 830

Leu Ile Gly Asn Glu Asn His Gly Leu Tyr Leu Ala Asp Gln Tyr Val
        835                 840                 845

Lys Gly Ile Ala Lys Ser Arg Lys Ser Gly Ser Arg Lys Arg Arg Ser
850                 855                 860

Gly Ser Gly Ala Pro Val Lys Gln Thr Leu Asn Phe Asp Leu Leu Lys
865                 870                 875                 880

Leu Ala Gly Asp Val Glu Ser Asn Pro Gly Pro Met Arg Ala Val Gly
                885                 890                 895

Val Phe Leu Ala Ile Cys Leu Val Thr Ile Phe Val Leu Pro Thr Trp
        900                 905                 910

Gly Asn Trp Ala Tyr Pro Cys Cys His Val Thr Gln Leu Arg Ala Gln
            915                 920                 925

His Leu Leu Ala Leu Glu Asn Ile Ser Asp Ile Tyr Leu Val Ser Asn
        930                 935                 940

Gln Thr Cys Asp Gly Phe Ser Leu Ala Ser Leu Asn Ser Pro Lys Asn
945                 950                 955                 960

Gly Ser Asn Gln Leu Val Ile Ser Arg Cys Ala Asn Gly Leu Asn Val
                965                 970                 975

Val Ser Phe Phe Ile Ser Ile Leu Lys Arg Ser Ser Ser Ala Leu Thr
        980                 985                 990

Gly His Leu Arg Glu Leu Leu Thr  Thr Leu Glu Thr Leu  Tyr Gly Ser
            995                 1000                1005

Phe Ser  Val Glu Asp Leu Phe  Gly Ala Asn Leu Asn  Arg Tyr Ala
    1010                1015                1020

Trp His  Arg Gly Gly
    1025

<210> SEQ ID NO 143
<211> LENGTH: 3825
<212> TYPE: DNA
<213> ORGANISM: Artificial Sequence
<220> FEATURE:
<223> OTHER INFORMATION: NAM encoding ferritin-gH-F2A-gL-F2A-gp42

<400> SEQUENCE: 143
atgcagctgc tgtgtgtgtt ctgtctggtc ctgctgtggg aagtcggagc cgcctctctg      60
agcgaagtga aactgcacct ggatattgaa gggcacgcct ctcattacac catcccttgg     120
acagagctga tggctaaggt gcctggactg agtccagaag ctctgtggcg cgaggcaaac     180
gtgaccgaag acctggcctc catgctgaat cgatacaaac tgatctacaa gacatctggg     240
actctgggaa tcgccctggc tgaacccgtg acattcctg ctgtcagtga gggctcaatg      300
caggtggatg caagcaaagt gcacccagga gtcatctctg gcctgaacag tcccgcctgc     360
atgctgtccg ctcctctgga gaagcagctg ttctactata ttgggacaat gctgccaaac     420
actagacccc acagctacgt gtttttatcag ctgaggtgtc atctgagcta cgtcgcactg     480
tccatcaatg gagacaaatt ccagtatact ggcgccatga cctctaagtt tctgatggga     540
acctacaaaa gggtgacaga aaagggcgat gagcacgtgc tgagcctggt cttcggcaaa     600
accaaggacc tgcccgatct cgcgcgggcct tttagctacc atccctgac atctgcccag     660 agtggcgact atagcctggt catcgtcacc acattcgtgc actacgctaa cttccataat     720 tatttttgtcc ctaacctgaa ggatatgttt tccagggcag tgactatgac cgccgcttct     780
tacgcccgct atgtgctgca gaaactggtc ctgctggaga tgaagggagg atgccgagaa     840

```
ccagagctgg acacagaaac tctgactacc atgttcgagg tgtccgtcgc tttctttaaa    900
gtggggcacg cagtcggaga acaggcaat  gggtgcgtgg acctgagatg gctggccaaa    960
agcttctttg agctgaccgt gctgaaggat atcattggca tctgttacgg gctacagtc    1020
aagggcatgc agtcctatgg gctggagcgg ctggcagcca tgctgatggc caccgtgaaa   1080
atggaggaac tgggacacct gacaactgaa aagcaggagt acgccctgag actggctact   1140
gtgggctacc caaaggccgg agtctatagc ggactgatcg gaggagcaac ctcagtgctg   1200
ctgagcgctt ataaccgaca ccccctgttc cagcctctgc atactgtgat gcgggaaacc   1260
ctgtttattg ctcccatgt  ggtcctgcga gagctgcggc tgaacgtgac cacacagggg   1320
cccaatctgg ctctgtacca gctgctgtct acagcactgt gcagtgccct ggaaatcgga   1380
gaggtgctga ggggactggc actgggaact gaatccggac tgttctctcc ctgttatctg   1440
agtctgaggt ttgacctgac tcgcgataag ctgctgtcaa tggctcctca ggaggcaacc   1500
ctggaccagc tgcagtgtc  aaacgcagtc gatggcttcc tggacgact  gagcctggaa   1560
agagaggaca gggatgcatg gcacctgcct gcctacaaat gcgtggacag actggataag   1620
gtcctgatga tcattccact gatcaatgtg accttcatca ttagctccga ccgagaagtc   1680
cgaggctccg cactgtacga ggcttctact acctatctgt ctagttcact gtttctgtca   1740
cccgtgatca tgaacaaatg tagccaggga gcagtcgcag agagccacg  acagatcccc   1800
aaaattcaga atttcacccg aacacagaag tcttgcattt tctgtggatt tgccctgctg   1860
agttacgatg aaaaggaggg cctggaaaca actacctata tcacaagtca ggaggtgcag   1920
aattcaattc tgagctccaa ctacttcgac tttgataatc tgcacgtgca ttatctgctg   1980
ctgacaacta cgggaccgt  catggaaatc gcaggactgt acgaggaaag agcacactca   2040
ggaggaagcg gagagtccca ggtgaggcag cagttctcta aagacattga gaagctgctg   2100
aacgaacaag tgaataagga gatgcagtct agtaacctgt acatgagtat gtcaagctgg   2160
tgctataccc actcactgga cggagcaggc ctgttcctgt tgatcacgc  cgctgaggaa   2220
tacgaacatg ccaagaaact gatcattttt ctgaacgaga caacgtgcc  tgtccagctg   2280
acatcaatca gcgctccaga acataaattc gagggcctga ctcagatctt tcagaaggca   2340
tacgaacacg agcagcatat ttccgaatct atcaacaata ttgtggacca cgccatcaag   2400
agcaaggatc atgcaacctt caattttctg cagtggtacg tggccgagca gcacgaggaa   2460
gaggtcctgt tcaaagacat cctggataag atcgaactga ttggaaacga gaatcatggc   2520
ctgtacctgg ccgatcagta tgtgaaaggc attgctaaat ctcgaaagag tgggtcacgg   2580
aagcgaagaa gcgggtccgg agctccagtg aaacagaccc tgaactttga cctgctgaag   2640
ctggcagggg atgtggagag caatcctggc ccaatgaggg ccgtgggggt cttcctggct   2700
atctgtctgg tgaccatttt tgtcctgcca acatgggaa  actgggccta cccatgctgt   2760
cacgtgaccc agctgcgagc tcagcatctg ctggcactgg agaacatcag cgacatctac   2820
ctggtgagca atcagacatg cgatgggttc tctctggcca gtctgaattc acctaaaaac   2880
ggatctaatc agctggtcat cagtaggtgt gctaacggcc tgaatgtggt cagtttcttt   2940
atctcaattc tgaagcggtc ctctagtgcc ctgacaggcc acctgagaga actgctgacc   3000
acactggaga ctctgtacgg gtctttcagt gtggaggacc tgtttggagc aaacctgaat   3060
cgctatgcat ggcatcgagg aggaagaaag aggcgatcag cagcggagc  acctgtcaaa   3120
cagaccctga acttcgacct gctgaagctg gctggagatg tggagagcaa tcccgggcct   3180
```

-continued

```
atgccaatgg gcagcctgca gccactggca actctgtacc tgctgggaat gctggtggca    3240
tccgtcctgg caggaggacg agtggcagca gctgcaatca catgggtccc caaacctaac    3300
gtggaagtct ggccagtgga ccccctcca ccagtcaact ttaataagac cgccgaacag     3360
gagtatggcg ataaagaggt gaagctgcct cactggactc caaccctgca tactttccag    3420
gtgcctcaga actacaccaa agccaattgc acatattgta acactagaga gtacaccttt    3480
tcttataagg ggtgctgttt ctactttaca aagaaaaagc acacttggaa cggatgcttc    3540
caggcttgtg cagagctgta tccatgcact tactttatg gaccaaccc agacatcctg     3600 ccagtggtca ccaggaacct gaatgccatt gaaagcctgt gggtgggagt ctaccgagtg    3660
ggagagggca attggacaag cctggatggg ggaactttca aagtgtacca gatctttggc    3720
tcccattgca cctatgtcag caagttctcc acagtgcccg tctcacacca tgagtgtagc    3780
tttctgaagc cttgcctgtg tgtgagccag cggtccaact cttga                    3825
```

<210> SEQ ID NO 144
<211> LENGTH: 1274
<212> TYPE: PRT
<213> ORGANISM: Artificial Sequence
<220> FEATURE:
<223> OTHER INFORMATION: Protein encoded by SEQ ID NO:143 (ferritin-gH-F2A-gL-F2A-gp42)

<400> SEQUENCE: 144

```
Met Gln Leu Leu Cys Val Phe Cys Leu Val Leu Leu Trp Glu Val Gly
1               5                   10                  15

Ala Ala Ser Leu Ser Glu Val Lys Leu His Leu Asp Ile Glu Gly His
            20                  25                  30

Ala Ser His Tyr Thr Ile Pro Trp Thr Glu Leu Met Ala Lys Val Pro
        35                  40                  45

Gly Leu Ser Pro Glu Ala Leu Trp Arg Glu Ala Asn Val Thr Glu Asp
    50                  55                  60

Leu Ala Ser Met Leu Asn Arg Tyr Lys Leu Ile Tyr Lys Thr Ser Gly
65                  70                  75                  80

Thr Leu Gly Ile Ala Leu Ala Glu Pro Val Asp Ile Pro Ala Val Ser
                85                  90                  95

Glu Gly Ser Met Gln Val Asp Ala Ser Lys Val His Pro Gly Val Ile
            100                 105                 110

Ser Gly Leu Asn Ser Pro Ala Cys Met Leu Ser Ala Pro Leu Glu Lys
        115                 120                 125

Gln Leu Phe Tyr Tyr Ile Gly Thr Met Leu Pro Asn Thr Arg Pro His
    130                 135                 140

Ser Tyr Val Phe Tyr Gln Leu Arg Cys His Leu Ser Tyr Val Ala Leu
145                 150                 155                 160

Ser Ile Asn Gly Asp Lys Phe Gln Tyr Thr Gly Ala Met Thr Ser Lys
                165                 170                 175

Phe Leu Met Gly Thr Tyr Lys Arg Val Thr Glu Lys Gly Asp Glu His
            180                 185                 190

Val Leu Ser Leu Val Phe Gly Lys Thr Lys Asp Leu Pro Asp Leu Arg
        195                 200                 205

Gly Pro Phe Ser Tyr Pro Ser Leu Thr Ser Ala Gln Ser Gly Asp Tyr
    210                 215                 220

Ser Leu Val Ile Val Thr Thr Phe Val His Tyr Ala Asn Phe His Asn
225                 230                 235                 240

Tyr Phe Val Pro Asn Leu Lys Asp Met Phe Ser Arg Ala Val Thr Met
```

```
                    245                 250                 255
Thr Ala Ala Ser Tyr Ala Arg Tyr Val Leu Gln Lys Leu Val Leu Leu
                260                 265                 270
Glu Met Lys Gly Gly Cys Arg Glu Pro Glu Leu Asp Thr Glu Thr Leu
                275                 280                 285
Thr Thr Met Phe Glu Val Ser Val Ala Phe Phe Lys Val Gly His Ala
            290                 295                 300
Val Gly Glu Thr Gly Asn Gly Cys Val Asp Leu Arg Trp Leu Ala Lys
305                 310                 315                 320
Ser Phe Phe Glu Leu Thr Val Leu Lys Asp Ile Ile Gly Ile Cys Tyr
                325                 330                 335
Gly Ala Thr Val Lys Gly Met Gln Ser Tyr Gly Leu Glu Arg Leu Ala
                340                 345                 350
Ala Met Leu Met Ala Thr Val Lys Met Glu Glu Leu Gly His Leu Thr
                355                 360                 365
Thr Glu Lys Gln Glu Tyr Ala Leu Arg Leu Ala Thr Val Gly Tyr Pro
            370                 375                 380
Lys Ala Gly Val Tyr Ser Gly Leu Ile Gly Gly Ala Thr Ser Val Leu
385                 390                 395                 400
Leu Ser Ala Tyr Asn Arg His Pro Leu Phe Gln Pro Leu His Thr Val
                405                 410                 415
Met Arg Glu Thr Leu Phe Ile Gly Ser His Val Val Leu Arg Glu Leu
                420                 425                 430
Arg Leu Asn Val Thr Thr Gln Gly Pro Asn Leu Ala Leu Tyr Gln Leu
                435                 440                 445
Leu Ser Thr Ala Leu Cys Ser Ala Leu Glu Ile Gly Glu Val Leu Arg
            450                 455                 460
Gly Leu Ala Leu Gly Thr Glu Ser Gly Leu Phe Ser Pro Cys Tyr Leu
465                 470                 475                 480
Ser Leu Arg Phe Asp Leu Thr Arg Asp Lys Leu Leu Ser Met Ala Pro
                485                 490                 495
Gln Glu Ala Thr Leu Asp Gln Ala Ala Val Ser Asn Ala Val Asp Gly
            500                 505                 510
Phe Leu Gly Arg Leu Ser Leu Glu Arg Glu Asp Arg Asp Ala Trp His
            515                 520                 525
Leu Pro Ala Tyr Lys Cys Val Asp Arg Leu Asp Lys Val Leu Met Ile
            530                 535                 540
Ile Pro Leu Ile Asn Val Thr Phe Ile Ile Ser Ser Asp Arg Glu Val
545                 550                 555                 560
Arg Gly Ser Ala Leu Tyr Glu Ala Ser Thr Thr Tyr Leu Ser Ser Ser
                565                 570                 575
Leu Phe Leu Ser Pro Val Ile Met Asn Lys Cys Ser Gln Gly Ala Val
                580                 585                 590
Ala Gly Glu Pro Arg Gln Ile Pro Lys Ile Gln Asn Phe Thr Arg Thr
                595                 600                 605
Gln Lys Ser Cys Ile Phe Cys Gly Phe Ala Leu Leu Ser Tyr Asp Glu
            610                 615                 620
Lys Glu Gly Leu Glu Thr Thr Tyr Ile Thr Ser Gln Glu Val Gln
625                 630                 635                 640
Asn Ser Ile Leu Ser Ser Asn Tyr Phe Asp Phe Asp Asn Leu His Val
                645                 650                 655
His Tyr Leu Leu Leu Thr Thr Asn Gly Thr Val Met Glu Ile Ala Gly
                660                 665                 670
```

-continued

```
Leu Tyr Glu Glu Arg Ala His Ser Gly Gly Ser Gly Glu Ser Gln Val
        675                 680                 685

Arg Gln Gln Phe Ser Lys Asp Ile Glu Lys Leu Leu Asn Glu Gln Val
690                 695                 700

Asn Lys Glu Met Gln Ser Ser Asn Leu Tyr Met Ser Met Ser Ser Trp
705                 710                 715                 720

Cys Tyr Thr His Ser Leu Asp Gly Ala Gly Leu Phe Leu Phe Asp His
                725                 730                 735

Ala Ala Glu Glu Tyr Glu His Ala Lys Lys Leu Ile Ile Phe Leu Asn
                740                 745                 750

Glu Asn Asn Val Pro Val Gln Leu Thr Ser Ile Ser Ala Pro Glu His
                755                 760                 765

Lys Phe Glu Gly Leu Thr Gln Ile Phe Gln Lys Ala Tyr Glu His Glu
                770                 775                 780

Gln His Ile Ser Glu Ser Ile Asn Asn Ile Val Asp His Ala Ile Lys
785                 790                 795                 800

Ser Lys Asp His Ala Thr Phe Asn Phe Leu Gln Trp Tyr Val Ala Glu
                805                 810                 815

Gln His Glu Glu Glu Val Leu Phe Lys Asp Ile Leu Asp Lys Ile Glu
                820                 825                 830

Leu Ile Gly Asn Glu Asn His Gly Leu Tyr Leu Ala Asp Gln Tyr Val
                835                 840                 845

Lys Gly Ile Ala Lys Ser Arg Lys Ser Gly Ser Arg Lys Arg Arg Ser
                850                 855                 860

Gly Ser Gly Ala Pro Val Lys Gln Thr Leu Asn Phe Asp Leu Leu Lys
865                 870                 875                 880

Leu Ala Gly Asp Val Glu Ser Asn Pro Gly Pro Met Arg Ala Val Gly
                885                 890                 895

Val Phe Leu Ala Ile Cys Leu Val Thr Ile Phe Val Leu Pro Thr Trp
                900                 905                 910

Gly Asn Trp Ala Tyr Pro Cys Cys His Val Thr Gln Leu Arg Ala Gln
                915                 920                 925

His Leu Leu Ala Leu Glu Asn Ile Ser Asp Ile Tyr Leu Val Ser Asn
                930                 935                 940

Gln Thr Cys Asp Gly Phe Ser Leu Ala Ser Leu Asn Ser Pro Lys Asn
945                 950                 955                 960

Gly Ser Asn Gln Leu Val Ile Ser Arg Cys Ala Asn Gly Leu Asn Val
                965                 970                 975

Val Ser Phe Phe Ile Ser Ile Leu Lys Arg Ser Ser Ser Ala Leu Thr
                980                 985                 990

Gly His Leu Arg Glu Leu Leu Thr Thr Leu Glu Thr Leu Tyr Gly Ser
                995                 1000                1005

Phe Ser Val Glu Asp Leu Phe Gly Ala Asn Leu Asn Arg Tyr Ala
                1010                1015                1020

Trp His Arg Gly Gly Arg Lys Arg Arg Ser Gly Ser Gly Ala Pro
                1025                1030                1035

Val Lys Gln Thr Leu Asn Phe Asp Leu Leu Lys Leu Ala Gly Asp
                1040                1045                1050

Val Glu Ser Asn Pro Gly Pro Met Pro Met Gly Ser Leu Gln Pro
                1055                1060                1065

Leu Ala Thr Leu Tyr Leu Leu Gly Met Leu Val Ala Ser Val Leu
                1070                1075                1080
```

```
Ala Gly Gly Arg Val Ala Ala Ala Ile Thr Trp Val Pro Lys
1085                1090                1095

Pro Asn Val Glu Val Trp Pro Val Asp Pro Pro Pro Val Asn
    1100                1105                1110

Phe Asn Lys Thr Ala Glu Gln Glu Tyr Gly Asp Lys Glu Val Lys
1115                1120                1125

Leu Pro His Trp Thr Pro Thr Leu His Thr Phe Gln Val Pro Gln
1130                1135                1140

Asn Tyr Thr Lys Ala Asn Cys Thr Tyr Cys Asn Thr Arg Glu Tyr
1145                1150                1155

Thr Phe Ser Tyr Lys Gly Cys Cys Phe Tyr Phe Thr Lys Lys Lys
1160                1165                1170

His Thr Trp Asn Gly Cys Phe Gln Ala Cys Ala Glu Leu Tyr Pro
1175                1180                1185

Cys Thr Tyr Phe Tyr Gly Pro Thr Pro Asp Ile Leu Pro Val Val
1190                1195                1200

Thr Arg Asn Leu Asn Ala Ile Glu Ser Leu Trp Val Gly Val Tyr
1205                1210                1215

Arg Val Gly Glu Gly Asn Trp Thr Ser Leu Asp Gly Gly Thr Phe
1220                1225                1230

Lys Val Tyr Gln Ile Phe Gly Ser His Cys Thr Tyr Val Ser Lys
1235                1240                1245

Phe Ser Thr Val Pro Val Ser His His Glu Cys Ser Phe Leu Lys
1250                1255                1260

Pro Cys Leu Cys Val Ser Gln Arg Ser Asn Ser
1265                1270

<210> SEQ ID NO 145
<211> LENGTH: 2595
<212> TYPE: DNA
<213> ORGANISM: Artificial Sequence
<220> FEATURE:
<223> OTHER INFORMATION: gH-(SGGG)2-ferritin sequence

<400> SEQUENCE: 145
atgcagctcc tgtgcgtgtt ctgtctggtg ctgctgtggg aagtgggagc cgcttctctg      60
agtgaggtga agctgcacct ggacattgaa ggccacgcct cccattacac tatcccttgg     120
accgagctga tggctaaagt gccaggactg tctcctgagg ctctgtggcg ggaagctaat     180
gtgaccgagg atctggcctc tatgctgaac agatacaagc tgatctataa aaccagtggc     240
acactgggga ttgctctggc tgagccagtg acatccccg ccgtgtcaga aggaagcatg     300
caggtggatg ctagtaaggt gcatccaggg gtgattagcg gactgaacag cccagcttgc     360
atgctgagcg ctcctctgga aaacagctc ttctactata tcggcaccat gctgcctaat     420
acacggccac acagctacgt gttttatcag ctcagatgtc atctgtccta cgtggccctg     480
tctattaacg gggacaagtt ccagtataca ggagctatga cttccaaatt tctgatggga     540
acttacaagc gggtgaccga aaaggcgat gaacacgtgc tgtctctggt gttcgggaag     600
acaaaagacc tgcccgatct gagaggaccc ttttcctacc cttctctgac tagtgcccag     660
tcaggcgact atagcctggt gatcgtgacc acattcgtgc actacgctaa cttccataat     720
tattttgtgc ccaatctgaa ggatatgttt tcccgggccg tgaccatgac agccgcttct     780
tacgctagat atgtgctgca gaagctggtg ctgctggaga tgaaaggcgg gtgccgggag     840
cctgaactgg acactgaaac cctgactacc atgttcgagg tgtccgtggc cttctttaaa     900
```

```
gtgggacacg ctgtgggaga cacaggaaac ggatgcgtgg acctgagatg gctggccaag    960
agcttctttg aactgaccgt gctgaaagat atcattggaa tctgttacgg cgccacagtg   1020
aaaggaatgc agagctatgg cctggagagg ctggccgcta tgctgatggc caccgtgaag   1080
atggaggaac tgggccacct gacaactgag aaacaggaat acgctctgag gctggctacc   1140
gtgggatacc caaaggccgg ggtgtattcc ggactgattg gaggcgccac atctgtgctg   1200
ctgagtgctt ataataggca cccactgttc cagcccctgc atacagtgat gcgcgagact   1260
ctgtttatcg ggtctcatgt ggtgctgcgg gaactgagac tgaatgtgac cacacaggga   1320
cccaacctgg ccctgtacca gctcctgagt actgccctgt gctcagctct ggagattgga   1380
gaagtgctga ggggactggc cctggggacc gagtcaggac tgttcagccc ttgttatctg   1440
tcactgaggt ttgacctgac tcgcgataag ctgctgagca tggccccaca ggaagctacc   1500
ctggaccagg ccgctgtgag caatgccgtg gatggattcc tgggcaggct gtccctggag   1560
agggaagacc gcgatgcctg gcacctgcca gcttacaagt gcgtggaccg cctggataaa   1620
gtgctgatga tcattcccct gatcaacgtg accttcatca ttagctccga cagggaagtg   1680
agaggcagcg ctctgtacga agcttccact acctatctgt ctagttcact gtttctgtca   1740
cctgtgatta tgaataagtg tagccaggga gctgtggctg gagagcccag acagatccca   1800
aagattcaga acttcacacg cactcagaaa agttgcatct tctgtggctt tgccctgctg   1860
tcatacgatg agaaagaagg gctggagaca actacctata ttcacatctca ggaagtgcag   1920
aacagtatcc tgagctccaa ttacttcgac tttgataacc tgcacgtgca ttatctgctg   1980
ctgacaacta acggcaccgt gatggagatc gctggactgt acgaggaaag ggctcactct   2040
ggcggcggta gcggcggtgg ctccggagag agccaggtga ggcagcagtt cagcaaggac   2100
atcgagaagc tgctgaacga gcaggtgaac aaggagatgc agagcagcaa cctgtacatg   2160
agcatgagca gctggtgcta cacccacagc ctggacggcg ccggcctgtt cctgttcgac   2220
cacgccgccg aggagtacga gcacgccaag aagctgatca tcttcctgaa cgagaacaac   2280
gtgcccgtgc agctgaccag catcagcgcc ccgagcaca gttcgaggg cctgacccag   2340
atcttccaga aggcctacga gcacgagcag cacatcagcg agagcatcaa caacatcgtg   2400
gaccacgcca tcaagagcaa ggaccacgcc accttcaact tcctgcagtg gtacgtggcc   2460
gagcagcacg aggaggaggt gctgttcaag gacatcctgg acaagatcga gctgatcggc   2520
aacgagaacc acggcctgta cctggccgac cagtacgtga agggcatcgc caagagcagg   2580
aagagcggat cctag                                                   2595
```

<210> SEQ ID NO 146
<211> LENGTH: 864
<212> TYPE: PRT
<213> ORGANISM: Artificial Sequence
<220> FEATURE:
<223> OTHER INFORMATION: Amino acid sequence encoded by SEQ ID NO:146
      (gH-(SGGG)2-ferritin sequence)

<400> SEQUENCE: 146

Met Gln Leu Leu Cys Val Phe Cys Leu Val Leu Leu Trp Glu Val Gly
1               5                   10                  15

Ala Ala Ser Leu Ser Glu Val Lys Leu His Leu Asp Ile Glu Gly His
            20                  25                  30

Ala Ser His Tyr Thr Ile Pro Trp Thr Glu Leu Met Ala Lys Val Pro
        35                  40                  45

Gly Leu Ser Pro Glu Ala Leu Trp Arg Glu Ala Asn Val Thr Glu Asp

```
                50              55              60
Leu Ala Ser Met Leu Asn Arg Tyr Lys Leu Ile Tyr Lys Thr Ser Gly
65                      70                  75                  80

Thr Leu Gly Ile Ala Leu Ala Glu Pro Val Asp Ile Pro Ala Val Ser
                    85                  90                  95

Glu Gly Ser Met Gln Val Asp Ala Ser Lys Val His Pro Gly Val Ile
                    100                 105                 110

Ser Gly Leu Asn Ser Pro Ala Cys Met Leu Ser Ala Pro Leu Glu Lys
                    115                 120                 125

Gln Leu Phe Tyr Tyr Ile Gly Thr Met Leu Pro Asn Thr Arg Pro His
        130                 135                 140

Ser Tyr Val Phe Tyr Gln Leu Arg Cys His Leu Ser Tyr Val Ala Leu
145                 150                 155                 160

Ser Ile Asn Gly Asp Lys Phe Gln Tyr Thr Gly Ala Met Thr Ser Lys
                    165                 170                 175

Phe Leu Met Gly Thr Tyr Lys Arg Val Thr Glu Lys Gly Asp Glu His
                    180                 185                 190

Val Leu Ser Leu Val Phe Gly Lys Thr Lys Asp Leu Pro Asp Leu Arg
            195                 200                 205

Gly Pro Phe Ser Tyr Pro Ser Leu Thr Ser Ala Gln Ser Gly Asp Tyr
        210                 215                 220

Ser Leu Val Ile Val Thr Thr Phe Val His Tyr Ala Asn Phe His Asn
225                 230                 235                 240

Tyr Phe Val Pro Asn Leu Lys Asp Met Phe Ser Arg Ala Val Thr Met
                    245                 250                 255

Thr Ala Ala Ser Tyr Ala Arg Tyr Val Leu Gln Lys Leu Val Leu Leu
                    260                 265                 270

Glu Met Lys Gly Gly Cys Arg Glu Pro Glu Leu Asp Thr Glu Thr Leu
                275                 280                 285

Thr Thr Met Phe Glu Val Ser Val Ala Phe Lys Val Gly His Ala
            290                 295                 300

Val Gly Glu Thr Gly Asn Gly Cys Val Asp Leu Arg Trp Leu Ala Lys
305                 310                 315                 320

Ser Phe Phe Glu Leu Thr Val Leu Lys Asp Ile Ile Gly Ile Cys Tyr
                    325                 330                 335

Gly Ala Thr Val Lys Gly Met Gln Ser Tyr Gly Leu Glu Arg Leu Ala
                340                 345                 350

Ala Met Leu Met Ala Thr Val Lys Met Glu Glu Leu Gly His Leu Thr
                355                 360                 365

Thr Glu Lys Gln Glu Tyr Ala Leu Arg Leu Ala Thr Val Gly Tyr Pro
    370                 375                 380

Lys Ala Gly Val Tyr Ser Gly Leu Ile Gly Ala Thr Ser Val Leu
385                 390                 395                 400

Leu Ser Ala Tyr Asn Arg His Pro Leu Phe Gln Pro Leu His Thr Val
                405                 410                 415

Met Arg Glu Thr Leu Phe Ile Gly Ser His Val Val Leu Arg Glu Leu
                420                 425                 430

Arg Leu Asn Val Thr Thr Gln Gly Pro Asn Leu Ala Leu Tyr Gln Leu
                435                 440                 445

Leu Ser Thr Ala Leu Cys Ser Ala Leu Glu Ile Gly Glu Val Leu Arg
    450                 455                 460

Gly Leu Ala Leu Gly Thr Glu Ser Gly Leu Phe Ser Pro Cys Tyr Leu
465                 470                 475                 480
```

```
Ser Leu Arg Phe Asp Leu Thr Arg Asp Lys Leu Leu Ser Met Ala Pro
                485                 490                 495

Gln Glu Ala Thr Leu Asp Gln Ala Ala Val Ser Asn Ala Val Asp Gly
            500                 505                 510

Phe Leu Gly Arg Leu Ser Leu Glu Arg Glu Asp Arg Asp Ala Trp His
            515                 520                 525

Leu Pro Ala Tyr Lys Cys Val Asp Arg Leu Asp Lys Val Leu Met Ile
        530                 535                 540

Ile Pro Leu Ile Asn Val Thr Phe Ile Ile Ser Ser Asp Arg Glu Val
545                 550                 555                 560

Arg Gly Ser Ala Leu Tyr Glu Ala Ser Thr Thr Tyr Leu Ser Ser Ser
                565                 570                 575

Leu Phe Leu Ser Pro Val Ile Met Asn Lys Cys Ser Gln Gly Ala Val
            580                 585                 590

Ala Gly Glu Pro Arg Gln Ile Pro Lys Ile Gln Asn Phe Thr Arg Thr
            595                 600                 605

Gln Lys Ser Cys Ile Phe Cys Gly Phe Ala Leu Leu Ser Tyr Asp Glu
        610                 615                 620

Lys Glu Gly Leu Glu Thr Thr Thr Tyr Ile Thr Ser Gln Glu Val Gln
625                 630                 635                 640

Asn Ser Ile Leu Ser Ser Asn Tyr Phe Asp Phe Asp Asn Leu His Val
                645                 650                 655

His Tyr Leu Leu Leu Thr Thr Asn Gly Thr Val Met Glu Ile Ala Gly
            660                 665                 670

Leu Tyr Glu Glu Arg Ala His Ser Gly Gly Ser Gly Gly Gly Ser
            675                 680                 685

Gly Glu Ser Gln Val Arg Gln Gln Phe Ser Lys Asp Ile Glu Lys Leu
        690                 695                 700

Leu Asn Glu Gln Val Asn Lys Glu Met Gln Ser Ser Asn Leu Tyr Met
705                 710                 715                 720

Ser Met Ser Ser Trp Cys Tyr Thr His Ser Leu Asp Gly Ala Gly Leu
                725                 730                 735

Phe Leu Phe Asp His Ala Ala Glu Glu Tyr Glu His Ala Lys Lys Leu
            740                 745                 750

Ile Ile Phe Leu Asn Glu Asn Asn Val Pro Val Gln Leu Thr Ser Ile
        755                 760                 765

Ser Ala Pro Glu His Lys Phe Glu Gly Leu Thr Gln Ile Phe Gln Lys
        770                 775                 780

Ala Tyr Glu His Glu Gln His Ile Ser Glu Ser Ile Asn Asn Ile Val
785                 790                 795                 800

Asp His Ala Ile Lys Ser Lys Asp His Ala Thr Phe Asn Phe Leu Gln
                805                 810                 815

Trp Tyr Val Ala Glu Gln His Glu Glu Val Leu Phe Lys Asp Ile
            820                 825                 830

Leu Asp Lys Ile Glu Leu Ile Gly Asn Glu Asn His Gly Leu Tyr Leu
        835                 840                 845

Ala Asp Gln Tyr Val Lys Gly Ile Ala Lys Ser Arg Lys Ser Gly Ser
850                 855                 860
```